US011970448B2

(12) United States Patent
Barany et al.

(10) Patent No.: US 11,970,448 B2
(45) Date of Patent: *Apr. 30, 2024

(54) MONOMERS CAPABLE OF DIMERIZING IN AN AQUEOUS SOLUTION, AND METHODS OF USING SAME

(71) Applicants: CORNELL UNIVERSITY, Ithaca, NY (US); PURDUE RESEARCH FOUNDATION, West Lafayette, IN (US)

(72) Inventors: Francis Barany, New York, NY (US); Maneesh Pingle, New York, NY (US); Donald E. Bergstrom, West Lafayette, IN (US); Sarah F. Giardina, New York, NY (US); Lee Daniel Arnold, Mt. Sinai, NY (US)

(73) Assignees: CORNELL UNIVERSITY, Ithaca, NY (US); PURDUE RESEARCH FOUNDATION, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/929,528

(22) Filed: Jul. 15, 2020

(65) Prior Publication Data
US 2020/0354319 A1 Nov. 12, 2020

Related U.S. Application Data

(63) Continuation of application No. 14/110,056, filed as application No. PCT/US2012/032809 on Apr. 9, 2012, now abandoned.

(60) Provisional application No. 61/473,093, filed on Apr. 7, 2011.

(51) Int. Cl.
| C07D 211/26 | (2006.01) |
| C07D 405/06 | (2006.01) |
| C07D 409/06 | (2006.01) |
| C07D 491/107 | (2006.01) |
| C07F 5/02 | (2006.01) |
| C07F 5/04 | (2006.01) |

(52) U.S. Cl.
CPC .......... *C07D 211/26* (2013.01); *C07D 405/06* (2013.01); *C07D 409/06* (2013.01); *C07D 491/107* (2013.01); *C07F 5/025* (2013.01); *C07F 5/04* (2013.01)

(58) Field of Classification Search
None
See application file for complete search history.

(56) References Cited

U.S. PATENT DOCUMENTS

| 5,401,751 A | 3/1995 | Crawley et al. |
| 6,326,011 B1 | 12/2001 | Miyazawa et al. |
| 6,977,263 B2 * | 12/2005 | Astles ............ A61P 43/00 514/318 |
| 7,511,139 B2 | 3/2009 | Zhou et al. |
| 7,713,994 B2 | 5/2010 | Tsou et al. |
| 8,853,185 B2 | 10/2014 | Barany et al. |
| 2002/0150890 A1 | 10/2002 | Nakayama et al. |
| 2003/0165772 A1 | 9/2003 | Takahashi et al. |
| 2004/0241748 A1 | 12/2004 | Ault-Richie et al. |
| 2004/0265902 A1 | 12/2004 | Fricker et al. |
| 2008/0255425 A1 | 10/2008 | Voegele et al. |
| 2009/0149399 A1 | 6/2009 | Tung |
| 2010/0081792 A1 | 4/2010 | Grant et al. |
| 2010/0159446 A1 | 6/2010 | Haff et al. |
| 2012/0295874 A1 | 11/2012 | Barany et al. |
| 2014/0161729 A1 | 6/2014 | Barany et al. |
| 2014/0163229 A1 | 6/2014 | Barany et al. |
| 2014/0194383 A1 | 7/2014 | Barany et al. |
| 2015/0105553 A1 | 4/2015 | Barany et al. |

FOREIGN PATENT DOCUMENTS

| JP | 63222153 | 9/1988 |
| JP | 2004-510697 A | 4/2004 |
| WO | 2000002896 A1 | 1/2000 |
| WO | 01-90101 A1 | 11/2001 |
| WO | 2009/018003 A2 | 2/2009 |
| WO | 2009-067202 A1 | 5/2009 |
| WO | 2009126290 A2 | 10/2009 |
| WO | 2011022449 A1 | 2/2011 |

(Continued)

OTHER PUBLICATIONS

Federal Register, vol. 76, No. 27, Feb. 9, 2011, 7162-7175, 7166.*
International Search Report and Written Opinion for PCT/US2012/000198, dated Oct. 1, 2012.
International Search Report and Written Opinion for PCT/US2012/032813, dated Sep. 24, 2012.
Supplementary European Search Report for EP 12842488, dated Sep. 4, 2014.
Supplementary European Search Report for EP 12842368, dated Aug. 8, 2014.
Bunyapaiboonsri et al., "Generation of Bis-Cationic Heterocyclic Inhibitors of Bacillus subtills HPr Kinase/Phosphatase from a Ditopic Dynamic Combinatorial Library", J. Med. Chem., 46:5803-5811 (2003).

(Continued)

*Primary Examiner* — Po-Chih Chen
(74) *Attorney, Agent, or Firm* — Troutman Pepper Hamilton Sanders LLP (Rochester)

(57) ABSTRACT

Described herein are monomers capable of forming a biologically useful multimer when in contact with one, two, three or more other monomers in an aqueous media. In one aspect, such monomers may be capable of binding to another monomer in an aqueous media (e.g. in vivo) to form a multimer, (e.g. a dimer). Contemplated monomers may include a ligand moiety, a linker element, and a connector element that joins the ligand moiety and the linker element. In an aqueous media, such contemplated monomers may join together via each linker element and may thus be capable of modulating one or more biomolecules substantially simultaneously, e.g., modulate two or more binding domains on a protein or on different proteins.

3 Claims, 12 Drawing Sheets

(56) References Cited

FOREIGN PATENT DOCUMENTS

| WO | 2011-043817 A1 | 4/2011 |
|---|---|---|
| WO | 2012154213 A1 | 11/2012 |
| WO | 2013058825 A1 | 4/2013 |

OTHER PUBLICATIONS

Burke et al., "Development and Application of Fluorescence Polarization Assays in Drug Discovery", Combinatorial Chemistry and High Throughput Screening, 6:183-194 (2003).
Shin et al., "Assembling Ligands In Situ Using Bloorthogonal Boronate Ester Synthesis", Chemistry and Biology, 17:1171-1176 (2010).
Trinquet et al., "Fluorescence Technologies for the Investigation of Chemical Libraries", Mol. Biosyst. 2:380-387 (2006).
West, Solid-State Chemistry and Its Applications, John Wiley & Sons (1984).
Procopiou et al., "Synthesis and Structure—Activity Relationships of Long-acting β2 Adrenergic Receptor Agonists Incorporating Metabolic Inactivation: An Antedrug Approach", J. Med. Chem. 53:4522-4530 (2010).
Soriano-Ursua et al., "Design, synthesis and in vitro evaluation of (R)-4-(2-tert-butylamino)-1-hydorxyethyl)-2-(hydroxymethyl)phenyl hydrogen phenylboronate: A novel salbutamol derivative with high intrinsic efficacy on the β2 adrenoceptor", Bioorg. Med. Chem. Lett. 20:5623-5629 (2010).
Office Action for corresponding European Patent Application No. 12842368.8 (dated Feb. 24, 2016).
Office Action for corresponding European Patent Application No. 12842368.8 (dated Jul. 14, 2015).
Office Action for corresponding European Patent Application No. 12842368.8 (dated Nov. 15, 2016).
Notice of Reasons for Rejection for corresponding Japanese Patent Application No. 2014-504078 (dated Feb. 17, 2016).
Notice of Reasons for Rejection for corresponding Japanese Patent Application No. 2014-504078 (dated Oct. 31, 2016).
Kumar et al., "Isolation and Characterization of Degradation Impurities in Epirubicin Hydrochloride Injection," J. Chromatogr. B 869:45-53 (2008).
Duke & Macleod, "Nuclear Magnetic Resonance Studies of p-Erythrose 4-Phosphate in Aqueous Solution, Structures of the Major Contributing Monomeric and Dimeric Forms," Carbohydrate Research 95:1-26 (1981).
Yaylayan et al., "Investigation of the Mechanism of Dissociation of Glycolaldehyde Dimer (2,5-dihydroxy-1,4-dioxane) by FTIR Spectroscopy," Carbohydrate Research 309:31-38 (1998).
Costall et al., "Characterisation of the Mechanisms for Hyperactivity Induction From the Nucleus Accumbens by Phenylethylamine Derivatives," Psychopharmacology 48:225-231 (1976).
Chemical Abstract Registry No. 1000524-64-0, indexed in the Registry File on STN CAS ONLINE Jan. 23, 2008.
Federal Register 76(27):7116 (2001).
Office Action for EP 12842368.8 dated Jun. 26, 2017.
Chemical Abstract Registry No. 1000518-95-5, indexed in the Registry File on STN CAS ONLINE Jan. 23, 2008.
Chemical Abstract Registry No. 854665-12-6, indexed in the Registry File on STN CAS ONLINE Jul. 12, 2005.
Rich et al., "Effect of Hydroxyl Group Configuration in Hydroxyethylamine Dipeptide Isosteres on HIV Protease Inhibition. Evidence for Multiple Binding Modes," Journal of Medicinal Chemistry 34:1222-1225 (1991).
Chemical Abstract Registry No. 746541-06-0, indexed in the Registry File on STN CAS ONLINE Sep. 17, 2004.
Chemical Abstract Registry No. 857020-02-1, indexed in the Registry File on STN CAS ONLINE Jul. 26, 2005.
International Search Report and Written Opinion for PCT/US2012/032809, filed Apr. 9, 2012 (dated Oct. 1, 2012).
Restriction Requirement in U.S. Appl. No. 14/110,056 (dated Feb. 19, 2015).
Office Action in U.S. Appl. No. 14/110,056 (dated Jul. 20, 2016).
Office Action in U.S. Appl. No. 14/110,056 (dated Mar. 22, 2017).
Office Action in U.S. Appl. No. 14/110,056 (dated Apr. 6, 2018).
Office Action in U.S. Appl. No. 14/110,056 (dated Oct. 1, 2018).
Office Action in U.S. Appl. No. 14/110,056 (dated Apr. 18, 2019).
Office Action in U.S. Appl. No. 14/110,056 (dated Jan. 15, 2020).

* cited by examiner

IUPAC name of tryptase-bound heterodimeric state
(2R)-5-({4-[3-(azaniumylmethyl)phenyl]piperidin-1-yl}carbonyl)-2-{3-[3-({4-[3-(azaniumylmethyl)phenyl]piperidin-1-yl}carbonyl)phenyl]-2-hydroxy-2H-1,3,2-benzodioxaborol-2-uide Traditional Name: (2R)-5-({4-[3-(aminiomethyl)phenyl]piperidin-1-yl}carbonyl)-2-{3-[3-({4-[3-(aminiomethyl)phenyl]piperidin-1-yl}carbonyl)phenyl]-2-hydroxy-2H-1,3,2-benzodioxaborol-2-uide

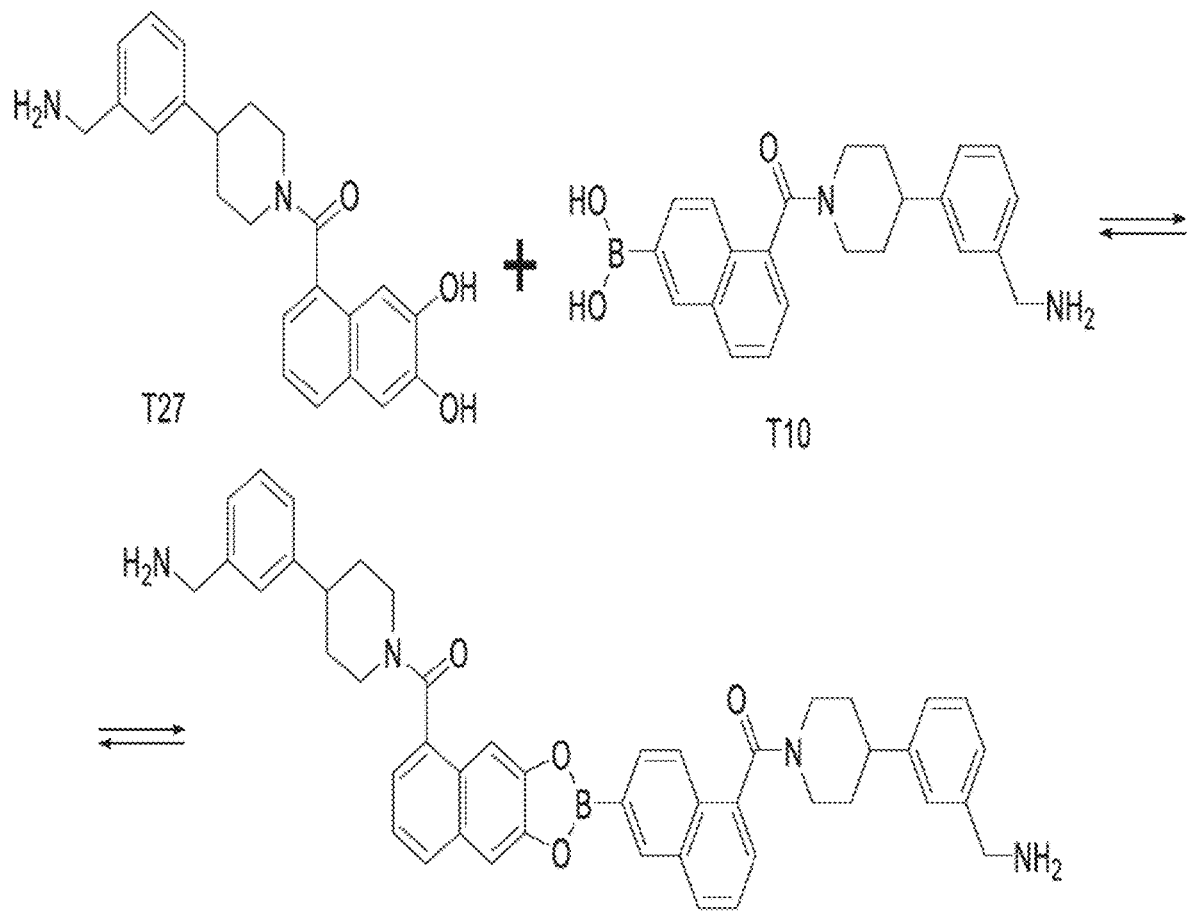

T27 IUPAC Name = [3-(1-{[6-(dihyroxyboranyl)naphthalen-1-yl]carbonyl}piperidin-4-yl)phenyl]methanaminium
T27 SMILES: [NH3+]CC1=CC=CC(=C1)C1CCN(CC1)C(=O)C1=CC=CC2=C1C=C(O)C(O)=C2
T10 IUPAC Name = [3-(1-{[6-(dihyroxyboranyl)naphthalen-1-yl]carbonyl}piperidin-4-yl)phenyl]methanaminium
T10 SMILES: [NH3+]CC1=CC=CC(=C1)C1CCN(CC1)C(=O)C1=CC=CC2=C1C=CC(=C2)B(O)O
T27+T10 heterodimer IUPAC Name = [3-[1-({6-[5-({4-[3-(azaniumylmethyl)phenyl]PIPERIDIN-1-yl}carbonyl)-2H-naphtho[2,3-d][1,3,2]dioxaborol-2-yl]naphthalene-1-yl}carbonyl)piperidin-4-yl]phenyl]methanaminium
T27+T10 SMILES
   [NH3+]CC1=CC=CC(=C1)C1CCN(CC1)C(=O)C1=CC=CC2=C1C=CC(=C2)B1OC2=CC
   3=C(C=C2O1)C(=CC=C3)C(=O)N1CCC(CC1)C1=CC(C[NH3+])=CC=C1

FIG. 4B

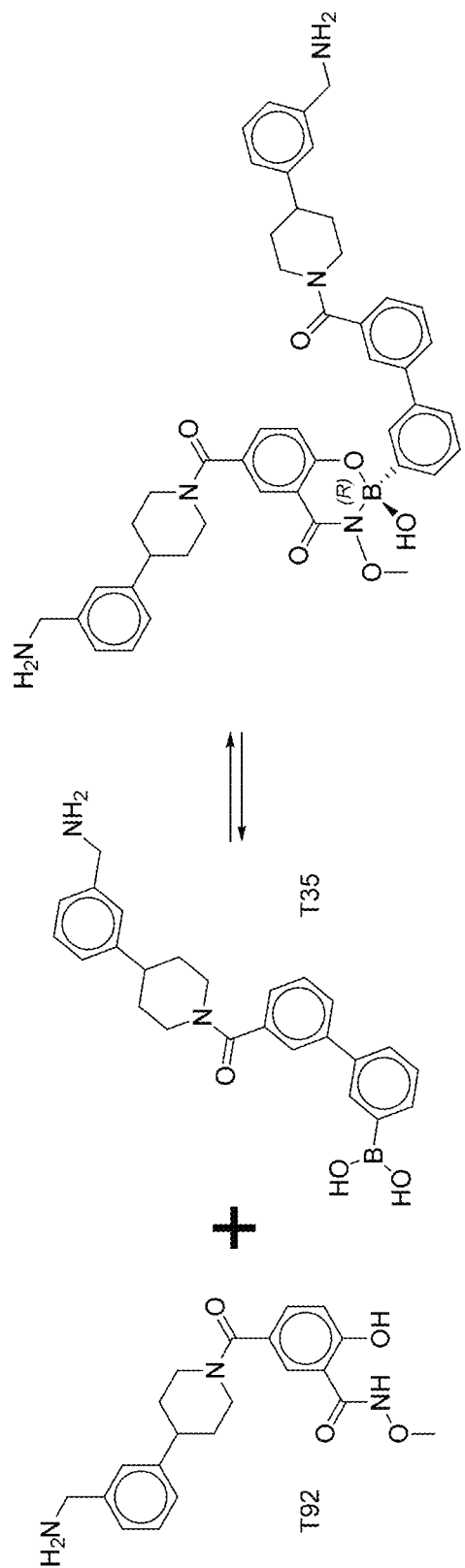

FIG. 5B

T92+T35 heterodimer forms a phenolic-hydroxamate/boronate complex bound in inhibiting tryptase. While the R-enantiomer of the boronate diester is observed, the S-isomer is also expected to be of similar potency.

T92 SMILES:
[CH3:30][O:29][NH:28][C:23](=[O:24])[c:22]1[cH:18][c:17](C(=[O:1])[N:3]1[CH2:4][CH2:5][CH:6]([CH2:15][CH2:16]1)[c:7]1[cH:8][cH:9][cH:10][c:11]([CH2:12][NH2:13])[cH:14]1

T92 IUPAC Name = 5-({4-[3-(aminomethyl)phenyl]piperidin-1-yl}carbonyl)-2-hydroxy-N-methoxybenzamide
See earlier slides for T35

T 55 Monomer

IUPAC Name: N-[3-({4-[3-(aminomethyl)phenyl]piperidin-1yl}carbonyl)phenyl]-3-hydroxy-3-methyl-2-oxobutanamide SMILES:
[CH3:29][C:28]([CH3:30])([OH:33])[C:26](=[O:31])[C:24](=[O:25])[NH:23]c:22]1[cH:20][cH:19][cH:18][c:17]([cH:21]1)[C:2](=[O:1])[N:3]1[CH2:4][CH2:5][CH:6]([CH2:15][CH2:16]1)[c:7]1[cH:14][cH:13][cH:12][c:9]([CH2:10][NH2:11])[cH:8]1

T 55 Homodimer

IUPAC Name: *(2R,4S)*-2-N,4-N-bis[3-({4-[3-(aminomethyl)phenyl]piperidin-1-yl}carbonyl)phenyl]-4-hydroxy 2-(2-hydroxypropan-2-yl)-5,5-dimethyl-1,3-dioxolane-2,4-dicarboxamide SMILES:
[CH3:35][C:34]([CH3:37])([OH:36])[C@:32]1([O:33][C:28]([CH3:29])([CH3:30])[C@:26]([OH:27])([O:31]1)[C:24](=[O:25])[NH:23][c:22]1[cH:20][cH:19][cH:18][c:17]([cH:21]1)[C:2](=[O:1])[N:3]1[CH2:4][CH2:5][CH:6]([CH2:15][CH2:16]1)[c:7]1[cH:14][cH:13][cH:12][c:9]([CH2:10][NH2:11])[cH8]1)[C:38](=[O:39])[NH:40][c:41]1[cH:46][cH:45][cH:44[c:43]([cH:42]1)[C:47](=[O:48])[N:49]1[CH2:50][CH2:51][CH:52]([CH2:53][CH2:54]1)[c:55]1[cH:62][cH:61][cH:60][c:57]([CH2:58][NH2:59])[cH:56]1

MONOMERS CAPABLE OF DIMERIZING IN AN AQUEOUS SOLUTION, AND METHODS OF USING SAME

CROSS-REFERENCE TO RELATED APPLICATIONS

This application is a continuation of U.S. patent application Ser. No. 14/110,056, filed Feb. 25, 2014, which is a National Stage Entry of PCT/US12/32809, filed Apr. 9, 2012, which claims priority to U.S. Provisional Application No. 61/473,093, filed Apr. 7, 2011, which is hereby incorporated by reference in its entirety.

BACKGROUND

Current drug design and drug therapies have not addressed the urgent need for therapies that interact with extended areas or multiple domains of biomolecules such as proteins. For example, there is an urgent need for therapies that are capable of, e.g., modulating protein-protein interactions, e.g., by modulating, simultaneously, domains on a single protein or both a domain on one protein and a domain on another protein. There is also an urgent need for such therapies that modulate fusion proteins, such as those that occur in cancer.

For example, signaling pathways are used by cells to generate biological responses to external or internal stimuli. A few thousand gene products control both ontogeny/development of higher organisms and sophisticated behavior by their many different cell types. These gene products can work in different combinations to achieve their goals and often do so through protein-protein interactions. Such proteins possess modular protein domains that recognize, bind, and/or modify certain motifs. Protein-protein and protein-nucleic acid recognition often function through protein interactions domains, for example, such as the SH2, SH3, and PDZ domains. These protein-interaction domains may represent a meaningful area for developing targeted therapies. Other macromolecular interactions that may serve as potential targets for effective therapies include protein-nucleic acid interactions, protein-carbohydrate interactions, and protein-lipid interactions.

Current drug design and drug therapy approaches do not address this urgent need to find drugs that interfere with intracellular protein-protein interactions or protein signaling. Although antibodies and other biological therapeutic agents may have sufficient specificity to distinguish among closely related protein surfaces, factors such as their high molecular weight prevent oral administration and uptake of the antibodies. Conversly, orally active pharmaceuticals are generally too small to disrupt protein-protein surface interactions, which can be much larger than the orally active pharmaceuticals. Further, previous attempts to link, e.g., two pharmacophores that each interact with e.g. different protein domains have focused on large covalently linked compounds assembled in organic solvents. These assemblies typically have a molecular weight too large for oral administration or effective cellular and tissue permeation.

SUMMARY

Described herein are monomers capable of forming a biologically useful multimer when in contact with one, two, three or more other monomers in an aqueous media. In one aspect, such monomers may be capable of binding to another monomer in an aqueous media (e.g. in vivo) to form a multimer, (e.g. a dimer). Contemplated monomers may include a ligand moiety (e.g. a pharmacophore for the target biomolecule), a linker element, and a connector element that joins the ligand moiety and the linker element. In an aqueous media, such contemplated monomers may join together via each linker element and may thus be capable of modulating one or more biomolecules substantially simultaneously, e.g., modulate two or more binding domains on a protein or on different proteins.

In one aspect, a first monomer capable of forming a biologically useful multimer when in contact with a second monomer in an aqueous media is provided. The first monomer is represented by the formula:

$X_1$—$Y_1$—$Z_1$ (Formula I) and pharmaceutically acceptable salts, stereoisomers, metabolites, and hydrates thereof, wherein $X_1$ is a first ligand moiety capable of binding to a first target biomolecule;

$Y_1$ is absent or is a connector moiety covalently bound to $X_1$ and $Z_1$;

$Z_1$ is a first linker as shown below; and the second monomer has a boronic acid or oxaborole moiety capable of binding with the $Z_1$ moiety of Formula I to form the multimer.

In another aspect, a method of administering a pharmaceutically effective amount of a multimeric compound to a patient in need thereof is provided. The method comprises administering to the patient thereof an amount of a first monomer as described above and an amount of a boronic acid or oxaborole monomer in amounts effective such that the pharmaceutically effective amount of the resulting multimer is formed in vivo.

In yet another aspect, a therapeutic multimer compound formed from the multimerization in an aqueous media of a first monomer is provided. The multimer is represented by the formula:

$$X_1\text{—}Y_1\text{—}Z_1 \qquad\qquad \text{(Formula I)}$$

and a second monomer represented by $$X_2\text{—}Y_2\text{—}Z_2 \qquad\qquad \text{(Formula II)},$$

wherein $X_1$ is a first ligand moiety capable of binding to a first target biomolecule;

$Y_1$ is absent or is a connector moiety covalently bound to $X_1$ and $Z_1$;

$Z_1$ is a first linker as shown below;

wherein $X_2$ is a second ligand moiety capable of binding to a second target biomolecule;

$Y_2$ is absent or is a connector moiety covalently bound to $X_2$ and $Z_2$; and $Z_2$ is a boronic acid or oxaborole moiety capable of binding with the $Z_1$ moiety of Formula I to form the multimer; and pharmaceutically acceptable salts, stereoisomers, metabolites and hydrates thereof.

In still another aspect, a method of modulating two or more target biomolecule domains substantially simultaneously is provided. The method comprises contacting an aqueous composition comprising said biomolecule domains with a first monomer represented by:

$X_1$—$Y_1$—$Z_1$ (Formula I) and pharmaceutically acceptable salts, stereoisomers, metabolites and hydrates thereof, wherein $X_1$ is a first ligand moiety capable of binding to a first target biomolecule domain; and a second monomer represented by:
$X_2$—$Y_2$—$Z_2$ (Formula II), wherein
$X_2$ is a ligand moiety capable of binding to a second target biomolecule domain;
wherein upon contact with the aqueous composition, said first monomer and said second monomer forms a dimer that binds to the first target biomolecule domain and the second target biomolecule domain.

In yet another aspect, a method of treating a disease associated with two or more target biomolecule domains in a patient in need thereof is provided. The method comprises administering to said patient a first monomer represented by:
$X_1$—$Y_1$—$Z_1$ (Formula I) and pharmaceutically acceptable salts, stereoisomers, metabolites and hydrates thereof, wherein
$X_1$ is a first ligand moiety capable of binding to a first target biomolecule domain; and
administering to said patient a second monomer represented by:
$X_2$—$Y_2$—$Z_2$ (Formula II), wherein
$X_2$ is a second ligand moiety capable of binding to a second target biomolecule domain, wherein upon administration, said first monomer and said second monomer forms a dimer in vivo that binds to the first target biomolecule domain and the second target biomolecule domain.

In still another aspect, a first monomer capable of forming a biologically useful dimer when in contact with a second monomer in vivo is provided. The first monomer is represented by the formula:
$X_3$—$Y_3$—$Z_3$ (Formula IV); and pharmaceutically acceptable salts, stereoisomers, metabolites and hydrates thereof,
and the second monomer is represented by:
$X_4$—$Y_4$—$Z_3$ (Formula V) and pharmaceutically acceptable salts, stereoisomers, metabolites and hydrates thereof,
wherein
$X_3$ is a first ligand moiety capable of binding to a first target biomolecule;
$Y_3$ is absent or is a connector moiety covalently bound to $X_4$ and $Z_3$;
$X_4$ is a second ligand moiety capable of binding to a second target biomolecule;
$Y_4$ is absent or is a connector moiety covalently bound to $X_4$ and $Z_3$;
$Z_3$ is as shown below.

In yet another aspect, a therapeutic dimerized compound formed from the dimerization in an aqueous media of a first monomer is provided. The first monomer is represented by:
$X_3$—$Y_3$—$Z_3$ (Formula IV); and pharmaceutically acceptable salts, stereoisomers, metabolites and hydrates thereof,
and a second monomer is represented by:
$X_4$—$Y_4$—$Z_3$ (Formula V) and pharmaceutically acceptable salts, stereoisomers, metabolites and hydrates thereof, wherein
$X_3$ is a first ligand moiety capable of binding to a first target biomolecule;
$Y_3$ is absent or is a connector moiety covalently bound to $X_4$ and $Z_3$;
$X_4$ is a second ligand moiety capable of binding to a second target biomolecule;
$Y_4$ is absent or is a connector moiety covalently bound to $X_4$ and $Z_3$;
$Z_3$ is as shown below.

In still another aspect, a method of treating a disease associated with two or more target biomolecule domains in a patient in need thereof is provided. The method comprises administering to said patient two or more monomers each independently selected from the group represented by:
$X_3$—$Y_3$—$Z_3$ (Formula IV); and pharmaceutically acceptable salts, stereoisomers, metabolites and hydrates thereof,
and a second monomer is represented by:
$X_4$—$Y_4$—$Z_3$ (Formula V) and pharmaceutically acceptable salts, stereoisomers, metabolites and hydrates thereof, wherein
$X_3$ is a first ligand moiety capable of binding to a first target biomolecule;
$Y_3$ is absent or is a connector moiety covalently bound to $X_4$ and $Z_3$;
$X_4$ is a second ligand moiety capable of binding to a second target biomolecule;
$Y_4$ is absent or is a connector moiety covalently bound to $X_4$ and $Z_3$;
$Z_3$ is as shown below, wherein upon administration, said first monomer and said second monomer forms a dimer in vivo that binds to the first target biomolecule domain and the second target biomolecule domain.

In yet another aspect, a first monomer capable of forming a biologically useful trimer when in contact with a second monomer and a third monomer in an aqueous media is provided. The first monomer is represented by the formula:
$X_2$—$Y_2$—$Z_2$ (Formula II) and pharmaceutically acceptable salts, stereoisomers, metabolites, and hydrates thereof, wherein
$X_2$ is a first ligand moiety capable of binding to a first target biomolecule;
$Y_2$ is absent or is a connector moiety covalently bound to $X_2$ and $Z_2$;
$Z_2$ is a first linker as shown below, and the second monomer and the third monomer each have a boronic acid moiety capable of binding with the $Z_2$ moiety of Formula II to form the trimer.

BRIEF DESCRIPTION OF THE FIGURES

FIG. 4B shows a reaction scheme for the formation of the 1:1 multimer in FIG. 4A, according to an embodiment;

FIG. 5B shows a reaction scheme for the formation of the 1:1 multimer in FIG. 5A, according to an embodiment;

DETAILED DESCRIPTION

Figure 1A:
FIG. 1A shows an x-ray co-crystal structure of a multimer bound to adjacent subunits of mast cell beta-tryptase-II, according to an embodiment. The cationic aminomethylphenyl-piperidine moieties of the multimer are bound in the pharmacophoric pockets of the tryptase subunits, and the linker elements are joined by a cyclic tetrahedral sp$^3$ boronate diester linkage.
Figure 1B:
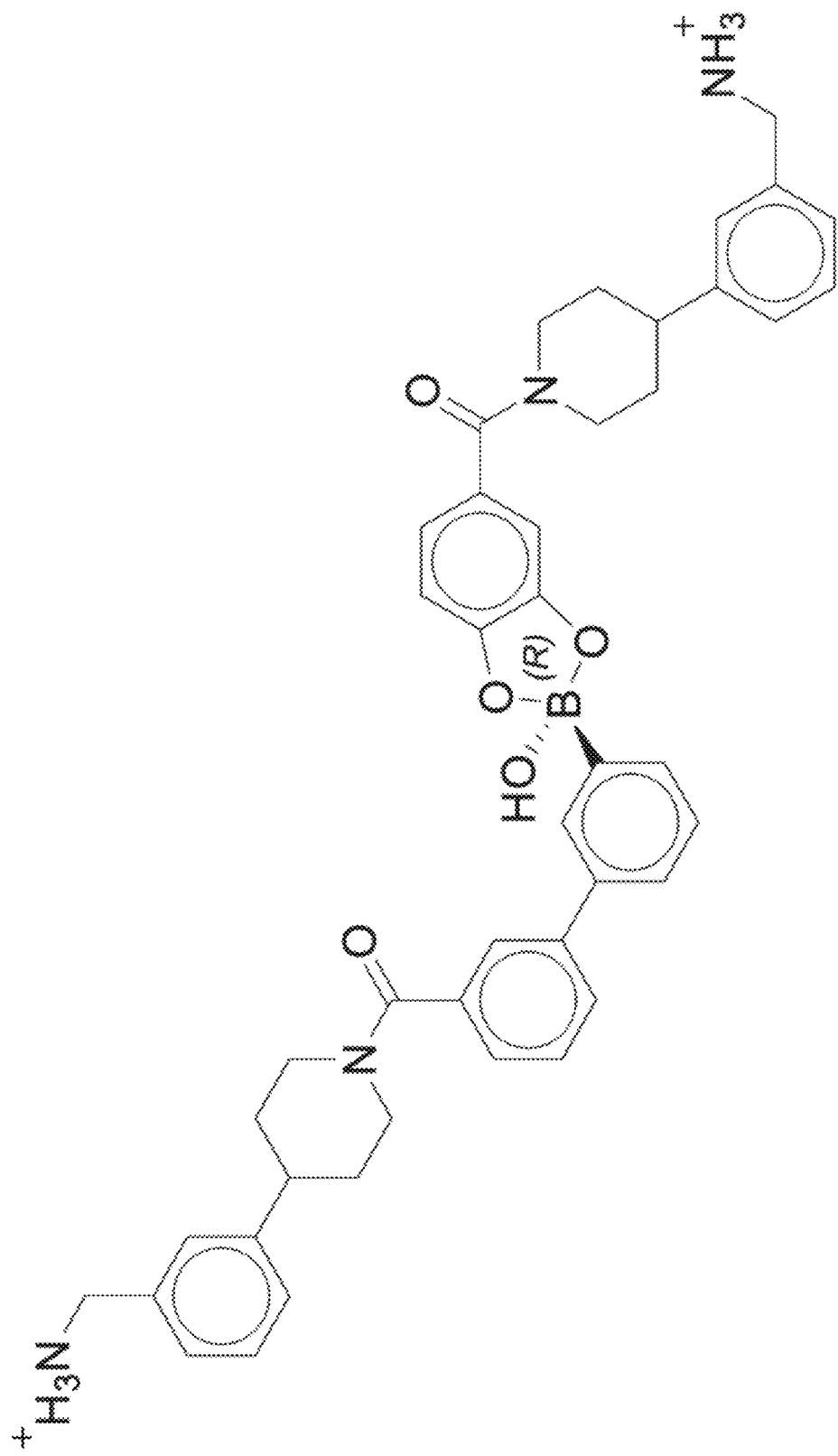
FIG. 1B shows the chemical structure of the multimer bound to tryptase in FIG. 1A, according to an embodiment.
Figure 2A:
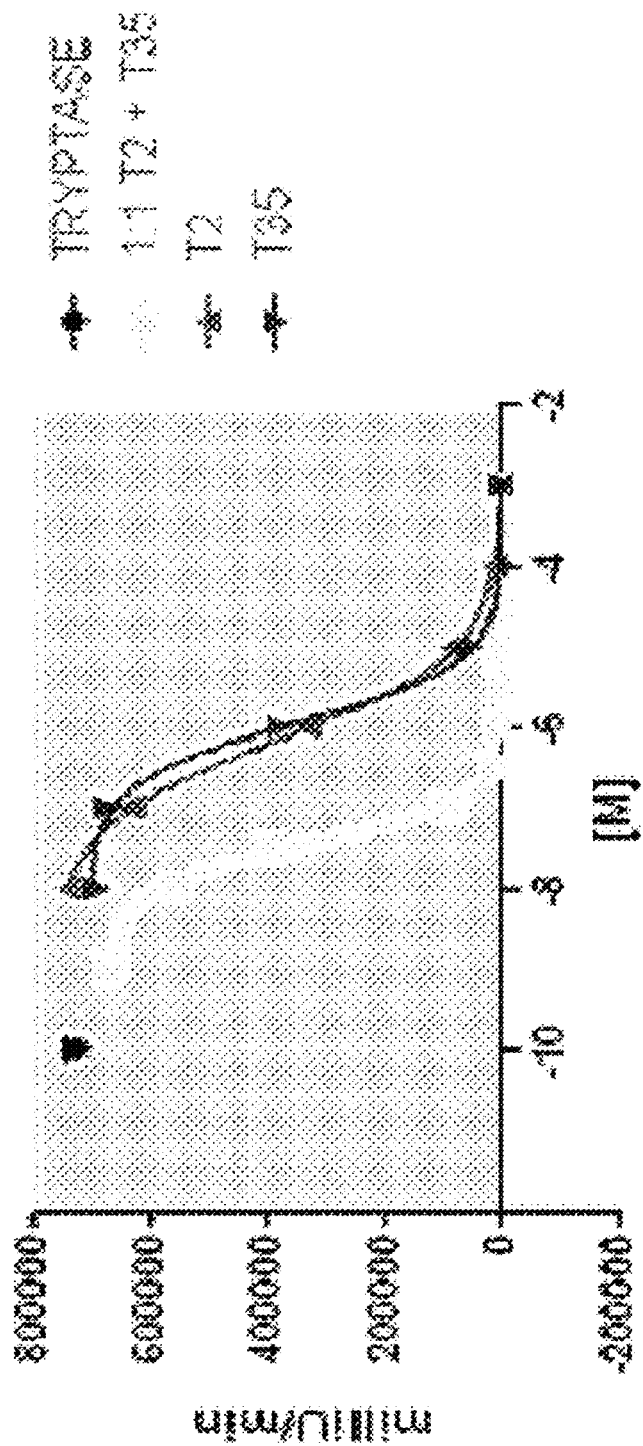
FIG. 2A shows dose response curves for T2 & T35 monomers and for T2 and T35 combined in a 1:1 ratio of T2:T35, according to an embodiment.
Figure 2B:
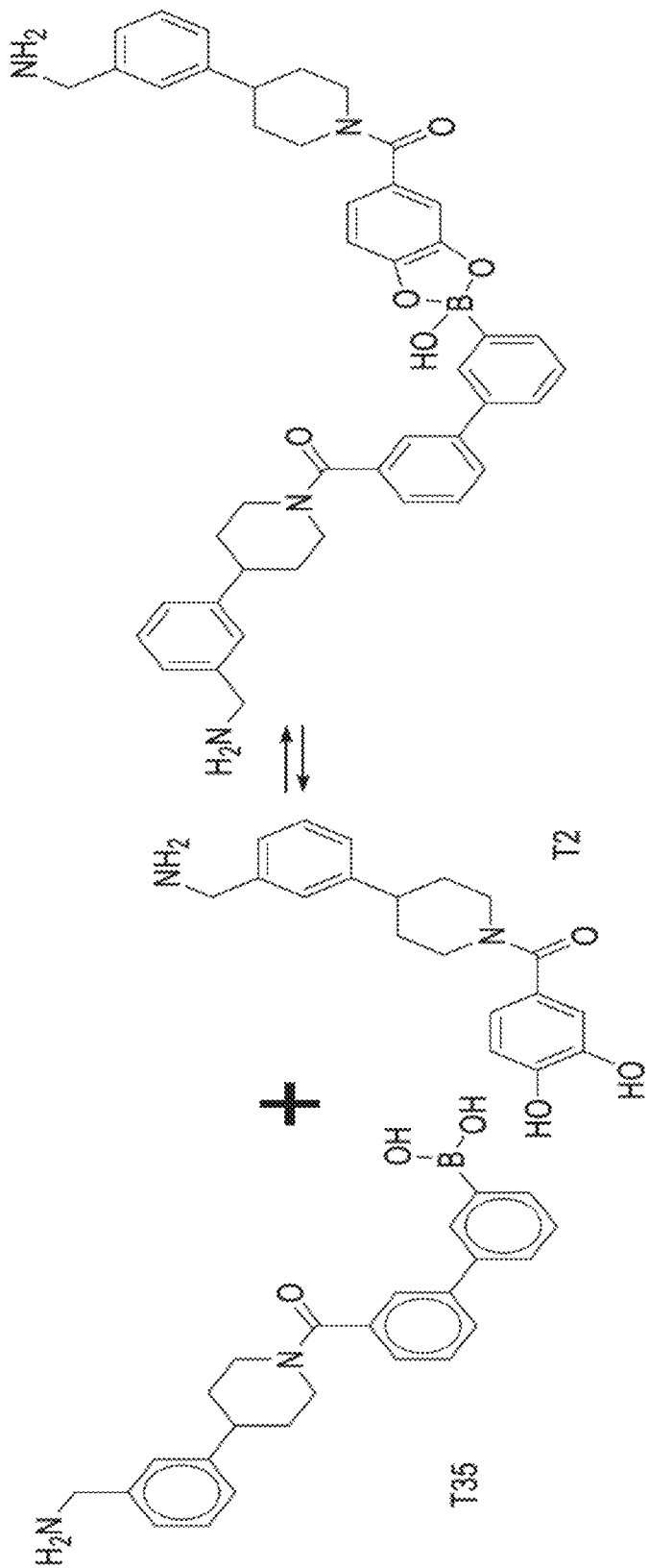
FIG. 2B shows a reaction scheme for the formation of the 1:1 multimer in FIG. 2A, according to an embodiment.
Figure 3:
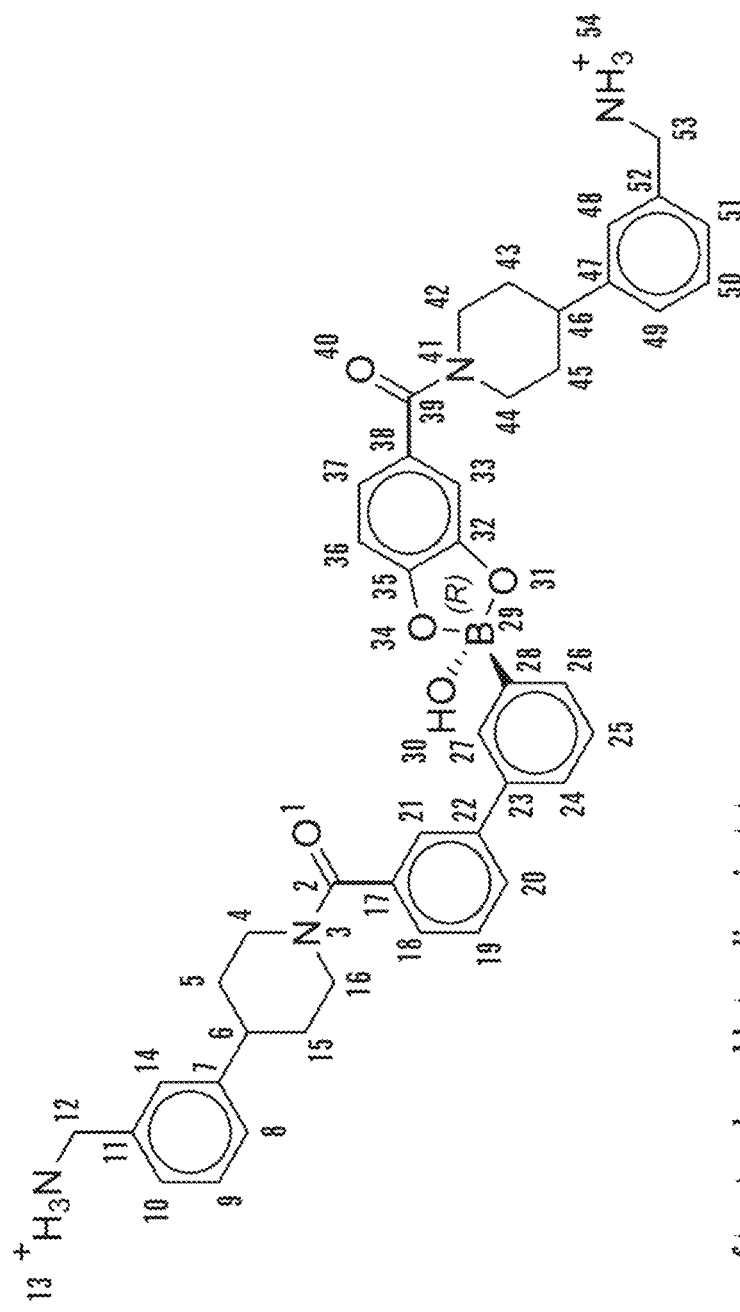
FIG. 3 shows the tryptase-bound state of the 1:1 multimer of T2:T35 shown in FIG. 1A, according to an embodiment.
Figure 4A:
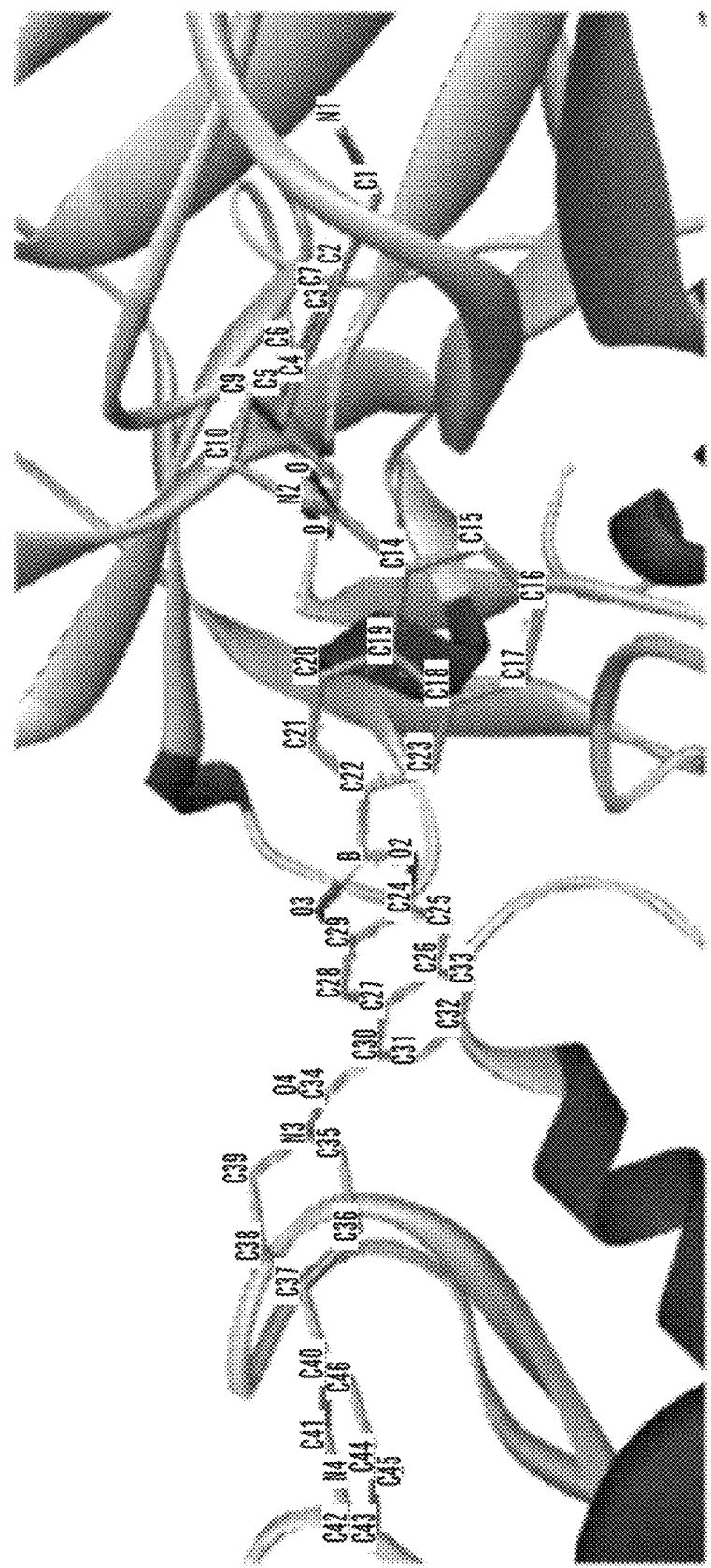
FIG. 4A shows an x-ray co crystal structure of a multimer bound to adjacent subunits of mast cell beta-tryptase, according to an embodiment. The cationic aminomethylphenyl-piperidine moieties of a 1:1 T27:T10 multimer are bound in the pharmacophoric pockets of the tryptase subunits, and the multimer is joined by a cyclic planar sp$^2$ boronic acid diester linkage.
Figure 5A:
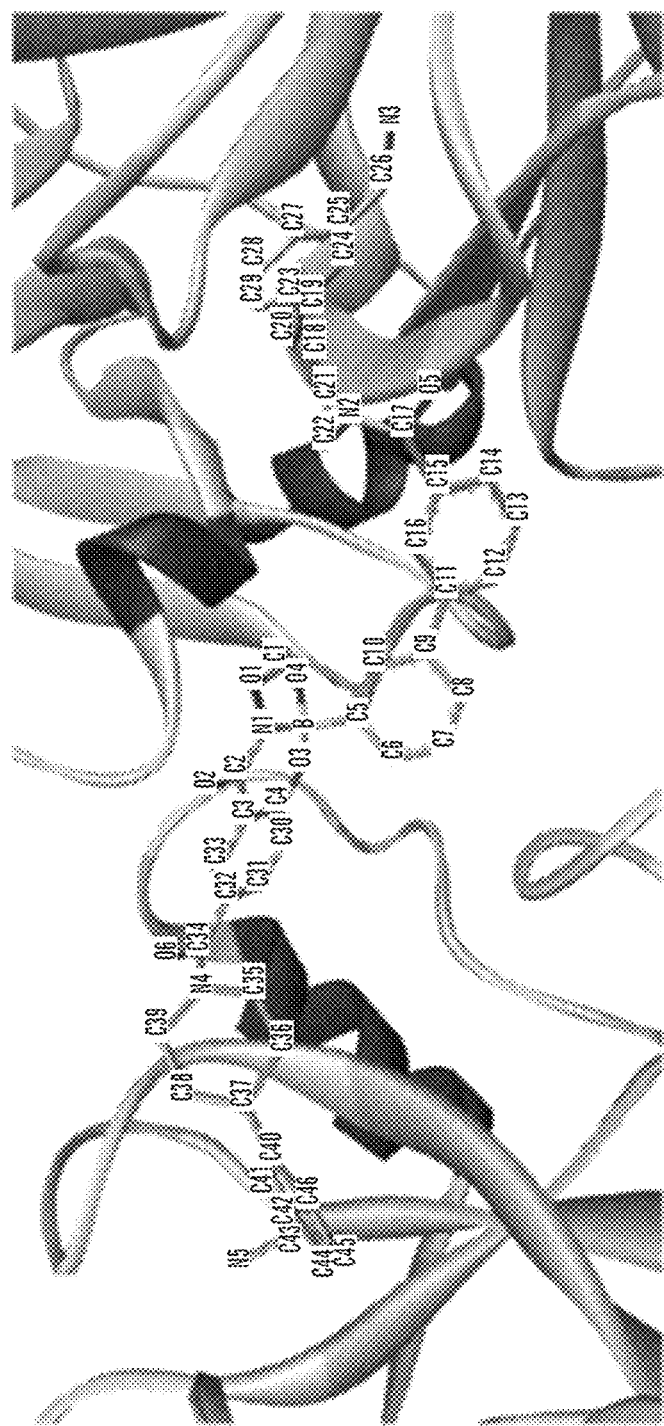
FIG. 5A shows an x-ray co-crystal structure of a T92+T35 heterodimer at pH5.5 and pH6.5 bound to tryptase, according to an embodiment. The structure confirms the $sp^3$ state of the phenolic-hydroxamate/boronate complex bound to tryptase under both conditions.
Figure 6A:
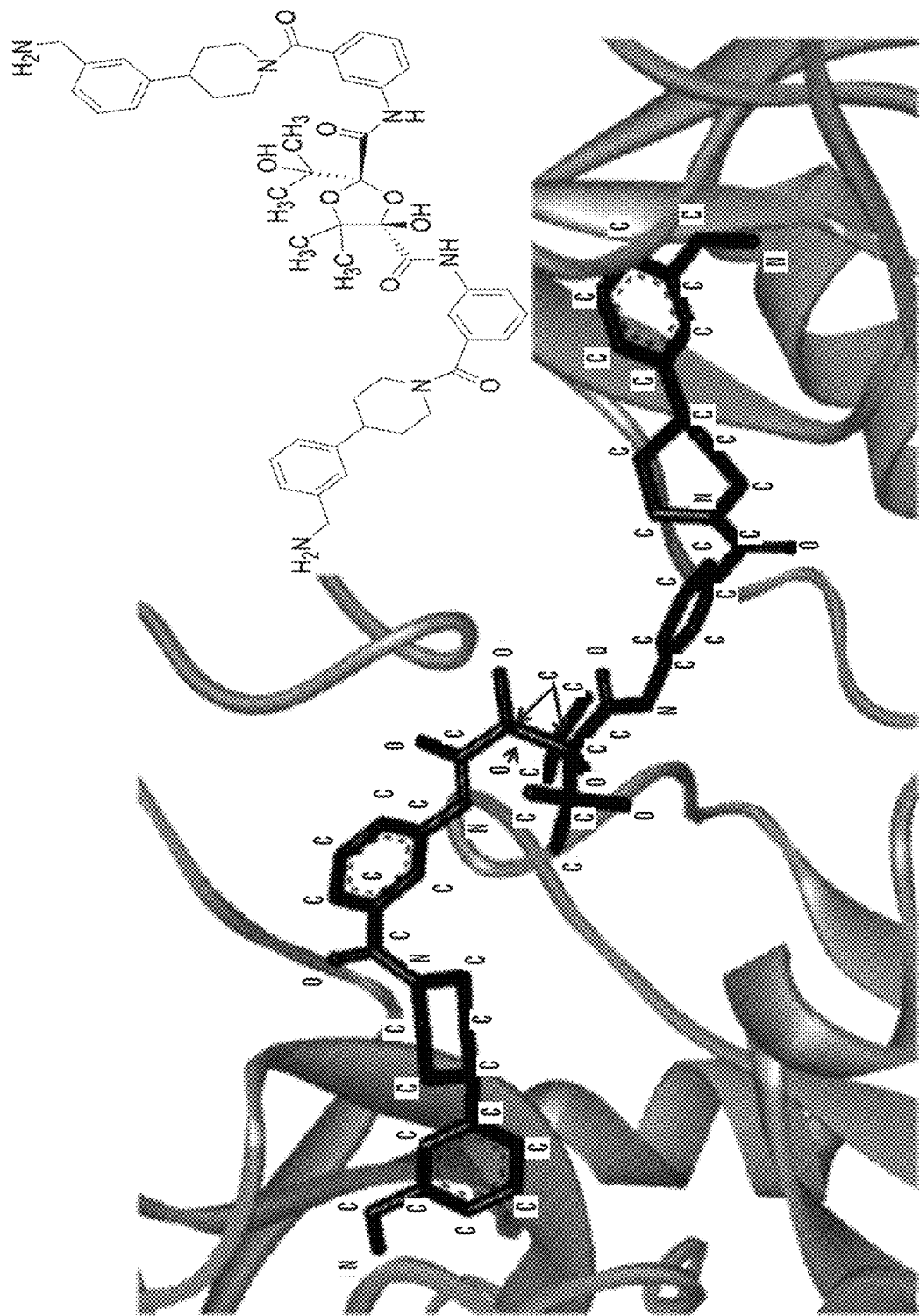
FIG. 6A shows an x-ray co-crystal structure of a T55 homodimer bound to tryptase, according to an embodiment. The cationic aminomethyl-phenyl-piperidine moieties of the multimer are bound in the pharmacophoric pockets of the tryptase subunits, and the monomers are joined by a covalent spiroketal linkage.
Figure 6B:
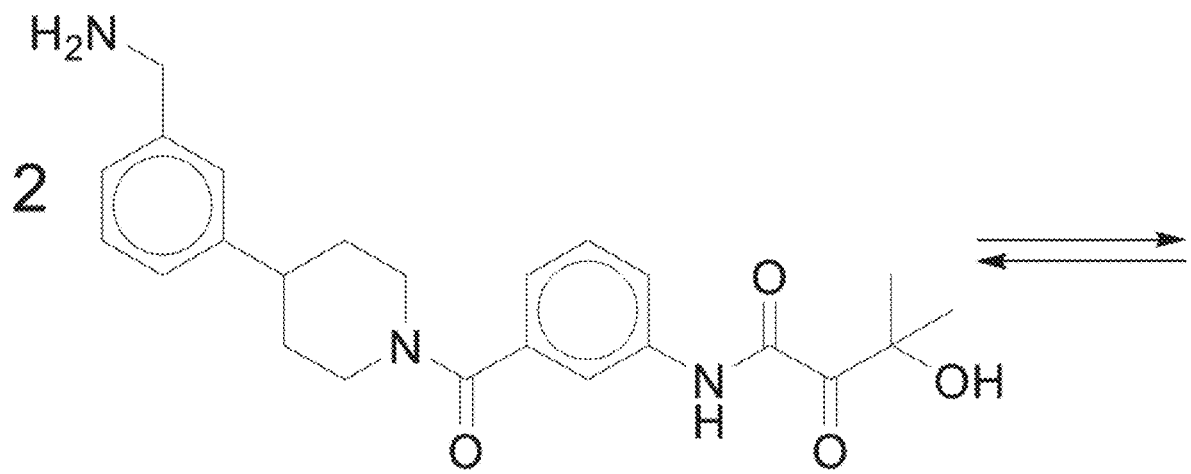
FIG. 6B shows a reaction scheme for the formation of the 1:1 multimer in FIG. 6A, according to an embodiment.
Figure 6B:
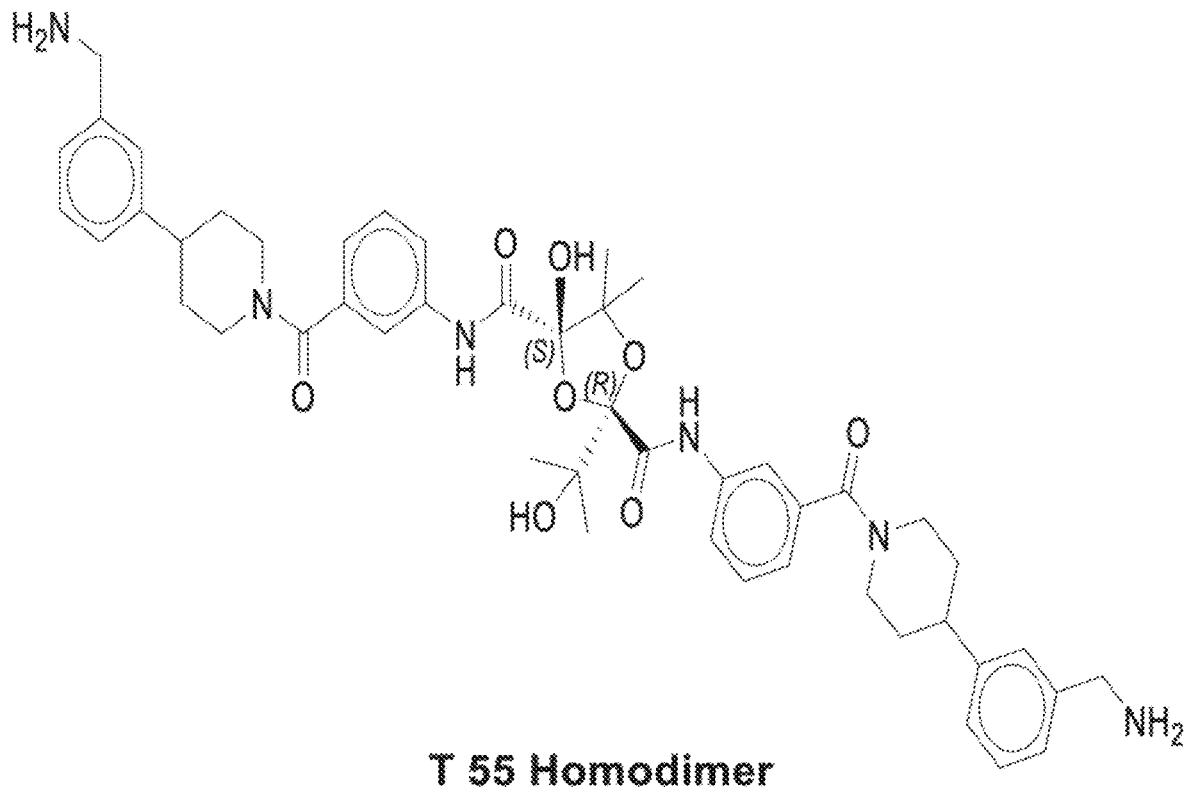

Described herein are monomers capable of forming a biologically useful multimer when in contact with one, two, three or more other monomers in an aqueous media. In one aspect, such monomers may be capable of binding to another monomer in an aqueous media (e.g. in vivo) to form a multimer, (e.g. a dimer). Contemplated monomers may include a ligand moiety (e.g. a pharmacophore moiety), a linker element, and a connector element that joins the ligand moiety and the linker element. In an aqueous media, such contemplated monomers may join together via each linker element and may thus be capable of modulating one or more biomolecules substantially simultaneously, e.g., modulate two or more binding domains on a protein or on different proteins. For example, contemplated monomers may be separate or separatable in a solid or in an aqueous media under one set of conditions, and when placed in an aqueous media having one or more biomolecules, with another (e.g., under a different set of conditions), can 1) form a multimer through the linker on each monomer; and either: 2a) bind to the biomolecule in two or more locations (e.g. protein domains) through each ligand moiety of the respective monomer or 2b) bind to two or more biomolecules through each ligand moiety of the respective monomer. In an exemplary embodiment, disclosed monomers may interact with another appropriate monomer (i.e. a monomeric pair) in an aqueous media (e.g., in vivo) to form a multimer (e.g. a dimer) that can bind to two separate target biomolecule domains (e.g. protein domains).

The ligand moiety of a contemplated monomer, in some cases, may be a pharmacophore or a ligand moiety that is e.g., capable of binding to a biomolecule, such as for example, a protein, e.g. a specific protein domain, a component of a biological cell such as ribosome (composed of proteins and nucleic acids), or an enzyme active site (e.g. a protease, such as tryptase). In some embodiments, the linker element comprises a functional group capable of forming a chemical bond with another linker element. In some embodiments, the linker moiety may also serve as a signaling entity or "reporter," and in some instances the assembly of two or more linkers can produce a fluorescent entity or fluorophore with properties distinct from the individual linker moiety. In another aspect, a plurality of monomers, each comprising a linker element, may react to form a multimer connected by the linker elements. In some embodiments, the multimer may be formed in vivo. In some instances, the multimer may have enhanced properties relative to the monomers that form the multimer. For example, in certain embodiments, the multimer may bind to a target with greater affinity than any of the monomers that form the multimer. Also described are methods of making the compositions and methods of administering the compositions.

In some embodiments, a plurality of monomers may assemble to form a multimer. The multimer may be used for a variety of purposes. For example, in some instances, the multimer may be used to perturb a biological system. As described in more detail below, in some embodiments, the multimer may bind to a target biomolecule, such as a protein, nucleic acid, or polysaccharide. In certain embodiments, the multimer may be used as a pharmaceutical.

Advantageously, in some embodiments, the multimer may form in vivo upon administration of suitable monomers to a subject. Also advantageously, the multimer may be capable of interacting with a relatively large target site as compared to the individual monomers that form the multimer. For example, a target may comprise, in some embodiments, two protein domains separated by a distance such that a multimer, but not a monomer, may be capable of binding to both domains essentially simultaneously. In some embodiments, contemplated multimers may bind to a target with greater affinity as compared to a monomer binding affinity alone.

In some embodiments, a contemplated multimer may advantageously exhibit enhanced properties relative to the monomers that form the multimer. As discussed above, a multimer may have improved binding properties as compared to the monomers alone. In some embodiments, a multimer may have improved signaling properties. For example, in some cases, the fluorescent properties of a multimer may be different as compared to a monomer. As discussed in more detail below, in some embodiments the fluorescent brightness of a multimer at a particular wavelength may be greater than the fluorescent brightness at the same wavelength of the monomers that form the multimer. Advantageously, in some embodiments, a difference in signaling properties between the multimer and the monomers that form the multimer may be used to detect formation of the multimer. In some embodiments, detection of the formation of the multimer may be used to screen monomers, as discussed in more detail below. Also as discussed in more detail below, in some embodiments, the multimers may be used for imaging or as diagnostic agents.

It should be understood that a multimer, as used herein, may be a homomultimer (i.e., a multimer formed from two or more essentially identical monomers) or may be a heteromultimer (i.e., a multimer formed from two or more substantially different monomers). In some embodiments, a contemplated multimer may comprise 2 to about 10 monomers, for example, a multimer may be a dimer, a trimer, a tetramer, or a pentamer.

In some embodiments, a monomer may comprise a ligand moiety, a linker element, and a connector element that associates the ligand moiety with the linker element. In some embodiments, the linker element of a first monomer may combine with the linker element of a second monomer. In some cases, the linker element may comprise a functional group that can react with a functional group of another linker element to form a bond linking the monomers. In some embodiments, the linker element of a first monomer may be substantially the same as the linker element of a second monomer. In some embodiments, the linker element of a first monomer may be substantially different than the linker element of a second monomer.

In some cases, the ligand moiety may be a pharmacophore. In some embodiments, the ligand moiety (e.g., a pharmacophore) may bind to a target molecule with a dissociation constant of less than 1 mM, in some embodiments less than 500 microM, in some embodiments less than 300 microM, in some embodiments less than 100 microM, in some embodiments less than 10 microM, in some embodiments less than 1 microM, in some embodiments less than 100 nM, in some embodiments less than 10 nM, and in some embodiments less than 1 nM.

In some embodiments, the $IC_{50}$ of the first monomer against a first target biomolecule and the $IC_{50}$ of the second monomer against a second target biomolecule may be greater than the apparent $IC_{50}$ of a combination of the monomers against the first target biomolecule and the second target biomolecule. The combination of monomers may be any suitable ratio. For example, the ratio of the first monomer to the second monomer may be between 10:1 to 1:10, in some embodiments between 5:1 and 1:5, and in some embodiments between 2:1 and 1:2. In some cases, the ratio of the first monomer to the second monomer may be essentially 1:1. In some instances, the ratio of the smaller of the $IC_{50}$ of the first monomer and the second monomer to the apparent $IC_{50}$ of the multimer may be at least 3.0. In other instances, the ratio of the smaller $IC_{50}$ of the first monomer or the second monomer to the apparent $IC_{50}$ of the multimer may be at least 10.0. In some embodiments, the ratio of the smaller $IC_{50}$ of the first monomer or the second monomer to the apparent $IC_{50}$ of the multimer may be at least 30.0.

For example, for disclosed monomers forming a heteromultimer, the apparent $IC_{50}$ resulting from an essentially equimolar combination of monomers against the first target biomolecule and the second target biomolecule is at least about 3 to 10 fold lower, at least about 10 to 30 fold lower, at least about 30 fold lower, or at least about 40 to 50 fold lower than the lowest of the $IC_{50}$ of the second monomer against the second target biomolecule or the $IC_{50}$ of the first monomer against the first target biomolecule.

It will be appreciated that for monomers forming homodimers (or homo-oligomeric or homomultimeric, as described below), in aqueous solution, there may an equilibrium between the monomeric and dimeric (or oligomeric) states with higher concentrations favoring greater extent of dimer formation. As the binding of monomers to the target biomolecule increases their proximity and effectively increases their local concentration on the target, the rate and extent of dimerization (oligomerization) is promoted when geometries are favorable. As a result, the occupancy of the target by favorable monomers maybe nearly completely in the homodimeric (or oligomeric) state. In this manner the target for example, may serve as a template for the dimerization of the monomers, significantly enhancing the extent and rate of dimerization.

While the affinity of the multimer for its target biomolecule(s) often cannot be measured directly due to the dynamic reversible equilibrium with its monomers in an aqueous or biological milieu, it may be possible to extract an apparent multimer-target dissociation constant from a series of experimental determinations. Exploring the effects of a matrix of monomer concentrations, monomer ratios, along with changes in concentration(s) in the target biomolecule(s), coupled with determinations of multimer-monomer dissociation constants, and in some cases additional binding competition, kinetic and biophysical methods, one can extract an estimate of the affinity of the multimeric assembly for its target(s). Through such approaches, one can demonstrate that in some embodiments, the affinity of the multimer for the target biomolecule(s) are less than 1 µM, in some embodiments less than 1 nM, in some embodiments less than 1 pM, in some embodiments less than 1 fM, and in some embodiments less than 1 aM, and in some embodiments less than 1 zM.

Affinities of heterodimerizing monomers for the target biomolecule can be assessed through the testing of the respective monomers in appropriate assays for the target activity or biology because they do not typically self-associate. In contrast, the testing of homodimerizing monomers may not, in some embodiments, afford an affinity for the monomeric or dimeric state, but rather the observed effect (e.g. $IC_{50}$) is a result of the monomer-dimer dynamics and equilibrium, with the apparent binding affinity (or $IC_{50}$) being e.g., a weighted measure of the monomer and dimeric inhibitory effects upon the target.

In some cases, the pH of the aqueous fluid in which the multimer forms may be between pH 1 and 9, in some embodiments between pH 1 and 3, in some embodiments between pH 3 and 5, in some embodiments between pH 5 and 7, and in some embodiments between pH 7 and 9. In some embodiments, the multimer may be stable in an aqueous solution having a pH between pH 1 and 9, in some embodiments between pH 1 and 3, in some embodiments between pH 3 and 5, in some embodiments between pH 5 and 7, and in some embodiments between pH 7 and 9. In some embodiments, the aqueous solution may have a physiologically acceptable pH.

In some embodiments, the ligand moiety may be capable of binding to a target and at least partially disrupting a biomolecule-biomolecule interaction (e.g., a protein-protein interaction). In some embodiments, the ligand moiety may be capable of binding to a target and at least partially disrupting a protein-nucleic acid interaction. In some cases, the ligand moiety may be capable of binding to a target and at least partially disrupting a protein-lipid interaction. In some cases, the ligand moiety may be capable of binding to a target and at least partially disrupting a protein-polysaccharide interaction. In some embodiments, the ligand moiety may be capable of at least partially stabilizing a biomolecule-biomolecule interaction. In certain embodiments, the ligand moiety may be capable of at least partially inhibiting a conformational change in a biomolecule target.

In some instances, the linker element may be capable of generating a signal. For example, in some embodiments, the linker element may be capable of fluorescing. In some cases, the linker element may have greater fluorescence when the monomer to which it is attached is part of a multimer as compared to when the monomer to which it is attached is not part of a multimer. In some embodiments, upon multimer formation, the fluorescent brightness of a linker element may increase by at least 2-fold, in some embodiments by at least 5-fold, in some embodiments by at least 10-fold, in some embodiments by at least 50-fold, in some embodiments by at least 100-fold, in some embodiments by at least 1000-fold, and in some embodiments by at least 10000-fold. In some embodiments, a linker element in a multimer may have a peak fluorescence that is red-shifted relative to the peak fluorescence of the linker element in a monomer. In other embodiments, a linker element may have a peak fluorescence that is blue-shifted relative to the peak fluorescence of a linker element in a monomer.

Monomers

In certain embodiments, a first monomer may be capable of forming a biologically useful multimer when in contact with a second monomer in an aqueous media, for example, when the first and second monomer are different and form e.g. a heteromultimer in aqueous media. For example, the first monomer can represented by the formula:

$X_1$—$Y_1$—$Z_1$(Formula I) and pharmaceutically acceptable salts, stereoisomers, metabolites, and hydrates thereof, wherein $X_1$ is a first ligand moiety capable of binding to a first target biomolecule;

$Y_1$ is absent or is a connector moiety covalently bound to $X_1$ and $Z_1$;

$Z_1$ is a first linker selected from the group consisting of:

a)

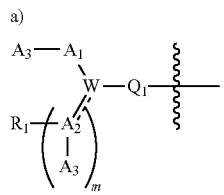

$A_1$ is (a) absent; or (b) selected from the group consisting of acyl, substituted or unsubstituted aliphatic, or substituted or unsubstituted heteroaliphatic;

$A_2$, independently for each occurrence, is (a) absent; or (b) selected from the group consisting of —N—, acyl, substituted or unsubstituted aliphatic, or substituted or unsubstituted heteroaliphatic, provided that at least one of $A_1$ and $A_2$ is present; or $A_1$ and $A_2$, together with the atoms to which they are attached, form a substituted or unsubstituted 4-8 membered cycloalkyl or heterocyclic ring;

$A_3$ is selected from the group consisting of —NHR', —SH, or —OH;

W is CR' or N;

R' is selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

m is 1-6;

═══ represents a single or double bond; and $R_1$ is (a) absent; or (b) selected from the group consisting of hydrogen, halogen, substituted or unsubstituted aliphatic, or substituted or unsubstituted heteroaliphatic, substituted or unsubstituted aryl, substituted or unsubstituted heteroaryl, —NH$_2$, —NO$_2$, —SH, or —OH;

$Q_1$ is (a) absent; or (b) selected from the group consisting of substituted or unsubstituted aliphatic or substituted or unsubstituted heteroaliphatic; or $R_1$ and $Q_1$ together with the atoms to which they are attached form a substituted or unsubstituted 4-8 membered cycloalkyl or heterocyclic ring;

b)

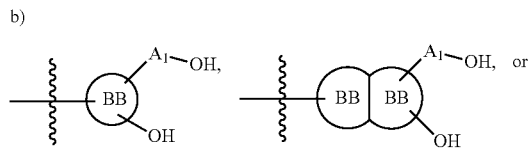

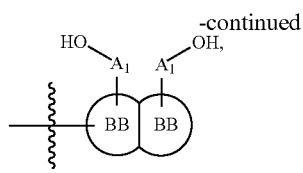

wherein

BB, independently for each occurrence, is a 4-8 membered cycloalkyl, heterocyclic, aryl, or heteroaryl moiety, wherein the cycloalkyl, heterocyclic, aryl, or heteroaryl moiety is optionally substituted with one or more groups represented by $R_2$, wherein the two substituents comprising —OH have a 1,2 or 1,3 configuration;

each $R_2$ is independently selected from hydrogen, halogen, oxo, sulfonate, —NO$_2$, —CN, —OH, —NH$_2$, —SH, —COOH, —CON(R')$_2$, substituted or unsubstituted aliphatic, substituted or unsubstituted heteroaliphatic, or two $R_2$ together with the atoms to which they are attached form a fused substituted or unsubstituted 4-6 membered cycloalkyl or heterocyclic bicyclic ring system;

$A_1$, independently for each occurrence, is (a) absent; or (b) selected from the group consisting of acyl, substituted or unsubstituted aliphatic, or substituted or unsubstituted heteroaliphatic;

R' is independently selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

c)

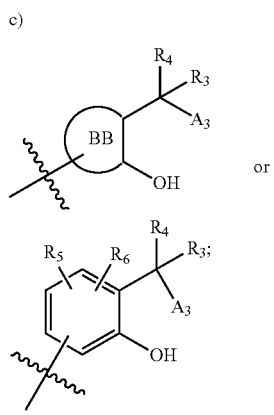

wherein

BB is a substituted or unsubstituted 5- or 6-membered cycloalkyl, heterocyclic, aryl, or heteroaryl moiety;

$A_3$, independently for each occurrence, is selected from the group consisting of —NHR', —OH, or —O—C$_{1-4}$alkyl;

$R_3$ and $R_4$ are independently selected from the group consisting of H, C$_{1-4}$alkyl, phenyl, or $R_3$ and $R_4$ taken together from a 3-6 membered ring;

$R_5$ and $R_6$ are independently selected from the group consisting of H, C$_{1-4}$alkyl optionally substituted by hydroxyl, amino, halogen, or thio; C$_{1-4}$alkoxy; halogen; —OH; —CN; —COOH; —CONHR'; or R$_5$ and R$_6$ taken together form phenyl or a 4-6 membered heterocycle; and R' is selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

d)

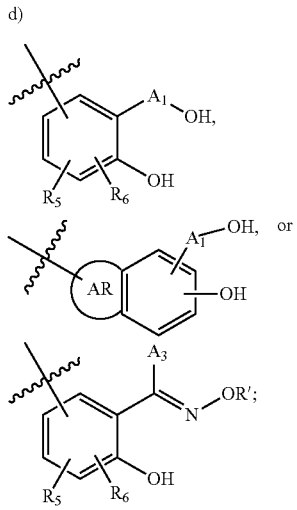

wherein
- A$_1$ is (a) absent; or (b) selected from the group consisting of acyl, substituted or unsubstituted aliphatic, or substituted or unsubstituted heteroaliphatic;
- A$_3$, independently for each occurrence, is selected from the group consisting of —NHR' or —OH;
- AR is a fused phenyl or 4-7 membered aromatic or partially aromatic heterocyclic ring, wherein AR is optionally substituted by oxo, C$_{1-4}$alkyl optionally substituted by hydroxyl, amino, halo, or thio; C$_{1-4}$alkoxy; —S— C$_{1-4}$alkyl; halogen; —OH; —CN; —COOH; —CONHR'; wherein the two substituents comprising —OH are ortho to each other;
- R$_5$ and R$_6$ are independently selected from the group consisting of H, C$_{1-4}$alkyl optionally substituted by hydroxyl, amino, halo, or thio; C$_{1-4}$alkoxy; halogen; —OH; —CN; —COOH; CONHR'; and
- R' is selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

e)

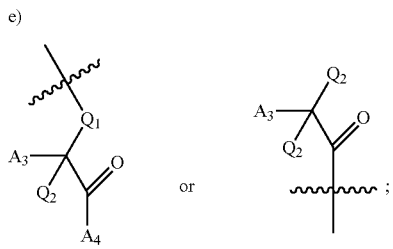

wherein
- Q$_1$ is selected from the group consisting of C$_{1-4}$alkyl, alkylene, or a bond; C$_{1-6}$cycloalkyl; a 5-6 membered heterocyclic ring; or phenyl;
- Q$_2$, independently for each occurrence, is selected from the group consisting of H, C$_{1-4}$alkyl, alkylene, or a bond; C$_{1-6}$cycloalkyl; a 5-6 membered heterocyclic ring; phenyl; substituted or unsubstituted aliphatic; substituted or unsubstituted heteroaliphatic; substituted or unsubstituted aryl; or substituted or unsubstituted heteroaryl;
- A$_3$, independently for each occurrence, is selected from the group consisting of —NH$_2$ or —OH;
- A$_4$, independently for each occurrence, is selected from the group consisting of —NH—NH$_2$; —NHOH, —NH—OR", or —OH;
- R" is selected from the group consisting of H or C$_{1-4}$alkyl; and f)

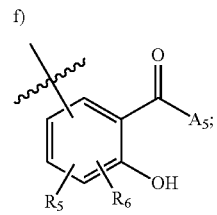

wherein
- A$_5$ is selected from the group consisting of —OH, —NH$_2$, —SH, —NHR'''; R''' is selected from —NH$_2$; —OH; —O-phenyl; and C$_{1-4}$alkoxy;
- R$_5$ and R$_6$ are independently selected from the group consisting of H, C$_{1-4}$alkyl optionally substituted by hydroxyl, amino, halo, or thio; C$_{1-4}$alkoxy; halogen; —OH; —CN; —COOH; —CONHR'; or R$_5$ and R$_6$ taken together may form a 5-6 membered ring; and the second monomer has a boronic acid or oxaborole moiety capable of binding with the Z$_1$ moiety of Formula I to form the multimer.

In some embodiments, A$_1$ may be selected from the group consisting of C$_1$-C$_3$alkylene optionally substituted with one, two, or three halogens, or —C(O)—.

In other embodiments, Z$_1$ may be

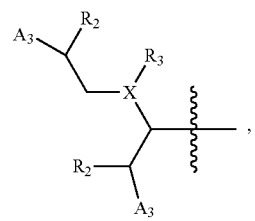

wherein R$_2$, independently for each occurrence, is selected from H, C$_{1-4}$alkyl, or two R$_1$ moities taken together form a 5- or 6-membered cycloalkyl or heterocyclic ring, wherein R$_3$ is H, or

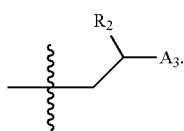

In certain embodiments, $Z_1$ may be

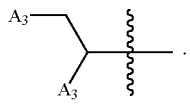

In some cases, $Z_1$ may be

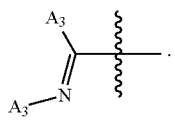

For example, in some instances, $Z_1$ may be

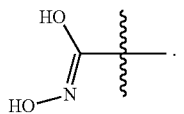

In some embodiments, $Z_1$ may be a monosaccharide or a disaccharide.

In some cases, $Z_1$ may be selected from the group consisting of

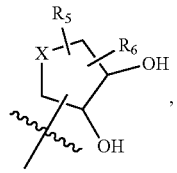 , 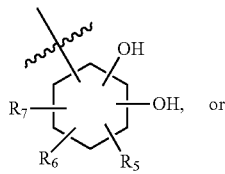 , or

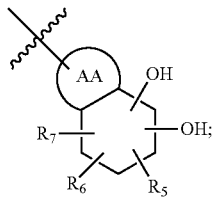

wherein
- X is selected from O, S, CH, NR', or when X is NR', N may be covalently bonded to Y of formula I;
- R' is selected from the group consisting of H and $C_{1-4}$alkyl;
- $R_5$, $R_6$, and $R_7$ are independently selected from the group consisting of H, $C_{1-4}$alkyl optionally substituted by hydroxyl, amino, halo, or thio; $C_{1-4}$alkoxy; halogen; —OH; —CN; —COOH; —CONHR'; or a mono- or bicyclic heterocyclic optionally substituted with amino, halo, hydroxyl, oxo, or cyano; and
- AA is a 5-6 membered heterocyclic ring optionally substituted by $C_{1-4}$alkyl optionally substituted by hydroxyl, amino, halo, or thio; $C_{1-4}$alkoxy; halogen; —OH; —CN; —COOH; —CONHR', or —S—$C_{1-4}$alkyl. For example, in some embodiments, $Z_1$ may be

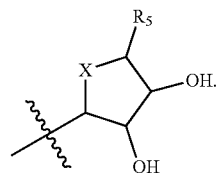

In some instances, $Z_1$ may be

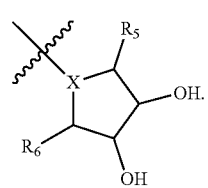

In certain cases, X may be nitrogen.

In some embodiments, $Z_1$ may be

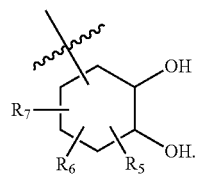

In other embodiments, $Z_1$ may be

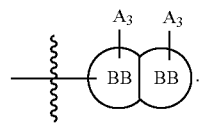

For example, in some cases, $Z_1$ may be

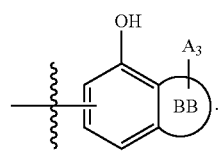

In other instances, $Z_1$ may be

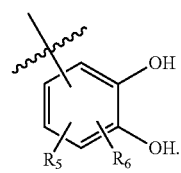

In some embodiments, $Z_1$ may be

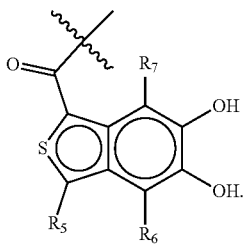

In some cases, $Z_1$ may be

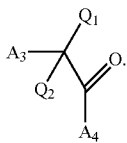

For example, $Z_1$ may be

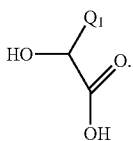

In other embodiments, $Z_1$ may be

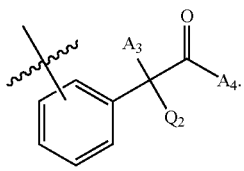

In some cases, $Z_1$ may be

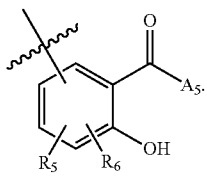

In some embodiments, $Z_1$ may be

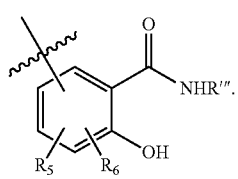

In some embodiments, $Z_1$ may be

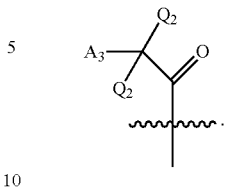

For example, $Z_1$ may be

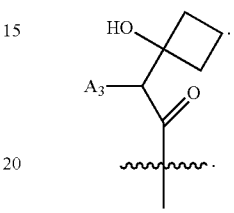

In certain embodiments, $Z_1$ may be

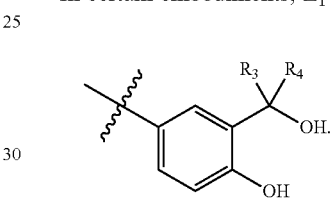

In other embodiments, $Z_1$ may be

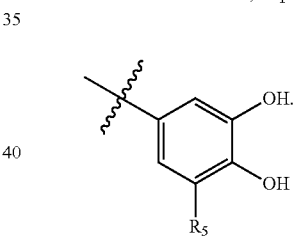

In some embodiments, the second monomer may be $X_2$—$Y_2$—$Z_2$ (Formula II), wherein $Z_2$ is the boronic acid or oxaborale moiety, and wherein $X_2$ is a second ligand moiety capable of binding to a second target biomolecule, and $Y_2$ is absent or is a connector moiety covalently bound to $X_2$ and $Z_2$. In some instances, $X_1$ and $X_2$ may be the same. In other instances, $X_1$ and $X_2$ may be different.

In some cases, the first target biomolecule and the second target biomolecule may be different. In other embodiments, the first target biomolecule and the second target biomolecule may be the same.

In some embodiments, $Z_2$ of the second monomer may be selected from the group consisting of:

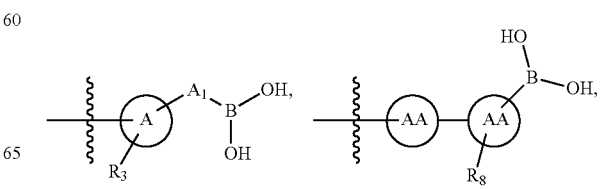

-continued

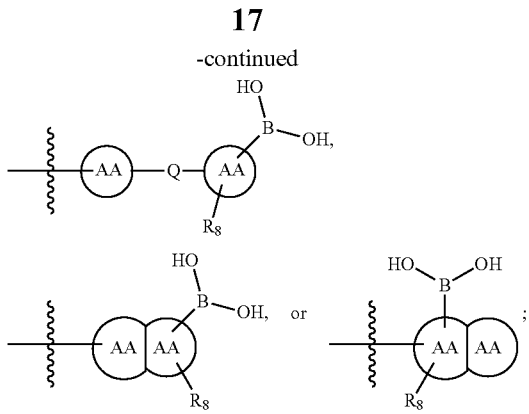

wherein
- $R_8$ is selected from the group consisting of H, halogen, oxo, $C_{1-4}$alkyl optionally substituted by hydroxyl, amino, halo or thio; $C_{2-4}$alkenyl, $C_{1-4}$alkoxy; —S—$C_{1-4}$alkyl; —CN; —COOH; or —CONHR';
- $A_1$ is (a) absent; or (b) selected from the group consisting of acyl, substituted or unsubstituted aliphatic, or substituted or unsubstituted heteroaliphatic;
- Q is selected from the group consisting of substituted or unsubstituted aliphatic, or substituted or unsubstituted heteroaliphatic;
- AA, independently for each occurrence, is phenyl, aryl, or a 5-7 membered heterocyclic or heteroaryl ring having one, two, or three heteroatoms, wherein AA is optionally substituted by one, two, or three substituents selected from the group consisting of halogen, $C_{1-4}$alkyl optionally substituted by hydroxyl, amino, halogen, or thio; $C_{2-4}$alkenyl; $C_{1-4}$alkoxy; —S—$C_{1-4}$alkyl; —CN; —NR$_2$''', wherein R''' is independently selected from the group consisting of H and $C_{1-4}$alkyl; —COOH; —CONHR'; or two substituents together with the atoms to which they are attached form a fused 4-6 membered cycloalkyl or heterocyclic bicyclic ring system; and
- R' is H or $C_{1-4}$alkyl.

In certain embodiments, $R_8$ and the substituent comprising boronic acid may be ortho to each other, and $R_8$ may be —CH$_2$NH$_2$. In some cases, $Z_2$ of the second monomer may be selected from the group consisting of:

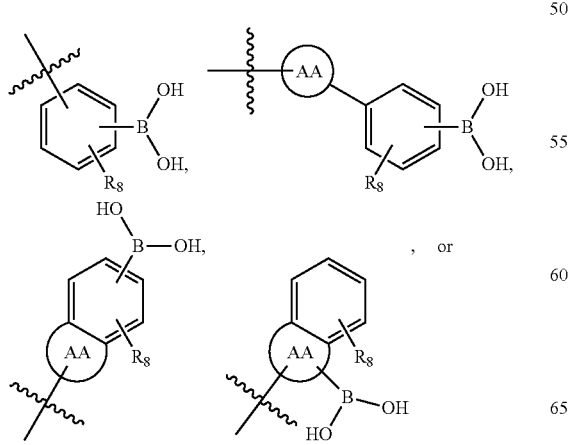

-continued

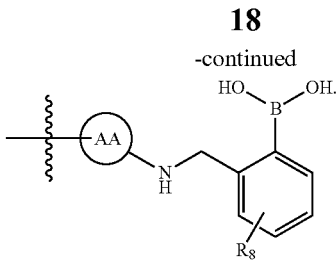

In some embodiments, $Z_2$ of the second monomer may be selected from the group consisting of:

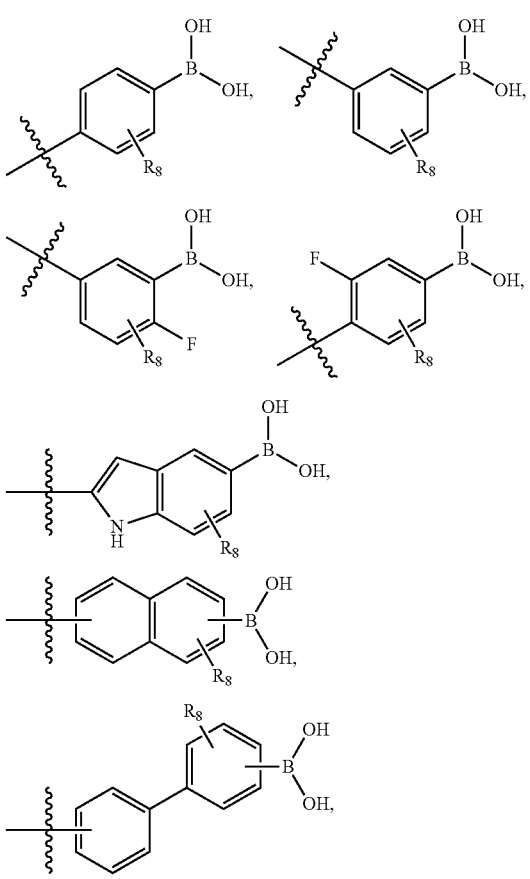

-continued

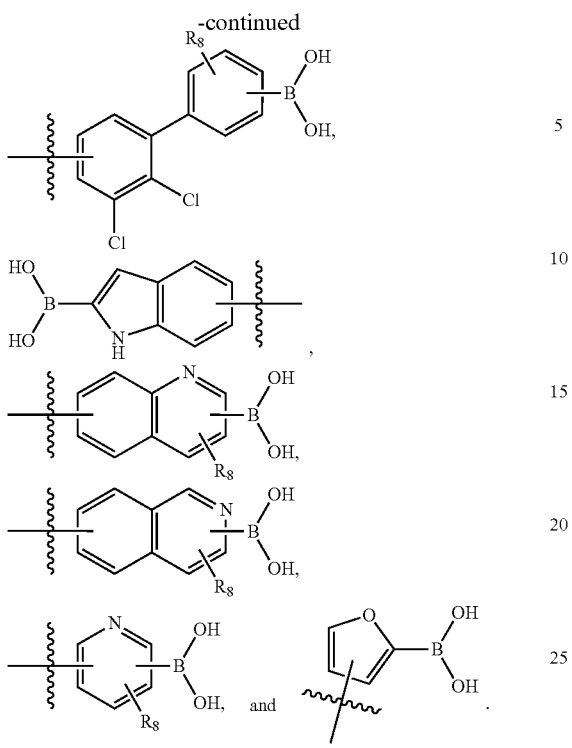

In some cases, $Z_2$ of the second monomer may be selected from the group consisting of:

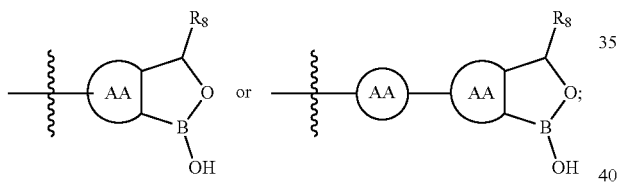

$R_8$ is selected from the group consisting of H, halogen, oxo, $C_{1-4}$alkyl optionally substituted by hydroxyl, amino, halo or thio; $C_{2-4}$alkenyl, $C_{1-4}$alkoxy; —S—$C_{1-4}$alkyl; —CN; —COOH; or —CONHR';

AA, independently for each occurrence, is a 5-7 membered heterocyclic ring having one, two, or three heteroatoms, or phenyl, wherein AA is optionally substituted by one, two, or three substituents selected from the group consisting of halo, $C_{1-4}$alkyl optionally substituted by hydroxyl, amino, halo, or thio; $C_{2-4}$alkenyl; $C_{1-4}$alkoxy; —S—$C_{1-4}$alkyl; —CN; —NR$_2$''', wherein R''' is independently selected from the group consisting of H and $C_{1-4}$alkyl; —COOH; —CONHR'; or two substituents together with the atoms to which they are attached form a fused 4-6 membered cycloalkyl or heterocyclic bicyclic ring system; and R' is H or $C_{1-4}$alkyl.

In some embodiments, a first monomer may be capable of forming a biologically useful dimer or multimer when in contact with a second monomer in vivo, wherein the first and second linkers are the same (e.g. forming a homodimer or homomultimer) wherein the first monomer is represented by the formula:

$X_3$—$Y_3$—$Z_3$ (Formula IV); and pharmaceutically acceptable salts, stereoisomers, metabolites and hydrates thereof, and the second monomer is represented by:

$X_4$—$Y_4$—$Z_3$ (Formula V) and pharmaceutically acceptable salts, stereoisomers, metabolites and hydrates thereof, wherein $X_3$ is a first ligand moiety capable of binding to a first target biomolecule;

$Y_3$ is absent or is a connector moiety covalently bound to $X_4$ and $Z_3$;

$X_4$ is a second ligand moiety capable of binding to a second target biomolecule;

$Y_4$ is absent or is a connector moiety covalently bound to $X_4$ and $Z_3$;

$Z_3$ is selected from the group consisting of:

a)

wherein $A_3$ is —OH, —SH, or —NHR';

$R_3$ is selected from the group consisting of H, halo, $C_{1-4}$alkyl, $C_{3-6}$ cycloalkyl, and heterocycle, wherein $C_{1-4}$alkyl, $C_{3-6}$cycloalkyl, or heterocycle may be optionally substituted by one, two, or three substituents selected from the group consisting of halo, cyano, amino, or hydroxyl;

$R_4$ is selected from the group consisting of H, halo, $C_{1-4}$alkyl, $C_{3-6}$cycloalkyl, and heterocycle, wherein $C_{1-4}$alkyl, $C_{3-6}$cycloalkyl, or heterocycle may be optionally substituted by one, two, or three substituents selected from the group consisting of halo, cyano, amino, or hydroxyl; or $R_3$ and $R_4$ taken together from a 3-6 membered ring; and b)

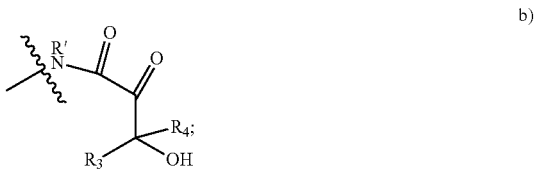

wherein

R' is selected from $C_{1-4}$alkyl optionally substituted with hydroxyl; —NH$_2$; —OH; and $C_{1-4}$alkoxy;

$R_3$ is selected from the group consisting of H, halo, $C_{1-4}$alkyl, $C_{3-6}$ cycloalkyl, and heterocycle, wherein $C_{1-4}$alkyl, $C_{3-6}$cycloalkyl, or heterocycle may be optionally substituted by one, two, or three substituents selected from the group consisting of halo, cyano, amino, or hydroxyl;

$R_4$ is selected from the group consisting of H, halo, $C_{1-4}$alkyl, $C_{3-6}$cycloalkyl, and heterocycle, wherein $C_{1-4}$alkyl, $C_{3-6}$cycloalkyl, or heterocycle may be optionally substituted by one, two or three substituents selected from the group consisting of halo, cyano, amino, or hydroxyl; or $R_3$ and $R_4$ taken together from a 3-6 membered ring.

In some embodiments, a first monomer may be capable of forming a biologically useful trimer when in contact with a second monomer and a third monomer in an aqueous media, wherein the first monomer is represented by the formula:

$X_2$—$Y_2$—$Z_2$ (Formula II) and pharmaceutically acceptable salts, stereoisomers, metabolites, and hydrates thereof, wherein $X_2$ is a first ligand moiety capable of binding to a first target biomolecule;

$Y_2$ is absent or is a connector moiety covalently bound to $X_2$ and $Z_2$;

$Z_2$ is a first linker selected from the group consisting of:

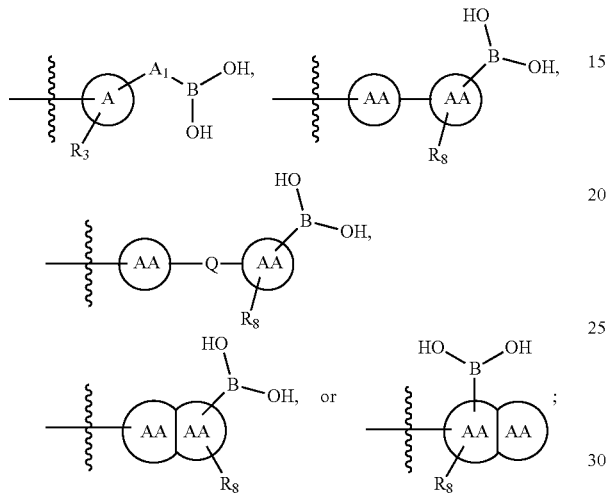

wherein $R_8$ is selected from the group consisting of H, halogen, oxo, $C_{1-4}$alkyl optionally substituted by hydroxyl, amino, halo, or thio; $C_{2-4}$alkenyl, $C_{1-4}$alkoxy; —S— $C_{1-4}$alkyl; —CN; —COOH; or —CONHR';

R' is H or $C_{1-4}$alkyl;

$A_1$ is (a) absent; or (b) selected from the group consisting of acyl, substituted or unsubstituted aliphatic, or substituted or unsubstituted heteroaliphatic;

Q is selected from the group consisting of substituted or unsubstituted aliphatic, or substituted or unsubstituted heteroaliphatic;

AA, independently for each occurrence, is phenyl, aryl, or a 5-7 membered heterocyclic or heteroaryl ring having one, two, or three heteroatoms, wherein AA is optionally substituted by one, two, or three substituents selected from the group consisting of halogen, $C_{1-4}$alkyl optionally substituted by hydroxyl, amino, halogen, or thio; $C_{2-4}$alkenyl; $C_{1-4}$alkoxy; —S— $C_{1-4}$alkyl; —CN; —$NR_2'''$, wherein R''' is independently selected from the group consisting of H and $C_{1-4}$alkyl; —COOH; —CONHR'; or two substituents together with the atoms to which they are attached form a fused 4-6 membered cycloalkyl or heterocyclic bicyclic ring system; and the second monomer and the third monomer each have a boronic acid moiety capable of binding with the $Z_2$ moiety of Formula II to form the trimer.

In some embodiments, $R_8$ and the substituent comprising boronic acid may be ortho to each other, and $R_8$ may be —$CH_2NH_2$.

In some instances, $Z_2$ of the first monomer may be selected from the group consisting of:

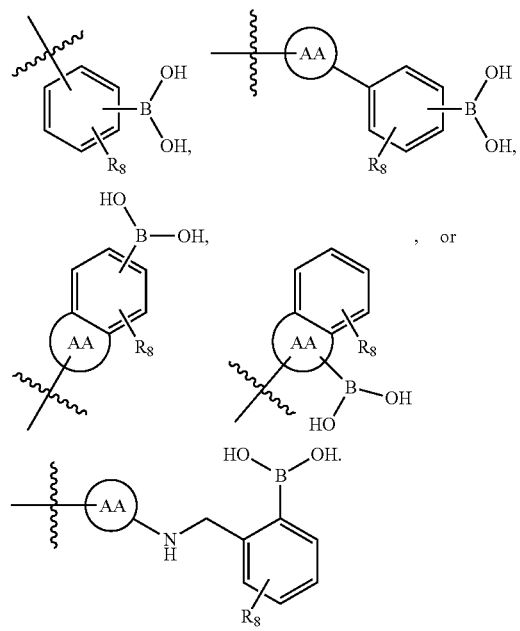

In certain instances, $Z_2$ of the first monomer may be selected from the group consisting of:

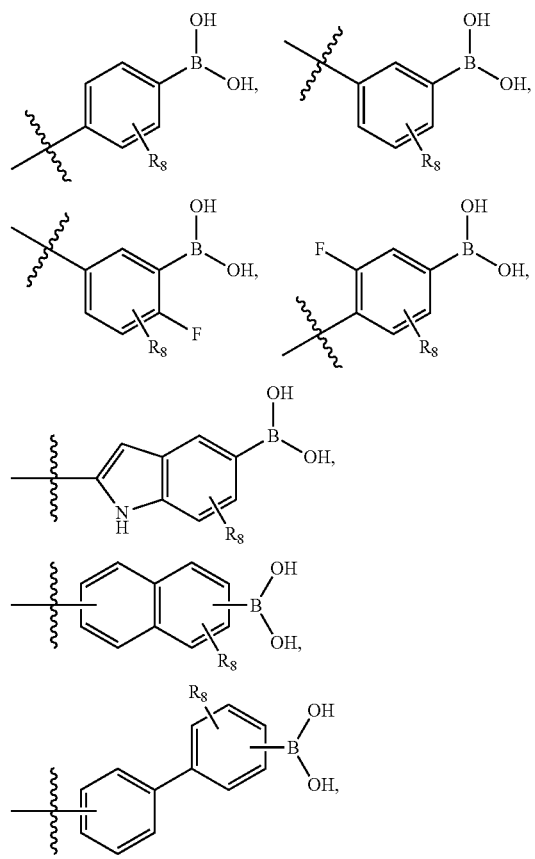

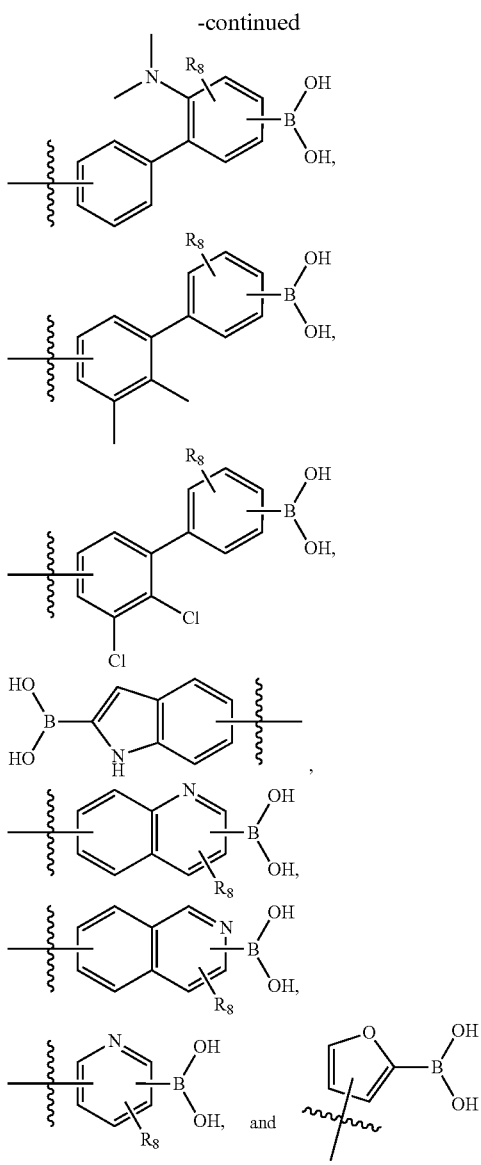

As discussed above, a monomer may be capable of reacting with one or more other monomers to form a multimer. In some embodiments, a first monomer may react with a second monomer to form a dimer. In other embodiments, a first monomer may react with a second monomer and a third monomer to form a trimer. In still other embodiments, a first monomer may react with a second monomer, a third monomer, and a fourth monomer to form a tetramer. In some embodiments, each of the monomers that form a multimer may be essentially the same. In some embodiments, each of the monomers that form a multimer may be substantially different. In certain embodiments, at least some of the monomers that form a multimer may be essentially the same or may be substantially different.

In some embodiments, the linker element of a first monomer and the linker element of a second monomer may be substantially different. In other embodiments, the connector element of a first monomer and the connector element of a second monomer may be substantially different. In still other embodiments, the ligand moiety (e.g., a pharmacophore) of a first monomer and the ligand moiety (e.g., a pharmacophore) of the second monomer may be substantially different.

In some cases, formation of a multimer from a plurality of monomers may be irreversible. In some embodiments, formation of a multimer from a plurality of monomers may be reversible. For example, in some embodiments, the multimer may have an oligomer or dimer dissociation constant between 10 mM and 1 nM, in some embodiments between 1 mM and 100 nM, in some embodiments between 1 mM and 1 mM, and in some embodiments between 500 mM and 1 mM. In certain embodiments, the multimer may have a dissociation constant of less than 10 mM, in some embodiments less than 1 mM, in some embodiments less than 500 mM, in some embodiments less than 100 mM, in some embodiments less than 50 mM, in some embodiments less than 1 mM, in some embodiments less than 100 nM, and in some embodiments less than 1 nM.

Multimers

In some embodiments, a first monomer and a second monomer may form a dimer in aqueous solution. For example, in some instances, the first monomer may form a biologically useful dimer with a second monomer in vivo.

Without wishing to be bound by any theory, it is believed that molecular self-assembly may be directed through non-covalent interactions, e.g., hydrogen bonding, metal coordination, hydrophobic forces, van der Waals forces, pi-pi interactions, electrostatic, and/or electromagnetic interactions.

Without wishing to be bound by any theory, pi-pi and pi-cation interactions can be used to drive multimerization. In addition, van der Waals and electromagnetic forces are other interactions that can help to drive multimerization. Alternatively, acid/base pairs and donor-acceptor pairs, e.g., amide and/or sulfonamide pairs, can be employed to help direct self-assembly. In other cases, use of hydrophobic interactions can be used for multimerization targeting a membrane-bound protein. Additionally, metal coordination might be used when the target itself incorporates the metal, but could also be used in other scenarios.

In some embodiments, a therapeutic multimer compound (e.g. a heteromultimer) may be formed from the multimerization in an aqueous media of a first monomer represented by:

 (Formula I)

and a second monomer represented by

 (Formula II), wherein
X$_1$ is a first ligand moiety capable of binding to a first target biomolecule;
Y$_1$ is absent or is a connector moiety covalently bound to X$_1$ and Z$_1$;
Z$_1$ is a first linker selected from the group consisting of:

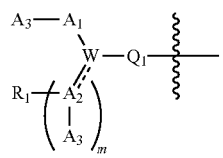

a)

wherein
A$_1$ is (a) absent; or (b) selected from the group consisting of acyl, substituted or unsubstituted aliphatic, or substituted or unsubstituted heteroaliphatic;

A$_2$, independently for each occurrence, is (a) absent; or (b) selected from the group consisting of —N—, acyl, substituted or unsubstituted aliphatic, or substituted or unsubstituted heteroaliphatic, provided that at least one of A$_1$ and A$_2$ is present; or A$_1$ and A$_2$, together with the atoms to which they are attached, form a substituted or unsubstituted 4-8 membered cycloalkyl or heterocyclic ring;

A$_3$ is selected from the group consisting of —NHR', —SH, or —OH;

W is CR' or N;

R' is selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

m is 1-6;

--- represents a single or double bond; and

R$_1$ is (a) absent; or (b) selected from the group consisting of hydrogen, halogen, substituted or unsubstituted aliphatic, or substituted or unsubstituted heteroaliphatic, substituted or unsubstituted aryl, substituted or unsubstituted heteroaryl, —NH$_2$, —NO$_2$, —SH, or —OH;

Q$_1$ is (a) absent; or (b) selected from the group consisting of substituted or unsubstituted aliphatic or substituted or unsubstituted heteroaliphatic; or R$_1$ and Q$_1$ together with the atoms to which they are attached form a substituted or unsubstituted 4-8 membered cycloalkyl or heterocyclic ring;

b)

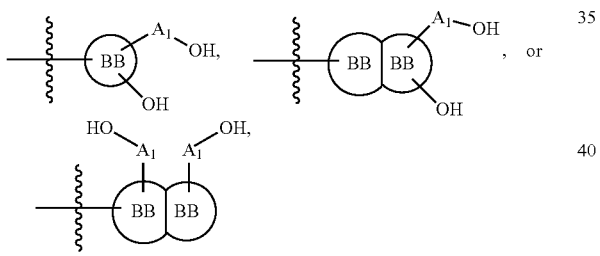

wherein

BB, independently for each occurrence, is a 4-8 membered cycloalkyl, heterocyclic, aryl, or heteroaryl moiety, wherein the cycloalkyl, heterocyclic, aryl, or heteroaryl moiety is optionally substituted with one or more groups represented by R$_2$, wherein the two substituents comprising —OH have a 1,2 or 1,3 configuration;

each R$_2$ is independently selected from hydrogen, halogen, oxo, sulfonate, —NO$_2$, —CN, —OH, —NH$_2$, —SH, —COOH, —CON(R')$_2$, substituted or unsubstituted aliphatic, substituted or unsubstituted heteroaliphatic, or two R$_2$ together with the atoms to which they are attached form a fused substituted or unsubstituted 4-6 membered cycloalkyl or heterocyclic bicyclic ring system;

A$_1$, independently for each occurrence, is (a) absent; or (b) selected from the group consisting of acyl, substituted or unsubstituted aliphatic, or substituted or unsubstituted heteroaliphatic;

R' is independently selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

c)

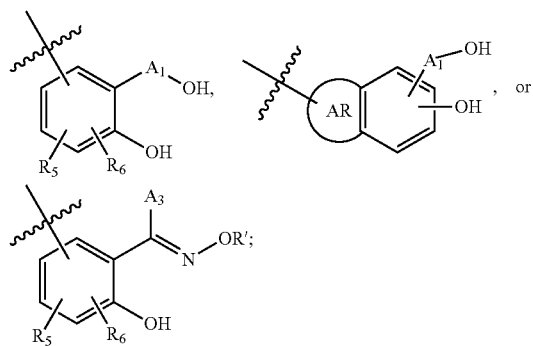

wherein

BB is a substituted or unsubstituted 5- or 6-membered cycloalkyl, heterocyclic, aryl, or heteroaryl moiety;

A$_3$, independently for each occurrence, is selected from the group consisting of —NHR', —OH, or —O—C$_{1-4}$alkyl;

R$_3$ and R$_4$ are independently selected from the group consisting of H, C$_{1-4}$alkyl, phenyl, or R$_3$ and R$_4$ taken together form a 3-6 membered ring;

R$_5$ and R$_6$ are independently selected from the group consisting of H, C$_{1-4}$alkyl optionally substituted by hydroxyl, amino, halogen, or thio; C$_{1-4}$alkoxy; halogen; —OH; —CN; —COOH; —CONHR'; or R$_5$ and R$_6$ taken together form phenyl or a 4-6 membered heterocycle; and R' is selected from the group consisting of hydrogen, halogen, substituted or unsubstituted aliphatic, substituted or unsubstituted heteroaliphatic, substituted or unsubstituted aryl, substituted or unsubstituted heteroaryl, —NH$_2$, —NO$_2$, —SH, or —OH;

d)

wherein

A$_1$ is (a) absent; or (b) selected from the group consisting of acyl, substituted or unsubstituted aliphatic, or substituted or unsubstituted heteroaliphatic;

A$_3$, independently for each occurrence, is selected from the group consisting of —NHR' or —OH;

AR is a fused phenyl or 4-7 membered aromatic or partially aromatic heterocyclic ring, wherein AR is optionally substituted by oxo, C$_{1-4}$alkyl optionally substituted by hydroxyl, amino, halo, or thio; C$_{1-4}$alkoxy; —S— C$_{1-4}$alkyl; halogen; —OH; —CN; —COOH; —CONHR'; wherein the two hydroxyl moieties are ortho to each other;

$R_5$ and $R_6$ are independently selected from the group consisting of H, $C_{1-4}$alkyl optionally substituted by hydroxyl, amino, halo, or thio; $C_{1-4}$alkoxy; halogen; —OH; —CN; —COOH; CONHR'; and R' is selected from the group consisting of hydrogen, halogen, substituted or unsubstituted aliphatic, substituted or unsubstituted heteroaliphatic, substituted or unsubstituted aryl, substituted or unsubstituted heteroaryl, —$NH_2$, —$NO_2$, —SH, or —OH;

e)

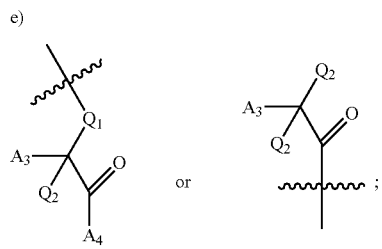

wherein $Q_1$ is selected from the group consisting of $C_{1-4}$alkyl, alkylene, or a bond; $C_{1-6}$cycloalkyl; a 5-6 membered heterocyclic ring; or phenyl;

$Q_2$, independently for each occurrence, is selected from the group consisting of H, $C_{1-4}$alkyl, alkylene, or a bond; $C_{1-6}$cycloalkyl; a 5-6 membered heterocyclic ring; phenyl; substituted or unsubstituted aliphatic; substituted or unsubstituted heteroaliphatic; substituted or unsubstituted aryl; or substituted or unsubstituted heteroaryl;

$A_3$, independently for each occurrence, is selected from the group consisting of —$NH_2$ or —OH;

$A_4$, independently for each occurrence, is selected from the group consisting of —NH—$NH_2$; —NHOH, —NH—OR", or —OH;

R" is selected from the group consisting of H or $C_{1-4}$alkyl; and f)

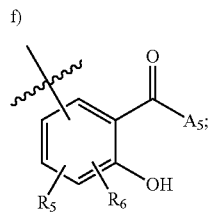

wherein $A_5$ is selected from the group consisting of —OH, —$NH_2$, —SH, —NHR'";

R'" is selected from $C_{1-4}$alkyl optionally substituted with hydroxyl; —$NH_2$; —OH; —O-phenyl; and $C_{1-4}$alkoxy;

$R_5$ and $R_6$ are independently selected from the group consisting of H, $C_{1-4}$alkyl optionally substituted by hydroxyl, amino, halo, or thio; $C_{1-4}$alkoxy; halogen; —OH; —CN; —COOH; —CONHR'; or $R_5$ and $R_6$ taken together may form a 5-6 membered ring;

wherein $X_2$ is a second ligand moiety capable of binding to a second target biomolecule;

$Y_2$ is absent or is a connector moiety covalently bound to $X_2$ and $Z_2$; and $Z_2$ is a boronic acid or oxaborale moiety capable of binding with the $Z_1$ moiety of Formula I to form the multimer; and pharmaceutically acceptable salts, stereoisomers, metabolites and hydrates thereof.

In some embodiments, a therapeutic dimerized compound may be formed from the dimerization in an aqueous media of a first monomer represented by:

$X_3$—$Y_3$—$Z_3$ (Formula IV); and pharmaceutically acceptable salts, stereoisomers, metabolites and hydrates thereof, and a second monomer is represented by:

$X_4$—$Y_4$—$Z_3$ (Formula V) and pharmaceutically acceptable salts, stereoisomers, metabolites and hydrates thereof, wherein $X_3$ is a first ligand moiety capable of binding to a first target biomolecule;

$Y_3$ is absent or is a connector moiety covalently bound to $X_4$ and $Z_3$;

$X_4$ is a second ligand moiety capable of binding to a second target biomolecule;

$Y_4$ is absent or is a connector moiety covalently bound to $X_4$ and $Z_3$;

$Z_3$ is selected from the group consisting of:

a)

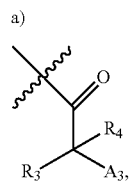

wherein $A_3$ is —OH, —SH, or —NHR';

$R_3$ is selected from the group consisting of H, halo, $C_{1-4}$alkyl, $C_{3-6}$cycloalkyl, and heterocycle, wherein $C_{1-4}$alkyl, $C_{3-6}$cycloalkyl, or heterocycle may be optionally substituted by one, two or three substituents selected from the group consisting of halo, cyano, amino, or hydroxyl;

$R_4$ is selected from the group consisting of H, halo, $C_{1-4}$alkyl, $C_{3-6}$cycloalkyl, and heterocycle, wherein $C_{1-4}$alkyl, $C_{3-6}$cycloalkyl, or heterocycle may be optionally substituted by one, two, or three substituents selected from the group consisting of halo, cyano, amino, or hydroxyl; and b)

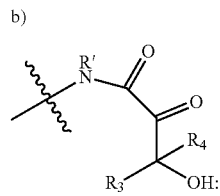

wherein

R' is selected from $C_{1-4}$alkyl optionally substituted with hydroxyl; —$NH_2$; —OH; and $C_{1-4}$alkoxy;

R$_3$ is selected from the group consisting of H, halo, C$_{1-4}$alkyl, C$_{3-6}$cycloalkyl, and heterocycle, wherein C$_{1-4}$alkyl, C$_{3-6}$cycloalkyl, or heterocycle may be optionally substituted by one, two, or three substituents selected from the group consisting of halo, cyano, amino, or hydroxyl;

R$_4$ is selected from the group consisting of H, halo, C$_{1-4}$alkyl, C$_{3-6}$cycloalkyl, and heterocycle, wherein C$_{1-4}$alkyl, C$_{3-6}$cycloalkyl, or heterocycle may be optionally substituted by one, two, or three substituents selected from the group consisting of halo, cyano, amino, or hydroxyl.

Connectors

In some embodiments, a monomer may comprise a connector that joins the ligand moiety with the linker element. In some instances, such connectors do not have significant binding or other affinity to an intended target. However, in certain embodiments, a connector may contribute to the affinity of a ligand moiety to a target.

In some embodiments, a connector element may be used to connect the linker element to the ligand moiety. In some instances, the connector element may be used to adjust spacing between the linker element and the ligand moiety. In some cases, the connector element may be used to adjust the orientation of the linker element and the ligand moiety. In certain embodiments, the spacing and/or orientation the linker element relative to the ligand moiety can affect the binding affinity of the ligand moiety (e.g., a pharmacophore) to a target. In some cases, connectors with restricted degrees of freedom are preferred to reduce the entropic losses incurred upon the binding of a multimer to its target biomolecule. In some embodiments, connectors with restricted degrees of freedom are preferred to promote cellular permeability of the monomer.

In some embodiments, the connector element may be used for modular assembly of monomers. For example, in some instances, a connector element may comprise a functional group formed from reaction of a first and second molecule. In some cases, a series of ligand moieties may be provided, where each ligand moiety comprises a common functional group that can participate in a reaction with a compatible functional group on a linker element. In some embodiments, the connector element may comprise a spacer having a first functional group that forms a bond with a ligand moiety and a second functional group that forms a bond with a linker element.

Contemplated connecters may be any acceptable (e.g. pharmaceutically and/or chemically acceptable) bivalent linker that, for example, does not interfere with multimerization of the disclosed monomers. For instance, such linkers may be substituted or unsubstituted C$_1$-C$_{10}$ alkylene, substituted or unsubstituted cycloalkylene, substituted or unsubstituted aryl, substituted or unsubstituted heteroaryl, acyl, sulfone, phosphate, ester, carbamate, or amide. Contemplated connectors may include polymeric connectors, such a polyethylene glycol or other pharmaceutically acceptable polymers. For example, contemplated connectors may be a covalent bond or a bivalent C$_{1-10}$ saturated or unsaturated, straight or branched, hydrocarbon chain, wherein one, two, or three or four methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, phenyl, or a mono or bicyclic heterocycle ring. In some embodiments, a connector may be from about 7 atoms to about 13 atoms in length, or about 8 atoms to about 12 atoms, or about 9 atoms to about 11 atoms in length. For purposes of counting connector length when a ring is present in the connector group, the ring is counted as three atoms from one end to the other. In another embodiment, a connecter group is from about 6 Å to about 15 Å in length.

Methods

In some embodiments, contemplated monomers and multimers may be administered to a patient in need thereof. In some embodiments, a method of administering a pharmaceutically effective amount of a multimeric compound to a patient in need thereof is provided. In some cases, the method comprises administering to the patient thereof an amount of the first monomer and an amount of a boronic acid monomer in amounts effective such that the pharmaceutically effective amount of the resulting multimer is formed in vivo.

In some embodiments, a first monomer and a second monomer may be administered substantially sequentially. In other embodiments, the first monomer and the second monomer are administered substantially simultaneously. In some embodiments the monomers may be administered, sequentially or simultaneously, by different routes of administration. In still further embodiments, a first monomer and a second monomer may be administered after forming a multimer.

In some instances, a method of modulating two or more target biomolecule domains is provided. In some embodiments, a first ligand moiety may bind to a first domain and a second ligand moiety may bind to a second domain. In certain embodiments, a multimer comprising the first and second ligand moieties may be form prior to binding the first and second domains. In other embodiments, the multimer may form after one and/or two of the monomers bind the first and second domains.

In some embodiments, the target biomolecule may be a protein. In other embodiments, the target biomolecule may be nucleic acid. In some cases, the ligand moiety may be a pharmacophore.

In some embodiments, a multimer may be used to inhibit or facilitate protein-protein interactions. For example, in some cases, a multimer may be capable of activating or inactivating a signaling pathway. Without wishing to be bound by any theory, a multimer may bind to a target protein and affect the conformation of the target protein such that the target protein is more biologically active as compared to when the multimer does not bind the target protein. In some embodiments monomers may be chosen such that a multimer formed from the monomers binds to at least two regions of a target molecule.

Without wishing to be bound by any theory, protein-protein and protein-nucleic acid recognition often work through protein interaction domains, such as the SH2, SH3, and PDZ domains. Currently, there are over 75 such motifs reported in the literature (Hunter, et al., *Cell* 100:113-127 (2000); Pawson et al., *Genes & Development* 14:1027-1047 (2000)). For example, SH2 domains are miniature receptors for protein regions containing a phosphorylated tyrosine. SH2 domains may be found in proteins that act as, or play a role in, for example, adaptors, scaffolds, kinases, phosphatases, ras signaling, transcription, ubiquitination, cytoskeletal regulation, signal regulation, and phospholipid second messenger signaling. As another non-limiting example, SH3 domains bind peptide loops with the motif RXXK or PXXP. Many proteins have both SH2 and SH3 domains, which act as "receptors" to bind one or more protein partners. Coferons may be designed to inhibit binding of a phosphotyrosine protein to its cognate SH2 domain. Alternatively, monomers and multimers may be designed so one ligand moiety binds one motif (i.e. SH2), and a second ligand moiety binds a second motif (i.e. SH3), either on the same or different proteins.

Many large proteins or macromolecular complexes (e.g., ribosomes) have multiple binding sites with known drug inhibitors. In some embodiments, linker elements may be used to bring together two pharmacophores on the same target to: (i) bind the target with higher affinity; (ii) exhibit a stronger inhibition than either pharmacophore alone; (iii) exhibit greater activation than either pharmacophore alone; or (iv) create a binding entity covering a larger surface area of the target, making it harder for the organism/cell/virus to develop resistance to the drug via point mutations.

In some embodiments, a multimer may target a tryptase. For example, a multimer may be used to treat conditions activated by a tryptase, such as mast cell mediated inflammatory conditions (e.g. asthma). Asthma is frequently characterized by progressive development of hyper-responsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by the binding of specific inhaled antigens to the IgE receptors and then release a number of chemical mediators. For example, degranulation of mast cells leads to the release of proteoglycans, peroxidase, arylsulfatase B, chymase, and tryptase, which results in bronchiole constriction.

Human mast cell β-tryptase-II is a tetrameric serine protease that is concentrated in mast cell secretory granules. The enzyme is involved in IgE-induced mast cell degranulation in an allergic response and is potentially a target for the treatment of allergic asthma, rhinitis, conjunctivitis and dermatitis. Tryptase has also been implicated in the progression of renal, pulmonary, hepatic, testicular fibrosis, chronic obstructive pulmonary disease (COPD), and inflammatory conditions such as ulcerative colitis, inflammatory bowel disease, rheumatoid arthritis, and various other mast cell-related diseases. In some embodiments, multimers may be used to treat such diseases.

Tryptase is stored in the mast cell secretory granules and is the major protease of human mast cells. Tryptase has been implicated in a variety of biological processes, including degradation of vasodilatory and bronchodilatory neuropeptides and modulation of bronchial responsiveness to histamine. As a result, tryptase inhibitors may be useful as anti-inflammatory agents for treatment of inflammatory disease and may also be useful in treating or preventing allergic rhinitis, inflammatory bowel disease, psoriasis, ocular or vernal or ulcerative conjunctivitis, dermatological conditions (e.g., psoriasis, eczema, or atopic dermatitis), arthritis (e.g., rheumatoid arthritis, osteoarthritis, hematoid arthritis, traumatic arthritis, rubella arthritis, psoriatic arthritis, or gouty arthritis), rheumatoid spondylitis, interstitial lung disease, chronic obstructive pulmonary disease, and diseases of joint cartilage destruction.

In addition, tryptase has been shown to be a potent mitogen for fibroblasts, suggesting its involvement in the pulmonary fibrosis in asthma and interstitial lung diseases. Therefore, in some embodiments, tryptase inhibitors may be useful in treating or preventing fibrotic conditions, for example, fibrosis, sceleroderma, pulmonary fibrosis, liver cirrhosis, myocardial fibrosis, neurofibromas, hepatic fibrosis, renal fibrosis, testicular, and hypertrophic scars.

Additionally, tryptase inhibitors may be useful in treating or preventing myocardial infarction, stroke, angina and other consequences of atherosclerotic plaque rupture.

Tryptase has also been discovered to activate prostromelysin that in turn activates collagenase, thereby initiating the destruction of cartilage and periodontal connective tissue, respectively. In some embodiments, tryptase inhibitors may be useful in the treatment or prevention of arthritis, periodontal disease, diabetic retinopathy, a condition relating to atherosclerotic plaque rupture, anaphylactic ulcerative colitis, and tumor growth. Also, tryptase inhibitors may be useful in the treatment of anaphylaxis, multiple sclerosis, peptic ulcers, and syncytial viral infections.

A variety of antibiotics elicit their antibacterial activity by binding to the bacterial ribosome and inhibiting protein synthesis. Many of these antibiotics bind the peptidyl transferase center of the ribosome (P site). In some embodiments, a multimer may bind to two or more sites on the ribosome. For example, a first pharmacophore of a multimer may bind to the peptidyl transferase center of the ribosome (i.e., the P site) and a second multimer may bind to site adjacent to the P site. As a non-limiting, illustrative example, Linezolid, an oxazolidinone antibiotic, is believed to bind adjacent to the binding site for Sparsomycin. The close juxtaposition of the linezolid binding site with the sparosmycin binding site presents a possible scenario for developing monomers based on linezolid and sparsomycin that can dimerize on binding to the ribosome, thereby creating a high affinity and high specificity inhibitor of bacterial protein synthesis.

Other non-limiting examples of target protein families are provided in Table 1 below. Also provided in Table 1 are endogenous ligands, agonists, and antagonists that bind to the protein families. Examples of detection assays are also provided in Table 1, which may be used in a screening assay to detect activation and/or inhibition of the target protein.

Provided in Table 2 are non-limiting examples of domains that can bind a ligand, proteins that contain the domains, known inhibitors, and $K_D$ values of binding partners (i.e., ligands). Examples of detection assays are also provided in Table 2, which may be used in a screening assay to find ligands for the domains.

TABLE 1

Examples of Protein Families and Their Pharmacological Targets

| TARGET FAMILY | TARGET EXAMPLE | ENDOGENOUS LIGAND (MOD- ULATORS) | EXAMPLES OF CURRENT AGONISTS (ACTIVATORS) | EXAMPLES OF CURRENT ANTAGONISTS (INHIBITORS) | EXAMPLE OF DETECTION ASSAYS |
|---|---|---|---|---|---|
| G-PROTEIN COUPLED RECEPTORS | $β_2$ adrenergic receptors | epinephrine, norepinephrine | albuterol, salbutamol, terbutaline, salmeterol | propranolol, butoxamine | HitHunter, PathHunter (DiscoverX), cAMP assay, Intracellnlar calcium flux, TANGO, |

TABLE 1-continued

Examples of Protein Families and Their Pharmacological Targets

| TARGET FAMILY | TARGET EXAMPLE | ENDOGENOUS LIGAND (MOD-ULATORS) | EXAMPLES OF CURRENT AGONISTS (ACTIVATORS) | EXAMPLES OF CURRENT ANTAGONISTS (INHIBITORS) | EXAMPLE OF DETECTION ASSAYS |
|---|---|---|---|---|---|
| G-PROTEIN COUPLED RECEPTORS | Muscarinic receptors | Acetylcholine | Acetylcholine, Pilocarpine | Scopolamine, atropine, ipratropium, caproctamine | GeneBlazer, ELISA, binding assays HitHunter, PathHunter (DiscoverX), cAMP assay, Intracellular calcium faix, TANGO, GeneBlazer, ELLSA, binding assays |
| G-PROTEIN COUPLED RECEPTORS | H1 histamine receptor | histamine | Histamine | diphenhydramine, doxylamine, pyrilamine, brompheniramine, chlorpheniramine, Loratadine, Fexofenadine, Cetrizine, Desoratadine | HitHunter, PathHunter (DiscoverX), cAMP assay, Intracellular calcium flux, TANGO, GeneBlazer, ELISA, binding assays |
| NUCLEAR RECEPTORS | Estrogen receptor | Estriol, estrone, estradiol | 17-beta-estradiel, Chlorotrianisene, Dienestrol, Fosfestrol, Diethylstilbestrol, Zeranol | Tamoxifen, ICI 164, 384, Keoxifene, Mepitiostane | Hit-hunter (Discoverx), reporter assays, TANGO, GeneBlazer, EL1SA, ligand binding assays, |
| VOLTAGE GATED ION CHANNELS | voltage-gated sodium channels | | veratridine, aconitine | tetrodotoxin, saxitoxin, | intracellutar ion flux assays |
| VOLTAGE GATED ION CHANNELS | voltage-gated calcium channels | | BAY K 8644, CGP 28392 | ω-conotoxin, ω-agatoxins, dihydropyridine, nifedipine | Intracellular ion flux assays |
| LIGAND GATED ION CHANNELS | kainate receptor | glutamate | kainic acid, domoic acid, LY339434, ATPA, iodowillardiine, (2S,4-R)-4-methylglutamic acid | CNQX, LY293558, LY294486 | HitHunter, PathHunter (DiscoverX), cAMP assay, Intracellular ion flux, TANGO, GeneBlazer, ELISA, ligand binding assays, |
| RECEPTOR TYROSINE KINASES | epidermal growth factor receptor (EGFR) | epidermal growth factor | EGF, TGFa, amphiregulin, betacellulin, epiregulin, neuregulins | PD153035, anti-EGFR antibody C225, acroplysinin-1 AG18, AG82, AG99, AG112, AG213, AG490, AG494, AG527, AG555, AG556 | reporter assays, kinase assays. CO-IP, BRET, FRET, TANGO, GeneBlazer, HitHunter, PathHunter (DiscoverX), ELISA |
| GROWTH FACTORS | Vascular endothelial growth factor | VEGFR | | Ranibizumab, bevacizumab, sunitinib, sorafenib, axitinb, pazopanib, Naphthamides | Hit-hunter (Discoverx), reporter assays, TANGO, GeneBlazer, ELISA. ligand binding assays, |
| PROTEASES | Caspase | granzyme B; caspase | Granzyme B, caspase | Z-VAD(OMc)-FMK, Z-VAD-CHO | caspase assays, apoptosis assays, mitochondrial Dy, CO-IP, BRET, FRET, TANGO, GeneBlazer, HitHunter, PathHunter (DiscoverX), ELISA |
| PHOSPHATASES | PP1 | phosphoserine/ threonine residues | | calyculin A, nodularin, tautomycin | protein tyrosine phosphatase assay, CO-IP, BRET, FRET, TANGO, GeneBlazer, HitHunter, PathHunter (DiscoverX), ELISA |
| PROTEIN KINASES | ERK | MEK | | AG126, apigenin, Ste-MPKKKPTPIQL, NP-NH2, H-GYGRKKRRQR | kinase assay, CO-IP, BRET, FRET, reporter assays, TANGO, GeneBlazer, HitHunter, PathHunter |

TABLE 1-continued

Examples of Protein Families and Their Pharmacological Targets

| TARGET FAMILY | TARGET EXAMPLE | ENDOGENOUS LIGAND (MOD-ULATORS) | EXAMPLES OF CURRENT AGONISTS (ACTIVATORS) | EXAMPLES OF CURRENT ANTAGONISTS (INHIBITORS) | EXAMPLE OF DETECTION ASSAYS |
|---|---|---|---|---|---|
| | | | | RR-G-MPKKKPTPIQLNP-NH2, PD98059, U0126, | (DiscoverX) |
| MISC ENZYMES | Adenyl-atecyclase | G proteins, calcium | bortetella pertussis, cholera toxin, forskolin | NKY80, 2',3'-Dideoxyadenosine, 2',5'-Dideoxyadenosine, SQ22536, MDL-12330A | BRET, FRET, calcium flux assays, cAMP assays, TANGO, GeneBlazer, HitHunter, PathHunter (DiscoverX) |
| MISC ENZYMES | Acetyl-cholinesterase | | | Caproctamine, Metrifonate, Physostigmine, Galantamine, Dyflos, Neostigmine | Acetylcholinesterase Assay, Amplex Red, Ellman method, HPLC |
| BIOACTIVE LIPIDS | Ceramide | sphingomyelin | TNF□, Fas ligand, 1, 25 dihydroxy vitamin D, □interferon | fumonisin B | TLC lipid charring, diacylglycerol kinase labeling in vitro |
| CYTOKINES | IL2 | IL2R | BAY 50-4798, P1-30, SP4206 | daclizumab, basiliximab, SP4206 | TANGO, GeneBlazer, HitHunter, PathHunter (DiscoverX), IL2 dependent mouse CTLL cell line, ELISA |
| MISC PROTEINS | BCLXL | BAD | | BH3I-1, A-371191, ABT-737 | TANGO, GeneBiazer, HitHunter, PathHunter (Discover, X) CO-IP, BRET, FRET, ELISA |
| MISC PROTEINS | p53 | MDM2, JNK1-3, ERK1-2, p38 MAPX, ATR, ATM, Chk1, Chk2, DNA-PK, CAK | PRIMA-1, MTRA-1, RITA, | Pifithrin-α | caspase assays, apoptosis assays, mitochondrial Dy, CO-IP, BRET, FRET, TANGO, GeneBlazer, HitHunter, PathHunter (DiscoverX, ELISA |
| MISC PROTEINS | Tubulin | tubulin | | ALB109564, ABT-751, D24851, D64131, benomyl, estramustine, LY290181 | Kinase assay, CO-IP, BRET, FRET reporter assays. TANGO, GeneBlazer, □-arrestin(DiscoverX |
| MISC PROTEINS | □-amyloid | | | L1, 10-phenanthroline derivatives, KLVFF, LVFFA, Memoquin, SLF-CR | Stagnant Amyloid Fibril Formation Assay, amyloid fibrillization assay |
| MISC PROTEINS | thymidylate synthase | | | raltitrexed, pemetrexed, nolatrexed, ZD9331, GS7904L, fluorouracil | caspase assays, apoptosis assays, mitochondrial Dy, CO-IP, BRET, FRET, TANGO, GeneBlazer, HitHunter, PathHunter (DiscoverX), ELISA |
| UBIQUITIN LIGASES | MDM2 | p53 | | trans-4-Iodo, 4'-boranyl-chalcone, Nutlins, MI-219. MI-63, RITA, HLI98 | TANGO, GeneBlazer, HitHunter, PathHunter (DiscoverX), CO-IP, BRET, FRET, ELISA, reporter assay |
| VIRAL REGULATORS | HPV E2 | HPV E1 | | indandiones, podophyllotoxin | E2 displacement assay, TANGO, GeneBlazer, HitHunter, PathHunter (DiscoverX, CO-IP, BRET, FRET, ELISA, reporter assay |
| BACTERIAL CELL | ZipA | FtsZ | | substituted 3-(2-indolyl)piperidines | TANGO, GeneBlazer, HitHunter, PathHunter |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLE OF DETECTION ASSAYS |
|---|---|---|---|---|---|
| DIVISION PROTEINS | | | | 2-phenylindoles | (DiscoverX), CO-IP, BRET, FRET, ELISA, reporter assay, polarization competition assay, |
| CYTOKINES | TNF | TNFR | | infliximab, adalimumab, elanercept | TANGO, GeneBlazer, HitHunter, PathHunter (DiscoverX), CO-IP, BRET, FRET, ELISA, |
| SCAFFOLD PROTEINS | JIP1 | JNK | | BI-78D3, TIJIP | TANGO, GeneBlazer, Hithunter, PathHunter (DiscoverX), CO-IP, BRET, FRET, ELISA, kinase assay |
| DNA REPAIR | PARP | | | INO-1001, AG014699, BS-201, AZD2281, BS-401 | TANGO, GeneBlazer, HitHunter, PathHunter (DiscoverX), CO-IP, BRET, FRET, ELISA. |
| RIBOSOMES | Antibiotics | ribosomes | | tetracyclins, macrolides, lincosamides, streptogramins | cell death assay, |
| HISTONE DEACETYLASES | HDAC1 | | | suberoylanilide hydroxamic acid, trichostatin A, LBH589 | TANGO, GeneBlazer, HitHunter, PathHunter (DiscoverX), CO-IP, BRET, FRET, ELISA, |
| APOPTOSIS REGULATORS | XIAP | SMAC/DIABLO, caspase 3, caspase 7, caspase 9 | | SM102-SM130 | CO-IP, BRET, FRET, reporter assays, TANGO, GeneBlazer HitHunter, PathHunter (DiscoverX), cell death assays |
| CHAPERONE PROTEINS | Hsp90 | Cdc37, survivin | | Celastrol, shepherdin | CO-IP, BRET, FRET, report assays, TANGO, GeneBlazer, HitHunter, PathHunter (DiscoverX), |
| SERINE/ THREONINE PROTEIN KINASES | mTOR | Raptor, mLST8/GβL | | Rapamycin, caffeine, farnesylthiosalicylic acid, curcumin, temsirolimus, everolimus | kinase assay, CO-IP, BRET, FRET, reporter assays, TANGO, GeneBlazer, HitHunter, PathHunter (DiscoverX) |
| SERINE/ THREONINE- PROTEIN KINASES | B-raf & B-raf V600E | K-ras | | PLX4720 | kinase assay, CO-IP, BRET, FRET, reporter assays, TANGO, GeneBlazer, HitHunter, PathHunter (DiscoverX), |
| CYCLIN DEPENDENT KINASES | CDK2 | Cyclin A, cyclin E | | Variolin, Meriolin | kinase assay, CO-IP, BRET, FRET, reporter assays, TANGO, GeneBlazer, HitHunter, PathHunter (DiscoverX), |
| GROWTH FACTOR RECEPTORS | IGF-1R | IGFII | | PQIP | CO-IP, BRET, FRET, reporter assays. TANGO, GeneBlazer, HitHunter, PathHunter (DiscoverX), |
| PROTEASOME | 20S | 19S | | Bortezomib, salinosporamide A, | CO-IP, BRET, FRET, cell viability |

TABLE 2

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| SH2 | Phospho-tyrosine residues | Grb2 | Fmoc-Glu-Tyr-Aib-Asa-NH2; Ac-SpYVNVQ-NH2, macrocycles, STATTIC | Surface plasmon resonance (SPR) technology, | 0.2-11 μM |
| FHA | Phospho-threonine and phospho-tyrosine residues | KIF13B | | | 1-100 μM |
| 14-3-3 | Phospho-serine residues | 14-3-3 | R18 | | 7 nM-20 μM |
| WW | ligands containing PpxY, Proline-rich sequences | Pin1 | Zn(II) Dipicolylamine-based artificial receptors | | 6 μM-190 μM |
| WD40 | | Apaf-1 | | | 1 μM |
| MH2 | phospho-serine residues | SMAD2 | | | 240 nM |
| BROMO | acetylated lysine residues | CBP | | | 1 μM-4 mM |
| UBA | mono-, di-, tri-, and tetra-ubiquitin | HHR23A | | | 6 μM-2.35 mM |
| PTB | Phospho-tyrosine residues, Asn-Pro-X-Tyr motifs | IRS-1 | LSNPTX-NH2, LYASSNOAX-NH2, LYASSNPAX-NH2 | PTB domain binding assays | 160 nM-10 μM |
| SH3 | Proline-rich peptides with consensus Pro-X-X-Pro, | Grb2 | Peptidimer-c, VPPPVPPRRR, (VPPPVPPRRR)2K) | | 1-500 μM |
| EVH1 | FPXΦP motifs, PPxxF motifs | ActA | | | 10-50 μM |
| GYF | proline-rich sequences, | CDBP2 | | | 10-160 μM |
| VHS | | TOM1 | | | 11-50 μM |
| PDZ | PDZ, Val-COOH | MNT1 | NSC668036, FJ9 | | 1-500 μM |
| PUF | RNA | PUM1 | | | 10-100 nM |
| TUBBY | DNA, phosphotidylinositol | TULP1 | | | |
| SAM | | CNK | | | 71 nM-1 μM |
| DD | DD | FADD | | | |
| CARD | CARD | Apaf-1 | | | 1.4 μM |
| PyD | PyD | Pyrin | | | 4 μM |
| PB1 | PB1 | Bem1 | | | 4-500 nM |
| BRCT | BRCT | BRCA1 | | | 113 nM-6 μM |
| PH | phosphatidylinositol-4,5-bisphosphate, PI-3, 4-P2 or PI-3, 4, 5-P3 | AKT1 | NSC 348900, perifosine, SH5, SH23, SH24, SH25, m114, m115, m116 | | 1.76 nM-350 μM |
| FYVE | Phosphatidylinositol 3-phosphate, zinc | SARA | | | 50 nM-140 μM |
| C1 | phorbol esters, diacylglycerol | PKC isoforms | | | 0.58-800 nM |
| FERM | PI(3)P, PI(4)P, PI(5)P, IP3, | PTLP1 | | | 200 nM-30 μM |
| C2 | Calcium, acidic phospholipids | Nedd4 | | | 250 nM-94 μM |
| PX | PI(3,4)P2, PI(3)P, PI(3,5)P2, PI(4)P, PI(5)P, PI(3,4,5)P3, PI(4,5)P2 | CISK | | | 1.8 nM-50 μM |
| ENTH | PtdIns(4,5)P2, PtdIns(1,4,5)P3, PI(3,4)P2; PI(3,5)P2 | Epsin1 | | | 98 nM-1 μM |

A pharmacophore is typically an arrangement of the substituents of a moiety that confers biochemical or pharmacological effects. In some embodiments, identification of a pharmacophore may be facilitated by knowing the structure of the ligand in association with a target biomolecule. In some cases, pharmacophores may be moieties derived from molecules previously known to bind to target biomolecules (e.g., proteins), fragments identified, for example, through NMR or crystallographic screening efforts, molecules that have been discovered to bind to target proteins after performing high-throughput screening of natural products libraries, previously synthesized commercial or non-commercial combinatorial compound libraries, or molecules that are discovered to bind to target proteins by screening of newly synthesized combinatorial libraries. Since most pre-existing combinatorial libraries are limited in the structural space and diversity that they encompass, newly synthesized combinatorial libraries may include molecules that are based on a variety of scaffolds.

Additionally pharmacophores may be derived from traditional approaches such as fragment based drug design and structure based drug design. Those skilled in the art will recognize that any pharmacophore including pre-existing pharmacophores such as approved drugs are amenable to be designed as monomers through the incorporation of the appropriate linker elements and connector elements. For example, previously approved drugs that have poor efficacy due to a low affinity for a first macromolecular target may be utilized as a pharmacophore component of a first monomer which when combined with a pharmacophore of a second monomer that also binds the first macromolecular target or a second macromolecular target that interacts with the first macromolecular target results in enhanced binding and, in some cases, higher efficacy. Likewise, previously approved drugs that have low efficacy as a result of size, molecular weight or other physicochemical attributes that reduce the cellular uptake of the drug may be amenable to being converted into one or more monomers that bear the appropriate pharmacophoric elements, such that each monomer has physicochemical attributes that allow for increased cellular uptake.

In some embodiments, a ligand moiety (e.g., a pharmacophore) may have a molecular weight between 50 Da and 2000 Da, in some embodiments between 50 Da and 1500 Da, in some embodiments, between 50 Da and 1000 Da, and in some embodiments, between 50 Da and 500 Da. In certain embodiments, a ligand moiety may have a molecular weight of less than 2000 Da, in some embodiments, less than 1000 Da, and in some embodiments less than 500 Da.

In certain embodiments, the compound utilized by one or more of the foregoing methods is one of the generic, subgeneric, or specific compounds described herein.

Disclosed compositions may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound may be administered orally, subcutaneously, topically, parenterally, by inhalation spray or rectally in dosage unit formulations containing conventional non-toxic pharmaceutically acceptable carriers, adjuvants, and vehicles. Parenteral administration may include subcutaneous injections, intravenous or intramuscular injections, or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a partial or total alleviation of symptoms, is achieved.

In another aspect, pharmaceutical compositions comprising monomers, dimers, and/or multimers as disclosed herein formulated together with a pharmaceutically acceptable carrier provided. In particular, the present disclosure provides pharmaceutical compositions comprising monomers, dimers, and/or multimers as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid, or liquid form, which contains one or more of the compounds, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, enteral pharmaceutical formulations including a disclosed pharmaceutical composition comprising monomers, dimers, and/or multimers, an enteric material; and a pharmaceutically acceptable carrier or excipient thereof are provided. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that may be used.

Advantageously, kits are provided containing one or more compositions each including the same or different monomers. Such kits include a suitable dosage form such as those described above and instructions describing the method of using such dosage form to treat a disease or condition. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent.

Also contemplated herein are methods and compositions that include a second active agent, or administering a second active agent.

Certain terms employed in the specification, examples, and appended claims are collected here. These definitions should be read in light of the entirety of the disclosure and understood as by a person of skill in the art. Unless defined otherwise, all technical and scientific terms used herein have the same meaning as commonly understood by a person of ordinary skill in the art.

Definitions

In some embodiments, the compounds, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "acyl," as used herein, refers to a moiety that includes a carbonyl group. In some embodiments, an acyl group may have a general formula selected from —C(O)R$_x$; —CO$_2$(R$_x$); —C(O)N(R$_x$)$_2$; —OC(O)R$_x$; —OCO$_2$R$_x$; and —OC(O)N(R$_x$)$_2$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments, aryl refers to a mono- or bicyclic carbocyclic ring system having one or two aromatic rings including, but not limited to, phenyl, naphthyl, tetrahydronaphthyl, indanyl, indenyl, and the like. In certain embodiments, the term heteroaryl, as used herein, refers to a cyclic aromatic radical having from five to ten ring atoms of which one ring atom is selected from the group consisting of S, O, and N; zero, one, or two ring atoms are additional heteroatoms independently selected from the group consisting of S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heterocyclic," as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from the group consisting of oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from the group consisting of O, S, and N (wherein the nitrogen and sulfur heteroatoms may be optionally oxidized), including, but not limited to, a bi- or tri-cyclic group, comprising fused six-membered rings having between one and three heteroatoms independently selected from the group consisting of the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_{2-6}$alkenyl, and $C_{3-4}$alkenyl, respectively. Exemplary alkenyl groups include, but are not limited to, vinyl, allyl, butenyl, pentenyl, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms referred to herein as $C_{3-6}$alkenyloxy. Exemplary "alkenyloxy" groups include, but are not limited to allyloxy, butenyloxy, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_{1-6}$alkoxy, and $C_2$-$C_6$alkoxy, respectively. Exemplary alkoxy groups include, but are not limited to methoxy, ethoxy, isopropoxy, etc.

The term "alkoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, for example, such as a straight or branched group of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "carboxylic acid" as used herein refers to a group of formula —$CO_2H$.

The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of for example 3-6, or 4-6 carbons, referred to herein, e.g., as $C_{3-6}$cycloalkyl or $C_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" as used herein refer to F, Cl, Br, or 1.

The term "heterocyclylalkoxy" as used herein refers to a heterocyclyl-alkyl-O— group.

The term "heterocyclyloxyalkyl" refers to a heterocyclyl-O-alkyl-group.

The term "heterocyclyloxy" refers to a heterocyclyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

The term "connector" as used herein to refers to an atom or a collection of atoms optionally used to link interconnecting moieties, such as a disclosed linker and a pharmacophore. Contemplated connectors are generally hydrolytically stable.

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic, or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal, or human that is being sought by the researcher, veterinarian, medical doctor, or other clinician. The compounds are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'- methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. Various stereoisomers of these compounds and mixtures thereof are encompassed by this disclosure. Stereoisomers include enantiomers and diastereomers. Mixtures of enantiomers or diastereomers may be designated "(+)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomers and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds. The symbol ⎯ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. Various stereoisomers of these compounds and mixtures thereof are encompassed by this disclosure.

Individual enantiomers and diasteriomers of the compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like. In one embodiment, the compound is amorphous. In one embodiment, the compound is a polymorph. In another embodiment, the compound is in a crystalline form.

Also embraced are isotopically labeled compounds which are identical to those recited herein, except that one or more atoms are replaced by an atom having an atomic mass or mass number different from the atomic mass or mass number usually found in nature. Examples of isotopes that can be incorporated into the compounds include isotopes of hydrogen, carbon, nitrogen, oxygen, phosphorus, sulfur, fluorine and chlorine, such as $^{10}B$, $^{2}H$, $^{3}H$, $^{3}C$, $^{14}C$, $^{15}N$, $^{18}O$, $^{17}O$, $^{31}P$, $^{32}P$, 35S, $^{18}F$, and $^{36}Cl$, respectively. For example, a compound may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood, or liver). Prodrugs are well known in the art (for example, see Rautio, Kumpulainen, et al, Nature Reviews Drug Discovery 2008, 7, 255). For example, if a compound or a pharmaceutically acceptable salt, hydrate, or solvate of the compound contains a carboxylic acid functional group, a prodrug can comprise an ester formed by the replacement of the hydrogen atom of the acid group with a group such as ($C_{1-8}$)alkyl, ($C_{2-12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound contains an alcohol functional group, a prodrug can be formed by the replacement of the hydrogen atom of the alcohol group with a group such as ($C_1$-6)alkanoyloxymethyl, 1-(($C_{1-6}$)alkanoyloxy)ethyl, 1-methyl-1-(($C_{1-6}$)alkanoyloxy)ethyl ($C_1$-6)alkoxycarbonyloxymethyl, N—($C_{1-6}$)alkoxycarbonylaminomethyl, succinoyl, ($C_{1-6}$)alkanoyl, α-amino($C_{1-4}$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($_{c1}$-$C_6$) alkyl)$_2$ or glycosyl (the radical resulting from the removal of a hydroxyl group of the hemiacetal form of a carbohydrate).

If a compound incorporates an amine functional group, a prodrug can be formed, for example, by creation of an amide or carbamate, an N-acyloxyakyl derivative, an (oxodioxolenyl)methyl derivative, an N-Mannich base, imine, or enamine. In addition, a secondary amine can be metabolically cleaved to generate a bioactive primary amine, or a tertiary amine can be metabolically cleaved to generate a bioactive primary or secondary amine. For examples, see Simplicio, et al., *Molecules* 2008, 13, 519 and references therein.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as active ingredients.

For ease of reading, intermediates are provided in Table 3. At least some of the compounds identified as "Intermediates" herein are contemplated as compounds of the invention. Example compounds are provided in Table 4.

TABLE 3

INTERMEDIATES INDEX

| Sr. No. | Structure | Compound Name | Cmpd. Code |
|---|---|---|---|
| | Sparsomycin analogues | | |
| 1. | 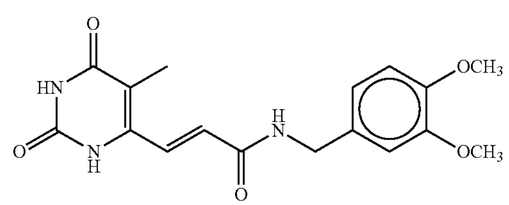 | (E)-N-(3,4-dimethoxybenzyl)-3-(5-methyl-2,6-dioxo-1,2,3,6-tetrahydropyrimidin-4-yl)acrylamide | SPARSO-10a |
| 2. | 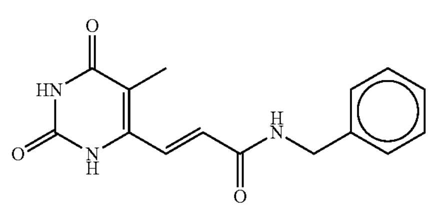 | (E)-N-benzyl-3-(5-methyl-2,6-dioxo-1,2,3,6-tetrahydropyrimidin-4-yl)acrylamide | SPARSO-17 |
| 3. | 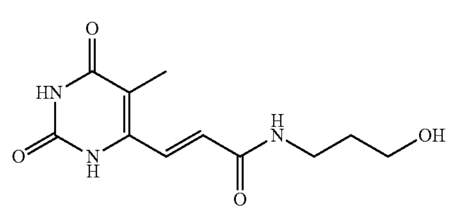 [SMILES: Cc1c(/C=C/C(=O)NCCCO)[nH]c(=O)[nH]c1=O] | (E)-N-(3-hydroxypropyl)-3-(5-methyl-2,6-dioxo-1,2,3,6-tetrahydropyrimidin-4-yl)acrylamide | SPARSO-18 |

TABLE 3-continued

INTERMEDIATES INDEX

| Sr. No. | Structure | Compound Name | Cmpd. Code |
|---|---|---|---|
| 4. | | (E)-3-(5-methyl-2,6-dioxo-1,2,3,6-tetrahydropyrimidin-4-yl)-N-propylacrylamide | SPARSO-19 |

Tryptase targets Method-D

| Sr. No. | Structure | Compound Name | Cmpd. Code |
|---|---|---|---|
| 5. | 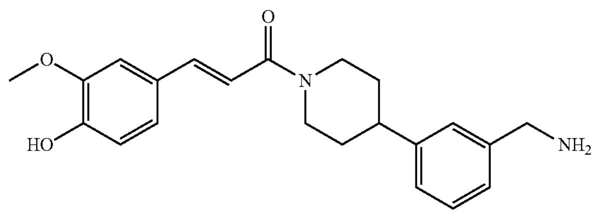 [SMILES: COc1cc(/C=C/C(=O)N2CCC(c3cccc(CN)c3)CC2)ccc1O] | (E)-1-(4-(3-(aminomethyl)phenyl)piperidin-1-yl)-3-(4-hydroxy-3-methoxyphenyl)prop-2-en-1-one | T-24 mono methoxy |
| 6. | 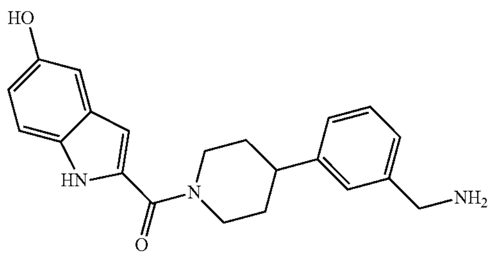 [SMILES: NCc1cccc(C2CCN(C(=O)c3cc4cc(O)ccc4[nH]3)CC2)c1] | (4-(3-(aminomethyl)phenyl)piperidin-1-yl)(5-hydroxy-1H-indol-2-yl)methanone | Target-31a |
| 7. | 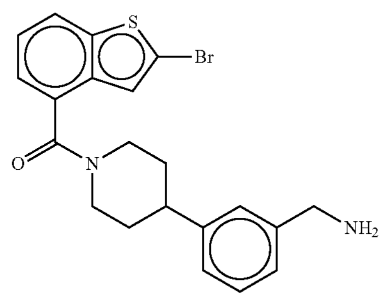 | (4-(3-(aminomethyl)phenyl)piperidin-1-yl)(2-bromobenzo[b]thiophen-4-yl)methanone | Target-37a |
| 8. | 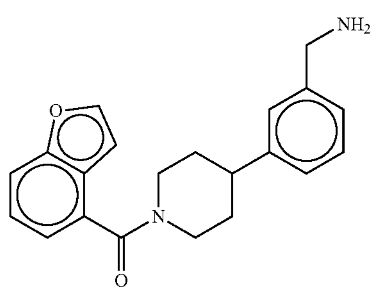 | (4-(3-(aminomethyl)phenyl)piperidin-1-yl)(benzofuran-4-yl)methanone | Target-38H |
| 9. | 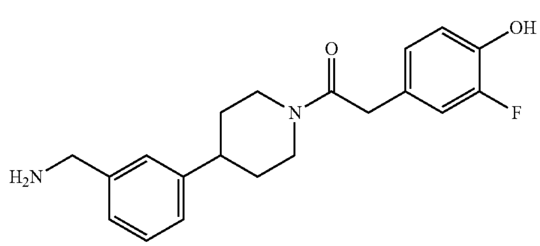 [SMILES: NCc1cccc(C2CCN(C(=O)Cc3ccc(O)c(F)c3)CC2)c1] | 1-(4-(3-(aminomethyl)phenyl)piperidin-1-yl)-2-(3-fluoro-4-hydroxyphenyl)ethanone | Target-54a |

TABLE 3-continued

INTERMEDIATES INDEX

| Sr. No. | Structure | Compound Name | Cmpd. Code |
|---|---|---|---|
| 10. | 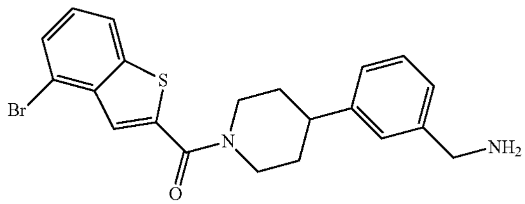 [SMILES: NCc1cccc(C2CCN(C(=O)c3cc4c(Br)cccc4s3)CC2)c1] | (4-(3-(aminomethyl)phenyl) piperidin-1-yl)(4-bromobenzo[b]thiophen-2-yl)methanone | Target-56a |
| 11. | 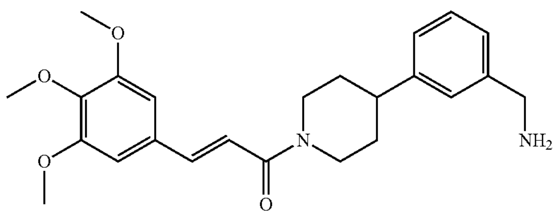 [SMILES: COc1cc(/C=C/C(=O)N2CCC(c3cccc(CN)c3)CC2)cc(OC)c1OC] | (E)-1-(4-(3-(aminomethyl)phenyl) piperidin-1-yl)-3-(3,4,5-trimethoxyphenyl)prop-2-ne-1-one | Target-43a |
| 12. | 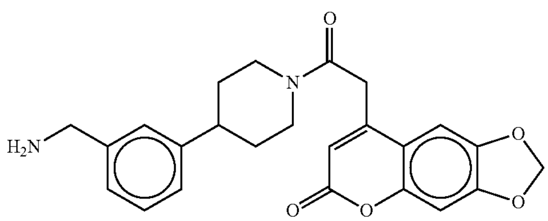 | 8-(2-(4-(3-(aminomethyl)phenyl) piperidin-1-yl)-2-oxoethyl)-6H-[1,3]dioxolo[4,5-g]chromen-6-one | Target-97a |

Tryptase targets Method-I

| Sr. No. | Structure | Compound Name | Cmpd. Code |
|---|---|---|---|
| 13. | | (4-(3-(aminomethyl)phenyl) piperidin-1-yl)(3-hydroxyphenyl)methanone | Target-53b |

Tryptase targets

| Sr. No. | Structure | Compound Name | Cmpd. Code |
|---|---|---|---|
| 14. | | (4-(3-(aminomethyl)phenyl)piperidin-1-yl)(3-((3S,4R)-3,4-dihydroxypyrrolidine-1-carbonyl)phenyl)methanone | Target-26 diol trans |
| 15. | | (E)-1-(4-(3-(aminomethyl)phenyl) piperidin-1-yl)-3-(4-cyclopropyl-3-hydroxyphenyl)prop-2-en-1-one | Target-41-Cyclopropyl |

TABLE 4

EXAMPLES INDEX

| Sr. No. | Cmpd. Code | Structure | Compound Name |
|---|---|---|---|
| | | Sparsomycin analogues | |
| 16. | SPARSO-10 | 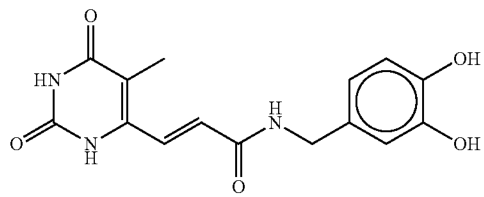 | (E)-N-(3,4-dihydroxybenzyl)-3-(5-methyl-2,6-dioxo-1,2,3,6-tetrahydropyrimidin-4-yl)acrylamide |
| | | Linezolid analogues | |
| 17. | LZD-2 | 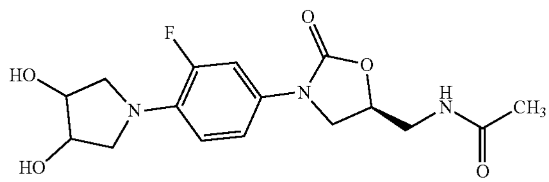 | N-(((5S)-3-(4-(3,4-dihydroxypyrrolidin-1-yl)-3-fluorophenyl)-2-oxooxazolidin-5-yl)methyl)acetamide |
| 18. | Lz-NA-19 | 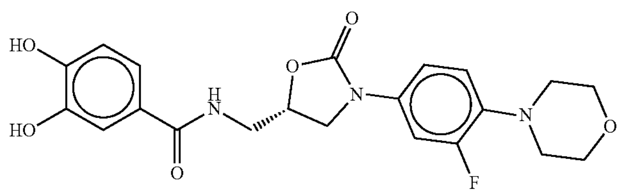 | (S)-N-((3-(3-fluoro-4-morpholinophenyl)-2-oxooxazolidin-5-yl)methyl)-3,4-dihydroxybenzamide |
| 19. | Lz-NA-20 | 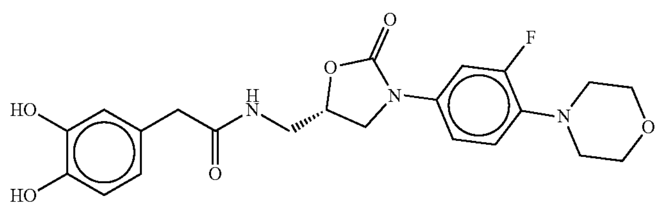 | (S)-2-(3,4-dihydroxyphenyl)-N-((3-(3-fluoro-4-morpholinophenyl)-2-oxooxazolidin-5-yl)methyl)acetamide |
| 20. | Lz-NA-21 | 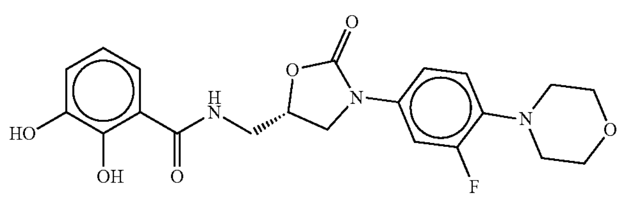 | (S)-N-((3-(3-fluoro-4-morpholinophenyl)-2-oxooxazolidin-5-yl)methyl)-2,3-dihydroxybenzamide |
| 21. | Lz-NA-22 | 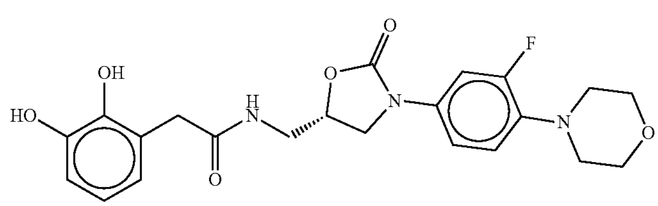 | (S)-2-(2,3-dihydroxyphenyl)-N-((3-(3-fluoro-4-morpholinophenyl)-2-oxooxazolidin-5-yl)methyl)acetamide |
| 22. | Lz-NA-23 | 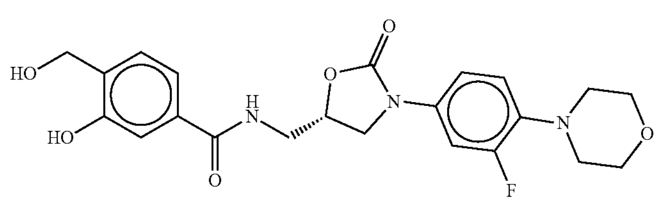 | (S)-N-((3-(3-fluoro-4-morpholinophenyl)-2-oxooxazolidin-5-yl)methyl)-3-hydroxy-4-(hydroxymethyl)benzamide |

TABLE 4-continued

EXAMPLES INDEX

| Sr. No. | Cmpd. Code | Structure | Compound Name |
|---|---|---|---|
| 23. | Lz-NA-24 | 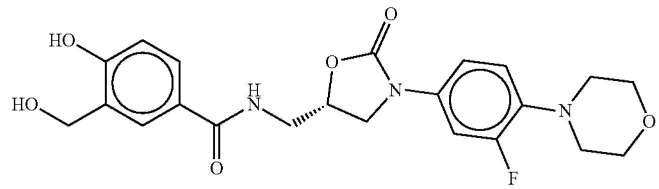 | (S)-N-((3-(3-fluoro-4-morpholinophenyl)-2-oxooxazolidin-5-yl)methyl)-4-hydroxy-3-(hydroxymethyl)benzamide |
| 24. | Lz-NA-27 | 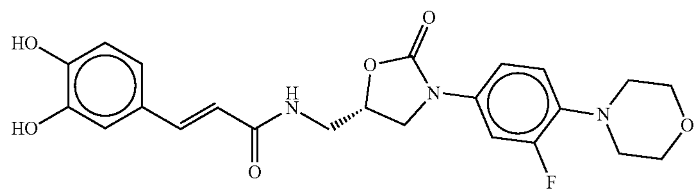 | (S,E)-3-(3,4-dihydroxyphenyl)-N-((3-(3-fluoro-4-morpholinophenyl)-2-oxooxazolidin-5-yl)methyl)acrylamide |
| 25. | Lz-NA-28 | 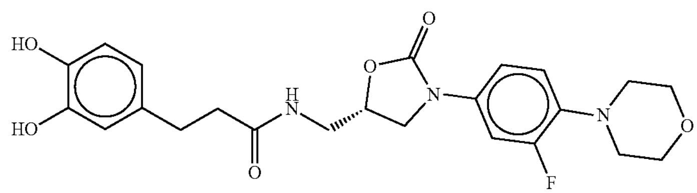 | (S)-3-(3,4-dihydroxyphenyl)-N-((3-(3-fluoro-4-morpholinophenyl)-2-oxooxazolidin-5-yl)methyl)propanamide |
| 26. | Lz-NA-34 | 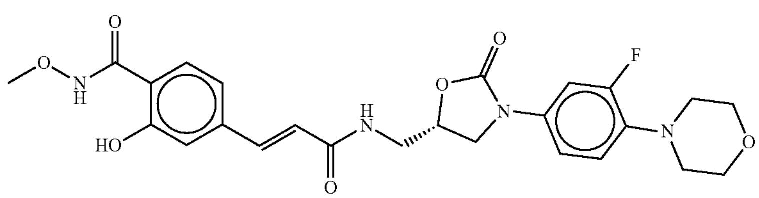 | (S,E)-4-(3-((3-(3-fluoro-4-morpholinophenyl)-2-oxooxazolidin-5-yl)methylamino)-3-oxoprop-1-enyl)-2-hydroxy-N-methoxybenzamide |
| 27. | Lz-NA-36 | 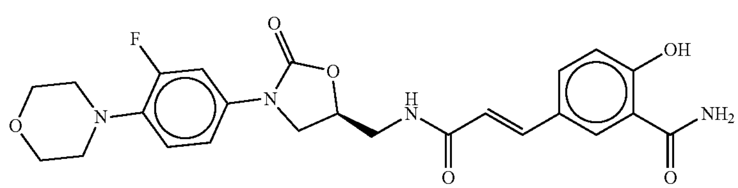 | (S,E)-5-(3-((3-(3-fluoro-4-morpholinophenyl)-2-oxooxazolidin-5-yl)methylamino)-3-oxoprop-1-enyl)-2-hydroxybenzamide |
| 28. | Lz-NA-12 | 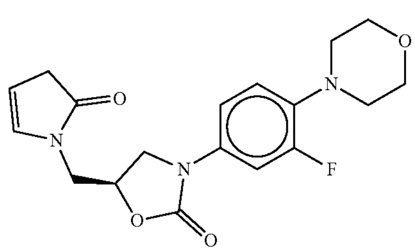 | (S)-3-(3-fluoro-4-morpholinophenyl)-5-((2-oxo-2,3-dihydro-1H-pyrrol-1-yl)methyl)oxazolidin-2-one |
| Fluorfenicol analogues | | | |
| 29. | NAFFLA-19 | 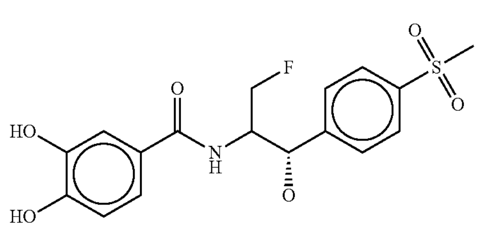 | N-((1S)-3-fluoro-1-hydroxy-1-(4-(methylsulfonyl)phenyl)propan-2-yl)-3,4-dihydroxybenzamide |

TABLE 4-continued

EXAMPLES INDEX

| Sr. No. | Cmpd. Code | Structure | Compound Name |
|---|---|---|---|
| 30. | NAFFLA-20 | 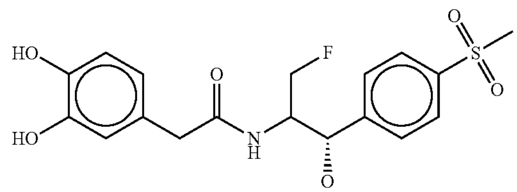 | 2-(3,4-dihydroxyphenyl)-N-((1S)-3-fluoro-1-hydroxy-1-(4-(methylsulfonyl)phenyl)propan-2-yl)acetamide |
| 31. | NAFFLA-21 | 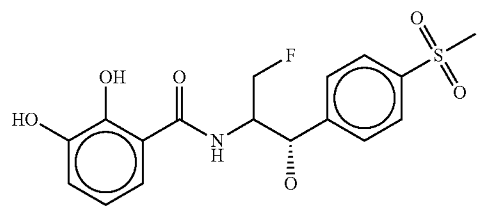 | N-((1S)-3-fluoro-1-hydroxy-1-(4-(methylsulfonyl)phenyl)propan-2-yl)-2,3-dihydroxybenzamide |
| 32. | NAFFLA-22 | 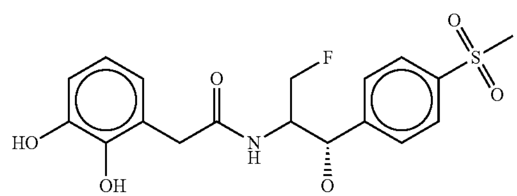 | 2-(2,3-dihydroxyphenyl)-N-((1S)-3-fluoro-1-hydroxy-1-(4-(methylsulfonyl)phenyl)propan-2-yl)acetamide |
| 33. | NAFFLA-23 | 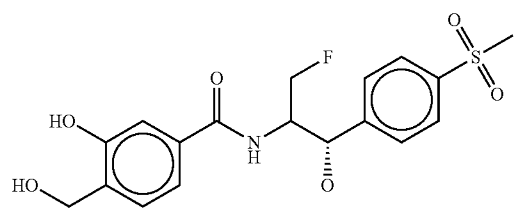 | N-((1S)-3-fluoro-1-hydroxy-1-(4-(methylsulfonyl)phenyl)propan-2-yl)-3-hydroxy-4-(hydroxymethyl)benzamide |
| 34. | NAFFLA-27 | 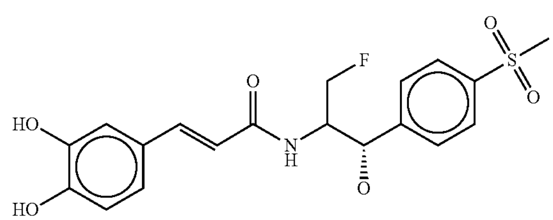 | (E)-3-(3,4-dihydroxyphenyl)-N-((1S)-3-fluoro-1-hydroxy-1-(4-(methylsulfonyl)phenyl)propan-2-yl)acrylamide |
| 35. | NAFFLA-28 | 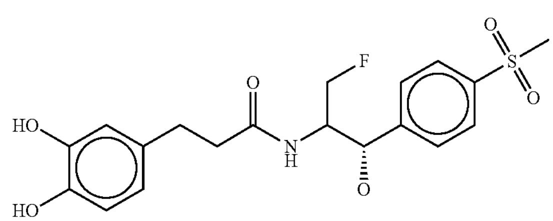 | 3-(3,4-dihydroxyphenyl)-N-((1S)-3-fluoro-1-hydroxy-1-(4-(methylsulfonyl)phenyl)propan-2-yl)propanamide |
| 36. | NAFFLA-34 | 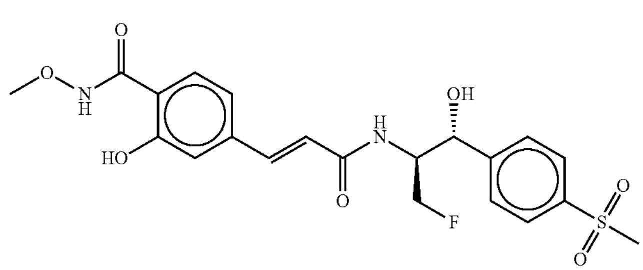 | 4-((E)-3-(((1R,2S)-3-fluoro-1-hydroxy-1-(4-(methylsulfonyl)phenyl)propan-2-ylamino)-3-oxoprop-1-enyl)-2-hydroxy-N-methoxybenzamide |

TABLE 4-continued

EXAMPLES INDEX

| Sr. No. | Cmpd. Code | Structure | Compound Name |
|---|---|---|---|
| 37. | NAFFLA-35 | 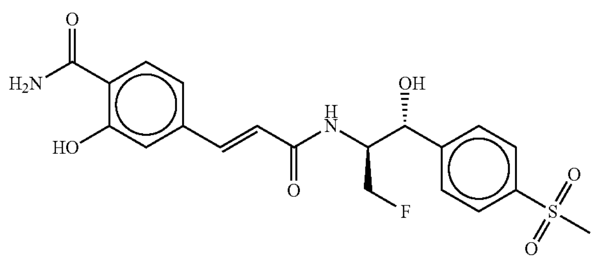 | 4-((E)-3-((1R,2S)-3-fluoro-1-hydroxy-1-(4-(methylsulfonyl)phenyl)propan-2-ylamino)-3-oxoprop-1-enyl)-2-hydroxybenzamide |
| 38. | NAFFLA-36 | 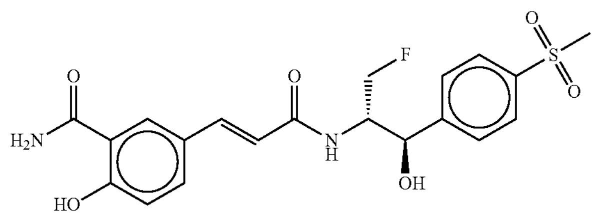 | 5-((E)-3-((1R,2S)-3-fluoro-1-hydroxy-1-(4-(methylsulfonyl)phenyl)propan-2-ylamino)-3-oxoprop-1-enyl)-2-hydroxybenzamide |
| 39. | NAFFLA-37 | 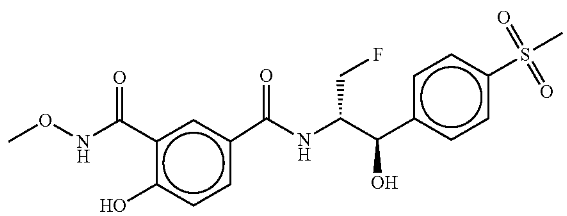 | $N^1$-((1R,2S)-3-fluoro-1-hydroxy-1-(4-(methylsulfonyl)phenyl)propan-2-yl)-4-hydroxy-$N^3$-methoxyisophthalamide |
| Tryptase targets Method-A | | | |
| 40. | Target-31 | 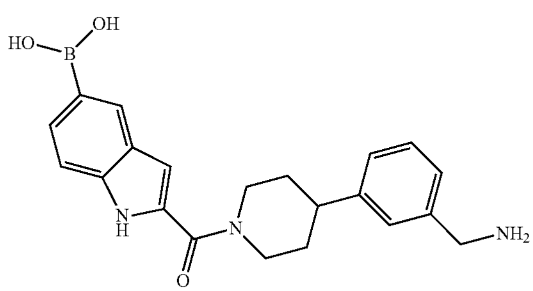 [SMILES: NCc1cccc(C2CCN(C(=O)c3cc4cc(B(O)O)ccc4[nH]3)CC2)c1] | ((2-(4-(3-(aminomethyl)phenyl)piperidine-1-carbonyl)-1H-indol-5-yl)(hydroxy)boryl)holmium |
| 41. | Target-62 | 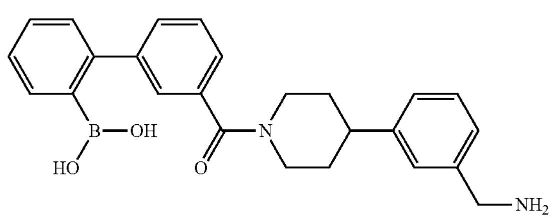 [SMILES: NCc1cccc(C2CCN(C(=O)c3cccc(-c4ccccc4B(O)O)c3)CC2)c1] | 3'-(4-(3-(aminomethyl)phenyl)piperidine-1-carbonyl)biphenyl-2-ylboronic acid |
| 42. | Target-64 | 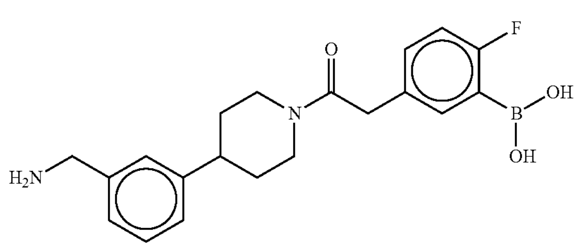 | 5-(2-(4-(3-(aminomethyl)phenyl)piperidin-1-yl)-2-oxoethyl)-2-fluorophenylboronic acid |

TABLE 4-continued

EXAMPLES INDEX

| Sr. No. | Cmpd. Code | Structure | Compound Name |
|---|---|---|---|
| 43. | Target-35 | 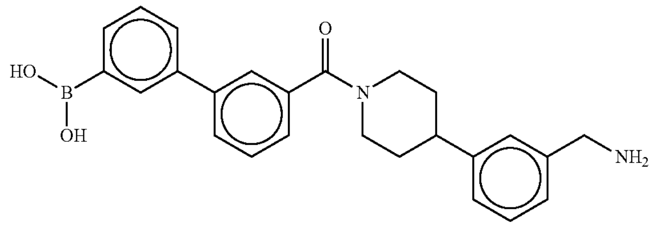 | 3'-(4-(3-(aminomethyl) phenyl)piperidine-1-carbonyl)biphenyl-3-ylboronic acid |
| 44. | Target-11F | 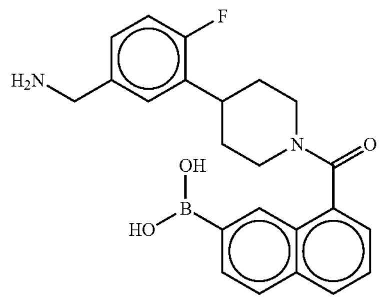 | 8-(4-(5-(aminomethyl)-2-fluorophenyl) piperidine-1-carbonyl)naphthalen-2-ylboronic acid |
| 45. | Target-58 | 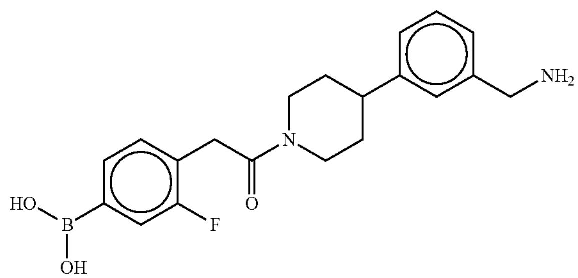 | 4-(2-(4-(3-(aminomethyl) phenyl)piperidin-1-yl)-2-oxoethyl)-3-fluorophenylboronic acid |
| 46. | Target-57 | 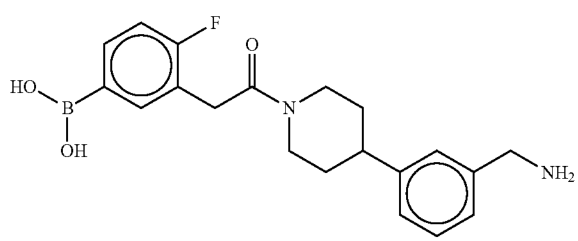 | 3-(2-(4-(3-(aminomethyl) phenyl)piperidin-1-yl)-2-oxoethyl)-4-fluorophenylboronic acid |
| 47. | Target-35F | 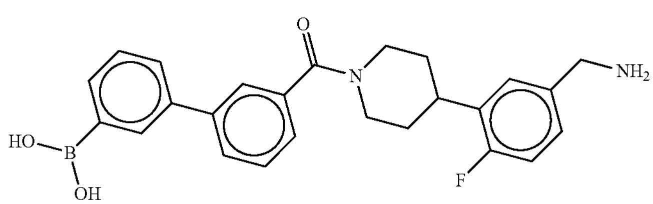 | 3'-(4-(5-(aminomethyl)-2-fluorophenyl) piperidine-1-carbonyl)biphenyl-3-ylboronic acid |
| 48. | Target-33 | 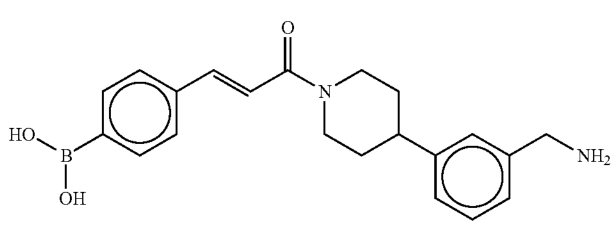 | (E)-4-(3-(4-(3-(aminomethyl) phenyl)piperidin-1-yl)-3-oxoprop-1-enyl)phenylboronic acid |

TABLE 4-continued

EXAMPLES INDEX

| Sr. No. | Cmpd. Code | Structure | Compound Name |
|---|---|---|---|
| 49. | Target-34 | 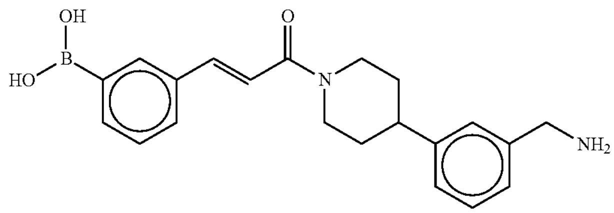 | (E)-3-(3-(4-(3-(aminomethyl)phenyl) piperidin-1-yl)-3-oxoprop-1-enyl)phenylboronic acid |
| 50. | Target-37 | 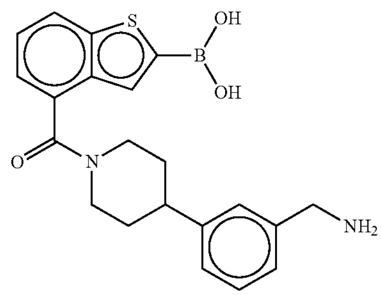 | 4-(4-(3-(aminomethyl)phenyl) piperidine-1-carbonyl) benzo[b]thiophen-2-ylboronic acid |
| 51. | Target-31 | 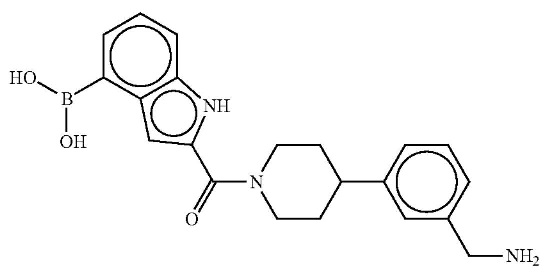 | 2-(4-(3-(aminomethyl) phenyl)piperidine-1-carbonyl)-1H-indol-4-ylboronic acid |
| 52. | Target-62 | 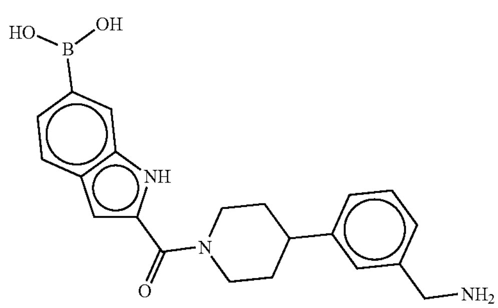 | 2-(4-(3-(aminomethyl) phenyl)piperidine-1-carbonyl)-1H-indol-6-ylboronic acid |
| 53. | Target-64 | 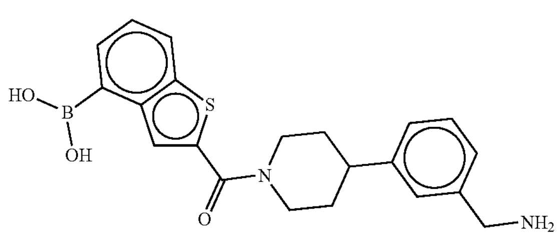 | 2-(4-(3-(aminomethyl) phenyl)piperidine-1-carbonyl)benzo[b] thiophen-4-ylboronic acid |

TABLE 4-continued

EXAMPLES INDEX

| Sr. No. | Cmpd. Code | Structure | Compound Name |
|---|---|---|---|
| | | Tryptase targets Method-B | |
| 54. | Target-32 | 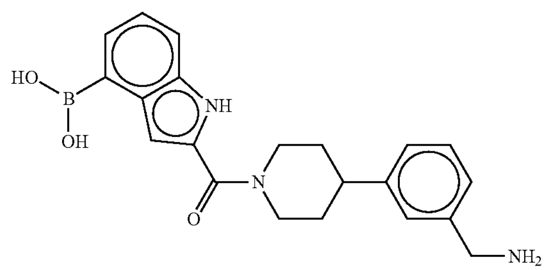 | 2-(4-(3-(aminomethyl) phenyl)piperidine-1-carbonyl)-1H-indol-4-ylboronic acid |
| 55. | Target-59 | 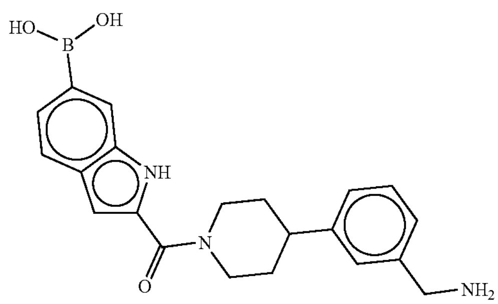 | 2-(4-(3-(aminomethyl) phenyl)piperidine-1-carbonyl)-1H-indol-6-ylboronic acid |
| 56. | Target-56 | 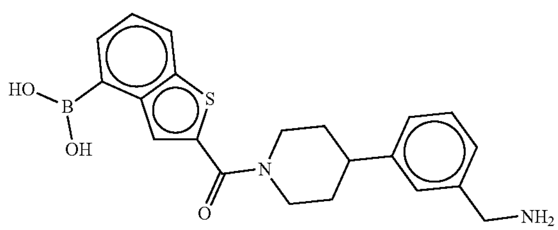 | 2-(4-(3-(aminomethyl) phenyl)piperidine-1-carbonyl)benzo[b]thiophen-4-ylboronic acid |
| | | Tryptase targets Method-C | |
| 57. | Target-28 | 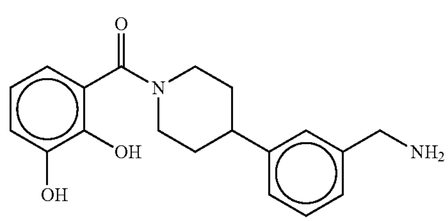 | (4-(3-(aminomethyl) phenyl)piperidin-1-yl)(2,3-dihydroxyphenyl)methanone |
| 58. | Target-27-F | 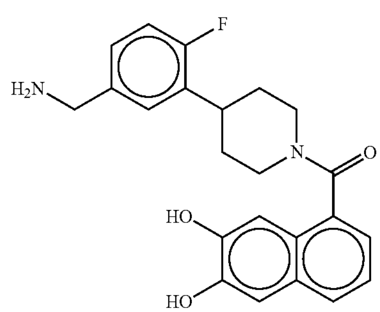 | (4-(5-(aminomethyl)-2-fluorophenyl)piperidin-1-yl)(6,7-dihydroxynaphthalen-1-yl)methanone |

TABLE 4-continued

EXAMPLES INDEX

| Sr. No. | Cmpd. Code | Structure | Compound Name |
|---|---|---|---|
| 59. | Target-68 | 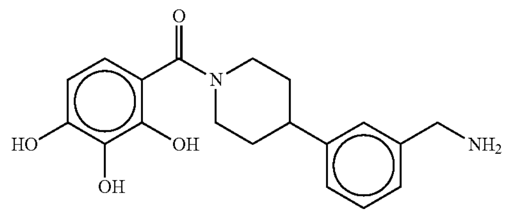 | (4-(3-(aminomethyl)phenyl)piperidin-1-yl)(2,3,4-trihydroxyphenyl)methanone |
| 60. | Target-69 | 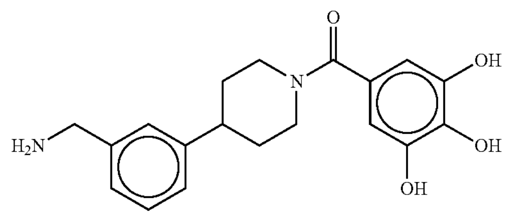 | (4-(3-(aminomethyl)phenyl)piperidin-1-yl)(3,4,5-trihydroxyphenyl)methanone |
| 61. | Target-77 | 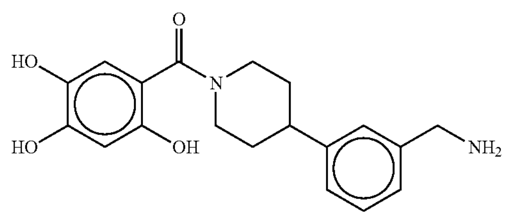 | (4-(3-(aminomethyl)phenyl)piperidin-1-yl)(2,4,5-trihydroxyphenyl)methanone |
| 62. | Target-78 | 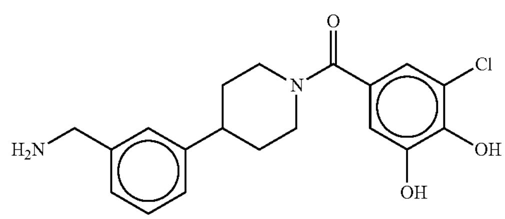 | (4-(3-(aminomethyl)phenyl)piperidin-1-yl)(3-chloro-4,5-dihydroxyphenyl)methanone |
| 63. | Target-43 | 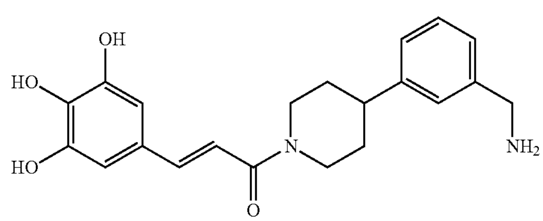 [SMILES: NCc1cccc(C2CCN(C(=O)/C=C/c3cc(O)c(O)c(O)c3)CC2)c1] | (E)-1-(4-(3-(aminomethyl)phenyl)piperidin-1-yl)-3-(3,4,5-trihydroxyphenyl)prop-2-en-1-one |
| 64. | Target-70 | 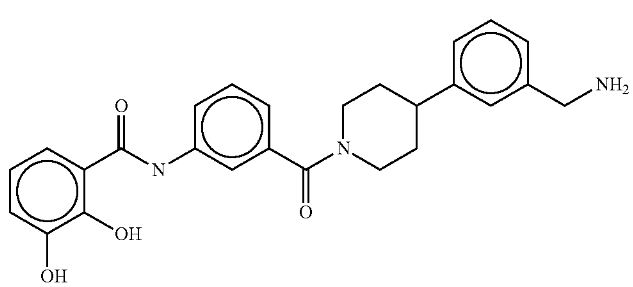 | N-(3-(4-(3-(aminomethyl)phenyl)piperidine-1-carbonyl)phenyl)-2,3-dihydroxybenzamide |

TABLE 4-continued

EXAMPLES INDEX

| Sr. No. | Cmpd. Code | Structure | Compound Name |
|---|---|---|---|
| 65. | Target-71 | 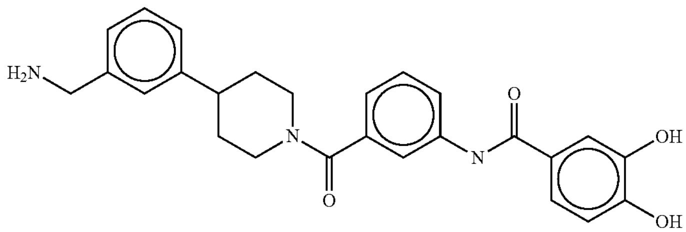 | N-(3-(4-(3-(aminomethyl) phenyl)piperidine-1-carbonyl)phenyl)-3,4-dihydroxybenzamide |
| 66. | Target-97 | 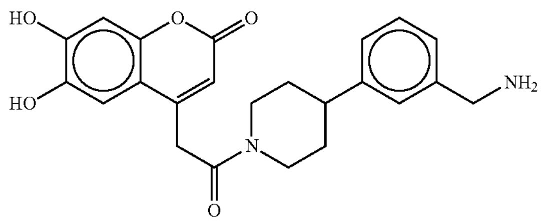 | 4-(2-(4-(3-(aminomethyl) phenyl)piperidin-1-yl)-2-oxoethyl)-6,7-dihydroxy-2H-chromen-2-one |
| 67. | Target-100 | 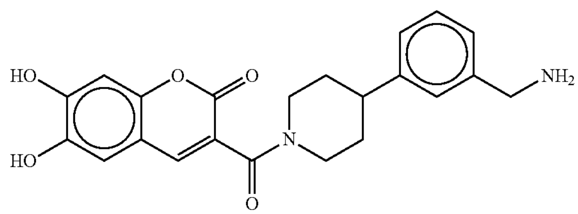 | 3-(4-(3-(aminomethyl) phenyl)piperidine-1-carbonyl)-6,7-dihydroxy-2H-chromen-2-one |
| 68. | Target-102 | 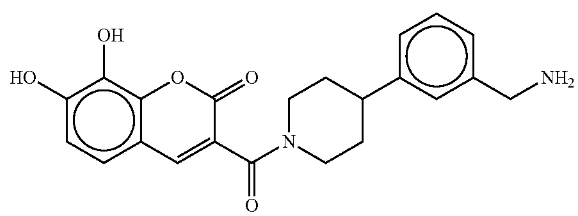 | 3-(4-(3-(aminomethyl) phenyl)piperidine-1-carbonyl)-7,8-dihydroxy-2H-chromen-2-one |

Tryptase targets Method-D

| 69. | Target-101 | | 3-(2-(4-(3-(aminomethyl) phenyl)piperidin-1-yl)-2-oxoethyl)-7,8-dihydroxy-4-methyl-2H-chromen-2-one |

Tryptase targets Method-E

| 70. | Target-74 | | (4-(3-(aminomethyl) phenyl)piperidin-1-yl)(3-hydroxy-4-(hydroxymethyl) phenyl)methanone |

TABLE 4-continued

EXAMPLES INDEX

| Sr. No. | Cmpd. Code | Structure | Compound Name |
|---|---|---|---|
| 71. | Target-65 | 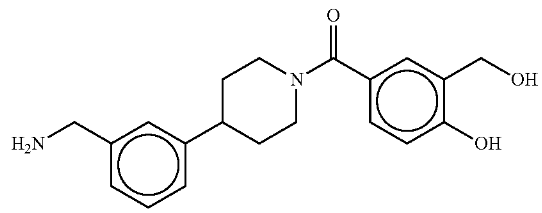 | (4-(3-(aminomethyl) phenyl)piperidin-1-yl)(4-hydroxy-3-(hydroxymethyl) phenyl)methanone |
| 72. | Target-40 | 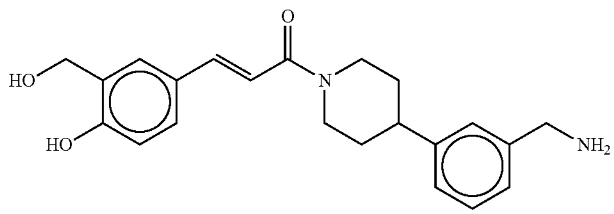 | (E)-1-(4-(3-(aminomethyl) phenyl)piperidin-1-yl)-3-(4-hydroxy-3-(hydroxymethyl) phenyl)prop-2-en-1-one |
| 73. | Target-44 | 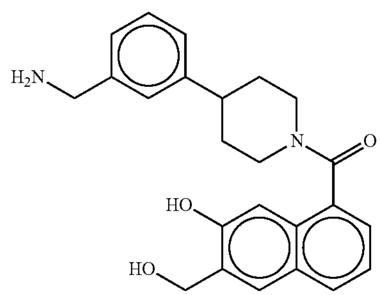 | (4-(3-(aminomethyl) phenyl)piperidin-1-yl)(7-hydroxy-6-(hydroxymethyl) naphthalen-1-yl)methanone |

Tryptase targets Method-F

| Sr. No. | Cmpd. Code | Structure | Compound Name |
|---|---|---|---|
| 74. | Target-75 | | 4-(4-(3-(aminomethyl) phenyl)piperidine-1-carbonyl)-2-hydroxybenzamide |
| 75. | Target-75a | | 4-(4-(3-(aminomethyl) phenyl)piperidine-1-carbonyl)-2-hydroxy-N-methoxybenzamide |
| 76. | Target-66 | | 5-(4-(3-(aminomethyl) phenyl)piperidine-1-carbonyl)-2-hydroxybenzamide |

TABLE 4-continued

EXAMPLES INDEX

| Sr. No. | Cmpd. Code | Structure | Compound Name |
|---|---|---|---|
| 77. | Target-86 | 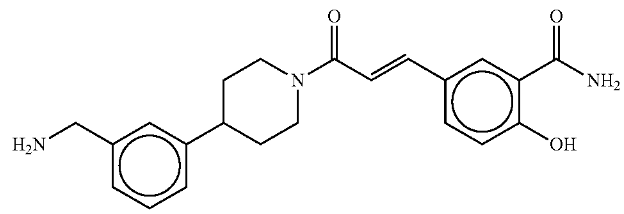 | (E)-5-(3-(4-(3-(aminomethyl) phenyl)piperidin-1-yl)-3-oxoprop-1-enyl)-2-hydroxybenzamide |
| 78. | Target-92 | 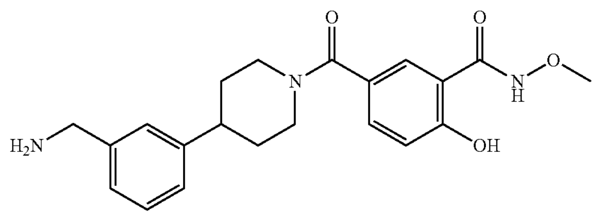 [SMILES: CONC(=O)c1cc(C(=O)N2CCC(c3cccc(CN)c3)CC2)ccc1O] | 5-(4-(3-(aminomethyl) phenyl)piperidine-1-carbonyl)-2-hydroxy-N-methoxybenzamide |
| Tryptase targets Method-H | | | |
| 79. | Target-72 | 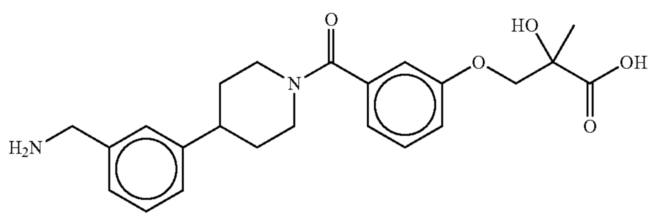 | 3-(3-(4-(3-(aminomethyl) phenyl)piperidine-1-carbonyl)phenoxy)-2-hydroxy-2-methylpropanoic acid |
| 80. | Target-73 | 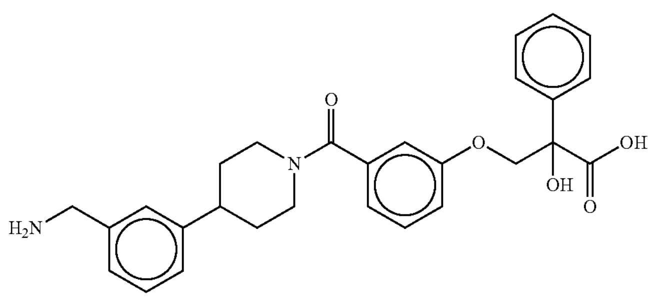 | 3-(3-(4-(3-(aminomethyl) phenyl)piperidine-1-carbonyl)phenoxy)-2-hydroxy-2-phenylpropanoic acid |
| 81. | Target-76 | 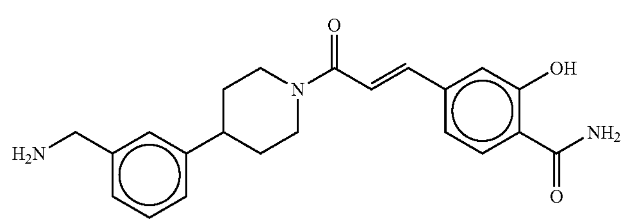 | (E)-4-(3-(4-(3-(aminomethyl) phenyl)piperidin-1-yl)-3-oxoprop-1-enyl)-2-hydroxybenzamide |
| 82. | Target-76a | 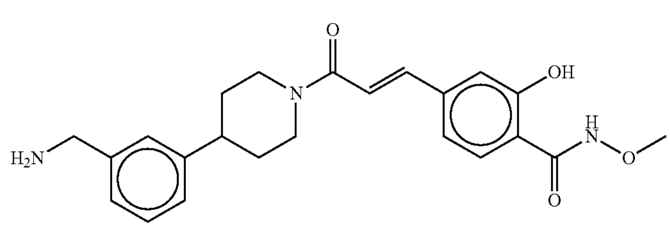 | (E)-4-(3-(4-(3-(aminomethyl) phenyl)piperidin-1-yl)-3-oxoprop-1-enyl)-2-hydroxy-N-methoxybenzamide |

TABLE 4-continued

EXAMPLES INDEX

| Sr. No. | Cmpd. Code | Structure | Compound Name |
|---|---|---|---|
| 83. | Target-81 | 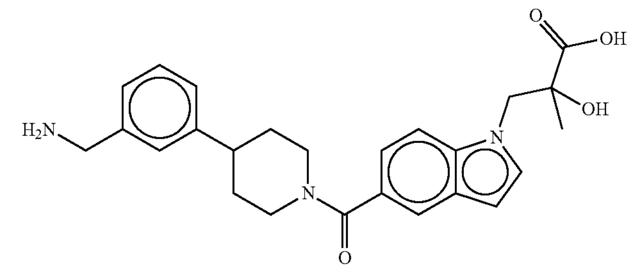 | 3-(5-(4-(3-(aminomethyl) phenyl)piperidine-1-carbonyl)-1H-indol-1-yl)-2-hydroxy-2-methylpropanoic acid |
| 84. | Target-82 | 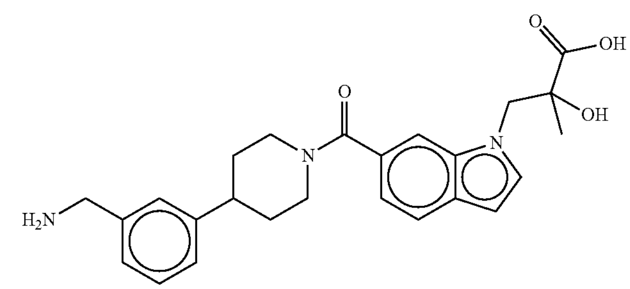 | 3-(6-(4-(3-(aminomethyl) phenyl)piperidine-1-carbonyl)-1H-indol-1-yl)-2-hydroxy-2-methylpropanoic acid |
| 85. | Target-83 | 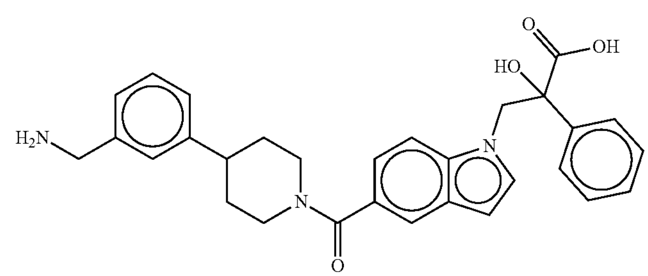 | 3-(5-(4-(3-(aminomethyl) phenyl)piperidine-1-carbonyl)-1H-indol-1-yl)-2-hydroxy-2-phenylpropanoic acid |
| 86. | Target-84 | 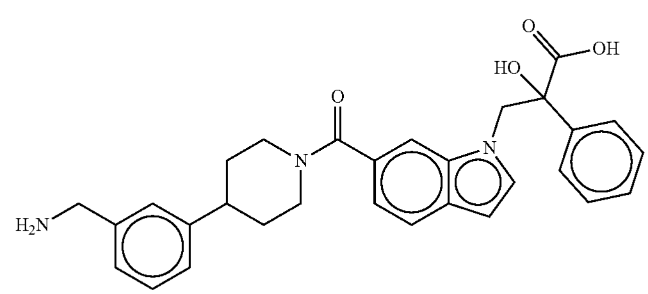 | 3-(6-(4-(3-(aminomethyl) phenyl)piperidine-1-carbonyl)-1H-indol-1-yl)-2-hydroxy-2-phenylpropanoic acid |
| 87. | Target-103 | 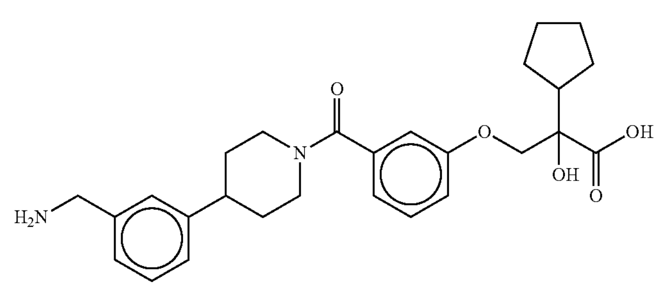 | 3-(3-(4-(3-(aminomethyl) phenyl)piperidine-1-carbonyl)phenoxy)-2-cyclopentyl-2-hydroxypropanoic acid |

TABLE 4-continued

EXAMPLES INDEX

| Sr. No. | Cmpd. Code | Structure | Compound Name |
|---|---|---|---|
| | | Tryptase targets Method-I | |
| 88. | Target-53 | 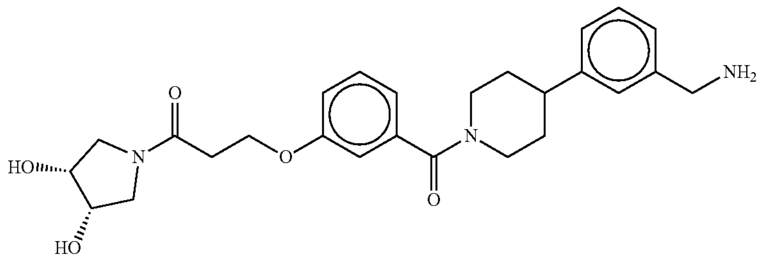 | 3-(3-(4-(3-(aminomethyl) phenyl)piperidine-1-carbonyl)phenoxy)-1-((3S,4R)-3,4-dihydroxypyrrolidin-1-yl)propan-1-one |
| 89. | Target-29 | 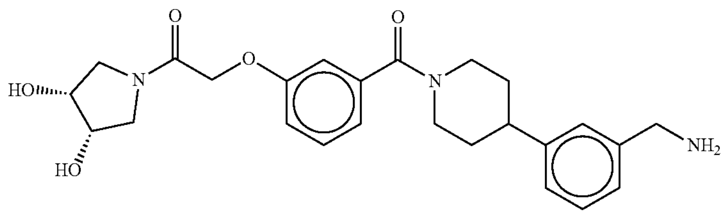 | 2-(3-(4-(3-(aminomethyl) phenyl)piperidine-1-carbonyl)phenoxy)-1-((3S,4R)-3,4-dihydroxypyrrolidin-1-yl)ethanone |
| 90. | Target-30 | 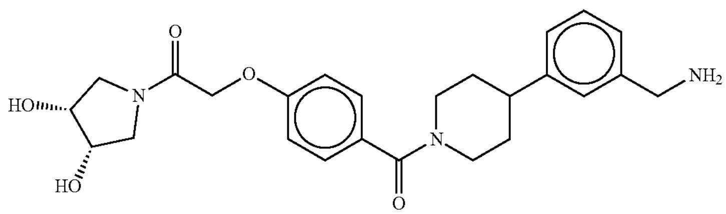 | 2-(4-(4-(3-(aminomethyl) phenyl)piperidine-1-carbonyl)phenoxy)-1-((3S,4R)-3,4-dihydroxypyrrolidin-1-yl)ethanone |
| | | Tryptase targets Method-J | |
| 91. | Target-35-Spiro | 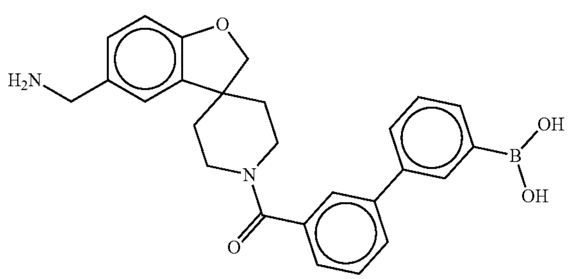 | 3'-(5-(aminomethyl)-2H-spiro[benzofuran-3,4'-piperidine]-1'-ylcarbonyl) biphenyl-3-ylboronic acid |
| 92. | Target-78-Spiro | 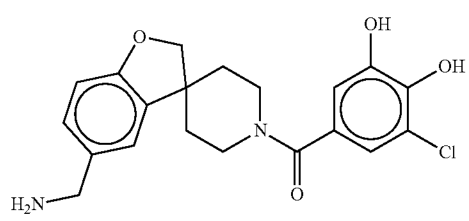 | (5-(aminomethyl)-2H-spiro[benzofuran-3,4'-piperidine]-1'-yl)(3-chloro-4,5-dihydroxyphenyl) methanone |
| 93. | Target-2 Spiro | 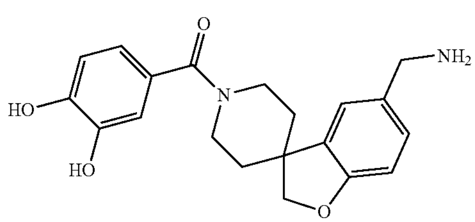 [SMILES: NCc1ccc2c(c1)C1(CCN(C(=O)c3ccc(O)c(O)c3)CC1)CO2] | (5-(aminomethyl)-2H-spiro[benzofuran-3,4'-piperidine]-1'-yl)(3,4-dihydroxyphenyl) methanone |

TABLE 4-continued

EXAMPLES INDEX

| Sr. No. | Cmpd. Code | Structure | Compound Name |
|---|---|---|---|
| 94. | Target-35-Spiro amidine | 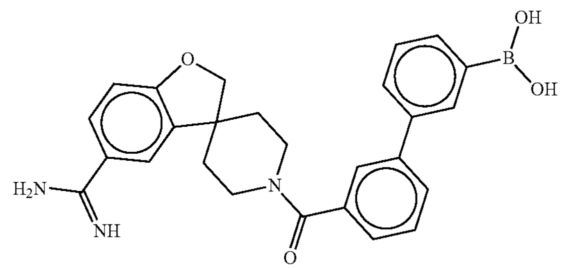 | 3'-(5-carbamimidoyl-2H-spiro[benzofuran-3,4'-piperidine]-1'-ylcarbonyl)biphenyl-3-ylboronic acid |
| 95. | T-33 spiro amidine | 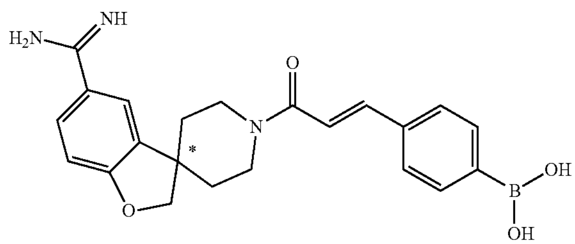 [SMILES: N=C(N)c1ccc2c(c1)C1(CCN(C(=O)/C=C/c3ccc(B(O)O)cc3)CC1)CO2] | (E)-4-(3-(5-carbamimidoyl-2H-spiro[benzofuran-3,4'-piperidine]-1'-yl)-3-oxoprop-1-enyl)phenylboronic acid |

Tryptase targets-Method-K

| 96. | Target-36 | | (4-(3-(aminomethyl)phenyl)piperidin-1-yl)(4-(1-hydroxy-1,3-dihydrobenzo[c][1,2]oxaborol-5-yl)phenyl)methanone |
| 97. | Target-36-meta | | (4-(3-(aminomethyl)phenyl)piperidin-1-yl)(3-(1-hydroxy-1,3-dihydrobenzo[c][1,2]oxaborol-5-yl)phenyl)methanone |

Tryptase targets

| 98. | Target-21 | | N-(3-(4-(3-(aminomethyl)phenyl)piperidine-1-carbonyl)phenyl)-2-(1-hydroxycyclobutyl)-2-oxoacetamide |

TABLE 4-continued

EXAMPLES INDEX

| Sr. No. | Cmpd. Code | Structure | Compound Name |
|---|---|---|---|
| 99. | Target-21-diol | 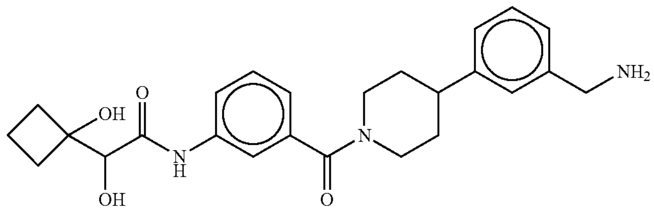 | N-(3-(4-(3-(aminomethyl) phenyl)piperidine-1-carbonyl)phenyl)-2-hydroxy-2-(1-hydroxycyclobutyl) acetamide |
| 100. | Target-22 | 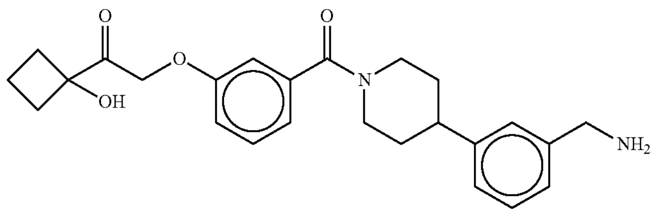 | 2-(3-(4-(3-(aminomethyl) phenyl)piperidine-1-carbonyl)phenoxy)-1-(1-hydroxycyclobutyl) ethanone |
| 101. | Target-42 | 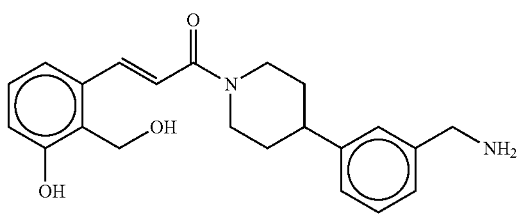 | (E)-1-(4-(3-(aminomethyl)phenyl) piperidin-1-yl)-3-(3-hydroxy-2-(hydroxymethyl)phenyl) prop-2-en-1-one |
| 102. | Target-55 | 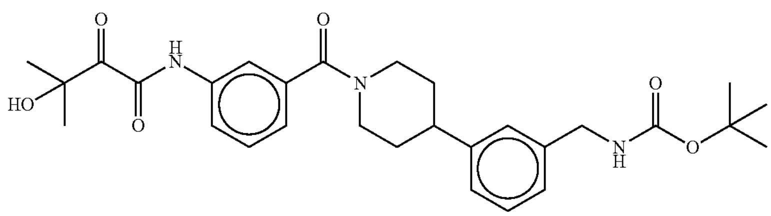 | tert-butyl 3-(1-(3-(3-hydroxy-3-methyl-2-oxobutanamido)benzoyl) piperidin-4-yl) benzylcarbamate |
| 103. | Target-55-diol | 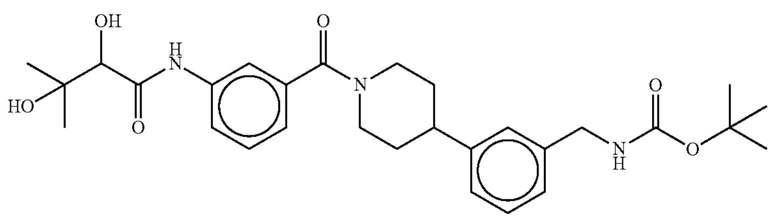 | tert-butyl 3-(1-(3-(2,3-dihydroxy-3-methylbutanamido) benzoyl)piperidin-4-yl)benzylcarbamate |
| 104. | Target-14 | 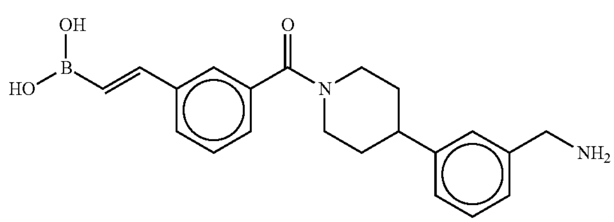 | (E)-3-(4-(3-(aminomethyl) phenyl)piperidine-1-carbonyl)styrylboronic acid |
| 105. | Target-24 cis | 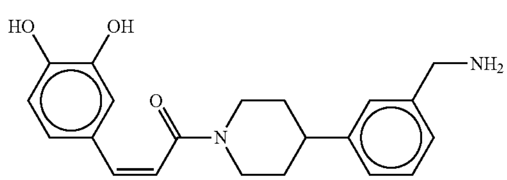 | (Z)-1-(4-(3-(aminomethyl)phenyl) piperidin-1-yl)-3-(3,4-dihydroxyphenyl) prop-2-en-1-one |

TABLE 4-continued

EXAMPLES INDEX

| Sr. No. | Cmpd. Code | Structure | Compound Name |
|---|---|---|---|
| 106. | Target-25b | 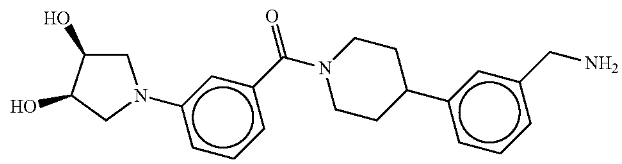 | (4-(3-(aminomethyl)phenyl)piperidin-1-yl)(3-((3S,4R)-3,4-dihydroxypyrrolidin-1-yl)phenyl)methanone |
| 107. | Target-26 diol cis | 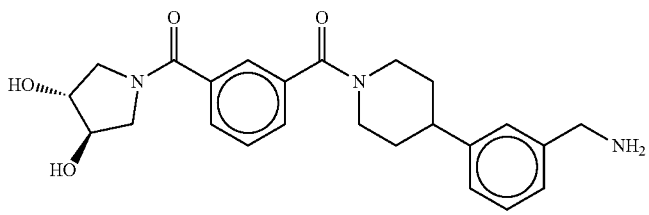 | (4-(3-(aminomethyl)phenyl)piperidin-1-yl)(3-((3R,4R)-3,4-dihydroxypyrrolidine-1-carbonyl)phenyl)methanone |
| 108. | Target-41 | 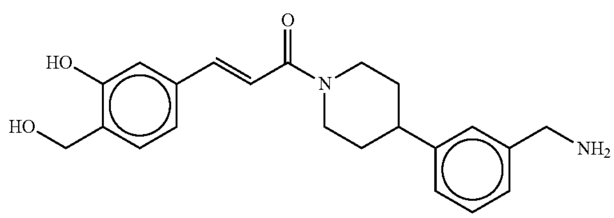 | (E)-1-(4-(3-(aminomethyl)phenyl)piperidin-1-yl)-3-(3-hydroxy-4-(hydroxymethyl)phenyl)prop-2-en-1-one |
| 109. | Target-67 | 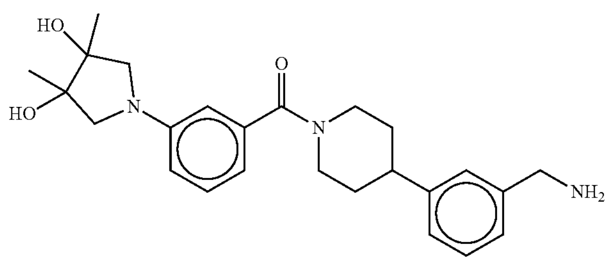 | (4-(3-(aminomethyl)phenyl)piperidin-1-yl)(3-(3,4-dihydroxy-3,4-dimethylpyrrolidin-1-yl)phenyl)methanone |
| 110. | Target-41 gem dimethyl | 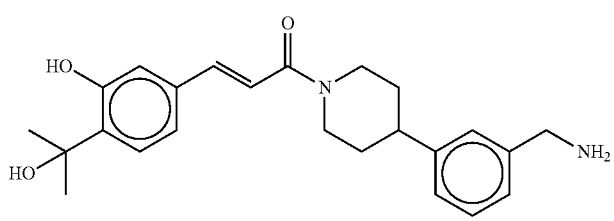 | (E)-1-(4-(3-(aminomethyl)phenyl)piperidin-1-yl)-3-(3-hydroxy-4-(2-hydroxypropan-2-yl)phenyl)prop-2-en-1-one |
| 111. | CF1 | 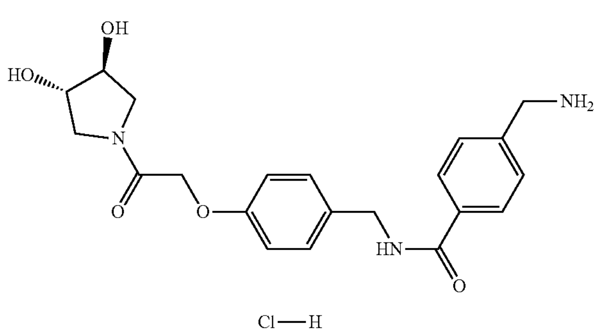 [SMILES: NCc1ccc(C(=O)NCc2ccc(OCC(=O)N3C[C@H](O)[C@@H](O)C3)cc2)cc1 ; Cl] | 4-(aminomethyl)-N-(4-(2-((3S,4S)-3,4-dihydroxypyrrolidin-1-yl)-2-oxoethoxy)benzyl)benzamide hydrochloride |

TABLE 4-continued

EXAMPLES INDEX

| Sr. No. | Cmpd. Code | Structure | Compound Name |
|---|---|---|---|
| 112. | CF2 | 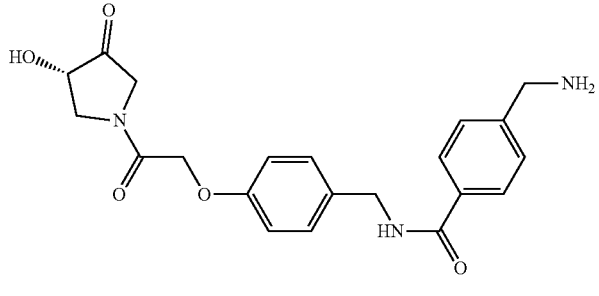 | (S)-4-(aminomethyl)-N-(4-(2-(3-hydroxy-4-oxopyrrolidin-1-yl)-2-oxoethyl)benzyl)benzamide hydrochloride |
| 113. | CF4 | 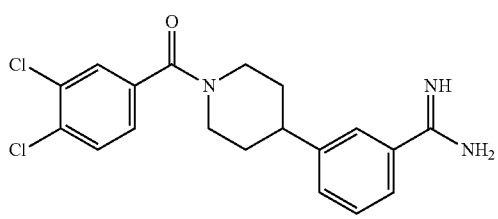 | 3-(1-(3,4-dichlorobenzoyl)piperidin-4-yl)benzimidamide hydrochloride |
| 114. | CF5 | 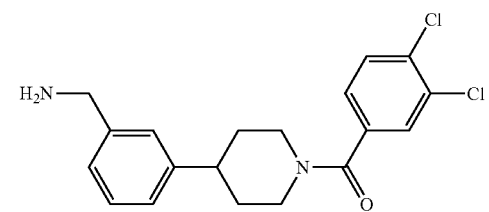 [SMILES: NCc1cccc(C2CCN(C(=O)c3ccc(Cl)c(Cl)c3)CC2)c1] | (4-(3-(aminomethyl)phenyl)piperidin-1-yl)(3,4-dichlorophenyl)methanone |
| 115. | CF6 | 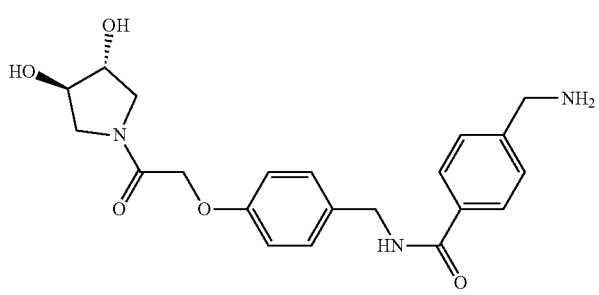 | 4-(aminomethyl)-N-(4-(2-((3R,4R)-3,4-dihydroxypyrrolidin-1-yl)-2-oxoethoxy)benzyl)benzamide hydrochloride |
| 116. | CF7 | 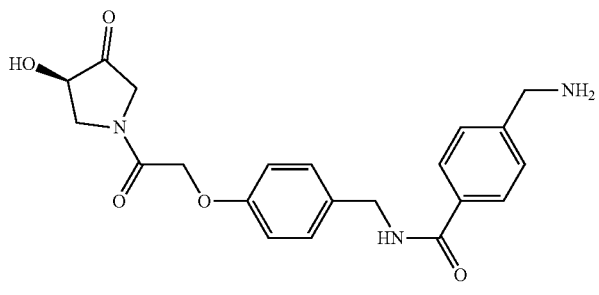 | (R)-4-(aminomethyl)-N-(4-(2-(3-hydroxy-4-oxopyrrolidin-1-yl)-2-oxoethoxy)benzyl)benzamide hydrochloride |

TABLE 4-continued

EXAMPLES INDEX

| Sr. No. | Cmpd. Code | Structure | Compound Name |
|---|---|---|---|
| 117. | CF10 | 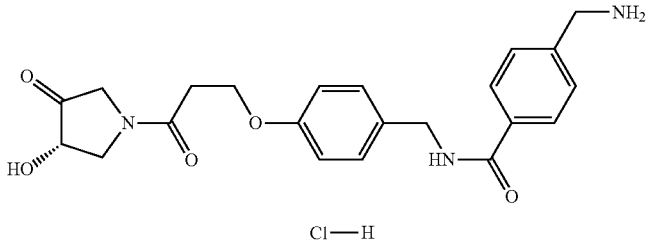 [SMILES: NCc1ccc(C(=O)NCc2ccc(OCCC(=O)N3CC(=O)[C@@H](O)C3)cc2)cc1 ; Cl] | (S)-4-(aminomethyl)-N-(4-(3-(3-hydroxy-4-oxopyrrolidin-1-yl)-3-oxopropoxy)benzyl)benzamide hydrochloride |
| 118. | CF12 | 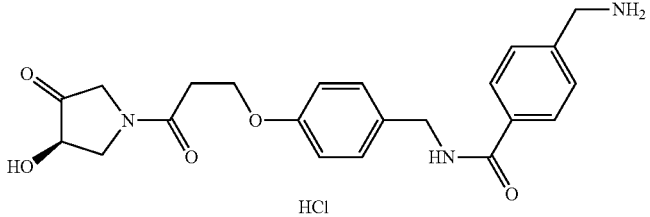 [SMILES: NCc1ccc(C(=O)NCc2ccc(OCCC(=O)N3CC(=O)[C@H](O)C3)cc2)cc1 ; Cl] | (R)-4-(aminomethyl)-N-(4-(3-(3-hydroxy-4-oxopyrrolidin-1-yl)-3-oxopropoxy)benzyl)benzamide hydrochloride |
| 119. | CF13 | 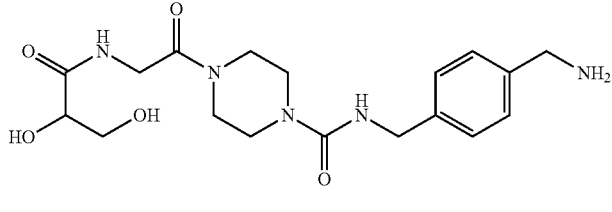 | N-(4-(aminomethyl)benzyl)-4-(2-(2,3-dihydroxypropanamido)acetyl)piperazine-1-carboxamide hydrochloride |
| 120. | CF15 | 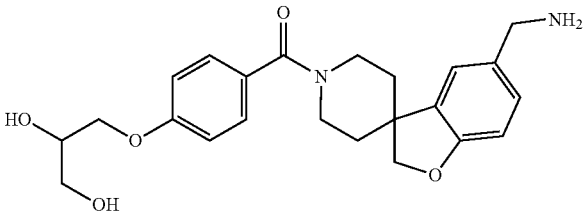 | (5-(aminomethyl)-2H-spiro[benzofuran-3,4'-piperidine]-1'-yl)(4-(2,3-dihydroxypropoxy)phenyl)methanone hydrochloride |
| 121. | CF17 | 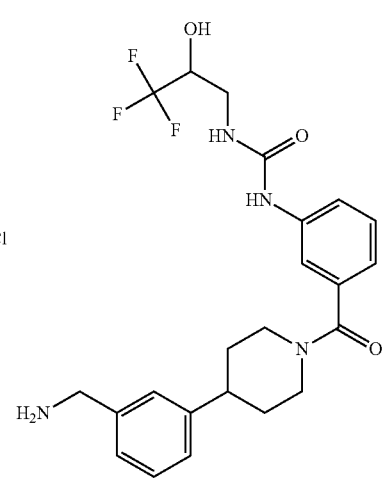 | 1-(3-(4-(3-(aminomethyl)phenyl)piperidine-1-carbonyl)phenyl)-3-(3,3,3-trifluoro-2-hydroxypropyl)urea hydrochloride |

TABLE 4-continued

EXAMPLES INDEX

| Sr. No. | Cmpd. Code | Structure | Compound Name |
|---|---|---|---|
| 122. | CF20 | 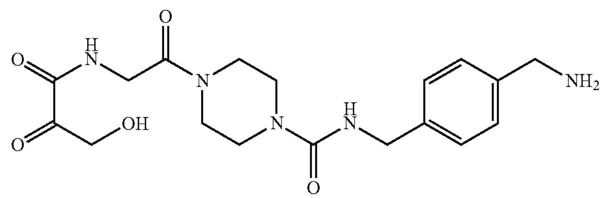 [SMILES: NCc1ccc(CNC(=O)N2CCN(C(=O)CNC(=O)C(=O)CO)CC2)cc1] | N-(4-(aminomethyl)benzyl)-4-(2-(3-hydroxy-2-oxopropanamido)acetyl)piperazine-1-carboxamide |

Example 1—Evaluation of Inhibition of Tryptase Activity by Monomers and Multimers Stock solutions of recominbant human tryptase, beta, from lung (Promega: catalog number G5631, or Enzo Life Sciences: catalog number BML-SE418) were made at 30 µM, in solution with 5 µM heparin sulfate and 1 M NaCl. Monomer tryptase inhibitor stock solutions were made at 50 mM in DMSO. Test substance plates were made at 1.2× the final concentration in assay buffer (50 mM HEPES, 150 mM NaCl, 100 µM EDTA, pH 7.4, 0.02% Tween-20). A final concentration of 1 nM tryptase was used. When required, test substances were diluted in water immediately before use in 10-fold serial dilutions. After the indicated incubation time, the test subtance-tryptase solution at 1.2× concentration, was diluted into assay buffer containing a final concentration of 200 µM N-tert-butoxycarbonyl-Gln-Ala-Arg-AMC HBr [AMC=7-amino-4-methylcoumarin] (Boc-Gln-Ala-Arg-AMC; Enzo Life Sciences: catalog number BML-P237) to a final volume of 50 µl in black opaque round bottom 96 well plates (Corning, catalog number 3792). The release of fluorescent AMC was immediately measured every 30 seconds over 15-30 minutes at an excitation wavelength of 367 nm, monitoring emission at 468 nm on a Spectramax M5 (Molecular Devices) microplate reader. The Softmax Pro (Molecular Devices) and Graphpad prism software were used to determine $V_{max}$, and concentration-response curve $IC_{50}$s, respectively. Combinations of monomeric test substancess were typically tested in a 1:1 ratio initially, and those displaying $IC_{50}$'s >4× lower than that of the most potent monomeric component were often retested with a range of ratios of manomeric concentrations.

Example 2—Evaluation of Inhibition of Ribosomal Protein Synthesis by Multimers Monomers with the potential to form heterodimers were evaluated in an in vitro Transcription and Translation assay (TnT assay) using the commercially available E. coli S30 Extract System for Circular DNA kit (Promega Catalog #L1020) according to the manufacturers instructions with minor modifications. Monomers were tested independently to determine individual $IC_{50}$ values. Pairs of monomers with the potential to form heterodimers were assayed at concentrations that ranged about their individual IC25 values. Each reaction uses 2 µl (250 ng/µl) of the pBESTluc™ DNA based circular luciferase plasmid (Promega Catalog #L492A), with 4 µl of complete amino acid mix (Promega Catalog #L4461), 13 µl of S30 Premix Without Amino Acids (Promega Catalog #L512A), 5 µl of S30 Extract (Promega Catalog #L464A), monomers at the appropriate concentration, and nuclease free water in a total volume of 35 µl. Assays were carried out in Costar 96 well white round bottom plates. Assay plates were setup with a master mix consisting of S30 extract and water, followed by the addition of compound, with the final addition of a master mix consisting of the plasmid, amino acid mix, and the S30 Premix. Plates were incubated at 37° C. for one hour followed by addition of 35 µl of the Bright-Glo Luciferase Reagent (Promega Catalog #E2620). After removal of 35 µl of the reaction mixture, the luminescence was recorded immediately in the Spectramax M5 plate reader (Molecular Devices). The data was plotted to generate dose-response curves using GraphPad Prism.

In Table 5 below, $IC_{50}$ ranges are provided for various exemplary monomers against tryptase. For the names of the monomers, the prefix "Target," as used elsewhere in the Examples, has been shortened to "T." For example, "Target-14" has been shortened to "T14." "A" refers to an $IC_{50}$ range of 0.1 nM to 1 µM, "B" refers to an $IC_{50}$ range of 1 µM to 10 µM, and "C" refers to an $IC_{50}$ range of 10 µM to 65 µM.

TABLE 5

MONOMER $IC_{50}$ VALUES

| Monomers | Monomer $IC_{50}$ range |
|---|---|
| T14 | A |
| T55 | A |
| T84 | A |
| T21 | A |
| T82 | A |
| T4 | A |
| T46 | A |
| T103 | A |
| CMI17 | A |
| T130 | A |
| CM121 | A |
| T25B | A |
| T74 | A |
| T55D | A |
| T81 | A |
| T102 | A |
| T67 | A |
| T75A | A |
| T14A | A |
| T22 | A |
| T21D | A |
| T70 | A |
| T56 | A |
| T3 | A |
| T56A | A |
| T36M | A |
| T76A | A |
| T78SPIRO | A |
| T31A | A |
| T27 | A |

TABLE 5-continued

MONOMER IC$_{50}$ VALUES

| Monomers | Monomer IC$_{50}$ range |
|---|---|
| T43 | A |
| T65 | A |
| CF17 | A |
| T41 | A |
| T71 | A |
| T78 | A |
| CF5 | A |
| T129A | A |
| T101 | A |
| T53 | A |
| T66 | A |
| T72 | A |
| T2 | A |
| T35F | A |
| T2SPIRO | A |
| T10 | A |
| T83 | A |
| T41CYCLO | A |
| T41GEM | A |
| T76 | A |
| T35AM | A |
| CF20 | A |
| T35 | A |
| T73 | A |
| T42 | B |
| T35SPIRO | B |
| CF14 | B |
| T24DI | B |
| T26DTRANS | B |
| T31 | B |
| T34 | B |
| T32 | B |
| T37 | B |
| T44i3 | B |
| CF12 | B |
| T1 | B |
| T69 | B |
| T86 | B |
| T24CIS | B |
| T24MON | B |
| T44 | B |
| T130A | B |
| T59 | B |
| T30 | B |
| T36 | B |
| T24 | B |
| T62 | B |
| T68 | B |
| T27F | B |
| T37A | B |
| T13A | B |
| CF15 | B |
| T26DCIS | B |
| T57 | B |
| T64 | B |
| T75 | B |
| T5 | B |
| T92 | B |
| T97 | B |
| T12 | B |
| T22D | B |
| T58 | B |
| T28 | B |
| T53B | B |
| T33AM | B |
| T54A | B |
| T33 | B |
| CF13 | B |
| T11F | B |
| CF7 | B |
| T10A | B |
| T29 | B |
| T40 | B |
| T12A | B |
| T27A | B |
| T11 | C |

TABLE 5-continued

MONOMER IC$_{50}$ VALUES

| Monomers | Monomer IC$_{50}$ range |
|---|---|
| CF10 | C |
| CF2 | C |
| T13 | C |
| CF1 | C |
| T100 | C |
| CF6 | C |
| T77 | C |
| T9 | C |

Additional Boronic Acid Monomers Belonging to Group A

T116SPIRO (1:10); T117; T131SPIRO; T56; T156; T35F; T10; T109SPIRO; T35SPAM; T35; T133SPIRO.

Additional Benzooxaborole Monomers Belonging to Group A

T117SPIRO; T117GEMMONO; T36M.

Additional Ligands Belonging to Group A

T75APSPIRO; T75AP (1:10); T84 (1:10); T82 (1:10); T103 (1:10); CMI9317 (1:10); T75ASPIRO 1:10; CMI9321 (1:10); T25b (1:10); T85 Å (1:10); T74 (1:10); T55D (1:10); T81 (1:10); T102 (1:10); T67; T75A; T114Spiro; T920 TB (1:10); T70; T21 (Diol); T3; T76A; T78SPIRO; T78SPIRO; T27; T113SPIRO; T43; T65; T41; T71; T78; T75AOTBSPIRO; T101; T53; T66; T142ENDOANTI; T72; T2; T141ENDOANTI; T2spiro; T92SPIRO; T83 (1:10); T74SPIRO; T41GEM; T76; T73; T136A; T104; T104SPIRO.

Additional Boronic Acid Monomers Belonging to Group B

T35SPIRO; T107; T147; T107SPIRO; T155SPIRO; T132SPIRO; T31; T34; T32; T37; T154; T143; T59; T62; T54BASPIRO; T57; T64; T12; T144; T58; T33SPAM; T33; T11F; T54BA.

Additional Benzooxaborole Monomers Belonging to Group B

T112SPIRO; T117METHYLSPIRO; T36.

Additional Ligands Belonging to Group B

T42; T126; T24Dihydro; T26diol trans; T920PH; T92PHSPIRO; T1; T86; T69; T24cis; T141EXOANTI; T44; T141EXOSYN; T139RACEENDO; T30; T24; T68; T27F; T99; T26diol cis; T75; T5; T92; T127; T97; T920TBSPIRO; T22_diol; T75AOTB; T28; T140RACEENDO; T40; T96.

Additional Boronic Acid Monomers Belonging to Group C

T11; T146; T13; T51.

Additional Ligands Belonging to Group C

T142EXOANTI; T142ENDOSYN; T98; T100; T77; T9; T8

In Table 6 below, $IC_{50}$ ratios are provided for various exemplary monomer pairs against tryptase. The $IC_{50}$ ratio is calculated by dividing the smallest monomer $IC_{50}$ value chosen from between monomer 1 and monomer 2 by the apparent $IC_{50}$ value for an essentially equimolar combination of monomer 1 and monomer 2. For the names of the monomers, the prefix "Target," as used elsewhere in the Examples, has been shortened to "T." For example, "Target-00" has been shortened to "T100." "AA" refers to an $IC_{50}$ ratio of 30 or greater, "BB" refers to an $IC_{50}$ ratio of 10-30, and "CC" refers to an $IC_{50}$ ratio of 3-10.

TABLE 6

$IC_{50}$ RANGES FOR 1:1 COMBINATIONS OF MONOMERS

| Monomer 1 | Monomer 2 | Ratio IC50 range |
|---|---|---|
| T100 | T11 | AA |
| T27F | T64 | AA |
| T28 | T33 | AA |
| T28 | T35SPIRO | AA |
| T2SPIRO | T35SPAM | AA |
| T2SPIRO | T35SPIRO | AA |
| T42 | T10 | AA |
| T68 | T35SPAM | AA |
| T69 | T35SPAM | AA |
| T69 | T35SPIRO | AA |
| T78 | T35 | AA |
| T78 | T35F | AA |
| T78 | T35SPAM | AA |
| T78 | T35SPIRO | AA |
| T78SPIRO | T35 | AA |
| T78SPIRO | T35F | AA |
| T78SPIRO | T35SPAM | AA |
| T78SPIRO | T35SPIRO | AA |
| T92 | T10 | AA |
| T92 | T11 | AA |
| T92 | T11F | AA |
| T92 | T35 | AA |
| T92 | T35SPAM | AA |
| T92 | T35SPIRO | AA |
| T100 | T11F | BB |
| T100 | T13 | BB |
| T100 | T33 | BB |
| T100 | T37 | BB |
| T100 | T64 | BB |
| T2 | T35 | BB |
| T2 | T35F | BB |
| T2 | T35SPAM | BB |
| T2 | T35SPIRO | BB |
| T24 | T11F | BB |
| T25diol cis | T33 | BB |
| T27F | T11 | BB |
| T27F | T12 | BB |
| T27F | T13 | BB |
| T27F | T32 | BB |
| T27F | T34 | BB |
| T27F | T35 | BB |
| T27F | T35F | BB |
| T27F | T35SPAM | BB |
| T27F | T35SPIRO | BB |
| T27F | T37 | BB |
| T27F | T57 | BB |
| T27F | T58 | BB |
| T28 | T35 | BB |
| T28 | T35F | BB |
| T28 | T35SPAM | BB |
| T2spiro | T35 | BB |
| T2spiro | T35F | BB |
| T40 | T11F | BB |
| T42 | T11F | BB |
| T42 | T35SPIRO | BB |
| T42 | T37 | BB |
| T68 | T33 | BB |
| T68 | T35 | BB |
| T68 | T35F | BB |
| T68 | T35SPIRO | BB |
| T68 | T58 | BB |
| T69 | T35 | BB |
| T69 | T35F | BB |
| T74 | T35SPAM | BB |
| T92 | T35F | BB |
| T92 | T37 | BB |
| T97 | T10 | BB |
| T97 | T11 | BB |
| T97 | T11F | BB |
| T97 | T33 | BB |
| T97 | T37 | BB |
| T97 | T58 | BB |
| T97 | T64 | BB |
| T1 | T11F | CC |
| T1 | T35SPIRO | CC |
| T1 | T37 | CC |
| T1 | T64 | CC |
| T100 | 110 | CC |
| T100 | T12 | CC |
| T100 | T32 | CC |
| T100 | T35SPAM | CC |
| T100 | T56 | CC |
| T100 | T58 | CC |
| T100 | T59 | CC |
| T101 | T56 | CC |
| T2 | T11F | CC |
| T21 (Diol) | T56 | CC |
| T22_diol | T33SPAM | CC |
| T22_diol | T57 | CC |
| T22_diol | T58 | CC |
| T22_diol | T64 | CC |
| T24 | T11 | CC |
| T24 | T32 | CC |
| T24 | T33 | CC |
| T24 | T34 | CC |
| T24 | T35 | CC |
| T24 | T35SPAM | CC |
| T24 | T35SPIRO | CC |
| T24 | T37 | CC |
| T24 | T57 | CC |
| T24 | T58 | CC |
| T24 | T59 | CC |
| T24 | T64 | CC |
| T24cis | T11 | CC |
| T24cis | T12 | CC |
| T24cis | T13 | CC |
| T24cis | T32 | CC |
| T24cis | T37 | CC |
| T24cis | T56 | CC |
| T24cis | T57 | CC |
| T24cis | T58 | CC |
| T24cis | T59 | CC |
| T24Dihydro | T32 | CC |
| T24Dihydro | T35SPAM | CC |
| T24Dihydro | T37 | CC |
| T24Dihydro | T58 | CC |
| T24Dihydro | T59 | CC |
| T25B | T36 | CC |
| T26diol cis | T11F | CC |
| T26diol cis | T32 | CC |
| T26diol cis | T64 | CC |
| T26diol trans | T36 | CC |
| T27 | T34 | CC |
| T27 | T35 | CC |
| T27 | T35F | CC |
| T27 | T35SPAM | CC |
| T27 | T64 | CC |
| T27F | T10 | CC |
| T27F | T11F | CC |
| T27F | T31 | CC |
| T27F | T33SPAM | CC |
| T27F | T36 | CC |
| T27F | T59 | CC |
| T27F | T62 | CC |
| T28 | T11 | CC |

TABLE 6-continued

IC$_{50}$ RANGES FOR 1:1 COMBINATIONS OF MONOMERS

| Monomer 1 | Monomer 2 | Ratio IC50 range |
|---|---|---|
| T28 | T11F | CC |
| T28 | T31 | CC |
| T28 | T33SPAM | CC |
| T28 | T34 | CC |
| T28 | T36 | CC |
| T28 | T58 | CC |
| T28 | T59 | CC |
| T29 | T11F | CC |
| T30 | T59 | CC |
| T40 | T33SPAM | CC |
| T40 | T35SPAM | CC |
| T40 | T58 | CC |
| T42 | T32 | CC |
| T42 | T34 | CC |
| T42 | T35 | CC |
| T42 | T35F | CC |
| T42 | T35SPAM | CC |
| T42 | T58 | CC |
| T42 | T59 | CC |
| T43 | T32 | CC |
| T43 | T34 | CC |
| T43 | T36 | CC |
| T43 | T37 | CC |
| T43 | T56 | CC |
| T44 | T12 | CC |
| T44 | T64 | CC |
| T5 | T32 | CC |
| T5 | T64 | CC |
| T65 | T35F | CC |
| T65 | T35SPAM | CC |
| T65 | T35SPIRO | CC |
| T68 | T11 | CC |
| T68 | T11F | CC |
| T68 | T33SPAM | CC |
| T68 | T34 | CC |
| T68 | T36 | CC |
| T68 | T37 | CC |
| T68 | T57 | CC |
| T68 | T59 | CC |
| T69 | T11F | CC |
| T69 | T37 | CC |
| T69 | T58 | CC |
| T69 | T64 | CC |
| T71 | T32 | CC |
| T73 | T32 | CC |
| T75 | T34 | CC |
| T75 | T35F | CC |
| T75 | T58 | CC |
| T75 | T59 | CC |
| T75A | T35 | CC |
| T75A | T35F | CC |
| T75A | T35SPAM | CC |
| T75A | T35SPIRO | CC |
| T76 | T10 | CC |
| T76 | T31 | CC |
| T76 | T35SPAM | CC |
| T76 | T59 | CC |
| T77 | T11 | CC |
| T77 | T13 | CC |
| T77 | T35F | CC |
| T77 | T35SPIRO | CC |
| T78 | T34 | CC |
| T78 | T37 | CC |
| T86 | T35SPIRO | CC |
| T92 | T12 | CC |
| T92 | T13 | CC |
| T92 | T58 | CC |
| T97 | T12 | CC |
| T97 | T13 | CC |
| T97 | T35 | CC |
| T97 | T34SPAM | CC |
| T97 | T35SPIRO | CC |
| T97 | T36 | CC |
| T97 | T57 | CC |
| T97 | T59 | CC |
| T97 | T62 | CC |

Additional 1:1 Combinations Belonging to Group AA

T104SPIRO+T35SPIRO; T104+T133SPIRO; T104SPIRO+T35SPAM; T104SPIRO+T133SPIRO; T104+T35SPAM; T78+T133SPIRO; T104+T35SPIRO; T78+T35; T74SPIRO+T133SPIRO; T27F+T133SPIRO; T92+T133SPIRO; T78+T35SPAM; T92+T132SPIRO; T92+T35SPAM; T104+T132SPIRO; T104SPIRO+T132SPIRO; T74SPIRO+T112SPIRO; T27F+T51; T104SPIRO+T35; T78+T35F; T78SPIRO+T35SPAM; T78+T35SPIRO; T74SPIRO+T35SPAM; T28+T133SPIRO; T78SPIRO+T133SPIRO; T104+T35; T28+T107SPIRO; T104+T112SPIRO; T78SPIRO+T35; T78+T132SPIRO; T74SPIRO+T35SPIRO; T104SPIRO+T35F; T2Spiro+T35SPAM; T78SPIRO+T35SPIRO; T28+T147; T28+T35SPIRO; T27F+T64; T78SPIRO+T35F; T68+T133SPIRO; T27F+T132SPIRO; T113SPIRO+T133SPIRO; T68+T147; T92+T112SPIRO; T2Spiro+T133SPIRO; T74SPIRO+T132SPIRO; T42+T112SPIRO; T69+T132SPIRO; T28+T132SPIRO; T28+T107; T92PHSPIRO+T35SPIRO; T104SPIRO+T112SPIRO; T92+T35SPIRO; T104+T35F; T69+T133SPIRO; T27F+T107SPIRO; T78SPIRO+T132SPIRO; T27F+T54BA; T92PHSPIRO+T133SPIRO; T28+T33; T27F+T109SPIRO; T68+T132SPIRO; T92PHSPIRO+T132SPIRO; T27F+T107; T92+T11F; T92PHSPIRO+T35SPAM; T78+T112SPIRO; T96+T11; T92SPIRO+T133SPIRO; T2+T133SPIRO; T68+T107SPIRO; T92+T11; T2SPIRO+T35SPIRO; T69+T35SPAM; T96+T11F; T92PHSPIRO+T109SPIRO; T92+T35; T92SPIRO+T35SPAM; T100+T11; T2Spiro+T132SPIRO; T69+T35SPIRO; T78+T131 SPIRO; T28+T109SPIRO; T74SPIRO+T35F; T74SPIRO+T35; T68+T107; T27+T133SPIRO; T139RACEENDO+T32; T78SPIRO+T112SPIRO; T2+T131SPIRO; T69+T131SPIRO; T104+T131SPIRO.

Additional 1:1 Combinations Belonging to Group BB

T2Spiro+T35F; T27F+T58; T78SPIRO+T131SPIRO; T69+T112SPIRO; T27F+T12; T92PHSPIRO+T35; T27F+T35; T42+T37; T92+T35F; T27F+T34; T27F+T35SPAM; T92SPIRO+T35SPIRO; T126+T112SPIRO; T92OPH+T35SPIRO; T92SPIRO+T132SPIRO; T92+T37; T2+T35SPAM; T28+T155SPIRO; T27F+T35SPIRO; T2Spiro+T131SPIRO; T100+T11F; T28+T146; T28+T35; T74SPIRO+T131SPIRO; T68+T109SPIRO; T92OPH+T35SPAM; T68+T146; T42+T10; T92+T109SPIRO; T92PHSPIRO+T112SPIRO; T27F+T112SPIRO; T92PHSPIRO+T35F; T26diol cis+T33; T2+T132SPIRO; T27F+T57; T28+T35F; T68+T33; T68+T35; T92SPIRO+T35F; T97+T133SPIRO; T92OPH+T35; T27F+T32; T92OPH+T133SPIRO; T92OPH+T132SPIRO; T2Spiro+T35; T113SPIRO+T35SPAM; T2+T35F; T27F+T54BASPIRO; T99+T32; T68+T35SPIRO; T27F+T147; T27F+

T155SPIRO; T96+T56; T98+T11; T141EXOSYN+T32; T2+T35; T96+T37; T104SPIRO+T131SPIRO; T74+T112SPIRO; T27F+T37; T68+T35F; T24+T11F; T2Spiro+T112SPIRO; T69+T35; T96+T132SPIRO; T92SPIRO+T35; T2+T35SPAM; T96+T54BA; T42+T35SPIRO; T28+T35SPAM; T113SPIRO+T35SPIRO; T97+T11F; T27F+T13; T104SPIRO+T109SPIRO; T69+T35F; T96+T133SPIRO; T92OPH+T35F; T97+T11; T2+T112SPIRO; T68+T58; T92OPH+T37; T92PHSPIRO+T131SPIRO; T77+T132SPIRO; T96+T32; T27F+T35F; T127+T147; T97+T33; T40+T11F; T141EXOSYN+T62; T78+T109SPIRO; T100+T37; T97+T64; T100+T51; T100+T13; T92OPH+T109SPIRO; T42+T133SPIRO; T97+T58; T98+T11F; T92OPH+T112SPIRO; T140RACEENDO+T54BA; T97+T37; T92+T131SPIRO; T28+T54BA; T42+T11F; T27F+T11; T96+T51; T65+T133SPIRO; T100+T133SPIRO; T92PHSPIRO+T107SPIRO; T74SPIRO+T109SPIRO; T74+T35SPAM; T127+T33; T100+T64.

Additional 1:1 Combinations Belonging to Group CC

T69+T109SPIRO; T68+T35SPAM; T100+T155SPIRO; T24+T11; T75A+T35F; T40+T58; T28+T59; T27+T51; T92+T54BASPIRO; T75+T112SPIRO; T28+T33SPAM; T140RACEENDO+T59; T29+T11F; T42+T35SPAM; T96+T35SPIRO; T78SPIRO+T109SPIRO; T24cis+T37; T68+T36; T68+T112SPIRO; T101+T56; T42+T132SPIRO; T139RACEENDO+T62; T113SPIRO+T132SPIRO; T92+T64; T104+T109SPIRO; T97+T132SPIRO; T24+T59; T127+T132SPIRO; T1+T133SPIRO; T27F+T146; T68+T155SPIRO; T142EXOANTI+T146; T24+T58; T28+T58; T75+T133SPIRO; T24+T133SPIRO; T140RACEENDO+T33; T27F+T131SPIRO; T27+T109SPIRO; T92+T54BA; T24cis+T132SPIRO; T99+T56; T74+T35SPAM; T27+T132SPIRO; T42+T11; T1+T37; T24+T37; T43+T56; T75+T35SPIRO; T75A+T35SPIRO; T75+T132SPIRO; T92+T58; T92OTB+T51; T92SPIRO+T131SPIRO; T100+T56; T96+T13; T96+T64; T77+T35SPAM; T27+T59; T98+T32; T127+T107SPIRO; T26diol cis+T32; T77+T11; T26diol cis+T11; T100+T54BA; T96+T109SPIRO; T27F+T10; T100+T32; T97+T59; T1+T11F; T127+T35SPIRO; T97+T32; T126+T35SPAM; T139RACEENDO+T117METHYLSPIRO; T140RACEENDO+T13; T27F+T36; T75A+T131SPIRO; T75A+T35SPAM; T24+T54BASPIRO; T100+T146; T66+T133SPIRO; T92+T107SPIRO; T44+T64; T75A+T112SPIRO; T27F+T33; T97+T54BA; T96+T58; T24cis+T13; T28+T51; T113SPIRO+T35F; T126+T155SPIRO; T97+T51; T22_diol+T51; T114SPIRO+T156; T127+T146; T24cis+T32; T82+T117; T126+T109SPIRO; T92+T57; T74+T133SPIRO; T114SPIRO+T131SPIRO; T127+T133SPIRO; T74+T35SPIRO; T24+T132SPIRO; T100+T132SPIRO; T68+T131SPIRO; T96+T54BASPIRO; T100+T35SPAM; T5+T32; T27F+T1 IF; T43+T64; T68+T37; T69+T11F; T69+T37; T126+T35SPIRO; T96+T35SPAM; T27+T107SPIRO; T24+T54BA; T75+T35SPAM; T69+T107SPIRO; T24+T64; T97+T35SPIRO; T92PHSPIRO+T155SPIRO; T26diol cis+T155SPIRO; T104+T107; T75A+T132SPIRO; T97+T34; T92+T107; T97+T12; T92+T13; T27+T107; T24+T32; T100+T35SPIRO; T75A+T133SPIRO; T68+T11; T75+T59; T114SPIRO+T35SPAM; T2+T11F; T140RACEENDO+T58; T2Spiro+T109SPIRO; T28+T112SPIRO; T96+T146; T77+T131SPIRO; T42+T54BASPIRO; T29+T11; T114SPIRO+T133SPIRO; T24+T34; T27+T35F; T24+T33; T92OPH+T107SPIRO; T86+T34; T92+T10; T22_diol+T58; T96+T12; T24cis+T54BASPIRO; T139RaceEndo+T154; T28+T154; T28+T34; T100+T12; T27+T131SPIRO; T114SPIRO+T35SPIRO; T69+T11; T68+T54BASPIRO; T98+T13; T83+T132SPIRO; T24cis+T12; T97+T35SPAM; T104+T107SPIRO; T126+T107SPIRO; T77+T35SPIRO; T24Dihydro+T11F; T75AOTB+T51; T68+T34; T71+T32; T98+T51; T75A+T35; T40+T57; T76+T31; T2+T109SPIRO; T127+T07; T69+T107; T24cis+T59; T24cis+T133SPIRO; T27F+T62; T73+T34; T24Dihydro+T133SPIRO; T27+T35SPAM; T75AOTB+T144; T92OPH+T131 SPIRO; T24+T57; T42+T34; T104+T155SPIRO; T100+T34; T42+T59; T99+T37; T65+T132SPIRO; T140RaceEndo+T51; T100+T109SPIRO; T113SPIRO+T35; T1+T112SPIRO; T24cis+T58; T43+T36; T40+T133SPIRO; T98+T54BA; T68+T54BA; T92OTBSPIRO+T12; T97+T109SPIRO; T29+T37; T78+T155SPIRO; T27+T35; T24Dihydro+T132SPIRO; T97+T13; T75+T34; T83+T133SPIRO; T1+T35SPAM; T5+T64; T24Dihydro+T32; T24Dihydro+T59; T114SPIRO+T35F; T75+T35; T92+T12; T104SPIRO+T107SPIRO; T141EXOANTI+T32; T92PHSPIRO+T37; T96+T131SPIRO; T99+T34; T126+T133SPIRO; T78+T34; T77+T112SPIRO; T92OTBSPIRO+T64; T98+T64; T43+T133SPIRO; T43+T37; T97+T56; T104Spiro+T07; T24cis+T11; T96+T112SPIRO; T104SPIRO+T155SPIRO; T99+T64; T92SPIRO+T112SPIRO; T100+T58; T114SPIRO+T155SPIRO; T76+T112SPIRO; T24+T35SPAM; T8+T35SPAM; T24cis+T54BA; T74SPIRO+T107SPIRO; T99+T54BASPIRO; T141EXOSYN+T147; T42+T58; T127+T35SPAM; T141EXOANTI+T155SPIRO; T141EXOSYN+T155SPIRO; T40+T132SPIRO; T24Dihydro+T37; T42+T35; T75+T58; T92OPH+T54BASPIRO; T78+T107; T114SPIRO+T132SPIRO; T100+T57; T97+T62; T68+T11F; T96+T35; T28+T31; T126+T51; T139RACEENDO+T64; T70+T56; T27+T64; T28+T11F; T22_diol+T54BA; T22_diol+T146; T97+T57; T22_diol+T144; T44+T132SPIRO; T100+T107SPIRO; T24Dihydro+T11; T24+T35; T68+T59; T24+T35SPIRO; T92OPH+T11; T142EXOANTI+T154; T126+T107; T42+T36; T98+T132SPIRO; T42+T54BA; T28+T143; T98+T12; T28+T11; T98+T133SPIRO; T139RACEENDO+T12; T97+T54BASPIRO; T126+T132SPIRO; T73+T32; T42+T35F; T77+T133SPIRO; T127+T154; T104+T37; T74SPIRO+T107; T77+T11F; T127+T58; T26diol cis+T1 IF; T43+T34; T92+T155SPIRO; T142EXOANTI+T107; T65+T35SPIRO; T69+T36; T73+T155SPIRO; T76+T35SPAM; T24Dihydro+T58; T69+T54BASPIRO; T75APSPIRO+T33SPAM; T1+T35SPIRO; T75A+T109SPIRO; T1+T107SPIRO;

T24cis+T64; T43+T32; T92PHSPIRO+T1 IF; T22_diol+T64; T40+T33SPAM; T127+T35; T66+T132SPIRO; T92OTBSPIRO+T132SPIRO; T71+T34; T26diol trans+T36; T113SPIRO+T131SPIRO; T97+T36; T92SPIRO+T109SPIRO; T86+T133SPIRO; T40+T35SPAM; T75AP+T54BASPIRO; T142EXOANTI+T107SPIRO; T24+T33SPAM; T113SPIRO+T146; T22_diol+T33SPAM; T86+T35SPIRO; T65+T35SPAM; T27+T54BA; T92+T36; T24Dihydro+T54BASPIRO; T42+T109SPIRO; T70+T131SPIRO; T98+T35SPIRO; T103+T56; T24Dihydro+T35SPAM; T69+T58; T41GEM+T112SPIRO; T99+T12; T42+T155SPIRO; T29+T54BA; T141EXOANTI+T37; T28+T36; T44+T133SPIRO; T139RaceEndo+T51; T24cis+T35SPAM; T30+T59; T21 (Diol)+T56; T40+T146; T127+T109SPIRO; T40+T51; T1+T64; T142EXOANTI+T147; T2+T107; T75+T36; T78+T37; T76+T10; T75AP+T54BA; T77+T13; T40+T54BA; T100+T59; T96+T35F; T98+T58; T127+T155SPIRO; T104SPIRO+T34; T78+T10; T65+T35F; T5+T107; T99+T58; T78+T107SPIRO; T24+T51; T75+T109SPIRO; T98+T109SPIRO; T22_diol+T57; T126+T35; T44+T12; T96+T57; T140RACEENDO+T155SPIRO; T113SPIRO+T156; T1+T54BASPIRO; T99+T62; T114SPIRO+T35; T98+T146; T74+T35F; T1+T107; T141EXOANTI+T12; T27+T112SPIRO; T92OPH+T107; T92+T56; T139RACEENDO+T146; T27+T34; T97+T112SPIRO; T27F+T31; T24cis+T57; T28+T64; T74SPIRO+T36; T97+T107SPIRO; T139RaceEndo+T143; T25B+T36; T104+T11F; T42+T32; T140RACEENDO+T34; T75+T35F; T104+T11; T75AOTBSPIRO+T10; T92+T144; T75A+T59; T99+T11F; T99+T54BA; T141EXOSYN+T34; T22_diol+T155SPIRO; T69+T155SPIRO; T136A+T109SPIRO; T140RACEENDO+T37; T24cis+T56; T40+T144; T68+T33SPAM; T75AP+T37; T69+T64; T22_diol+T109SPIRO; T24Dihydro+T112SPIRO; T140RACEENDO+T146; T127+T12; T29+T33; T140RACEENDO+T36; T100+T54BASPIRO; T27F+T144; T76+T59; T139RACEENDO+T147; T97+T35; T98+T34; T69+T54BA; T78SPIRO+T155SPIRO; T27F+T33SPAM; T75APSPIRO+T117METHYLSPIRO; T104+T36; T75AOTB+T143; T26diol cis+T64; T75AP+T64; T98+T35SPAM; T92PHSPIRO+T36; T68+T57; T24Dihydro+T10; T24cis+T10; T75AOTB+T12; T77+T35F; T44+T107SPIRO.

Example 3: Synthesis of Sparsomycin Analogues 3-(6-methyl-2, 4-dioxo-1, 2, 3, 4-tetrahydropyrimidin-5-yl) acrylic acid Synthesis of 3-(6-methyl-2, 4-dioxo-1, 2, 3, 4-tetrahydropyrimidin-5-yl) acrylic acid was carried out as shown in the scheme below and described in the literature.

SCHEME 1

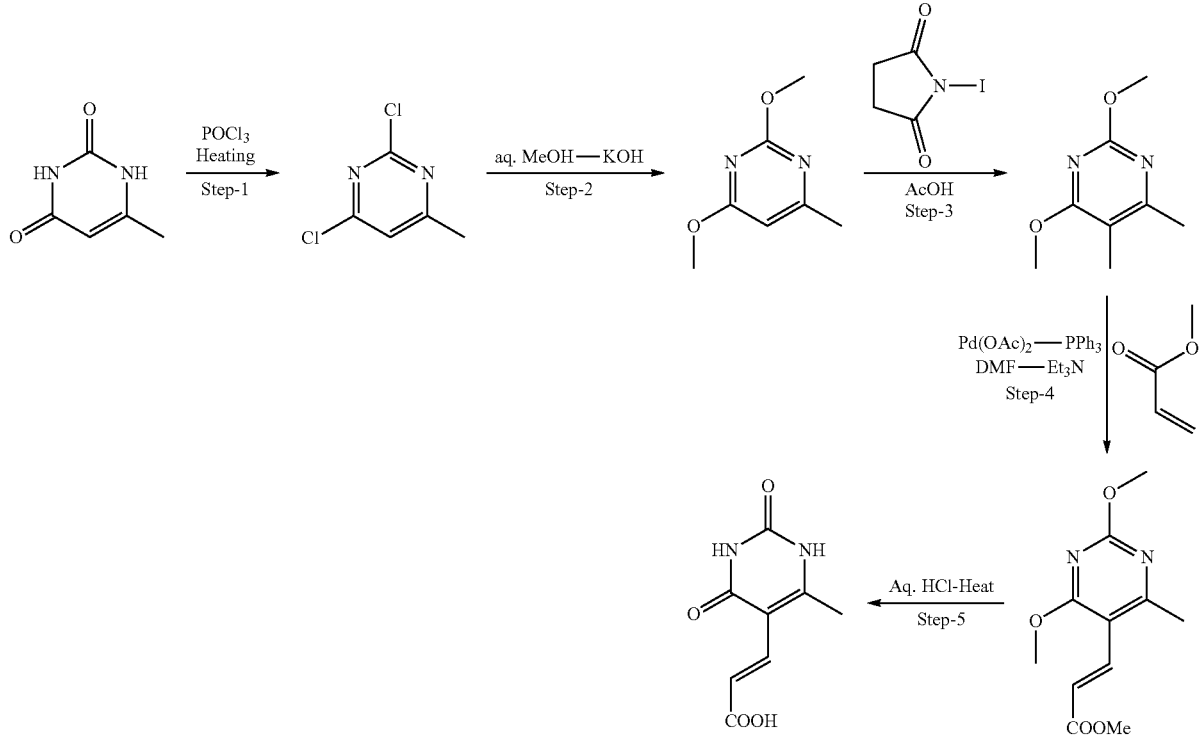

Step-1:- *Journal of Heterocyclic Chemistry*; vol. 21; (1984); 741-744
Step-2:- *Journal of Chemical Society*; (1951); vol. 24, 1004-1015;
Step-3 to 5:- *Synthesis*; 10; (1988); p. 771-775

Coupling Reactions of 3-(6-methyl-2, 4-dioxo-1, 2, 3, 4-tetrahydropyrimidin-5-yl) acrylic acid General Procedure for Coupling Reactions 100 mg (0.510 mmol) 3-(6-methyl-2,4-dioxo-1,2,3,4-tetrahydropyrimidin-5-yl)acrylic acid, desired amine (1.5 eq.), N-Ethoxycarbonyl-2-ethoxy-1,2-Dihydroquinoline (EEDQ 2 eq.) in dimethyl formamide (DMF, 5 mL) were heated to 100° C. and monitored by TLC & LCMS. After consumption of starting material the crude product was isolated either by diluting reaction mass by ethyl acetate followed by filtration of precipitated crude product, or concentrating the DMF in GeneVac® to obtain the crude product.

Dihydroxy compound (Sparso-10) was synthesized by de-methylation of corresponding dimethoxy compound (Sparso-10a) by boron tribromide in dichloromethane at room temperature.

Crude products were purified by preparative HPLC.

Analytical data of the coupled product synthesized is tabulated below in Table 7.

SCHEME 2

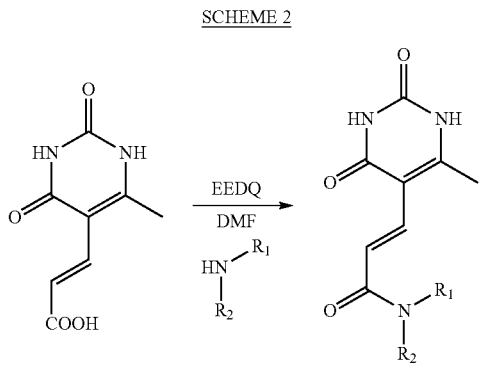

TABLE 7

ANALYTICAL DATA

| Sr. No | Code | Structure | Analytical data |
|---|---|---|---|
| 2 | SPARSO-10 | 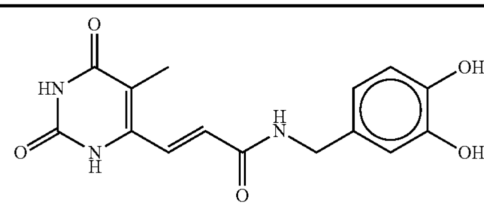 | Mol. Wt:- 317.29<br>M.I. Peak observed : 318.20<br>HPLC Purity:- 99.37%<br>$^1$H NMR DMSO-d6:- 2.25(s,3H), 4.15-4.16(d,2H), 6.48-6.50(d,1H), 6.62-6.64(d,2H), 7.06-7.10(d,1H), 7.20-7.24(d,1H), 8.43(t,1H),<br>8.68(s,1H),8.82(s,1H), 11.21(bs,2H). |

Example 4: Synthesis of Linezolid Analogues cis N-(((5S)-3-(4-(3,4-dihydroxypyrrolidin-1-yl)-3-fluorophenyl)-2-oxooxazolidin-5-yl)methyl)acetamide (LZD-2)

This compound was synthesized by oxidation of (S)—N-((3-(4-(2, 5-dihydro-1H-pyrrol-1-yl)-3-fluorophenyl)-2-oxooxazolidin-5-yl)methyl) acetamide by osmium tetroxide as in the reaction scheme below (see Scheme 3).

SCHEME 3.

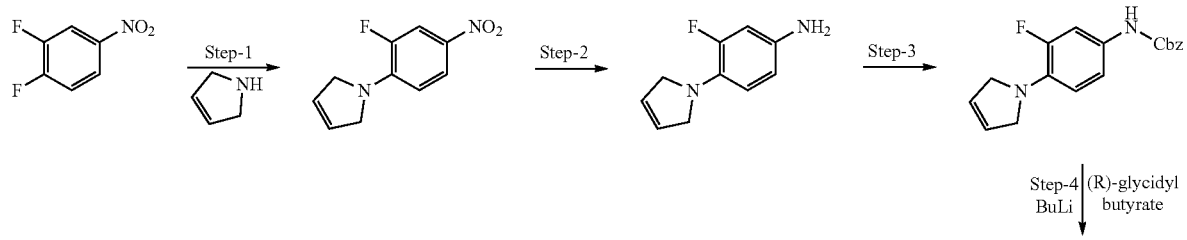

Step-4 BuLi | (R)-glycidyl butyrate

109 -continued 110

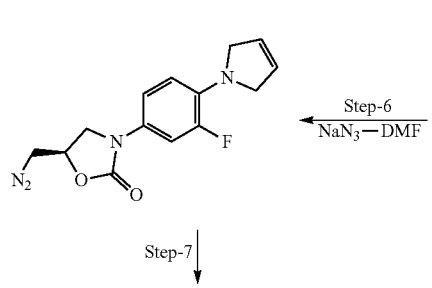

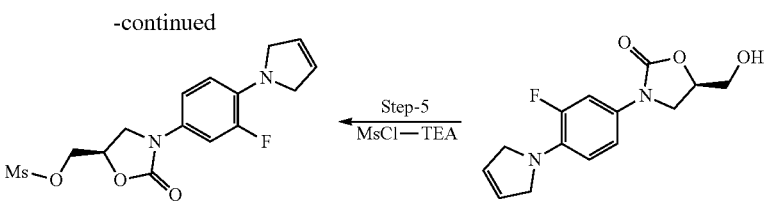

Steps 1 to 7

These reactions were carried out as per literature method (J. Med. Chem. 1996, 39, 673-679) described for synthesis of Linezolid. 2, 5-dihydro-1H-pyrrole was used instead of morpholine in step-1.

Step 8

Synthesis of N-(((5S)-3-(4-(3, 4-dihydroxypyrrolidin-1-yl)-3-fluorophenyl)-2-oxooxazolidin-5-yl)methyl) acetamide

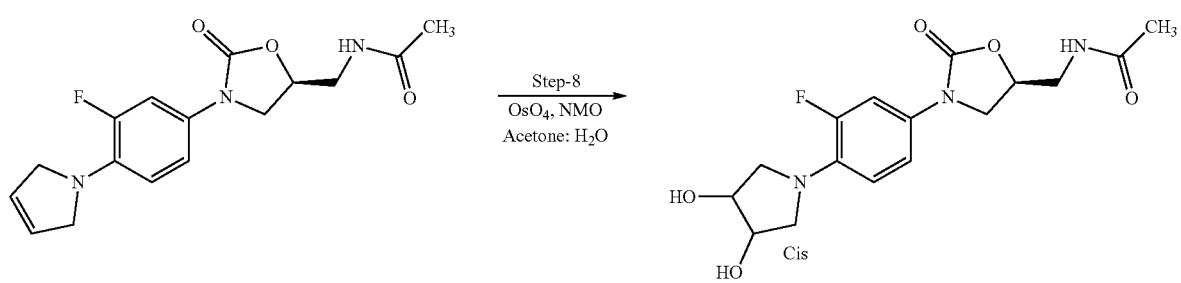

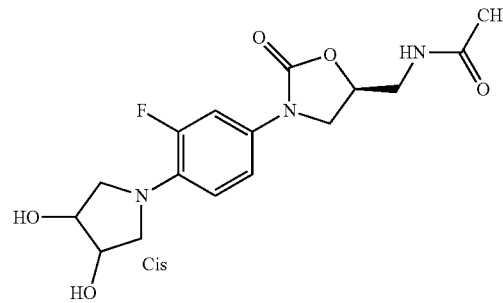

To a solution of (S)—N-((3-(4-(2, 5-dihydro-1H-pyrrol-1-yl)-3-fluorophenyl)-2-oxooxazolidin-5-yl)methyl) acetamide (0.4 g, 1.25 mmol) in acetone (10 mL) and water (3 mL), Osmium tetroxide (3.1 mg, 0.012 mmol), was added at room temperature. The reaction mixture was stirred for 15 min. N-methyl morpholine oxide (161 mg, 1.3 mmol) was added and the reaction mixture was allowed to stir at room temperature overnight. TLC (Mobile phase 60% ethyl acetate in n-hexane) indicated absence of starting material (Rf 0.7) and product formation (Rf 0.25). 10% sodium bisulphite solution (40 mL) was added and the reaction mixture was stirred for 10 min. The compound was extracted in ethyl acetate. The organic layer was dried over sodium sulfate and concentrated. The compound was purified by column chromatography using Hexane: ethyl acetate as eluent to give the desired product as white solid. (0.07 g, 15.9%)

Mol. Wt: 353.34, M.I. Peak observed: 354.20, HPLC Purity: 99.09%

$^1$H NMR DMSO-d6: 1.83 (s, 3H), 3.16-3.19 (m, 2H), 3.38 (t, 2H), 3.47-3.49 (m, 2H), 3.64-3.68 (q, 1H), 4.01-4.08 (m, 3H), 4.65-4.68 (m, 2H), 4.84-4.85 (d, 1H), 6.65 (t, 1H), 7.05-7.07 (dd, 1H), 7.33-7.38 (dd, 1H), 8.23 (t, 1H). LCMS: (M+1) 354.2 Example 5: Synthesis of Linezolid derivatives with catechol, (o-hydroxy amido) aryl or o-hydroxy methyl phenol groups.

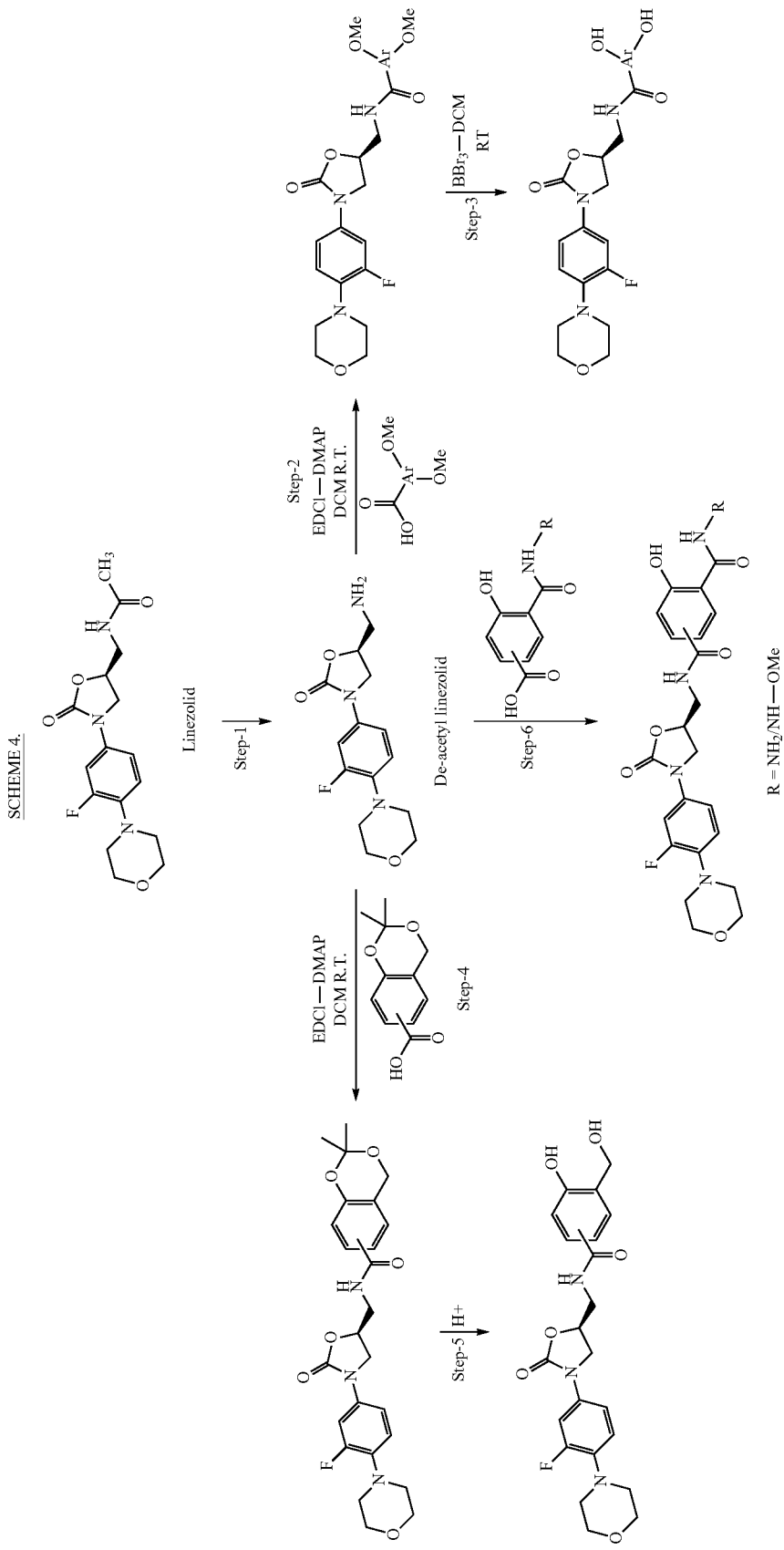
SCHEME 4.

De-methylated Linezolid was synthesized and acylated with desired carboxylic acids by the procedure described earlier. Demethylation of the compounds obtained after acylation with dimethoxy aryl carboxylic acids to get desired diol was carried out as per general procedure below. (Step-3 in the Scheme 4, above)

General Procedure for De-Methylation

Dimethoxy intermediates were dissolved in dichloromethane (10-50 vol depending on solubility) the reaction mass was cooled to 0° C., Boron tribromide (3 eq) was added and reaction mass was gradually warmed to room temperature. Stirring was continued at room temperature and reaction was monitored by LCMS till maximum starting was consumed (~1-8 hrs required). Reaction mass was then concentrated and excess $BBr_3$ was removed by multiple strippings of methanol to get the products as hydrobromide salts.

The (o-hydroxy amido) aryl analogues were synthesized by coupling of corresponding suitably substituted carboxylic acid with de-acetyl Linezolid (Step-6 in the above reaction scheme) as per the general procedure described earlier.

Analogues with o-hydroxy methyl phenol group were synthesized by coupling desired aryl carboxylic acid with 2-(hydroxymethyl) phenol functionality that was protected with isopropylidine group and subsequent deprotection of coupled product in methanolic HCl at room temperature (Step 4 & 5 in reaction Scheme 4.)

All the crude products were purified by reverse phase preparative HPLC. Pure products were isolated as TFA salts. Analytical data of the compounds synthesized is as below in Table 8.

TABLE 8

ANALYTICAL DATA

| Sr. No. | Code | Structure | Analytical data |
|---|---|---|---|
| 7 | Lz-NA-19 | 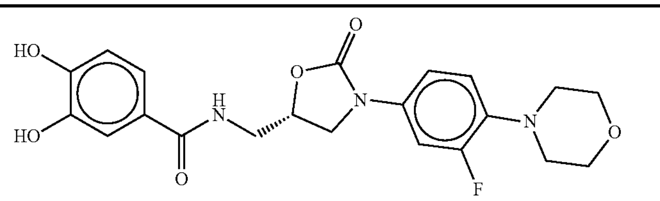 | Mol. Wt:- 431.41<br>M.I. Peak observed : 432.30<br>HPLC Purity:- 99.40%<br>$^1$H NMR DMSO-d6:- 2.95(t,4H), 3.51-3.57(m,2H), 3.73(t,4H), 3.80-3.84(m,2H), 4.09-4.14(m,2H), 4.78-4.80-(m,1H), 6.73-6.76(d 1H),7.06(t,1H),7.17-7.19(d,2H),7.27(s,1H),7.46-7.50(1H),8.49(t,1H). |
| 8 | Lz-NA-20 | 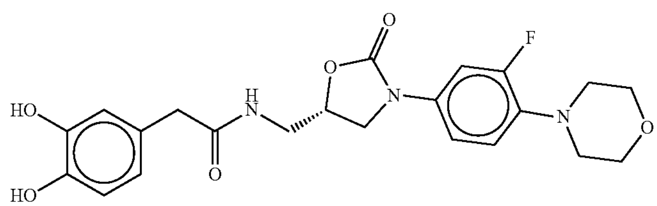 | Mol. Wt:- 445.41<br>M.I. Peak observed : 446.30<br>HPLC Purity:- 99.27%<br>$^1$H NMR DMSO-d6:- 2.96(t,4H), 3.22 (s,3H), 3.39(t,2H), 3.65-3.67(m,1H), 3.73(t,4H), 4.05(t,1H), 4.66-4.73(m,2H), 6.41-6.43(d 1H), 6.54-6.56(d,1H), 6.63(s,1H), 7.04-7.14(m,2H),7.45-7.49(dd,1H),8.35(t,1H). |
| 9 | Lz-NA-21 | 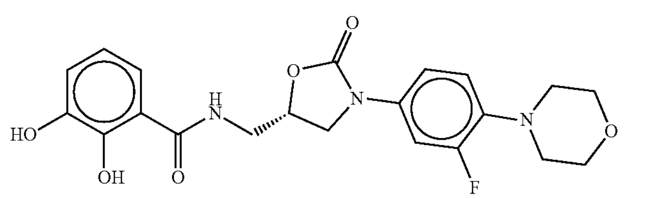 | Mol. Wt:- 431.14<br>M.I. Peak observed :432.30<br>HPLC Purity:- 99.18%<br>$^1$H NMR DMSO-d6:- 2.95(t,4H), 3.65(t,2H), 3.73(t,4H), 3.83(t,1H), 4.15(t,2H), 4.85-4.88(m,1H), 6.71(t,1H), 6.91-6.93(d,1H), 7.05(t,1H), 7.07-7.13(d,1H), 7.17-7.20(d,1H), 7.28-7.30(d,1H), 7.45-7.49(d,1H),9.04(t,1H). |
| 10 | Lz-NA-22 | 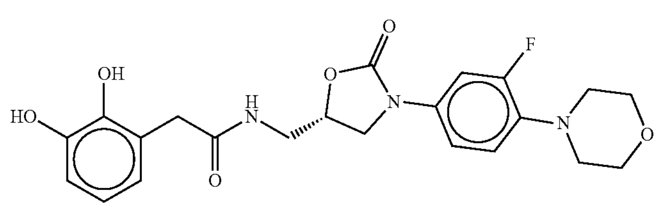 | Mol. Wt:- 445.44<br>M.I. Peak observed : 446.00<br>HPLC Purity:- 97.59%<br>$^1$H NMR DMSO-d6:- 2.96(t,4H), 3.41-3.45(m,4H), 3.68-3.74(m,5H), 4.07(t,1H), 4.70-4.74(m,1H), 6.46-6.47(m,2H), 6.61-6.63(m,1H), 7.06(t,1H), 7.15-7.17(d,1H), 7.44-7.49(dd,1H), 8.37(t,1H). |
| 11 | Lz-NA-23 | 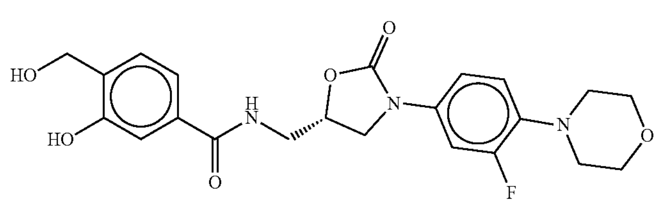 | Mol. Wt:- 445.41<br>M.I. Peak observed : 446.10<br>HPLC Purity:- 99.92%<br>$^1$H NMR DMSO-d6:- 2.95(t,4H), 3.55-3.59(m,2H), 3.72(t,4H), 3.81-3.84(m,1H), 4.13(t,1H), 4.49(s,2H), 4.81-4.84(m,1H), 7.05(t,1H), 7.17-7.19(d,1H), 7.24-7.28(t,2H), 7.33-7.35(d,1H), 7.46-7.50(dd,1H), 8.66(t,1H), 9.63(s,1H). |

TABLE 8-continued

ANALYTICAL DATA

| Sr. No. | Code | Structure | Analytical data |
|---|---|---|---|
| 12 | Lz-NA-24 | 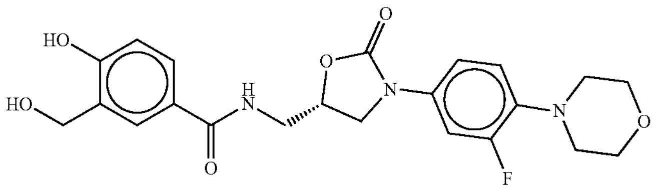 | Mol. Wt:- 445.44<br>M.I. Peak observed : 446.35<br>HPLC Purity:- 94.37%<br>$^1$H NMR DMSO-d6:- 2.95(t,4H), 3.52-3.61(m,3H), 3.73(t,4H), 3.81-3.85(m,1H), 4.10-4.14(m,1H), 4.47(s,2H), 4.80-4.83-(m,1H), 6.78-6.80(d 1H),7.05(t,1H),7.17-7.19(d,1H), 7.46-7.50(dd,1H) 7.58-7.61(dd,1H), 7.87(s,1H), 8.56(t,1H),10.00(bs,1H). |
| 13 | Lz-NA-27 | 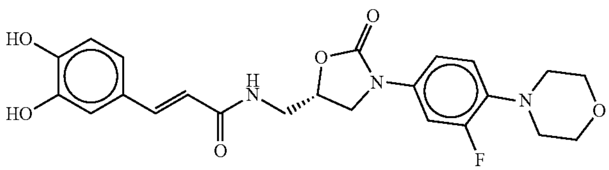 | Mol. Wt:- 457.45<br>M.I. Peak observed : 458.40<br>HPLC Purity:- 95.46%<br>$^1$H NMR DMSO-d6:- 2.94(t,4H), 3.52-3.55(m,3H), 3.72-3.77(m,5H), 4.11(t,1H), 4.75-4.79(m,1H), 6.35-6.39(d,1H), 6.72-6.74(d,1H), 6.81-6.84(dd,1H), 6.93(s,1H), 7.07(t,1H), 7.16-7.19(dd,1H), 7.23-7.27(d,1H), 7.46-7.51(dd,1H), 8.36(t,1H) , 9.25(bs, 1H). |
| 14 | Lz-NA-28 | 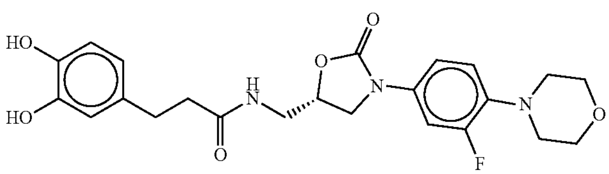 | Mol. Wt:- 459.47<br>M.I. Peak observed : 460.30<br>HPLC Purity:- 99.42%<br>$^1$H NMR DMSO-d6:- 2.30(t,2H), 2.57(t,2H), 2.95(t,4H), 3.36-3.46(m, 3H), 3.64-3.68(m,1H), 3.73(t,4H), 4.03(t,1H), 4.65-4.70(m,1H), 6.37-6.39(d, 1H), 6.53(s,1H), 6.57-6.59 (d,1H), 7.06(t,1H), 7.13-7.15(d, 1H), 7.46-7.50(d,1H), 8.20(t,1H), 8.7(bs,1H). |
| 15 | Lz-NA-34 | 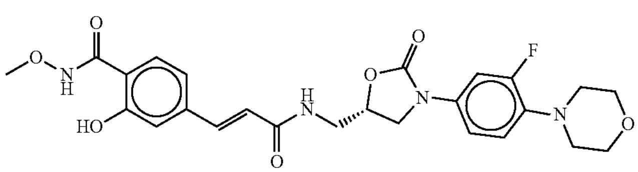 | Mol. Wt:- 514.50<br>M.I. Peak observed : 515.15<br>HPLC Purity:- 98.69%<br>$^1$H NMR DMSO-d6:- 2.94(t,4H), 3.56(t,4H), 3.72(t,6H), 4.11(t,1H), 4.79(m,1H), 6.69-6.73(d,1H, , J = 15.6 Hz), 7.02-7.07(m,3H), 7.16-7.18(d,1H, , J = 8.8 Hz), 7.34-7.38(d,1H, , J = 16 Hz), 7.46-7.50(d,1H, , J = 15.2 Hz), 7.64-7.66(d,1H, , J = 8 Hz),8.55(t,1H0, 11.81(bs,1H). |
| 16 | Lz-NA-36 | 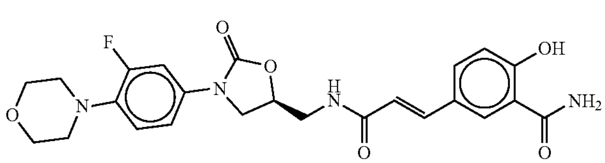 | Mol. Wt:- 484.47<br>M.I. Peak observed : 484.95<br>HPLC Purity:- 96.2% |

Example 6: Synthesis of N-Substituted Florfenicol Derivatives

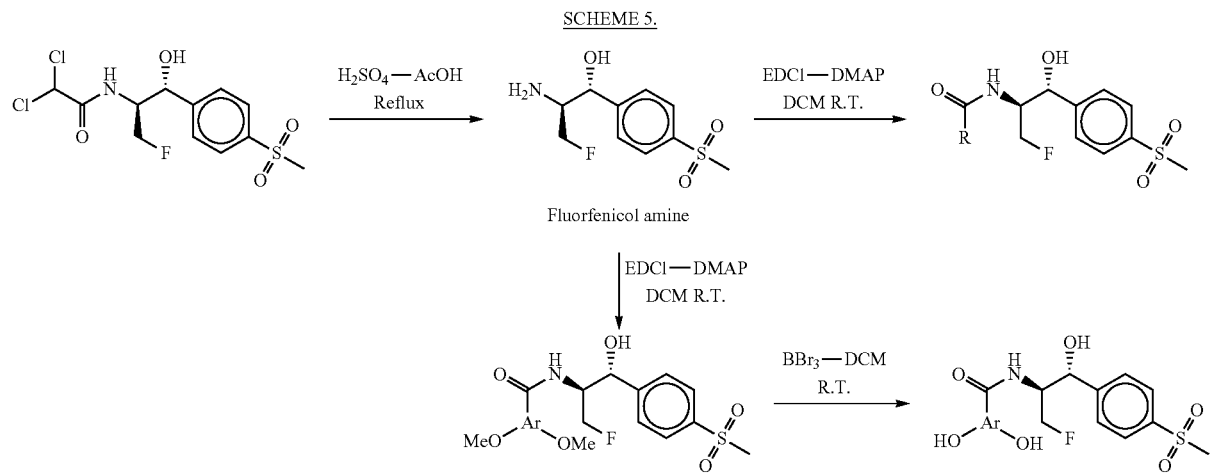

SCHEME 5.

Fluorfenicol amine

Florfenicol amine was synthesized from commercially available florfenicol by the procedure reported in the literature (WO2005185266). Coupling & subsequent demethylation reactions were carried out as per the general procedure described earlier for similar analogues of Linezolid.

TABLE 9

ANALYTICAL DATA

| Sr. No. | Code | Structure | Analytical data |
|---|---|---|---|
| 1 | NAFFLA-19 | 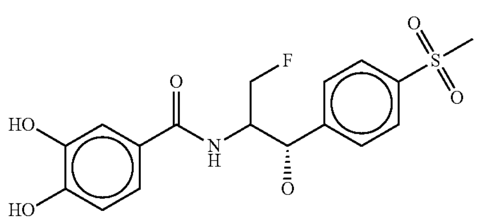 | Mol. Wt:- 383.39<br>M.I. Peak observed : 384.15<br>HPLC Purity:- 99.38%<br>$^1$H NMR DMSO-d6:- 3.22(s,3H), 3.60(m,1H), 4.3-4.72(m,3H), 4.98(s,1H), 6.71-6.73(d,1H), 7.11-7.13(d,1H), 7.17(s,1H), 7.59-7.60(d,2H), 7.80-7.85(m,3H), 9.11(s,1H), 9.46(s,1H). |
| 2 | NAFFLA-20 | 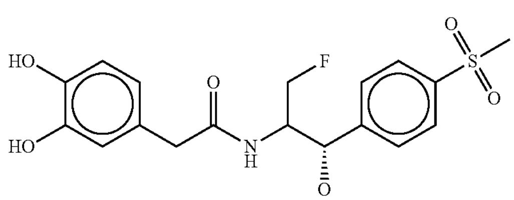 | Mol. Wt:- 397.42<br>M.I. Peak observed : 398.25<br>HPLC Purity:- 99.87%<br>$^1$H NMR DMSO-d6:- 3.15(s,3H), 3.20-3.23(m,2H), 4.19-4.61(m,3H), 4.88(s,1H), 6.32-6.34(m,1H), 6.55(s,1H, J = 8 Hz ), 6.58-6.60(d,1H, J = 8 Hz,), 7.49-7.51(d,2H, J = 8 Hz), 7.77-7.79(d,2H, J = 8 Hz) |
| 3 | NAFFLA-21 | 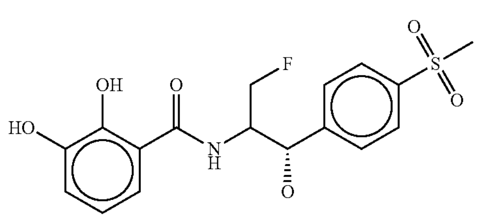 | Mol. Wt:- 383.39<br>M.I. Peak observed : 384.15<br>HPLC Purity:- 98.60%<br>$^1$H NMR DMSO-d6:- 3.16(s,3H), 4.52-4.70(m,3H), 5.03(s,1H), 6.11-6.12(d,1H), 6.67(t,1H), 6.89-6.91(d,1H, J = 7.2 Hz ), 6.727-6.29(d,1H J = 8 Hz, ), 7.63-7.65(d,2H, J = 8 Hz), 7.83-7.85(d,2H, J = 8.4 Hz), 8.67-8.69(d,1H), 9.43(bs,1H), 11.30(bs,1H). |

TABLE 9-continued

ANALYTICAL DATA

| Sr. No. | Code | Structure | Analytical data |
|---|---|---|---|
| 4 | NAFFLA-22 | 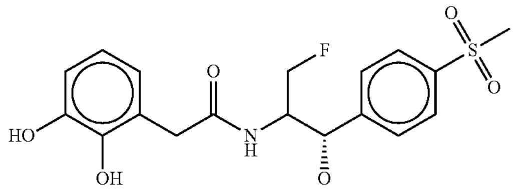 | Mol. Wt:- 397.42<br>M.I. Peak observed : 398.00<br>HPLC Purity:- 94.48%<br>$^1$H NMR DMSO-d6:- 3.14(s,3H), 3.21-3.41(m, 3H), 4.19-4.26(m,1H), 4.37(t,1H), 4.49-4.65(m,1H), 4.90(s,1H), 6.32-6.34(d,1H), 6.51(t,1H), 6.63-6.66(d,1H), 7.50-7.52(d,2H), 7.74-7.76(d,2H), 7.86-7.88(d,1H), 8.7(bs,1H), 9.12(bs,1H). |
| 5 | NAFFLA-23 | 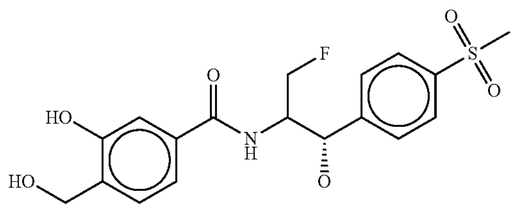 | Mol. Wt:- 397.42<br>M.I. Peak observed : 398.00<br>HPLC Purity:- 96.44%<br>$^1$H NMR DMSO-d6:- 3.16(s,3H), 4.36(t,1H), 4.48(s,2H), 4.59-4.74(m,2H), 4.99-5.00(d,1H), 7.13(s,1H), 7.20-7.22(d,1H, , J = 8.8 Hz), 7.32-7.34(d,1H, , J = 7.6 Hz), 7.60-7.62(d,2H, , J = 8 Hz), 7.83-7.85(d,2H, , J = 8 Hz), 8.024-8.045(d,1H, , J = 8.4 Hz), 9.62(bs,1H). |
| 6 | NAFFLA-27 | 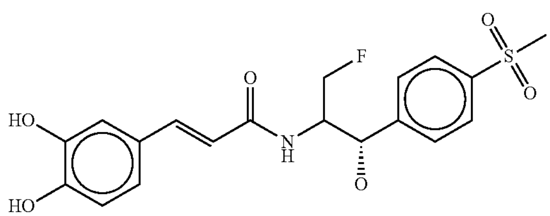 | Mol. Wt:- 409-42<br>M.I. Peak observed:- 410.20<br>HPLC Purity:- 96.02%<br>$^1$H NMR DMSO-d6:- 3.17(s,3H), 4.28(t,1H), 4.37-4.40(m,1H), 4.55-4.65(m,1H), 4.96(s,1H), 6.06-6.07(d,1H), 6.45-6.49(d,1H, , J = 15.6 Hz), 6.70-6.72 (d, 1H), 6.77-6.79(d,1H), 6.89(s,1H), 7.09-7.13(d,1H, , J = 15.6 Hz), 7.61-7.63(d, 2H), 7.84-7.86(d,2H), 7.96-7.98(d,1H), 9.10(bs,1H), 9.36(bs,1H). |
| 7 | NAFFLA-28 | 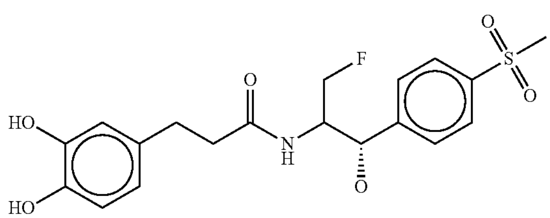 | Mol. Wt:- 411.44<br>M.I. Peak observed:- 412.25<br>HPLC Purity:- 98.12%<br>$^1$H NMR CD3OD:- 2.37(t,2H), 2.61(t,2H), 3.09(s,3H), 4.20-4.59(m,3H), 4.97(s,1H), 6.46-6.48(d,1H), 6.59(s,1H), 6.64-6.66(d,1H), 7.51-7.54(d,2H), 7.86-7.88(d,2H). |
| 8 | NAFFLA-34 | 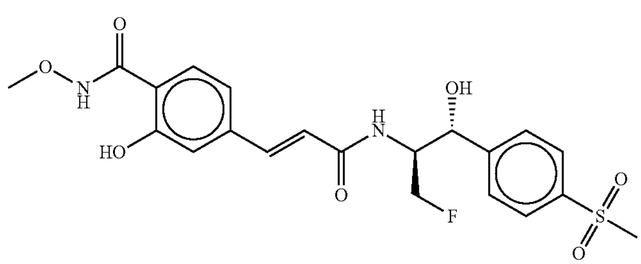 | Mol. Wt:- 466.48<br>M.I. Peak observed:- 467.00<br>HPLC Purity:- 97.56%<br>$^1$H NMR DMSO-d6:- 3.17(s,3H), 3.72(s,3H), 4.28-4.67(m, 3H), 4.98(s,1H), 6.12(bs,1H), 6.81-6.85(d,1H, J = 16 Hz), 7.03(s,2H),7.20-7.24(d,1H, J = 15.6 Hz), 7.63-7.65(d, 3H), 7.85-7.87(d,2H), 8.16-8.18(d,1H), 11,82(bs,2H). |
| 9 | NAFFLA-35 | 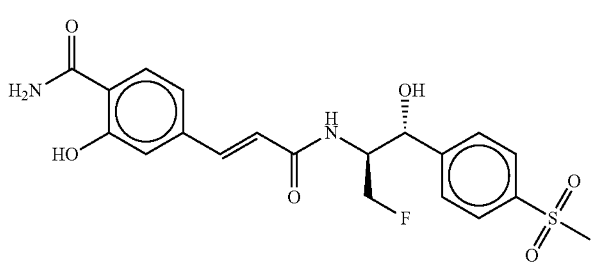 | Mol. Wt:- 436.45<br>M.I. Peak observed:- 437.00<br>HPLC Purity:- 98.36%<br>$^1$H NMR DMSO-d6:- 3.17(s,3H), 4.29(t, 1H), 4.42(m,1H), 4.56(t,1H), 4.98(bs,1H), 6.11(s,1H), 6.83-6.87(d,1H, J = 15.6 Hz), 6.99(s,2H), 7.21-7.24(d,1H, J = 15.6 Hz),7.63-7.65(d,2H), 7.85-7.87(t,4H), 7.96(bs,1H), 8.14-8.16(d,1H), 8.41(bs,1H),13.09(s,1H). |

TABLE 9-continued

ANALYTICAL DATA

| Sr. No. | Code | Structure | Analytical data |
|---|---|---|---|
| 10 | NAFFLA-36 | 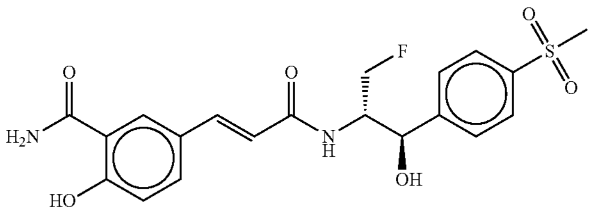 | Mol. Wt:- 436.45<br>M.I. Peak observed:- 437.05<br>HPLC Purity:- 98.78%<br>$^1$H NMR DMSO-d6:- 3.1(s,3H), 4.29-4.31(t,1H), 4.42(m,1H), 4.53-4.55(m,1H), 4.63(bs,1H), 4.98(s,1H), 6.61-6.65(d,1H, J = 15.6Hz), 6.91-6.93(d,1H), 7.20-7.24(d,1H, J = 15.6Hz), 7.57-7.60(m,3H), 7.85-8.02(m,5H), 8.41(bs,1H). |
| 11 | NAFFLA-37 | 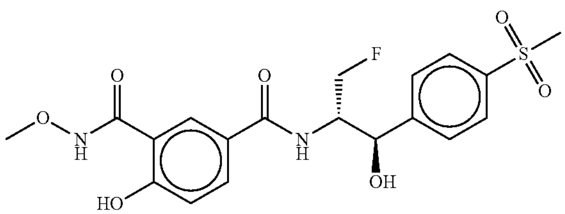 | Mol. Wt:- 440.44<br>M.I. Peak observed:- 441.15<br>HPLC Purity:- 97.02%<br>$^1$H NMR DMSO-d6:- 3.16(s,3H), 3.72(s,3H),4.34-4.75(m,3H), 4.49-4.50(d,1H), 6.1(bs,1H), 6.93-6.95(d,1H), 7,60-7.62(d,2H), 7.73-7.87(m,3H), 8.11(s,1H), 11.74(bs,1H), 11.92(bs,1H). |

Example 7: Synthesis of Tryptase Inhibitors with Boronic Acid Functionality

These compounds were synthesized by either of the two methods (Method A & Method B) as below. Required aryl halo carboxylic acids in step-1 of both the methods were either procured commercially or synthesized in house by known methods in the literature.

Method A

Required aryl pinacolato boronate esters/boronic acids with carboxylic acid groups were synthesized and coupled with desired tert-butyl 3-(piperidin-4-yl) benzylcarbamate. Later boronate ester functionality was hydrolyzed to boronic acid in acidic media.

SCHEME 6.

Method-A

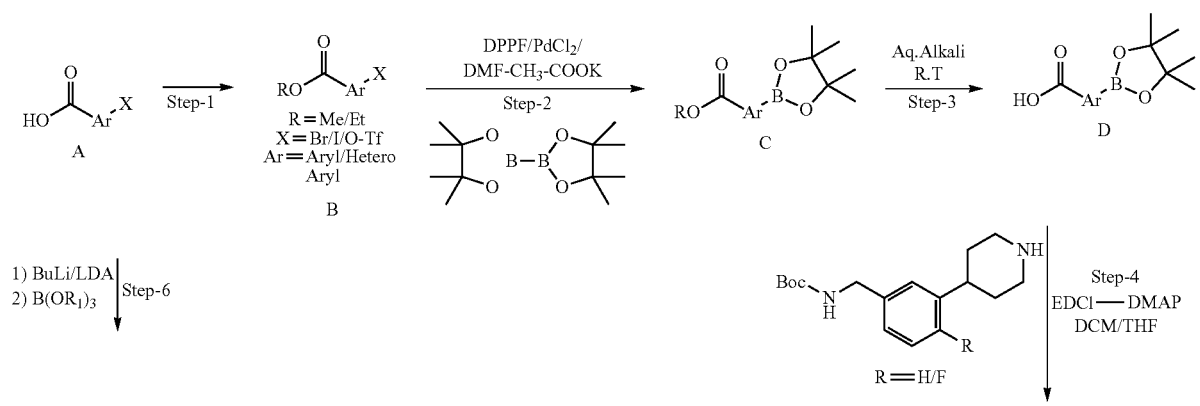

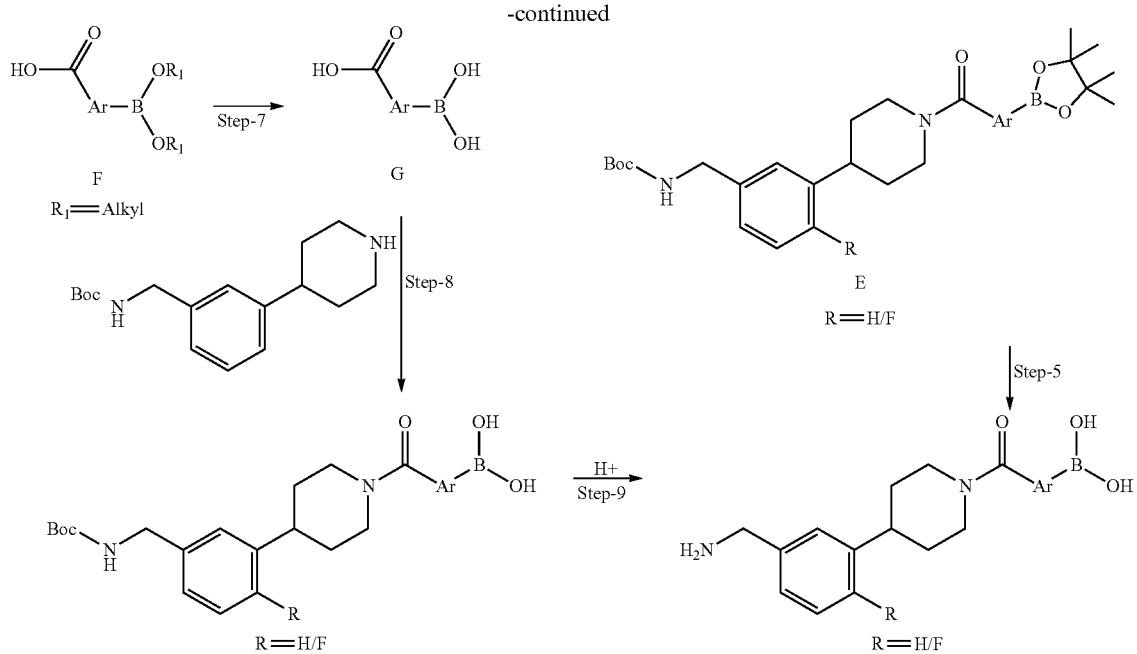

Step 1

Required aryl halo/hydroxy carboxylic acids were esterified by refluxing with excess methanol/ethanol in presence of catalytic sulfuric acid or refluxing the required aryl halo/hydroxy carboxylic acid with thionyl chloride-Methanol/ethanol followed by standard work up involving distillation of excess alcohol and subsequent treatment of residue with aq. sodium bicarbonate followed by extraction with dichloromethane/ethyl acetate. Purification was carried out by column chromatography over 100-200 mesh silica gel using hexane-ethyl acetate.

O-triflate derivatives of hydroxy esters were synthesized as per procedure described in the literature. (*J. Med. Chem.* 53(5), 2010-2037, 2010)

The details of compounds synthesized are as below in Table 10.

TABLE 10

REACTION CONDITIONS & ANALYTICAL DATA

| Comp. No. | Structure | Brief Reaction conditions | Analytical data |
|---|---|---|---|
| B-31 | (TfO-indole-2-carboxylate methyl ester) | 1) Thionyl chloride (1.5 eq.), Methanol (25 vol), 4 h,65° C., 93%<br>2) As per J. Med. Chem. 53(5), 2010-2037, 2010, 81% | Ionization not observed in LCMS<br>$^1$H NMR (400 MHz, CDCl$_3$): δ 9.10 bs, 1H), 7.62 (d, J = 4.0 Hz, 1H), 7.47 (d, J = 8.0 Hz, 1H), 7.28-7.20 (m, 2H), 3.97 (S, 3H) |
| B-62 | (ethyl 2'-bromo-biphenyl-3-carboxylate) | Analogously as per Angew, Chem, Int. Edn. 43(40), 5331-5335, 2004. | Mol. Wt:- 305.17<br>M.I. Peak observed : 306<br>$^1$H NMR (400 MHz, CDCl3): δ 1.40 (t, J = 7 Hz, 3H), 4.35-4.50 (q, J = 7 Hz, 2H), 7.20-7.44 (m, 3H), 7.46-7.56 (m, 1H), 7.61 (d, J = 7.6 Hz, 1H), 7.68 (d, J = 8.0 Hz, 1H), 8.04-8.10 (m, 2H). |
| B-64 | (methyl 2-(3-bromo-4-fluorophenyl)acetate) | Thionyl chloride (1.5 eq.), Methanol (25 vol) , 4 h,65° C., 96% | Mol. Wt:- 247.06<br>M.I. Peak observed : 247, 249.20[MH$^+$] |

TABLE 10-continued

REACTION CONDITIONS & ANALYTICAL DATA

| Comp. No. | Structure | Brief Reaction conditions | Analytical data |
|---|---|---|---|
| B-35 | 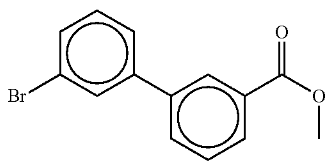 | Thionyl chloride (1.5 eq.), Methanol (25 vol), 4 h, 65° C., 92% | $^1$HNMR (400 MHz, CDCl3) :- 3.9(s,1H), 7.3(t,1H), 7.48(m,3H), 7.68(d,2H), 8.05(d,1H), 8.21(s,1H). |
| B-11F | 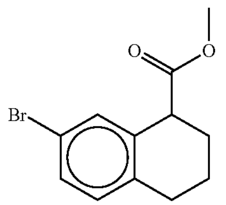 | Synthesized using Lit. Procedures (Helvetica Chimica Acta, 1938, 21, 1519-1520; USP4391816, Bull. Chem. Soc. Japan. 1975, 48, 3356-3366; WO2008/100480 A1 | $^1$HNMR (400 MHz, CDCl3) 4 (s, 3H), 7.66(t, 1H), 7.65(d, 1H), 7.8 (d, 1H) 8.02(d, 1H), 8.23(d, 1H), 9.03 (s, 1H). |
| B-58 | 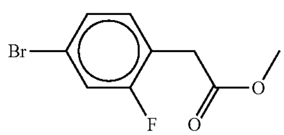 | Thionyl chloride (2 eq.), Methanol (10 vol), 4 h, 65° C., 94% | $^1$HNMR (400 MHz, CDCl3) :- 3.62(s, 2H), 3.72(s, 3H), 7.18(t, 1H), 7.25(d, 2H). |
| B-57 | 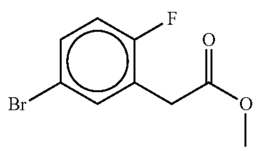 | Thionyl chloride (2 eq.), Methanol (10 vol), 4 h, 65° C., 95% | Mol. Wt:- 247.06 M.I. Peak observed : 247.95, 249 [MH$^+$] |

Step-2

A solution of aryl halo/O-trifluoromethyl sulfonyl carboxylate in common solvents like toluene, dimethyl sulfoxide, dioxane etc was degassed with Argon, to this solution (bis-pinacolato)diboron, Potassium acetate, and Pd(dppf)$_2$Cl$_2$ were added at room temperature and the mixture was heated at 80-100° C. and monitored by TLC & LCMS till starting was consumed to maximum extent. The reaction mixture was then diluted with water and extracted with ethyl acetate, and ethyl acetate extract was evaporated under vacuum to give the crude products that were purified by column chromatography over silica gel (Gradient: 0-10% ethyl acetate in hexane) The details of compounds synthesized by above method are as below in Table 11.

TABLE 11

REACTION CONDITIONS & ANALYTICAL DATA

| Comp. No. | Structure | Brief Reaction conditions | Analytical data |
|---|---|---|---|
| C-31 | 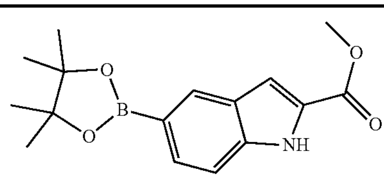 | bispinacoiato diboron (1.5 eq.), PdCl2(dppf) (3 mol %), dppf (3 mol %), Potassium acetate (3.0 eq.), dioxane, 20 hr, 100° C., Yield 54% | Ionization not observed in LCMS, $^1$H NMR (400 MHz, CDCl3): δ 8.97 (bs, 1H), 8.23 (s, 1H), 7.75 (d, J = 8.0 Hz, 1H), 7.41 (d, J = 8.0 Hz, 1H), 7.26-7.22 (m, 1H), 3.95 (s, 3H), 1.37 (s, 12H) |
| C-62 | 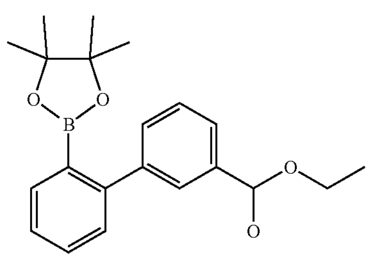 | Ethyl 2'-bromo-[1,1'-biphenyl]-3-carboxylate (1 eq), potassium acetate (3 eq) bispinacolato diboron (10 eq) PdCl2 (dppf).DCM adduct (0.03 eq) DMSO (46 V) 110° C. for 5h. inorganics removed by column Chromatography & carried forward to next step | Ionization not observed in LCMS, $^1$HNMR (400 MHz, CDCl3): δ 1.19 (s, 12H), 1.38 (t, J = 7.2 Hz, 3H), 4.33-4.42 (q, J = 7.1 Hz, 2H), 7.30-7.65 (m, 5H), 7.78 (d, J = 7.2 Hz, 1H), 8.00-8.10 (m, 2H). |

TABLE 11-continued

REACTION CONDITIONS & ANALYTICAL DATA

| Comp. No. | Structure | Brief Reaction conditions | Analytical data |
|---|---|---|---|
| C-64 | 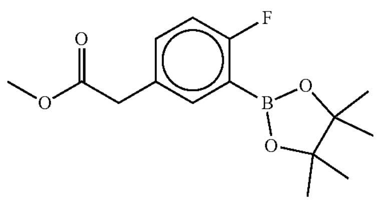 | KOAc (3 eq), Bis Pin. Borane (3 eq), DPPF-PdCl2.DCM( 6 mol %), Toluene (100 vol ), Reflux, 3 hrs. Crude product carried forward to next step without purification as it was sufficient pure. | Mol. Wt:- 294.13 M.I. Peak observed : 295.1 |
| C-35 | 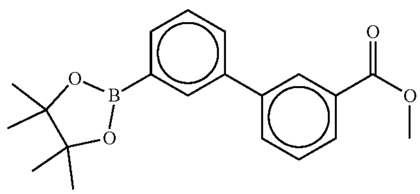 | KOAc(3 eq), Bis Pin. Borane (10 eq), DPPF-PdCl2.DCM (6 Mol %), DMSO (12.5 vol), 80° C., 4 hrs. 65%. | Ionization not observed in LCMS. Crude product carried forward for next step |
| C-11F | 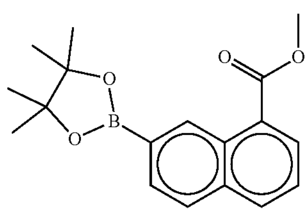 | KOAc(3 eq), Bis Pin. Borane (10 eq), DPPF-PdCl2.DCM (3 Mol %), DMSO (10 vol), 80° C., 5 hrs. 57.8%. | Ionization not observed in LCMS, $^1$H NMR (400 MHz; CDCl3):- δ 1.39(s, 12H), 4.02 (s 3H, 7.52 (t 1H), 7.85-7.93 (m 2H), 8.00 (d, 1H J = 8), 8.13-8.14 (d 1H, J = 6.8), 9.32 (s 1H) |
| C-58 | 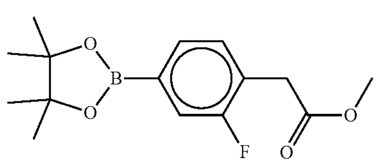 | KOAc (3 eq), Bis Pin. Borane (10 eq.), DPPF-PdCl2.DCM (6 Mol %), DMSO(12.5 vol ), 80° C., 3 hrs, 61%. | Ionization not observed in LCMS. Crude product carried forward for next step. |
| C-57 | 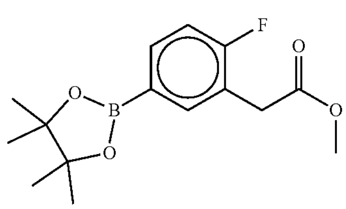 | KOAc (3 eq), Bis Pin. Borane (10 eq), DPPF-PdCl2.DCM(6%), DMSO(12.5 vol ), 80° C., 4 hrs. 65%. | Ionization not observed in LCMS $^1$HNMR (400 MHz, CDCl3) :- 1.32(s,12H), 3.70(m,5H), 7.05(t,1H), 7.70(m,2H). |

Step-3

Boronate ester form step-2 was dissolved in mix of Water and solvents like THF/methanol/Acetone that are miscible in water. To this, lithium hydroxide was added and mixture was stirred at room temperature and monitored by TLC & LCMS till maximum starting was consumed (6-12 hrs required) THF was then concentrated and reaction mass was extracted with ethyl acetate and water. Organic layer was washed with water and combined aq. washings were acidified with 2N HCl and extracted with ethyl acetate. Ethyl acetate extract was dried over sodium sulphate and concentrated in vacuum to get crude product. In most of the cases products were sufficient pure to be used for the next step. The details of compounds synthesized by above method are as below.

The details of compounds synthesized are as below in Table 12.

TABLE 12

REACTION CONDITIONS & ANALYTICAL DATA

| Comp. No. | Structure | Brief Reaction conditions | Analytical data |
|---|---|---|---|
| D-31 | 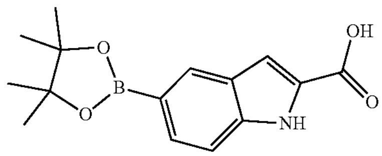 [SMILES: CC1(C)OB(c2ccc3[nH]c(C(=O)O)cc3c2)OC1(C)C] | LiOH (2.0 eq.), THF:H2O (2:1), RT, 90%. | Ionization not observed in LCMS. Crude product used for next step |
| D-62 | 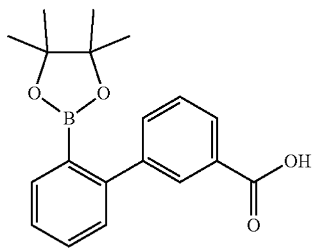 [SMILES: CC1(C)OB(c2ccccc2-c2cccc(C(=O)O)c2)OC1(C)C] | LiOH (3.0 eq.), THF:H2O (1:1), RT, 25%. | Ionization not observed in LCMS, $^1$H NMR (400 MHz, CDCl3): δ 1.12 (s, 12H), 7.24-7.46 (m, 4H), 7.55 (d, J = 7.2 Hz, 1H), 7.71 (d, J = 7.2 Hz, 1H), 8.00 (d, J = 7.6 Hz, 1H), 8.06 (s, 1H). |
| D-64 | 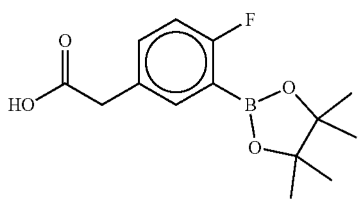 | LiOH (3.0 eq.), THF:H2O (1:1), RT, 4h, 65%. | Mol. Wt:- 280.10 M.I. Peak observed ESMS(-Ve mode) :- 279 |
| D-35 | 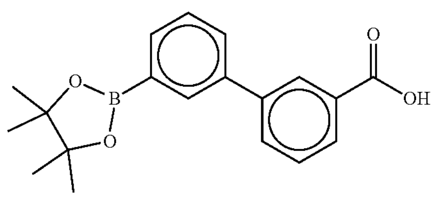 | LiOH (3.0 eq.), THF:H2O (1:1), RT, 4h, 80%. | Mol. Wt:- 324.18 M.I. Peak observed ESMS(-Ve mode) :- 323.52 |
| D-11F | 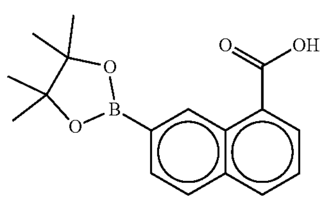 | LiOH (3.0 eq.), THF:H2O (1:1), RT, 8h, 84%.. Purified by column chromatography over silica gel using 0-20% ethyl acetate in n-hexane | Mol. Wt:- 298.14 M.I. Peak observed ESMS(-Ve mode) :- 297.48 |
| D-58 | 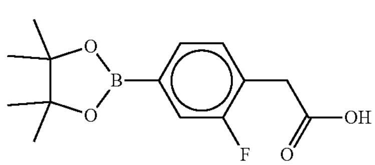 | LiOH (3.0 eq.), THF:H2O (1:1), RT, 8h, 84%. | Ionization not observed in LCMS $^1$HNMR (400 MHz, DMSO-d6) :- 1.35(s,14H), 3.62(s,2H)7.29-7.42(m,2H)7.98(s,1H) |
| D-57 | 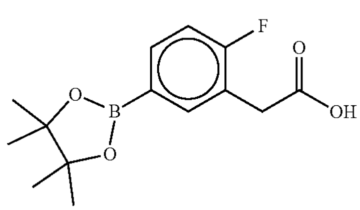 | LiOH (3.0 eq.), THF:H2O (1:1), RT, 8h, 78.8%. | Ionization not observed in LCMS, $^1$HNMR (400 MHz, DMSO-d6) :- 1.35(d,14H),3.70(d,2H), 6.91 (t,1H )7.40(m,1H),7.79(m,1H) |

Step-4

To a stirred solution of carboxylic acid from step-3 in DCM or DMF was added and EDCI, HOBT (in some cases) & DMAP or DIPEA. The solution was stirred for 15 min. at 0° C. followed by addition of desired tert-butyl 3-(piperidin-4-yl) benzylcarbamate. Stirring was continued at room temperature and reaction was monitored by LCMS till maximum, starting materials were consumed. Reaction mixture was then quenched with Water and aq. layer was extracted with dichloromethane and combined organic layers were dried over sodium sulphate and concentrated under vacuum to afford the product which was used for next step without purification. The details of compounds synthesized by above method are as below in Table 13.

TABLE 13

REACTION CONDITIONS & ANALYTICAL DATA

| Comp. No | Structure | Brief Reaction conditions | Analytical data |
|---|---|---|---|
| E-31 | 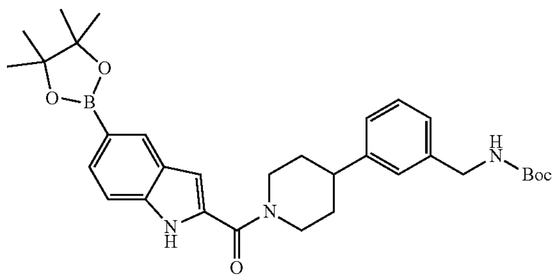 [SMILES: CC(C)(C)OC(=O)NCc1cccc(C2CCN(C(=O)c3cc4cc(B5OC(C)(C)C(C)(C)O5)ccc4[nH]3)CC2)c1] | tert-butyl 3-(piperidin-4-yl) benzyl carbamate (1.0 eq.) EDCI (1.5 eq.), HOBT (1.5 eq.), DIPEA (2.5 eq.), DMF, RT, 15 h, 57% | Mol. Wt:- 559.50 M.I. Peak observed : 582 (M + Na ) $^1$H NMR (400 MHz, CD3OD): δ 8.10, (s, 1H), 7.60 (d, J = 8.0 Hz, 1H), 7.43 (d, J = 8.0 Hz, 1H), 7.30-7.20 (m, 4H), 6.88 (s, 1H), 4.80-4.66 (m, 2H), 4.26-4.15 (m, 2H), 2.96-2.86 (m, 2H), 2.00-1.92 (m, 2H), 1.86-1.72 (m, 2H), 1.45 (s, 9H), 1.36 (s, 12H) |
| E-62 | 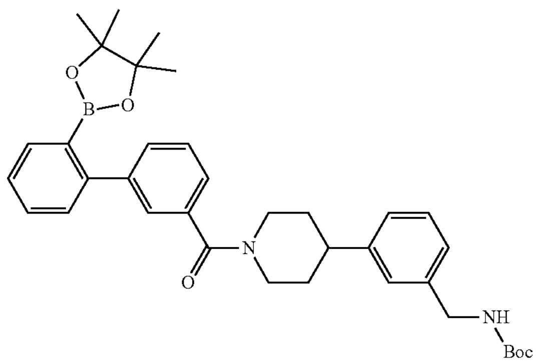 [SMILES: CC(C)(C)OC(=O)NCc1cccc(C2CCN(C(=O)c3cccc(-c4ccccc4B4OC(C)(C)C(C)(C)O4)c3)CC2)c1] | tert-butyl 3-(piperidin-4-yl) benzyl carbamate (1.1 eq.), EDCI (1.5 eq.), DMAP (0.5 eq.), DCM (125 vol), RT, 24 h, 48%. | Mol. Wt:- 596.56 M.I. Peak observed : 619.15 (M + Na ) |
| E-64 | 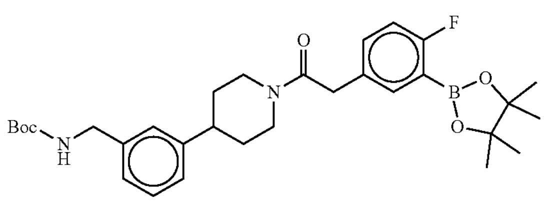 | tert-butyl 3-(piperidin-4-yl) benzyl carbamate (1.1 eq.), EDCI (1.5 eq.), DMAP (1.2 eq.), DCM(100 vol), RT, 4 h, 81% | Mol. Wt:- 552.48 M.I. Peak observed : 575.15 (M + Na ) |
| E-35 | 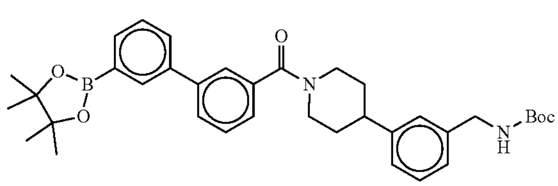 | tert-butyl 3-(piperidin-4-yl) benzyl carbamate (1.1 eq.), EDCI (1.5 eq.), DMAP (1.2 eq.), DCM(1.00 vol), RT, 4 h, 90%, Crude product used for next step | Mol. Wt:- 596.56 M.I. Peak observed : 597.45 |
| E-11F | 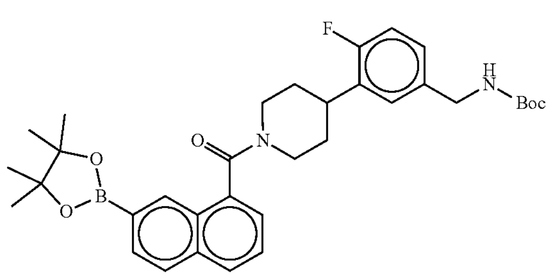 | tert-butyl 4-fluoro-3-(piperidin-4-yl) benzyl carbamate (1.3 eq.), EDCI (1.5 eq.), DMAP (1.2 eq.), DCM(100 vol), RT, 4 h, 86% Crude product used for next step | Mol. Wt:- 588.52 M.I. Peak observed : 589.40 |

TABLE 13-continued

REACTION CONDITIONS & ANALYTICAL DATA

| Comp. No | Structure | Brief Reaction conditions | Analytical data |
|---|---|---|---|
| E-58 | [structure] | tert-butyl 3-(piperdin-4-yl) benzyl carbamate (1.2 eq.), EDCI (1.5 eq.), DMAP (1.2 eq.), DCM(100 vol), RT, 4 h, 81.6%, Crude product used for next step | Mol. Wt:- 552.48 M.I. Peak observed : 575.25 (M + Na ) |
| E-57 | [structure] | tert-butyl 3-(piperidin-4-yl) benzyl carbamate (1.3 eq.), EDCI (1.5 eq.), DMAP (1.2 eq.), DCM(100 vol), RT, 4 h, 98%, Crude product used for next step | Mol. Wt:- 552.48 M.I. Peak observed : 553.55 |
| E-35F | [structure] | tert-butyl 4-fluoro-3-(piperidin-4-yl)benzylcarbamate (1.2 eq.), EDCI (1.5 eq.), DMAP (1.2 eq.), DCM(100 vol), RT, 4 h, 92%, Crude product used for next step. | Mol. Wt:- 614.55 M.I. Peak observed : 615.45 |

Step-5

Products from step-4 were stirred with aq. hydrochloric acid or trifluoracetic acid (TFA) in a co-solvent like Acetonitrile, methanol, THF, DCM etc. Reaction was monitored by LCMS till maximum, starting materials were consumed. Reaction mass was then concentrated in vacuum to remove the solvents and residue obtained was purified by reverse phase preparative HPLC. The pure fraction of mobile phase was lyophilized to get the products as TFA salts.

TFA salts were converted to hydrochloride salts by stirring with 2N HCl for 30 min under nitrogen atmosphere followed by lyophilization.

Sometimes only Boc deprotection observed to be taking place with boronate ester functionality intact. In such cases further hydrolysis of isolated Boc de-protected boronate esters was carried out followed by purification using preparative HPLC.

The details of compounds synthesized are as below in Table 14.

TABLE 14

ANALYTICAL DATA

| Comp. No. | Structure | Brief Reaction conditions | Analytical data |
|---|---|---|---|
| Target-31 | [structure] | Conc. HCl (8.0 eq.), MeOH, 15 h, RT, followed by prep HPLC. Isolated as TFA salt of boronate ester, 50% Converted to hydrochloride by aq. HCl (4.0 eq.), 4 h , RT and lyophilization, 60% | Mol. Wt:- 377.24 LCMS (m/z): 378 [M + 1] HPLC Purity: 93.98% $^1$H NMR (400 MHz, D$_2$O): δ 8.22-8.12 (m, 1H), 7.54-7.28 (m, 6H), 7.04-6.96 (m, 1H), 4.66-4.52 (m, 2H), 4.24-4.10 (m, 2H), 3.50-3.34 (m, 1H), 3.20-2.94 (m, 2H), 2.10-1.70 (m, 4H) |
| Target-62 | [structure] | HCl (5.7 v), MeOH (85V), 24 h, RT, followed by prep HPLC. Isolated as TFA salt, 26%. | Mol. Wt:- 414.3 M.I. Peak observed :415.4 $^1$H NMR DMSO-d6:- $^1$HNMR (400 MHz, DMSO) 1.50-1.95 (br, 4H), 2.80-2.90 (m, 1H), 3.20-3.40 (m, 4H), 3.84 (brs, 1H), 3.95-4.10 (m, 2H), 4.65 (brs, 1H), 7.25-7.55 (m, 10H), 8.00 (s, 2H), 8.10 (brs, 2H) |

TABLE 14-continued

ANALYTICAL DATA

| Comp. No. | Structure | Brief Reaction conditions | Analytical data |
|---|---|---|---|
| Target-64 | 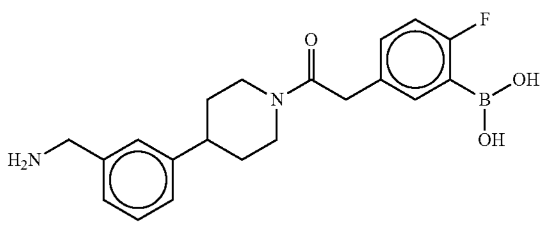 | TFA (10 eq) DCM (65 vol), R.T. 12 hrs, 58% | Mol. Wt.:- 370.22<br>M.I. Peak observed : 371.00<br>HPLC Purity:- 99.09%<br>$^1$H NMR DMSO-d6:- $^1$HNMR (400 MHz, DMSO) 1.36-1.50(m,2H),1.71-1.77(m,2H), 2.60-2.79(m,2H), 3.06-3.13(m,1H), 3,72(s,2H), 3.98-4.08(m,3H), 4.54-4.57(d,1H), 7.03(t,1H), 7.21-7.43(m,6H), 8.29(bs,2H). |
| Target-65 | 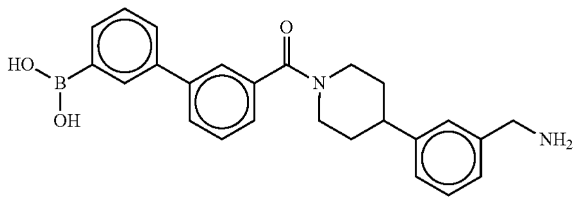 | Conc. HCl (10 vol), THF(66 vol), 15 h, RT, 14.4% | Mol. Wt:- 414.30<br>M.I. Peak observed : 415.05<br>HPLC Purity:- 94.79%<br>$^1$H NMR DMSO-d6:- $^1$HNMR (400 MHz, DMSO) 1.64-1.86 (m,4H),2.84-2.87 (m,2H),3.23(m,2H) 3.65-3.73 (m,1H),3.99-4.01(d,2H), 4.69(bs,1H), 7.29-7.57(m,7H), 7.70-7.80(m,4H), 8.15(bs,1H), 8.24(bs,1H). |
| Target-11F | 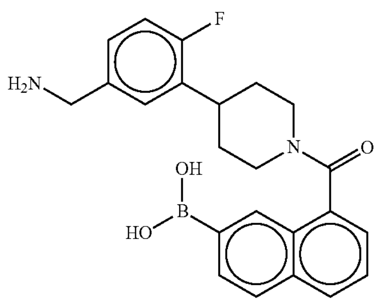 | Conc. HCl (4 vol), THF(66 vol), 15 h, RT, 12.7% | Mol. Wt:- 406.26<br>M.I. Peak observed : 407.30<br>HPLC Purity:- 96.62%<br>$^1$H NMR DMSO-d6:- $^1$HNMR (400 MHz, DMSO) 1.15-1.91(m,4H),2.97-3.47 (m,3H),3.64(t,1H) 4.01(bs,2H), 4.84-4.87(m,1H),7.21(t,1H) 7.37-7.61(m,4H),7.93-7.95(m,3H),8.19-8.34(m,4H D$_2$O exchangable). |
| Target-58 | 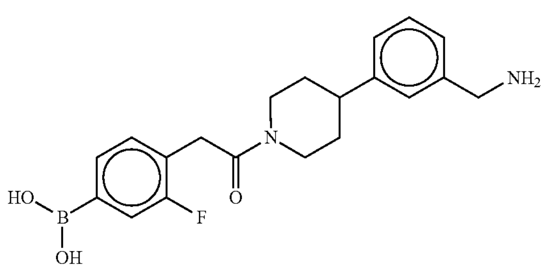 | Conc. HCl (3.75 vol), THF(25 vol), 16 h, RT, 19.2% | Mol. Wt:- 370.23<br>M.I. Peak observed : 371.30<br>HPLC Purity:- 95.81%<br>$^1$H NMR DMSO-d6:- $^1$HNMR (400 MHz, DMSO) 1.46-1.79(m,4H),2.64-3.20 (m,4H), 3.97-4.02(m,2H),4.07-4.10(m,1H),4.52-4.55(d,2H),7.21-7.37(m,5H),7.47-7.55(m,2H), 8.29(bs,4H). |
| Target-57 | 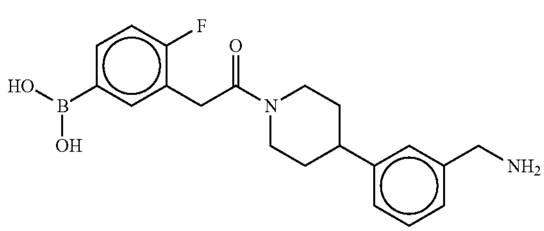 | Conc. HCl (5.7 vol), THF(25 vol), 16 h, RT, 26% | Mol. Wt:- 370.22<br>M.I. Peak observed : 371.30<br>HPLC Purity:- 95.77%<br>$^1$H NMR DMSO-d6:- $^1$HNMR (400 MHz, DMSO) 1.48-1.54(m,2H), 1.77-1.80(d,2H) 2.67(t,1H), 2.80(t,1H), 3.17(t,1H), 3.75(s,2H), 3.99-4.01(q,2H), 4.08-4.12(d,1H), 4.55-4.58(d,1H), 7.11(t,1H), 7.24-7.36(m,4H), 7.67-7.27(m,2H), 8.26(bs,2H). |

TABLE 14-continued

ANALYTICAL DATA

| Comp. No. | Structure | Brief Reaction conditions | Analytical data |
|---|---|---|---|
| Target-35F | 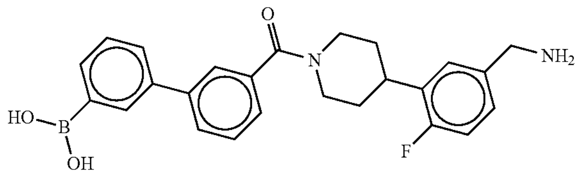 | Conc. HCl (8 vol), THF(25 vol), 16 h, RT, 25.7% | Mol. Wt:- 432.29<br>M.I. Peak observed : 433.40<br>HPLC Purity:- 98.83%<br>$^1$H NMR DMSO-d6:- $^1$HNMR (400 MHz, DMSO) 1.69-1.84(m,4H), 2.93-3.19(m,3H),3.74(bs,1H),3.99-4.01(q,2H), 4.67(bs,1H), 7.21(t,1H), 7.34-7.47(m,3H), 7.54-7.58(m,2H), 7.69-7.80(m,4H), 8.15(bs,2H),8.21(bs,2H). |

Step-6 & 7

Non commercial aryl/hetero aryl carboxy boronic acids were synthesized from corresponding aryl halo carboxylic acids by reaction with LDA & Tri alkyl borate followed by hydrolysis as per method described in the literature (US-patent application 2008/306082; 2008 example 20B)

Step-8

Coupling reaction of aryl boronic acids were carried out as per general procedure described in Step-4 above. The details of compounds synthesized are as below in Table 15.

TABLE 15

ANALYTICAL DATA

| Comp. No. | Structure | Brief Reaction conditions | Analytical data |
|---|---|---|---|
| H-33 | 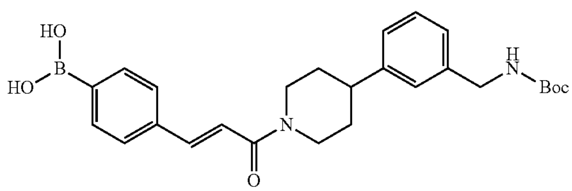 [SMILES: CC(C)(C)OC(=O)NCc1cccc(C2CCN(C(=O)/C=C/c3ccc(B(O)O)cc3)CC2)c1] | tert-butyl 3-(piperidin-4-yl) benzylcarbamate. (1.0 eq.), EDCI (1.5 eq.), HOBT (1.1 eq.), DMAP (1.1 eq.), DCM(100 vol),DMF(2 vol) RT, 2 h, 88%. Crude product was used for next step | Mol. wt:- 464.36<br>M.I. Peak observed : 465.65 |
| H-34 | 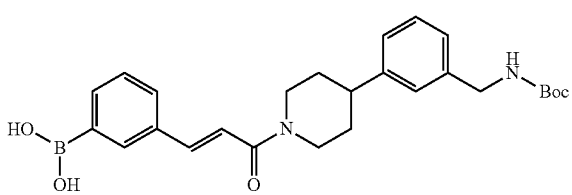 [SMILES: CC(C)(C)OC(=O)NCc1cccc(C2CCN(C(=O)/C=C/c3cccc(B(O)O)c3)CC2)c1] | tert-butyl 3-(piperidin-4-yl) benzylcarbamate. (1.0 eq.), EDCI (1.5 eq.), HOBT (1.1 eq.), DMAP (1.1 eq.), DCM(100 vol),DMF(2 vol) RT, 2 h, 88%, Crude product was used for next step | Mol. Wt:- 464.36<br>M.I. Peak observed : 464.85 |
| H-37 | 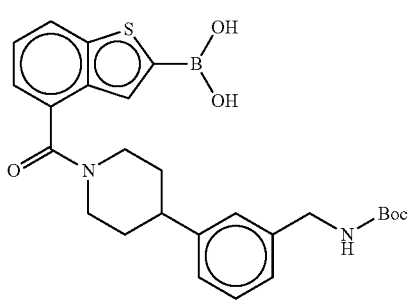 | tert-butyl 3-(piperidin-4-yl) benzylcarbamate. (1.1 eq.), EDCI (1.3 eq.), DMAP (2 eq.), DCM (50 vol), RT, 2 h, 50%, Crude product was used for next step | Mol. Wt:- 494.41<br>M.I. Peak observed : 118.71 (M + Na) |

Step-9

Products from step-8 were stirred with Trifluoro acetic acid in dichloromethane at room temperature and reactions were monitored by TLC & LCMS till maximum, starting materials were consumed. Reaction mass was concentrated in vacuum to remove excess trifluoro acetic acid and dichloromethane. Crude products obtained were purified by reverse phase preparative HPLC. The pure fraction of mobile phase was lyophilized to get the products as TFA salts.

TFA salts were converted to hydrochloride salts by stirring with 2N HCl for 30 min under nitrogen atmosphere followed by lyophilization.

The details of compounds synthesized are as below in Table 16.

TABLE 16

REACTION CONDITIONS & ANALYTICAL DATA

| Comp. No. | Structure | Brief Reaction conditions | Analytical data |
|---|---|---|---|
| Target-33 | (4-boronic acid cinnamoyl piperidine benzylamine structure) | TFA (1.5 eq) DCM (66 vol), R.T. 14 hrs 12% | Mol. Wt:- 364.24 M.I. Peak observed: 364.90 HPLC Purity:- 97.22% $^1$H NMR DMSO-d6:- $^1$HNMR (400 MHz, DMSO) 1.53-1.59(m, 2H), 1.83 (t, 2H), 2.69-2.88(m, 2H), 3.20-3.23(m, 1H), 3.97-4.01(q, 2H), 4.42-4.47(d, 1H), 4.64-4.67(d, 1H), 7.27-7.39 (m, 4H), 7.48-7.52(d, 2H), 7.67-7.69 (d, 2H), 7.80-7.82(d, 2H), 8.23(bs, 4H). |
| Target-34 | (3-boronic acid cinnamoyl piperidine benzylamine structure) | TFA (1.5 eq) DCM (66 vol), R.T. 14 hrs 12% | Mol. Wt:- 364.25 M.I. Peak observed: 364.90 HPLC Purity:- 95.01% $^1$H NMR DMSO-d6:- $^1$HNMR (400 MHz, DMSO) 1.57-1.84(m, 4H), 2.67-2.88 (m, 2H), 3.20-3.23(m, 1H) 3.99-4.01 (q, 2H), 4.41-4.44(d, 1H), 4.65-4.68 (d, 1H), 7.27-7.39(m, 6H), 7.48-7.52 (d, 2H), 7.76(t, 2H), 8.08(bs, 2H), 8.21 (bs, 2H). |
| Target-37 | (benzothiophene boronic acid carbonyl piperidine benzylamine structure) | HCl (10 vol) THF (50 vol), R.T. 5 hrs 40% | Mol. Wt:- 394.29 M.I. Peak observed: 395.00 HPLC Purity:- 97.24% $^1$H NMR DMSO-d6:- $^1$HNMR (400 MHz, DMSO) 1.49-1.91(m, 4H), 2.81-3.19 (m, 4H), 3.42-3.55(m, 2H), 3.99-4.00 (d, 2H), 4.78-4.80(d, 1H), 7.30-7.46 (m, 6H), 8.04-8.06 (d, 2H), 8.34(bs, 2H). |

Method B

Desired halo aryl carboxylic acids were first coupled with tert-butyl 3-(piperidin-4-yl) benzylcarbamate and coupled products were reacted with bis pinacolato diborane to get boronate esters which were hydrolyzed to corresponding boronic acids.

SCHEME 7.

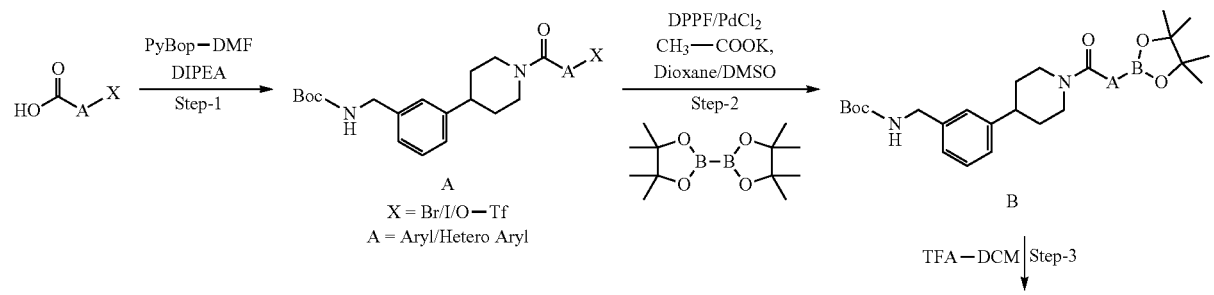

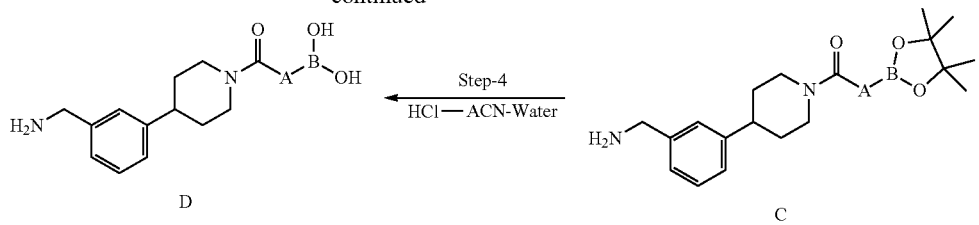

Step-1 tert-butyl 3-(piperidin-4-yl) benzylcarbamate & desired aryl halo carboxylic acids were stirred with PyBop & Di isopropyl ethyl amine in DMF for 24 hrs at room temperature. Reaction mixture was then quenched with water and extracted with ethyl acetate. Ethyl acetate extract was dried over sodium sulfate and concentrated to get the crude product which was purified by column chromatography.

The details of compounds synthesized are as below in Table 17.

TABLE 17

ANALYTICAL DATA

| Comp. No. | Structure | Brief Reaction conditions | Analytical data |
|---|---|---|---|
| A-32 | 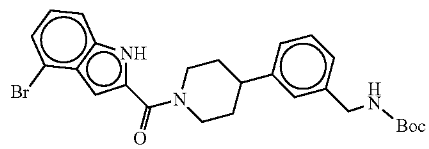 | tert-butyl 3-(piperidin-4-yl) benzyl carbamate (1 eq.) Py Bop(2 eq) in DMF(30 vol) & DIPEA(2.5 eq), 24 h. RT, Yield 93% | Mol. Wt:- 512.4<br>M.I. Peak observed: 512, 514 [MH$^+$]<br>$^1$H NMR DMSO-d6:- $^1$HNMR (400 MHz, DMSO) 1.38 (s, 9H), 1.60-1.95 (m, 4H), 2.80-2.91 (m, 1H), 2.95-3.05 (m, 2H), 4.11 (d, J = 5.6 Hz, 2H), 4.55 (br, 2H), 6.80 (s, 1H), 7.00-7.20 (m, 4H), 7.20-7.40 (m, 3H), 7.44 (d, J = 8.4 Hz, 1H), 12.0 (s, 1H). |
| A-59 | 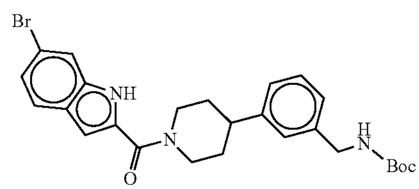 | tert-butyl 3-(piperidin-4-yl) benzyl carbamate (1 eq) Py Bop(2 eq) in DMF(30 vol) & DIPEA(2.5 eq), 24 h. RT , Yield 71% | Mol. Wt:- 512.4<br>M.I. Peak observed: 536 (MH$^+$ + Na)<br>$^1$H NMR DMSO-d6:- $^1$HNMR (400 MHz, DMSO) 1.46 (s, 9H), 1.70-1.90 (m, 2H), 1.95-2.05 (m, 2H), 2.80-2.90 (m, 1H), 3.0-3.4 (brm, 2H), 4.31 (brd, 2H), 4.84 (brd, 2H), 6.78 (s, 1H), 7.10-7.19 (m, 3H), 7.20-7.32 (m, 2H), 7.50 (d, J = 8.4 Hz, 1H), 7.60 (s, 1H), 9.50 (brs, 1H). |
| A-56 | 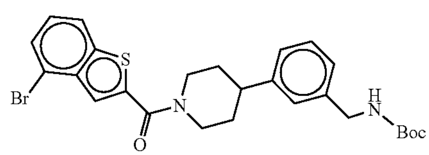 | tert-butyl 3-(piperidin-4-yl) benzyl carbamate (1 eq) Py Bop(2 eq) in DMF(10 vol) & DIPEA(2.5 eq), 24 h. RT , Yield 65% | Mol. Wt.:- 529.5<br>M.I. Peak observed: 529.35, 531 [MH$^+$]<br>$^1$H NMR CDCl3:- $^1$HNMR (400 MHz, CDCl3) 1.43 (s, 1H), 1.70-2.00 (m, 4H), 2.75-2.92 (m, 1H), 3.00-3.40 (br, 2H), 4.30 (d, 2H), 4.40-5.00 (br, 2H), 7.00-7.40 (m, 5H), 7.55 (d, 1H), 7.60 (s, 1H), 7.80 (d, 1H). |

Step-2

Product of step-1, was converted boronate ester by reacting with Bis Pinacolato Borane in presence of Potassium acetate DPPF—PdCl$_2$·DCM by heating in 1,4-dioxane/Dimethyl sulfoxide for 12 hrs. R.M was then concentrated in vacuum and residue was purified by column chromatography.

The details of compounds synthesized are as below in Table 18.

TABLE 18

ANALYTICAL DATA

| Comp. No. | Structure | Brief Reaction conditions | Analytical data |
|---|---|---|---|
| B-32 | 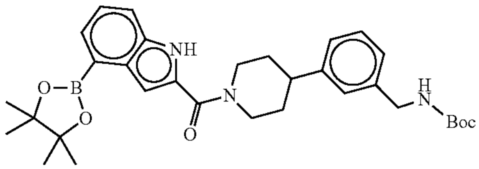 | KOAc (3 eq.), Bis Pin, Borane (10 eq.), DPPF-PdCl2•DCM (Mol. 6%), Dioxane (40 vol), Reflux, 12 hrs. inorganics removed by column Chromatography & carried forward to next step | Mol. Wt:- 559.5 M.I. Peak observed: 560 |
| B-59 | 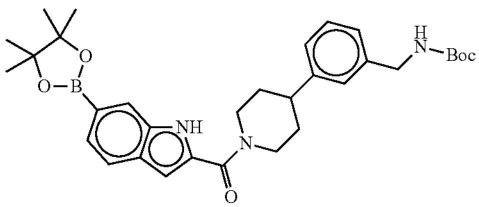 | KOAc(3 eq.), Bis Pin. Borane (10 eq.), DPPF-PdCl2•DCM (Mol. 3%), DMSO(35 vol), 80° C. deg, 12 hrs. purified Column Chromatography, Yield 59% | Mol. Wt:- 559.5 M.I. Peak observed: 560 $^1$H NMR CDCl3:- $^1$HNMR (400 MHz, CDCl3) 1.37 (s, 12H), 1.46 (s, 9H), 1.71-1.35 (m, 2H), 1.95-2.05 (m, 2H), 2.80-2.91 (m, 1H), 3.01-3.30 (brm, 2H), 4.30 (brd, 2H), 4.84 (brd, 2H), 6.80 (s, 1H), 7.10-7.20 (m, 3H), 7.27-7.32 (m, 1H), 7.56 (d, J = 8.4 Hz, 1H), 7.64 (d, J = 8.0 Hz, 1H), 7.92 (s, 1H), 9.11 (brs, 1H). |
| C-56 | 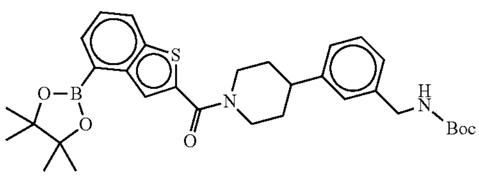 | KOAc(3 eq), Bis Pin. Borane (10 eq), DPPF-PdCl2•DCM (Mol 3%), Dioxane (200 vol), 110° C. deg, 12 hrs. purified by Column Chromatography, Yield 74% | Mol. Wt:- 576.6 M.I. Peak observed: 599.15 (M + Na) $^1$H NMR CDCl3:- $^1$HNMR (400 MHz, CDCl3) 1.23 (s, 12H), 1.38 s, 9H, 1.70-2.00 (m, 4H), 2.77-2.90 (m, 1H), 2.91-3.50 (br, 2H), 4.31 (brs, 2H), 4.50-5.20 (br, 2H), 7.10-7.45 (m, 5H), 7.50-7.70 (m, 1H), 7.85-8.00 (m, 1H), 8.23 (s, 1H). |

Step-3

Products of step-2 were stirred with trifluoro acetic acid in dichloromethane at room temp. Reaction mass was then concentrated in vacuum and used for next step without purification. The details of compounds synthesized are as below in Table 19.

TABLE 19

ANALYTICAL DATA

| Comp. No. | Structure | Brief Reaction conditions | Analytical data |
|---|---|---|---|
| C-32 | 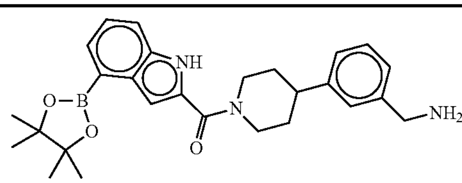 | TFA (3 vol) DCM (100 vol), R.T. 24 hrs subjected to next step without purification | Mol. Wt:- 459.4 M.I. Peak observed: 460 |
| C-59 | 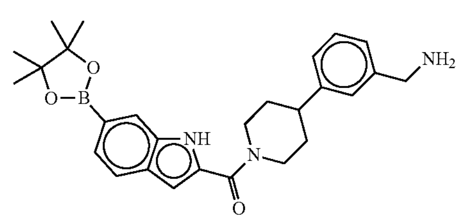 | TFA (2 Vol) DCM (200 Vol), R.T. 24 hrs subjected to next step without purification | Mol. Wt:- 459.4 M.I. Peak observed: 460 |

TABLE 19-continued

ANALYTICAL DATA

| Comp. No. | Structure | Brief Reaction conditions | Analytical data |
|---|---|---|---|
| C-56 | (structure) | TFA (7.5 Vol) DCM (100 vol), R.T. 24 hrs subjected to next step without purification | Mol. Wt:- 476.6<br>M.I. Peak observed: 477 |

Step-4

Products of step-3 were stirred with conc. HCl, acetonitrile & water for about 5 hrs under nitrogen atmosphere. There after reaction mass was concentrated in vacuum and crude boronic acid was purified by preparative HPLC. Products were isolated either as TFA salts or acetate salts depending on the buffer used during purification by prep HPLC. The details of compounds synthesized are as below in Table 20.

TABLE 20

ANALYTICAL DATA

| Comp. No. | Structure | Brief Reaction conditions | Analytical data |
|---|---|---|---|
| Target-32 | (structure) | Conc. HCl (3 eq) ACN:Water 1:1 200 vol. R.T. 5 hrs. and prep purification isolated as acetate salt, Yield, 41% | Mol. Wt:- 377.2<br>M.I. Peak observed: 378<br>HPLC Purity:- 96.55 % (220 nm)<br>$^1$H NMR CD$_3$CN + D$_2$O:- $^1$HNMR (400 MHz, CD$_3$CN + D$_2$O) 1.80-1.91 (m, 2H), 1.94 (s, 3H, acetate), 2.05-2.15 (m, 2H), 3.00-3.10 (m, 1H), 3.20-3.50 (brm, 2H), 4.15 (s, 2H), 4.80 (brd, 2H), 7.35-7.52 (m, 6H), 7.65 (d, J = 6.8 Hz, 1H), 7.70 (d, J = 8.0 Hz, 1H). |
| Target-59 | (structure) | Conc. HCl (3 eq) ACN:Water 1:1 200 vol. R.T. 5 hrs. and prep purification isolated as acetate salt, Yield 17% | Mol. Wt:- 377.2<br>M.I. Peak observed: 378<br>HPLC Purity:- 97.3% (220 nm)<br>$^1$H NMR CD$_3$CN + D$_2$O:- $^1$HNMR (400 MHz, CD$_3$CN + D$_2$O) 1.80-1.90 (m, 2H), 1.94 (s, 3H, acetate), 2.05-2.15 (m, 2H), 3.00-3.10 (m, 1H), 3.20-3.50 (brm, 2H), 4.15 (s, 2H), 4.75 (brd, 2H), 6.97 (s, 1H), 7.35-7.52 (m, 4H), 7.61 (d, J = 8.0 Hz, 1H), 7.75 (d, J = 8.0 Hz, 1H), 8.06 (s, 1H) |
| Target-56 | (structure) | Conc. HCl (3 eq) ACN: Water 1:1 200 vol. R.T. 5 hrs. and prep purification isolated as TFA salt, Yield 15% | Mol. Wt:- 394.3<br>M.I. Peak observed: 395<br>HPLC Purity:- 97.37% (220 nm)<br>$^1$H NMR DMSO-d6:- $^1$HNMR (400 MHz, DMSO) 1.60-1.95 (br, 4H), 2.85-2.95 (m, 1H), 3.25-3.40 (br, 4H), 3.95-4.10 (m, 2H), 4.30-4.70 (br, 2H), 7.22-7.48 (m, 5H), 7.83 (d, J = 6.8 Hz, 1H), 8.05 (d, J = 8.0 Hz, 1H), 8.15 (s, 1H), 8.41 (br, 2H). |

Example 8: Synthesis of tryptase inhibitors with phenolic hydroxy functionality

Method C

Desired dimethoxy analogues of carboxylic acids were first coupled with tert-butyl 3-(piperidin-4-yl) benzylcarbamate and coupled products were de-methylated using boron tribromide.

2-(6-oxo-6H-[1,3]dioxolo[4,5-g]chromen-8-yl)acetic acid, required for targets 97 was synthesized by Pechmann reaction of Sesamol & diethyl 3-oxopentanedioate using toluene as a solvent and following the procedure described in the literature for analogous substrate (*Chemistry Letters*, 2, 110-111, 2001)

6,7-dimethoxy-2-oxo-2H-chromene-3-carboxylic acid & 7,8-dimethoxy-2-oxo-2H-chromene-3-carboxylic acid required for target-100 & 102 were prepared by the reaction of Meldrums acid with 2-hydroxy-4,5-dimethoxybenzaldehyde or 2-hydroxy-3,4-dimethoxybenzaldehyde in water at 75° C. for 2 hrs. Precipitated products were sufficient pure to be used for the next step. Required aldehydes for this were prepared from corresponding trimethoxy benzaldehydes by demethylation using AlCl$_3$ in benzene (*JOC*, 54, 4112, 1989)

SCHEME 8.

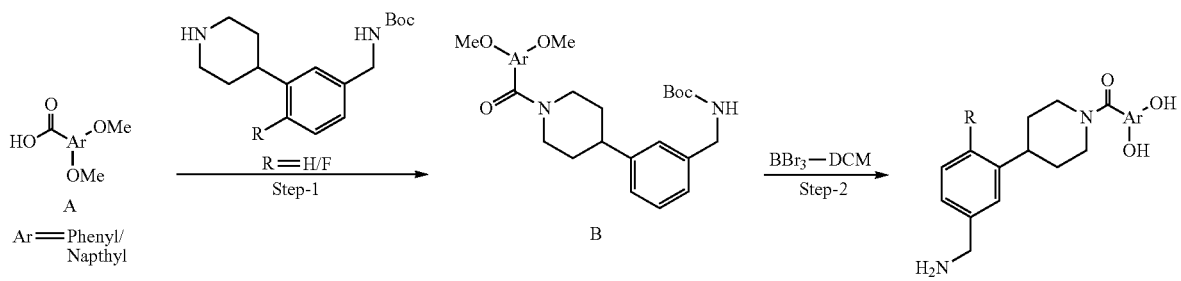

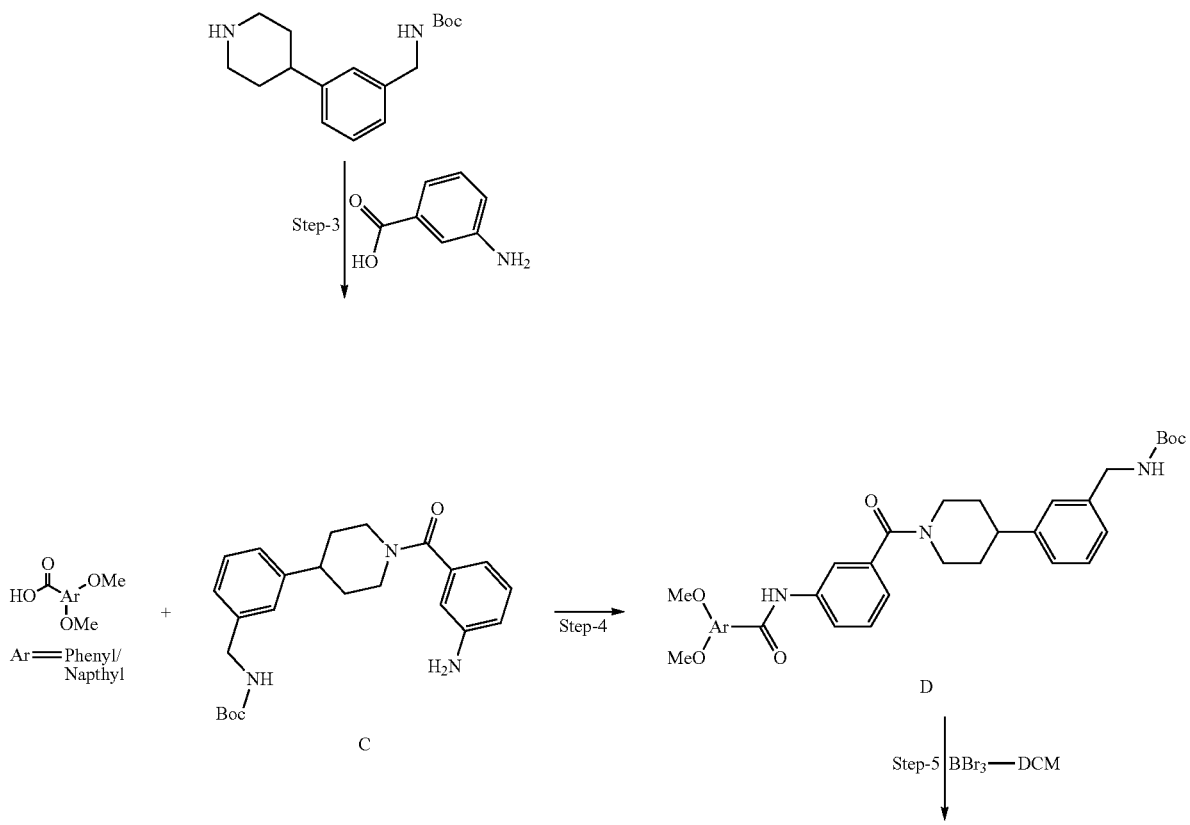

-continued

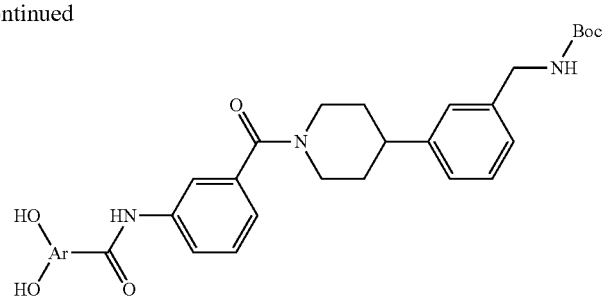

Step-1

These reactions were performed as per general procedure described in method-A (step-4) or method-B (step-1). The details of compounds synthesized are as below in Table 20.

Crude products were used for next step without purification.

TABLE 20

ANALYTICAL DATA

| Comp. No. | Structure | Brief Reaction conditions | Analytical data |
|---|---|---|---|
| B-28 | 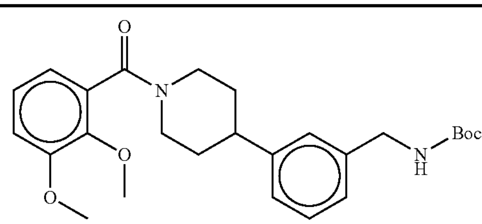 | Common core (1.1 eq.), EDCI (1.5 eq.), DMAP (1.2 eq.), DCM(85 vol), RT, 4 h, 42% | Mol. Wt:- 454.56<br>M.I. Peak observed:- 455.40<br>Crude product used for next step |
| B-27-F | 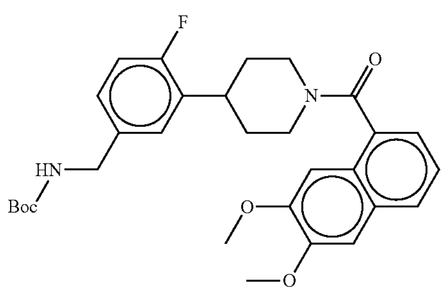 | Common core (1 eq.), EDCI (1.5 eq.), DMAP (1.2 eq.), DCM(85 vol), RT, 4 h, 89% | Mol. Wt:- 522.61<br>M.I. Peak observed:- 545.10(M + Na)<br>Crude product used or next step |
| B-68 | 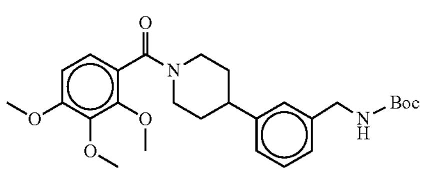 | Common core (1.1 eq.), EDCI (1.5 eq.), DMAP (1.2 eq.), DCM(85 vol), RT, 4 h, 93% | Mol. Wt:- 484.28<br>M.I. Peak observed:- 485.40<br>Crude product used for next step |
| B-69 | 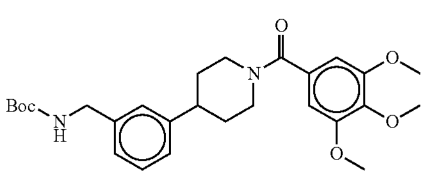 | Common core (1.1 eq.), EDCI (1.5 eq.), DMAP (1.2 eq.), DCM(85 vol), RT, 4 h, 96% | Mol. Wt:- 484.28<br>M.I. Peak observed:- 485.40<br>Crude product used for next step |
| B-77 | 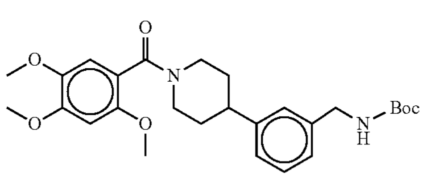 | Common core (1.1 eq.), EDCI (1.5 eq.), DMAP (1.2 eq.), DCM(85 vol), RT, 4 h, 89.4% | Mol. Wt:- 484.58<br>M.I. Peak observed:- 485.00<br>Crude product used for next step |

TABLE 20-continued

ANALYTICAL DATA

| Comp. No. | Structure | Brief Reaction conditions | Analytical data |
|---|---|---|---|
| B-78 | 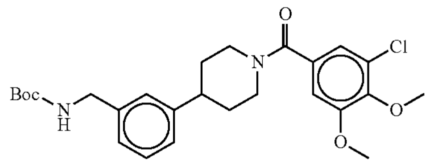 | Common core (1.1 eq.), EDCI (1.5 eq.), DMAP (1.2 eq.), DCM(85 vol), RT, 4 h, 89.5% | Mol. Wt:- 489.00<br>M.I. Peak observed:-<br>512(M + Na)<br>Crude product used for next step |
| B-43 | 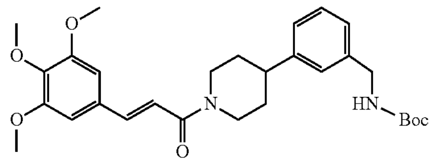 [SMILES: COc1cc(/C=C/C(=O)N2CCC(c3cccc(CNC(=O)OC(C)(C)C)c3)CC2)cc(OC)c1OC] | (E)-3-(3,4,5-trimethoxy phenyl) acrylic acid (1 eq.), tert-butyl 3-(piperidln-4-yl) benzylcarbamate (1 eq.), Pybop (2 eq.), DIPEA (2.5 eq.), DMF (5 V), 24 h, RT, 63%. | Mol. Wt:- 510.62<br>M.I. Peak observed:- 533 (M + Na)<br>$^1$H NMR (400 MHz, CDCl3): □ 1.46 (s, 9H), 1.65-1.80 (m, 2H), 1.90-2.05 (m, 2H), 2.72-2.85 (m, 1H), 3.10-3.50 (br, 2H), 3.88 (s, 3H), 3.90 (s, 6H), 4.30 (d, J = 5.2 Hz, 2H), 4.75-5.00 (br, 2H), 6.75 (s, 2H), 6.82 (d, J = 15 Hz, 1H), 7.09-7.20 (m, 3H), 7.26-7.32 (m, 1H), 7.60 (d, J = 15 Hz, 1H). |
| B-97 | 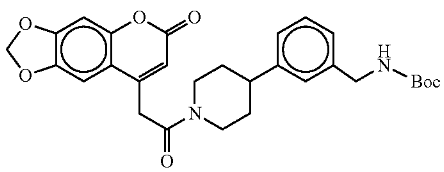 | 2-(6-oxo-6H-[1,3]dioxolo[4,5-g]chromen-8-yl)acetic acid (1 eq) tert-butyl 3-(piperidin-4-yl) benzylcarbamate (1 eq.), EDCI (2 eq.), DMAP (0.5 eq.), DCM (20 V), 12 h, RT, 86%. | Mol. Wt:- 520.57<br>M.I. Peak observed:-543 (M + Na) |
| B-100 | 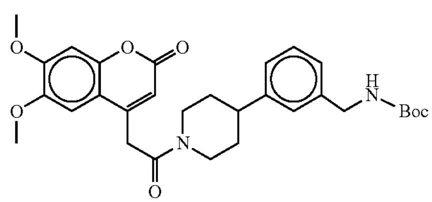 | 6,7-dimethoxy-2-oxo-2H-chromene-3-carboxylic add (1 eq) tert-butyl 3-(piperidin-4-yl) benzylcarbamate (1 eq.), EDCI (1.5 eq.), DMAP (0.5 eq.), DCM (100 V), 12 h, RT, 80%. | Mol. Wt:- 522.59<br>M.I. Peak observed:- 523 |
| B-102 | 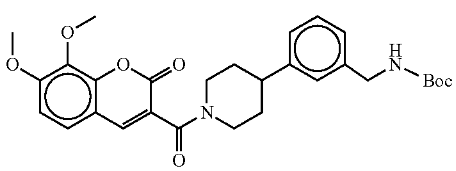 | 7,8-dimethoxy-2-oxo-2H-chromene-3-carboxylic acid (1 eq) tert-butyl 3-(piperidin-4-yl) benzylcarbamate (1.2 eq.), EDCI (1.5 eq.), DMAP (0.5 eq.), DCM (66 vol), 12 h, RT, 80.6%. | Mol. Wt:- 522.59<br>M.I. Peak observed:- 523<br>$^1$H NMR (400 MHz, DMSO-d6): 1.39 (s, 9H), 1.50-1.90 (m, 4H), 2.60-2.90 (m, 2H), 3.10-3.25 (m, 1H), 3.84 (s, 3H), 3.92 (s, 3H), 4.09 (s, 2H), 4.29 (brd, 1H), 4.59 (brd, 1H), 7.00-7.55 (m, 6H), 8.02 (s, 1H), 3.13 (s, 1H). |

Step-2

Product from step-1 was dissolved in dichloromethane and the solution was cooled to 0° C. Boron tribromide (3 eq) was added and reaction mass was gradually warmed to room temperature. Stirring was continued at room temperature and reaction was monitored by TLC & LCMS till maximum starting was consumed (1-8 hrs required). Reaction mass was then concentrated and excess BBr3 was removed by multiple strippings of methanol. Residue containing crude product as hydrobromide was purified by reverse phase preparative HPLC. Pure product isolated as TFA salts were converted to hydrochloride by dissolving in 2N hydrochloric acid followed by lyophilization to get the title compounds as hydrochloride salts.

The details of compounds synthesized are as below in Table 21.

TABLE 21

ANALYTICAL DATA

| Comp. No. | Structure | Brief Reaction conditions | Analytical data |
| --- | --- | --- | --- |
| Target-28 | 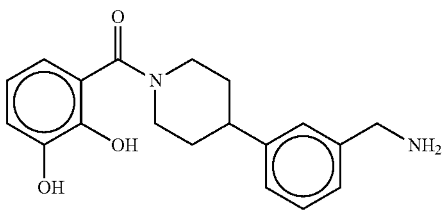 | BBr$_3$ (3 eq) DCM (85 vol), R.T. 2 hrs, 42% | Mol. Wt:- 326.39<br>M.I. Peak observed:- 327.25<br>HPLC Purity:- 99. 42<br>$^1$H NMR DMSO-d6:- 1.53-1.75(m, 4H), 2.76-2.82(m, 4H), 3.9-4.0(q, 2H), 6.56(d, 1H), 6.67(t, 1H), 6.80(d, 1H), 7.24-7.38(m, 4H), 8.32(bs, 2H-D$_2$O exchangable). |
| Target-27-F | 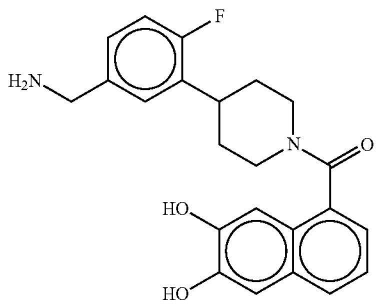 | BBr$_3$ (3 eq) DCM (85 vol), R.T. 2 hrs, 16% | Mol. Wt:- 394.43<br>M.I. Peak observed: 395.30<br>HPLC Purity:- 96.75<br>$^1$H NMR DMSO-d6:- $^1$HNMR (400 MHz, DMSO) 1.53-1.88(m, 4H), 2.91-3.33(m, 4H), 4.0(bs, 2H), 4.82(m, 1H), 6.99(s, 1H), 7.15-7.36(m, 5H), 7.59-7.64(m, 2H), 7.82-7.84(d, 1H-D$_2$O exchangable), 8.34-8.43(m, 2H-D$_2$O exchangable). |
| Target-68 | 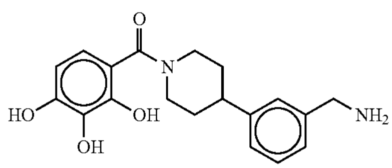 | BBr$_3$ (3 eq) DCM (85 vol), R.T. 2 hrs, 22% | Mol. Wt:- 342.38<br>M.I. Peak observed:- 343.20<br>HPLC Purity:- 97.94<br>$^1$H NMR CD$_3$OD:- 1.75-1.94(m, 4H), 2.90-3.31(m, 4H), 4.10(s, 2H), 4.35(bs, 1H), 6.43(d, 1H, J = 8.4 Hz), 6.66(d, 1H, J = 8.4 Hz), 7.29-7.41(m, 4H). |
| Target-69 | 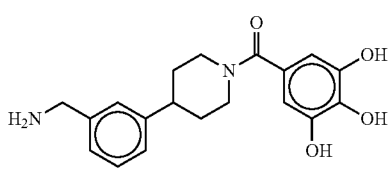 | BBr$_3$ (3 eq) DCM (85 vol), R.T. 2 hrs, 23.6% | Mol. Wt:- 342.38<br>M.I. Peak observed:- 343.25<br>HPLC Purity:- 97.41<br>$^1$H NMR CD$_3$OD:- 1.75-1.94 (m, 4H), 2.90-3.31(m, 4H), 4.10(s, 2H), 6.47(s, 2H), 7.03-7.38(m, 4H). |
| Target-77 | 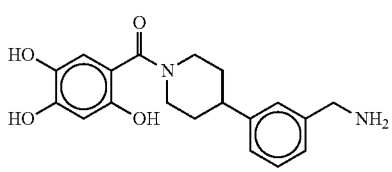 | BBr$_3$ (3 eq) DCM (85 vol), R.T. 2 hrs, 22.7% | Mol. Wt:- 342.38<br>M.I. Peak observed:- 343.25<br>HPLC Purity:- 99.73<br>$^1$H NMR DMSO-d6:- 1.54-1.60(m, 2H), 1.74-1.77(d, 4H), 2.75-2.96(m, 4H), 3.96-4.14(m, 2H), 6.34(s, 1H), 6.54(s, 1H), 7.24-7.39(4H), 8.34(bs, 3H). |
| Target-78 | 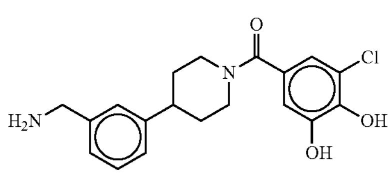 | BBr$_3$ (3 eq) DCM (85 vol), R.T. 2 hrs, 34% | Mol. Wt:- 360.83<br>M.I. Peak observed:- 361.20<br>HPLC Purity:- 99.91<br>$^1$H NMR DMSO-d6:- 1.57-1.79(m, 4H), 2.78-2.84(m, 4H), 3.98-4.02(q, 3H), 6.85(s, 2H), 7.28-7.42(m, 4H), 8.28(bs, 3H), 9.57(bs, 1H), 10.14(bs, 1H). |
| Target-43 | 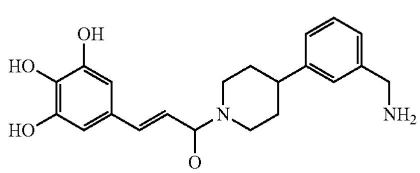 [SMILES: NCc1cccc(C2CCN(C(O)/C=C/c3cc(O)c(O)c(O)c3)CC2)c1] | BBr3 (1M in DCM, 5 eq.), DCM (100 Vol), 24 h, RT, 15%. | Mol. Wt:- 368.43<br>M.I. Peak observed:- 369<br>HPLC Purity:- 99.49%<br>$^1$H NMR (400 MHz, DMSO-d6): δ 1.55 (brs, 2H), 1.80 (brs, 2H), 2.79-2.88 (m, 1H), 3.10-3.40 (br, 2H), 3.95-4.20 (m, 2H), 4.30-4.70 (br, 2H), 6.62 (s, 2H), 6.89 (d, J = 15.2 Hz, 1H), 7.20-7.40 (m, 5H), 8.11 (brs, 2H), 8.64 (brs, 1H), 8.97 (brs, 2H). |

TABLE 21-continued

ANALYTICAL DATA

| Comp. No. | Structure | Brief Reaction conditions | Analytical data |
|---|---|---|---|
| Target-97 | (structure: 6,7-dihydroxycoumarin-CH2-C(O)-N-piperidine-phenyl-CH2-NH2) | BBr3 (1M in DCM, 4 eq.), DCM (66 Vol), 12 h, RT, 15%. Isolated as TFA salt, Yield:- 20% | Mol. Wt:- 408.45<br>M.I. Peak observed:- 409<br>HPLC: 98.37% (220 nm)<br>$^1$H NMR (400 MHz, CD$_3$OD): δ 1.60-2.0 (m, 4H), 2.78-3.0 (m, 2H), 3.30-3.45 (brm, 1H, merged in solvent peak), 3.90-4.10 (m, 2H), 4.11 (s, 2H), 4.12 (br, 1H), 4.60-4.80 (brd, 1H), 6.14 (s, 1H), 6.78 (s, 1H), 7.04 (s, 1H), 7.28-7.50 (m, 4H). |
| Target-100 | (structure: 6,7-dihydroxycoumarin-3-C(O)-N-piperidine-phenyl-CH2-NH2) | BBr3 (1M in DCM, 4 eq.), DCM (100 Vol), 12 hr, RT, Isolated as TFA salt; yield:- 19.4% | Mol. Wt:- 394.42<br>M.I. Peak observed:- 395.25<br>HPLC: 98.83% (220 nm)<br>$^1$H NMR (400 MHz, CD$_3$OD): δ 1.70-2.00 (m, 4H), 2.35-3.00 (m, 2H), 3.75-3.75 (brd, 1H), 4.10 (s, 2H), 4.70-4.80 (brd, 2H), 6.80 (s, 1H), 7.02 (s, 1H), 7.26-7.44 (m, 4H), 7.95 (s, 1H). |
| Target-102 | (structure: 7,8-dihydroxycoumarin-3-C(O)-N-piperidine-phenyl-CH2-NH2) | BBr3 (1M in DCM, 4 eq.), DCM (80 Vol), 12 hr, RT, isolated as TFA salt; yield:- 25% | Mol. Wt:- 394.42<br>M.I. Peak observed:- 395.25<br>HPLC: 99.27% (220 nm)<br>$^1$H NMR (400 MHz, CD$_3$OD): δ 1.77-1.99 (m, 4H), 2.92-2.98 (m, 2H), 3.31(brs, 1.0 merged in solvent peak), 3.81-3.85 (m, 1H), 4.11 (brs, 2H), 4.76 (brs, 1H, merged in solvent water peak), 6.87 (d, J = 8.4 Hz, 1H), 7.09 (d, J = 8.4 Hz, 1H), 7.29-7.42 (m, 4H), 7.98 (brs, 1H) |

Step-3

Reaction was performed as per General procedure described in method-A (step-4)

Reaction details and analytical data is as below in Table 22.

TABLE 22

ANALYTICAL DATA

| Comp. No. | Structure | Brief Reaction conditions | Analytical data |
|---|---|---|---|
| C | (structure: H2N-phenyl-CH(O-)-piperidine-phenyl-CH2-NH-Boc) | tert-butyl 3-(piperidin-4-yl) benzyl carbamate (1 eq.), EDCI (1.5 eq.), DMAP (1.2 eq.), DCM(85 vol), RT, 4 h, 99% | Step-3:-<br>Mol. Wt:- 409.24<br>M.I. Peak observed:- 432.05(M + Na)<br>Crude product used for next step |

These reactions were performed as per General procedure described in Step-4 (method A); the details of compounds synthesized are as below in Table 23.

TABLE 23

ANALYTICAL DATA

| Comp. No. | Structure | Brief Reaction conditions | Analytical data |
|---|---|---|---|
| D-70 | 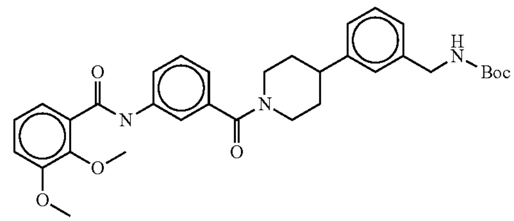 | Step-4:- 2,3-dimethoxy benzoic acid (1 eq.), EDCI (1.5 eq.), DMAP (1.2 eq.), DCM(85 vol), RT, 4 h, 79.5% | Step-4:-<br>Mol. Wt:- 573.68<br>M.I. Peak observed:- 574.50<br>Crude product used for next step |
| D-71 | 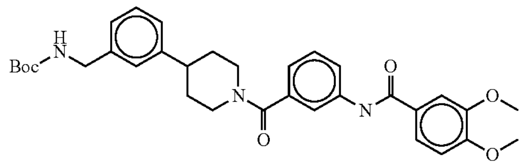 | Step-4:- 3,4-dimethoxy benzoic acid (1 eq.), EDCI (1.5 eq.), DMAP (1.2 eq.), DCM(85 vol), RT, 4 h, 81.6% | Step-4:-<br>Mol. Wt:- 573.68<br>M.I. Peak observed:-<br>596.15(M + Na)<br>Crude product used for next step |

Step-5

These reactions were performed as per General procedure described in Step-2 above. The details of compounds synthesized are as below in Table 24.

TABLE 24

ANALYTICAL DATA

| Comp. No. | Structure | Brief Reaction conditions | Analytical data |
|---|---|---|---|
| Target-70 | 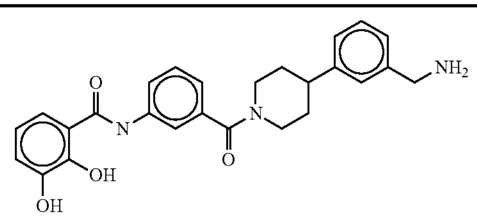 | $BBr_3$ (3 eq) DCM (85 vol), R.T., 2 hrs, Compound purified by prep HPLC yield:- 21% | Mol. Wt.:- 445.51<br>M.I. Peak observed:- 446.40<br>HPLC Purity:- 99.41<br>$^1$H NMR DMSO-d6:- 1.63-1.86(m, 4H), 2.82-3.29(m, 3H), 3.78(bs, 1H), 4.00-4.01(q, 2H), 4.63(bs, 1H), 6.77(t, 1H), 6.98-7.00(d, 1H, J = 7.2 Hz), 7.18-7.20(d, 1H, , J = 7.6 Hz), 7.31-7.47(m, 5H), 7.71-7.73(d, 1H), 7.84(s, 2H), 8.23(bs, 2H), 9.47(bs, 1H), 10.47(bs, 1H), 11.42(s, 1H). |
| Target 71 | 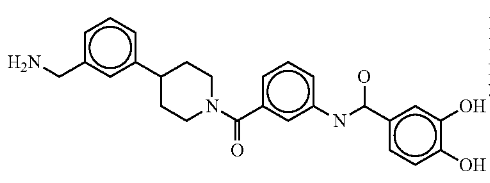 | $BBr_3$ (3 eq) DCM (85 vol), R.T., 2 hrs, Compound purified by prep HPLC yield:- 16.7% | Mol. Wt:- 445.51<br>M.I. Peak observed:- 446.35<br>HPLC Purity:- 98.41<br>$^1$H NMR DMSO-d6:- 1.61-1.86(m, 4H), 2.82-3.19(m, 3H), 3.75(s, 1H), 3.98-4.02(q, 2H), 4.63(bs, 1H), 6.82-6.84(d, 1H, J = 8.4 Hz), 7.09-7.11(d, 1H, , J = 7.6 Hz), 7.28-7.42(m, 7H), 7.76-7.78(d, 1H), 7.90(s, 1H), 8.26(bs, 2H), 9.27(bs, 1H), 9.69(bs, 1H), 10.09(s, 1H). |

Method D

Desired carboxylic acid (A) was coupled with tert-butyl 3-(piperidin-4-yl) benzylcarbamate followed by deprotection of Boc functionality.

2-(7,8-dihydroxy-4-methyl-2-oxo-2H-chromen-3-yl)acetic acid required for Target-101 was synthesized Pechmann reaction of Pyrogallol & Diethyl acetyl succinate using toluene as a solvent and following the procedure described in the literature for analogous substrate i.e. resorcinol (*Chemistry Letters*, 2, 110 111, 2001)

Some halo analogues of the Boronic acids in method-A were also synthesized by this approach.

SCHEME 9.

Method D

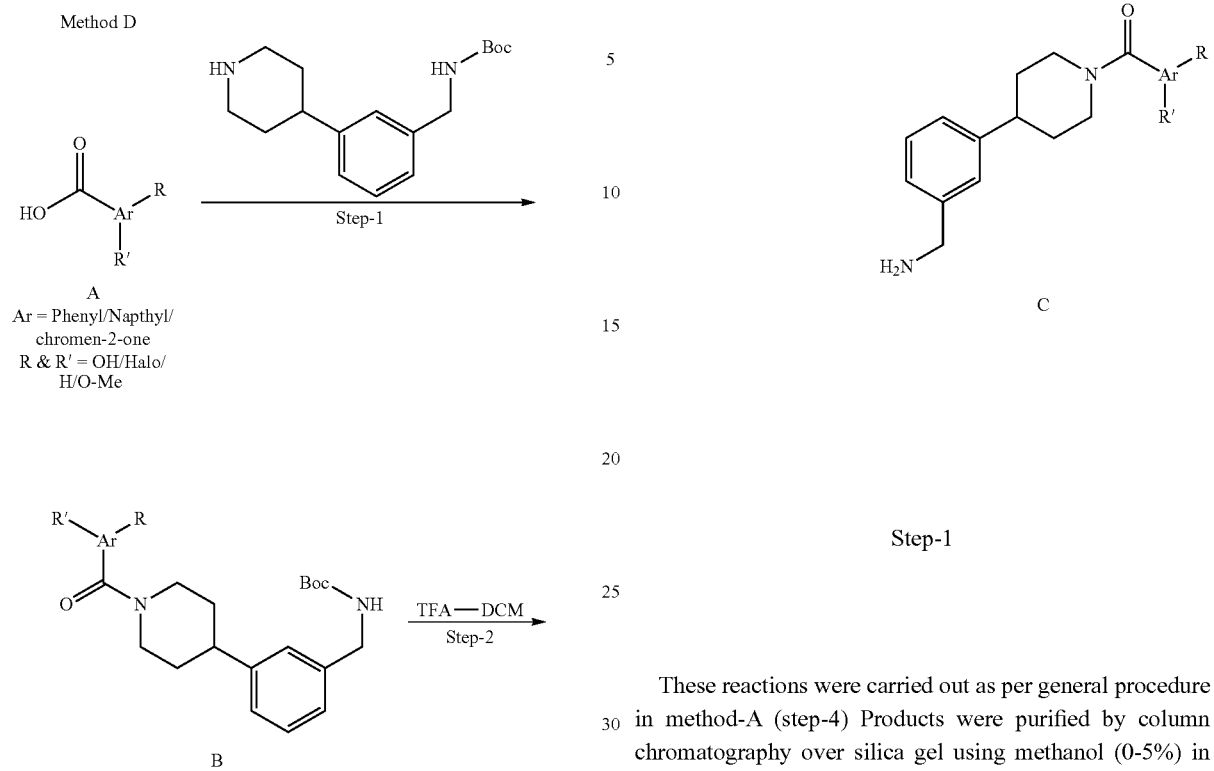

Ar = Phenyl/Napthyl/chromen-2-one
R & R' = OH/Halo/H/O-Me

Step-1

These reactions were carried out as per general procedure in method-A (step-4) Products were purified by column chromatography over silica gel using methanol (0-5%) in Chloroform.

TABLE 25

| Comp. No | Structure | Brief Reaction conditions | Analytical data |
|---|---|---|---|
| B-101 | [structure] | 2-(7,8-dihydroxy-4-methyl-2-oxo-2H-chromen-3-yl)acetic acid (1 eq) tert-butyl 3-(piperidin-4-yl) benzyl carbamate (1.2 eq.), EDCI (1.2 eq.), HOBT (1.5 eq.), DIPEA (1.5 eq.), DMF(50 vol), RT, 12 h, Yield:- 30% | Mol. Wt.: 522.59<br>M.I. Peak observed in LCMS:- 573.2<br>$^1$H NMR (400 MHz, DMSO-d6): δ 1.39 (s, 9H), 1.46-1.90 (m, 4H), 2.28 (s, 3H), 2.60-2.90 (m, 2H), 3.12-3.30 (m, 1H), 3.60-3.80 (m, 2H), 4.11 (d, J = 5.2 Hz, 1H), 4.19 (brd, 1H), 4.49 (brd, 1H), 6.81 (d, J = 8.8 Hz, 1H), 7.00-7.40 (m, 5H), 9.23 (s, 1H), 9.92 (s, 1H) |

Step-2

Boc deprotection of the products from step-1 was carried out by stirring it with hydrochloric acid in presence of co-solvent like methanol or dioxane at room temperature. Solvents were then evaporated and residue was purified by reverse phase preparative HPLC. Products were isolated as TFA salts. Details of the compounds synthesized are as below in Table 26.

TABLE 26

ANALYTICAL DATA

| Comp. No. | Structure | Brief Reaction conditions | Analytical data |
|---|---|---|---|
| Target-101 | 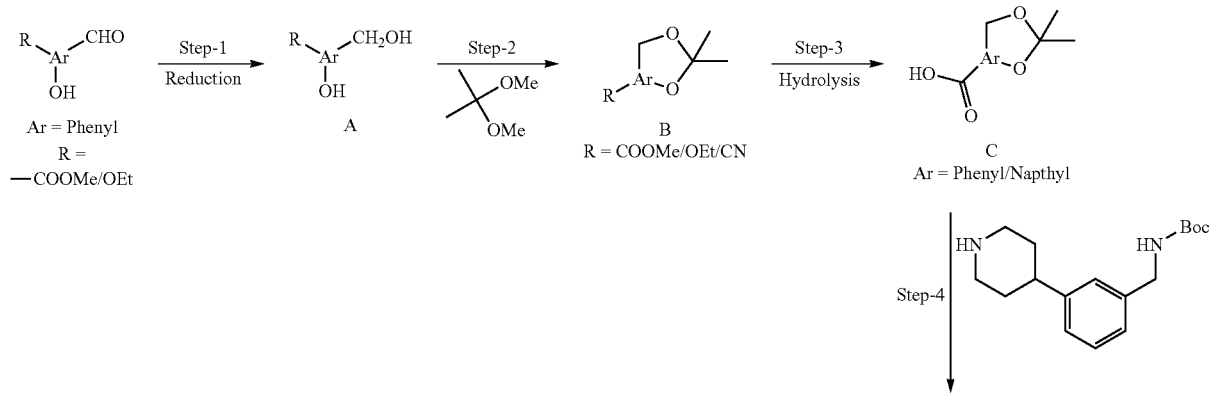 | conc. HCl (10 V), Methanol (100 V), 24 h, RT, isolated as hydrochloride in pure form after work-up Yield:- 81.3% | Mol. Wt.: 422.47 LCMS: (M + 1) 423.2 $^1$H NMR (400 MHz, DMSO-d6): δ 1.40-1.90 (m, 4H), 2.28 (s, 3H), 2.60-2.89 (m, 2H), 3.16-3.27 (m, 1H), 4.00 (d, 2H), 4.05 (s, 2H), 4.21 (brd, 1H), 4.51 (brd, 1H), 6.84 (d, J = 8.8 Hz, 1H), 7.13 (d, J = 8.8 Hz, 1H), 7.25-7.43 (m, 4H), 8.36 (br, 2H) |

Example 9: Synthesis of Tryptase Inhibitors with o-Hydroxy Methyl Phenol Functionality Method E Ortho hydroxy aromatic aldehyde with carbethoxy/methoxy functionality at suitable position was reduced to get o-hydroxy methyl phenols which were then protected and ester functionality hydrolyzed to get required protected carboxylic acid, which upon coupling with tert-butyl 3-(piperidin-4-yl) benzylcarbamate and subsequent deprotection in acidic media afforded the title compounds.

In case of napthyl derivative, corresponding cyano derivative instead of carbethoxy/methoxy derivative analogue was synthesized by the route described in scheme-2 and used during step-3.

SCHEME 10.

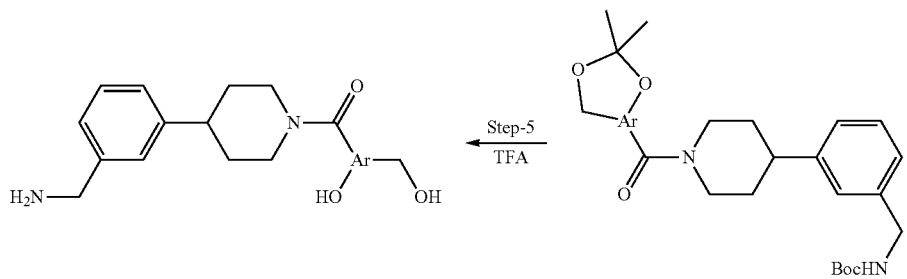

Scheme:-2

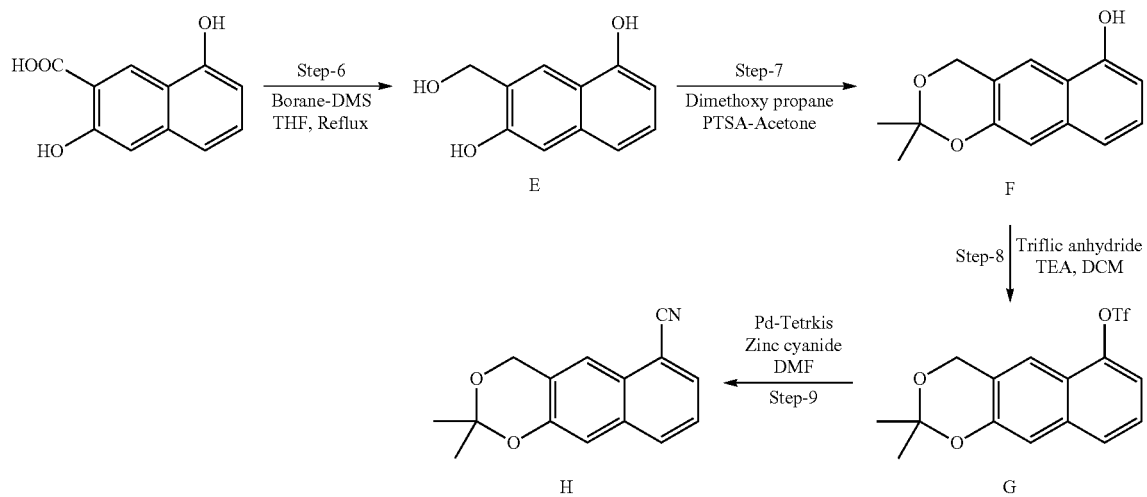

Step-1

Required ortho hydroxy aromatic aldehydes with carbethoxy/methoxy functionality were synthesized either by esterification of corresponding carboxylic acid available commercially using reaction conditions described in method-A step-1 (for 4-formyl-3-hydroxy methyl benzoate) or synthesized as per methods in the literature (*JACS*, 131, 15608-15609, 2009 for methyl 3-formyl-4-hydroxybenzoate; *Syn. Comm*, 29, 2061-2068, 1999. for 3-formyl-4-hydroxy ethyl cinnamate). (E)-ethyl 3-(3-formyl-4-hydroxyphenyl)acrylate was synthesized as per methods in the literature (*Syn. Comm.* 30 1003-1008 2000). Aldehyde functionality was reduced either by catalytic hydrogenation or using sodium borohydride in methanol. The details of compounds synthesized are as below in Table 27.

TABLE 27

| | | ANALYTICAL DATA | |
|---|---|---|---|
| Comp. No. | Structure | Brief Reaction conditions | Analytical data |
| A-74 | methyl 3-hydroxy-4-(hydroxymethyl)benzoate | 10% Pd/C (10% w/w.), Hydrogen (balloon pressure), Methanol (50 vol), 4 h, RT, 79% | Mol. Wt:- 182.17<br>M.I. Peak observed(ESMS):- 181.40(-Ve mode)<br>$^1$H NMR DMSO-d6:- 3.79(s, 1H), 4.5(s, 2H), 7.3(m, 3H). |
| A-65 | methyl 4-hydroxy-3-(hydroxymethyl)benzoate | MeOH (80 V) at 0° C.<br>NaBH4(1 eq) 0° C. 1 h. 70% | Mol. Wt:- 182.17<br>LCMS: (M + 1) 182.8<br>$^1$H NMR (400 MHz, DMSO-d6): δ 3.78 (s, 3H), 4.48 (s, 2H), 6.84 (d, J = 8.4 Hz, 1H), 7.68-7.72 (dd, J = 2.4 and 8.4 Hz, 1H), 7.97 (s, 1H), 10.31 (s, 1H) |
| A-40 | (E)-ethyl 3-(4-hydroxy-3-(hydroxymethyl)phenyl)acrylate | EtOH(30 V) at 0° C. NaBH4(1 eq) 0° C. 30 min. Crude taken for next step | Mol. Wt:- 222.24<br>LCMS: (M + 1) 223<br>$^1$H NMR (400 MHz, CDCl$_3$): δ 1.32 (t, J = 7.0 Hz, 3H), 4.20-4.27 (q, J = 7.0 Hz, 2H), 4.88 (s, 2H), 6.25 (d, J = 16 Hz, 1H), 6.88 (d, J = 8.4 Hz, 1H), 7.20 (s, 1H), 7.36 (d, J = 8.4 Hz, 1H), 7.55 (d, J = 16 Hz, 1H), 8.0 (brs, 1H). |

Step-2

Protection of step-1 products was carried out using 2,2-dimethoxy propane by refluxing in acetone in presence of catalytic p-toluene sulfonic acid. Reaction was monitored by LCMS and after completion of reaction solvents were distilled and crude product obtained was purified by column chromatography using ethyl acetate (0-10%) in hexane. The details of compounds synthesized are as below in Table 27.

TABLE 27

ANALYTICAL DATA

| Comp. No. | Structure | Brief Reaction conditions | Analytical data |
|---|---|---|---|
| B-74 | 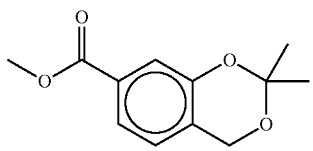 | 2,2-dimethoxy propane (4 eq.), acetone (50 vol), PTSA (catalytic), 3 h, RT, Yield:- 59% | $^1$H NMR CDCl3:- 1.48(s, 6H), 3.95(s, 3H), 4.86(s, 2H), 7.1(d, 1H), 7.45(s, 1H) 7.5(d, 1H). |
| B-65 | 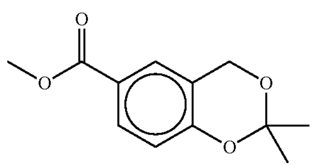 | Acetone (72 V) 2,2-dimethoxy propane (3 eq) and PPTS (0.1 eq) RT overnight. Yield:- 59% | Mol. Wt:- 222.24 LCMS: (M + 1) 222.75 $^1$H NMR (400 MHz, CDCl$_3$): δ 1.52 (s, 6H), 3.85 (s, 3H), 4.84 (s, 2H), 6.81 (d, J = 8.4 Hz, 1H) 7.68 (d, J = 1.2 Hz, 1H), 7.82 (dd, J = 1.2 and 8.6 Hz, 1H) |
| B-40 | 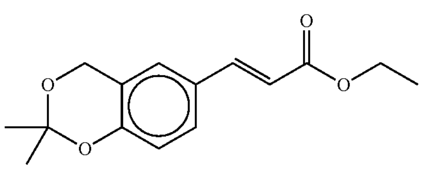 | Acetone (250 V), 2,2 dimethoxy propane (3 eq) PPTS (0.1 eq) RT overnight. Yield:- 65% | Mol. Wt:- 262.30 LCMS: (M + 1) 262.9 $^1$H NMR (400 MHz, CDCl$_3$): δ 1.33 (t, J = 7 Hz, 3H), 1.55 (s, 6H), 4.22-4.27 (m, 2H), 4.85 (s, 2H), 6.29 (d, J = 16.4 Hz, 1H), 6.82 (d, J = 8.8 Hz, 1H), 7.15 (s, 1H), 7.35-7.37 (m, 1H), 7.60 (d, J = 15.6 Hz, 1H). |

Step-3

Hydrolysis of step-2 products was carried out as per procedure described in Method-A (step-3). In case of C-44, hydrolysis of corresponding cyano compound (G-44) was carried out using ethanolic potassium hydroxide under reflux to get mixture of acid and corresponding amide. This mixture was used for next step without purification. The details of compounds synthesized are as below in Table 28.

TABLE 28

REACTION CONDITIONS & ANALYTICAL DATA

| Comp. No. | Structure | Brief Reaction conditions | Analytical data |
|---|---|---|---|
| C-74 | 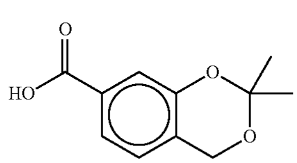 | LiOH (3.0 eq.), THF:H2O (1:1), RT, 4 h, 62%. | Ionisation not observed in LCMS. HPLC purity-90%. Used as such for next step. |
| C-65 | 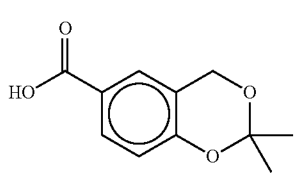 | THF:H2O:MeOH (50:50:10 V) LiOH•H2O (1.5 eq) RT overnight. 93% | LCMS: Ionization was not observed $^1$H NMR (400 MHz, DMSO-d$_6$): δ 1.49 (s, 6H), 4.88 (s, 2H), 6.86 (d, J = 8.4 Hz, 1H), 7.70 (s, 1H), 7.73 (d, J = 8.8 Hz, 1H). |

TABLE 28-continued

REACTION CONDITIONS & ANALYTICAL DATA

| Comp. No. | Structure | Brief Reaction conditions | Analytical data |
|---|---|---|---|
| C-40 | 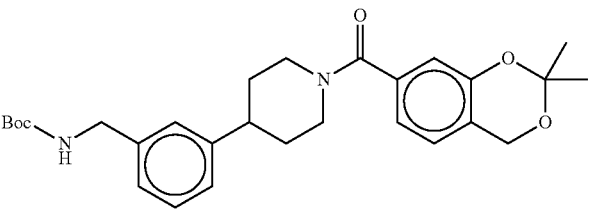 | THF:H2O:MeOH (17:17:5 V), LiOH•H2O (1.5 eq) RT overnight. 92% | Mol. Wt:- 234.25 LCMS: (M + Na) 256.8 $^1$H NMR (400 MHz, DMSO-d$_6$) δ 1.47 (s, 6H), 4.83 (s, 2H), 6.35 (d, J = 16 Hz, 1H), 6.81 (d, J = 8.4 Hz, 1H), 7.43-7.52 (m, 3H). |
| C-44 | 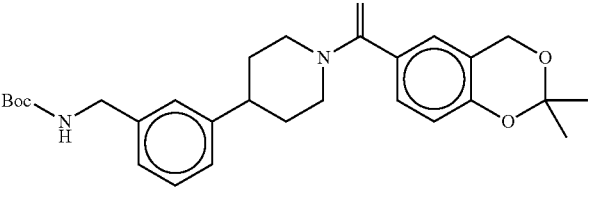 | EtOH (8 V) 30% solution of KOH (8 V mL) 80° C. 24 h. 2:1 mix of acid:amide obtained used as such for next step. | LCMS: ionization was not observed |

Step-4

Coupling reactions of protected carboxylic acids from step-3 were carried out as per general procedure described in Method-A (Step-4). The details of compounds synthesized are as below in Table 29.

TABLE 29

REACTION CONDITIONS & ANALYTICAL DATA

| Comp. No. | Structure | Brief Reaction conditions | Analytical data |
|---|---|---|---|
| D-74 | 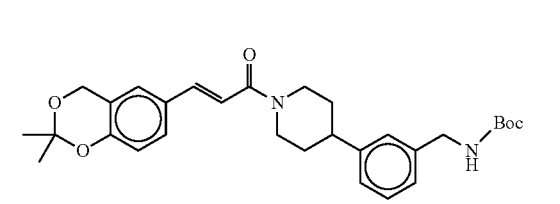 | tert-butyl 3-(piperidin-4-yl) benzylcarbamate (1.1 eq.), EDCI (1.5 eq.), DMAP (1.2 eq.), DCM(85 vol), RT, 4 h, 89% | Mol. Wt: ~480.60 M.I. Peak observed: ~503.25 (M + Na) |
| D-65 | 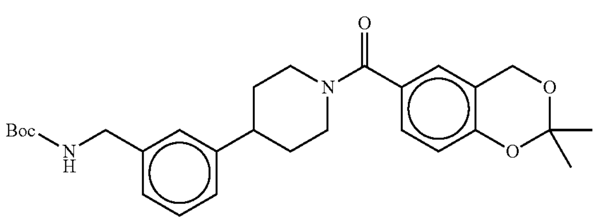 | tert-butyl 3-(piperidin-4-yl) benzylcarbamate (1 eq) DCM (100 V), DMAP (0.5 eq), EDCI (1.5 eq) RT overnight. 79% | Mol. Wt: ~480.60 LCMS: (M + 1) 481.5 |
| D-40 | 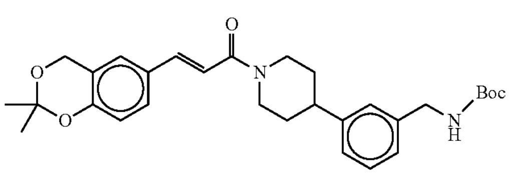 | tert-butyl 3-(piperidin-4-yl) benzylcarbamate (1.2 eq) DCM (66 V), DMAP (0.5 eq) EDCI (1.5 eq) RT overnight. 50% | Mol. Wt: ~506.63 LCMS: (M + Na) 529.2 |

TABLE 29-continued

REACTION CONDITIONS & ANALYTICAL DATA

| Comp. No. | Structure | Brief Reaction conditions | Analytical data |
|---|---|---|---|
| D-44 | 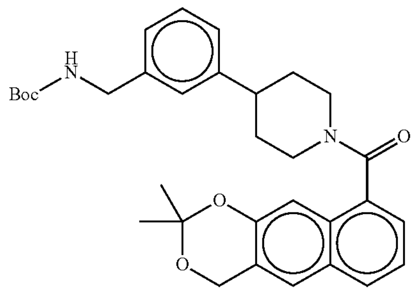 | tert-butyl 3-(piperidin-4-yl) benzylcarbamate (1.2 eq) DCM (66 V), DMAP (0.5 eq), EDCI (1.5 eq), RT overnight. 40% | LCMS: (M + Na) 553.15 $^1$H NMR (400 MHz, CDCl$_3$): δ 1.47 (s, 9H), 1.63 (s, 6H), 1.60-2.00 (m, 4H), 2.70-2.81 (m, 1H), 2.85-3.20 (m, 2H), 3.45-3.65 (m, 1H), 4.30 (s, 2H), 4.82 (br, 1H), 5.00-5.25 (m, 2H), 7.00-7.22 (m, 3H), 7.28-7.43 (m 4H), 7.50 (s, 1H), 7.74 (d, J = 7.6 Hz, 1H). |

Step-5

Boc and isopropylidine deprotection of the compounds was carried out by stirring with Methanolic HCl or Trifluoro acetic acid in dichloromethane at room temperature. Reactions were monitored by LCMS and after reaction completion, reaction mass was concentrated and residue was purified by reverse phase preparative HPLC. Products were isolated as TFA salts. The details of 6 compounds synthesized are as below in Table 30.

TABLE 30

REACTION CONDITIONS & ANALYTICAL DATA

| Comp. No. | Structure | Brief Reaction conditions | Analytical data |
|---|---|---|---|
| Target-74 | 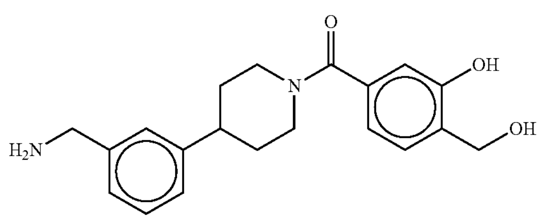 | Methanolic HCl (25 vol), 4 h, RT, Prep purification Isolated as TFA Salt Yield: ~17.2% | Mol. Wt: ~340.41 M.I. Peak observed: ~340.95 HPLC Purity: ~99.14 $^1$H NMR DMSO-d6: ~1.59-1.77(m, 4H), 2.80-2.86(m, 4H), 4.00-4.04(q, 2H), 4.49(s, 2H), 6.79(s, 1H), 6.82-6.84(d, 1H), 7.27-7.38 (m, 5H), 8.13(bs, 3H), 9.64(bs, 1H) |
| Target-65 | 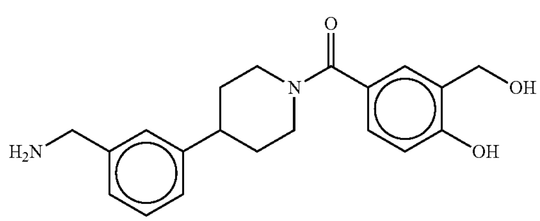 | DCM (100 V), TFA (3 eq) RT overnight Prep purification. Isolated as TFA Salt Yield: ~32% | Mol. Wt: ~340.42 LCMS: (M + 1) 341 HPLC: 99.56% (220 nm) $^1$H NMR (400 MHz, CD$_3$OD): δ 1.60-2.10 (br, 4H), 2.88-3.00 (m, 1H), 3.30 (br, 4H, merged in solvent peak), 4.10 (s, 2H), 4.67 (s, 2 H), 6.84 (d, J = 8.4 Hz, 1H), 7.22-7.45 (m, 6H). |
| Target-40 | 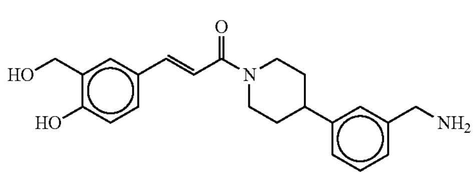 | DCM (100 V) TFA (3 eq) RT 2 h. Prep purification. Isolated as TFA Salt Yield: ~30.5% | Mol. Wt: ~366.45 LCMS: (M + Na) 389 HPLC: 92% trans 7% cis (220 nm) $^1$H NMR (400 MHz, CD$_3$OD): δ 1.55-1.81 (m, 2H), 1.90-2.10 (m, 2H), 2.80-3.00 (m, 1H), 3.31 (br, 4H, merged in solvent peak), 4.10 (s, 2H), 4.66 (s, 2H), 6.80 (d, J = 8.4 Hz, 1H), 7.00 (s, J = 15.2 Hz, 1H), 7.20-7.50 (m, 5H), 7.56 (d, J = 15.2 Hz, 1H), 7.60 (s, 1H). |

TABLE 30-continued

REACTION CONDITIONS & ANALYTICAL DATA

| Comp. No. | Structure | Brief Reaction conditions | Analytical data |
|---|---|---|---|
| Target-44 | (structure) | DCM (100 V)<br>TFA (3 eq)<br>0° C.<br>2 h. Prep purification.<br>Isolated as TFA Salt Yield: ~42% | Mol. Wt: ~390.47<br>LCMS: (M + Na) 413<br>HPLC: 99.07% (220 nm)<br>$^1$H NMR (400 MHz, CD$_3$OD): δ 1.50-2.10 (m, 4H), 2.82-3.00 (m, 1H), 3.00-3.29 (m, 2H), 3.40-3.60 (br, 2H), 4.10 (s, 2H), 4.80 (s, 2H), 7.01 (s, 1H), 7.20 (s, 1H), 7.23-7.42 (m, 5H), 7.80-7.90 (m, 2H). |

Step-6 (Synthesis of E-44)

To a solution of 3, 5 dihydroxy-2-napthoic acid (5 g, 24.5 mmol) in THF dry (100 mL), DMS-Borane (7 mL, 73.5 mmol) was added drop wise at room temperature. The reaction mixture was then allowed to reflux for 4 h. TLC (Mobile phase 50% ethyl acetate in n-hexane) indicated absence of starting material (Rf 0.2) and product formation (Rf-0.4) The reaction mixture was cooled and quenched with saturated solution of ammonium chloride. The compound was extracted in ethyl acetate. The organic layer was dried over sodium sulphate, concentrated and purified by column chromatography using ethyl acetate (0-20%) in hexane afford 6-(hydroxymethyl)naphthalene-1,7-diol as an off white solid. Yield: (3.9 g, 83.8%).

LCMS: Ionization not observed; $^1$H NMR (400 MHz, DMSO-d$_6$): δ 4.61 (d, J=5.2 Hz, 2H), 5.11 (t, J=5.8 Hz, 1H, —OH), 6.71 (d, J=7.6 Hz, 1H), 7.02 (t, J=7.8 Hz, 1H), 7.20 (d, J=8.4 Hz, 1H), 7.36 (s, 1H), 7.70 (s, 1H), 9.64 (bs, 1H), 9.71 (bs, 1H).

Step-7 (Synthesis of F-44)

To a solution of 6-(hydroxymethyl)naphthalene-1,7-diol (1 g, 5.26 mmol) in acetone (120 mL), pyridinium-p-toluenesulfonate (0.13 g, 0.52 mmol) followed by 2,2 dimethoxy propane (0.77 mL, 6.31 mmol) were added at room temperature. The reaction mixture was then allowed to stir at room temperature overnight. TLC (Mobile phase 50% ethyl acetate in n-hexane) indicated absence of starting material (Rf 0.4) and product formation (Rf-0.7) The reaction mixture was concentrated to dryness and purified by column chromatography using neutral 60-120 mesh silica to give 2,2-dimethyl-4H-naphtho[2,3-d][1,3]dioxin-9-ol. NMR is in agreement with the structure. Yield: (1.2 g, 99%)

LCMS: Ionization not observed; $^1$H NMR (400 MHz, CDCl$_3$): δ 1.60 (s, 6H) 5.06 (s, 2H), 5.39 (bs, 1H, —OH), 6.74 (d, J=7.2 Hz, 1H), 7.14 (t, J=7.8 Hz, 1H), 7.30 (d, J=8.4 Hz, 1H), 7.44 (s, 1H), 7.54 (s, 1H).

Step-8 (Synthesis of G-44)

To a solution of 2,2-dimethyl-4H-naphtho[2,3-d][1,3]dioxin-9-ol (1.2 g, 5.21 mmol) in DCM (130 mL) triethylamine (2.2 mL, 15.6 mmol) was added and the reaction mixture was cooled to 0° C. Triflic anhydride (1.3 mL, 7.82 mmol) was added drop wise during which the reaction mixture became black in color. The reaction mixture was allowed to stir as such for 2 h. TLC (Mobile phase 10% ethyl acetate in n-hexane) indicated absence of starting material (Rf 0.3) and product formation (Rf-0.6). The reaction mixture was diluted with water. The organic layer was separated dried over sodium sulphate concentrated to give 2, 2-dimethyl-4H-naphtho[2,3-d][1,3]dioxin-9-yl trifluoromethanesulfonate. The product was used as such for further reaction without purification. Yield: (1.88 g, Crude)

LCMS: Ionization not observed; $^1$H NMR (400 MHz, CDCl$_3$): δ 1.62 (s, 6H), 5.08 (s, 2H), 7.30 (t, J=8 Hz, 1H), 7.38 (d, J=7.6 Hz, 1H), 7.42 (s, 1H), 7.55 (s, 1H), 7.73 (d, J=8.4 Hz, 1H).

Step-9 (Synthesis of H-44)

To a solution of 2, 2-dimethyl-4H-naphtho[2,3-d][1,3]dioxin-9-yl trifluoromethanesulfonate (0.37 g, 1.02 mmol) in degassed DMF (5 mL) zinc cyanide (0.23 g, 2.04 mmol) was added and the reaction mixture was further degassed for 15 min. Palladium tetrakis (0.23 g, 0.2 mmol) was added and the reaction mixture was degassed for 15 min. The reaction mixture was then heated in a bottle at 80° C. for 3 h. TLC (Mobile phase 10% ethyl acetate in n-hexane) indicated absence of starting material (Rf 0.6) and product formation (Rf-0.4). The reaction mixture was cooled and filtered through a celite pad. The compound was extracted in ethyl acetate and washed with water and brine. The organic layer was dried over sodium sulphate concentrated and purified by column chromatography using Hexane ethyl acetate as eluent (60-120 mesh neutral silica) to give 2,2-dimethyl-4H-naphtho[2,3-d][1,3]dioxine-9-carbonitrile. Yield: (0.13 g, 54%).

LCMS: Ionization not observed; $^1$H NMR (400 MHz, CDCl$_3$): δ 1.62 (s, 6H), 5.09 (s, 2H), 7.34 (t, J=7.8 Hz, 1H), 7.56 (s, 1H), 7.62 (s, 1H), 7.82 (d, J=7.2 Hz, 1H), 7.93 (d, J=8.4 Hz, 1H).

Example 10: Synthesis of 1-Amido Phenols

Method F

Ortho hydroxy aromatic aldehydes, with carbethoxy or methoxy functionality at suitable position were oxidized to get o-carboxy phenols which were then converted to amide by reaction either with ammonia/o-Methyl hydroxyl amine. Ester functionality was then hydrolyzed to get required o-Hydroxy amido carboxylic acid, which upon coupling with tert-butyl 3-(piperidin-4-yl) benzylcarbamate and subsequent deprotection in acidic media afforded the title compounds.

SCHEME 11.

Method F

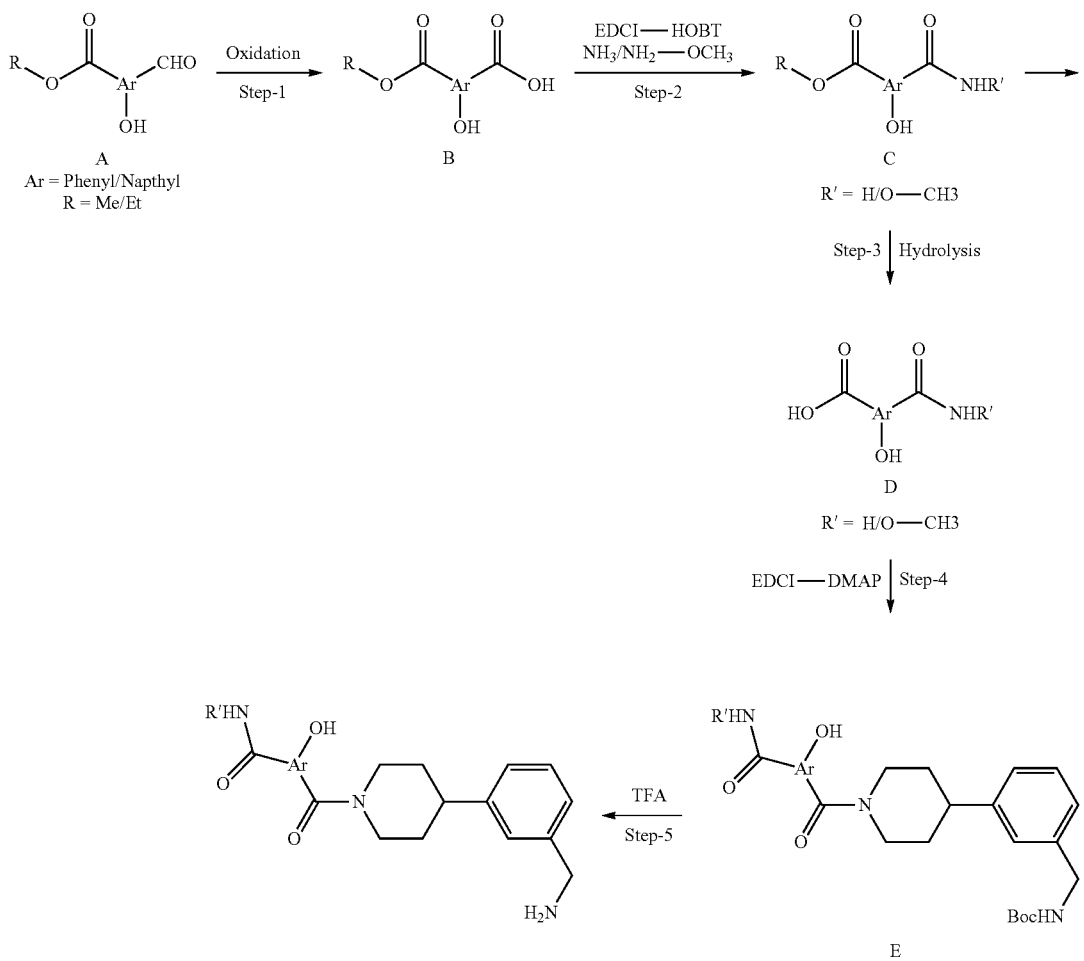

Ar = Phenyl/Napthyl
R = Me/Et

R' = H/O—CH3

R' = H/O—CH3

Step-1

Desired Carbmethoxy hydroxy benzaldehyde was dissolved in Acetonitrile and aq solution of di-sodium hydrogen phosphate & 30% hydrogen peroxide was then added and reaction mass cooled to 0° C. Aq. solution of Sodium chlorite was added to the reaction mass drop wise and reaction mass was allowed to warm to room temperature. Stirring continued at room temperature and reaction was monitored by LCMS till maximum starting was consumed. Reaction mass was then concentrated, residue was acidified with aq. HCl and product extracted in ethyl acetate. Ethyl acetate extract dried over sodium sulfate and concentrated to get the crude product which was sufficient pure for the use in next step. The details of the compounds synthesized are as below in Table 31.

TABLE 31

REACTION CONDITIONS & ANALYTICAL DATA

| Comp. No. | Structure | Brief Reaction conditions | Analytical data |
|---|---|---|---|
| B-75 | 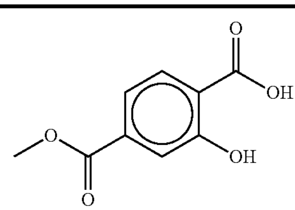 | 4-Formyl, 3-Hydroxy methyl benzoate, (1 eq) ACN (65 V), NaH2PO4•2H2O (0.32 eq in 11 V water), H2O2 30% solution (5 eq) NaClO2 (1.4 eq in 10 V of water) RT 2 h. Yield ~35.46% | Ionization not observed in LCMS $^1$H NMR DMSO-d6: −3.91(s, 3h) 7.42(d, 1H) 7.60 s(1H) 7.78 (d, 1H) 10.19(s, 1H), 11.1 (s, 1H) |

TABLE 31-continued

REACTION CONDITIONS & ANALYTICAL DATA

| Comp. No. | Structure | Brief Reaction conditions | Analytical data |
|---|---|---|---|
| B-66 | 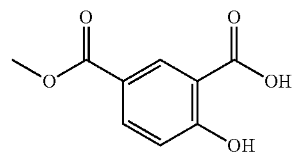 | 3-Formyl, 4-Hydroxy methyl benzoate ACN (37.5 V), NaH2PO4•2H2O (0.32 eq in 11 V water), H2O2 30% solution (5 eq) NaClO2 (1.4 eq in 10 V of water) RT 2 h. Yield –53.4% | Ionization not observed in LCMS $^1$H NMR (400 MHz, DMSO-d6): δ 3.83 (s, 3H), 7.06 (d, J = 8.8 Hz, 1H), 8.02-8.07 (dd, J = 1.6 and 8.6 Hz, 1H), 8.38 (d, J = 1.2 Hz, 1H). |

Step-2

Products from step-1 were converted to desired amides either by conversion to acid chloride and subsequent reaction with ammonia/desired amine or by coupling reaction using EDCI—HOBT in DMF followed by usual work-up as described in method-A (step-4.) Crude products were purified by column chromatography over silica gel using methanol (0-30%) in chloroform.

Intermediates C-76 & D-76 were synthesized by Heck reaction of the desired o-Hydroxy-4-bromo benzamides (Synthesized form 4-bromo-2-hydroxybenzoic acid as per general procedure described earlier) using ethyl acrylate and following the procedure described in the literature for analogous compounds (*Bull. Korean Chem. Soc.* 1999, Vol. 20, 232-236)

Intermediate C-86 was synthesized by the procedure described in the literature (*J. Med. Chem.* 43, 1670-1683, 2000)

The details of compounds synthesized are as below in Table 32.

TABLE 32

REACTION CONDITIONS & ANALYTICAL DATA

| Comp. No. | Structure | Brief Reaction conditions | Analytical data |
|---|---|---|---|
| C-75 | 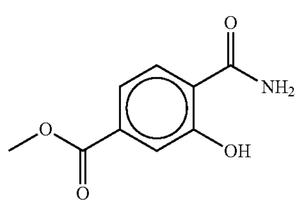 | EDCI (1.1 eq.), HOBT (1.1 eq.), aq ammonia (4 eq.), DMF(60 vol), RT, 14 h, purified by column chromatography(0-30% Methanol-chloroform), Yield –10%, | Mol. Wt: –195.17 M.I. Peak observed: –196.00 |
| C-75a | 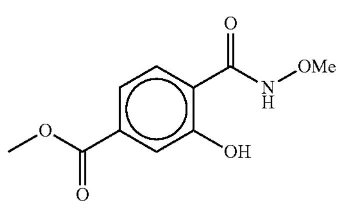 | B-75 (1 eq), DCM (75 Vol), TEA (1.5 eq) Thionyl chloride (1.5 eq) 0° C. 1 h. NH2OMe•HCl (1.5 eq) DCM (32 vol), TEA (2 eq) was added and stirred for 2 h. purified by column chromatography(0-30% Methanol-chloroform), Yield –64%, | Mol Wt: –225.20 M.I. Peak observed: –225.75 |
| C-66 | 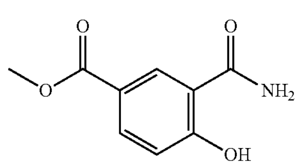 | DMF (35 Vol), EDCI (1.2 eq) HOBt (1.2 eq) Aq NH3 (1 Vol) RT overnight. 91% | Mol. Wt: –195.17 M.I. Peak observed: –195.75 $^1$H NMR (400 MHz, DMSO-d6): δ 3.82 (s, 3H), 6.98 (d, J = 8.8 Hz, 1H), 7.25 (brs, 2H), 7.95-7.98 (dd, J = 2 and 8.6 Hz, 1H), 8.54 (d, J = 2 Hz, 1H). |
| C-92 | 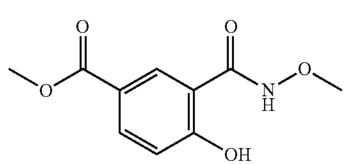 | B-66 (1 eq), DCM (100 Vol), TEA (3 eq) Thionyl chloride (1.5 eq) 0° C. 1 h. NH2OMe•HCl (1 eq) DCM (32 vol), TEA (2 eq) was added and stirred for 2 h. Yield –52.6% | Mol. Wt: –225.20 M.I. Peak observed: –225.7 $^1$H NMR (400 MHz, CDCl3): δ 3.91 (s, 3H), 3.92 (s, 3H), 7.03 (d, J = 8.8 Hz, 1H), 8.05-8.09, (dd, J = 1.8 and 8.6 Hz, 1H), 8.16 (s, 1H), 9.48 (s, 1H), 12.2 (s, 1H) |

TABLE 32-continued

REACTION CONDITIONS & ANALYTICAL DATA

| Comp. No. | Structure | Brief Reaction conditions | Analytical data |
|---|---|---|---|
| C-76 | (structure) | Bull. Korean Chem. Soc. 1999, Vol. 20, 232-236 White solid; Yield: ~60% | Mol. Wt.: 235.24 M.I. Peak observed: ~236 |
| C-76a | (structure) | As above White solid; Yield: ~93% | Mol. Wt: 265.26 M.I. Peak observed: ~266 |
| C-86 | (structure) | J. Med. Chem. 43, 1670-1683, 2000 Yield: ~71.4% | Mol. Wt.: 235.24 M.I. Peak observed: ~277 (M + ACN) $^1$H NMR (400 MHz, DMSO-d6): δ 1.25 (t, J = 7.0 Hz, 3H), 4.10-4.23 (q, J = 7 Hz, 2H), 6.57 (d, J = 16 Hz, 1H), 6.91 (d, J = 8.4 Hz, 1H), 7.55 (d, J = 16 Hz, 1H), 7.74-7.80 (dd, J = 2.0 and 8.6 Hz, 1H), 8.06 (s, 1H), 8.28 (d, J = 2 Hz, 1H), 8.50 (s, 1H), 13.5 (s, 1H). |

Step-3

Hydrolysis of step-2 products was carried out as per general procedure followed in method-A (step-3) crude products were used for next step unless specified.

The details of compounds synthesized are as below in Table 33.

TABLE 33

REACTION CONDITIONS & ANALYTICAL DATA

| Comp. No. | Structure | Brief Reaction conditions | Analytical data |
|---|---|---|---|
| D-75 | (structure) | LiOH (3.0 eq.), THF:H2O (1:1), RT, 4 h, Yield: ~60%. | Ionization not observed in LCMS Crude product subjected to next step. |
| D-75a | (structure) | LiOH (3.0 eq.), THF:H2O (1:1), RT, 4 h, Yield: ~86%. | Mol. Wt.: 211.17 M.I. Peak observed: ~212 |
| D-66 | (structure) | Acetone (25 V) 1N NaOH (25 V) RT 12 hrs Yield: ~60% | Mol. Wt: ~181.15 M.I. Peak observed: ~181.7 $^1$H NMR (400 MHz, DMSO-d6): δ 6.94-6.97 (m, 1H), 7.94-7.96 (m, 1H), 8.01 (br, 1H), 8.52 (d, J = 2 Hz, 1H), 8.64 (br, 1H), 12.76 (br, 1H), 13.67 (s, 1H). |

TABLE 33-continued

REACTION CONDITIONS & ANALYTICAL DATA

| Comp. No. | Structure | Brief Reaction conditions | Analytical data |
|---|---|---|---|
| D-92 | (structure: 2-hydroxy-5-carboxy-N-methoxybenzamide derivative) | Acetone (25 Vol) 1N NaOH (25 Vol) RT stir 12 hrs. Crude product contaminated with Sodium chloride was used for next step without purification. | Mol. Wt: ~211.17<br>M.I. Peak observed: ~211.8<br>$^1$H NMR (400 MHz, DMSO-d6): δ 3.70 (s, 3H), 7.05 (d, J = 8.4 Hz, 1H), 7.89-7.93 (dd, J = 1.4 and 8.6 Hz, 1H), 8.26 (s, 1H). |
| D-76 | (structure: cinnamic acid with hydroxy and carboxamide substituents) | LiOH (4.0 eq.), MeOH:H2O (4:1), RT, 4 h, Acidified with aq. Citric acid instead of HCl during work-up.<br>Yield: ~75%. | Mol. Wt.: 207.18<br>M.I. Peak observed: ~208 [M + 1] |
| D-76a | (structure: cinnamic acid with hydroxy and N-methoxy carboxamide) | LiOH (4.0 eq.), MeOH:H2O (4:1), RT, 4 h, Acidified with aq. Citric acid instead of HCl during work-up.<br>Yield: ~70%. | Mol. Wt.: 237.21<br>M.I. Peak observed: ~238 [M + 1] |
| D-86 | (structure: cinnamic acid with hydroxybenzamide) | Acetone (25 Vol) 1N NaOH (25 Vol) RT stir 12 hrs. Crude product was taken for further step. | Mol. Wt: ~207.18<br>M.I. Peak observed: ~208 |

Step-4

Coupling reactions of step-3 products with tert-butyl 3-(piperidin-4-yl) benzylcarbamate were carried out as per general procedure followed in method-A (step-4) Crude products The details of compounds synthesized are as below in Table 34. Unless specified crude products ere used for next step without further purification.

TABLE 34

REACTION CONDITIONS & ANALYTICAL DATA

| Comp. No. | Structure | Brief Reaction conditions | Analytical data |
|---|---|---|---|
| E-75 | (Boc-NH-CH2-phenyl-piperidine-N-CO-phenyl(OH)-CONH2) | tert-butyl-3-(piperidin-4-yl) benzylcarbamate (1.1 eq.), EDCI (1.5 eq.), DMAP (1.2 eq.), DCM(85 vol), RT, 4 h, yield: ~40%, | Mol. Wt: ~453.53<br>M.I. Peak observed: ~476.15 (M + Na) |
| E-75a | (Boc-NH-CH2-phenyl-piperidine-N-CO-phenyl-CO-N-O) | tert-butyl-3-(piperidin-4-yl) benzylcarbamate (1.1 eq.), EDCI (1.5 eq.), DMAP (1.2 eq.), DCM(85 vol), RT, 4 h, yield: ~61%, | Mol. Wt: ~483.56<br>M.I. Peak observed: ~484.10 |

TABLE 34-continued

REACTION CONDITIONS & ANALYTICAL DATA

| Comp. No. | Structure | Brief Reaction conditions | Analytical data |
|---|---|---|---|
| E-66 | (structure) | tert-butyl-3-(piperidin-4-yl)benzyl carbamate (1.2 eq) DCM (100 Vol), DMAP (0.5 eq), EDCI (1.5 eq) RT overnight. 50% | Mol. Wt: ~453.53<br>M.I. Peak observed: ~454.3<br>$^1$H NMR (400 MHz, DMSO-d6): δ 1.38 (s, 9H), 1.50-1.90 (m, 4H), 2.70-2.85 (m, 1H), 2.90-3.20 (br, 1H), 3.60-4.00 (br, 1H), 4.00-4.15 (brm, 2H), 4.20-4.80 (br, 2H), 6.90-7.51 (m, 6H), 7.99 (s, 1H), 8.01 (brs, 1H), 8.51 (brs, 1H), 13.3 (s, 1H). |
| E-92 | (structure) | tert-butyl-3-(piperidin-4-yl)benzylcarbamate (1.2 eq) DCM (100 Vol), DMAP (0.5 eq), EDCI (1.5 eq) RT 12 hrs, Purified by column chromatography on silica gel using methanol(0-10%) in chloroform. Yield: ~61% | Mol. Wt: ~483.56<br>M.I. Peak observed: ~506 (M + Na)<br>$^1$H NMR (400 MHz, CDCl3): δ 1.46 (s, 9H), 1.64-2.00 (m, 4H), 2.70-2.82 (m, 1H), 2.90-3.40 (br, 2H), 4.29 (s, 2H), 4.50-5.00 (br, 2H), 6.97 (d, J = 8.4 Hz, 1H), 7.00-7.20 (m, 4H), 7.26-7.30 (m, 1H), 7.42 (d, J = 8.4 Hz, 1H), 7.70 (s, 1H), 10.7 (s, 1H), 12.1 (s, 1H). |
| E-76 | (structure) | tert-butyl-3-(piperidin-4-yl)benzylcarbamate (1.2 eq) DMF (10 Vol), HOBT (1.5 eq), EDCI (1.5 eq) DIEA (2.5 eq) RT 12 hrs, Yield: ~71% | Mol. Wt.: 479.57<br>M.I. Peak observed: ~480 [M + 1] |
| E-76a | (structure) | tert-butyl-3-(piperidin-4-yl)benzylcarbamate (1.2 eq) DMF (10 Vol), HOBT (1.5 eq), EDCI (1.5 eq) DIEA (2.5 eq) RT 12 hrs, Yield: ~36% | Mol. Wt.: 509.59<br>M.I. Peak observed: ~532.25 [M + Na] |
| E-86 | (structure) | tert-butyl-3-(piperidin-4-yl)benzylcarbamate (1.2 eq) DCM (60 Vol), DMAP (0.5 eq), EDCI (1.5 eq) RT 12 hrs, Purified by column chromatography on silica gel using methanol(0-10%) in chloroform. Yield: ~45% | Mol. Wt: ~479.57<br>M.I. Peak observed: ~480<br>$^1$H NMR (400 MHz, DMSO-d6): δ 1.37 (s, 9H), 1.53 (br, 2H), 1.83 (br, 2H), 2.60-2.90 (m, 2H), 3.10-3.30 (m, 1H), 4.10 (d, J = 5.6 Hz, 2H), 4.40 (br, 1H), 4.63 (br, 1H), 6.91 (d, J = 8.4 Hz, 1H), 7.00-7.40 (m, 6H), 7.44 (d, J = 15.2 Hz, 1H), 7.80 (d, J = 8.8 Hz, 1H), 8.07 (brs, 1H), 8.20 (s, 1H), 8.48 (brs, 1H), 13.5 (s, 1H). |

Step-5

Boc deprotection of Step-4 products was carried out by stirring with Aq. hydrochloric acid-methanol or methanolic HCl at room temperature. Crude products were purified by reverse phase preparative HPLC and isolated as TFA salts.

The details of compounds synthesized are as below in Table 35.

TABLE 35

REACTION CONDITIONS & ANALYTICAL DATA

| Comp. No. | Structure | Brief Reaction conditions | Analytical data |
|---|---|---|---|
| Target-75 | (structure) | Methanolic HCl (25 vol), 4 h, RT Purified by prep. HPLC, isolated as TFA Salt, Yield: ~20% | Mol. Wt: ~353.41<br>M.I. Peak observed: ~354.05<br>HPLC Purity: ~96.79<br>$^1$H NMR DMSO-d6: ~1.61-1.83(m, 4H), 2.80-2.85(m, 2H), 3.16(m, 1H), 3.61-3.64(d, 1H), 4.00-4.04 (q, 2H), 4.60-4.63 (d, 1H), 6.87 (s, 2H), 7.27-7.39(m, 4H), 7.90-7.92(d, 1H), 8.03(bs, 1H), 8.13(bs, 2H), 8.48(bs, 1H), 13.20(bs, 1H). |

TABLE 35-continued

REACTION CONDITIONS & ANALYTICAL DATA

| Comp. No. | Structure | Brief Reaction conditions | Analytical data |
|---|---|---|---|
| Target-75a | 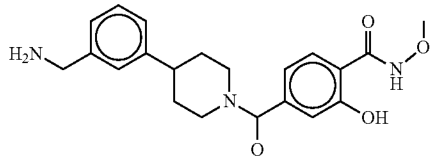 | Methanolic HCl (25 vol), 4 h, RT Purified by prep. HPLC, isolated as TFA Salt, Yield: ~11% | Mol. Wt: ~383.44<br>M.I. Peak observed: ~384.20<br>HPLC Purity: ~97.05<br>$^1$H NMR DMSO-d6: ~1.61-1.83(m, 4H), 2.08(m, 2H), 3.15-3.16(m, 2H), 3.76(s, 1H), 4.00(s, 2H), 4.58(m, 1H), 6.89-6.92(m, 2H), 7.26-7.36(m, 4H), 7.67-7.69(d, 1H). |
| Target-66 | 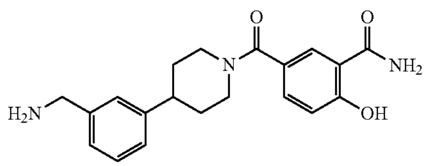 [SMILES: NCc1cccc(C2CCN(C(=O)c3ccc(O)c(C(N)=O)c3)CC2)c1] | Methanol (100 V), concentrated HCl (10 V) RT overnight. 70% HCl salt | Mol. Wt: ~353.41<br>M.I. Peak observed: ~353.66<br>HPLC: 96% (220 nm).<br>$^1$H NMR (400 MHz, DMSO-d6): δ 1.50-1.85 (m, 4H), 2.79-2.90 (m, 1H), 3.20-3.45 (br, 4H), 3.95-4.05 (m, 2H), 6.94 (d, J = 8.4 Hz, 1H), 7.20-7.60 (m, 5H), 8.00 (s, 1H), 8.02 (s, 1H), 8.22 (brs, 2H), 8.51 (brs, 1H), 13.30 (brs, 1H). |
| Target-92 | 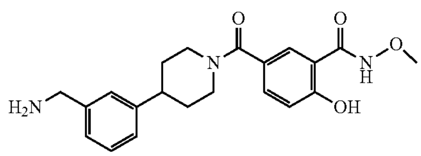 [SMILES: CONC(=O)c1cc(C(=O)N2CCC(c3cccc(CN)c3)CC2)ccc1O] | Methanol (100 V), concentrated HCl (10 V) RT 12 hrs. Purified by prep. HPLC isolated as TFA Salt. Yield: ~70% | Mol. Wt: ~383.44<br>M.I. Peak observed: ~384.2<br>HPLC: 99.5% (220 nm)<br>$^1$H NMR (400 MHz, DMSO-d6): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H) 11.7 (br, 1H), 11.9 (br, 1H). |
| Target-76 | 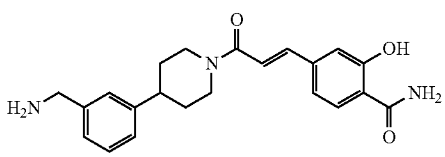 [SMILES: NCc1cccc(C2CCN(C(=O)/C=C/c3ccc(C(N)=O)c(O)c3)CC2)c1] | Methanol (30 Vol), concentrated HCl (1 Vol) RT 3 hrs. Isolated as hydrochloride salt in pure form after work-up. Yield: ~45% | Mol. Wt.: 379.45<br>M.I. Peak observed: ~380 [M + 1]<br>HPLC Purity: 95.60%<br>$^1$H NMR (400 MHz, CD$_3$OD): 7.80 (d, J = 8.0 Hz, 1H), 7.51 (d, J = 15.6 Hz, 1H), 7.45-7.30 (m, 4H), 7.26 (d, J = 15.6 Hz, 1H), 7.20-7.12 (m, 2H), 4.82-4.74 (m, 1H), 4.48-4.36 (m, 1H), 4.10 (s, 2H), 3.00-2.82 (m, 2H), 2.04-1.90 (m, 2H), 1.80-1.62 (m, 2H) |
| Target-76a | 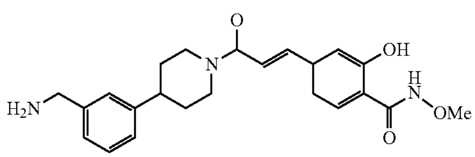 [SMILES: CONC(=O)C1=CCC(/C=C/C(O)N2CCC(c3cccc(CN)c3)CC2)C=C1O] | Methanol (30 Vol), concentrated HCl (1 Vol) RT 3 hrs. Isolated as hydrochloride salt in pure form after work-up. Yield: ~72%. | Mol. Wt.: 409.48<br>M.I. Peak observed: ~410 [M + 1]<br>HPLC: Purity: 96.93%<br>$^1$H NMR (400 MHz, CD$_3$OD): 7.69 (d, J = 8.4 Hz, 1H), 7.50 (d, J = 15.2 Hz, 1H) 7.43-7.18 (m, 6H), 7.16 (s, 1H), 4.82-4.74 (m 1H), 4.46-4.36 (m, 1H), 4.10 (s, 2H), 3.83 (s, 3H), 3.02-2.84 (m, 2H), 2.06-1.90 (m, 2H), 1.80-1.64 (m, 2H). |
| Target-86 | 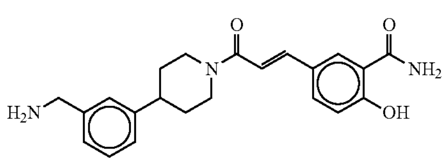 | Methanol (100 V), concentrated HCl (10 V) RT 12 hrs. Isolated as hydrochloride salt in pure form after work-up Yield : ~92.30% | Mol. Wt: ~379.45<br>M.I. Peak observed: ~380.2<br>HPLC: 94.8% (220 nm) $^1$H NMR (400 MHz, DMSO-d6): δ 1.40-1.70 (br, 2H), 1.84 (br, 2H), 2.60-2.91 (m, 2H), 3.10-3.30 (m, 1H), 3.98 (d, J = 5.6 Hz, 2H), 4.40-4.70 (br, 2H), 6.91 (d, J = 8.4 Hz, 1H), 7.20-7.50 (m, 6H), 7.78 (d, J = 8.8 Hz, 1H), 8.07 (br, 1H), 8.32 (br, 2H), 8.37 (br, 2H), 8.65 (br, 1H). |

Example 11. Synthesis of d-hydroxy carboxylic acids

Method H

Alfa hydroxy carboxylic acids were synthesized by reacting desired epoxide with tert-butyl 3-(1-(3-hydroxybenzoyl) piperidin-4-yl) benzyl carbamate in presence of base to yield Alfa hydroxy carboxylic esters that were hydrolyzed and de-protected to get the title compounds (Scheme-1).

Similarly indole 5/6 carboxylic acids were coupled with tert-butyl 3-(piperidin-4-yl) benzyl carbamate and resulting coupled products were treated with desired epoxides. Alfa hydroxy ester formed in the reaction gets hydrolyzed during the work-up to yield alpha hydroxy acids which were subjected to Boc De-protection to get the title compounds (SCHEME 12, part Scheme-2).

SCHEME 12.
Method H
Scheme-1
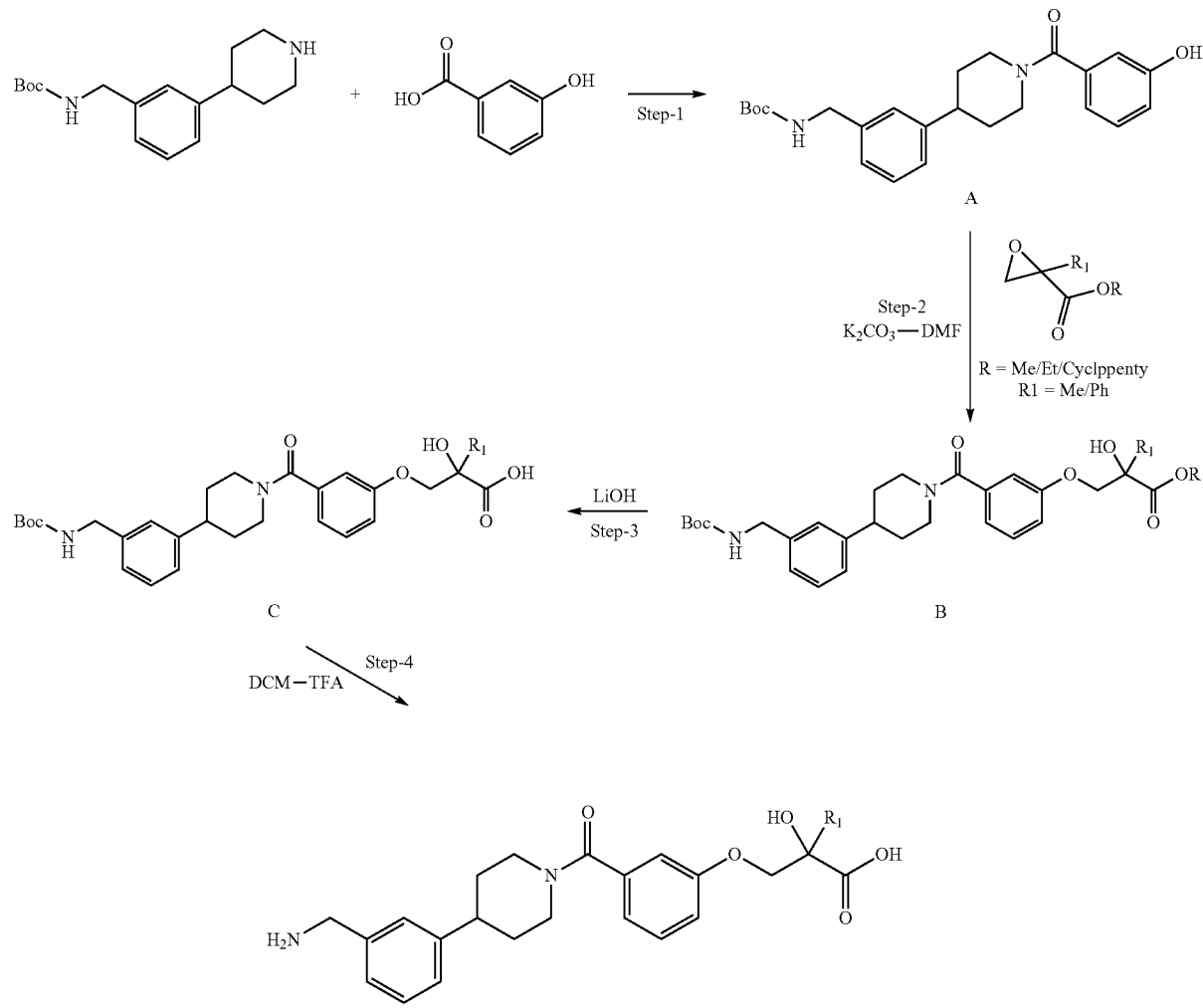
Scheme-2
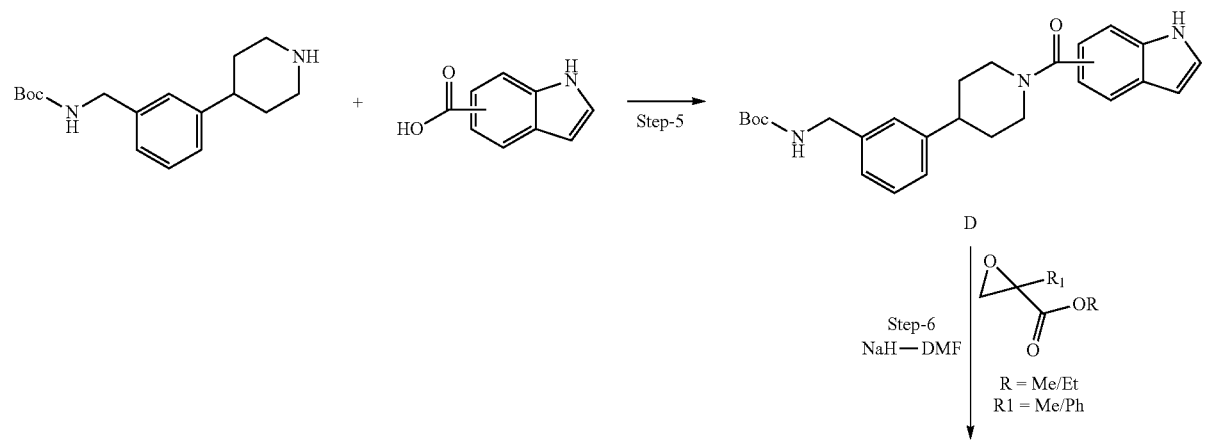

-continued

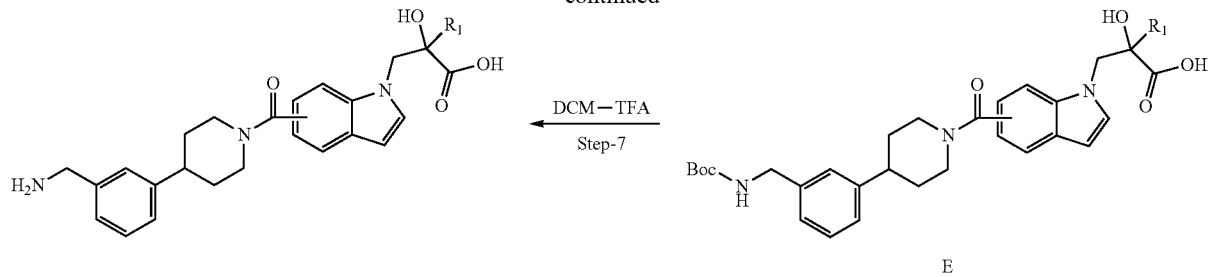

E

Step-1 & 5

Coupling of desired carboxylic acid was carried out with tert-butyl 3-(piperidin-4-yl) benzylcarbamate as per general procedure described in Method-A step-4 was followed. The details of compounds synthesized are as below in Table 36.

TABLE 36

REACTION CONDITIONS & ANALYTICAL DATA

| Comp. No. | Structure | Brief Reaction conditions | Analytical data |
|---|---|---|---|
| A | 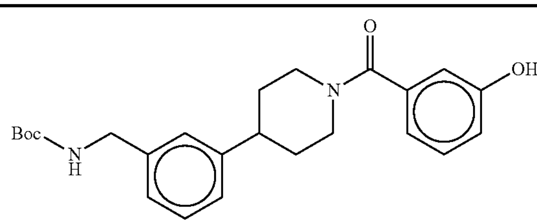 | tert-butyl 3-(piperidin-4-yl) benzylcarbamate (1.0 eq.), EDCI (1.5 eq.), HOBT (1.5 eq.), DIPEA (2.5 eq.), DMF, RT, 24 h, Yield: ~87% | Mol. Wt: ~410.51 M.I. Peak observed: ~433.55 (M + Na) |
| D-81/83 | 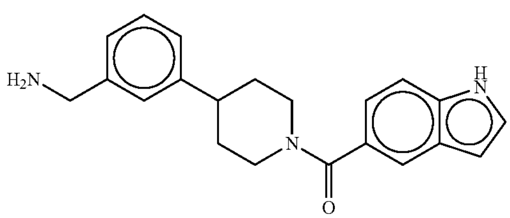 | Indole-5-carboxylic acid (1 eq), tert-butyl 3-(piperidin-4-yl) benzyl carbamate (1.3 eq.), EDCI (1.2 eq.), DMAP (2.0 eq.), DMF, DCM, RT, 3 h, Yield: ~75% | Mol. Wt: ~433.54 M.I. Peak observed: ~434.05 |
| D-82/84 | 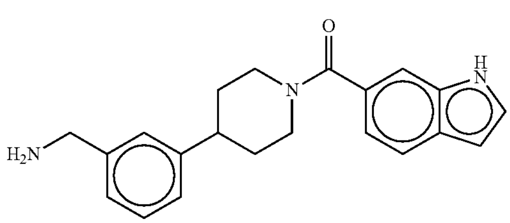 | Indole-6-carboxylic acid (1 eq), tert-butyl 3-(piperidin-4-yl) benzyl carbamate (1.3 eq.), EDCI (1.2 eq.), DMAP (2.0 eq.), DMF, DCM, RT, 3 h, Yield: ~73% | Mol. Wt: ~433.54 M.I. Peak observed: ~434.10 |

Step-2

Stirred suspension of Product from step-1 (intermediate A) in dimethyl formamide was added using potassium carbonate followed by desired epoxide. Reaction mass was heated to 100° C. and reaction monitored by LCMS till maximum starting was consumed. There after reaction mass was cooled to room temperature and diluted with water and extracted with ethyl acetate. Ethyl acetate extract was washed with water, dried over sodium sulfate and concentrated in vacuum to get the crude product which was purified by column chromatography over silica gel using 0-25% ethyl acetate in hexane. Epoxide required for Synthesis of target-103 was synthesized by the procedure described in the literature (*J. Am. Chem. Soc.* 113, 3096-3106, 1991)

Details of the compounds synthesized are as below in Table 37.

TABLE 37

REACTION CONDITIONS & ANALYTICAL DATA

| Comp. No. | Structure | Brief Reaction conditions | Analytical data |
|---|---|---|---|
| B-72 | 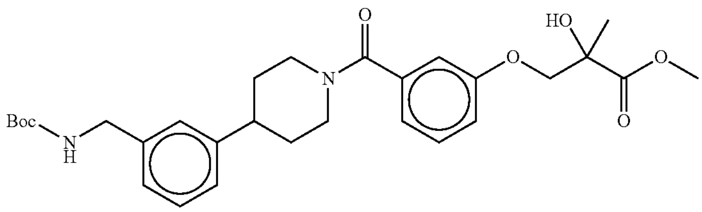 | K2CO3 (4.0 eq.), DMF, 100° C., 5 h, 79% | Mol. Wt: 540.65<br>M.I. Peak observed: −563.40<br>(M + Na in ESMS) |
| B-73 | 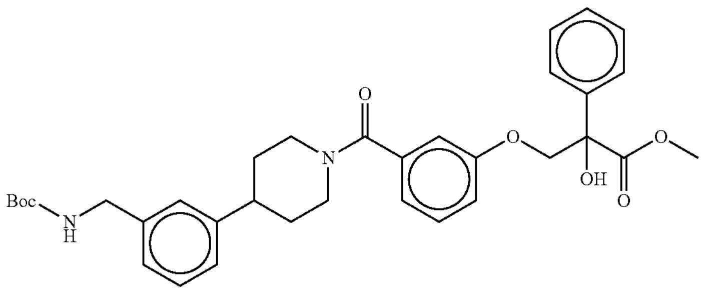 | K2CO3 (4.0 eq.), DMF, 100° C., 5 h, 68% | Mol. Wt.: 602.72<br>M.I. Peak observed: −603<br>(ESMS) |
| B-103 | 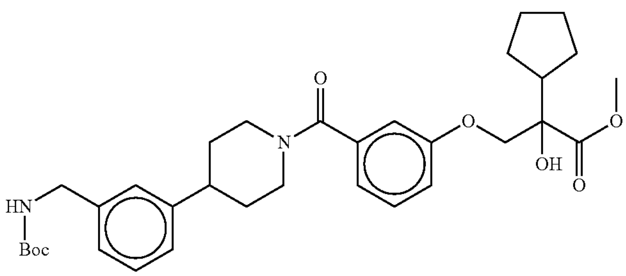 | K2CO3 (4.0 eq.), DMF, 100° C., 5 h, 80% | Mol. Wt.: 594.33<br>ESMS (m/z): 617<br>[M + Na] |

Step-3

Hydroxy ester from step-2 was hydrolyzed to acid following general procedure in method-A, step 3. Compounds were purified by column chromatography over silica gel using methanol (1-15%) in chloroform. The details of the compounds synthesized are as below in Table 38.

TABLE 38

REACTION CONDITIONS & ANALYTICAL DATA

| Comp. No. | Structure | Brief Reaction conditions | Analytical data |
|---|---|---|---|
| C-72 | 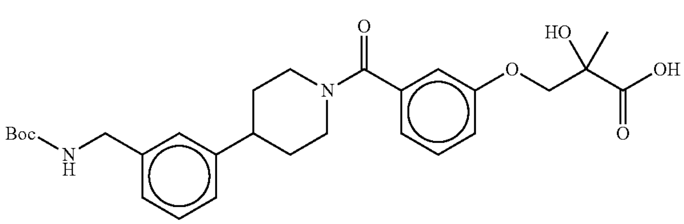 | LiOH (2.0 eq.), THF:H2O (1:1), RT, Yield: −79%. | Mol. Wt: 512.59<br>LCMS (m/z): 535.15<br>[M + 1] |

TABLE 38-continued

REACTION CONDITIONS & ANALYTICAL DATA

| Comp. No. | Structure | Brief Reaction conditions | Analytical data |
|---|---|---|---|
| C-73 | 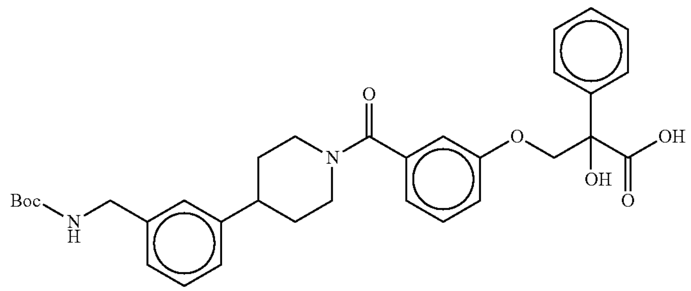 | LiOH (2.0 eq.), THF:H2O (1:1), RT, Yield: ~70%. | Mol. Wt: 574.66 LCMS (m/z): 597 [M + Na] |
| C-103 | 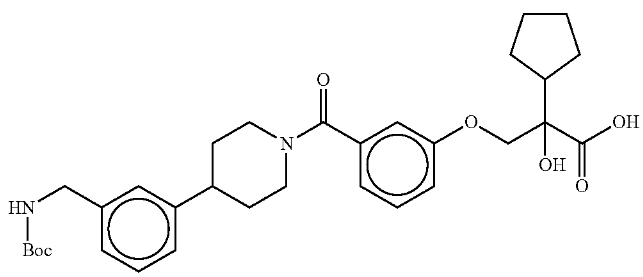 | KOH (10.0 eq.), EtOH:H2O (1:1), RT, Yield: ~75%. | Mol. Wt: 566.69 LCMS (m/z): 567.20 [M + Na] |

Step-4

Boc deprotection of the step-3 products was carried out by stirring with methanolic HCl at room temperature. Reactions were monitored by LCMS and after reaction completion, solvents were evaporated in vacuum and residue was purified by reverse phase preparative HPLC to get the products as TFA salts. The details of the compounds synthesized are as below in Table 39.

TABLE 39

REACTION CONDITIONS & ANALYTICAL DATA

| Comp. No. | Structure | Brief Reaction conditions | Analytical data |
|---|---|---|---|
| Target-72 | 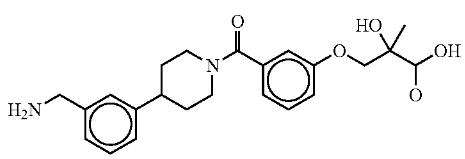 | Conc. HCl (8.0 eq.), MeOH, 15 h, RT, 62% isolated as TFA salt from prep HPLC and later converted to hydrochloride. | Mol. Wt: 412.48 M.I. Peak observed: ~413.10 [M + 1] HPLC Purity: 98.83% $^1$H NMR (400 MHz, DMSO): ~7.45-7.25 (m, 5H), 7.12-7.00 (m, 2H), 6.92-6.82 (m, 1H), 4.84-4.74 (m, 1H), 4.25 (d, J = 9.4 Hz, 1H), 4.10 (s, 2H), 4.03 (d, J = 9.4 Hz, 1H), 3.94-3.82 (m, 1H), 3.28-3.20 (m, 1H), 3.00-2.86 (m, 2H), 2.02-1.92 (m, 1H), 1.88-1.60 (m, 3H), 1.48 (s, 3H) |
| Target-73 | 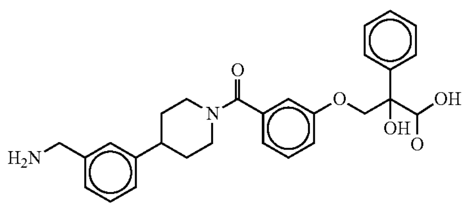 | Conc. HCl (8.0 eq.), MeOH, 15 h, RT, Prep HPLC. isolated as TFA, salt Yield: ~36% | Mol. Wt: 474.55 M.I. Peak observed: ~475 [M + 1] HPLC Purity: 98.44% $^1$H NMR (400 MHz, CD$_3$OD): δ 7.73-7.70 (m, 2H), 7.42-7.28 (m, 8H), 7.12-7.08 (m, 1H), 7.05-7.00 (m, 2H), 4.82-4.75 (m, 1H), 4.71 (d, J = 9.4 Hz, 1H), 4.22 (d, J = 9.4 Hz, 1H), 4.10 (s, 2H), 3.92-3.84 (m, 1H), 3.28-3.20 (m, 1H), 3.00-2.88 (m, 2H), 2.03-1.92 (m, 1H), 1.85-1.60 (m, 3H) |

TABLE 39-continued

REACTION CONDITIONS & ANALYTICAL DATA

| Comp. No. | Structure | Brief Reaction conditions | Analytical data |
|---|---|---|---|
| Target-103 | (structure) | DCM (20 Vol), TFA (10 Vol), 2 h, RT, 50% isolated as TFA salt from prep HPLC and later converted to hydrochloride. | Mol. Wt: 466.57<br>M.I. Peak observed: −467.10<br>HPLC Purity: 97.58%<br>¹H NMR (400 MHz, DMSO):- δ 1.47-1.83 (m, 11H), 2.21(t, 1H), 2.82-2.84 (m, 2H), 3.16(bs, 1H), 3.94-4.00(m, 3H), 4.18-4.20(d, 1H), 4.62(bs, 1H), 6.93-7.00(m, 4H), 7.30-7.36(m, 4H) |

Step-6

Stirred suspension of coupled product form step-1 in THF was added sodium hydride. Stirring continued for 30 min and desired epoxy ester was added to it. Stirring continued at room temp and reaction monitored by LCMS. LCMS indicated peak of corresponding carboxylic acid instead of ester. After completion of reaction, Reaction mass was concentrated in vacuum and quenched with ice. pH of the reaction mass was then adjusted to 3-4 by potassium hydrogen sulfate and extracted with ethyl acetate. Ethyl acetate extract was dried over sodium sulfate and concentrated in vacuum to get the crude product which was used for next step without purification.

TABLE 40

REACTION CONDITIONS & ANALYTICAL DATA

| Comp. No. | Structure | Brief Reaction conditions | Analytica data |
|---|---|---|---|
| E-81 | (structure) | NaH(10 eq), THF(20 Vol), Methyl-2-methyloxirane-2-carboxylate(4.0 eq), R.T. Yield: ~70% | Mol. Wt: ~535.63<br>M.I. Peak observed: ~558.10(Na+) |
| E82 | (structure) | NaH(10 eq), THF(20 Vol), Methyl-2-methyloxirane-2-carboxylate(4.0 eq) Yield: ~65% | Mol. Wt: ~535.63<br>M.I. Peak observed: ~536.00 |
| E-83 | (structure) | NaH(10 eq), THF(20 Vol), Methyl-2-phenyloxirane-2-carboxylate (4.0 eq) Yield: ~72.63% | Mol. Wt: ~597.70<br>M.I. Peak observed: ~598.15 |

TABLE 40-continued

REACTION CONDITIONS & ANALYTICAL DATA

| Comp. No. | Structure | Brief Reaction conditions | Analytical data |
|---|---|---|---|
| E-84 | 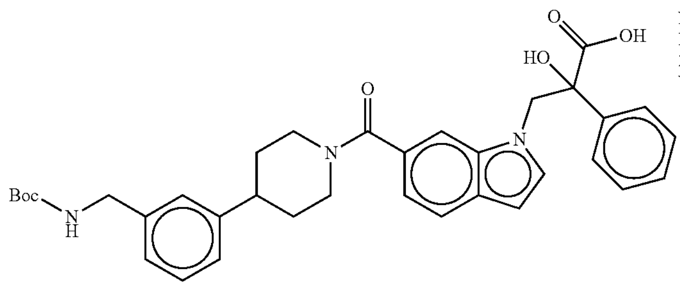 | NaH(10 eq), THF(20 Vol) Methyl-2-phenyloxirane-2-carboxylate (4.0 eq) Yield: ~77.48% | Mol. Wt: ~597.70 M.I. Peak observed: 598.45 |

Step-7

Boc de-protection of Product from step-6 was carried out as per general procedure described in method-A, step-9.

TABLE 41

REACTION CONDITIONS & ANALYTICAL DATA

| Comp. No. | Structure | Brief Reaction conditions | Analytical data |
|---|---|---|---|
| Target-81 | 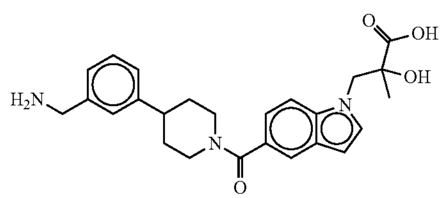 | TFA (10 Vol), DCM (20 Vol), 4 Hrs, Isolated as TFA Salt by prep. HPLC. Yield: ~20%. | Mol. Wt: ~435.52 M.I. peak observed: ~436.15 HPLC Purity: ~97.17% 1H NMR DMSO-d6: ~1.266(s, 3H), 1.63-1.722(m, 4H), 2.835-2.913(m, 4H), 4.029-4.015(d, 2H, 4.294-4.331 (d, 1H, J = 14.4 Hz), 4.402-4.438 (d, 1H, J = 14.8 Hz), 6.492(s, 1H), 7.166-7.187(d, 1H, J = 8.4 Hz), 7.291-7.398 (m, 5H), 7.607(S, 1H), 7.557-7.578 (d, 1H, J = 8.4 Hz), 8.132(S, 3H). |
| Target-82 | 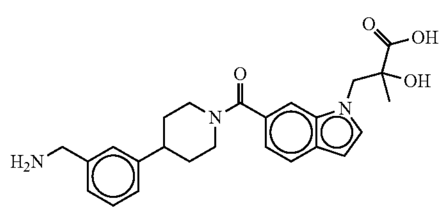 | TFA (10 Vol), DCM (20 Vol), 4 Hrs, Isolated as TFA Salt by prep. HPLC, Yield: ~10%. | Mol. Wt: ~435.52 M.I. peak observed: ~436.05 HPLC Purity: ~97.79% 1H NMR DMSO-d6: ~1.265(s, 3H), 1.615-1.751(m, 4H), 2.871-2.812 (m, 4H),, 4.004-4.033 (d, 2H), 4.305-4.342 (d, 1H, J = 14.8 Hz), 4.452-4.416 (d, 1H, J = 14.4 Hz), 5.538 (m, 1H), 6.472-6.479(d, 1H), 7.059-7.081 (d, 1H), 7.550-7.571(d, 1H), 7.277-7.406(m, 2H), 7.626 (s, 1H), 6.902-6.934(t, 1H), 8.135 (s, 3H), 12.9(s, 1H). |
| Target-83 | 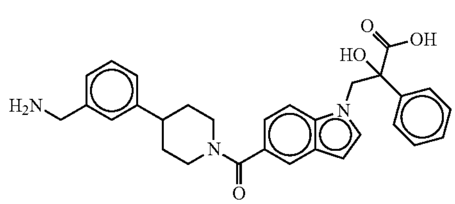 | TFA (20 Vol), DCM (40 Vol), 4 Hrs, Isolated as TFA Salt by prep. HPLC and converted to hydrochloride Yield: ~30% | Mol. Wt: ~497.58 M.H. peak observed: ~498 HPLC Purity: ~99.85% $^1$H NMR DMSO-d6: ~1.586-1.768(m, 4H), 2.796-2.855(m, 2H), 3.427-3.523(m, 2H), 3.055-2.988(m, 1H), 4.022-3.972(d, 2H), 4.503-4.539(d, 1H J = 14.4 Hz), 4.875-4.911 (d, 1H, J = 14.4 Hz), 6.418-6.424 (d, 1H), 7.101-7.105 (dd, 1H, J = 1.6 Hz), 7.256-7.368 (m, 7H), 7.446 (s, 1H), 7.512 (s, 1H), 7.629-7.625(dd, 1H, J = 1.6 Hz), 7.446-7.560(m, 2H), 8.371(bs, 2H),. |

TABLE 41-continued

REACTION CONDITIONS & ANALYTICAL DATA

| Comp. No. | Structure | Brief Reaction conditions | Analytical data |
|---|---|---|---|
| Target-84 | 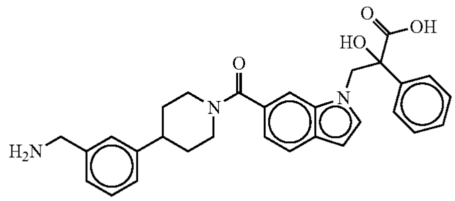 | TFA (20 Vol), DCM (40 Vol), 4 Hrs, Isolated as TFA Salt by prep. HPLC and converted to hydrochloride Yield: ~30% | Mol. Wt: ~497.58 M.I. peak observed: ~498.40 HPLC Purity: ~98.03% $^1$H NMR DMSO-d6: ~1.633-1.799 (m, 4H), 2.820-2.879 (m, 2H), 3.988-4.015 (d, 2H), 4.493-4.532 (d, 1H, J = 15.6 Hz), 4.838-4.924(d, 1H, J = 14.4 Hz), 6.397-6.405 (d, 1H), 7.033-7.053(d, 1H, J = 8 Hz), 7.442(s, 1H), 7.448-7.518(d, 1H, J = 8 Hz), 7.632-7.613(d, 3H), 8.326(bs, 3H) |

Example 12: Synthesis of Tryptase Inhibitors with Cis Pyrrolidine Diol Functionality

Method 1

Meta/para hydroxy benzoic acid was coupled with tert-butyl 3-(1-(3-hydroxybenzoyl)piperidin-4-yl) benzylcarbamate. Coupled product was reacted with ethyl bromo acetate/methyl acrylate in presence of base to yield corresponding O-Alky product with aliphatic ester functionality which was hydrolyzed and coupled with cis-pyrrolidine diol (e.g. as shown in EP1961750 & WO2009/61879) the coupled products were de-protected to yield the title compounds.

SCHEME 13.

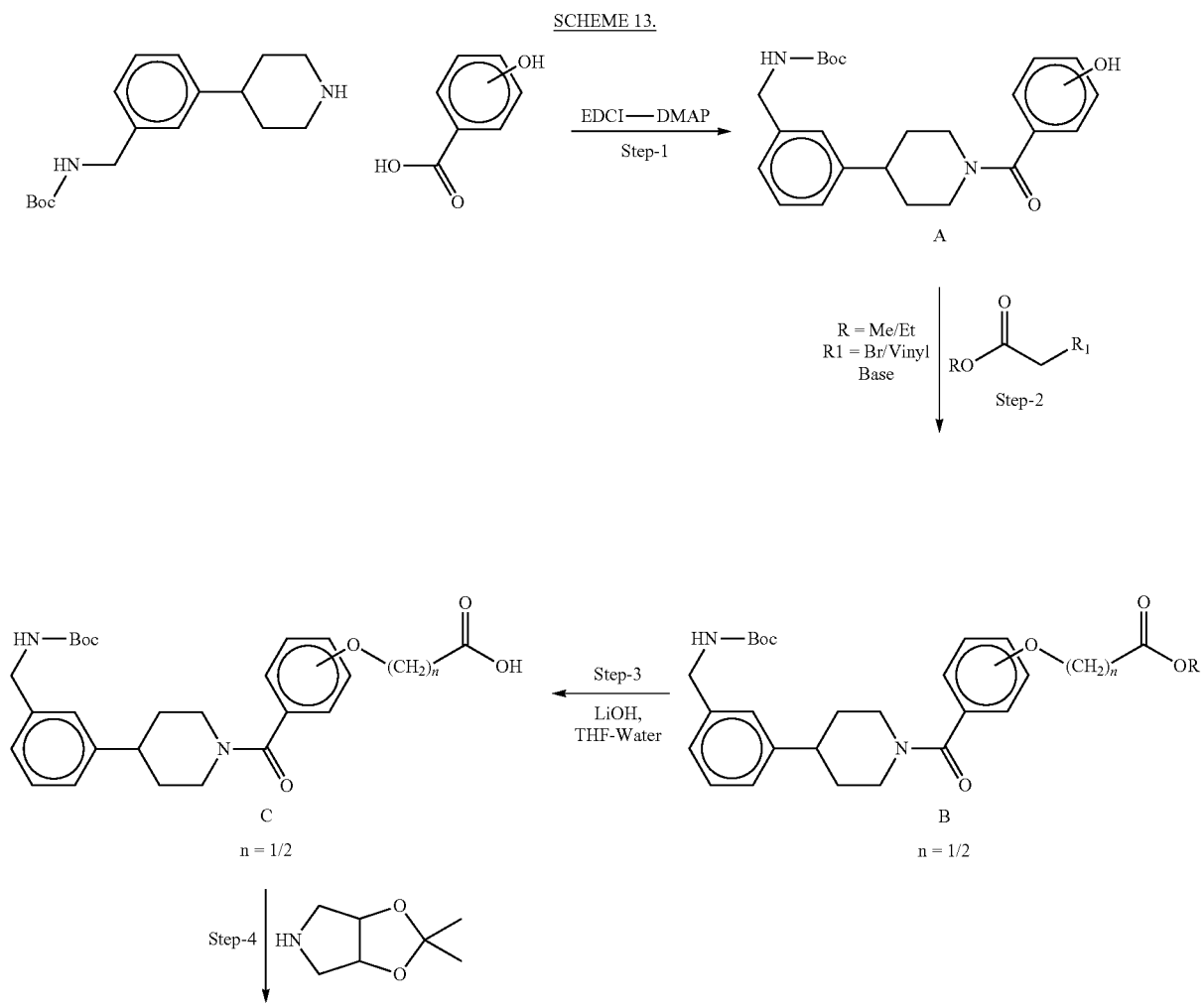

-continued

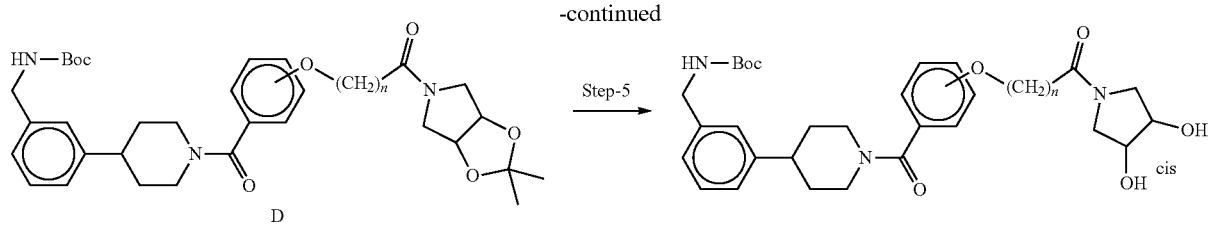

Step-1

This reaction was performed as per the general procedure described for step-4 in method "A" using meta or para hydroxy benzoic acid.

The details of compounds synthesized are as below in Table 42.

TABLE 42

REACTION CONDITIONS & ANALYTICAL DATA

| Comp. No. | Structure | Brief Reaction conditions | Analytical data |
|---|---|---|---|
| A-30 | 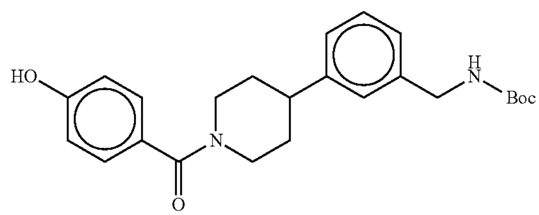 | Common core (1.1 eq.), EDCI (1.5 eq.), DMAP (1.2 eq.), DCM(100 vol), DMF(10 vol), RT, 2 h, yield: ~58%, | Crude product carried forward for next step |

Step-2

Synthesis of B-53: Product from step-1 was dissolved in methyl acrylate. To this catalytic hydroquinone was added as polymerization inhibitor followed by sodium metal. Reaction mass was then refluxed for 48 hrs and monitored by LCMS. After consumption of maximum starting, the reaction mass was concentrated and the residue was purified by column chromatography over neutral alumina using Methanol (0-10%) in dichloromethane.

Synthesis of B29 & B30: Product from step-1 was added to suspension of potassium carbonate in acetone at room temperature. Ethyl bromo acetate was then added to this and refluxed and reaction was monitored by LCMS. After maximum starting was consumed, Reaction mass was concentrated and residue was diluted with dichloromethane and washed with water. Organic layer was filtered, dried over a=sodium sulfate and concentrated to get the crude product which was used for next step without further purification.

TABLE 42

REACTION CONDITIONS & ANALYTICAL DATA

| Comp. No. | Structure | Brief Reaction conditions | Analytical data |
|---|---|---|---|
| B-53 | 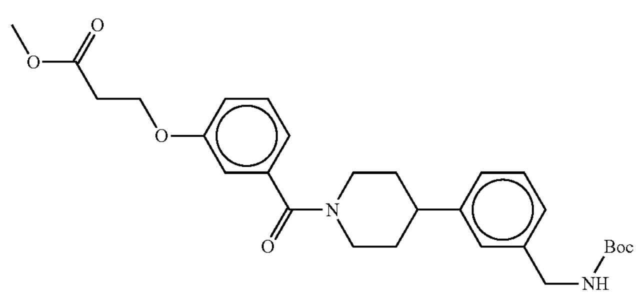 | Methyl acrylate (20 vol), Na metal (10 eq), hydroqunone (catalytic), 48 h, 75° C., Yield: ~82.9% | Mol. Wt: ~496.60 M.I. Peak observed: ~519.45 (M + Na) Purity: ~83% |

TABLE 42-continued

REACTION CONDITIONS & ANALYTICAL DATA

| Comp. No. | Structure | Brief Reaction conditions | Analytical data |
|---|---|---|---|
| B-29 | 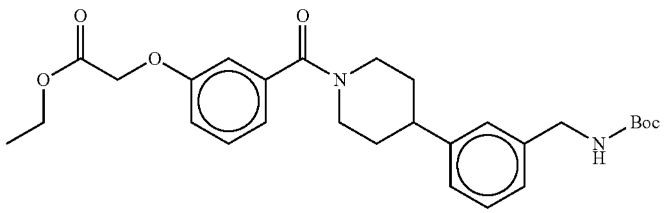 | Ethyl bromo acetate (1 eq.), K₂CO₃(3 eq), acetone(100 vol), relux temp, 3 h, Yield: ~100%, Crude product carried forward | Mol. Wt: ~496.60 M.I. Peak observed: ~519.35 (M + Na) Crude product used for next step |
| B-30 | 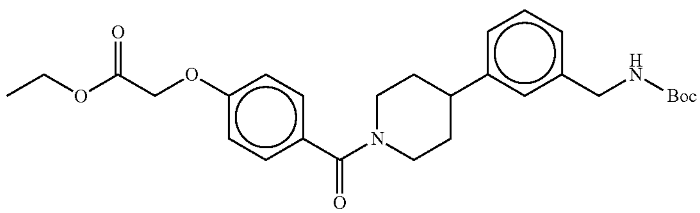 | Ethyl bromo acetate (1 eq.), K₂CO₃ (3 eq), acetone(100 vol), reflux temp, 3 h, 98%, | Crude product carried forward for next step. |

Step-3

These reactions were performed as per general procedure followed for step-3 of method A. In some cases sodium hydroxide was used instead of lithium hydroxide as reactions were unsuccessful with lithium hydroxide The details of compounds synthesized are as below in Table 43.

TABLE 43

REACTION CONDITIONS & ANALYTICAL DATA

| Comp. No. | Structure | Brief Reaction conditions | Analytical data |
|---|---|---|---|
| C-53 | 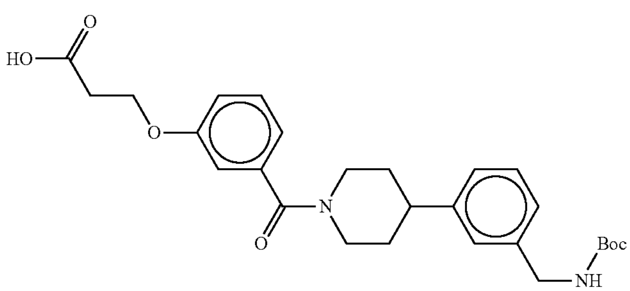 | LiOH (2.0 eq.), THF:H2O (1:1), RT, 12, h, Yield:- 77%. | Mol. Wt:- 482.57 M.I. Peak observed:- 505.45 (M + Na) Crude product used for nex step |
| C-29 | 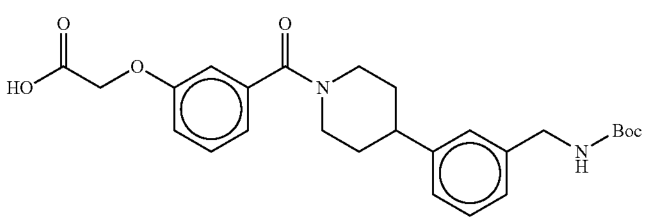 | NaOH (3.0 eq.), THF:H2O (1:1), RT, Yield:- 74%. | Mol. Wt:- 468.54 M.I. Peak observed:- 491.20 (M + Na) Crude product used for next step |
| C-30 | 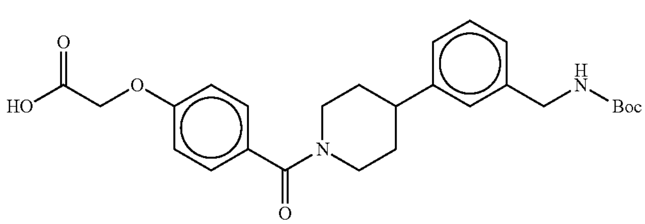 | NaOH (3.0 eq.), THF:H2O (1:1), RT, Yield:- 70%. | Mol. Wt:- 468.54 M.I. Peak observed:- 491.20 (M + Na) Crude product used for next step |

Step-4

Protected cis-pyrrolidine diol required was synthesized as per procedure described in the literature (EP1961750 & WO2009/61879). Coupling reactions were carried out as per the general procedure described in method-A (step-4).

The details of compounds synthesized are as below in Table 44.

TABLE 44

REACTION CONDITIONS & ANALYTICAL DATA

| Comp. No. | Structure | Brief Reaction conditions | Analytical data |
|---|---|---|---|
| D-53 | 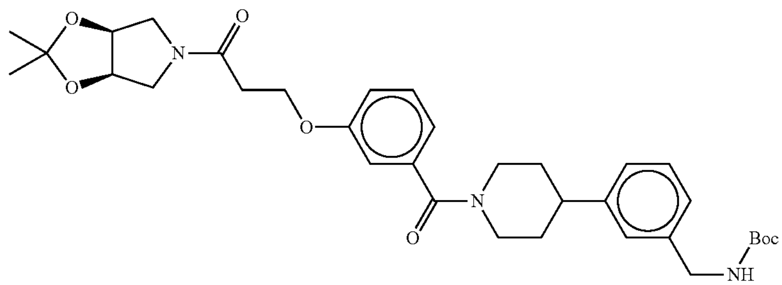 | protected cis pyrrolidine diol (1.1 eq) EDCI (1.5 eq), DMAP (1.2 eq) DCM (100 vol), RT, 3 h, Yield:- 82.2% | Mol. Wt:- 607.74 M.I. Peak observed:- 630.15 (M + Na) Crude product used for next step |
| D-29 | 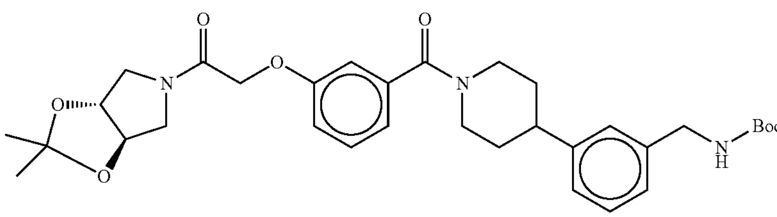 | protected cis pyrrolidine diol (1.3 eq) EDCI (1.5 eq), DMAP (1.2 eq) DCM (100 vol), RT, 3 h, Yield:- 44.6% | Mol. Wt.:- 593.71 M.I. Peak observed:- 594.41 Crude product used for next step |
| D-30 | 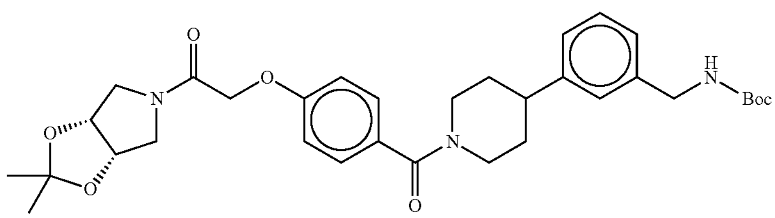 | protected cis pyrrolidine diol (1.3 eq) EDCI (1.5 eq), DMAP (1.2 eq) DCM (100 vol), RT, 3 h, Yield:- 40% | Mol. Wt:- 593.71 M.I. Peak observed:- 594.48 Crude product used for next step |

Step-5

Products form step-4 were deprotected as per procedure described in method A (Step-5) the details of compounds synthesized are as below in Table 45.

TABLE 45

REACTION CONDITIONS & ANALYTICAL DATA

| Comp. No. | Structure | Brief Reaction conditions | Analytical data |
|---|---|---|---|
| Target-53 | 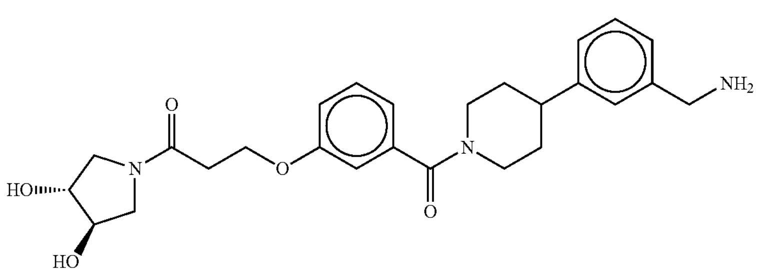 | Methanolic HCl (25 vol), 4 h, RT, 89%. Isolated by prep HPLC As TFA salt and converted to hydrochloride | Mol. Wt:- 467.56 M.I. Peak observed:- 468.10 HPLC Purity:- 95.41 $^1$H NMR (DMSO-d6:- 1.62-1.83 (m, 4H) 2.69 (t, 2H), 2.79-2.85 (m, 2H), 3.16-3.50 (m, 7H), 3.99 (t, 2H), 4.04-4.08 (m, 2H), 4.21 (t, 2H), 4.65 (bs, 1 H), 6.93-7.05 (m, 3H), 7.18 (s, 1H), 7.29-7.42 (m, 4H), 8.26 (bs, 2H). |

TABLE 45-continued

REACTION CONDITIONS & ANALYTICAL DATA

| Comp. No. | Structure | Brief Reaction conditions | Analytical data |
|---|---|---|---|
| Target-29 | 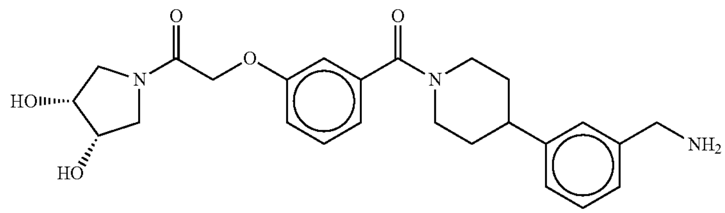 | TFA (6 eq) DCM (100 vol), R.T., 7 hrs, Isolated by prep HPLC As TFA salt 33%. | Mol. Wt:- 453.53 M.I. Peak observed:- 454.50 HPLC Purity:- 98.79 ¹H NMR (DMSO-d6:- 1.60-1.83 (m, 4H), 2.83 (t, 2H), 3.18-3.33 (m, 5H), 3.62-3.66 (m, 2H), 3.97-4.07 (m, 4H), 4.62 (bs, 1H), 4.74 (s, 2H), 6.92-6.99 (m, 3H), 7.27-7.39 (m, 5H), 8.12 (bs, 2H). |
| Target-30 | 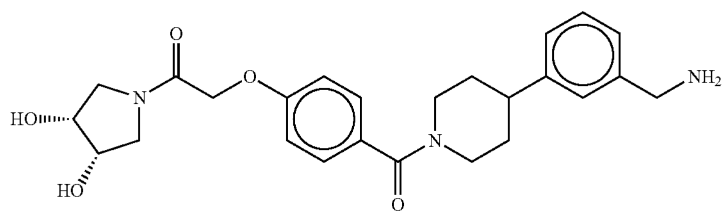 | TFA (6 eq) DCM (100 vol), R.T., 7 hrs, Isolated by prep HPLC As TFA salt 21%. | Mol. Wt:- 453.53 M.I. Peak observed:- 454.40 HPLC Purity:- 95.34 ¹H NMR DSO-d6:- 1.59-1.77 (m, 4H), 2.83 (t, 2H), 3.16-3.40 (m, 5H), 3.62-3.66 (m, 2H), 4.00-4.08 (m, 4H), 4.76 (s, 2H), 6.94-6.96 (d, 2H), 7.27-7.37 (m, 6H), 8.12 (bs, 2H). |

Example 13: Synthesis of Spiro Analogues of Tryptase Inhibitors

Method J

Spiro key intermediate (E) was synthesized from 2H-spiro[benzofuran-3, 4'-piperidine]-5-carbonitrile (US 2009/0163527, & B.org. Med. Chem. Lett. 2008, 18, 2114-2121.) through the reaction sequence described in the scheme below.

Boronic acids or hydroxy compounds were synthesized form it through the identical reaction sequence followed earlier (Method A & C). Spiro amidines were synthesized as per the reaction sequence mentioned in steps 7 & 8.

SCHEME 14.

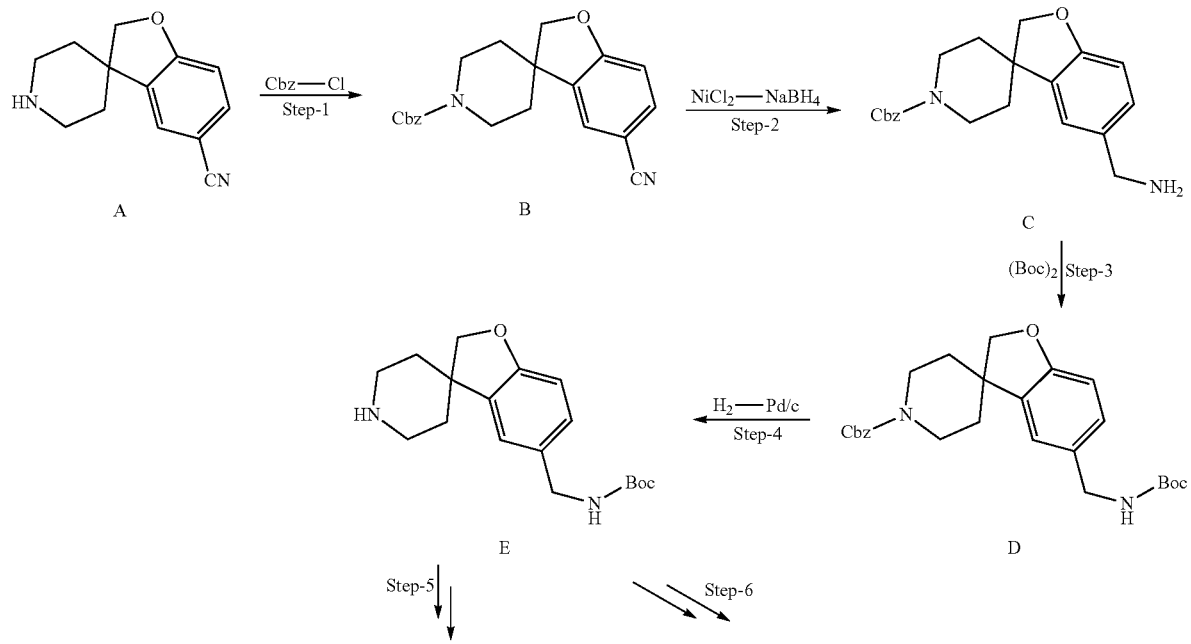

-continued

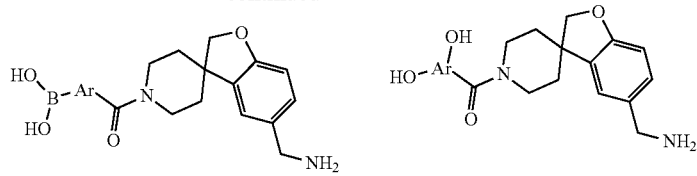

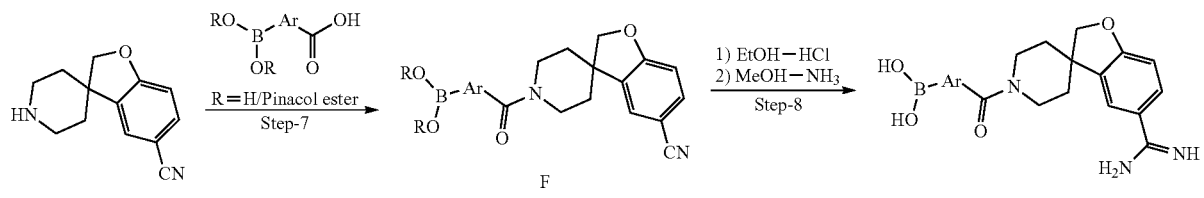

Step-1

To a stirred solution of 2H-spiro [benzofuran-3,4'-piperidine]-5-carbonitrile (5 g, 0.023 mol) in THF (10 vol) and aq. solution of sodium bicarbonate (10 vol) was added benzyl chloroformate (1.3 eq 0.030 mol) at 0-5° C. and the reaction mixture was stirred for 3 hrs at same temperature. There after it was warmed to room temperature and stirring continued for additional 2 hrs. Solvents were then evaporated under reduced pressure and aq layer was extracted with ethyl acetate. Ethyl acetate extracts were dried over sodium sulphate and concentrated to get the Crude product which purified by column chromatography over silica gel using ethyl acetate (0-20%) in hexane to get the pure product.
Yield: 60%
Mol. Wt: 348.40
M.I peak observed: 348.95

Step-2 & 3

To a stirred solution of benzyl-5-cyano-2H-spiro[benzofuran-3,4'-piperidine]-1'-carboxylate (4 g, 0.011 mol) in methanol (10 vol) was added Boc anhydride (5.01 g, 2.0 eq 0.022 mol)& $NiCl_2$ (0.372 g, 0.25 eq, 0.0028 mol) at 0-5° C. Sodium borohydride (0.869 g, 2.0 eq, 0.22 mol) was then added portion wise maintaining the temperature. Reaction mixture was allowed to warm to room temperature and stirring continued for 3 hrs there after. Solvents were evaporated under reduced pressure. Residue was diluted with water (~20 volumes) and extracted with ethyl acetate. Ethyl acetate extract was dried over sodium sulphate and concentrated to get the crude product which was purified by column chromatography over silica gel using ethyl acetate (0-40%) in hexane to get the pure product.
Yield: 3.2 g (62.7%)
Mol. Wt: 438.52
M.I peak observed: 475.55 (M+Na)

Step-4

To a stirred solution of benzyl5-((tert-butoxycarbonyl)amino)-2H-spiro[benzofuran-3,4'-piperidine]-1'-carboxylate (3 g, 0.0066 mol) in methanol (15 vol) was added 10% Pd/C (500 mg) at room temperature under nitrogen atmosphere. The mixture was then stirred under hydrogen pressure (~10 Kg) at room temperature in an autoclave till no more hydrogen was consumed & LCMS there after indicated formation of product and absence of starting material (~4 hrs required). Vessel was depressurized and the reaction mass was filtered through celite; solvent was evaporated in vacuum, and the residue was purified by column chromatography get pure product which was characterized by LCMS. Yield: 63%
Mol. Wt: (318.41)
M.I peak observed: (319.05)

Step-5

Procedure described in method-A step-4 & 5 was followed.

TABLE 46

REACTION CONDITIONS & ANALYTICAL DATA

| Comp. No. | Structure | Brief Reaction conditions | Analytical data |
|---|---|---|---|
| Target-35-Spiro | 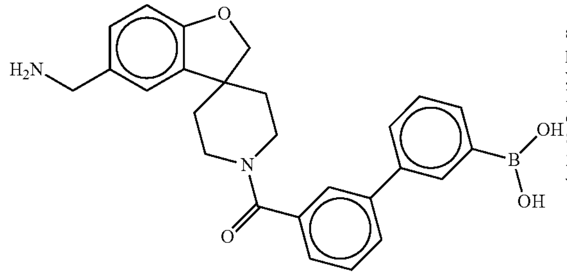 | 1) tert-butyl ((2H-spiro[benzofuran-3,4'-piperidin]-5-yl)methyl)carbamate (1.1 eq.), EDCI (1.5 eq.), DMAP (1.2 eq.), DCM (100 vol), RT, 12 h, 81% 2) TFA (10 eq) Acetonitrile (65 vol), R.T. 12 hrs, 57% | Mol. Wt:- 442.31 M.I. Peak observed: 443.40 HPLC Purity:- 95.81% $^1$H NMR (DMSO-d6:- $^1$HNMR (400 MHz, DMSO):- 1.67-1.79 (m, 4H), 3.16-3.29 (m, 2H), 3.92-3.93 (q, 4H), 4.50 (s, 3H), 6.81-6.83 (d, 1H), 7.23-7.25 (d, 1H), 7.40-7.58 (m, 4H), 7.71-7.81 (m, 4H), 8.15 (s, 1H), 8.25 (bs, 2H). |

Step-6

Procedure described in method-C, step-1 & 2 was followed for Target-78-spiro & and Procedure as per method-A, step-4 & 9 was followed for Target-2 spiro.

TABLE 47

REACTION CONDITIONS & ANALYTICAL DATA

| Comp. No. | Structure | Brief Reaction conditions | Analytical data |
|---|---|---|---|
| Target-78-Spiro | 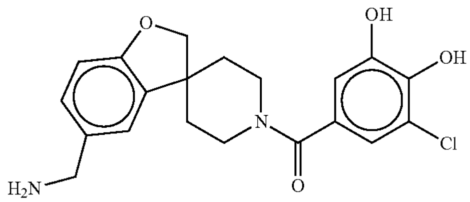 | 1) tert-butyl ((2H-spiro[benzofuran-3,4'-piperidin]-5-yl)methyl)carbamate (1.1 eq.), EDCI (1.5 eq.), DMAP (1.2 eq.), DCM (100 vol), RT, 12 h, Yield- 90%<br>2) BBr₃ (3 eq) DCM (85 vol), R.T. 1 hrs, Yield-74% | Mol. Wt:- 388.84<br>M.I. Peak observed 411.00 (M + Na)<br>HPLC Purity:- 99.60%<br>¹H NMR DMSO-d6:- ¹HNMR (400 MHz, DMSO):- 1.72 (m ,4H), 3.14 (m, 4H), 3.94-3.95 (q, 2H), 4.49 (s, 2H), 6.80-6.86 (m, 3H) 7.20-7.23 (d, 1H), 7.41(s, 1H), 8.02 (bs, 2H), 9.59( bs, 1H), 10.11 (bs, 1H). |
| Target-2 Spiro | 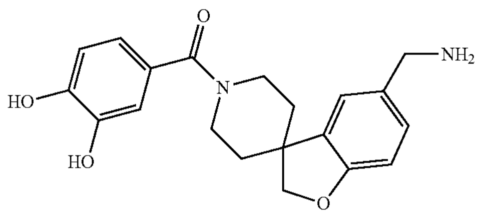 [SMILES: NCc1ccc2c(c1)C1(CCN(C(=O)c3ccc(O)c(O)c3)CC1)CO2] | 1) tert-butyl ((2H-spiro [benzofuran-3,4'-piperidin]-5-yl) methyl)carbamate (1.1 eq.), EDCI (1.5 eq.), DMAP (1.2 eq.), DMF (10 vol), RT, 12 h, Yield-60%<br>2) TFA (3 eq) DCM (25 vol), R.T. 4 hrs, Yield-51% | Mol. Wt:- 354.40<br>M.I. Peak observed: 377.00 (M + Na)<br>HPLC Purity:- 99.33%<br>¹H NMR CD3OD:- 1.814-1.930 (m, 4H), 3.14 (m, 4H), 4.04 (s, 2H), 4.56 (s, 2H), 6.90 (s, 1H), 6.18-6.83 (m, 3H), 7.31 (s, 1H), 7.224-7.244 (dd, 1H). |

These reactions were carried out as per procedure described in method-A (step-4 or step-8).

TABLE 48

REACTION CONDITIONS & ANALYTICAL DATA

| Comp. No. | Structure | Brief Reaction conditions | Analytical data |
|---|---|---|---|
| F-35-Spiro amidine | 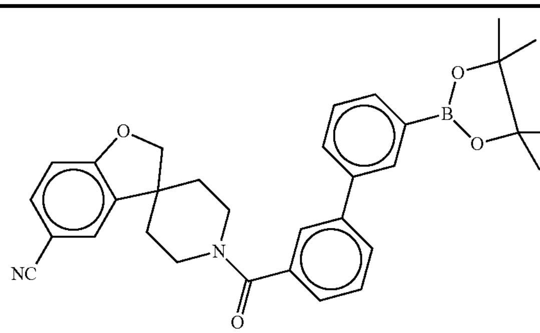 | 2H-spiro[benzofuran-3,4'-piperidine]-5-carbonitrile (1.1 eq.), EDCI (1.5 eq.), DMAP (1.2 eq.), DCM (100 vol), RT, 12 h, purified by column chromatography, over silica gel using 0-40% ethyl acetate in hexane. Yield-75% | Mol. Wt:- 520.43<br>M.I. Peak observed: 543.22 (M + Na) |
| F-33 spiro amidine | 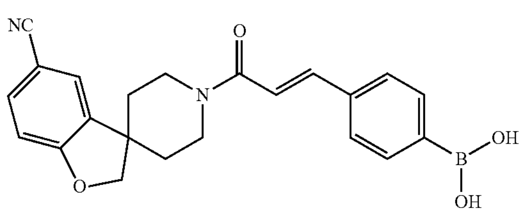 [SMILES: N#Cc1ccc2c(c1)C1(CCN(C(=O)/C=C/c3ccc(B(O)O)cc3)CC1)CO2] | 2H-spiro[benzofuran-3,4'-piperidine]-5-carbonitrile (1.1 eq.), EDCI (1.5 eq.), DMAP (1.2 eq.), DCM (100 vol), RT, 12 h, column chromatography, over silica gel using 0-40% ethyl acetate in hexane, Yield-52% | Mol. Wt:- 388.22<br>M.I. Peak observed: 389.35 |

Products from step-7 were treated Ethanolic HC at ambient temperature followed by methanolic ammonia in a sealed bottle to get the title compounds which were isolated by prep. HPLC as TFA salts which were later converted to hydrochloride salts by stirring with 2N HC for 30 min and subsequent lyophilization.

TABLE 49

REACTION CONDITIONS & ANALYTICAL DATA

| Comp. No. | Structure | Brief Reaction conditions | Analytical data |
|---|---|---|---|
| Target-35-Spiro amidine | 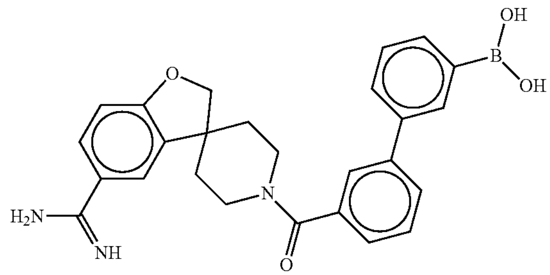 | 1) Ethanolic HCl (5 vol) RT, 4H, purified by column chromatography, over silica gel using 0-40% methanol in chloroform Yield- 75% 2) Methanolic ammonia (10 vol), heating in sealed tube, 12 h, purified by prep HPLC, isolated as TFA salt, converted to HCl salt. Yield- 43% | Mol. Wt:- 455.31 M.I. peak observed:- 456.20 HPLC Purity:- 98.66% 1H NMR (DMSO-d6:- 1.703-1.847 (m, 4H), 3.057 (m, 2H), 3.657 (m, 2H), 4.657 (s, 2H), 7.038-7.018 (d, 1H), 7.413-7.457 (m, 2H), 7.570 (t, 1H), 7.790 (t, 1H), 7.866 (s, 1H), 8.142 (s, 1H), 7.675-7.746 (m, 4H), 8.746 (bs, 2H), 9.079 (s, 2H), 8.142 (s, 1H), |
| T-33 spiro amidine | 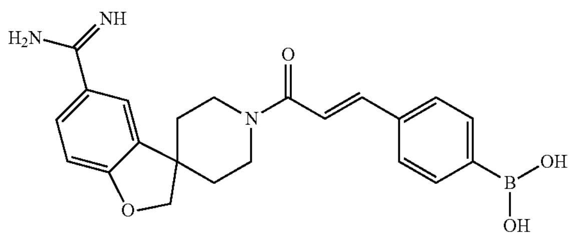 [SMILES: N=C(N)c1ccc2c(c1)C1(CCN(C(=O)/C=C/c3ccc(B(O)O)cc3)CC1)CO2] | 1) Ethanolic HCl (5 vol) RT, 4H, purified by column chromatography, over silica gel using 0-40% methanol in chloroform Yield-61% 2) Methanolic acmmonia (10 vol), heating in sealed tube, 12 h, purified by prep HPLC, isolated as TFA salt, converted to HCl salt. Yield- 13% | Mol. Wt:- 405.25 M.I. peak observed:- 406.10 HPLC Purity:- 98.36% 1H NMR (DMSO-d6:- 1.784-1.815 (m, 4H), 2.900 (m, 1H), 4.340-4.493 (m, 2H), 4.862 (s, 2H), 7.029-7.050 (d, 1H), 7.364-7.403 (d, 1HJ = 15.6 Hz), 7.513-7.551 (d, 1H, J = 15.2 Hz), 7.689-7.822 (d, 5H), 7.804 (s, 1H), 9.050 (bsa, 2H), 8.710 (bs, 2H), 8.134 (bs, 2H). |

Example 14. Synthesis of Tryptase Inhibitors with Benzo oxaborol-1-ol Functionality Method-K These targets were synthesized by reaction sequence below in Scheme 15.

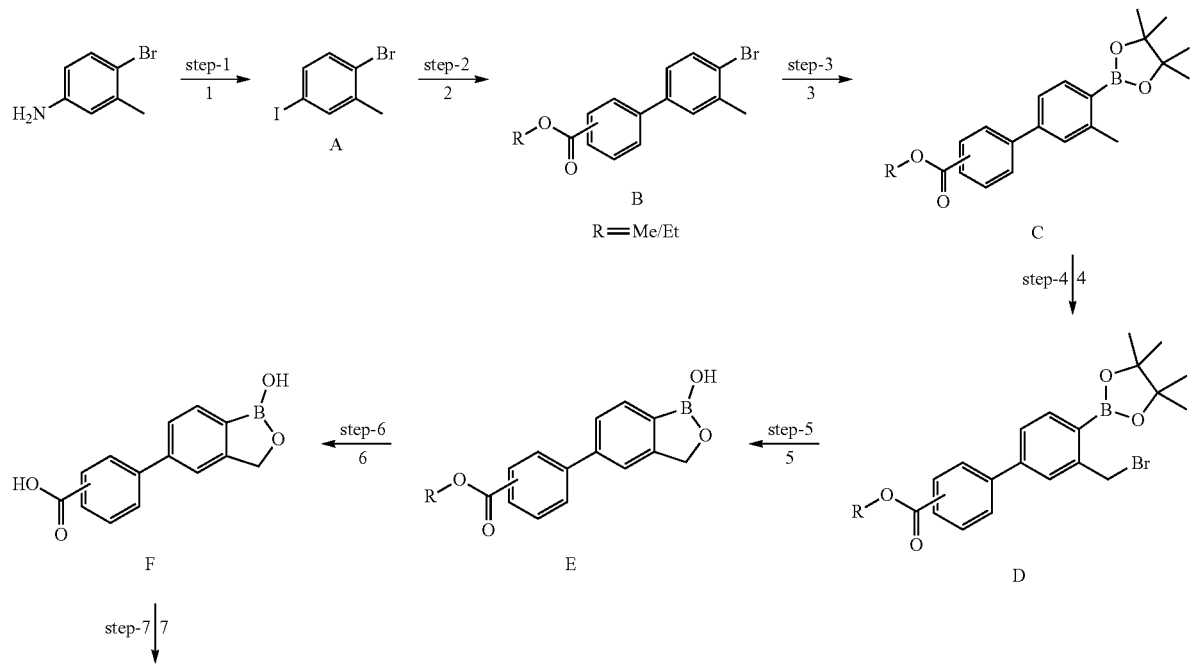

SCHEME 15.

-continued

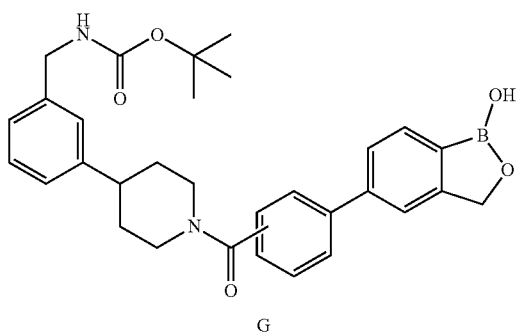

G

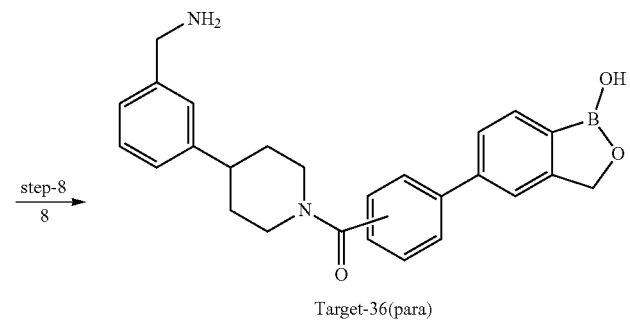

Target-36(para)
Target-36-meta

Reagents and Conditions: a) NaNO₂-HCl, Water-0 to 5° C, 30 min then KI-K₂CO₃, water, 0-25° C, 1 h; b) (3-(ethoxycarbonyl)phenyl)boronic acid, Dioxane, Water, Pd(Tetrakis), 80° C, 14 h; c) 1, 1'-Bis(Diphenyl phosphino) Ferrocene Palladium (II) chloride, complex with Dichloromethane, Toluene, Potassium acetate, Bis pinacolato diborane, Reflux, 4 h; d) NBS, Dibenzoyl peroxide Carbon tetrachloride, Reflux, 2 h; e) TFA, Water, Acetonitrile 91° C, 12 h; f) LiOH-THF Water, 60° C; g) EDCI, 4-DMAP, tert-butyl 3-(piperidin-4-yl) benzylcarbamate, CH₂Cl₂, 5 h; h) TFA-CH₂Cl₂ Room temperature, 4 h.

Step-1

1-bromo-4-iodo-2-methylbenzene was synthesized as per procedures available in the literature (*Bioorganic and Medicinal Chemistry*, 16, 6764-6777, 2008; *J. Am. Chem. Soc.*, 122, 6871-6883, 2000.)

Step-2

Suzuki coupling of Step-1 product with meta/para carbethoxy/methoxy phenyl boronic acid was carried out in presence of Palladium (0) Tetrakis (Triphenyl phosphene) in dioxane and sodium carbonate as base. After completion of reaction, the reaction mixture was filtered through celite pad and filtrate was concentrated under reduced pressure residue was diluted with water and extracted with ethyl acetate to get crude product. Crude products obtained were purified by column chromatography over silica gel using 5-10% ethyl acetate in hexane. The details of the intermediates synthesized are as below in Table 50.

TABLE 50

REACTION CONDITIONS & ANALYTICAL DATA

| Comp. No. | Structure | Brief Reaction conditions | Analytical data |
|---|---|---|---|
| B-36 | (structure) | Boronic acid (1.2 eq.), Water (5 vol) Dioxane (20 vol), Pd-Tetrakis (10 mol %), Sodium carbonate (2 eq.), 80° C., 15 hrs. Yield 64.8% | 1H NMR (CDCl3:- 2.447 (s, 3H), 3.942 (s, 3H), 7.260 (s, 1H), 7.308-7.327 (d, 1H, J = 7.6 Hz), 7.452-7.472 (d, 1H, J = 8 Hz), 7.608-7.628 (d, 2H, J = 8 Hz), 7.802 (s, 1H), 8.086-8.106 (d, 2H, J = 8 Hz). |
| B-36-meta | (structure) | Same as above Yield:- 60% | Mol. Wt:- 319.19 M.I. Peak observed:- 362.25 ACN adduct. |

Step-3

Stirred suspension of step-2 products in toluene was degassed with argon and to this were added potassium acetate, PdCl2-DPPF—CH₂Cl₂ and Bis (Pinacolato)Diborane. Reaction mass was heated to reflux & monitored by LCMS till maximum starting material was consumed. The mixture was the filtered through celite pad and filtrate was concentrated under reduced pressure to yield the crude product. The crude product was purified by column chromatography over silica gel using 1-5% ethyl acetate in hexane. The details of the compounds synthesized are as below in Table 51.

TABLE 51

REACTION CONDITIONS & ANALYTICAL DATA

| Comp. No. | Structure | Brief Reaction conditions | Analytical data |
|---|---|---|---|
| C-36 | 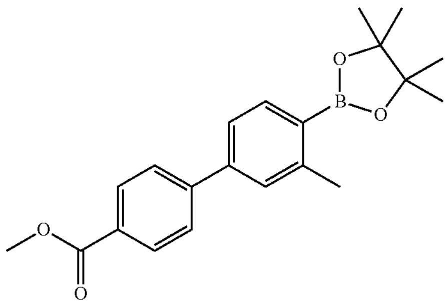 | Bispinacolato diborane (2.5 eq.), PdCl2 (dppf) (5 mol %), dppf (3 mol %), Potassium acetate (3.0 eq.), Toluene (30 vol), Reflux, 5 hrs., Yield 50% | 1H NMR CDCl3:- 1.362 (s, 12H), 2.586 (s, 3H), 3.936 (s, 3H), 7.257-7.275 (d, 1H, J = 7.2 Hz), 7.570-7.589 (d, 1H, J = 7.6 Hz), 7.667-7.688 (d, 2H, J = 8.4 Hz), 8.023 (s, 1H), 8.070-8.091 (d, 2H, J = 8.4 Hz). |
| C-36-meta | 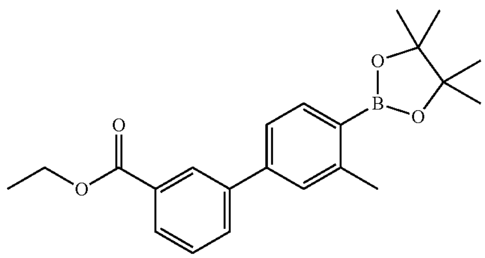 [SMILES: CCOC(=O)c1cccc(-c2ccc(B3OC(C)(C)C(C)(C)O3)c(C)c2)c1] | Same as above Yield:- 75% | Mol. Wt:- 366.26 M.I. Peak observed:- 367.20 |

Step-4

To a stirred solution of step-3 product in Carbon tetrachloride, Dibenzoyl peroxide & N-bromo succinamide were added. The resulting mixture was heated to 75° C. and reaction was monitored by LCMS. After consumption of maximum starting the reaction mixture was diluted with water and extracted with dichloromethane. Organic phase was again washed with water followed by brine, and dried over anhydrous sodium sulfate and concentrated under reduced pressure to get the crude product. The crude product was purified by column chromatography over silica gel using 1-5% ethyl acetate in hexane. The details of the compounds synthesized are as below in Table 52.

TABLE 52

REACTION CONDITIONS & ANALYTICAL DATA

| Comp. No. | Structure | Brief Reaction conditions | Analytical data |
|---|---|---|---|
| D-36 | 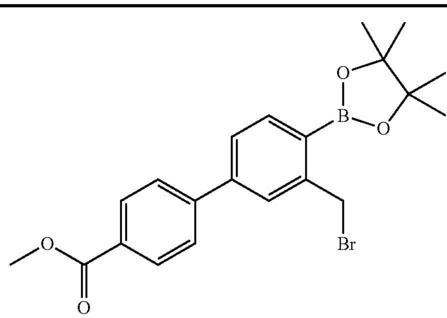 | Benzoyl peroxide (0.2 eq.), NBS (1.2 eq.) CCl4 (20 vol), 75° C. for 3 hrs. Yield:- 60% | 1H NMR (CDCl3:- 1.392 (s, 12H), 3.943 (s, 3H), 4.967 (s, 3H), 7.479-7.499 (d, 1H, J = 8 Hz), 7.644-7.650 (d, 1H), 7.692-7.671 (d, 2H, J = 8.4 Hz), 8.071 (s, 1H), 8.108-8.088 (d, 2H, J = 8 Hz). |
| D-36-meta | 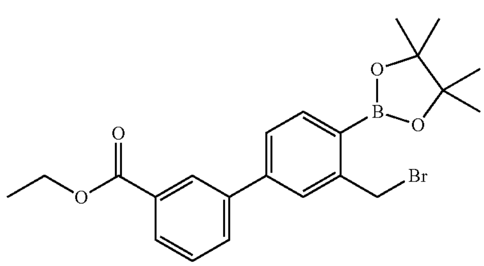 [SMILES: CCOC(=O)c1cccc(-c2ccc(B3OC(C)(C)C(C)(C)O3)c(CBr)c2)c1] | Same as above Yield:- 65% | Mol. Wt: -445.15 M.I. Peak observed:- 446.20 |

Step-5

To a stirred solution of Step-4 product in acetonitrile, trifluoro acetic acid and water were added and mixture was heated to 91° C. and monitored by LCMS. After maximum starting was consumed, The reaction mixture was concentrated and residue obtained was diluted with water and extracted with ethyl acetate. Concentration of ethyl acetate layer yielded crude product which was purified by column chromatography over silica gel using 10-35% ethyl acetate in hexane.

The details of the compounds synthesized are as below in Table 53.

TABLE 53

REACTION CONDITIONS & ANALYTICAL DATA

| Comp. No. | Structure | Brief Reaction conditions | Analytical data |
|---|---|---|---|
| E-36 | [structure] | Acetonitrile (30 vol), TFA (10 vol) Water (5 Vol), 91° C. 14 hrs, Yield:- 50% | 1H NMR DMSO-d6:- 3.881 (s, 3H), 5.055 (s, 2H), 7.536-7.556 (d, 1H, J = 8 Hz), 7.778-7.855 (m, 3H), 8.032-8.073 (m, 3H), 9.286 (s, 1H). |
| E-36-meta | [structure] | Same as above Yield:- 50% | Mol. Wt:- 282.10 M.I. Peak observed:- 283.25 |

Step-6

A mixture of step-5 product, lithium hydroxide, THF & water was heated to 60° C. Reaction was monitored by LCMS till maximum starting was consumed. The reaction mixture was concentrated and diluted with water. pH of the reaction mass was then adjusted to ~2 using Conc. HCl. Precipitated product was filtered, washed with water and dried in vacuum oven. The details of the compounds synthesized are as below in Table 54.

TABLE 54

REACTION CONDITIONS & ANALYTICAL DATA

| Comp. No. | Structure | Brief Reaction conditions | Analytical data |
|---|---|---|---|
| F-36 | [structure] | LiOH (10 eq), THF (10 vol), Water (20 Vol), 60° C., 2 hrs. Yield:- 60% | 1H NMR (DMSO-d6:- 5.054 (s, 2H), 7.141-7.165 (d, 1H, J = 9.6 Hz), 7.531-7.551 (d, 1H, J = 8 Hz), 7.778-7.846 (m, 2H), 7.992-8.058 (m, 2H), 7.084 (s, 1H). |
| F-36-meta | [structure] | Same as above Yield:- 75% | 1H NMR (DMSO-d6:- 5.051 (s, 2H), 7.523-7.543 (d, 1H, J = 8 Hz), 7.618- (t, 1H), 7.812-7.832 (d, 1H), 7.922-7.955 (d, 2H), 8.076 (s, 1H), 8.216 (s, 1H), 9.275 (S, 1H), 13.10 (s, 1H) |

Step-7

These reactions were carried out as per general procedure described in method-A, Step-4. DMF was used as co-solvent. pH of the reaction mass was adjusted to ~5 by adding dilute HCl prior to the extraction. The details of the compounds synthesized are as below in Table 55.

TABLE 55

REACTION CONDITIONS & ANALYTICAL DATA

| Comp. No. | Structure | Brief Reaction conditions | Analytical data |
|---|---|---|---|
| G-36 | (structure) | tert-butyl 3-(piperidin-4-yl) benzyl carbamate (1.3 eq.), EDCI•HCl (1.5 eq.), DMAP (2 eq.), DCM (20 vol), DMF (10 vol), RT, 4 h, Yield:- 50%. | Mol. Wt:-526.43 M.I. peak observed:- 527.5 |
| G-36-meta | (structure) | Same as above Yield:- 70% | Mol. Wt:- 526.43 M.I. peak observed:- 549.05 (M + Na) |

Step-8

Boc de-protection of Product from step-6 was carried out as per general procedure described in method-A, step-9.

TABLE 56

REACTION CONDITIONS & ANALYTICAL DATA

| Comp. No. | Structure | Brief Reaction conditions | Analytical data |
|---|---|---|---|
| Target-36 | (structure) | TFA (20 eq.), Dichloromethane (20 vol), R.T. 4 hr. Prep HPLC. isolated as TFA salt converted to hydrochloride Yield:- 12.76% | Mol. Wt:- 426.32 M.I. peak observed:- 427.05 HPLC Purity:- 99.10% 1H NMR (DMSO-d6:- 1.646-1.769 (m, 4H), 4.653-4.681 (m, 1H), 2.822-2.881 (m, 2H), 3.104-3.218 (m, 2H), 3.997-4.011 (d, 2H), 5.047 (s, 2H), 7.458 (s, 1H), 8.055 (s, 1H), 7.535-7.554 (m, 2H), 7.298-7.375 (m, 3H), 7.726-7.746 (d, 2H, J = 8 Hz), 7.816-7.796 (d, 2H, J = 8 Hz) 8.372 (s, 3H). |
| Target-36-meta | (structure) | Same as above isolated as TFA salt & converted to hydrochloride Yield:- 50% | Mol. Wt:- 426.32 M.I. peak observed:- 427.06 HPLC Purity:- 99.47% $^1$H NMR DMSO-d6:- 1.670-2.070 (m, 4H), 2.813-2.873 (m, 2H), 3.166-3.230 (m, 1H), 3.989-4.003 (d, 2H), 3.578-3.558 (m, 1H), 5.046 (s, 2H), 7.469 (s, 1H), 7.669, (s, 1H), 8.095 (s, 1H), 7.288-7.340 (m, 3H), 7.819-7.816 (d, 1H, J = 8 Hz), 7.757-7.737 (d, 1H, J = 8 Hz), 7.433-7.414 (d, 1H, J = 7.6 Hz), 7.512-7.532, (d, 1H, J = 8 Hz), 8.406 (s, 3H) |

Example 15. Uncategorized Targets

Synthesis of N-(3-(4-(3-(aminomethyl) phenyl) piperidine-1-carbonyl) phenyl)-2-(1-hydroxycyclobutyl)-2-oxoacetamide (Target-21)

Synthesis of the N-(3-(4-(3-(aminomethyl) phenyl) piperidine-1-carbonyl) phenyl)-2-(1-hydroxycyclobutyl)-2-oxoacetamide was carried out as shown in the scheme below

SCHEME 16.

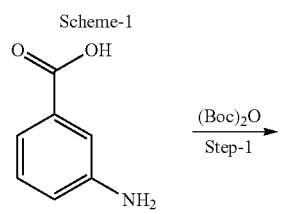

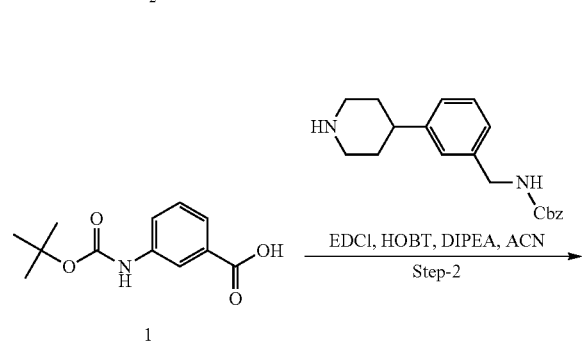

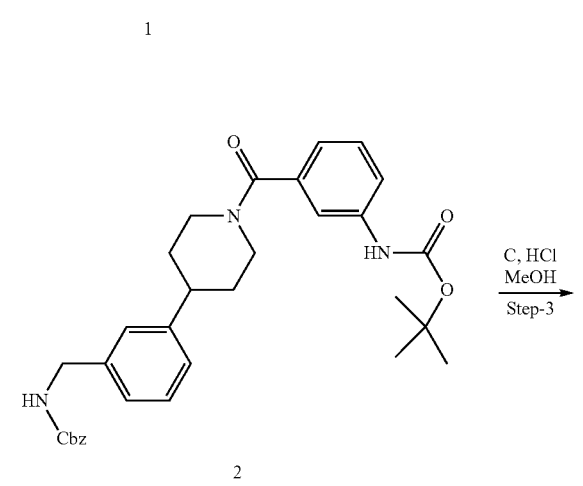

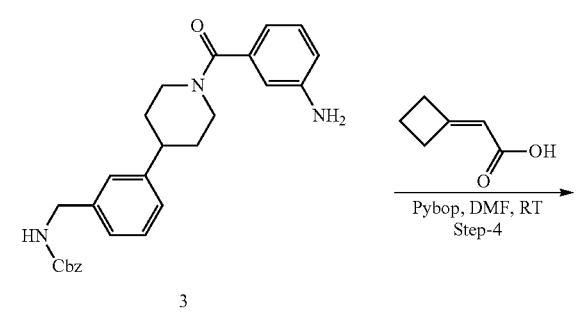

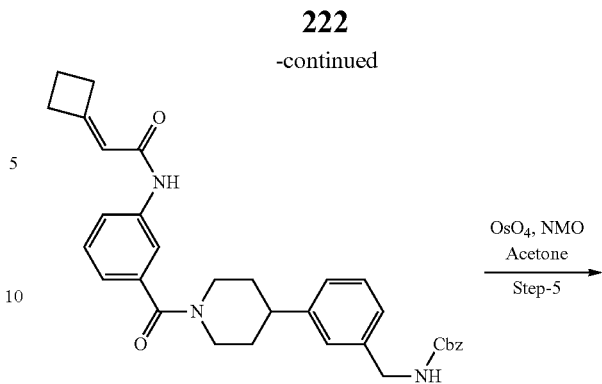

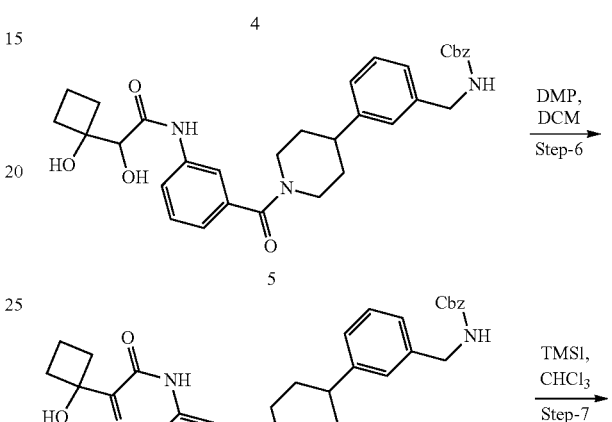

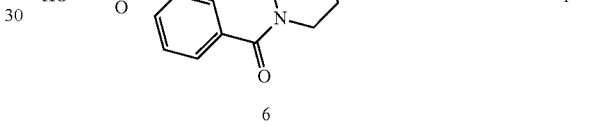

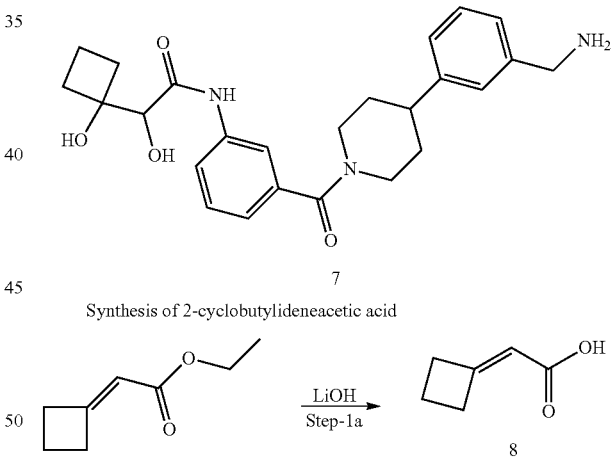

Synthesis of 2-cyclobutylideneacetic acid

Detailed experimental procedure and analytical data is as follows.

Synthesis of 2-cyclobutylidene-acetic acid

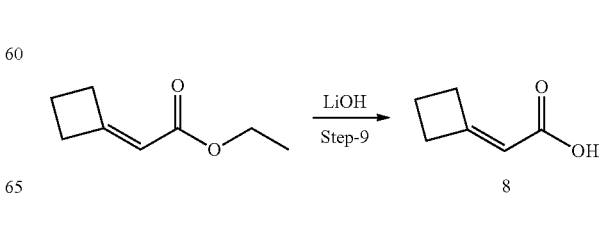

| Sr. No. | Chemical | Mol. Wt. | Quantity | mmol | Molar Ratio |
|---|---|---|---|---|---|
| 1 | ethyl 2-cyclobutylideneacetate | 140 | 1.2 g | 8.57 | 1 |
| 2 | Lithium hydroxide monohydrate | 41.9 | 2.15 g | 51.4 | 6 |
| 3 | THF:H₂O:MeOH | — | 10:10:5 mL | — | — |

In 1:1:0.5 THF/water/Methanol (10:10:5 mL each), ethyl 2-cyclobutylideneacetate (1.2 g, 8.57 mmol) and lithium hydroxide monohydrate (2.15 g, 51.4 mmol) was added at room temperature. Reaction mixture was allowed to stir at room temperature for 16 h. TLC showed absence of starting material (Rf=0.4, 30% ethyl acetate/n-hexane). THF and Methanol was removed under reduced pressure. Aqueous layer was acidified with citric acid and extracted with ethyl acetate. Crude product was purified by column chromatography (silica gel 60-120 mesh ethyl acetate/n-hexane as eluent) to afford white solid.

Yield: 0.6 g (62%)

$^1$H NMR (400 MHz, CDCl$_3$): δ 2.02-2.20 (m, 2H). 2.86 (t, J=7.8 Hz, 2H), 3.14 (t, J=7.8 Hz, 2H), 5.59 (t, J=2 Hz, 1H).

Step 1: Synthesis of 3-((tert-butoxycarbonyl) amino) benzoic acid

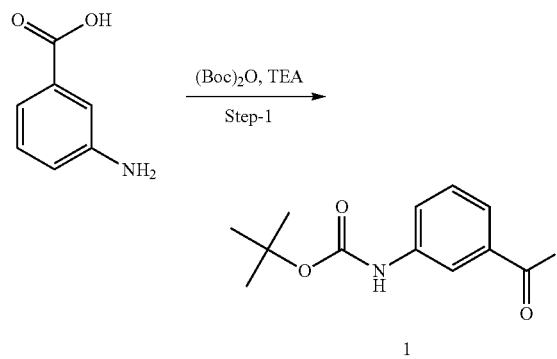

| Sr. No. | Chemical | Mol. Wt. | Quantity | mmol | Molar Ratio |
|---|---|---|---|---|---|
| 1 | 3-aminobenzoic acid | 137 | 6 g | 43.8 | 1 |
| 2 | Triethyl amine | 101 | 12.1 mL | 87.6 | 2 |
| 3 | Boc anhydride | 218 | 15 mL | 65.7 | 1.5 |
| 4 | 1-4 Dioxane | — | 100 mL | — | — |
| 5 | H₂O | — | 50 mL | — | — |

To a solution of 3-aminobenzoic acid (6 g, 0.043 mmol), Triethyl amine (12.1 mL, 87.6 mmol), water (50 mL) in 1-4 Dioxane (100 mL) was added Boc anhydride (15 mL, 65.7 mmol) at room temperature. Reaction mixture was allowed to stir for 16 h at room temperature. TLC showed absence of starting material (R$_f$=0.7, 70% ethyl acetate/n-hexane). 1-4 Dioxane was removed under reduced pressure and 3N HCl solutions (60 mL) was added drop wise in the reaction mixture. White precipitate obtained was filter out, washed with hexane and dried.

Yield: 10 g (97%)

$^1$H NMR (400 MHz, CDCl$_3$): δ 1.47 (s, 9H), 7.35 (t, J=8 Hz, 1H), 7.53 (d, J=8 Hz, 1H), 7.61 (d, J=8 Hz, 1H), 8.14 (s, 1H), 9.53 (s, 1H), 12.9 (br, 1H).

Step 2: Synthesis of Intermediate 2

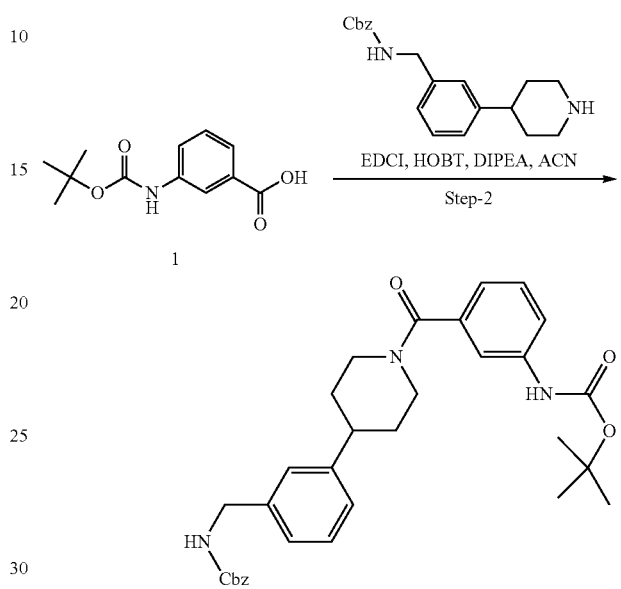

| Sr. No. | Chemical | Mol. Wt. | Quantity | mmol | Molar Ratio |
|---|---|---|---|---|---|
| 1 | 3-((tert-butoxycarbonyl)amino)benzoic acid | 237 | 2.19 g | 9.24 | 1 |
| 2 | Benzyl 3-(piperidin-4-yl) benzyl carbamate | 324 | 3 g | 9.24 | 1 |
| 3 | EDCI | 191.5 | 1.9 g | 10.2 | 1.1 |
| 4 | HOBT | 135 | 2.5 g | 18.5 | 2.0 |
| 5 | DIPEA | 129 | 4 mL | 23.1 | 2.5 |
| 6 | CAN | — | 30 mL | — | — |

To a solution of 3-((tert-butoxycarbonyl)amino)benzoic acid (2.19 g, 9.24 mmol) in acetonitrile (30 mL), benzyl 3-(piperidin-4-yl)benzylcarbamate (3 g, 9.24 mmol), EDCI (1.9 g, 10.2 mmol), HOBt (2.5 g, 18.5 mmol), DIPEA (4 mL, 23.1 mmol) were added and the reaction mixture was allowed to stir at room temperature overnight under nitrogen atmosphere. TLC showed absence of starting material (R$_f$=0.67, 60% ethyl acetate/n-hexane). Acetonitrile was removed under reduced pressure; the reaction mixture was washed with water. The organic layer was separated, dried over sodium sulphate, concentrated and purified by column chromatography (Silica gel 100-200 mesh using 0-80% ethyl acetate in hexane as eluent) to give the desired product as brown semi solid. This was used as such for the next step.

Yield: 1.6 g (32%)

LCMS: m/z (M+Na) 566

$^1$H NMR (400 MHz, CDCl$_3$): δ 1.51 (s, 9H), 1.60-2.00 (br, 4H), 2.70-2.80 (m, 1H), 2.90-3.30 (br, 2H), 3.80-4.00 (br, 1H), 4.38 (d, J=5.6 Hz, 2H), 4.84 (br, 1H), 5.14 (s, 2H), 6.64 (s, 1H), 7.00-7.50 (m, 12H).

Step 3: Synthesis of benzyl 3-(1-(3-aminobenzoyl) piperidin-4-yl) benzylcarbamate

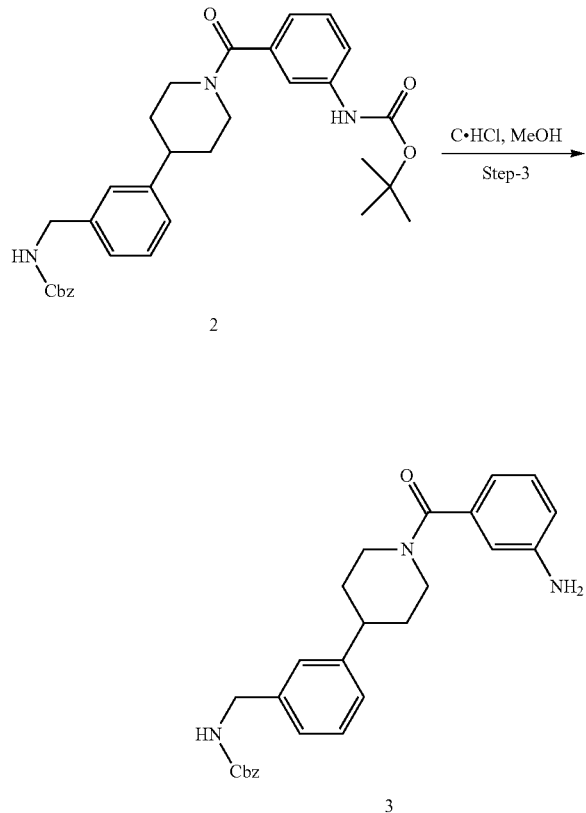

| Sr. No. | Chemical | Mol. Wt. | Quantity | mmol | Molar Ratio |
|---|---|---|---|---|---|
| 1 | Step-2 compound | 543 | 1.6 g | 2.94 | 1 |
| 2 | HCl (35%) | — | 6.4 mL | — | 4 vol |
| 3 | Methanol | — | 16 mL | — | 10 vol |

In 16 mL of methanol, product from step 2 (1.6 g, 2.94 mmol) and 6.4 mL of conc. HCl was allowed to stir at room temperature for 16 h. Methanol was removed under reduced pressure. Water (20 ml) was added in reaction mixture and basified by 2 N NaOH solution. Aqueous layer was extracted with ethyl acetate. Organic layer was washed with brine and water. Further organic layer was dried over sodium sulphate and evaporated under reduced pressure. Crude compound was purified by column chromatography (Silica gel 60-120 mesh using 0-80% ethyl acetate in hexane as eluent) to give the desired product as white solid.

Yield: 1.1 g (84%)

LCMS: m/z (M+23) 466

$^1$H NMR (400 MHz, CDCl$_3$): δ 1.70-2.00 (br, 4H), 2.70-2.81 (m, 1H), 2.82-3.20 (br, 1H), 3.92 (br, 1H), 4.38 (d, J=5.6 Hz, 2H), 4.70-5.10 (br, 2H), 5.15 (s, 2H), 6.70-6.82 (m, 3H), 7.00-7.50 (m, 1H).

Step 4: Synthesis of benzyl 3-(1-(3-(2-cyclobutylideneacetamido) benzoyl) piperidin-4-yl) benzylcarbamate

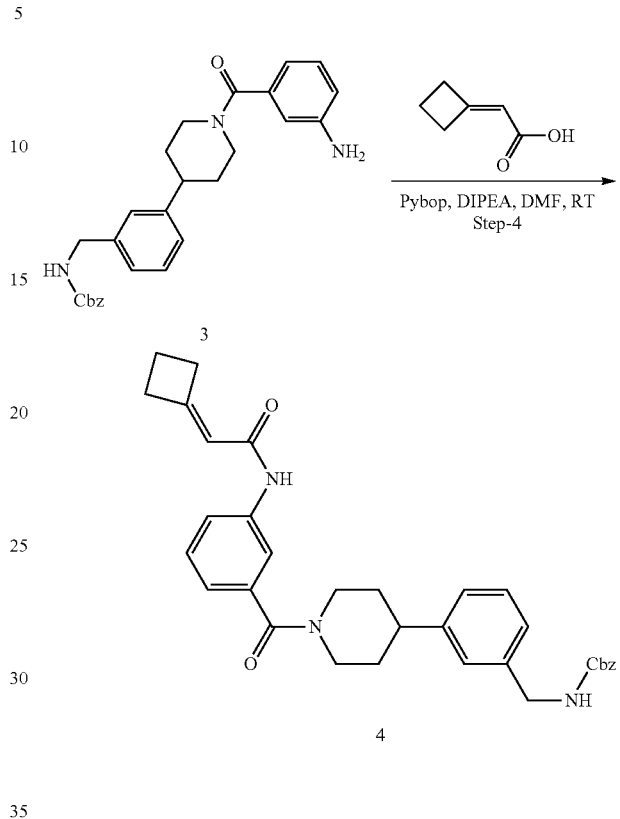

| Sr. No. | Chemical | Mol. Wt. | Quantity | mmol | Molar Ratio |
|---|---|---|---|---|---|
| 1 | 2-cyclobutylideneacetic acid | 112 | 0.27 g | 2.41 | 1 |
| 2 | 3-(1-(3-aminobenzoyl) piperidin-4-yl) benzylcarbamate | 443 | 1.09 g | 2.41 | 1 |
| 3 | Pybop | 520 | 2.5 g | 4.82 | 2 |
| 4 | DIPEA | 129 | 1.1 mL | 6.02 | 2.5 |
| 5 | DMF | — | 8 mL | — | — |

To a solution of 2-cyclobutylideneacetic acid (0.27 g, 2.41 mmol) in DMF (8 mL), 3-(1-(3-aminobenzoyl) piperidin-4-yl) benzylcarbamate (1.09 g, 2.41 mmol), Pybop (2.5 g, 4.82 mmol), DIPEA (1.1 mL, 6.02 mmol) were added and the reaction mixture was allowed to stir at room temperature for overnight under nitrogen atmosphere. TLC showed absence of starting material (R$_f$=0.37, 80% ethyl acetate/n-hexane). Reaction mixture was quenched with water, extracted by ethyl acetate, organic layer washed with water and brine. Organic layer was dried over sodium sulphate and evaporated under reduced pressure. Crude compound was purified by column chromatography (Silica gel 100-200 mesh using 0-80% ethyl acetate in hexane as eluent) to give the desired product as white solid.

Yield: 0.84 g (65%)

LCMS: m/z (M+Na) 560

$^1$H NMR (400 MHz, DMSO-d$_6$): δ 1.40-1.92 (br, 4H), 2.0-2.15 (m, 2H), 2.70-2.90 (m, 4H), 3.00-3.20 (m, 3H), 3.70 (br, 1H), 4.19 (d, J=6 Hz, 2H), 4.62 (brs, 1H), 5.05 (s, 2H), 5.80 (s, 1H), 7.00-7.50 (m, 10H), 7.61 (d, J=8 Hz, 1H), 7.73 (s, 1H), 7.77-7.83 (m, 1H), 9.92 (s, 1H).

Step 5: Synthesis of benzyl 3-(1-(3-(2-hydroxy-2-(1-hydroxycyclobutyl) acetamido)benzoyl)piperidin-4-yl)benzylcarbamate

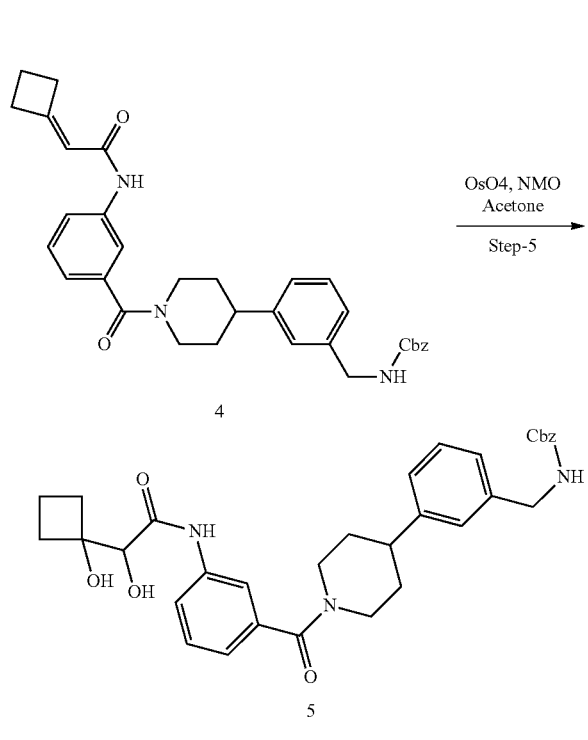

| Sr. No. | Chemical | Mol. Wt. | Quantity | µmol | Molar Ratio |
|---|---|---|---|---|---|
| 1 | benzyl 3-(1-(3-(2-cyclobutylidene acetamido)benzoyl)piperidin-4-yl)benzylcarbamate | 537 | 0.012 g | 22 | 1 |
| 2 | OsO₄ (4% aq.) | 254 | 6 µL | 0.9 | 0.04 |
| 3 | N-Methylmorpholine oxide [NMO] (50% aq.) | 117 | 6 µL | 26 | 1.2 |
| 4 | Acetone | — | 2 mL | — | — |
| 5 | Water | — | 0.3 mL | — | — |

In 2 mL acetone and 0.3 mL of water benzyl 3-(1-(3-(2-cyclobutylideneacetamido)benzoyl)piperidin-4-yl)benzylcarbamate (0.012 g, 22 µmol), OsO₄ (4% aqueous solution, 6 µL, 0.9 µmol) was added and stirred for 10 min at room temperature. Then NMO (50% aqueous solution, 6 µL, 26 µmol) was added and allowed to stir at room temperature overnight. TLC showed absence of starting material ($R_f$=0.2, 80% ethyl acetate/n-hexane). Reaction mixture was quenched with 10% aqueous sodium bisulphite solution and stirred for ~1 h at room temperature. Aqueous layer was extracted with ethyl acetate, dried over sodium sulphate. Crude product obtained was purified by column chromatography (silica 60-120 mesh, ethyl acetate/n-hexane) afforded semi solid.

Yield: 0.011 g (91%)
LCMS: m/z (M+Na) 594
¹H NMR (400 MHz, CDCl3): δ 1.50-2.30 (m, 9H), 2.50-2.70 (br, 2H), 2.72-3.00 (br, 2H), 3.12 (br, 2H), 3.75-3.95 (m, 2H), 4.36 (d, J=5.6 Hz, 2H), 4.84 (br, 1H), 5.14 (s, 2H), 7.00-7.50 (m, 12H), 7.72 (s, 1H), 8.86 (s, 1H).

Step 6: Synthesis of Intermediate 6

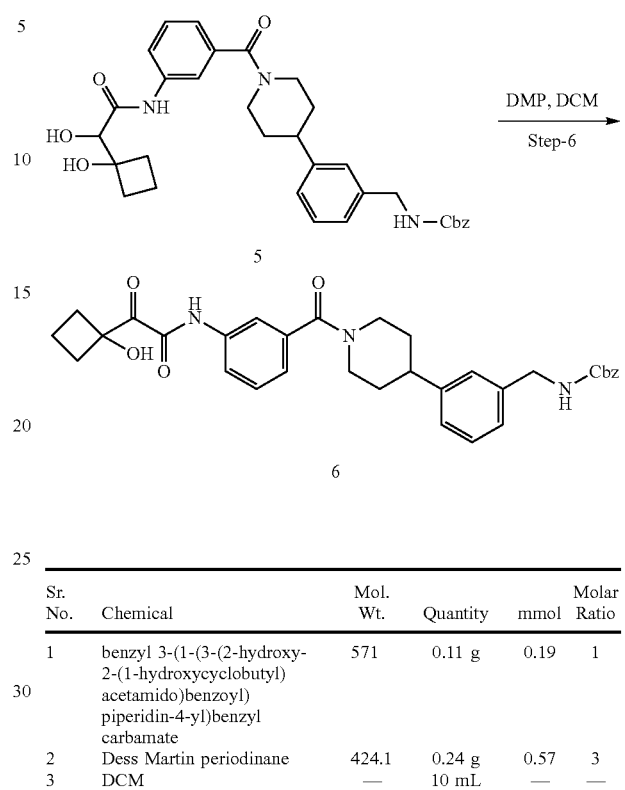

| Sr. No. | Chemical | Mol. Wt. | Quantity | mmol | Molar Ratio |
|---|---|---|---|---|---|
| 1 | benzyl 3-(1-(3-(2-hydroxy-2-(1-hydroxycyclobutyl) acetamido)benzoyl) piperidin-4-yl)benzyl carbamate | 571 | 0.11 g | 0.19 | 1 |
| 2 | Dess Martin periodinane | 424.1 | 0.24 g | 0.57 | 3 |
| 3 | DCM | — | 10 mL | — | — |

To a solution of benzyl 3-(1-(3-(2-hydroxy-2-(1-hydroxycyclobutyl)acetamido)-benzoyl)piperidin-4-yl)benzylcarbamate (0.011 g, 0.019 mmol), DCM (10 mL), Dess Martin periodinane (0.24 g, 0.57 mmol) was added at room temperature. Reaction mixture was stirred under nitrogen atmosphere for 2 h. TLC showed absence of starting material ($R_f$=0.4, 100% ethyl acetate). Reaction mixture was quenched with carbonate resin, filter through cotton. DCM was evaporated under reduced pressure. Further crude compound was purified by preparative TLC and taken ahead as such for the next step.

Yield: 0.01 g (9%)
LCMS: m/z (M+1) 570

Step 7: Synthesis of N-(3-(4-(3-(aminomethyl)phenyl)piperidine-1-carbonyl) phenyl)-2-(1-hydroxycyclobutyl)-2-oxoacetamide

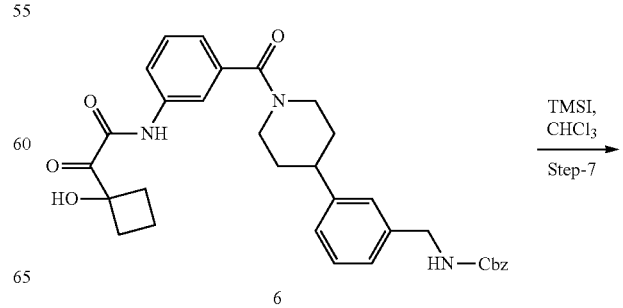

-continued

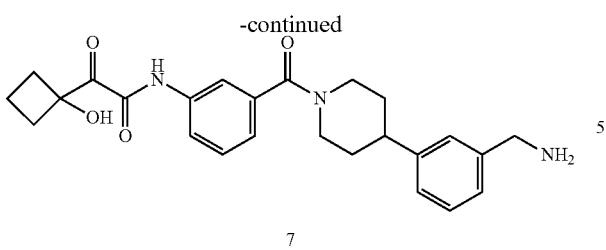

| Sr. No. | Chemical | Mol. Wt. | Quantity | mmol | Molar Ratio |
|---|---|---|---|---|---|
| 1 | Intermediate-6 | 569 | 0.009 g | 0.016 | 1 |
| 2 | TMSI | 200 | 3 drop | — | — |
| 3 | CHCl₃ | — | 5 mL | — | — |

To a solution of intermediate-6 (0.009 g, 0.016 mmol), CHCl$_3$ (5 mL), TMSI (1 drop) was added at room temperature. Reaction mixture was stirred under nitrogen atmosphere for 16 h. LCMS showed 46% starting material. In reaction mixture TMSI (2 drops) was added at room temperature. Further reaction mixture was stirred for 6 h. TLC showed absence of starting material (R$_f$=0.2, 100% ethyl acetate). Reaction mixture was quenched with aq. ammonium formate solution (3 mL), DCM layer was separated out, aq layer lyophilized and further purified by Prep. HPLC to isolate the compound as a TFA salt.

Yield: 0.0047 g (47%, TFA salt)
LCMS: m/z (M+1) 436
HPLC: 85.13% (220 nm)
$^1$H NMR (400 MHz, CD$_3$OD): δ 1.55-2.00 (m, 4H), 2.02-2.20 (m, 2H), 2.35-2.65 (m, 3H), 2.80-3.20 (m, 2H), 3.10-3.30 (br, 3H, merged in the solvent peak), 3.87 (br, 1H), 4.10 (s, 2H), 7.18-7.50 (m, 6H), 7.62 (d, J=8.0 Hz, 1H), 7.85 (s, 1H).

Example 16: Synthesis of 2-(3-(4-(3-(aminomethyl) phenyl) piperidine-1-carbonyl) phenoxy)-1-(1-hydroxycyclobutyl) ethanone (Target-22)

Title compound was synthesized as shown in Scheme 17 below.

SCHEME 17.

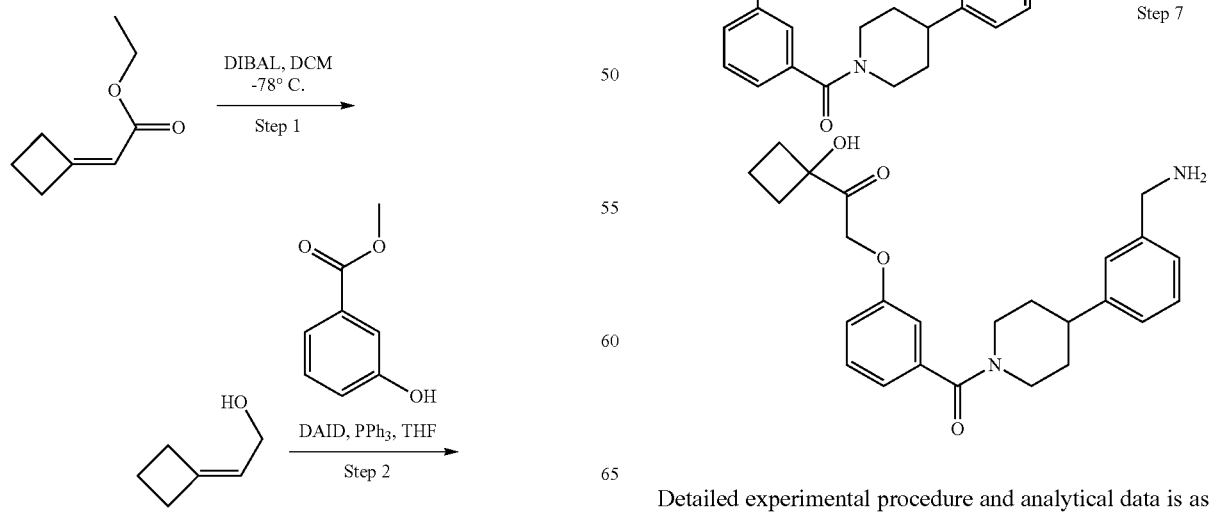

Detailed experimental procedure and analytical data is as follows.

Step 1: Synthesis of 2-cyclobutylideneethanol

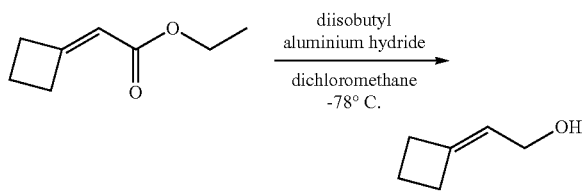

| Sr. No. | Chemical | Mol. Wt. | Quantity | mmol | Molar Ratio |
|---|---|---|---|---|---|
| 1 | ethyl 2-cyclobutylideneacetate | 140 | 0.85 g | 6.07 | 1 |
| 2 | diisobutyl aluminium hydride 1M in toluene) | 142 | 1.72 g | 12.1 | 2 |
| 3 | Dichloromethane (DCM) | — | 40 mL | — | — |

In 40 mL of dry DCM ethyl 2-cyclobutylideneacetate (0.85 g, 6.07 mmol) was allowed to cool to −78° C. under nitrogen atmosphere. To this solution DIBAL-H (1M in toluene) (1.72 g, 12.1 mL, 12.1 mmol) was added dropwise. Reaction was monitored by TLC. When the starting material was consumed completely the reaction mixture was quenched with MeOH/H$_2$O (1:1) (R$_f$=0.28, 20% ethyl acetate/n-hexane). DCM layer was separated and dried over sodium sulphate. DCM was removed under reduced pressure. Crude product was purified by column chromatography (silica gel 60-120 mesh, 0-20% ethyl acetate and n-hexane as eluent) afforded colorless oil.

Yield: 0.5 g (84%)

$^1$H NMR (400 MHz, CDCl$_3$): δ 1.61 (br, 1H), 1.91-2.05 (m, 2H), 2.65-2.74 (m, 4H), 4.02 (d, J=7.2 Hz, 2H), 5.30-5.36 (m, 1H).

Step 2: Synthesis of methyl 3-(2-cyclobutylideneethoxy)benzoate

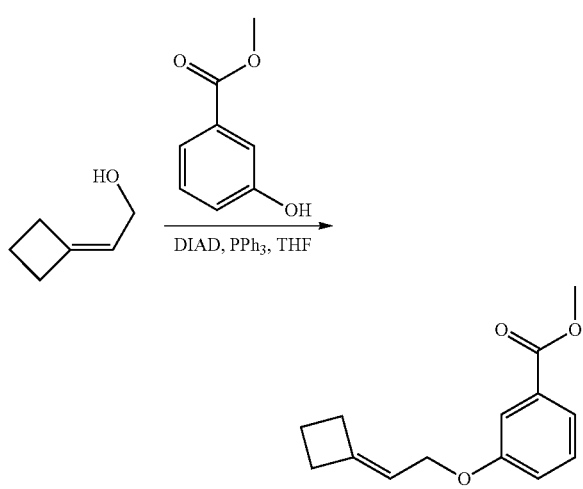

| Sr. No. | Chemical | Mol. Wt. | Quantity | mmol | Molar Ratio |
|---|---|---|---|---|---|
| 1 | 2-cyclobutylideneethanol | 98 | 0.17 g | 1.73 | 1 |
| 2 | methyl 3-hydroxybenzoate | 152 | 0.26 g | 1.73 | 1 |
| 3 | Triphenyl phosphine | 262 | 0.59 g | 2.25 | 1.3 |
| 4 | DIAD | 202 | 0.45 g | 2.25 | 1.3 |
| 5 | THF | — | 16 mL | — | — |

In 10 mL of dry THF, triphenyl phosphine (0.56 g, 2.25 mmol) was allowed to stir at −20° C. To this solution, DIAD (0.45 g, 0.44 mL, 2.25 mmol) was added. Yellow precipitate was observed in the reaction mixture. Methyl 3-hydroxybenzoate (0.26 g, 1.73 mmol) in 3 mL THF was added dropwise to the reaction mixture and stirred for 10-15 min. 2-cyclobutylideneethanol (0.17 g, 1.73 mmol) in 3 mL of dry THF was added dropwise (after complete addition clear yellow solution was observed) and resulting reaction mixture was stirred at RT overnight (R$_f$=0.62, 20% ethyl acetate/n-Hexane). Water was added to the reaction mixture. Aqueous layer was washed with diethyl ether. Crude product was purified by column chromatography (silica gel 60-120 mesh, ethyl acetate and n-hexane) to afford light yellow oil.

Yield: 0.2 g (50%)

LCMS: m/z (M+1) 233

$^1$H NMR (400 MHz, CDCl$_3$): δ 1.95-2.06 (m, 2H), 2.70-2.81 (m, 4H), 3.91 (s, 3H), 4.44 (d, J=7.2 Hz, 2H), 5.38-5.46 (m, 1H), 7.06-7.14 (dd, J=2.4 and 8.4 Hz, 1H), 7.32 (t, J=8.0 Hz, 1H), 7.57 (t, J=2.4 Hz, 1H), 7.62 (d, J=7.6 Hz, 1H).

Step 3: Synthesis of 3-(2-cyclobutylideneethoxy)benzoic acid

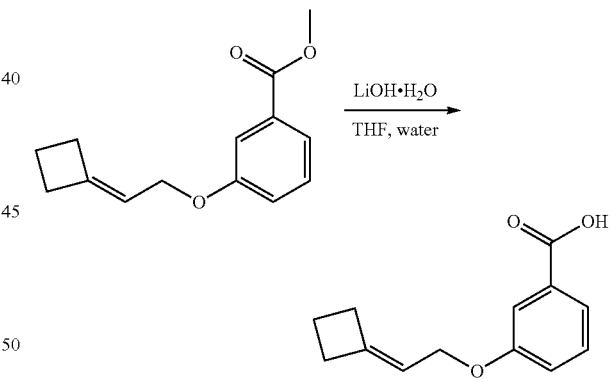

| Sr. No. | Chemical | Mol. Wt. | Quantity | mmol | Molar Ratio |
|---|---|---|---|---|---|
| 1 | methyl 3-(2-cyclobutylideneethoxy)benzoate | 232 | 0.2 g | 0.86 | 1 |
| 2 | Lithium hydroxide monohydrate | 41.9 | 0.21 g | 5.17 | 6 |
| 3 | THF | — | 5 mL | — | — |
| 4 | water | — | 5 mL | — | — |

In 1:1 THF/water (5 mL each) product from step 2 (0.2 g, 0.86 mmol) and lithium hydroxide monohydrate (0.1 g, 2.58 mmol) was allowed to stir at room temperature. After 2 h TLC showed desired product and starting material, 3 eq. of lithium hydroxide monohydrate (0.1 g, 2.58 mmol) was added and stirred for ~2 h. TLC showed complete consumption of starting material ($R_f$=0.35 in 50% ethyl acetate/n-hexane). THF was removed under reduced pressure. Aqueous layer was acidified with citric acid and extracted with ethyl acetate. Crude product was purified by column chromatography (silica gel 60-120 mesh ethyl acetate/n-hexane as eluent) to afford colorless oil.

Yield: 0.14 g (77%)

$^1$H NMR (400 MHz, CDCl$_3$): δ 1.96-2.07 (m, 2H), 2.72-2.82 (m, 4H), 4.46 (d, J=6.8 Hz, 2H), 5.38-5.47 (m, 1H), 7.12-7.18 (dd, J=2.4 and 8.0 Hz, 1H), 7.37 (t, J=8.0 Hz, 1H), 7.62 (s, 1H), 7.70 (d, J1=7.6 Hz, 1H).

Step 4: Synthesis of tert-butyl 3-(1-(3-(2-cyclobutylidene ethoxy) benzoyl) piperidin-4-yl) benzylcarbamate mixture was washed with sat. NaHCO$_3$ solution. The organic layer was separated, dried over sodium sulphate, concentrated and purified by column chromatography (Silica gel 60-120 mesh using 0-40% ethyl acetate in hexane as eluent) to give the desired product as colorless oil.

Yield: 0.23 g (73%)

LCMS: m/z (M+1) 491

$^1$H NMR (400 MHz, CDCl$_3$): δ 1.46 (s, 1H), 1.95-2.0 (m, 2H), 2.71-2.84 (m, 7H), 3.09 (br, 1H), 3.91 (br, 1H), 4.30 (br, 2H), 4.41 (d, J=6.8 Hz, 2H), 4.82 (br, 2H), 5.40-5.45 (m, 1H), 6.90-7.00 (m, 3H), 7.10-7.20 (m, 3H), 7.26-7.33 (m, 2H).

Step 5: Synthesis of tert-butyl 3-(1-(3-(2-cyclobutylideneethoxy) benzoyl)piperidin-4-yl)benzylcarbamate

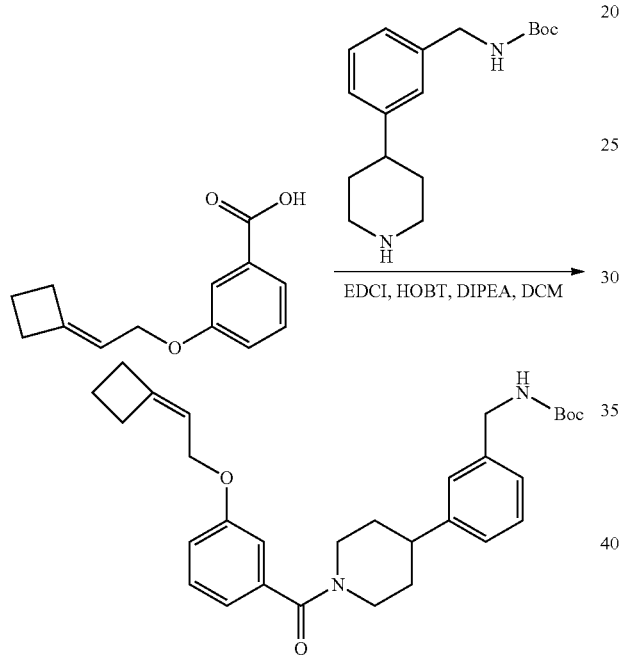

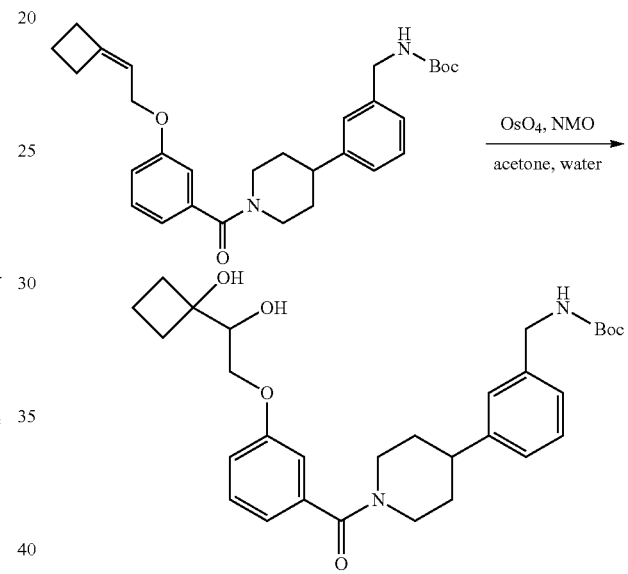

| Sr. No. | Chemical | Mol. Wt. | Quantity | mmol | Molar Ratio |
|---|---|---|---|---|---|
| 1 | 3-(2-cyclobutylideneethoxy) benzoic acid | 218 | 0.14 g | 0.64 | 1 |
| 2 | tert-butyl 3-(piperidin-4-yl) benzyl carbamate (Int-E, Boc) | 290 | 0.18 g | 0.64 | 1 |
| 3 | EDCI | 191 | 0.14 g | 0.70 | 1.1 |
| 4 | HOBT | 135 | 0.17 g | 1.28 | 2.0 |
| 5 | DIPEA | 129 | 0.2 g | 1.6 | 2.5 |
| 6 | Dichloromethane | — | 10 mL | — | — |

To a solution of Step 3 product (0.14 g, 0.64 mmol) in dry dichloromethane (10 mL), Int-E (Boc protected) (0.18 g, 0.64 mmol), EDCI (0.14 g, 0.70 mmol), HOBt (0.17 g, 1.28 mmol), DIPEA (0.27 mL, 1.6 mmol) were added and the reaction mixture was allowed to stir at RT overnight under nitrogen atmosphere. TLC showed absence of starting material ($R_f$=0.75, 30% ethyl acetate/n-hexane). The reaction

| Sr. No. | Chemical | Mol. Wt. | Quantity | mmol | Molar Ratio |
|---|---|---|---|---|---|
| 1 | tert-butyl 3-(1-(3-(2-cyclobutylideneethoxy)benzoyl) piperidin-4-yl)benzylcarbamate | 490 | 0.23 g | 0.47 | 1 |
| 2 | OsO$_4$ (4% aq.) | 254 | 0.0047 g | 18.5 µmol | 0.04 |
| 3 | N-Methylmorpholine oxide [NMO] (50% aq.) | 117 | 0.066 g | 0.56 | 1.2 |
| 4 | Acetone | — | 7 mL | — | — |
| 5 | Water | — | 1.5 mL | — | — |

In 7 mL acetone and 1.5 mL of water Step 4 product (0.23 g, 0.47 mmol), OsO$_4$ (4% aqueous solution, 0.012 mL, 18.5 µmol) was added and stirred for 10 min at room temperature. Then NMO (50% aqueous solution, 0.13 mL, 0.56 mmol) was added and allowed to stir at room temperature overnight. Reaction mixture was quenched with 10% aqueous sodium bisulphite solution and stirred for ~1 h at room temperature. Aqueous layer was extracted with ethyl acetate, dried over sodium sulphate. Crude product obtained was purified by column chromatography (silica 60-120 mesh, ethyl acetate/n-hexane; $R_f$=0.14, 50% ethyl acetate/n-hexane) afforded colorless oil.

Yield: 0.18 g (73%)

LCMS: m/z (M+1) 525

$^1$H NMR (400 MHz, CDCl$_3$): δ 1.47 (s, 9H), 1.61-1.76 (m, 4H), 2.05-2.16 (m, 4H), 2.35-2.40 (m, 1H), 2.70-2.90 (m, 4H), 3.11 (br, 1H), 3.86 (br, 1H), 4.05-4.20 (m, 3H), 4.30 (br, 2H), 4.85 (s, 2H), 6.93-7.06 (m, 3H), 7.11-7.17 (m, 3H), 7.26-7.35 (m, 2H).

Step 6: Synthesis of tert-butyl 3-(1-(3-(2-(1-hydroxycyclobutyl)-2-oxoethoxy) benzoyl)piperidin-4-yl)benzylcarbamate

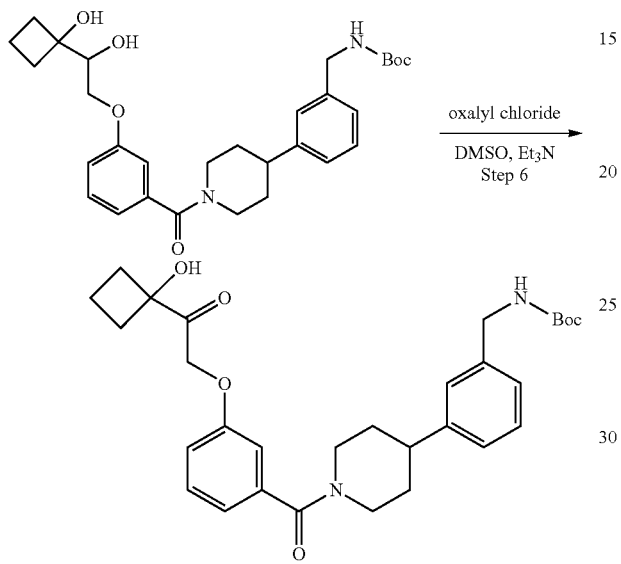

| Sr. No. | Chemical | Mol. Wt. | Quantity | mmol | Molar Ratio |
|---|---|---|---|---|---|
| 1 | tert-butyl 3-(1-(3-(2-hydroxy-2-(1-hydroxycyclobutyl)ethoxy)benzoyl)piperidin-4-yl)benzylcarbamate | 524 | 0.1 g | 0.19 | 1 |
| 2 | Oxalyl chloride | 127 | 0.032 mL | 0.38 | 2 |
| 3 | DMSO | 78 | 0.028 mL | 0.40 | 2.1 |
| 4 | Triethyl amine | 101 | 0.2 mL | 1.52 | 8 |
| 5 | Dichloromethane | — | 8 mL | — | — |

A solution of DMSO (0.028 mL, 0.40 mmol) in DCM (5 mL) was cooled to −78° C. To this solution oxalyl chloride (0.032 mL, 0.38 mmol) in 1 mL DCM was added dropwise. Then step 5 product (0.1 g, 0.19 mmol) in 2 mL of DCM was added. Resulting reaction mixture was allowed to stir at −78° C. for 1 h under nitrogen. To this solution triethyl amine (0.2 mL, 1.52 mmol) was added and reaction mixture was allowed to warm to room temperature and stir overnight. Reaction mixture was quenched with sat. NH$_4$Cl solution, aq. layer washed with DCM, dried over sodium sulphate. Crude reaction mixture was purified by column chromatography (60-120 mesh, ethyl acetate/n-hexane)

Yield: 0.028 g, 28%.

LCMS: (M+Na) 545

$^1$H NMR (400 MHz, CDCl$_3$): δ 1.47 (s, 9H), 1.60-1.80 (br, 4H), 1.90-2.10 (m, 4H), 2.30-2.50 (m, 2H), 2.70-3.20 (m, 4H), 3.85 (br, 1H), 4.03 (s, 2H), 4.30 (d, J=4.8 Hz, 2H), 4.84 (br, 1H), 6.90-7.04 (m, 3H), 7.10-7.20 (m, 3H), 7.28-7.34 (m, 2H).

Step 7: Synthesis of 2-(3-(4-(3-(aminomethyl)phenyl)piperidine-1-carbonyl) phenoxy)-1-(1-hydroxycyclobutyl)ethanone

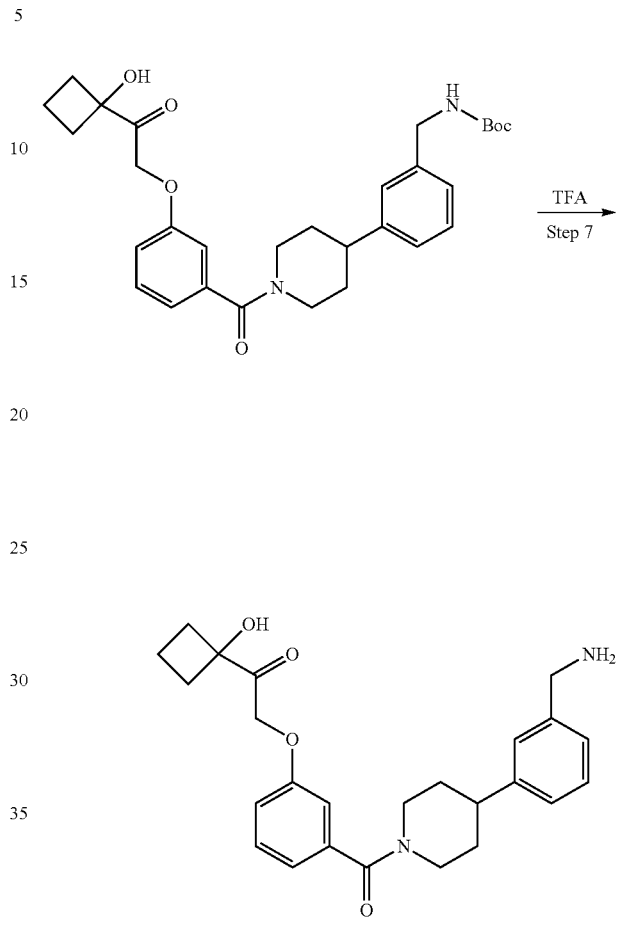

| Sr. No. | Chemical | Mol. Wt. | Quantity | mmol | Molar Ratio |
|---|---|---|---|---|---|
| 1 | tert-butyl 3-(1-(3-(2-(1-hydroxycyclobutyl)-2-oxoethoxy) benzoyl)piperidin-4-yl)benzyl carbamate | 523 | 0.02 g | 0.038 | 1 |
| 2 | Trifluoroacetic acid (TFA) | — | 3 mL | — | — |
| 3 | water | — | 0.3 mL | — | — |

In 9:1 TFA/water (3/0.3 mL) product from step 6 (0.020 g, 0.038 mmol) allowed to stir at RT for ~2 h. As TLC showed complete consumption of starting material reaction mixture was concentrated under vacuum. Compound was purified by preparative HPLC.

Yield: 8.31 mg (41.5%, TFA salt).

LCMS: (M+1) 423

HPLC purity: 92.5% (220 nm)

$^1$H NMR (400 mHz, CD$_3$OD): δ 1.60-1.90 (m, 3H), 1.90-2.10 (m, 4H), 2.25-2.50 (m, 3H), 2.85-3.00 (m, 2H), 3.20-3.30 (m, 1H), 3.84 (br, 1H), 3.95-4.15 (m, 4H), 4.80 (br, 1H), 6.90-7.10 (m, 3H), 7.22-7.44 (m, 5H).

Example 17: Synthesis of (E)-1-(4-(3-(aminomethyl)phenyl)piperidin-1-yl)-3-(3-hydroxy-2-(hydroxymethyl)phenyl)prop-2-en-1-one (Target-42)

SCHEME 18.

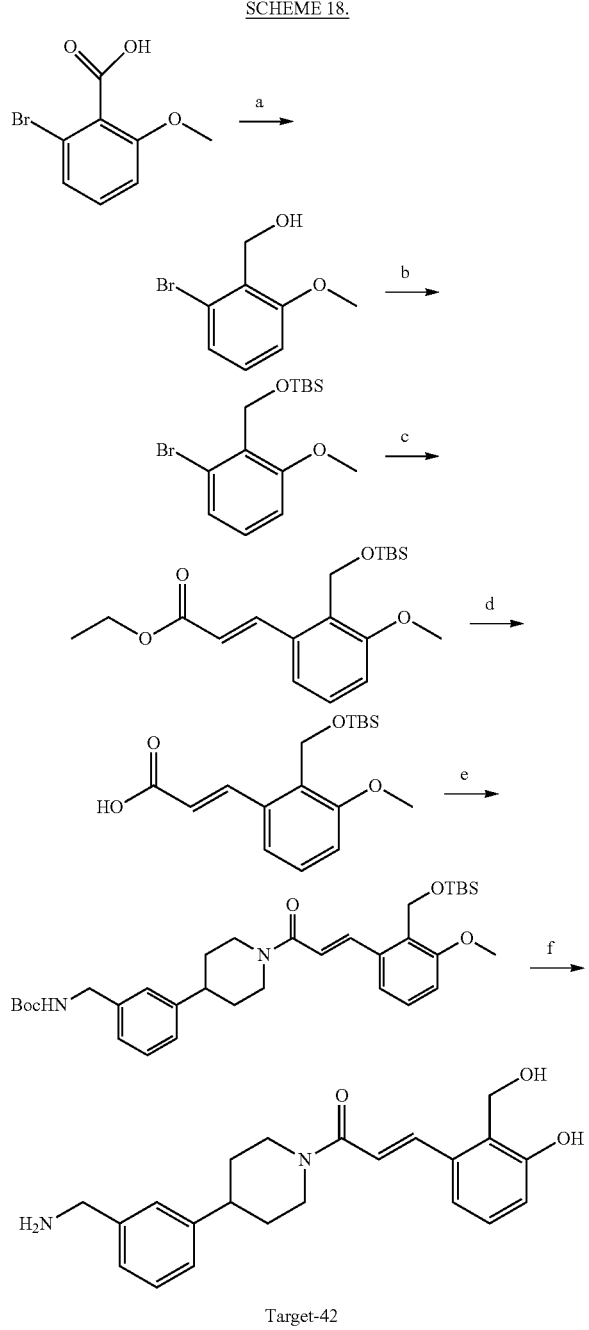

Target-42

Reagents and Conditions: a) BH₃·DMS, THF, 0° C.-rt, 10 h; b) TBDMS-Cl, NEt₃, DMAP, DCM, rt, 6 h; c) Tri-o-tolylphosphine, ethylacrylate, Pd(OAc)₂, NEtU, acetonitrile, 80° C., 4 h; d) LiOH, THF:H₂O, rt, 5 h; e) tert-Butyl 3-(piperidin-4-yl)benzylcarbamate, EDCi, HOBt, DIEA, DMF, rt, 15 h; f) 2 N HCl, Dioxane, 0° C., 2 h.

Detailed experimental procedure and analytical data is as follows.

Step-1: Synthesis of (2-bromo-6-methoxyphenyl)methanol

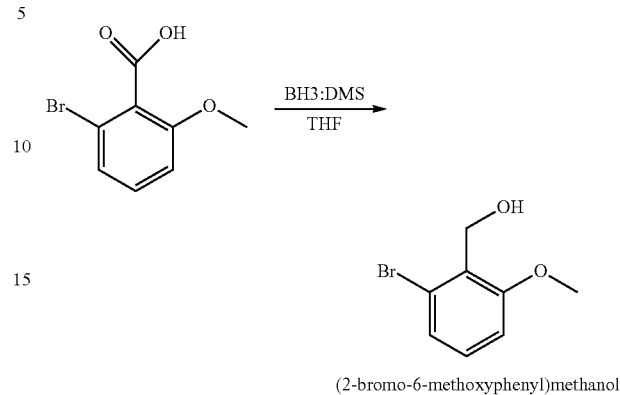

(2-bromo-6-methoxyphenyl)methanol

| Sr. No. | Chemical | Mol. Wt. | Quantity | Mmol | Molar Ratio |
|---|---|---|---|---|---|
| 1 | 2-Bromo-6-methoxybenzoic acid | 231.04 | 4.0 g | 17.3 | 1.0 |
| 2 | BH3:DMS (1M in THF) | 76 | 34.6 mL | 34.6 | 2.0 |
| 3 | THF | — | 80 mL | — | — |

To a cold solution of 2-bromo-6-methoxybenzoic acid (4.0 g, 17.3 mmol) in THF (80 mL), BH₃:DMS (34.6 mL, 34.6 mmol) was added dropwise. The reaction mixture was stirred at room temperature for 10 h. The reaction mixture was slowly poured onto ice and then extracted with EtOAc. The organic layer was washed with brine, dried over anhydrous sodium sulfate, concentrated under reduced pressure to afford (2-bromo-6-methoxyphenyl) methanol as a white solid.

Yield: 3.4 g, (91%)

Mol. Wt.: 217.06

LCMS (m/z): 240 [M+Na]

Step-2: Synthesis of ((2-bromo-6-methoxybenzyl)oxy)(tert-butyl) dimethyl silane

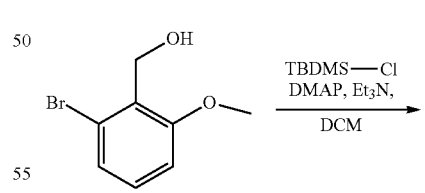

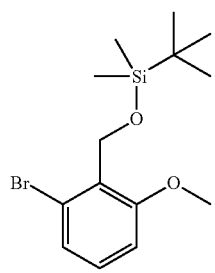

| Sr. No. | Chemical | Mol. Wt. | Quantity | mmol | Molar Ratio |
|---|---|---|---|---|---|
| 1 | (2-Bromo-6-methoxyphenyl) methanol | 217.06 | 2.45 g | 11.4 | 1.0 |
| 2 | TBDMS—Cl | 150.7 | 5.16 g | 34.2 | 3.0 |
| 3 | DMAP | 122.17 | 0.14 g | 1.14 | 0.1 |
| 4 | Et₃N | 101.19 | 4.0 mL | 28.5 | 2.5 |
| 5 | DCM | | 50 mL | | |

To a solution of (2-bromo-6-methoxyphenyl) methanol (2.45 g, 11.4 mmol) in DCM (50 mL), DMAP (0.14 g, 1.14 mmol) and Et₃N (4.0 mL, 28.5 mmol) was added. The reaction mixture was stirred at room temperature for 10 min followed by addition of TBDMS-Cl (5.16 g, 34.2 mmol). The reaction mixture was stirred at room temperature for 6 h and was concentrated under reduced pressure and purified by column chromatography (0-10% EtOAc in hexane) to yield ((2-bromo-6-methoxybenzyl)oxy)(tert-butyl)dimethylsilane.

Yellow liquid; Yield: 3.0 g, (80%)
Mol. Wt.: 331.32
$^1$H NMR (400 MHz, CDCl$_3$): δ 7.15 (d, J=8.0 Hz, 1H), 7.09 (t, J=8.0 Hz, 1H), 6.80 (d, J=8.0 Hz, 1H), 4.85 (s, 2H), 3.82 (s, 3H), 0.91 (s, 9H), 0.09 (s, 6H).

Step-3: Synthesis of (E)-ethyl 3-(2-(((tert-butyldimethylsilyl)oxy)methyl)-3-methoxyphenyl)acrylate

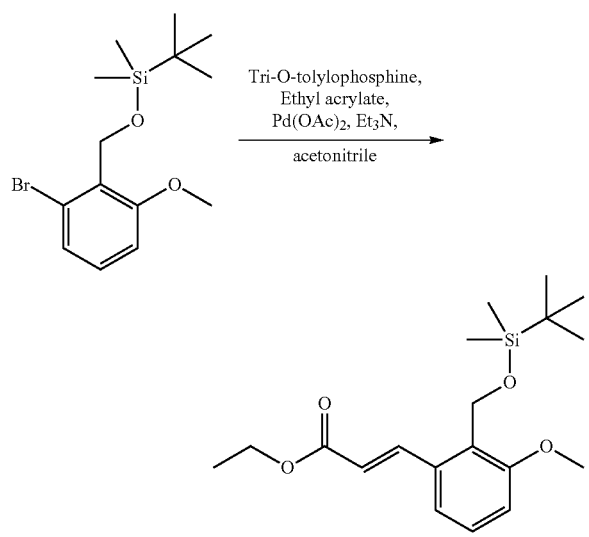

| Sr. No. | Chemical | Mol. Wt. | Quantity | mmol | Molar Ratio |
|---|---|---|---|---|---|
| 1 | ((2-bromo-6-methoxybenzyl)oxy)(tert-butyl)dimethylsilane | 331.32 | 1.0 g | 3.02 | 1.0 |
| 2 | Ethyl acrylate | 100.11 | 1.32 mL | 12.0 | 4.0 |
| 3 | Tri-O-Tolylphosphine | 304.37 | 0.23 g | 0.75 | 0.25 |
| 4 | Pd(OAc)₂ | 224.5 | 0.17 g | 0.75 | 0.25 |
| 5 | Et₃N | 101.19 | 1.68 mL | 12.0 | 4.0 |
| 6 | Acetonitrile | — | 25 mL | — | — |

A solution of ((2-bromo-6-methoxybenzyl)oxy)(tert-butyl)dimethylsilane (1.0 g, 3.02 mmol), ethyl acrylate (1.32 mL, 12.0 mmol), triethyl amine (1.68 mL, 12.0 mmol), tri-o-tolyl phosphine (0.23 g, 0.75 mmol) in acetonitrile (25 mL) was degassed with argon for 10 min. Palladium acetate (0.17 g, 0.75 mmol) was added and degassed with argon for 10 min. The reaction mixture was refluxed at 80° C. for 4 h. The reaction mixture was concentrated under vacuo, diluted with ethyl acetate, filtered over celite and purified by silica gel column chromatography (0-5%, EtOAc in hexane) to yield (E)-ethyl 3-(2-(((tert-butyldimethylsilyl)oxy)methyl)-3-methoxyphenyl)acrylate as white solid.

Yield: 0.9 g, (86%)
Mol. Wt.: 350.19
LCMS (m/z): 391 [M+K].

Step-4: Synthesis of (E)-3-(2-(((tert-butyldimethylsilyl)oxy)methyl)-3-methoxyphenyl)acrylic acid

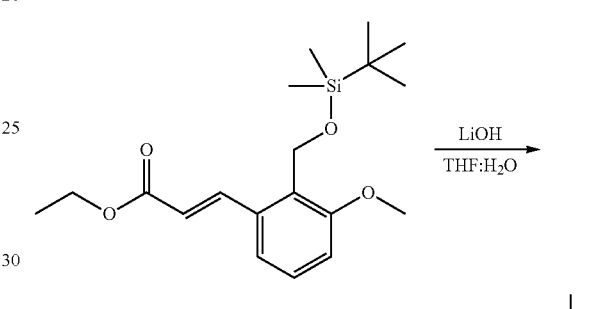

| Sr. No. | Chemical | Mol. Wt. | Quantity | mmol | Molar Ratio |
|---|---|---|---|---|---|
| 1 | (E)-ethyl 3-(2-(((tert-butyldimethylsilyl)oxy)methyl)-3-methoxyphenyl)acrylate | 350.19 | 0.5 g | 1.42 | 1.0 |
| 2 | LiOH | 42.0 | 0.12 g | 2.85 | 2.0 |
| 3 | THF:H₂O (2:1) | — | 15 ml | — | — |

To a solution of methyl (E)-ethyl 3-(2-(((tert-butyldimethylsilyl)oxy)methyl)-3-methoxyphenyl)acrylate (0.5 g, 1.42 mmol) in THF:H₂O (15 mL) was added LiOH (0.12 g, 2.85 mmol), the resulting solution was stirred at room temperature for 5 h. The organic solvent was concentrated, residue acidified with 10% citric acid solution, extracted with EtOAc. The combined organic layer was dried over anhydrous sodium sulfate, concentrated under reduced pressure and triturated with diethyl ether to yield the (E)-3-(2-(((tert-butyldimethylsilyl)oxy)methyl)-3-methoxyphenyl) acrylic acid as a white solid.

Yield: 0.33 g, (72%)
Mol. Wt.: 322.47.

Step-5: Synthesis of (E)-tert-butyl 3-(1-(3-(2-(((tert-butyldimethylsilyl) oxy) methyl)-3-hydroxyphenyl) acryloyl) piperidin-4-yl) benzylcarbamate

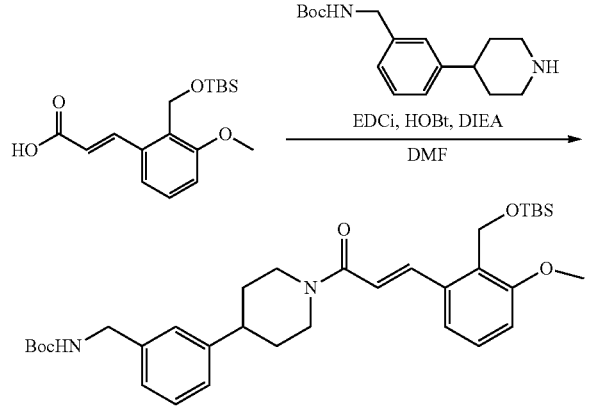

| Sr. No. | Chemical | Mol. Wt. | Quantity | mmol | Molar Ratio |
|---|---|---|---|---|---|
| 1 | (E)-3-(2-(((tert-butyldimethylsilyl)oxy)methyl)-3-methoxyphenyl)acrylic acid | 322.47 | 0.33 g | 1.02 | 1.0 |
| 2 | tert-butyl 3-(piperidin-4-yl)benzylcarbamate | 290.4 | 0.29 g | 1.02 | 1.0 |
| 3 | EDCI | 191.7 | 0.29 g | 1.53 | 1.5 |
| 4 | HOBt | 135.1 | 0.21 g | 1.53 | 1.5 |
| 5 | DIEA | 129.25 | 0.35 mL | 2.04 | 2.0 |
| 6 | DMF | — | 10 mL | — | — |

To a solution of (E)-3-(2-(((tert-butyldimethylsilyl)oxy)methyl)-3-methoxyphenyl)acrylic acid (0.33 g, 1.02 mmol) in anhydrous DMF (10 mL) at 0° C., was added HOBt (0.21 g, 1.53 mmol). The reaction mixture was stirred for 10 minutes and EDCI (0.29 g, 1.53 mmol), tert-butyl 3-(piperidin-4-yl) benzylcarbamate (0.29 g, 1.02 mmol) and DIEA (0.35 mL, 2.04 mmol) were added. The resulting solution was allowed to stir at RT for 15 h. The reaction mixture was diluted with EtOAc and washed with $H_2O$, dried ($Na_2SO_4$) and evaporated under vacuo. The crude product was purified by silica gel column chromatography (5-10% MeOH in $CHCl_3$) to afford (E)-tert-butyl 3-(1-(3-(2-(((tert-butyldimethylsilyl)oxy)methyl)-3-hydroxyphenyl)acryloyl)piperidin-4-yl)benzylcarbamate as a yellow solid.

Yield: 0.35 g, (55%)
Mol. Wt.: 594.35
LCMS (m/z): 617 [M+Na].

Step-6: Synthesis of (E)-1-(4-(3-(aminomethyl)phenyl)piperidin-1-yl)-3-(3-hydroxy-2-(hydroxymethyl) phenyl)prop-2-en-1-one

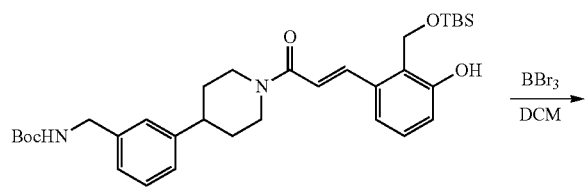

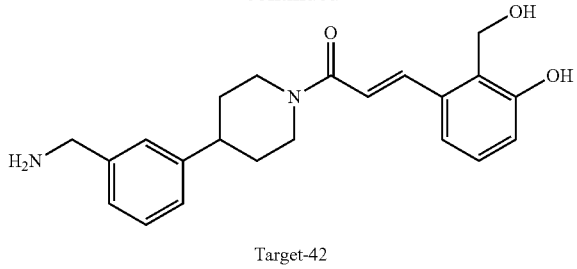

Target-42

| Sr. No. | Chemical | Mol. Wt. | Quantity | mmol | Molar Ratio |
|---|---|---|---|---|---|
| 1 | (E)-tert-butyl 3-(1-(3-(2-(((tert-butyldimethylsilyl)oxy)methyl)-3-hydroxyphenyl)acryloyl)piperidin-4-yl)benzylcarbamate | 594.35 | 0.1 g | 0.17 | 1.0 |
| 2 | $BBr_3$ (1M in DCM) | — | 0.68 mL | 0.68 | 4.0 |
| 3 | DCM | — | 5 mL | — | — |

To a stirred solution of (E)-tert-butyl 3-(1-(3-(2-(((tert-butyldimethylsilyl)oxy)methyl)-3-hydroxyphenyl)acryloyl) piperidin-4-yl) benzylcarbamate (0.1 g, 0.17 mmol) in DCM (5 mL) was added $BBr_3$ (0.68 mL, 1 M in DCM) at 0° C. The resulting solution was stirred at 0° C. for 2 h and the reaction was monitored by LCMS. The reaction mixture was evaporated under vacuo and purified by prep-HPLC to afford (E)-1-(4-(3-(aminomethyl) phenyl) piperidin-1-yl)-3-(3-hydroxy-2-(hydroxymethyl) phenyl) prop-2-en-1-one as a TFA salt.

Yield: 0.028 g, (46%)
Mol. Wt.: 366.45
LCMS (m/z): 367 [M+1]
HPLC Purity: 99.78%
$^1$H NMR (400 MHz, $CD_3OD$): δ 7.99 (d, J=15.2 Hz, 1H), 7.44-7.26 (m, 4H), 7.22-7.12 (m, 2H), 7.07 (d, J=15.2 Hz, 1H), 6.85 (d, J=7.6 Hz, 1H), 4.80-4.72 (m, 1H), 4.46-4.34 (m, 1H), 4.10 (s, 2H), 3.00-2.80 (m, 2H), 2.02-1.90 (m, 2H), 1.80-1.64 (m, 2H).

Example 18: Synthesis of N-(3-(4-(3-(aminomethyl) phenyl)piperidine-1-carbonyl)phenyl)-3-hydroxy-3-methyl-2-oxobutanamide (Target-55)

Synthesis of the N-(3-(4-(3-(aminomethyl)phenyl)piperidine-1-carbonyl)phenyl)-3-hydroxy-3-methyl-2-oxobutanamide was carried out as shown in the scheme below.

SCHEME 19.

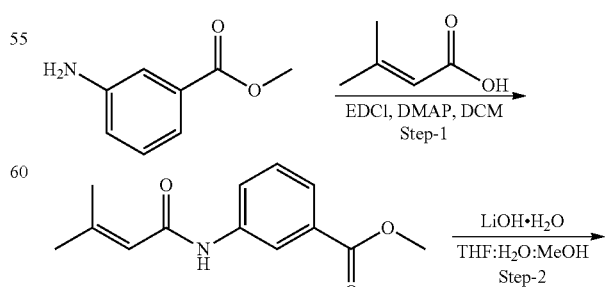

-continued

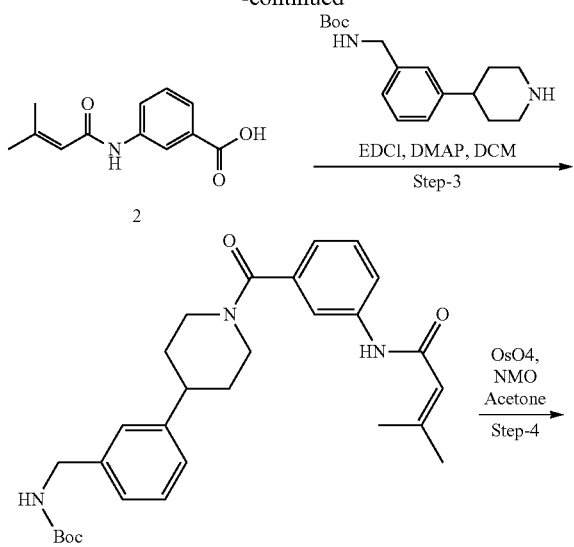

Step 1: Synthesis of methyl 3-(3-methylbut-2-enamido) benzoate

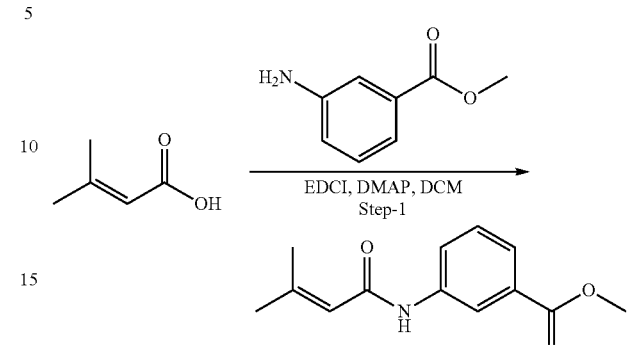

| Sr. No. | Chemical | Mol. Wt. | Quantity | mmol | Molar Ratio |
|---|---|---|---|---|---|
| 1 | 3-methylbut-2-enoic acid | 100 | 2.5 g | 25 | 1 |
| 2 | methyl 3-aminobenzoate | 151 | 4.5 g | 30 | 1.2 |
| 3 | EDCI | 191.5 | 7.2 g | 37.5 | 1.5 |
| 4 | DMAP | 122 | 1.5 g | 12.5 | 0.5 |
| 5 | DCM | — | 30 mL | — | — |

To a solution of 3-methylbut-2-enoic acid (2.5 g, 25 mmol) in DCM (30 mL), methyl 3-aminobenzoate (4.5 g, 30 mmol), EDCI (7.2 g, 37.5 mmol), DMAP (1.5 g, 12.5 mmol) were added and the reaction mixture was allowed to stir at room temperature for overnight under nitrogen atmosphere. TLC showed absence of starting material ($R_f$=0.5, 30% ethyl acetate/n-hexane). The reaction mixture was washed with water and 2N HCl. The organic layer was separated, dried over sodium sulphate, concentrated. Solid was washed with diethyl ether three times get off white solid.

Yield: 4.5 g (77%)

LCMS: m/z (M+1) 234

$^1$H NMR (400 MHz, CDCl$_3$): δ 1.89 (s, 3H), 2.23 (s, 3H), 3.90 (s, 3H), 5.73 (s, 1H), 7.31-7.50 (m, 2H), 7.75 (d, J=7.2 Hz, 1H), 7.92 (br, 1H), 8.06 (s, 1H).

Step 2: Synthesis of 3-(3-methylbut-2-enamido) benzoic acid

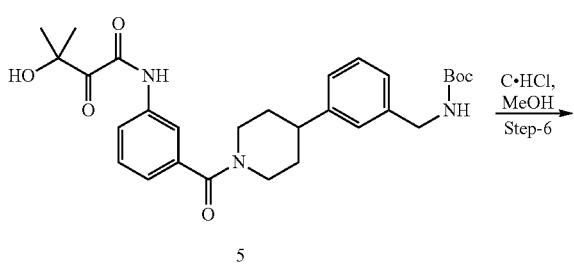

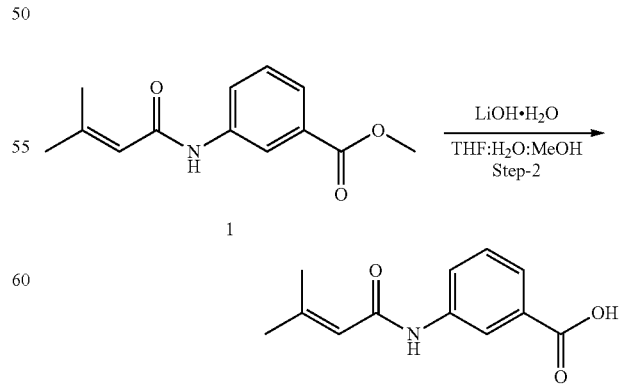

Detailed experimental procedure and analytical data is as follows.

| Sr. No. | Chemical | Mol. Wt. | Quantity | mmol | Molar Ratio |
|---|---|---|---|---|---|
| 1 | methyl 3-(3-methylbut-2-enamido)benzoate | 233 | 4.5 g | 19.3 | 1 |
| 2 | LiOH•H₂O | 42 | 2.43 g | 58 | 3 |
| 3 | THf:H₂0:MeOH | — | 10:10:5 mL | — | — |

A solution of methyl 3-(3-methylbut-2-enamido) benzoate (4.5 g, 19.3 mmol), Lithium hydroxide monohydrate (2.43 g, 58 mmol) in THF (10 mL), H₂O (10 mL), MeOH (5 mL) allowed to stir for 16 h at room temperature. TLC showed absence of starting material ($R_f$=0.3, 50% ethyl acetate/n-hexane). Solvent was removed under reduced pressure. Reaction mixture was acidified with 10% citric acid solution; white precipitate obtained was filtered out and washed with hexane and dried under vacuum.

Yield: 4 g (95%)

LCMS: m/z (M+1) 219.9

¹H NMR (400 MHz, DMSO-d₆): δ 1.86 (s, 3H), 2.15 (s, 3H), 5.86 (s, 1H), 7.40 (t, J=7.6 Hz, 1H), 7.59 (d, J=7.6 Hz, 1H), 7.82 (d, J=7.6 Hz, 1H), 8.27 (s, 1H), 10.0 (s, 1H), 12.8 (br, 1H).

Step-3: Synthesis of tert-butyl 3-(1-(3-(3-methylbut-2-enamido) benzoyl)piperidin-4-yl)benzylcarbamate

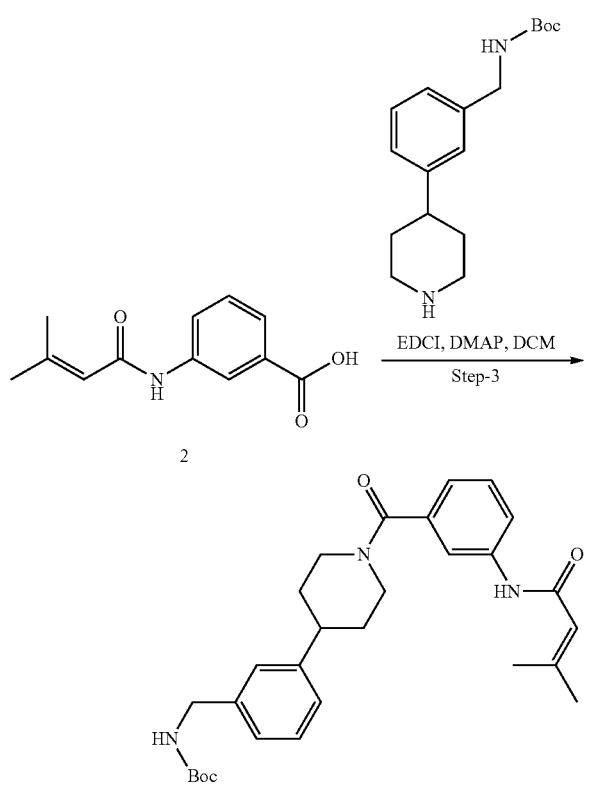

| Sr. No. | Chemical | Mol. Wt. | Quantity | mmol | Molar Ratio |
|---|---|---|---|---|---|
| 1 | 3-(3-methylbut-2-enamido)benzoic acid | 219 | 0.03 g | 0.136 | 1 |
| 2 | tert-butyl 3-(piperidin-4-yl)benzylcarbamate | 290 | 0.047 g | 0.16 | 1.2 |
| 3 | EDCI | 191.5 | 0.039 g | 0.2 | 1.5 |
| 4 | DMAP | 122 | 0.008 g | 0.07 | 0.5 |
| 5 | DCM | — | 2 mL | — | — |

To a solution of 3-(3-methylbut-2-enamido)benzoic acid (0.03 g, 0.136 mmol) in DCM (2 mL), tert-butyl 3-(piperidin-4-yl)benzylcarbamate (0.047 g, 0.16 mmol), EDCI (0.039 g, 0.2 mmol), DMAP (0.008 g, 0.07 mmol) were added and the reaction mixture was allowed to stir at room temperature for overnight under nitrogen atmosphere. TLC showed absence of starting material ($R_f$=0.53, 80% ethyl acetate/n-hexane). The reaction mixture was washed with water, 2N HCl, followed by brine. The organic layer was separated, dried over sodium sulphate concentrated under reduced pressure. Compound was used as it is for next step.

Yield: 0.027 g (40%)

LCMS: m/z (M+Na) 514.4

¹H NMR (400 MHz, CDCl₃): δ 1.46 (s, 9H), 1.66-1.90 (br, 4H), 1.91 (s, 3H), 2.22 (s, 3H), 2.70-2.90 (m, 1H), 3.13 (br, 1H), 3.90 (br, 1H), 4.30 (d, J=4.8 Hz, 2H), 4.87 (br, 2H), 5.74 (s, 1H), 7.00-7.40 (m, 7H), 7.50-7.70 (m, 3H).

Step 4: Syntheses of Intermediate 4

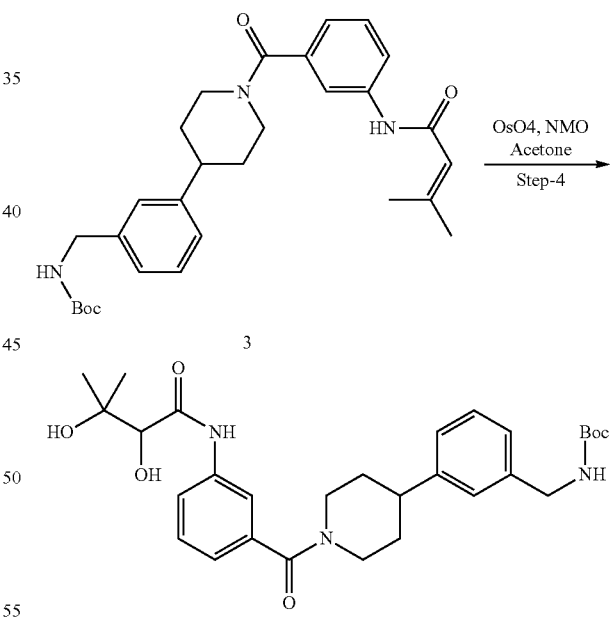

| Sr. No. | Chemical | Mol. Wt. | Quantity | Mmol | Molar Ratio |
|---|---|---|---|---|---|
| 1 | tert-butyl 3-(1-(3-(3-methylbut-2-enamido)benzoyl)piperidin-4-yl)benzylcarbamate. | 491 | 0.027 g | 55 μmol | 1 |
| 2 | OsO₄ (4% aq.) | 254 | 13 μL | 2.2 μmol | 0.04 |

| Sr. No. | Chemical | Mol. Wt. | Quantity | Mmol | Molar Ratio |
|---|---|---|---|---|---|
| 3 | N-Methylmorpholine oxide [NMO] (50% aq.) | 117 | 15 µL | 66 µmol | 1.2 |
| 4 | Acetone | — | 2 mL | — | — |
| 5 | Water | — | 0.3 mL | — | — |

In 2 mL acetone and 0.3 mL of water tert-butyl 3-(1-(3-(3-methylbut-2-enamido)benzoyl)piperidin-4-yl)benzylcarbamate (0.027 g, 55 µmol), OSO$_4$ (4% aqueous solution, 13 µL, 2.2 µmol) was added and stirred for 10 min at room temperature. Then NMO (50% aqueous solution, 15 µL, 66 µmol) was added and allowed to stir at room temperature overnight. TLC showed absence of starting material ($R_f$=0.4, 100% ethyl acetate). Reaction mixture was quenched with 10% aqueous sodium bisulphite solution and stirred for ~1 h at room temperature. Aqueous layer was extracted with ethyl acetate, dried over sodium sulphate. Crude product obtained was purified by column chromatography (100-200 mesh, ethyl acetate/n-hexane) afforded off white solid.

Yield: 0.017 g (60%)
LCMS: m/z (M+Na) 548.15
$^1$H NMR (400 MHz, CDCl$_3$): δ 1.20 (s, 3H), 1.34 (s, 3H), 1.46 (s, 9H), 1.70-2.00 (br, 4H), 2.70-3.25 (br, 3H), 3.76 (s, 1H), 3.90 (br, 1H), 4.31 (s, 2H), 4.50-5.00 (br, 2H), 7.10-7.50 (m, 8H), 7.69 (bs, 1H), 8.90 (bs, 1H).

Step 5: Synthesis of tert-butyl 3-(1-(3-(3-hydroxy-3-methyl-2-oxobutanamido)benzoyl)-piperidin-4-yl)benzylcarbamate

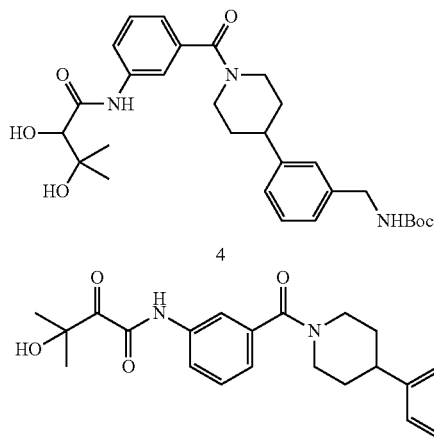

| Sr. No. | Chemical | Mol. Wt. | Quantity | mmol | Molar Ratio |
|---|---|---|---|---|---|
| 1 | Intermediate 4 | 525 | 0.1 g | 0.19 | 1 |
| 2 | Dess Martin periodinane | 424.1 | 0.24 g | 0.57 | 3 |
| 3 | DCM | — | 5 mL | — | — |

To a solution of Intermediate 4 (0.01 g, 0.019 mmol), DCM (5 mL), Dess Martin periodinane (0.24 g, 0.57 mmol) was added at room temperature. Reaction mixture was stirred under nitrogen atmosphere for 2 h. TLC showed absence of starting material ($R_f$=0.4, 100% ethyl acetate). Reaction mixture was quenched with carbonate resin, filter through cotton. DCM was evaporated under reduced pressure. Crude compound was purified by preparative TLC (100% ethyl acetate as a mobile phase).

Yield: 0.018 g (18%)
LCMS: m/z (M+Na) 546.

Step 6: Synthesis of N-(3-(4-(3-(aminomethyl)phenyl)piperidine-1-carbonyl) phenyl)-3-hydroxy-3-methyl-2-oxobutanamide

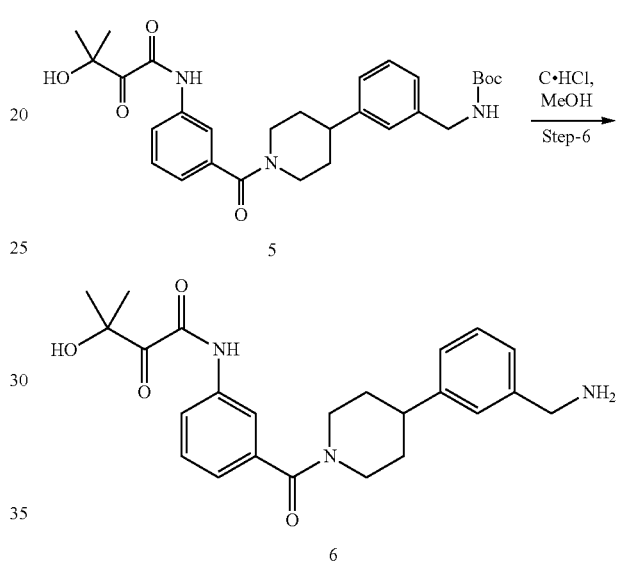

| Sr. No. | Chemical | Mol. Wt. | Quantity | mmol | Molar Ratio |
|---|---|---|---|---|---|
| 1 | tert-butyl 3-(1-(3-(3-hydroxy-3-methyl-2-oxobutanamido)benzoyl)piperidin-4-yl)benzylcarbamate | 523 | 0.01 g | 0.019 | 1 |
| 2 | Conc. HCl | — | 0.12 mL | — | — |
| 3 | Methanol | — | 2.5 mL | — | — |

To a solution of tert-butyl 3-(1-(3-(3-hydroxy-3-methyl-2-oxobutanamido)benzoyl)piperidin-4-yl)benzylcarbamate (0.01 g, 0.019 mmol), methanol (2.5 mL), Conc. HCl (0.12 mL) was added at room temperature. Reaction mixture was stirred for 16 h. Methanol was evaporated under reduced pressure. Crude compound was purified by Preparative HPLC.

Yield: 4.8 mg (60%, TFA salt)
LCMS: m/z (M+MeOH) 446
$^1$H NMR (400 MHz, CD$_3$OD): δ 1.24 (s, 3H), 1.29 (s, 3H), 1.65-2.10 (br, 4H), 2.88-3.10 (m, 2H), 3.20-3.30 (br, 2H), 3.90 (br, 1H), 4.11 (s, 2H), 7.20-7.50 (m, 6H), 7.61 (d, J=8.0 Hz, 1H), 7.90 (s, 1H).

Example 19: Synthesis of (E)-(3-(4-(3-(aminomethyl)phenyl)piperidine-1-carbonyl) styryl)boronic acid hydrochloride (Target-14)

SCHEME 20.

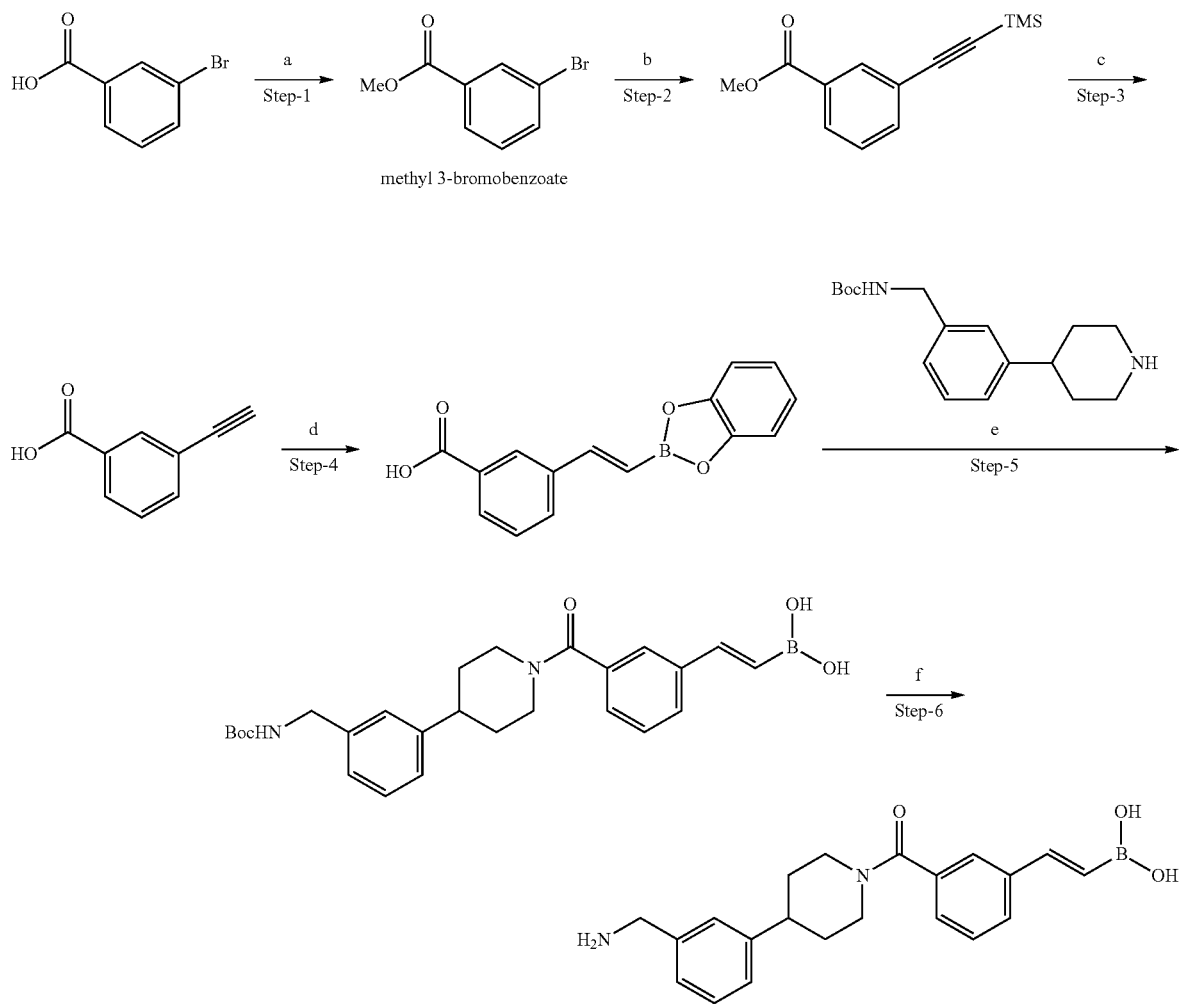

Reagents and Conditions: a) SOCl₂, MeOH, reflux, 5 h; b) CuI, Pd(PPh₃)₄, Ethynyl (trimethyl)silane, Et₃N, 50° C., 24 h; c) K₂CO₃, MeOH, rt, 5 h; d) Catechol borane, THF, 0° C.-rt, 5 h; e) tert-Butyl 3-(piperidin-4-yl)benzylcarbamate, EDCI, HOBt, DIEA, DMF, rt, 15 h; f) Conc. HCl, MeOH, rt, 2 h.

Detailed experimental procedure and analytical data is as follows.

Methyl 3-bromobenzoate was synthesized from 3-bromobenzoic acid by esterification with thionyl chloride in methanol. Further Sonogashira coupling was carried out with ethynyl (trimethyl)silane to afford methyl 3-((trimethylsilyl)ethynyl)benzoate, which upon hydrolysis with lithium hydroxide in methanol yielded 3-ethynylbenzoic acid as per known procedures.

Step-4: Synthesis of (E)-3-(2-(benzo[d][1,3,2]dioxaborol-2-yl)vinyl)benzoic acid

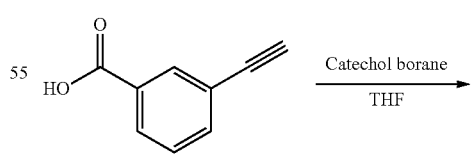
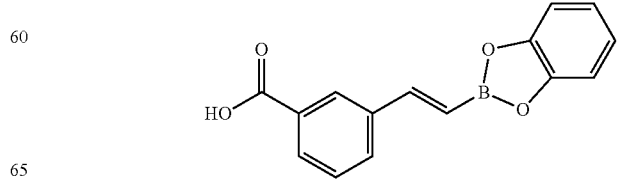

| Sr. No. | Chemical | Mol. Wt. | Quantity | mmol | Molar Ratio |
|---|---|---|---|---|---|
| 1 | 3-Ethynylbenzoic acid | 146.14 | 0.2 g | 1.37 | 1.0 |
| 2 | Catechol borane | 119.92 | 0.15 mL | 1.37 | 1.0 |
| 3 | THF | | 10 mL | | |

To a cold solution of 3-ethynylbenzoic acid (0.2 g, 1.37 mmol) in anhydrous THF (10 mL), was added catechol borane (0.15 mL, 1.37 mmol). The reaction mixture was stirred at room temperature for 2 h. The resulting solution was poured into cold water and extracted with EtOAc. The organic layer was washed with $H_2O$, dried over $Na_2SO_4$ and evaporated under vacuo. The crude product was purified by silica gel column chromatography (0-20%, EtOAc in hexane) to afford (E)-3-(2-(benzo[d][1,3,2]dioxaborol-2-yl)vinyl)benzoic acid as a white solid.

Yield: 0.27 g (75%)

$^1$H NMR (400 MHz, Acetone-$d_6$): δ 8.18-8.12 (m, 1H), 7.95 (d, J=7.2 Hz, 1H), 7.92-7.86 (m, 1H), 7.76 (d, J=7.2 Hz, 1H), 7.51 (t, J=7.2 Hz, 1H), 7.43 (d, J=18.2 Hz, 1H), 7.12-7.02 (m, 1H), 6.84-6.76 (m, 1H), 6.70-6.62 (m, 1H), 6.32 (d, J=18.2 Hz, 1H).

Step-5: Synthesis of (E)-(3-(4-(3-(((tert-butoxycarbonyl) amino)methyl) phenyl)piperidine-1-carbonyl) styryl)boronic acid

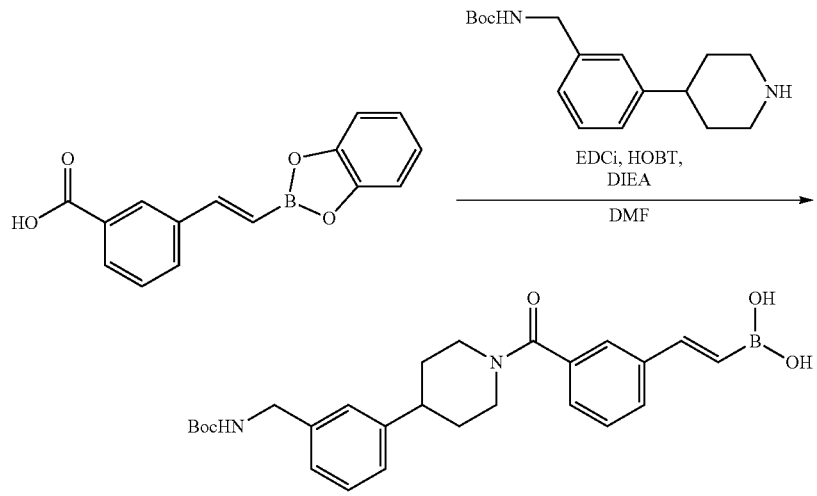

| Sr. No. | Chemical | Mol. Wt. | Quantity | mmol | Molar Ratio |
|---|---|---|---|---|---|
| 1 | (E)-3-(2-(benzo[d][1,3,2] dioxaborol-2-yl)vinyl) benzoic acid | 266.06 | 0.1 g | 0.38 | 1.0 |
| 2 | tert-butyl 3-(piperidin-4-yl) benzylcarbamate | 290.35 | 0.11 g | 0.38 | 1.2 |
| 3 | EDCi | 191.7 | 0.11 g | 0.57 | 1.5 |
| 4 | HOBt | 135.12 | 0.077 g | 0.57 | 1.5 |
| 5 | DIEA | 129.25 | 0.13 mL | 0.76 | 2.0 |
| 6 | DMF | — | 5 mL | — | — |

To a solution of (E)-3-(2-(benzo[d][1,3,2]dioxaborol-2-yl)vinyl)benzoic acid (0.1 g, 0.38 mmol) in anhydrous DMF (5 mL) at 0° C., was added HOBt (0.077 g, 0.57 mmol). The reaction mixture was stirred for 10 minutes and EDCI (0.11 g, 0.57 mmol), tert-butyl 3-(piperidin-4-yl) benzylcarbamate (0.11 g, 0.38 mmol) and DIEA (0.13 mL, 0.76 mmol) were added. The resulting solution was allowed to stir at room temperature for overnight. The reaction mixture was then diluted with EtOAc and was washed with $H_2O$. The organic layer was dried over $Na_2SO_4$ and evaporated under vacuo. The crude product was purified by silica gel column chromatography (0-15%, EtOAc in hexane) to afford (E)-(3-(4-(3-(((tert-butoxycarbonyl)amino)methyl)phenyl)piperidine-1-carbonyl)styryl)boronic acid.

White solid; Yield: 0.06 g (35%)

Mol. Wt.: 464.36

LCMS (m/z): 465 [M+1].

Step-6: Synthesis of (E)-(3-(4-(3-(aminomethyl)phenyl)piperidine-1-carbonyl)styryl)boronic acid hydrochloride

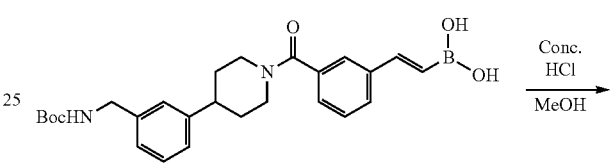

-continued

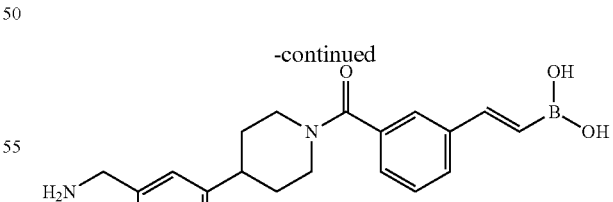

| Sr. No. | Chemical | Mol. Wt. | Quantity | mmol | Molar Ratio |
|---|---|---|---|---|---|
| 1 | (E)-(3-(4-(3-(((tert-butoxycarbonyl) amino)methyl)phenyl)piperidine-1-carbonyl) styryl)boronic add | 464.36 | 0.04 g | 0.09 | 1.0 |

| Sr. No. | Chemical | Mol. Wt. | Quantity | Molar mmol Ratio |
|---|---|---|---|---|
| 2 | Conc. HCl | — | 0.05 mL | — — |
| 3 | MeOH | — | 3 mL | — — |

To a stirred solution of (E)-(3-(4-(3-(((tert-butoxycarbonyl)amino) methyl)phenyl)piperidine-1-carbonyl)styryl)boronic acid (0.05 g, 0.09 mmol) in MeOH (3 mL) was added 2 N HCl (0.05 mL) at room temperature. The resulting solution was stirred at room temperature for 5 h. The reaction mixture was evaporated under vacuo and the resultant residue was triturated with diethyl ether to afford (E)-(3-(4-(3-(aminomethyl)phenyl)piperidine-1-carbonyl)styryl)boronic acid hydrochloride as a white solid.

Yield: 0.02 g (64%)
Mol. Wt.: 364.25
LCMS (m/z): 365 [M+1], 387 [M+Na]
HPLC Purity: 94.17%
$^1$H NMR (400 MHz, CD$_3$OD): δ 7.62-7.54 (m, H), 7.52-7.46 (m, 1H), 7.42-7.18 (m, 7H), 6.37 (d, J=18.0 Hz, 1H), 4.02 (s, 3H), 3.82-3.70 (m, 1H), 3.20-3.10 (m, 1H), 2.95-2.76 (m, 2H), 1.95-1.82 (m, 1H), 1.80-1.52 (m, 3H).

Example 20: Synthesis of (Z)-1-(4-(3-(aminomethyl)phenyl)piperidin-1-yl)-3-(3,4-dihydroxyphenyl)prop-2-en-1-one hydrochloride (Target-24 cis) and Synthesis of 1-(4-(3-(aminomethyl)phenyl)piperidin-1-yl)-3-(3,4-dihydroxyphenyl)propan-1-one (TFA salt) (Target-24 dihydro)

SCHEME 21.

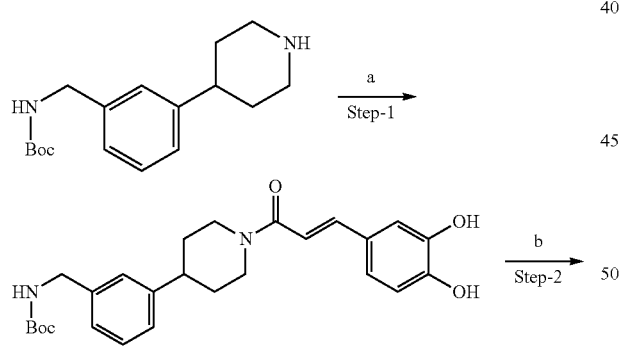

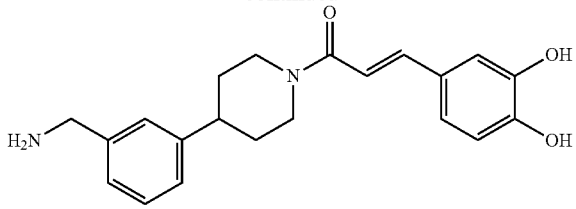

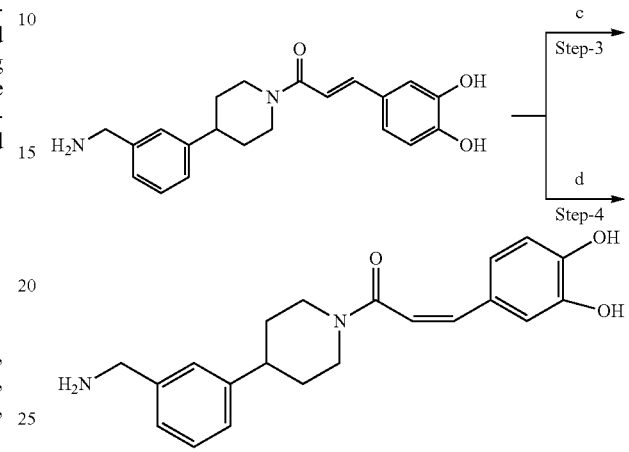

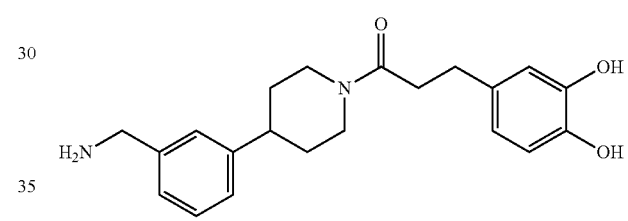

Reagents and Conditions: a) (E)-3-(3,4-dihydroxyphenyl)acrylic acid, EDCi, HOBt, DIEA, DMF, rt, overnight; b) HCl, MeOH, rt, 1 h; c) Exposed to sunlight in ethanol for 2 h; d) H$_2$/Pd—C, MeOH, rt, 1 h.

Detailed experimental procedure and analytical data is as follows.

Synthesis of (E)-1-(4-(3-(aminomethyl) phenyl) piperidin-1-yl)-3-(3,4-dihydroxyphenyl)prop-2-en-1-one hydrochloride Step-3: Synthesis of (Z)-1-(4-(3-(aminomethyl)phenyl)piperidin-1-yl)-3-(3,4-dihydroxyphenyl)prop-2-en-1-one hydrochloride

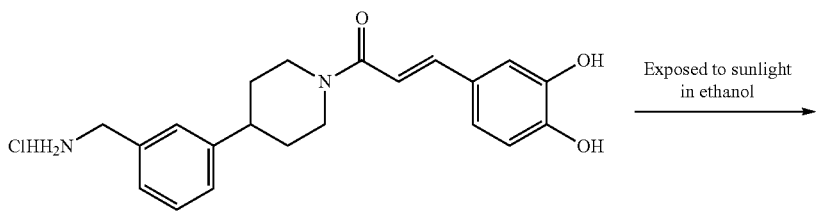

Exposed to sunlight in ethanol

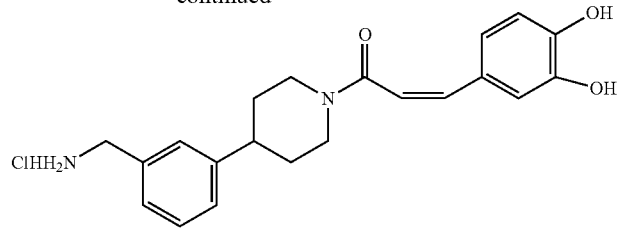

Target-24 cis

| Sr. No. | Chemicals | Mol. wt. | Quantity | mmol | Molar Ratio |
|---|---|---|---|---|---|
| 1 | (E)-1-(4-(3-(aminomethyl)phenyl) piperidin-1-yl)-3-(3,4-dihydroxy phenyl)prop-2-en-1-one hydrochloride | 352.43 | 0.02 g | 0.06 | 1.0 |
| 2 | Ethanol | | 3.0 mL | | |

(E)-1-(4-(3-(Aminomethyl)phenyl)piperidin-1-yl)-3-(3,4-dihydroxyphenyl)prop-2-en-1-one hydrochloride was taken in ethanol (3.0 mL) and exposed to sunlight for 2 h. The organic layer was concentrated under vacuo to afford (Z)-1-(4-(3-(aminomethyl)phenyl)piperidin-1-yl)-3-(3,4-dihydroxyphenyl)prop-2-en-1-one hydrochloride as a white solid.

Yield: 0.018 g, (90%)

Mol. Wt.: 352.43

LCMS (m/z): 353 [M+1], 375 [M+Na]

HPLC Purity: 89.73%

$^1$H NMR (400 MHz, CD$_3$OD): δ 7.33 (t, J=7.6 Hz, 1H), 7.25 (d, J=7.6 Hz, 1H), 7.16 (d, J=7.6 Hz, 1H), 7.10 (s, 1H), 6.94 (d, J=1.8 Hz, 1H), 6.80 (d, J=8.2 Hz, 1H), 6.74 (dd, J=8.2, 1.8 Hz, 1H), 6.67 (d, J=12.0 Hz, 1H), 5.91 (d, J=12.0 Hz, 1H), 4.80-4.70 (m, 1H), 4.13 (ABq, J=13.6 Hz, 2H), 4.08-3.98 (m, 1H), 3.08-2.95 (m, 1H), 2.80-2.65 (m, 2H), 1.82-1.74 (m, 1H), 1.68-1.54 (m, 1H), 1.45-1.36 (m, 1H), 0.80-0.65 (m, 1H).

Step-4: Synthesis of 1-(4-(3-(aminomethyl)phenyl) piperidin-1-yl)-3-(3,4-dihydroxyphenyl)propan-1-one (TFA Salt)

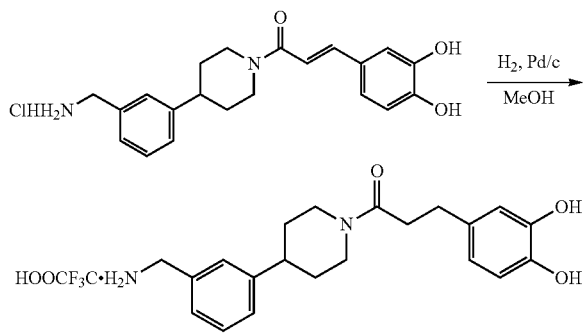

Target-24 dihydro

| Sr. No. | Chemicals | Mol. Wt. | Quantity | mmol | Molar Ratio |
|---|---|---|---|---|---|
| 1 | (E)-1-(4-(3-(aminomethyl) phenyl) piperidin-1-yl)-3-(3,4-dihydroxy phenyl)prop-2-en-1-one hydrochloride | 352.43 | 0.08 g | 0.23 | 1.0 |
| 2 | 10% Pd/C | — | 20 mg | — | — |
| 3 | MeOH | — | 10 mL | — | — |

To a solution of (E)-1-(4-(3-(aminomethyl)phenyl)piperidin-1-yl)-3-(3,4-dihydroxyphenyl)prop-2-en-1-one hydrochloride (0.08 g, 0.23 mmol) in methanol (10 mL), 10% Pd/C (0.02 g) was added and the reaction mixture was stirred under H$_2$ atmosphere (using a 2 Lit. bladder) at room temperature for 1 h. The reaction mixture was filtered through a pad of celite and the filtrate was concentrated under reduced pressure. The crude compound was purified by prep-HPLC to yield TFA salt of 1-(4-(3-(aminomethyl)phenyl)piperidin-1-yl)-3-(3,4-dihydroxyphenyl)propan-1-one as a white solid.

Yield: (0.024 g, 30%)

Mol. Wt.: 354.44

LCMS (m/z): 377 [M+Na]

HPLC Purity: 99.13%

$^1$H NMR (400 MHz, CD$_3$OD): δ 7.35 (t, J=7.6 Hz, 1H), 7.28-7.16 (m, 3H), 6.74 (d, J=8.0 Hz, 1H), 6.68 (s, 1H), 6.62 (d, J=8.0 Hz, 1H) 4.74-4.64 (m, 1H), 4.14 (ABq, J=13.6 Hz, 2H), 3.94-3.84 (m, 1H), 3.10-2.98 (m, 1H), 2.95-2.80 (m, 3H), 2.76-2.55 (m, 1H), 2.48-2.38 (m, 1H), 1.78-1.68 (m, 1H), 1.54-1.44 (m, 1H), 1.43-1.30 (m, 1H), 0.75-0.60 (m, 1H).

Example 21: Synthesis of (4-(3-(aminomethyl)phenyl)piperidin-1-yl)(3-(3,4-dihydroxypyrrolidin-1-yl)phenyl)methanone hydrochloride (Target-25b)

SCHEME 22.

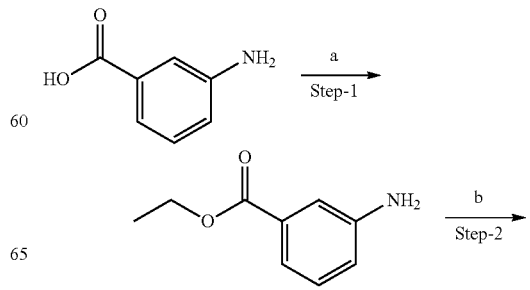

257
-continued

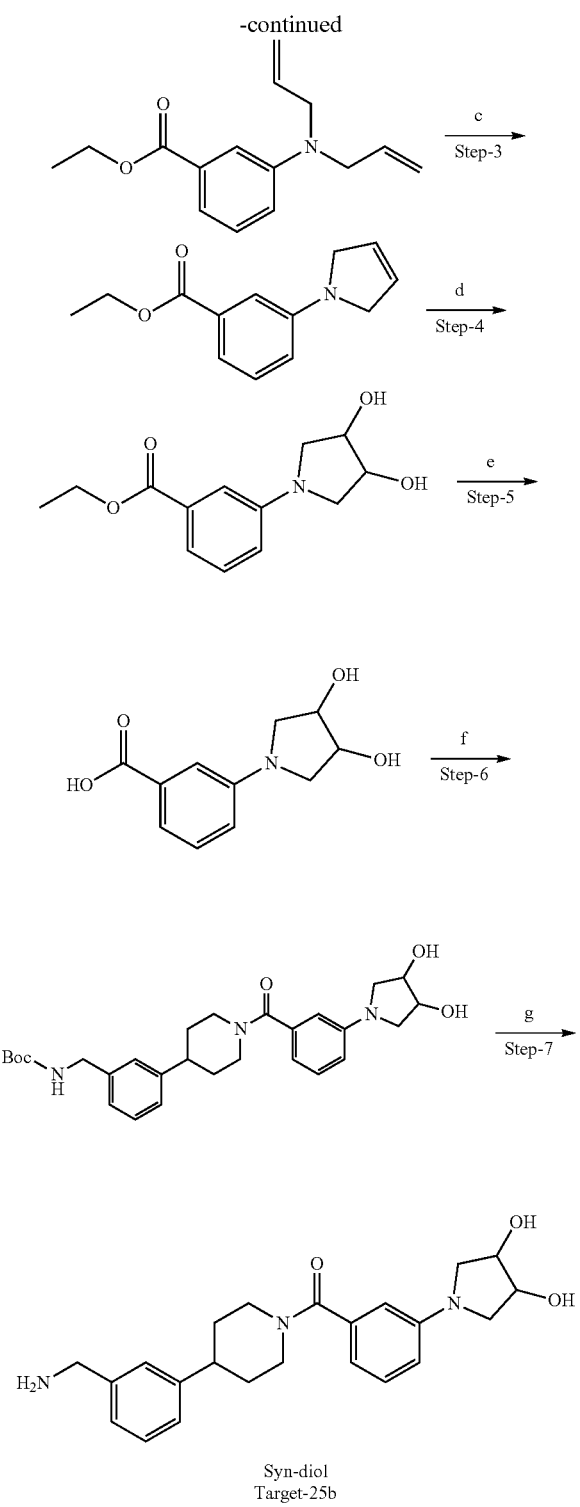

Syn-diol
Target-25b

Reagents and Conditions: a) SOCl₂, EtOH, reflux, 15 h; b) Allyl bromide, Na₂CO₃, ethanol: H₂O, 90° C., 15 h; c) Grubb's II$^{nd}$ generation catalyst, Benzene, 80° C., 15 h; d) OsO₄, NMO,THF rt, 15 h; e) LiOH·H₂O, MeOH:H₂O, rt, 4 h; f) tert-butyl 3-(piperidin-4-yl)benzylcarbamate, EDCI, HOBt, DIEA, DMF, rt, overnight; g) HCl, MeOH, rt, 1 h.

Detailed experimental procedure and analytical data is as follows.

258

Synthesis of ethyl 3-(2,5-dihydro-1H-pyrrol-1-yl) benzoate as per reported synthesis of (4-(3-(Aminomethyl)phenyl)piperidin-1-yl)(3-(pyrrolidin-1-yl) phenyl)methanone hydrochloride (Target-25a)

Step-4: Synthesis of ethyl 3-(3,4-dihydroxypyrrolidin-1-yl)benzoate

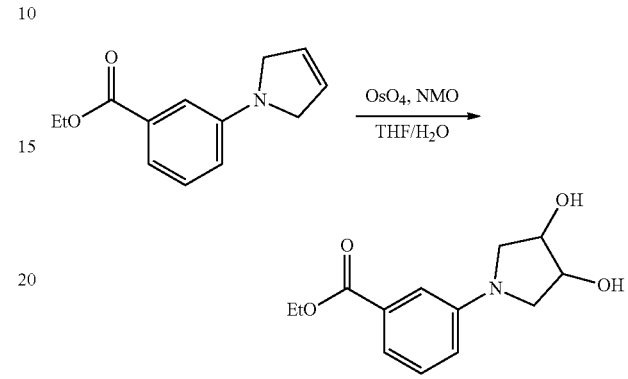

| Sr. No. | Chemical | Mol. Wt. | Quantity | mmol | Molar Ratio |
|---|---|---|---|---|---|
| 1 | ethyl 3-(2,5-dihydro-1H-pyrrol-1-yl)benzoate | 217.26 | 0.16 g | 0.74 | 1.0 |
| 2 | Osmium tetroxide | 254.10 | 0.002 g | 0.007 | 0.01 |
| 3 | N-Methylmorpholine oxide [NMO] (50% aq.) | 117.15 | 0.095 g | 0.81 | 1.1 |
| 4 | THF | — | 2.0 mL | — | — |
| 5 | Water | — | 1.0 mL | — | — |

To a solution of ethyl 3-(2,5-dihydro-1H-pyrrol-1-yl)benzoate (0.16 g, 0.74 mmol) in THF:water (3.0 mL, 2:1), NMO (0.095 g 0.81 mmol) and osmium tetroxide (0.002 g 0.007 mmol) were added. The reaction mixture was stirred at room temperature for 15 h. The reaction mixture was concentrated under vacuo and the residue obtained was partitioned between EtOAc and water. The combined organic layer was washed with brine, dried over Na₂SO₄ and concentrated under reduced pressure to yield the crude compound which was purified by silica gel column chromatography (10-40%, EtOAc in hexane) to yield ethyl 3-(3,4-dihydroxypyrrolidin-1-yl)benzoate as a white solid.

Yield: 0.15 g, (83%)

Mol. Wt.: 251.28

LCMS (m/z): 252 [M+1].

Step-5: Synthesis of 3-(3,4-dihydroxypyrrolidin-1-yl)benzoic acid

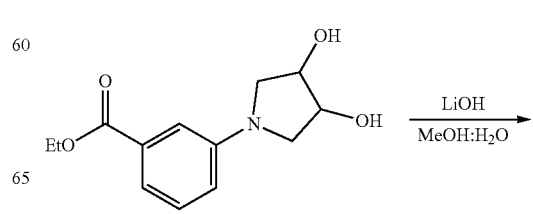

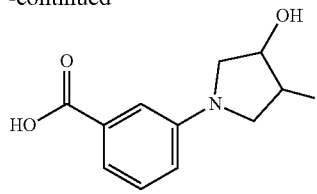

| Sr. No. | Chemical | Mol. Wt. | Quantity | mmol | Molar Ratio |
|---|---|---|---|---|---|
| 1 | Ethyl 3-(3,4-dihydroxypyrrolidin-1-yl)benzoate | 251.28 | 0.15 g | 0.59 | 1.0 |
| 2 | LiOH·H₂O | 41.96 | 0.05 g | 1.19 | 2.0 |
| 3 | MeOH | — | 4 mL | — | — |
| 4 | H₂O | — | 1 mL | — | — |

To a solution of ethyl 3-(3, 4-dihydroxypyrrolidin-1-yl) benzoate (0.15 g, 0.59 mmol) in MeOH: H2O (5.0 mL, 4:1), LiOH (0.05 g, 1.19 mmol) was added and the resulting solution was stirred at room temperature for 4 h. The organic solvent was concentrated under vacuo and the resultant residue was acidified with 10% citric acid solution. The mixture was then extracted with ethyl acetate, the combined organic layer was dried over Na₂SO₄, concentrated under reduced pressure to give a residue which was triturated with diethyl ether to yield the 3-(3,4-dihydroxypyrrolidin-1-yl) benzoic acid as a white solid.

Yield: 0.13 g, (98%)
Mol. Wt.: 223.08
LCMS (m/z): 224.00 [M+1].

Step-6: Synthesis of tert-butyl 3-(1-(3-(3,4-dihydroxypyrrolidin-1-yl)benzoyl)piperidin-4-yl)benzyl-carbamate

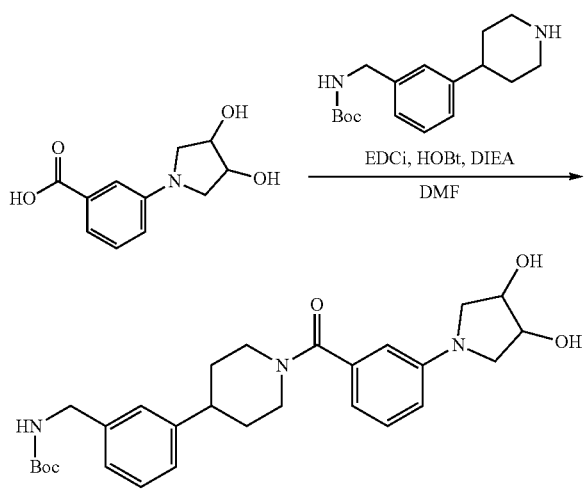

| Sr. No. | Chemical | Mol. Wt. | Quantity | mmol | Molar Ratio |
|---|---|---|---|---|---|
| 1 | 3-(3,4-dihydroxypyrrolidin-1-yl)benzoic acid | 223.08 | 0.13 g | 0.58 | 1.0 |
| 2 | tert-butyl 3-(piperidin-4-yl)benzyl carbamate | 290.40 | 0.17 g | 0.58 | 1.0 |
| 3 | EDCi | 191.70 | 0.17 g | 0.87 | 1.5 |
| 4 | HOBt | 135.12 | 0.12 g | 0.87 | 1.5 |
| 5 | DIEA | 129.25 | 0.2 mL | 1.16 | 2.0 |
| 6 | DMF | — | 4 mL | — | — |

A mixture of tert-butyl 3-(piperidin-4-yl) benzylcarbamate (0.17 g, 0.58 mmol), 3-(3,4-dihydroxypyrrolidin-1-yl) benzoic acid (0.13 g, 0.58 mmol), EDCi (0.17 g, 0.87 mmol), HOBt (0.12 g, 0.87 mmol), DIEA (0.2 mL, 1.16 mmol) in DMF (4 mL) was stirred at room temperature for overnight. The reaction mixture was diluted with EtOAc, washed with brine and dried over Na₂SO₄. The organic layer concentrated under reduced pressure to give the crude compound which was purified by silica gel column chromatography (0-5%, MeOH in CHC₃) to tert-butyl 3-(1-(3-(3,4-dihydroxypyrrolidin-1-yl)benzoyl)piperidin-4-yl)benzylcarbamate as a white solid.

Yield: 0.08 g, (27%)
Mol. Wt: 495.61
LCMS (m/z): 518 [M+Na]

Step-7: Synthesis of (4-(3-(aminomethyl)phenyl) piperidin-1-yl)(3-(3,4-dihydroxypyrrolidin-1-yl) phenyl)methanone hydrochloride

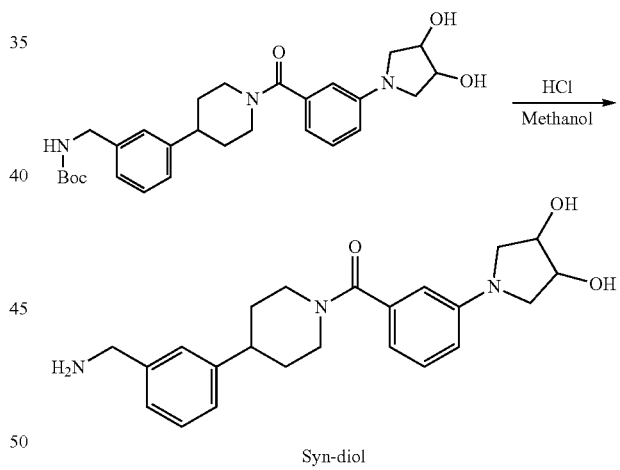

Syn-diol

| Sr. No. | Chemical | Mol. Wt. | Quantity | mmol | Molar Ratio |
|---|---|---|---|---|---|
| 1 | tert-Butyl 3-(1-(3-(3,4-dihydroxy pyrrolidin-1-yl)benzoyl)piperidin-4-yl)benzylcarbamate | 495.61 | 0.08 g | 0.16 | 1.0 |
| 2 | Methanol | — | 2.0 mL | — | — |
| 3 | Conc. HCl | — | 0.1 mL | — | — |

A solution of tert-Butyl 3-(1-(3-(3,4-dihydroxypyrrolidin-1-yl)benzoyl)piperidin-4-yl)benzylcarbamate (0.08 g, 0.16 mmol) in MeOH (2.0 mL) was treated with conc. HCl (0.1 mL) at room temperature for 1 h. The reaction mixture was then evaporated under vacuo and the residue was triturated with ether to yield (4-(3-(aminomethyl)phenyl)piperidin-1-yl)(3-(3,4-dihydroxypyrrolidin-1-yl)phenyl)methanone hydrochloride as a white solid.

Yield: 0.04 g, (63%)
Mol. Wt: 395.49
LCMS (m/z): 418 [M+Na]
HPLC Purity: 98.59%

$^1$H NMR (400 MHz, CD$_3$OD): δ 7.44-7.28 (m, 6H), 6.94-6.82 (m, 3H), 4.80-4.74 (m, 1H), 4.41-4.32 (m, 2H), 4.11 (s, 2H), 3.96-3.84 (m, 1H), 3.66 (dd, J=5.6 10.0 Hz, 2H), 3.39 (dd, J=5.6 10.0 Hz, 2H), 3.29-3.20 (m, 1H), 3.04-2.88 (m, 2H), 2.05-1.92 (m 1H), 1.90-1.64 (m, 3H)

Example 22: Synthesis of (4-(3-(aminomethyl)phenyl)piperidin-1-yl)(3-((3R,4R)-3,4-dihydroxypyrrolidine-1-carbonyl)phenyl)methanone hydrochloride (Target-26 diol trans)

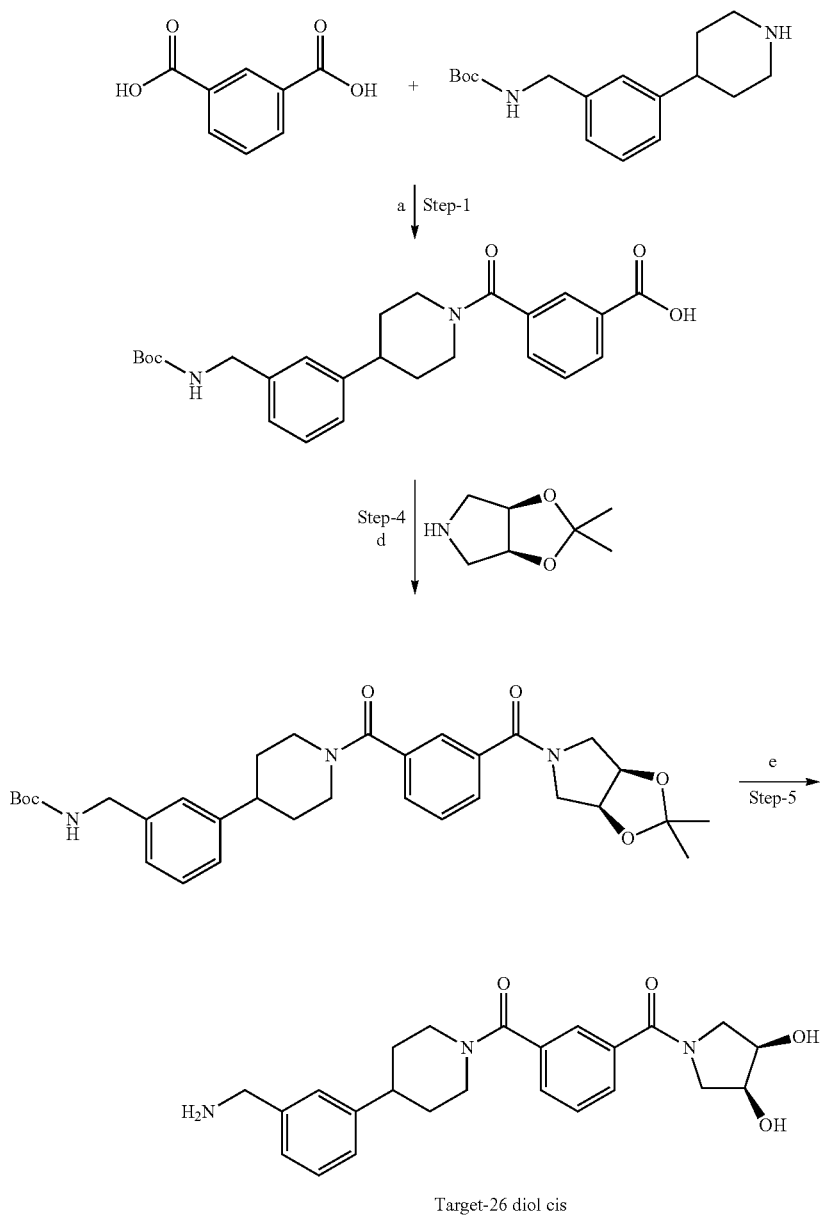

SCHEME 23.

Target-26 diol cis

Reagents and Conditions: a) Isophthalic acid, tert-butyl 3-(piperidin-4-yl)benzylcarbamate, EDCi, HOBt, DIEA, DMF, rt, 15 h; b) PyBOP, DMSO, rt, 15 h; c) 2 N HCl, MeOH, rt, 2 h., d) PyBOP, DMF, rt, 16 h; e) 2 N HCl, MeOH, 0° C.-rt, 4 h.

Detailed experimental procedure and analytical data is as follows.

Step-1: 3-(4-(3-(((tert-butoxycarbonyl)amino)methyl)phenyl)piperidine-1-carbonyl)benzoic acid

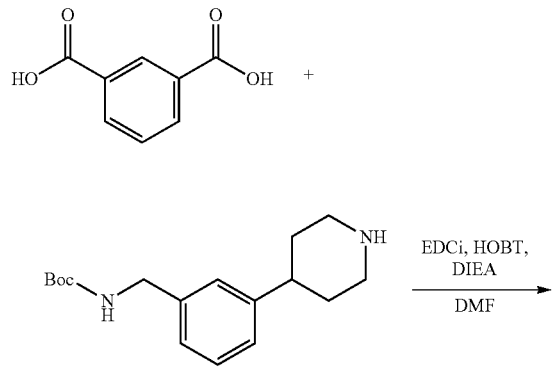

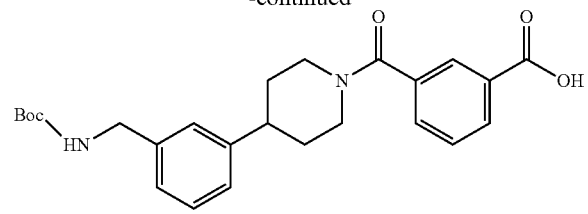

| Sr. No. | Chemical | Mol. Wt. | Quantity | mmol | Molar Ratio |
|---|---|---|---|---|---|
| 1 | Isophthalic acid | 166.13 | 0.3 g | 1.8 | 1.0 |
| 2 | tert-butyl 3-(piperidin-4-yl)benzylcarbamate | 290.4 | 0.63 g | 2.16 | 1.2 |
| 3 | EDCi | 191.7 | 0.52 g | 2.7 | 1.5 |
| 4 | HOBt | 135.1 | 0.36 g | 2.7 | 1.5 |
| 5 | DIEA | 129.25 | 0.62 mL | 3.6 | 2.0 |
| 6 | DMF | — | 5 mL | — | — |

To an ice-cold solution of isophthalic acid (0.3 g, 1.8 mmol) in anhydrous DMF (5 mL), was added HOBt (0.36 g, 2.7 mmol). The reaction mixture was stirred for 10 minutes and EDCI (0.52 g, 2.7 mmol), tert-butyl 3-(piperidin-4-yl)benzylcarbamate (0.63 g, 2.16 mmol) and DIEA (0.62 mL, 3.6 mmol) were added. The resulting solution was allowed to stir at room temperature overnight. The reaction mixture was then diluted with EtOAc and was washed with $H_2O$. The organic layer was dried over $Na_2SO_4$ and evaporated under vacuo to yield the crude product which was purified by silica gel column chromatography (5-10% MeOH in $CHCl_3$) to afford 3-(4-(3-(((tert-butoxycarbonyl)amino)methyl)phenyl)piperidine-1-carbonyl)benzoic acid as a white solid.

Yield: 0.35 g (44%)

Mol. Wt.: 438.52

LCMS (m/z): 461 [M+Na]

Step-4: Synthesis of tert-butyl 3-(1-(3-((3aR,6aS)-2,2-dimethyltetrahydro-3aH-[1,3]dioxolo[4,5-c]pyrrole-5-carbonyl)benzoyl)piperidin-4-yl)benzyl carbamate

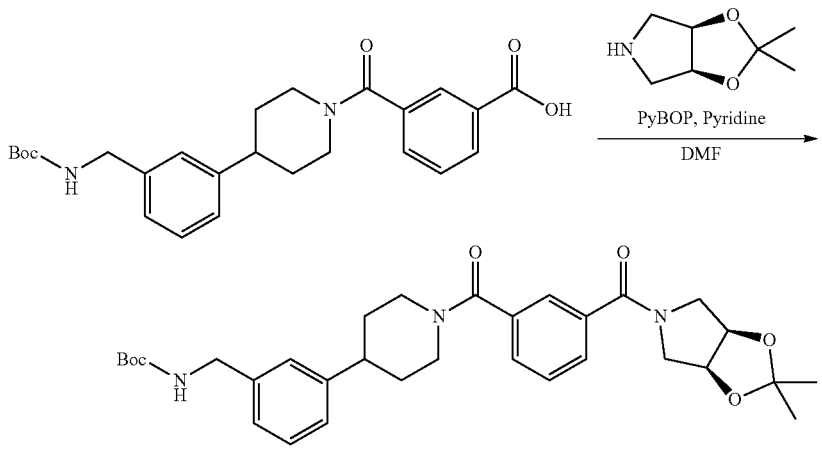

| Sr. No. | Chemical | Mol. Wt.1 | Quantity | Mmol | Molar Ratio |
|---|---|---|---|---|---|
| 1 | 3-(4-(3-(((tert-butoxycarbonyl)amino)methyl)phenyl)piperidine-1-carbonyl)benzoic acid | 438.52 | 0.2 g | 0.46 | 1.0 |
| 2 | (3aR,6aS)-2,2-dimethyltetrahydro-3aH-[1,3]diaxolo[4,5-c]pyrrole | 143.18 | 0.098 g | 0.68 | 1.5 |
| 3 | PyBOP | 520.4 | 0.48 g | 0.92 | 2.0 |
| 4 | Pyridine | — | 1.2 mL | — | — |
| 5 | DMF | — | 5 mL | — | — |

To a stirred solution of 3-(4-(3-(((tert-butoxycarbonyl)amino)methyl) phenyl)piperidine-1-carbonyl)benzoic acid (0.2 g, 0.46 mmol) in DMF (5 mL), pyridine (1.2 ml) and PyBOP (0.48 g, 0.92 mmol) were added. The reaction mixture was cooled to 0° C. and a solution of (3aR,6aS)-2,2-dimethyltetrahydro-3aH-[1,3]dioxolo[4,5-c]pyrrole (0.098 g, 0.68 mmol) in DMF (5 mL) was added. The reaction mixture was allowed to warm to room temperature and stirred for 16 h. After completion, the reaction mixture was quenched with saturated $CuSO_4$ solution and extracted with $Et_2O$. The combined organic layer was dried over $Na_2SO_4$ and evaporated under vacuo. The crude compound was purified by silica gel column chromatography (5-10%

MeOH in CHCl₃) to afford tert-butyl 3-(1-(3-((3aR,6aS)-2,2-dimethyltetrahydro-3aH-[1,3]dioxolo[4,5-c]pyrrole-5-carbonyl)benzoyl)piperidin-4-yl)benzylcarbamate as a white solid.

Yield: 0.1 g (39%)
Mol. Wt: 563.68
LCMS (m/z): 586 [M+Na]

Step-5: Synthesis of (4-(3-(aminomethyl)phenyl)piperidin-1-yl)(3-((3S,4R)-3,4-dihydroxypyrrolidine-1-carbonyl)phenyl)methanone LCMS (m/z): 424.25 [M+1], 446.25 [M+23]
HPLC Purity: 99.58%
¹H NMR (400 MHz, CD₃OD): δ 7.68-7.62 (m, 1H), 7.61-7.54 (m, 3H), 7.44-7.34 (m, 3H), 7.32-7.26 (m, 1H), 4.82-4.74 (m, 1H), 4.31-4.26 (m, 1H), 4.20-4.14 (m, 1H), 4.11 (s, 2H), 3.88-3.80 (m, 1H), 3.77 (dd, J=12.8, 6.0 Hz, 1H), 3.63 (dd, J=10.8, 6.0 Hz, 1H), 3.57 (dd, J=12.8, 4.2 Hz, 1H), 3.50-3.40 (m, 2H), 3.04-2.88 (m, 2H), 2.05-1.94 (m, 1H), 1.90-1.60 (m, 3H).

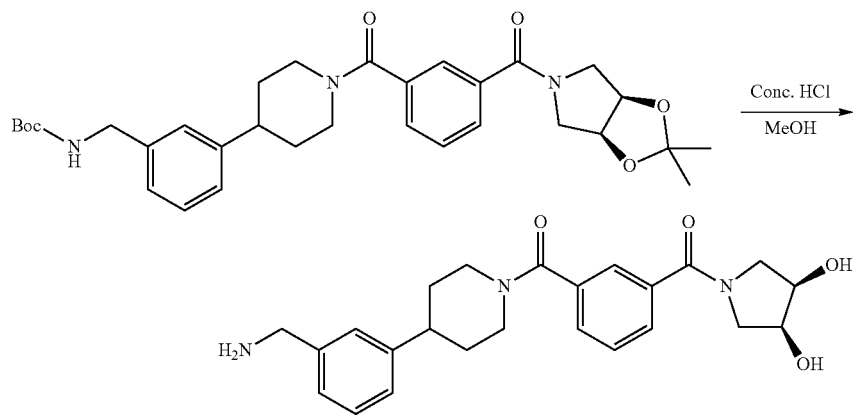

| Sr. No. | Chemical | Mol. Wt. | Quantity | mmol | Molar Ratio |
|---|---|---|---|---|---|
| 1 | tert-butyl 3-(1-(3-((3aR,6aS)-2,2-dimethyltetrahydro-3aH-[1,3]dioxolo[4,5-c]pyrrole-5-carbonyl)benzoyl)piperidin-4-yl)benzyl carbamate | 563.3 | 0.08 g | 0.14 | 1.0 |
| 2 | Conc. HCl | — | 0.1 mL | — | — |
| 3 | MeOH | — | 5 mL | — | — |

To a stirred solution of tert-butyl 3-(1-(3-((3aR,6aS)-2,2-dimethyltetrahydro-3aH-[1,3]dioxolo[4,5-c]pyrrole-5-carbonyl)benzoyl)piperidin-4-yl)benzylcarbamate (0.08 g, 0.14 mmol) in MeOH (5 mL) was added 2 N HCl (0.1 mL) at 0° C. The resulting solution was warmed to room temperature and stirred for further 1 h. The reaction mixture was evaporated under vacuo to yield the crude product which was purified by prep-HPLC to afford the TFA salt of (4-(3-(aminomethyl)phenyl)piperidin-1-yl)(3-((3S,4R)-3,4-dihydroxypyrrolidine-1-carbonyl)phenyl)methanone as white solid.

Yield: 0.02 g (33%)
Mol. Wt.: 423.22

Example 23: Synthesis of (E)-1-(4-(3-(aminomethyl)phenyl)piperidin-1-yl)-3-(3-hydroxy-4-(hydroxymethyl)phenyl)prop-2-en-1-one (acetate salt) (Target-41)

SCHEME 24.

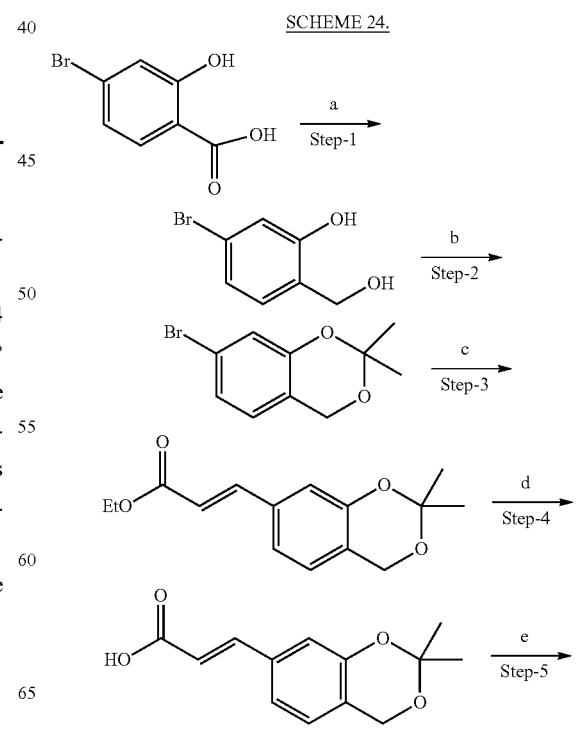

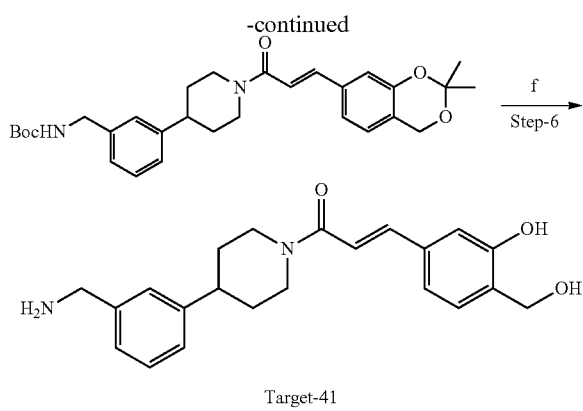

Target-41

Reagents and Conditions: a) BH₃:DMS, THF, 0° C.-70° C., 2 h; b) p-TSA, 2,2-DMP, acetone, rt, 4 h; c) Tri-o-tolyl phosphine, TEA, ethyl acrylate, palladium acetate, acetonitrile, 80° C., 5 h; d) LiOH·H₂O, MeOH:H₂O, rt, 4 h; e) tert-butyl 3-(piperidin-4-yl)benzylcarbamate, EDCI, HOBt, DIEA, DMF, rt, overnight; f) HCl, MeOH, rt, 3 h.

Detailed experimental procedure and analytical data is as follows.

Step-1: Synthesis of 5-bromo-2-(hydroxymethyl) phenol

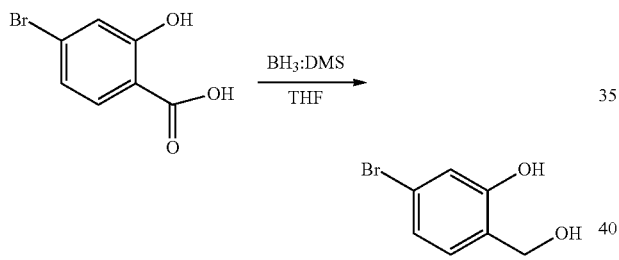

| Sr. No. | Chemical | Mol. Wt. | Quantity | mmol | Molar Ratio |
|---|---|---|---|---|---|
| 1 | 4-bromo-2-hydroxybenzoic acid | 217.02 | 2.0 g | 9.2 | 1.0 |
| 2 | Borane:DMS | 75.97 | 1.8 mL | 18.4 | 2.0 |
| 3 | THF | — | 30 mL | — | — |

To an ice-cooled solution of 4-Bromo-2-hydroxybenzoic acid (2.0 g, 9.2 mmol) in dry THF (30 mL) under N₂ atmosphere, BH₃: DMS (1.8 mL, 18.4 mmol) was added dropwise and stirred for 10 min. Then reaction mixture was warmed to room temperature and heated at 70° C. overnight. The reaction mixture was cooled to room temperature and poured onto ice and extracted with EtOAc. The organic layer was washed with saturated NaHCO₃ solution, dried over Na₂SO₄, concentrated under reduced pressure to yield the crude product which was purified by silica gel column chromatography (0-10%, EtOAc in hexane) to yield 5-bromo-2-(hydroxymethyl) phenol as a white solid.

Yield: (1.5 g, 80%)
Mol. Wt.: 203.03
LCMS (m/z): 203, 205 [MH⁺]

Step-2: Synthesis of 7-bromo-2,2-dimethyl-4H-benzo[d][1,3]dioxine

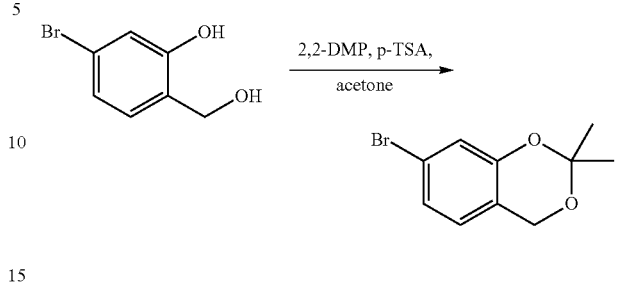

| Sr. No. | Chemical | Mol. Wt. | Quantity | mmol | Molar Ratio |
|---|---|---|---|---|---|
| 1 | 5-bromo-2-(hydroxymethyl)phenol | 203.03 | 1.5 g | 7.4 | 1 |
| 2 | p-TSA | 172.20 | 0.25 g | 1.4 | 0.2 |
| 3 | 2,2-DMP | 104.15 | 1.8 mL | 14.8 | 2.0 |
| 4 | Acetone | — | 15 mL | — | — |

A solution of 5-bromo-2-(hydroxymethyl) phenol (1.5 g, 7.4 mmol), p-TSA (0.25 g 1.4 mmol) and 2,2-DMP (1.8 mL, 14.8 mmol) in acetone (15 mL) was stirred at room temperature for 4 h. Triethyl amine was added to the reaction mixture and stirred for 10 min. The reaction mixture was concentrated under reduced pressure to give the crude product which was purified by silica gel column chromatography (0-5%, EtOAc in hexane) to yield 7-bromo-2,2-dimethyl-4H-benzo[d][1,3]dioxine as a white solid.

Yield: 1.4 g, (78%)
Mol. Wt.: 243.10
LCMS (m/z): 243, 245 [MH⁺]

Step-3: Synthesis of (E)-ethyl 3-(2,2-dimethyl-4H-benzo[d][1,3]dioxin-7-yl)acrylate

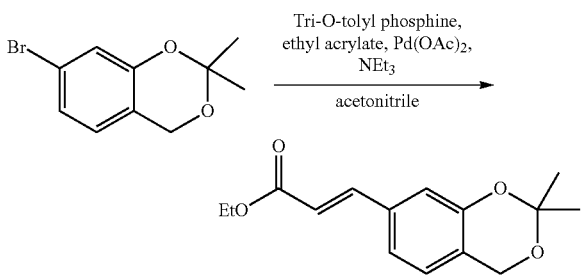

| Sr. No. | Chemical | Mol. Wt. | Amount | mmol | Molar Ratio |
|---|---|---|---|---|---|
| 1 | 7-bromo-2,2-dimethyl-4H-benzo[d][1,3]dioxine | 243.10 | 1.4 g | 5.76 | 1.0 |
| 2 | Ethyl acrylate | 100.11 | 1.22 mL | 11.5 | 2.0 |
| 3 | Triethyl amine | 101.19 | 1.6 mL | 11.5 | 2.0 |
| 4 | Palladium acetate | 224.50 | 0.064 g | 0.28 | 0.05 |
| 5 | Tri-o-tolyl phosphine | 304.37 | 0.17 g | 0.57 | 0.1 |
| 6 | Acetonitrile | — | 15 mL | — | — |

A solution of 7-bromo-2,2-dimethyl-4H-benzo[d][1,3]dioxine (1.4 g, 5.76 mmol), ethyl acrylate (1.22 mL, 11.5 mmol), triethyl amine (1.6 mL, 11.5 mmol), tri-O-tolyl phosphine (0.17 g, 0.57 mmol) in acetonitrile (15 mL) was degassed using argon for 10 min. Palladium acetate (0.064 g, 0.28 mmol) was added and the reaction mixture was again degassed with argon for 10 min. The reaction mixture was refluxed at 80° C. for 5 h, cooled to room temperature, diluted with ethyl acetate and filtered over celite. The filtrate was concentrated under vacuo to give a residue which was purified by silica gel column chromatography (0-20%, EtOAc in hexane) to yield (E)-ethyl 3-(2,2-dimethyl-4H-benzo[d][1,3]dioxin-7-yl)acrylate as a white solid.

Yield: 1.2 g, (80%)
Mol. Wt.: 262.12
LCMS (m/z): 263 [M+1].

Step-4: Synthesis of (E)-3-(2,2-dimethyl-4H-benzo [d][1,3]dioxin-7-yl) acrylic acid

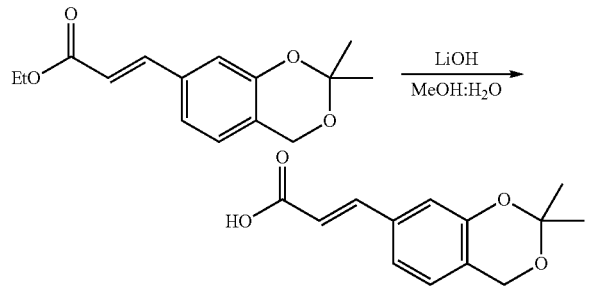

| Sr. No. | Chemical | Mol. Wt. | Amount | mmol | Molar Ratio |
|---|---|---|---|---|---|
| 1 | (E)-ethyl 3-(2,2-dimethyl-4H-benzo[d][1,3]dioxin-7-yl)acrylate | 262.12 | 1.0 g | 3.8 | 1.0 |
| 2 | LiOH·H₂O | 41.96 | 0.32 g | 7.6 | 2.0 |
| 3 | MeOH | — | 8 mL | — | — |
| 4 | H₂O | — | 4 mL | — | — |

To a solution of (E)-ethyl 3-(2,2-dimethyl-4H-benzo[d][1,3]dioxin-7-yl)acrylate (1.0 g, 3.8 mmol) in MeOH:H₂O (12 mL, 2:1), LiOH (0.32 g, 7.6 mmol) was added and the resulting solution was stirred at room temperature for 4 h. The reaction mixture was concentrated under vacuo and the residue was acidified with 10% citric acid solution and extracted with EtOAc. The combined organic layer was dried over Na₂SO₄ and concentrated under reduced pressure to give a residue which was triturated with diethyl ether to yield the (E)-3-(2, 2-dimethyl-4H-benzo[d][1,3]dioxin-7-yl) acrylic acid as a white solid.

Yield: 0.8 g, (89%)
Mol. Wt.: 234.25
LCMS (m/z): 235 [M+1]

Step-5: Synthesis of (E)-tert-butyl 3-(1-(3-(2,2-dimethyl-4H-benzo [d][1,3]dioxin-7-yl)acryloyl)piperidin-4-yl)benzylcarbamate

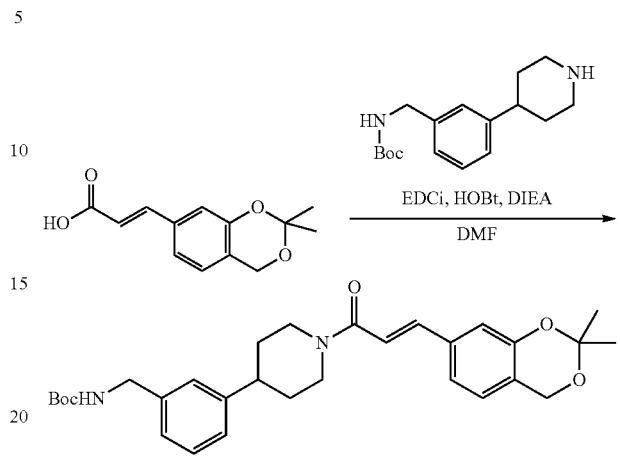

| Sr. No. | Chemical | Mol. Wt. | Amount | mmol | Molar Ratio |
|---|---|---|---|---|---|
| 1 | (E)-3-(2,2-dimethyl-4H-benzo[d][1,3]dioxin-7-yl)acrylic acid | 234.25 | 0.16 g | 0.68 | 1.0 |
| 2 | tert-butyl 3-(piperidin-4-yl)benzylcarbamate | 290.40 | 0.2 g | 0.68 | 1.0 |
| 3 | EDCi | 191.70 | 0.2 g | 1.02 | 1.5 |
| 4 | HOBt | 135.12 | 0.14 g | 1.02 | 1.5 |
| 5 | DIEA | 129.25 | 0.3 mL | 1.7 | 2.5 |
| 6 | DMF | — | 4 mL | — | — |

A mixture of tert-butyl 3-(piperidin-4-yl) benzylcarbamate (0.2 g, 0.68 mmol), (E)-3-(2,2-dimethyl-4H-benzo[d][1,3]dioxin-7-yl)acrylic acid (0.16 g, 0.68 mmol), EDCi (0.2 g, 1.02 mmol), HOBt (0.14 g, 1.02 mmol), DIEA (0.3 mL, 1.7 mmol) in DMF (4 mL) was stirred at room temperature for overnight. The reaction mixture was diluted with EtOAc, washed with brine, dried over Na₂SO₄ and concentrated under reduced pressure. The crude compound was purified by silica gel column chromatography (0-5%, MeOH in CHCl₃) to obtain (E)-tert-butyl 3-(1-(3-(2,2-dimethyl-4H-benzo[d][1,3]dioxin-7-yl)acryloyl)piperidin-4-yl)benzylcarbamate as a white solid.

Yield: 0.3 g, (88%)
Mol. Wt.: 506.63
LCMS (m/z): 529 [M+23]

Step-6: Synthesis of (E)-1-(4-(3-(aminomethyl)phenyl)piperidin-1-yl)-3-(3-hydroxy-4-(hydroxymethyl) phenyl)prop-2-en-1-one (acetate salt)

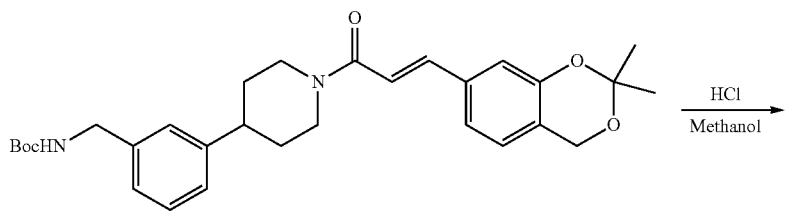

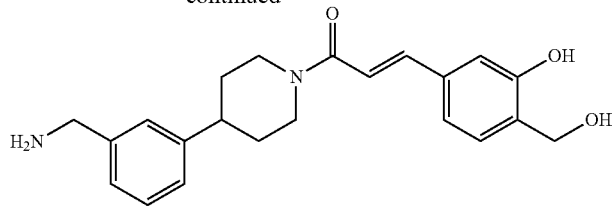

| Sr. No. | Chemical | Mol. Wt. | Amount | mmol | Molar Ratio |
|---|---|---|---|---|---|
| 1 | (E)-tert-Butyl 3-(1-(3-(2,2-dimethyl-4H-benzo[d][1,3] dioxin-7-yl) acryloyl) piperidin-4-yl) benzylcarbamate | 506.63 | 0.2 g | 0.39 | 1.0 |
| 2 | Methanol | — | 2 mL | — | — |
| 3 | Conc. HCl | — | 0.2 mL | — | — |

A solution of (E)-tert-butyl 3-(1-(3-(2,2-dimethyl-4H-benzo[d][1,3]dioxin-7-yl)acryloyl)piperidin-4-yl)benzylcarbamate (0.2 g, 0.39 mmol) in MeOH (2 mL) was treated with conc. HCl (0.2 mL) at room temperature for 3 h. The reaction mixture was evaporated under vacuo and the residue was purified by prep-HPLC to yield the acetate salt of (E)-1-(4-(3-(aminomethyl)phenyl)piperidin-1-yl)-3-(3-hydroxy-4-(hydroxymethyl)phenyl)prop-2-en-1-one as a white solid.

Yield: 0.03 g, (20%)
Mol. Wt.: 366.45
LCMS (m/z): 389 [M+23]
HPLC Purity: 99.77%
$^1$H NMR (400 MHz, CD$_3$OD): δ 7.50 (d, J=15.6 Hz, 1H) 7.40-7.26 (m, 5H), 7.13 (s, 1H), 7.09 (d, J=15.6 Hz, 1H), 6.99 (s, 1H), 4.84-4.72 (m, 1H), 4.66 (s, 2H), 4.45-4.34 (m, 1H), 4.06 (s, 2H), 3.37-3.25 (m, 1H), 2.97-2.80 (m, 2H), 2.02-1.92 (m, 2H), 1.78-1.62 (m, 2H).

Example 24: (4-(3-(aminomethyl)phenyl)piperidin-1-yl)(3-(3,4-dihydroxy-3,4-dimethylpyrrolidin-1-yl) phenyl)methanone hydrochloride (Target-67)

SCHEME 25

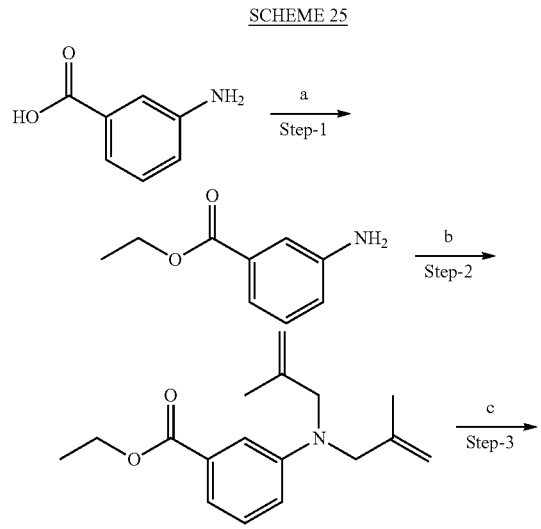

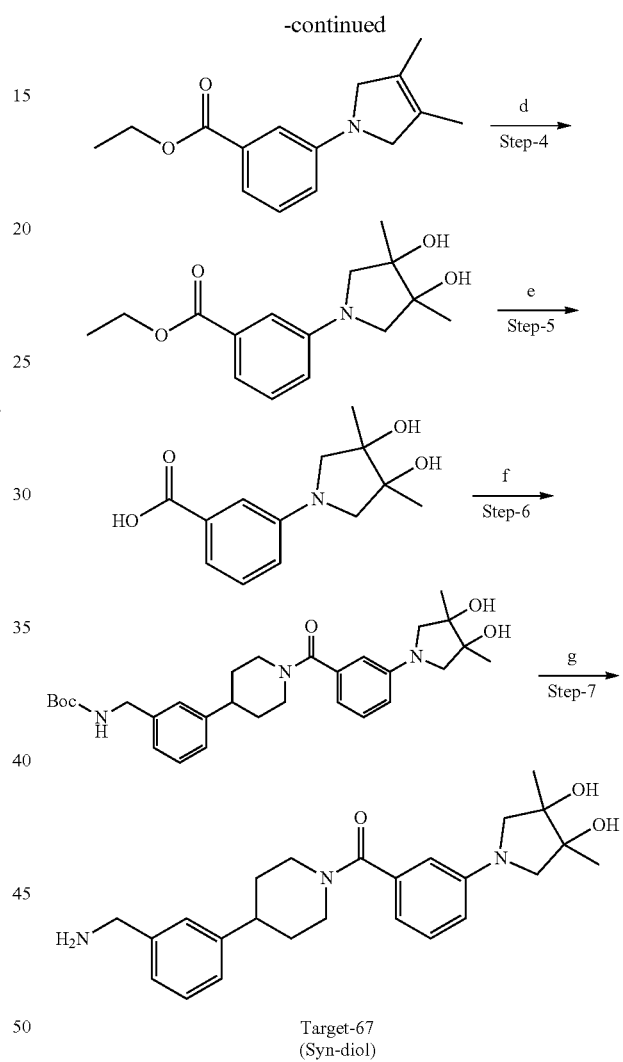

Target-67
(Syn-diol)

Reagents and Conditions: a) SOCl$_2$, EtOH, 80° C., 15 h; b) 3-Bromo-2-methylprop-1-ene, Na$_2$CO$_3$, Ethanol:H$_2$O, 90° C., 15 h; c) Grubb's II$^{nd}$ generation catalyst, Benzene, 80° C., 15 h; d) OsO$_4$, NMO, THF/H$_2$O, rt, 15 h; e) LiOH·H$_2$O, MeOH:H$_2$O, rt, 1 h; f) tert-butyl 3-(piperidin-4-yl)benzylcarbamate, EDCI, HOBt, DIEA, DMF, rt, overnight; g) HCl, MeOH, rt, 2 h.

Detailed experimental procedure and analytical data is as follows.

Ethyl 3-aminobenzoate was synthesized as per reported synthesis of (4-(3-(Aminomethyl)phenyl)piperidin-1-yl)(3-(pyrrolidin-1-yl) phenyl)methanone hydrochloride (Target-25a)

Step-2: Synthesis of ethyl 3-(bis(2-methylallyl)amino)benzoate

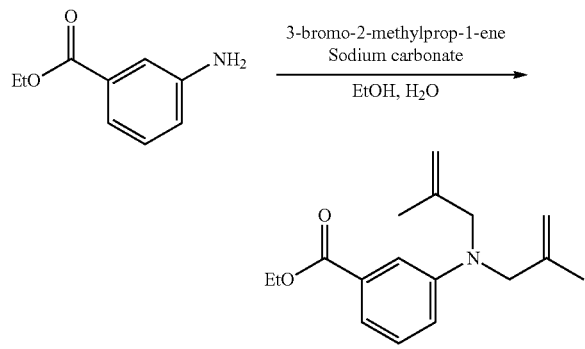

| Sr. No. | Chemical | Mol. Wt. | Quantity | Mmol | Molar Ratio |
|---|---|---|---|---|---|
| 1 | Ethyl 3-aminobenzoate | 165.19 | 3.0 g | 18.16 | 1 |
| 2 | 3-Bromo-2-methylprop-1-ene | 135.00 | 4.57 mL | 45.40 | 2.5 |
| 3 | Sodium carbonate | 105.96 | 2.31 g | 21.79 | 1.2 |
| 4 | Ethanol:water (4:1) | — | 120 mL | — | — |

A solution of ethyl 3-aminobenzoate (3.0 g, 18.16 mmol), 3-bromo-2-methylprop-1-ene (4.57 mL 45.40 mmol) and sodium carbonate (2.30 g, 21.79 mmol) in ethanol:water (120 mL, 4:1) was heated in a sealed tube at 90° C. for 15 h. The reaction mixture was cooled to room temperature and concentrated under vacuo. The residue was diluted with EtOAc and washed with $H_2O$. The combined organic layer was washed with brine, dried over $Na_2SO_4$ and concentrated under reduced pressure to give a crude compound which was purified by silica gel column chromatography (0-5%, EtOAc in hexane) to yield ethyl 3-(bis(2-methylallyl)amino)benzoate as a white solid.

Yield: 4.5 g, (91%)
Mol. Wt.: 273.37
LCMS (m/z): 274 [M+1].

Step-3: Synthesis of ethyl 3-(3,4-dimethyl-2,5-dihydro-1H-pyrrol-1-yl) benzoate

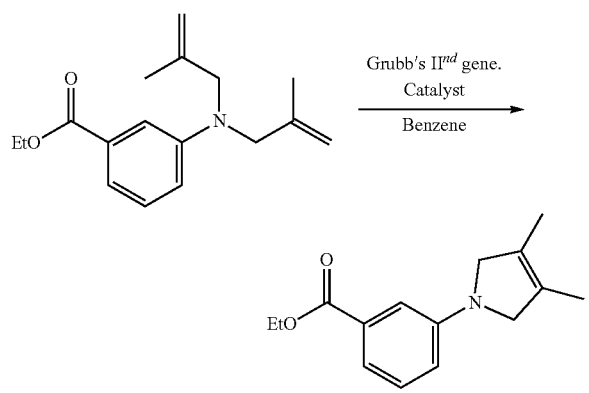

| Sr. No. | Chemical | Mol. Wt. | Quantity | mmol | Molar Ratio |
|---|---|---|---|---|---|
| 1 | Ethyl 3-(bis(2-methylallyl)amino)benzoate | 273.37 | 1.0 g | 3.66 | 1.0 |
| 2 | Grubb's $II^{nd}$ generation catalyst | 848.97 | 3.1 mg | 0.0036 | 0.001 |
| 3 | Benzene | — | 300 mL | — | — |

To a solution of ethyl 3-(bis(2-methylallyl)amino)benzoate (1.0 g, 3.66 mmol) in benzene (300 mL) under Argon atmosphere, Grubb's $II^{nd}$ generation catalyst (3.1 mg, 0.0036 mmol) was added. The reaction mixture was refluxed at 80° C. for 15 h. The reaction mixture was cooled to room temperature and concentrated under vacuo to give a crude product which was purified by silica gel column chromatography (0-5%, EtOAc in hexane) to yield ethyl 3-(3,4-dimethyl-2,5-dihydro-1H-pyrrol-1-yl)benzoate as a white solid.

Yield: 0.29 g, (33%)
Mol. Wt.: 245.32
LCMS (m/z): 246 [M+1].

Step-4: Synthesis of ethyl 3-(3,4-dihydroxy-3,4-dimethylpyrrolidin-1-yl) benzoate

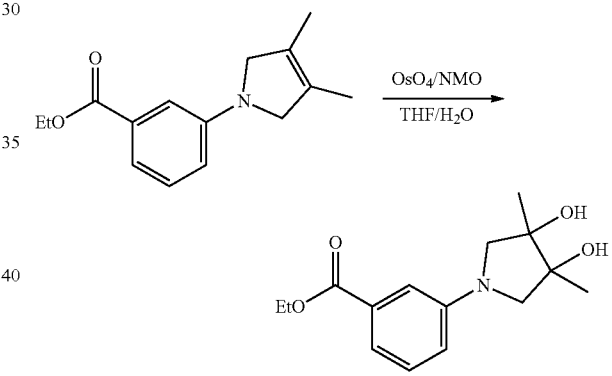

| Sr. No. | Chemical | Mol. Wt. | Quantity | mmol | Molar Ratio |
|---|---|---|---|---|---|
| 1 | Ethyl 3-(3,4-dimethyl-2,5-dihydro-1H-pyrrol-1-yl)benzoate | 245.32 | 0.29 g | 1.2 | 1.0 |
| 2 | OsO4 | 254.1 | 0.003 g | 0.012 | 0.01 |
| 3 | N-Methylmorpholine oxide [NMO] | 117.15 | 0.15 g | 1.32 | 1.1 |
| 4 | THF | — | 4 mL | — | — |
| 5 | $H_2O$ | — | 2 mL | — | — |

To a solution of ethyl 3-(3,4-dimethyl-2,5-dihydro-1H-pyrrol-1-yl)benzoate (0.29 g, 1.2 mmol) in THF:water (6.0 mL, 2:1), NMO (0.15 g 1.32 mmol) and osmium tetroxide (0.003 g, 0.012 mmol) were added and reaction mixture was stirred at room temperature for 15 h. The reaction mixture was concentrated under vacuo and the residue obtained was partitioned between EtOAc and water. The combined organic layer was washed with brine, dried over $Na_2SO_4$ and concentrated under reduced pressure to yield the crude compound which was purified by silica gel column chromatography (0-40%, EtOAc in hexane) to afford ethyl 3-(3,4-dihydroxy-3,4-dimethylpyrrolidin-1-yl) benzoate as a white solid.
Yield: 0.15 g, (45%)
Mol. Wt.: 279.33
LCMS (m/z): 280 [M+1].

Step-5: Synthesis of 3-(3,4-dihydroxy-3,4-dimethylpyrrolidin-1-yl)benzoic acid

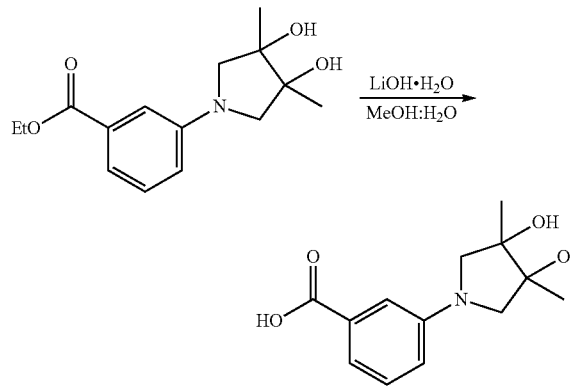

| Sr. No. | Chemical | Mol. Wt. | Quantity | mmol | Molar Ratio |
|---|---|---|---|---|---|
| 1 | ethyl 3-(3,4-dihydroxy-3, 4-dimethyl-pyrrolidin-1-yl) benzoate | 279.33 | 0.15 g | 0.53 | 1.0 |
| 2 | LiOH·H₂O | 41.96 | 0.045 g | 1.07 | 2.0 |
| 3 | MeOH:H₂O | — | 3 mL | — | — |

To a solution of ethyl 3-(3,4-dihydroxy-3,4-dimethylpyrrolidin-1-yl)benzoate (0.15 g, 0.53 mmol) in MeOH:H₂O (3 mL, 2:1), LiOH (0.045 g, 1.07 mmol) was added and the resulting solution was stirred at room temperature for 1 h. The reaction mixture was concentrated under vacuo and the residue was acidified with 10% citric acid solution and extracted with EtOAc. The combined organic layer was dried over Na₂SO₄ and concentrated under reduced pressure to give a crude compound which was triturated with diethyl ether to yield the 3-(3,4-dihydroxy-3,4-dimethylpyrrolidin-1-yl)benzoic acid as a white solid.
Yield: 0.13 g, (97%)
Mol. Wt.: 251.28
LCMS (m/z): 252 [M+1].

Step-6: Synthesis of tert-butyl 3-(1-(3-(3,4-dihydroxy-3,4-dimethyl pyrrolidin-1-yl)benzoyl)piperidin-4-yl)benzylcarbamate

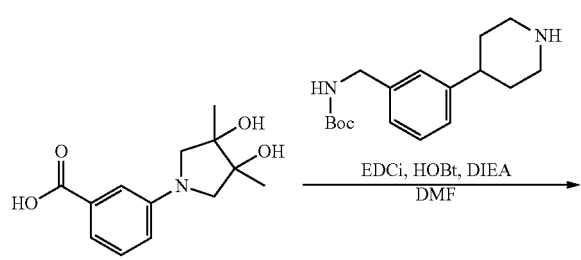

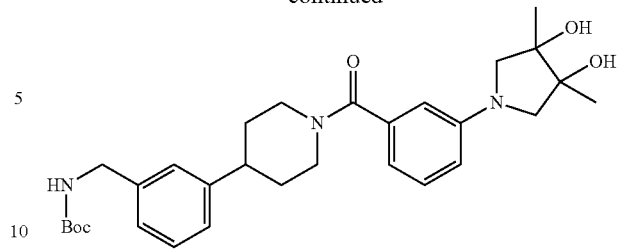

| Sr. No. | Chemical | Mol. Wt. | Quantity | mmol | Molar Ratio |
|---|---|---|---|---|---|
| 1 | 3-(3,4-dihydroxy-3,4-dimethylpyrrolidin-1-yl)benzoic acid | 251.28 | 0.13 g | 0.52 | 1.0 |
| 2 | tert-butyl 3-(piperidin-4-yl)benzylcarbamate | 290.40 | 0.15 g | 0.52 | 1.0 |
| 3 | EDCi | 191.70 | 0.15 g | 0.77 | 1.5 |
| 4 | HOBt | 135.12 | 0.1 g | 0.77 | 1.5 |
| 5 | DIEA | 129.25 | 0.22 mL | 1.2 | 2.0 |
| 6 | DMF | — | 4 mL | — | — |

A mixture of tert-butyl 3-(piperidin-4-yl) benzylcarbamate (0.15 g, 0.52 mmol), 3-(3,4-dihydroxy-3,4-dimethylpyrrolidin-1-yl)benzoic acid (0.13 g, 0.52 mmol), EDCi (0.15 g, 0.77 mmol), HOBt (0.1 g, 0.77 mmol), DIEA (0.22 mL, 1.2 mmol) in DMF (4 mL) was stirred at room temperature overnight. The reaction mixture was diluted with EtOAc, washed with brine and dried over Na₂SO₄. The EtOAc layer was concentrated under reduced pressure to afford a residue which was purified by silica gel column chromatography (0-5%, MeOH in CHC₃) to yield tert-butyl 3-(1-(3-(3,4-dihydroxy-3,4-dimethylpyrrolidin-1-yl)benzoyl)piperidin-4-yl)benzylcarbamate as a white solid.
Yield: 0.25 g, (92%)
Mol. Wt: 523.66
LCMS (m/z): 546 [M+Na]

Step-7: Synthesis of (4-(3-(aminomethyl)phenyl) piperidin-1-yl)(3-(3,4-dihydroxy-3,4-dimethylpyrrolidin-1-yl)phenyl)methanone hydrochloride

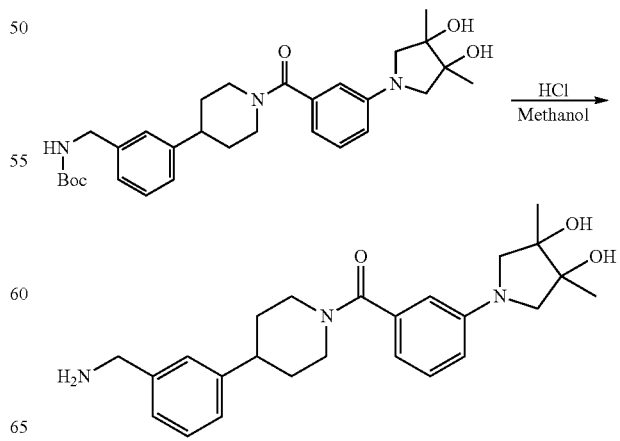

| Sr. No. | Chemical | Mol. Wt. | Quantity | mmol | Molar Ratio |
|---|---|---|---|---|---|
| 1 | tert-butyl 3-(1-(3-(3,4-dihydroxy-3,4-dimethyl pyrrolidin-1-yl) benzoyl) piperidin-4-yl) benzyl carbamate | 523.66 | 0.15 g | 0.29 | 1.0 |
| 2 | Methanol | — | 3 mL | — | — |
| 3 | Conc. HCl | — | 0.1 mL | — | — |

A solution of tert-butyl 3-(1-(3-(3,4-dihydroxy-3,4-dimethylpyrrolidin-1-yl)benzoyl)piperidin-4-yl)benzylcarbamate (0.15 g, 0.29 mmol) in MeOH (3 mL) was treated with conc. HCl (0.1 mL) at room temperature for 2 h. The reaction mixture was evaporated in vacuo and the resultant residue was triturated with ether to yield (4-(3-(aminomethyl) phenyl)piperidin-1-yl)(3-(3,4-dihydroxy-3,4-dimethylpyrrolidin-1-yl)phenyl)methanone hydrochloride as a white solid.

Yield: 0.06 g, (50%)
Mol. Wt: 423.55
LCMS (m/z): 446 [M+Na]
HPLC Purity: 97.27%
$^1$H NMR (400 MHz, CD$_3$OD): δ 7.44-7.22 (m, 5H), 6.70-6.60 (m, 2H), 6.52 (s, 1H), 4.11 (s, 2H), 4.00-3.85 (m, 1H), 3.38 (ABq, J=9.6 Hz, 4H), 3.25-3.15 (m, 1H), 3.02-2.86 (m, 2H), 2.05-1.92 (m, 1H), 1.88-1.58 (m, 3H), 1.30 (s, 6H).

Example 25: Synthesis of (E)-1-(4-(3-(aminomethyl)phenyl)piperidin-1-yl)-3-(3-hydroxy-4-(2-hydroxypropan-2-yl)phenyl)prop-2-en-1-one (Target-41 gemdimethyl) and (E)-1-(4-(3-(aminomethyl) phenyl)piperidin-1-yl)-3-(4-cyclopropyl-3-hydroxyphenyl)prop-2-en-1-one (Target-41 cyclopropyl)

SCHEME 26.

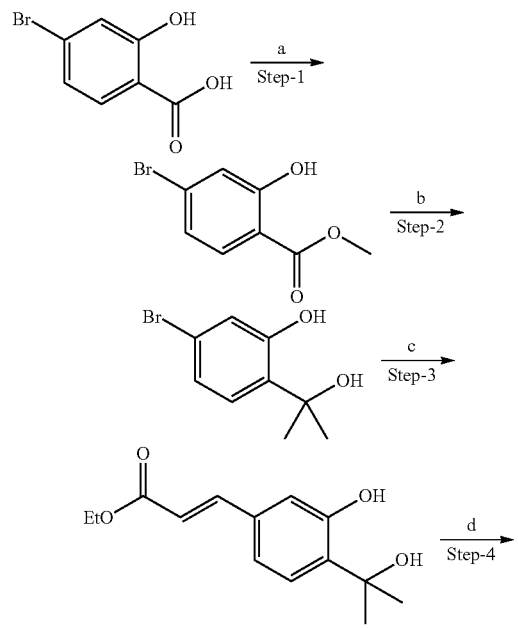

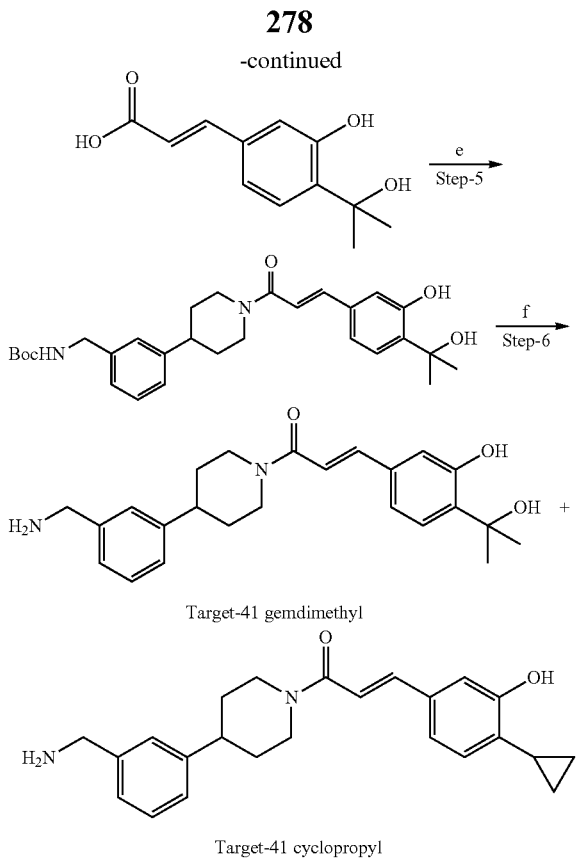

Target-41 gemdimethyl

Target-41 cyclopropyl

Reagents and Conditions: a) SOCl$_2$, Methanol, 60° C., 5 h; b) MeLi, THF −78° C.-t, 5 h; c) Tri-o-tolyl phosphine, TEA, ethyl acrylate, palladium acetate, acetonitrile, 80° C., 5 h; d) LiOH·H$_2$O, MeOH:H$_2$O, rt, 4 h; e) tert-Butyl 3-(piperidin-4-yl)benzylcarbamate, EDCi, HOBt, DIEA, DMF, rt, overnight; f) HCl, MeOH, rt, 3 h.

Step-1: Synthesis of methyl 4-bromo-2-hydroxybenzoate

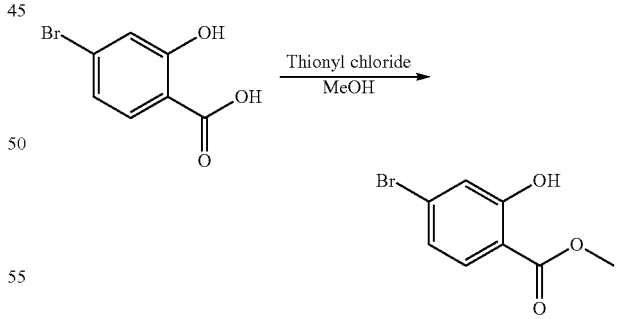

| Sr. No. | Chemical | Mol. Wt. | Amount | mmol | Molar Ratio |
|---|---|---|---|---|---|
| 1 | 4-Bromo-2-hydroxybenzoic acid | 217.02 | 2.0 g | 9.21 | 1.0 |
| 2 | Thionyl chloride | 118.97 | 1.3 mL | 18.43 | 2.0 |
| 3 | MeOH | — | 20 mL | — | — |

To an ice-cooled solution of 4-bromo-2-hydroxybenzoic acid (2.0 g, 9.21 mmol) in methanol (20 mL), thionyl chloride (1.3 mL, 18.43 mmol) was added dropwise. The reaction mixture was allowed to warm to room temperature and refluxed at 60° C. for 5 h. The reaction mixture was concentrated under vacuo, diluted with EtOAc, washed with saturated NaHCO₃ solution followed by brine. The organic layer was dried over Na₂SO₄ and concentrated under reduced pressure to give the crude product which was purified by silica gel column chromatography (0-10%, EtOAc in hexane) to yield methyl 4-bromo-2-hydroxybenzoate.

White solid; Yield: 1.5 g, (70%)

Mol. Wt.: 231.04

LCMS (m/z): 231, 233 [M+1].

Step-2: Synthesis of 5-bromo-2-(2-hydroxypropan-2-yl) phenol

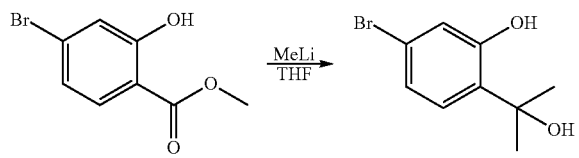

| Sr. No. | Chemical | Mol. Wt. | Amount | mmol | Molar Ratio |
|---|---|---|---|---|---|
| 1 | Methyl 4-bromo-2-hydroxybenzoate | 231.04 | 1.5 g | 6.5 | 1.0 |
| 2 | MeLi (3.0M in DME) | — | 13.0 mL | 38.9 | 2.0 |
| 3 | THF | — | 50 mL | — | — |

To a solution of methyl 4-bromo-2-hydroxybenzoate (1.5 g, 6.5 mmol) in THF (50 mL) at −78° C. under N₂ atmosphere, methyl lithium (13.0 mL, 38.9 mmol) was added. The reaction mixture was stirred for 30 min. before it was warmed to room temperature and stirred for 2 h. The reaction mixture was quenched with saturated NH₄Cl solution and extracted with EtOAc. The combined organic layer was dried over Na₂SO₄ and concentrated under reduced pressure to afford crude product which was purified by silica gel column chromatography (0-5%, EtOAc in hexane) to yield 5-bromo-2-(2-hydroxypropan-2-yl)phenol.

White solid; Yield: 1.2 g, (80%)

Mol. Wt.: 231.09

¹H NMR (400 MHz, CDCl₃): δ 9.06 (s, 1H), 7.03 (s, 1H), 6.93 (ABq, J=8.4 Hz, 2H), 2.33 (s, 1H), 1.65 (s, 6H).

Step-3: Synthesis of ((E)-ethyl 3-(3-hydroxy-4-(2-hydroxypropan-2-yl) phenyl) acrylate

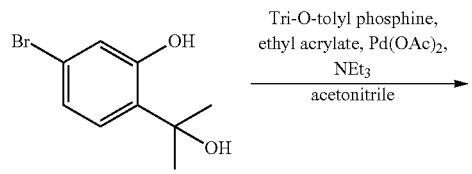

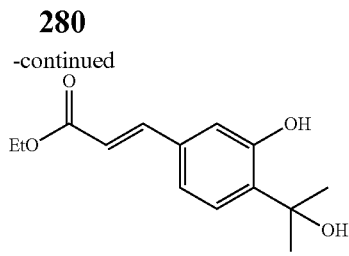

| Sr. No. | Chemical | Mol. Wt. | Quantity | mmol | Molar Ratio |
|---|---|---|---|---|---|
| 1 | 5-Bromo-2-(2-hydroxypropan-2-yl)phenol | 231.09 | 1.2 g | 5.2 | 1.0 |
| 2 | Ethyl Acrylate | 100.11 | 1.13 mL | 10.4 | 2.0 |
| 3 | Triethyl amine | 101.19 | 1.5 mL | 10.4 | 2.0 |
| 4 | Palladium acetate | 224.50 | 0.12 g | 0.52 | 0.1 |
| 5 | Tri-o-tolyl phosphine | 304.37 | 0.16 g | 0.52 | 0.1 |
| 6 | Acetonitrile | — | 50 mL | — | — |

A solution of 5-bromo-2-(2-hydroxypropan-2-yl) phenol (1.2 g, 5.2 mmol), ethyl acrylate (1.13 mL, 10.4 mmol), triethyl amine (1.5 mL, 10.4 mmol), tri-O-tolyl phosphine (0.16 g, 0.52 mmol) in acetonitrile (50 mL) was degassed using argon for 10 min. Palladium acetate (0.12 g, 0.52 mmol) was added and the reaction mixture was again degassed using argon for 10 min. The reaction mixture was then refluxed at 80° C. for 4 h. The reaction mixture was cooled to room temperature and diluted with ethyl acetate and the slurry was then filtered over celite. The filtrate was concentrated under vacuo to yield the crude product which was purified by silica gel column chromatography (0-5%, EtOAc in hexane) to yield (E)-ethyl 3-(3-hydroxy-4-(2-hydroxypropan-2-yl) phenyl) acrylate.

White solid; Yield: 1.0 g, (77%)

Mol. Wt.: 250.29

LCMS (m/z): 251 [M+1].

Step-4: Synthesis of (E)-3-(3-hydroxy-4-(2-hydroxypropan-2-yl) phenyl) acrylic acid

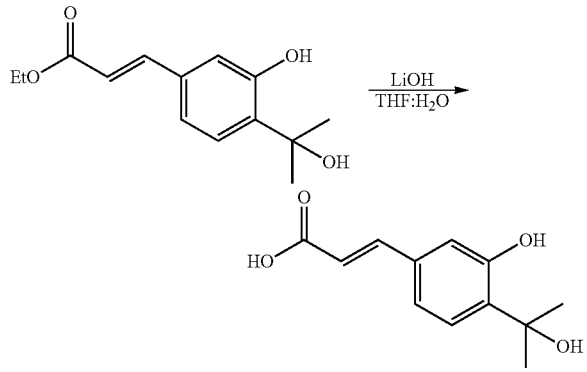

| Sr. No. | Chemical | Mol. Wt. | Quantity | mmol | Molar Ratio |
|---|---|---|---|---|---|
| 1 | (E)-ethyl 3-(3-hydroxy-4-(2-hydroxypropan-2-yl) phenyl) acrylate | 250.29 | 0.3 g | 1.19 | 1.0 |

| Sr. No. | Chemical | Mol. Wt. | Quantity | mmol | Molar Ratio |
|---|---|---|---|---|---|
| 2 | LiOH·H₂O | 41.96 | 0.2 g | 4.79 | 4.0 |
| 3 | MeOH | — | 4 mL | — | — |
| 4 | H₂O | — | 1 mL | — | — |

To a solution of (E)-ethyl 3-(3-hydroxy-4-(2-hydroxypropan-2-yl) phenyl) acrylate (0.3 g, 1.19 mmol) in THF:H₂O (5 mL, 4:1), LiOH (0.2 g, 4.79 mmol) was added and the resulting solution was stirred at room temperature for 4 h. The organic solvent was concentrated under reduced pressure and the residue was acidified with 10% citric acid solution. The mixture was extracted with EtOAc and dried over Na₂SO₄ and concentrated under reduced pressure to yield a residue which was triturated with diethyl ether to afford the (E)-3-(3-hydroxy-4-(2-hydroxypropan-2-yl) phenyl) acrylic acid.

White solid; Yield: 0.2 g, (76%)
Mol. Wt: 222.24
$^1$H NMR (400 MHz, CD₃OD): δ 7.56 (d, J=16.0 Hz, 1H), 7.26 (d, J=8.0 Hz, 1H), 7.02 (d, J=8.0 Hz, 1H), 6.97 (s, 1H), 6.38 (d, J=16.0 Hz, 1H), 1.59 (s, 6H).

Step-5: Synthesis of (E)-tert-butyl 3-(1-(3-(3-hydroxy-4-(2-hydroxypropan-2-yl) phenyl) acryloyl) piperidin-4-yl) benzylcarbamate

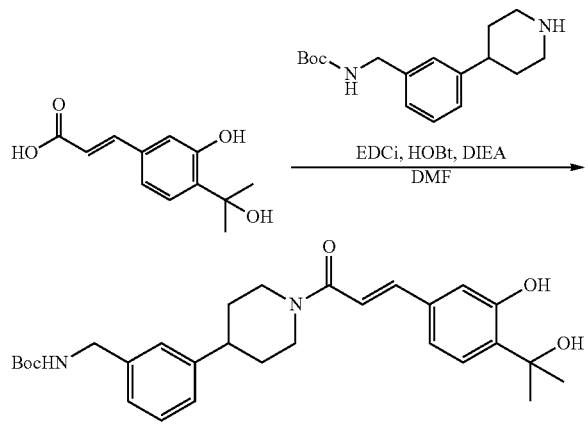

| Sr. No. | Chemical | Mol. Wt. | Quantity | mmol | Molar Ratio |
|---|---|---|---|---|---|
| 1 | (E)-3-(3-hydroxy-4-(2-hydroxypropan-2-yl)phenyl) acrylic acid | 222.24 | 0.15 g | 0.67 | 1.0 |
| 2 | tert-butyl 3-(piperidin-4-yl) benzyl carbamate | 290.40 | 0.19 g | 0.67 | 1.0 |
| 3 | EDCI | 191.70 | 0.19 g | 1.01 | 1.5 |
| 4 | HOBt | 135.12 | 0.13 g | 1.01 | 1.5 |
| 5 | DIEA | 129.25 | 0.3 mL | 1.67 | 2.5 |
| 6 | DMF | — | 4 mL | — | — |

A mixture of tert-butyl 3-(piperidin-4-yl) benzylcarbamate (0.19 g, 0.67 mmol), (E)-3-(3-hydroxy-4-(2-hydroxypropan-2-yl) phenyl) acrylic acid (0.15 g, 0.67 mmol), EDCi (0.19 g, 1.01 mmol), HOBt (0.13 g, 1.01 mmol), DIEA (0.3 mL, 1.67 mmol) in DMF (4 mL) was stirred at room temperature overnight. The reaction mixture was extracted with EtOAc and washed with brine. The combined organic layer was dried over Na₂SO₄ and concentrated under reduced pressure to afford the crude compound which was purified by silica gel column chromatography (0.5%, MeOH in CHCl₃) to yield (E)-tert-butyl 3-(1-(3-(3-hydroxy-4-(2-hydroxypropan-2-yl) phenyl) acryloyl) piperidin-4-yl) benzylcarbamate.

White solid; Yield: 0.25 g, (33%)
Mol. Wt: 494.62
LCMS (m/z): 495 [M+1].

Synthesis of (E)-1-(4-(3-(aminomethyl)phenyl)piperidin-1-yl)-3-(3-hydroxy-4-(2-hydroxy-propan-2-yl) phenyl)prop-2-en-1-one (TFA salt)

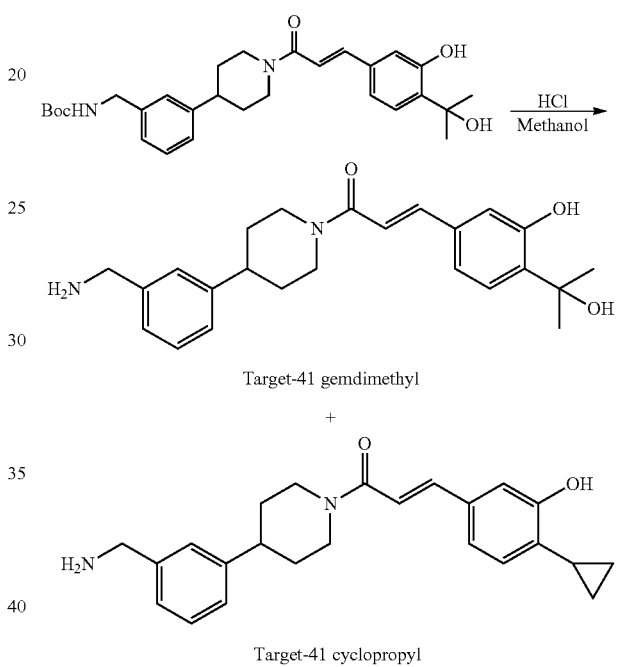

Target-41 gemdimethyl

+

Target-41 cyclopropyl

| Sr. No. | Chemical | Mol. Wt. | Quantity | mmol | Molar Ratio |
|---|---|---|---|---|---|
| 1 | (E)-tert-butyl 3-(1-(3-(3-hydroxy-4-(2-hydroxypropan-2-yl) phenyl) acryloyl)piperidin-4-yl) benzyl carbamate | 494.62 | 0.1 g | 0.2 | 1.0 |
| 2 | Methanol | — | 2 mL | — | — |
| 3 | Conc. HCl | — | 0.2 mL | — | — |

A solution of (E)-tert-butyl 3-(1-(3-(3-hydroxy-4-(2-hydroxypropan-2-yl) phenyl) acryloyl) piperidin-4-yl) benzylcarbamate (0.1 g, 0.2 mmol) in MeOH (2 mL) was treated with conc. HCl (0.2 mL) at room temperature for 1 h. The reaction mixture was concentrated in vacuo and the residue was purified by prep-HPLC to yield (E)-1-(4-(3-(aminomethyl)phenyl)piperidin-1-yl)-3-(3-hydroxy-4-(2-hydroxypropan-2-yl)phenyl)prop-2-en-1-one and (E)-1-(4-(3-(aminomethyl)phenyl)piperidin-1-yl)-3-(4-cyclopropyl-3-hydroxyphenyl)prop-2-en-1-one as a TFA salt. Analytical data for (E)-1-(4-(3-(aminomethyl) phenyl) piperidin-1-yl)-3-(3-hydroxy-4-(2-hydroxypropan-2-yl) phenyl) prop-2-en-1-one (TFA salt)

White solid; Yield: 0.002 g, (3%)

Mol. Wt.: 366.45

LCMS (m/z): 389 [M+23]

HPLC Purity: 99.11%

$^1$H NMR (400 MHz, CD$_3$OD): δ 7.49 (d, J=15.6 Hz, 1H), 7.42-7.22 (m, 5H), 7.10 (d, J=16.4 Hz, 1H), 7.07 (d, J=8.0 Hz, 1H), 7.01 (s, 1H), 4.80-4.74 (m, 1H), 4.46-4.35 (m, 1H), 4.09 (s, 2H), 3.00-2.80 (m, 2H), 2.04-1.90 (m, 2H), 1.78-1.64 (m, 2H), 1.60 (s, 6H).

Example 26—Synthesis of CMI Monomers

The compound 1-{3-[4-(3-aminomethyl-phenyl)-piperidine-1-carbonyl]-phenyl}-3,4-dihydroxy-4-methyl-pyrrolidin-2-one hydrochloride (10) was prepared starting from 3-methyl-but-2-enoic acid methyl ester (1) as shown in Scheme 27 below. In a similar way the other isomer Compound 13 was prepared as shown in Scheme 28, also below.

SCHEME 27.

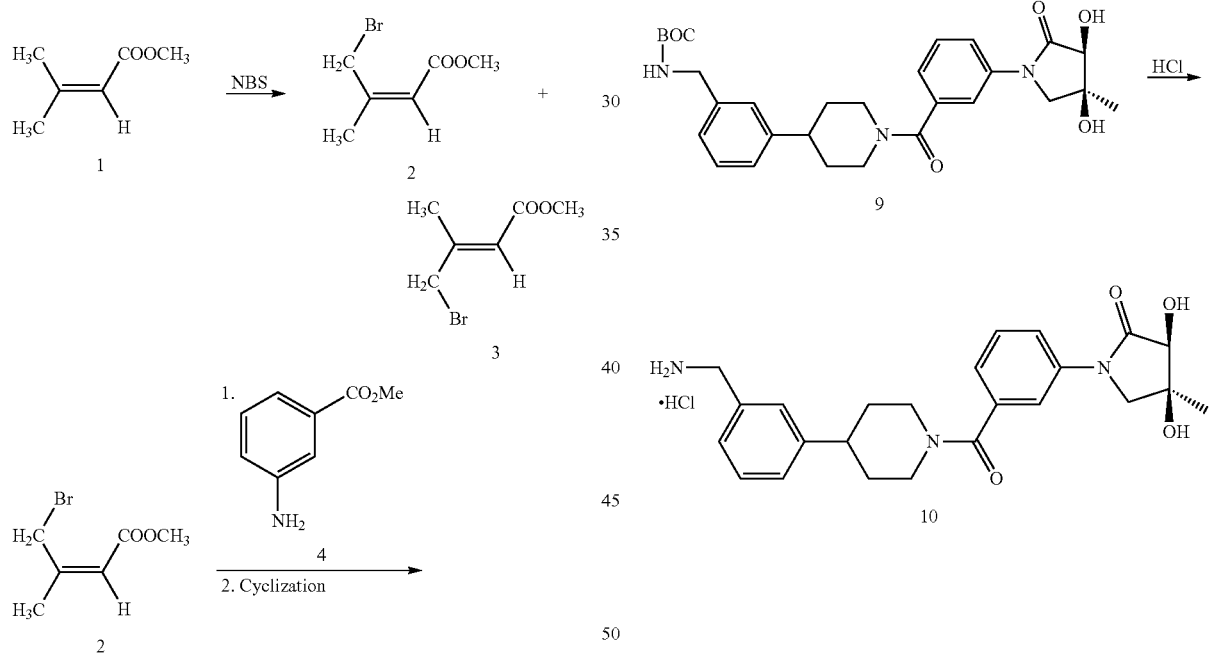

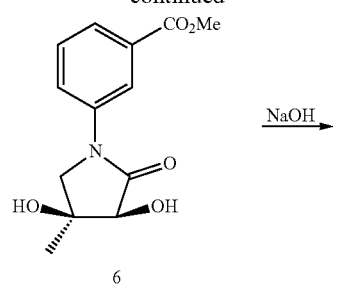

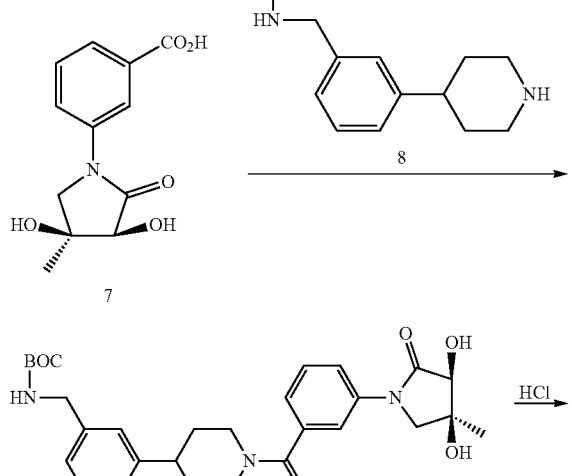

SCHEME 28

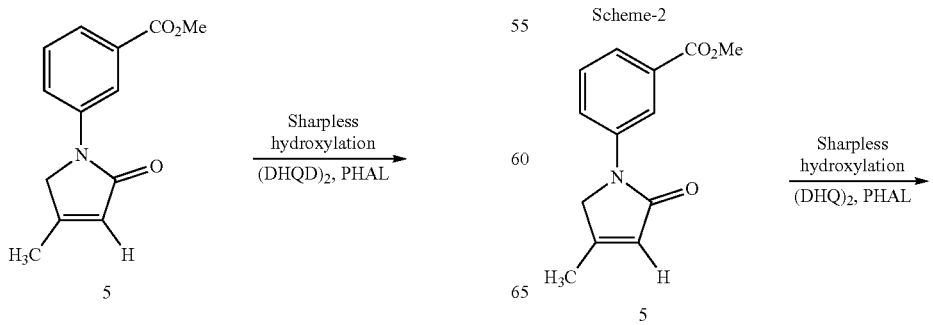

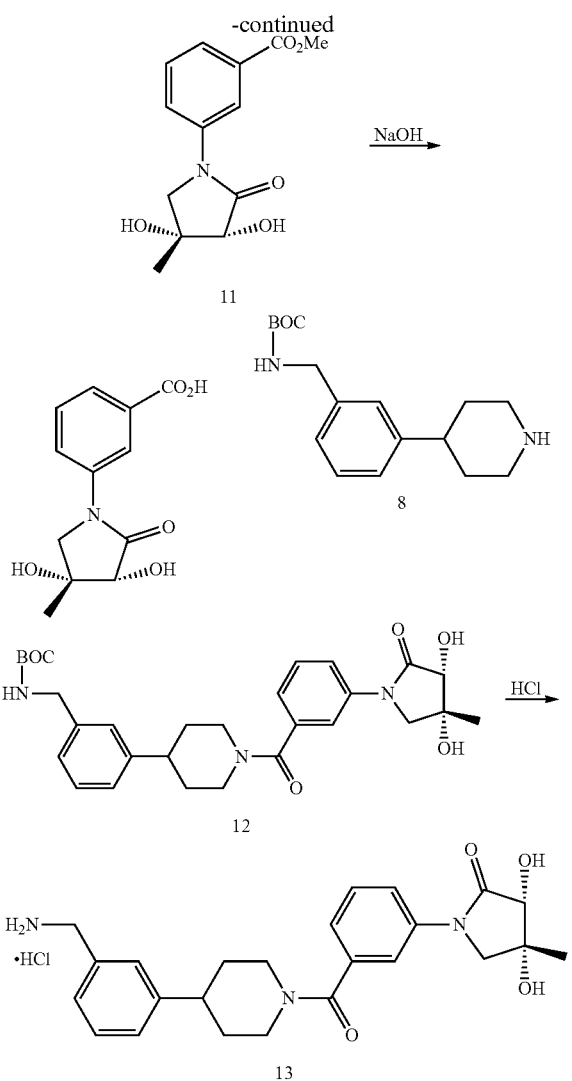

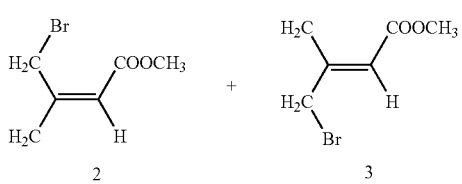

Synthesis of 4-bromo-3-methyl-but-2-enoic acid methyl ester (2 & 3)

To a solution of 3-methylbut-2-enoic acid methyl ester (20 g, 175.4 mmol) in carbon tetrachloride (88 mL) was added N-bromosuccinimide (31.2 g, 175.4 mmole) and benzoyl peroxide (235 mg) under nitrogen. The mixture was heated under reflux for 2 h. A small aliquot was worked up and the $^1$H NMR indicated the reaction to be complete. The reaction mixture was filtered to remove the succinimide which was washed with carbon tetrachloride (40 mL) and the combined filtrates were evaporated to give the crude title product (33.8 g) as a mixture of cis and trans isomers. The crude residue was used as such in the next reaction.

Synthesis of 3-(4-methyl-2-oxo-2,5-dihydropyrrol-1-yl)benzoic acid methyl ester (5) (CMI-89-24)

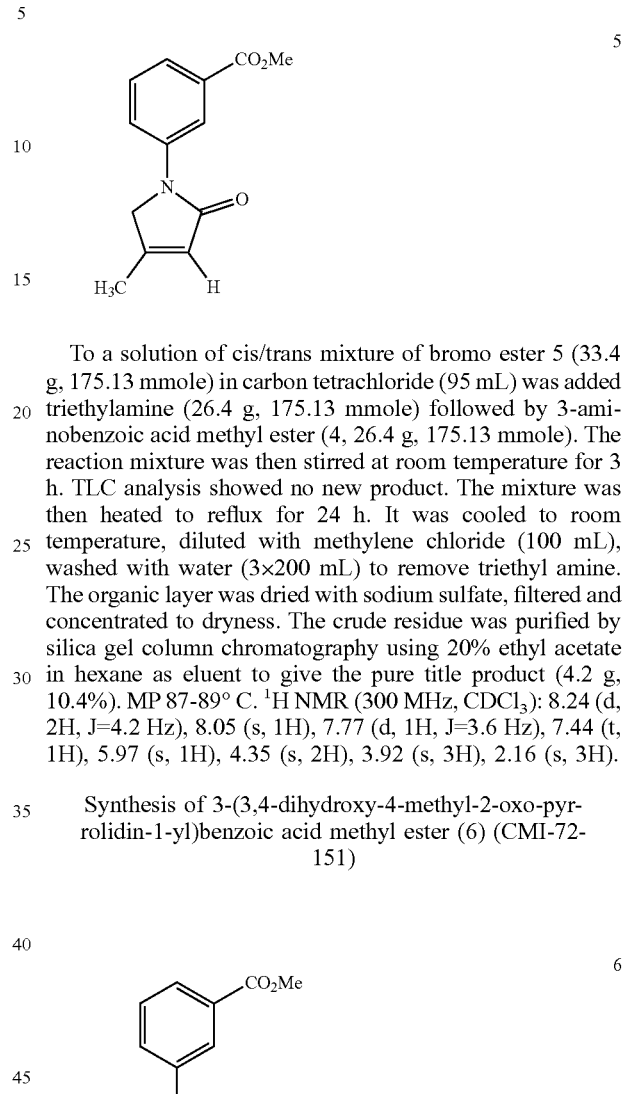

To a solution of cis/trans mixture of bromo ester 5 (33.4 g, 175.13 mmole) in carbon tetrachloride (95 mL) was added triethylamine (26.4 g, 175.13 mmole) followed by 3-aminobenzoic acid methyl ester (4, 26.4 g, 175.13 mmole). The reaction mixture was then stirred at room temperature for 3 h. TLC analysis showed no new product. The mixture was then heated to reflux for 24 h. It was cooled to room temperature, diluted with methylene chloride (100 mL), washed with water (3×200 mL) to remove triethyl amine. The organic layer was dried with sodium sulfate, filtered and concentrated to dryness. The crude residue was purified by silica gel column chromatography using 20% ethyl acetate in hexane as eluent to give the pure title product (4.2 g, 10.4%). MP 87-89° C. $^1$H NMR (300 MHz, CDCl$_3$): 8.24 (d, 2H, J=4.2 Hz), 8.05 (s, 1H), 7.77 (d, 1H, J=3.6 Hz), 7.44 (t, 1H), 5.97 (s, 1H), 4.35 (s, 2H), 3.92 (s, 3H), 2.16 (s, 3H).

Synthesis of 3-(3,4-dihydroxy-4-methyl-2-oxo-pyrrolidin-1-yl)benzoic acid methyl ester (6) (CMI-72-151)

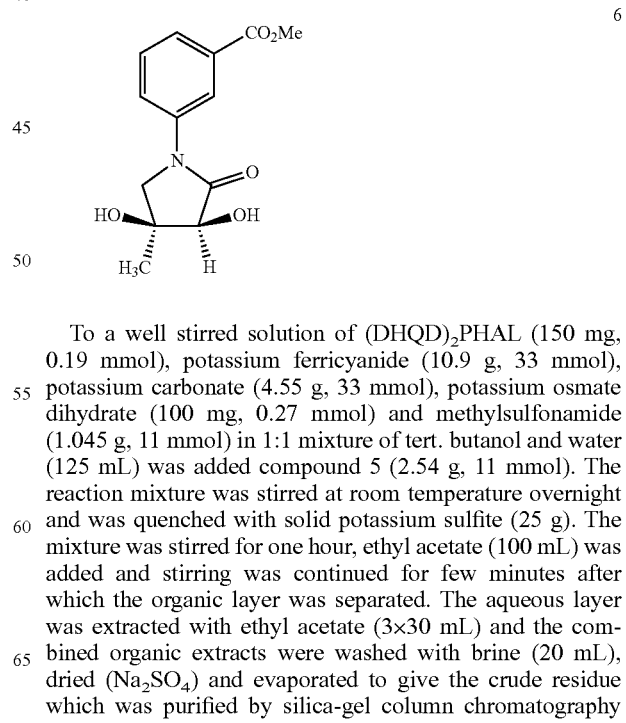

To a well stirred solution of (DHQD)$_2$PHAL (150 mg, 0.19 mmol), potassium ferricyanide (10.9 g, 33 mmol), potassium carbonate (4.55 g, 33 mmol), potassium osmate dihydrate (100 mg, 0.27 mmol) and methylsulfonamide (1.045 g, 11 mmol) in 1:1 mixture of tert. butanol and water (125 mL) was added compound 5 (2.54 g, 11 mmol). The reaction mixture was stirred at room temperature overnight and was quenched with solid potassium sulfite (25 g). The mixture was stirred for one hour, ethyl acetate (100 mL) was added and stirring was continued for few minutes after which the organic layer was separated. The aqueous layer was extracted with ethyl acetate (3×30 mL) and the combined organic extracts were washed with brine (20 mL), dried (Na$_2$SO$_4$) and evaporated to give the crude residue which was purified by silica-gel column chromatography using 1 to 5% methanol in dichloromethane as the eluent. The pure dihydroxy compound 6 thus obtained as an off-white solid (800 mg, 27.5%). MP 98-100° C. ¹HNMR (300 MHz, CDCl₃): δ 1.56 (s, 3H), 2.96 (s, OH), 3.58 (s, OH), 3.84 (dd, J=26 & 8 Hz, 2H), 3.92 (s, 3H), 4.22 (s, 1H), 7.46 (t, J=8.1 Hz, 1H), 7.84 (dd, J=8.1 & 3 Hz, 1H), 8.05-8.12 (m, 2H). ESMS: 266 (MH+). [α]_D-23.3 (CH₂C₂, C=1.06).

Synthesis of 3-(3,4-dihydroxy-4-methyl-2-oxo-pyrrolidin-1-yl)benzoic acid (7)

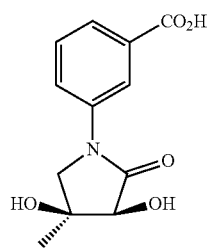

7

To a solution of dihydroxy ester 6 (530 mg, 2 mmol) in methanol (10 mL) was added 1.25 M aqueous sodium hydroxide (2 mL) and the mixture was stirred at room temperature overnight. The solvent was evaporated and the residue dried by co-evaporation with toluene (2×10 mL). Methanol (10 mL) was added to the residue, and the residual NaCl was removed by filtration. The filtrate was evaporated to give the title compound as a sticky gum. (500 mg, 100%). ¹HNMR (300 MHz, CD₃OD): δ 1.50 (s, 3H), 3.70 (d, J=10.2 Hz, 1H), 3.81 (d, J=10.2 Hz, 1H), 4.24 (s, 1H), 7.49 (t, J=8.1 Hz, 1H), 7.81 (d, J=8.1 Hz, 1H), 7.93 (d, J=8.1 Hz, 1H), 8.28 (d, J=3 Hz, 1H). ESMS: 252(MH+). It was used as such in the next reaction.

Synthesis of (3-{1-[3-(3,4-dihydroxy-4-methyl-2-oxo-pyrrolidin-1-yl)benzoyl]-piperidin-4-yl}benzyl) carbamic acid tert-butyl ester (9) (CMI-93-20)

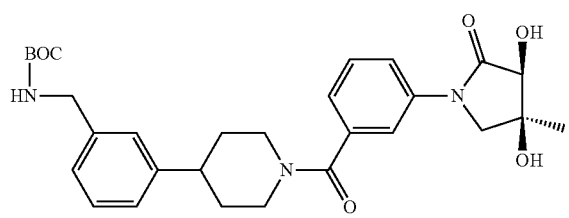

9

To a solution of the dihydroxy acid 7 (450 mg, 1.8 mmol) and (3-piperidin-4-yl-benzyl)-carbamic acid tert-butyl ester (8, 420 mg, 1.45 mmol) in CH₂Cl₂ (30 mL) was added EDCI (575 mg, 3 mmol) followed by N-hydroxybenzotriazole (30 mg, 0.25 mmol) and DIPEA (0.8 mL, 4.5 mmol). The reaction mixture was stirred at room temperature overnight. The solvent was evaporated and the residue was purified by silica-gel column chromatography using 1 to 5% methanol in dichloromethane as the eluent. The pure title compound thus obtained as off-white solid (320 mg, 42%). MP>105° C. (dec). ¹H NMR (300 MHz, CD₃OD): δ 1.44, (s, 9H), 1.48 (s, 3H), 1.65-2.05 (m, 5H), 2.83-3.35 (m, 4H), 3.69 (d, J=10.5 Hz, 1H), 3.82 (s, 1H), 3.85 (d, J=10.5 Hz, 1H), 4.20 (s, 2H), 7.09-7.25 (m, 5H), 7.46 (t, J=8.1 Hz, 1H), 7.58 (d, J=8.1 Hz, 1H) and 7.90 (s, 1H). ESMS: 524(MH+). [α]_D-19.25 (CH₂Cl₂, 1.03).

Synthesis of 1-{3-[4-(3-aminomethyl-phenyl)-piperidine-1-carbonyl]-phenyl}-3,4-dihydroxy-4-methyl-pyrrolidin-2-one hydrochloride (10) (CMI-93-21)

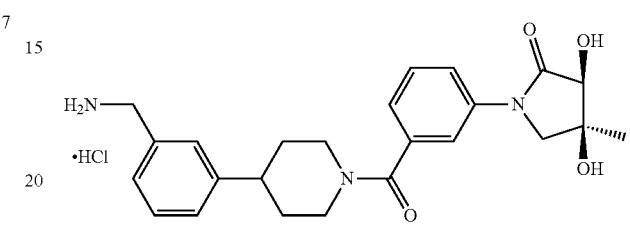

10

The Boc derivative 9 (112 mg, 0.21 mmol) was dissolved in CH₂Cl₂ (5 mL) and the solution was cooled in an ice-bath. To this was added 2 M HCl in ether (1.5 mL) and the mixture was stirred at room temperature overnight. On evaporation of the solvent, a white solid was obtained, which was dried at 50° C. overnight in a vacuum oven to give desired product as the hydrochloride salt. (82 mg, 85%) MP>185° C. (dec). ¹HNMR (300 MHz, CD₃OD): 1.49 (s, 3H), 1.65-2.05 (m, 5H), 2.85-3.01 (m, 3H), 3.65-3.95 (m, 3H), 4.12 (s, 2H), 4.22 (s, 1H), 7.22-7.52 (m, 8H), 8.08 (s, 1H). ESMS: 424(MH+). Synthesis of 3-(3,4-dihydroxy-4-methyl-2-oxo-pyrrolidin-1-yl)benzoic acid methyl ester (11) (CMI-72-153):

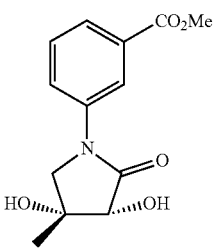

11

To a well stirred solution of (DHQ)₂PHAL (150 mg, 0.19 mmol), potassium ferricyanide (10.9 g, 33 mmol), potassium carbonate (4.55 g, 33 mmol), potassium osmate dihydrate (100 mg, 0.27 mmol) and methylsulfonamide (1.045 g, 11 mmol) in a 1:1 mixture of tert. butanol and water (125 mL) was added compound 5 (2.54 g, 11 mmol). The reaction mixture was stirred at room temperature overnight and then quenched with solid potassium sulfite (25 g). It was stirred for one hour, after which ethyl acetate (100 mL) was added and the mixture was stirred for a few minutes then the organic layer was separated. The aqueous layer was extracted with ethyl acetate (3×30 mL) and the combined organic extracts were washed with brine (20 mL), dried (Na₂SO₄) and evaporated to give the crude diol. This was purified by silica-gel column chromatography using 1 to 5% methanol in dichloromethane as the eluent. The pure dihydroxy compound 11 was obtained as an off-white solid (773 mg, 26.5%). MP 95-97° C. ¹HNMR (300 MHz, CDCl₃): δ

1.56 (s, 3H), 2.96 (s, OH), 3.58 (s, OH), 3.84 (dd, J=26 & 8 Hz, 2H), 3.92 (s, 3H), 4.22 (s, 1H), 7.46 (t, J=8.1 Hz, 1H), 7.84 (dd, J=8.1 & 3 Hz, 1H), 8.05-8.12 (m, 2H). ESMS: 266(MH+). [α]$_D$+23.59 (CH$_2$Cl$_2$, C=1.06).

Synthesis of (3-{1-[3-(3,4-dihydroxy-4-methyl-2-oxo-pyrrolidin-1-yl)benzoyl]-piperidin-4-yl}benzyl)carbamic acid tert-butyl ester (12): (CMI-72-159)

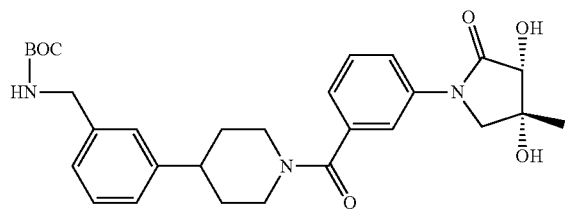

The ester 11 was hydrolyzed to the corresponding acid and converted to amide 12 in a way similar to that reported for compound 9. MP>68° C. (dec). [α]$_D$+19.05 (CH$_2$Cl$_2$, 1.03). Mass and $^1$H NMR were in agreement with the proposed structure.

Synthesis of 1-{3-[4-(3-aminomethyl-phenyl)-piperidine-1-carbonyl]-phenyl}-3,4-dihydroxy-4-methyl-pyrrolidin-2-one hydrochloride (13) (CMI-93-17)

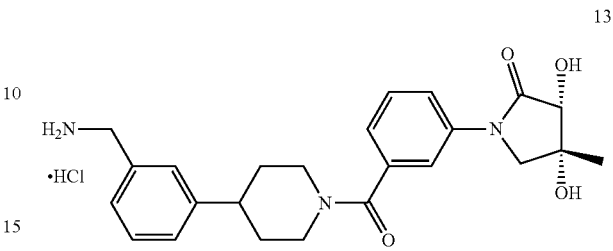

It was prepared in a similar way to that reported for Compound 10 starting from 83 mg of compound 12. The hydrochloride salt of 13 obtained as a sticky solid. Mass and $^1$H NMR were in agreement with the proposed structure.

Example 27

The following table contains exemplary compounds.

| No. | Structure | Compound Code | Homo/Hetero-Dimerizing Monomer |
|---|---|---|---|
| 1 | 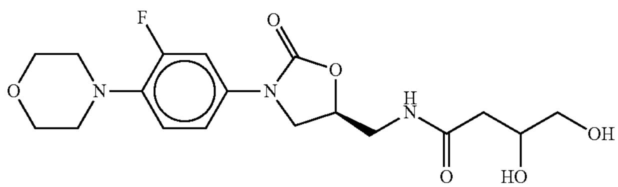 | 12 | Hetero |
| 2 | 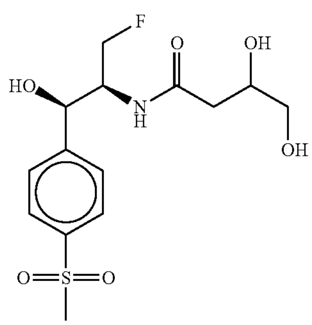 | NAFFLA-29 | Hetero |
| 3 | 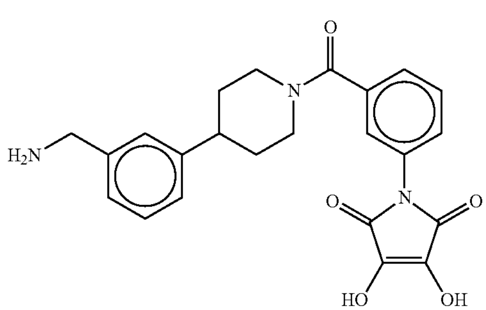 | T25e | Hetero |

-continued

| No. | Structure | Compound Code | Homo/Hetero-Dimerizing Monomer |
|---|---|---|---|
| 4 | 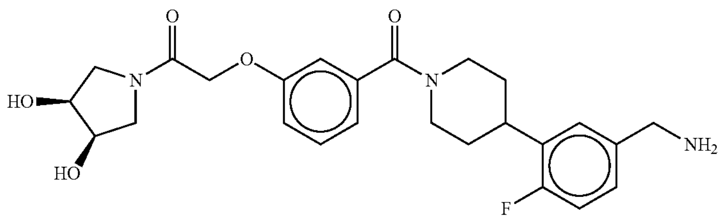 | T29-F | Hetero |
| 5 | 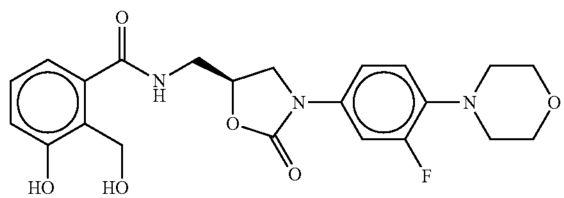 | Lz-NA-25 | Hetero |
| 6 | 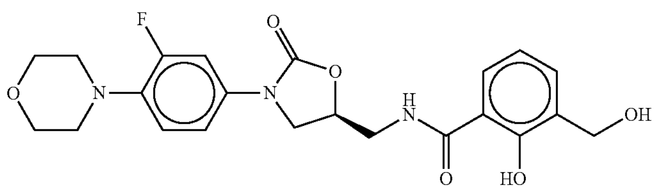 | Lz-NA-26 | Hetero |
| 7 | 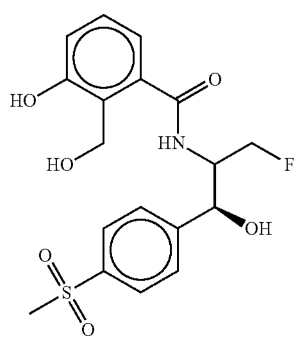 | NAFFLA-25 | Hetero |
| 8 | 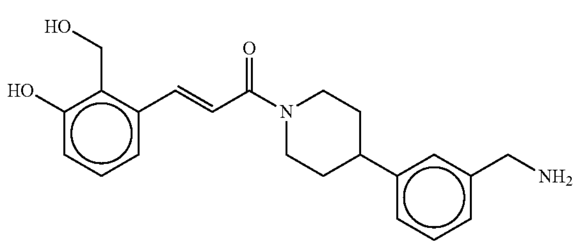 | t42 | Hetero |
| 9 | 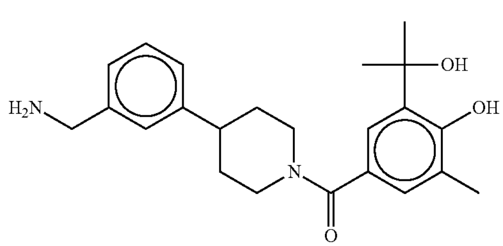 | | Hetero |

-continued

| No. | Structure | Compound Code | Homo/Hetero-Dimerizing Monomer |
|---|---|---|---|
| 10 | 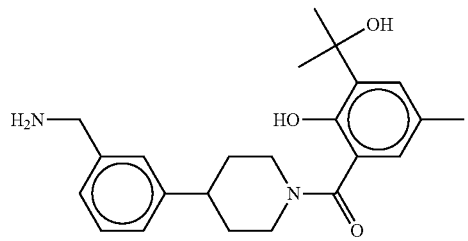 | | Hetero |
| 11 | 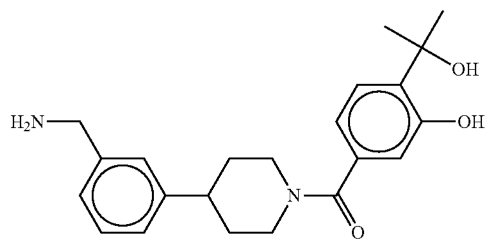 | T126 | Hetero |
| 12 | 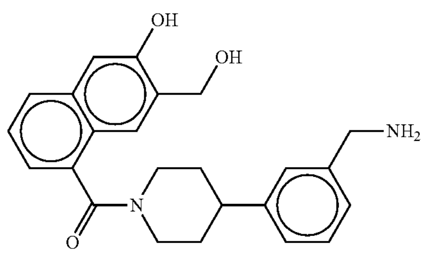 | T45 | Hetero |
| 13 | 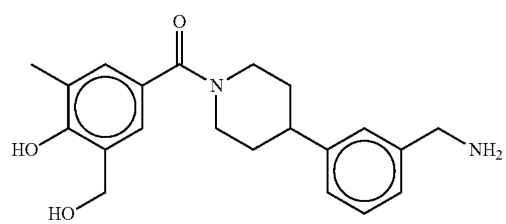 | T113 | Hetero |
| 14 | 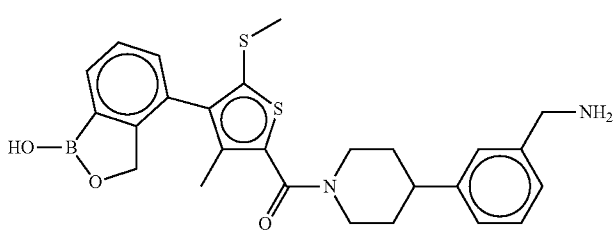 | | Hetero |
| 15 | 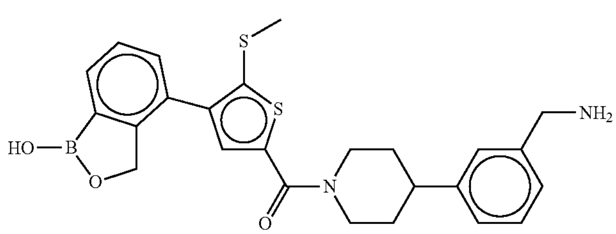 | T117 | Hetero |

-continued

| No. | Structure | Compound Code | Homo/Hetero-Dimerizing Monomer |
|-----|-----------|---------------|-------------------------------|
| 16 | 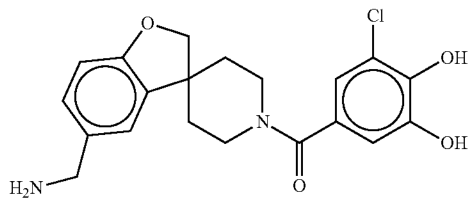 | T78spiro | Hetero |
| 17 | 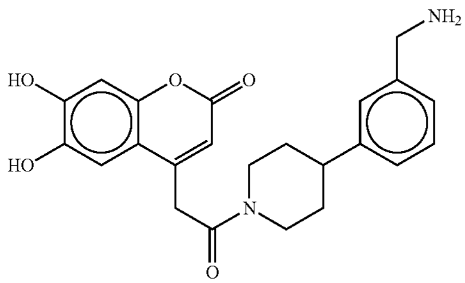 | T97 | Hetero |
| 18 | 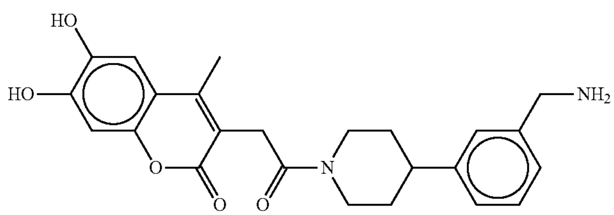 | | Hetero |
| 19 | 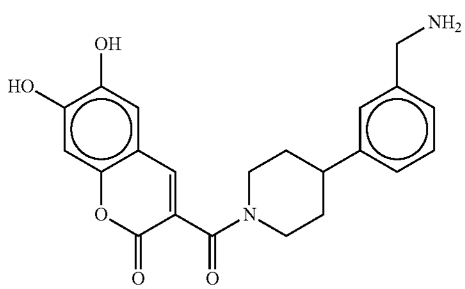 | T100 | Hetero |
| 20 | 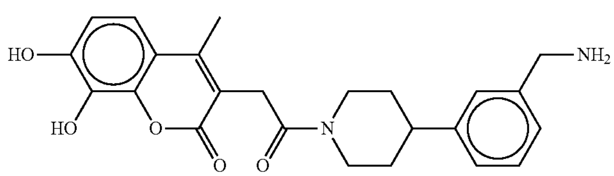 | T101 | Hetero |
| 21 | 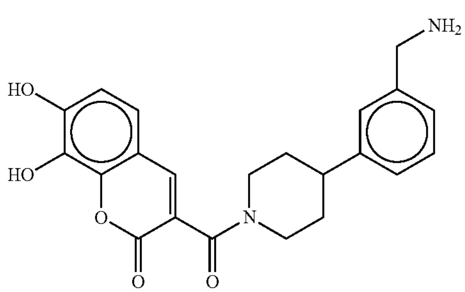 | T102 | Hetero |

-continued
| No. | Structure | Compound Code | Homo/Hetero-Dimerizing Monomer |
|---|---|---|---|
| 22 | 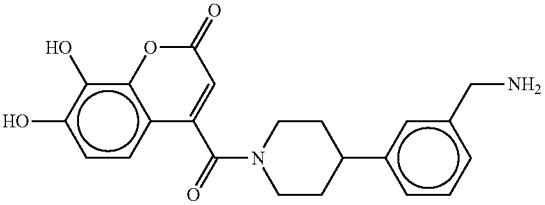 | T96 | Hetero |
| 23 | 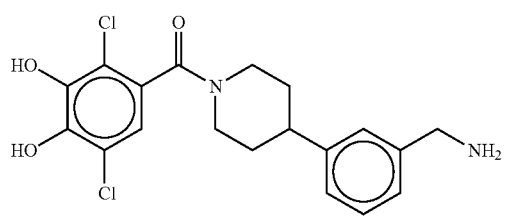 | | Hetero |
| 24 | 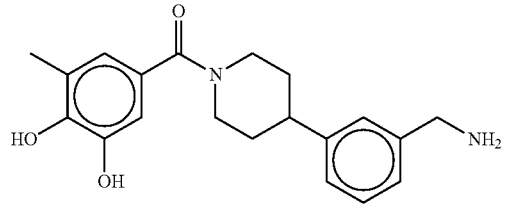 | | Hetero |
| 25 | 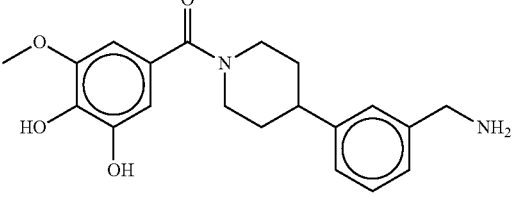 | T104 | Hetero |
| 26 | 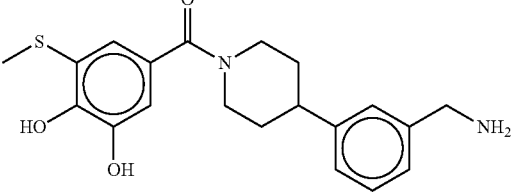 | | Hetero |
| 27 | 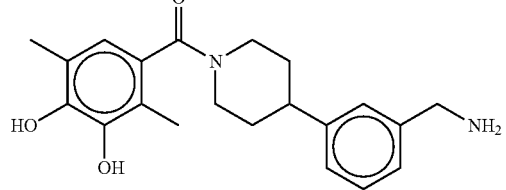 | | Hetero |
| 28 | 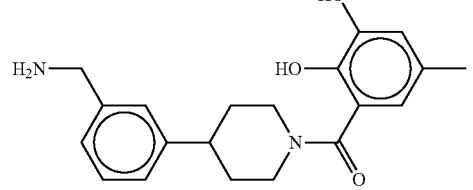 | | Hetero |

-continued

| No. | Structure | Compound Code | Homo/Hetero-Dimerizing Monomer |
|---|---|---|---|
| 29 | 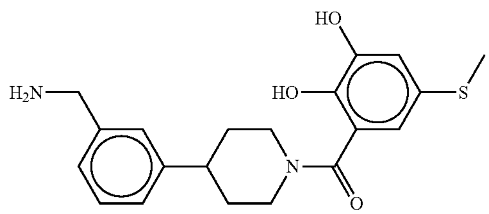 | | Hetero |
| 30 | 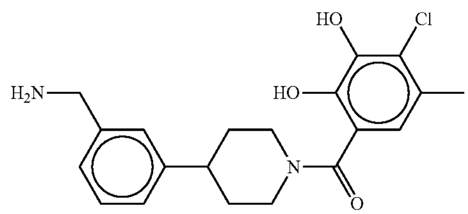 | | Hetero |
| 31 | 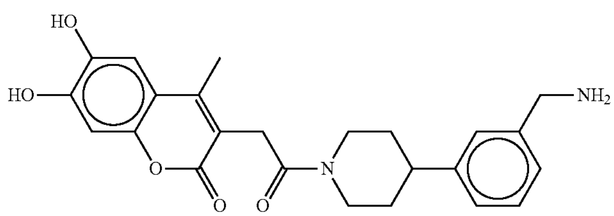 | T99 | Hetero |
| 32 | 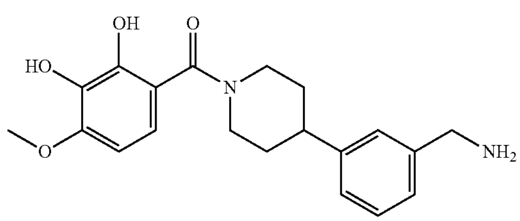 [SMILES: COc1ccc(C(=O)N2CCC(c3cccc(CN)c3)CC2)c(O)c1O] | T127 | Hetero |
| 33 | 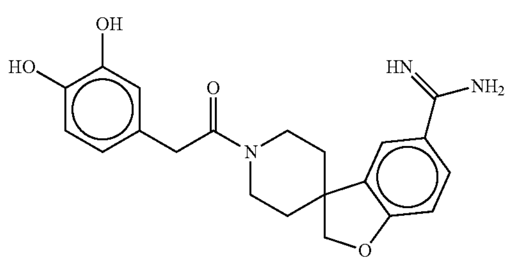 | T20 | Hetero |
| 34 | 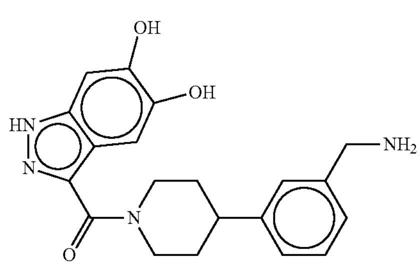 | Target 60 | Hetero |

-continued

| No. | Structure | Compound Code | Homo/Hetero-Dimerizing Monomer |
|---|---|---|---|
| 35 | 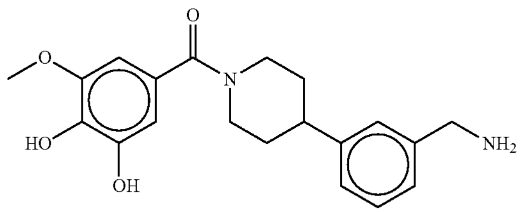 | T104 | Hetero |
| 36 | 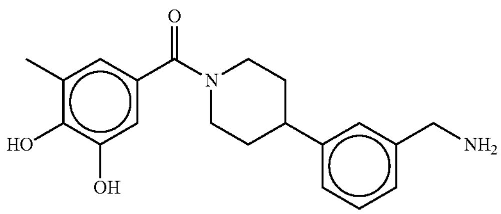 | T105 | Hetero |
| 37 | 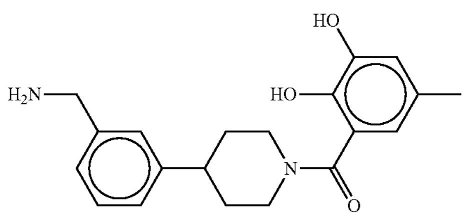 | T123 | Hetero |
| 38 | 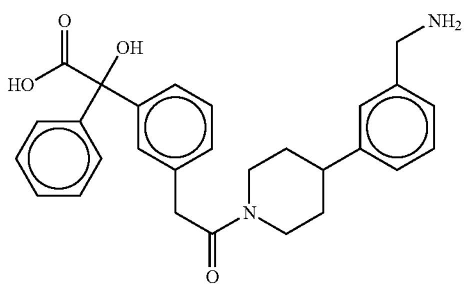 | T87 | Hetero |
| 39 | 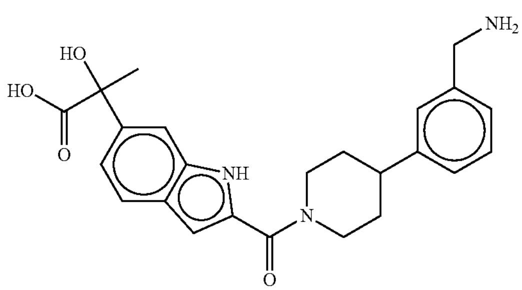 | T89 | Hetero |
| 40 | 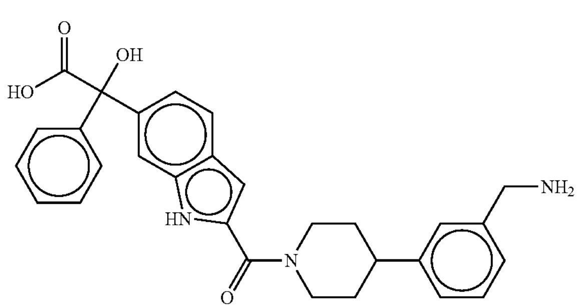 | T90 | Hetero |

-continued

| No. | Structure | Compound Code | Homo/Hetero-Dimerizing Monomer |
|---|---|---|---|
| 41 | 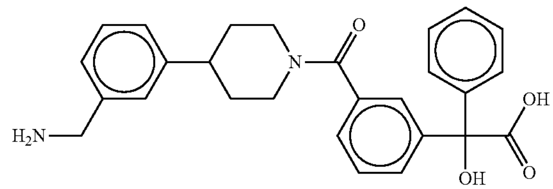 | T88 | Hetero |
| 42 | 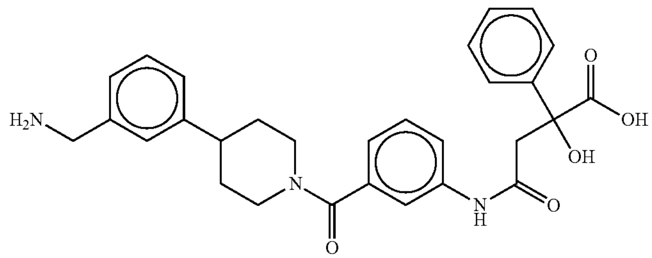 | T95 | Hetero |
| 43 | 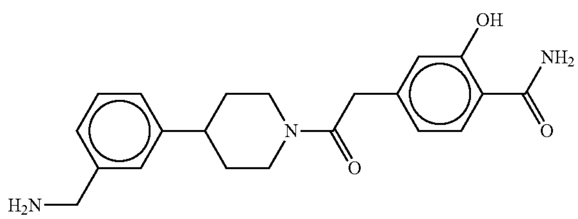 | T85 | Hetero |
| 45 | 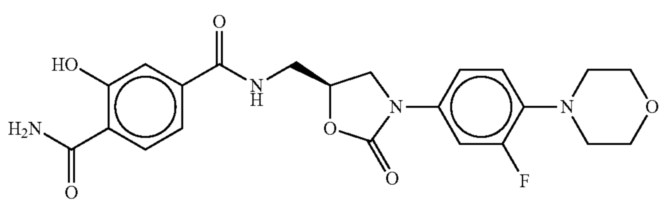 | Lz-NA-32 | Hetero |
| 46 | 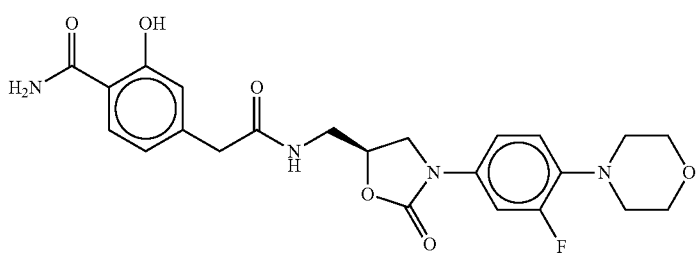 | Lz-NA-33 | Hetero |
| 47 | 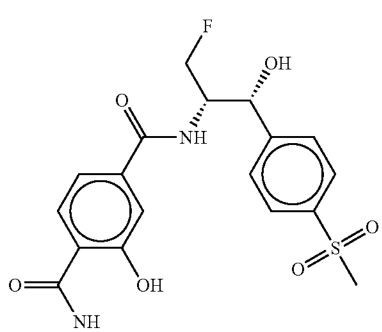 | NAFFLA-32 | Hetero |

-continued

| No. | Structure | Compound Code | Homo/Hetero-Dimerizing Monomer |
|---|---|---|---|
| 48 | 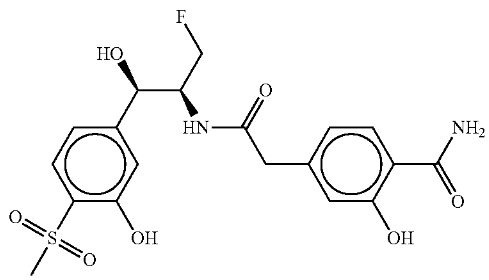 | NAFFLA-33 | Hetero |
| 49 | 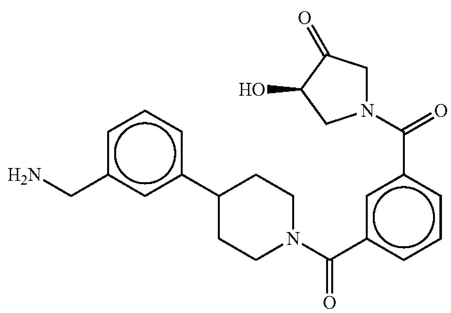 | T26 | Homo |
| 50 | 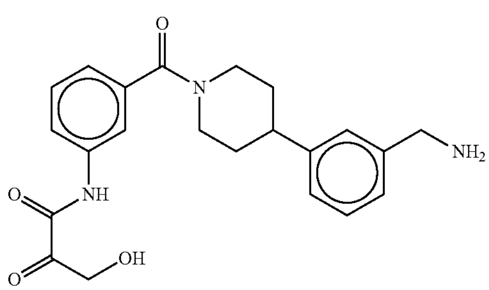 | T6 | Homo |
| 51 | 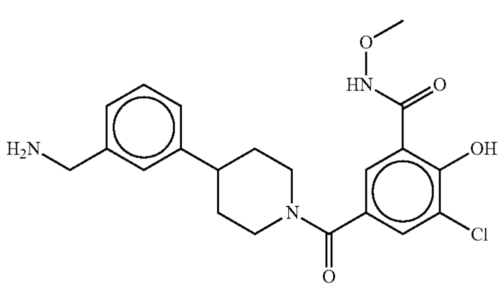 | T125 | Hetero |
| 52 | 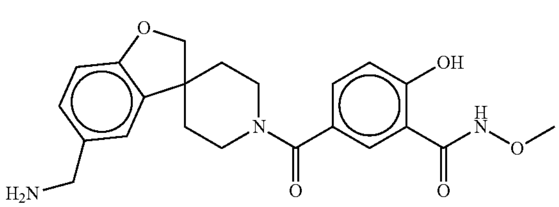 | Target 92-Spiro | Hetero |

-continued

| No. | Structure | Compound Code | Homo/Hetero-Dimerizing Monomer |
|---|---|---|---|
| 53 | 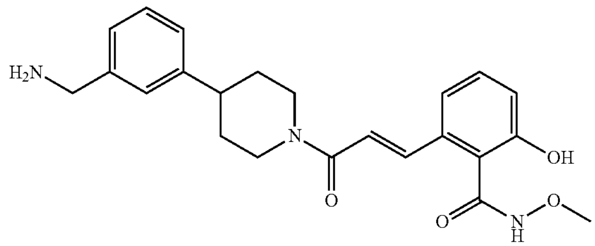 [SMILES: CONC(=O)c1c(O)cccc1/C=C/C(=O)N1CCC(c2cccc(CN)c2)CC1] | T124 | Hetero |
| 54 | 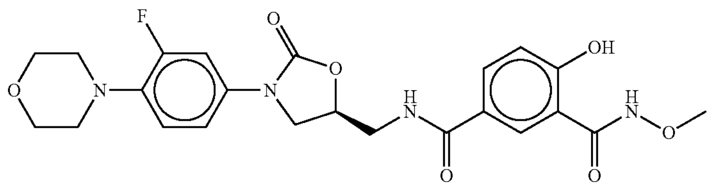 | Lz-NA-37 | Hetero |
| 55 | 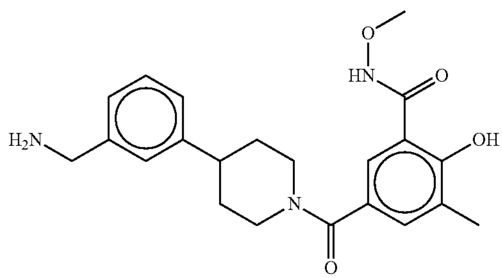 | T114 | Hetero |
| 56 | 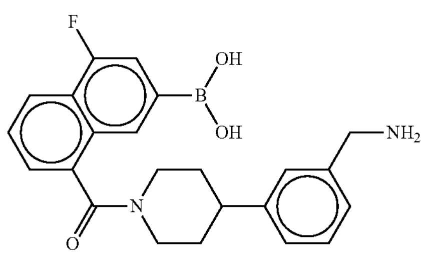 | T39 | Hetero |
| 57 | 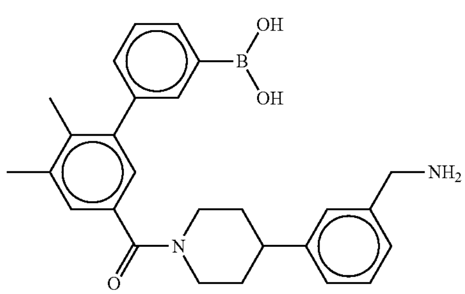 | T107 | Hetero |
| 58 | 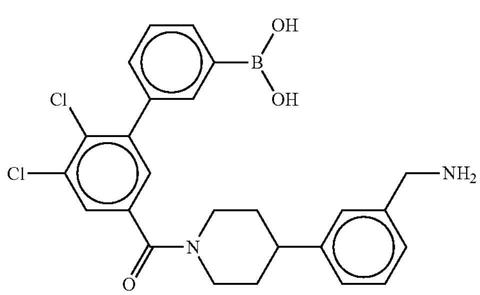 | | Hetero |

-continued

| No. | Structure | Compound Code | Homo/Hetero-Dimerizing Monomer |
|---|---|---|---|
| 59 | 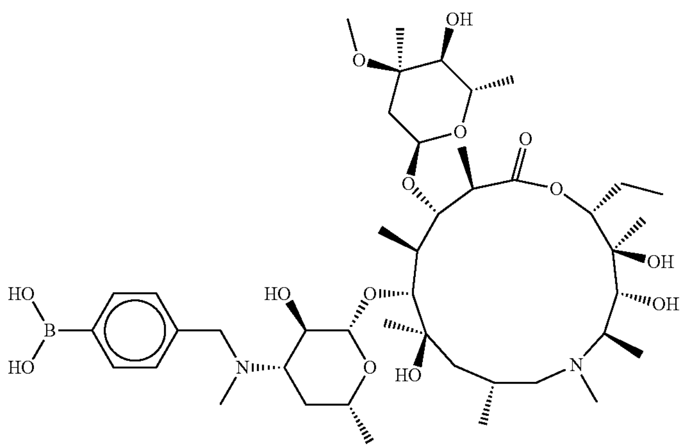 | AzBOR-1 | Hetero |
| 60 | 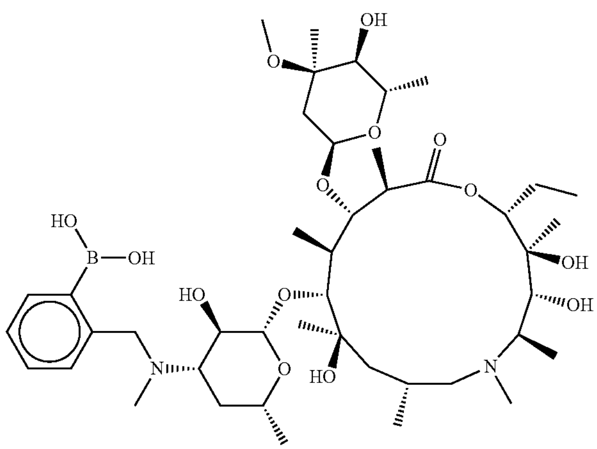 | AzBOR-2 | Hetero |
| 61 | 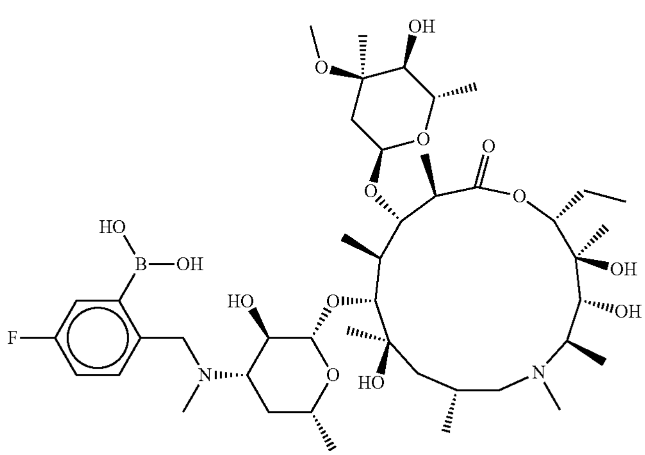 | AzBOR-3 | Hetero |

-continued

| No. | Structure | Compound Code | Homo/Hetero-Dimerizing Monomer |
|---|---|---|---|
| 62 | 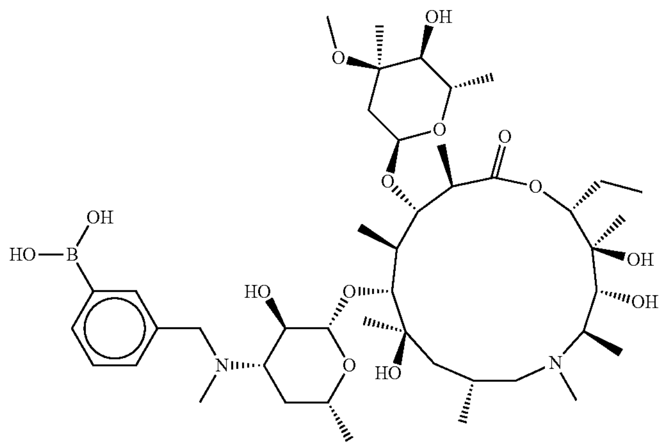 | AzBOR-4 | Hetero |
| 63 | 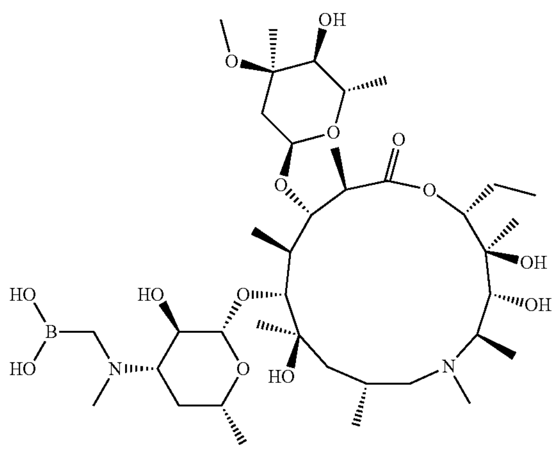 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CB(O)O)[C@H]2O)[C@](C)(O)C[C@@H](C)CN(C)[C@H](C)[C@@H](O)[C@]1(C)O] | AzBOR-5 | Hetero |
| 64 | 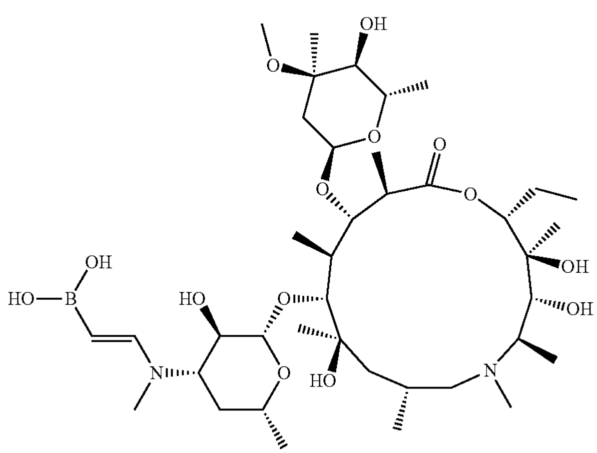 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)/C=C/B(O)O)[C@H]2O)[C@](C)(O)C[C@@H](C)CN(C)[C@H](C)[C@@H](O)[C@]1(C)O] | AzBOR-6 | Hetero |
| 65 | 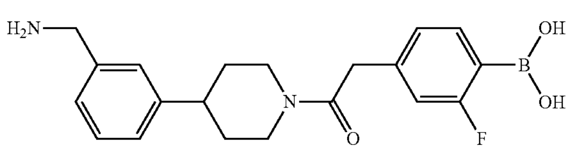 [SMILES: NCc1cccc(C2CCN(C(=O)Cc3ccc(B(O)O)c(F)c3)CC2)c1] | T54BA | Hetero |

-continued
| No. | Structure | Compound Code | Homo/Hetero-Dimerizing Monomer |
|---|---|---|---|
| 66 | 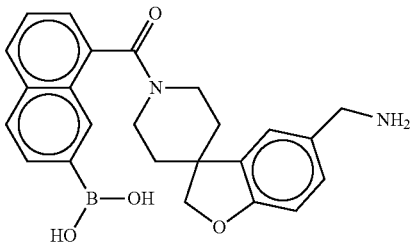 | T16 | Hetero |
| 67 | 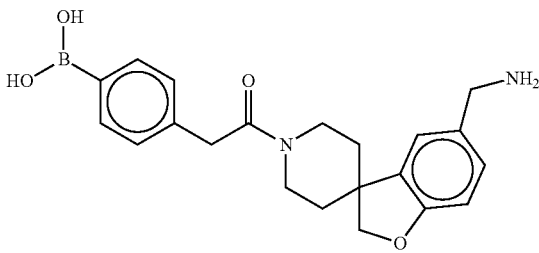 | T17 | Hetero |
| 68 | 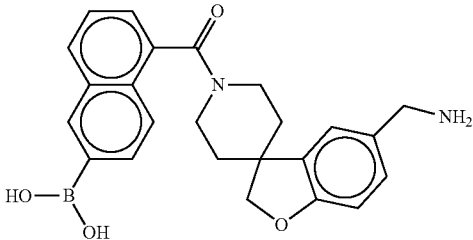 | T18 | Hetero |
| 69 | 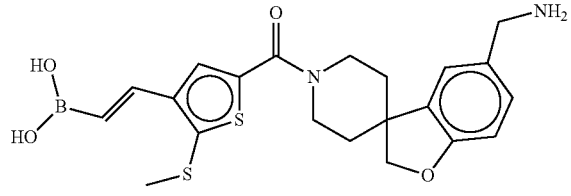 | T19 | Hetero |
| 70 | 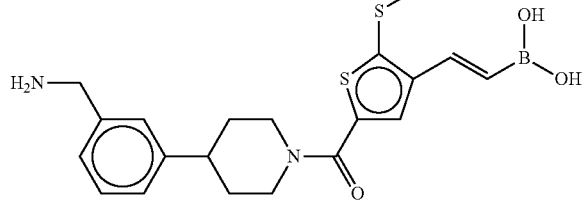 | T15 | Hetero |
| 71 | 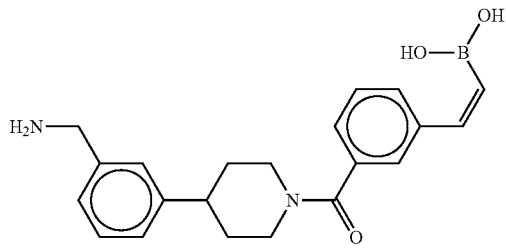 | T14-cis | Hetero |

-continued

| No. | Structure | Compound Code | Homo/Hetero-Dimerizing Monomer |
|---|---|---|---|
| 72 | 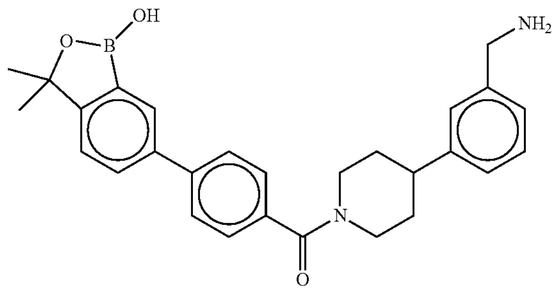 | T36-Gemdimethyl | Hetero |
| 73 | 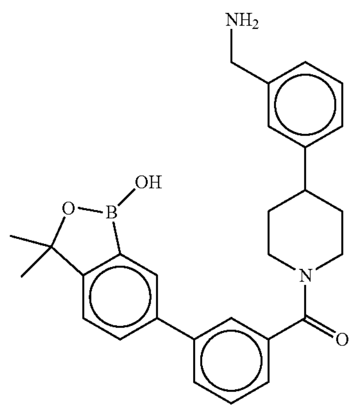 | T36-meta-Gemdimethyl | Hetero |
| 74 | 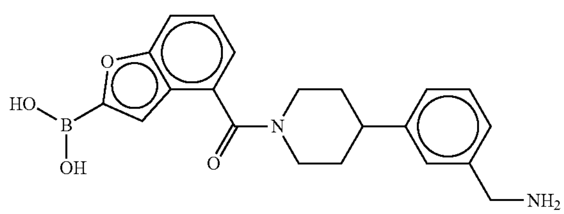 | T38 | Hetero |
| 75 | 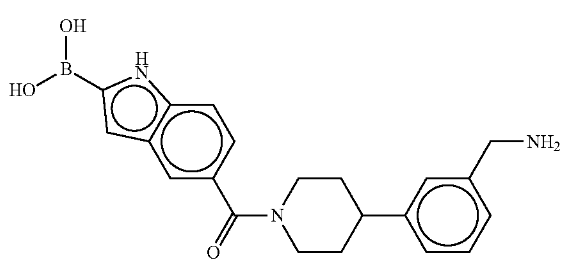 | Target 63 | Hetero |
| 76 | 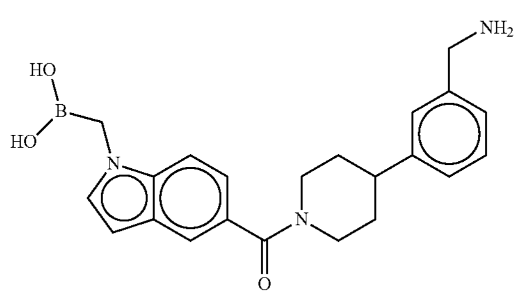 | T79 | Hetero |

-continued
| No. | Structure | Compound Code | Homo/Hetero-Dimerizing Monomer |
|---|---|---|---|
| 77 | 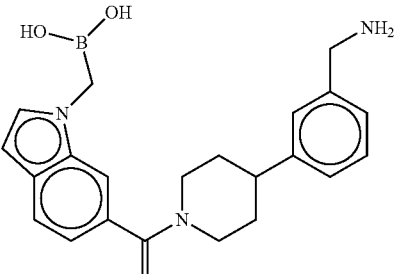 | T80 | Hetero |
| 78 | 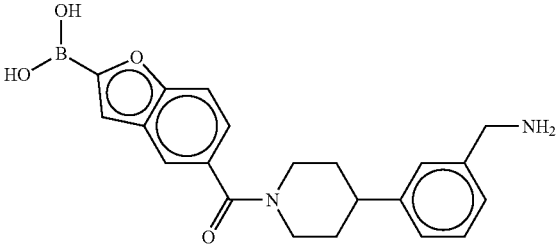 | T91 | Hetero |
| 79 | 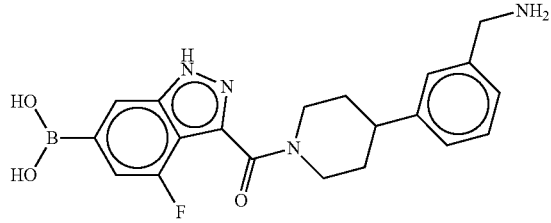 | Target 61 | Hetero |
| 80 | 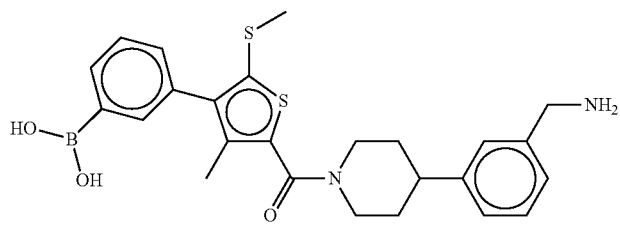 | T118 | Hetero |
| 81 | 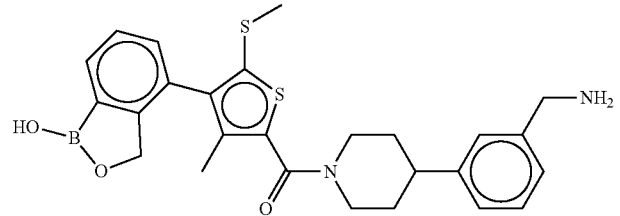 | T119 | Hetero |
| 82 | 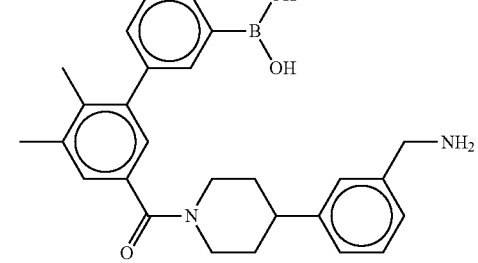 | T107 | Hetero |

-continued

| No. | Structure | Compound Code | Homo/Hetero-Dimerizing Monomer |
|---|---|---|---|
| 83 | 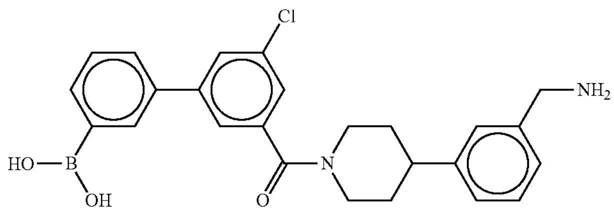 | T108 | Hetero |
| 84 | 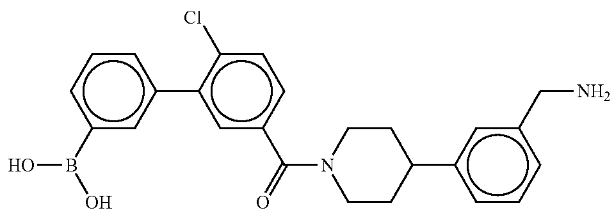 | T109 | Hetero |
| 85 | 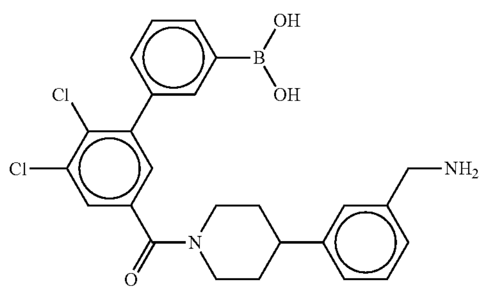 | T110 | Hetero |
| 86 | 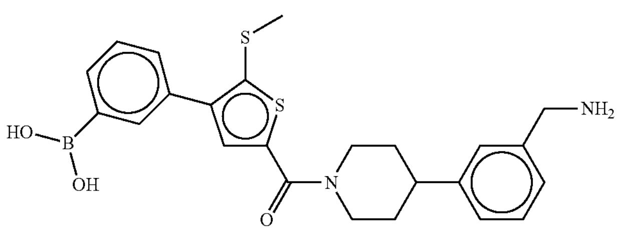 | T116 | Hetero |
| 87 | 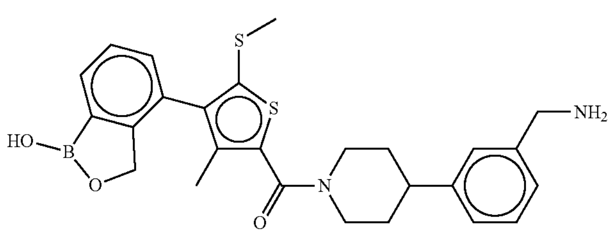 | T117 | Hetero |
| 88 | 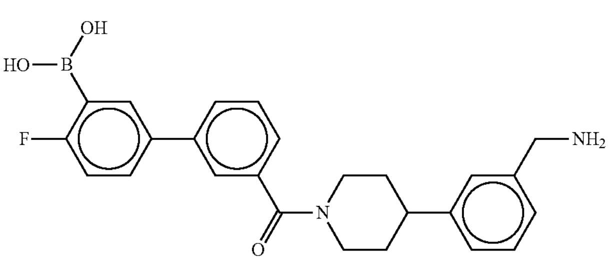 | T131 | Hetero |

| No. | Structure | Compound Code | Homo/Hetero-Dimerizing Monomer |
|---|---|---|---|
| 89 | 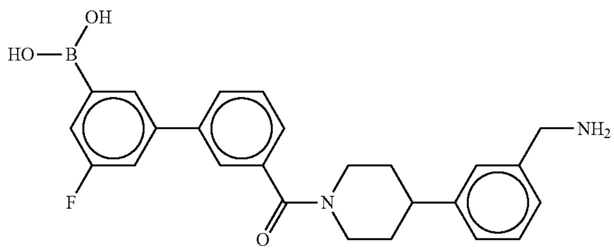 | T132 | Hetero |
| 90 | 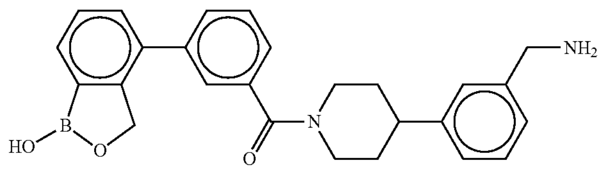 | T112 | Hetero |
| 91 | 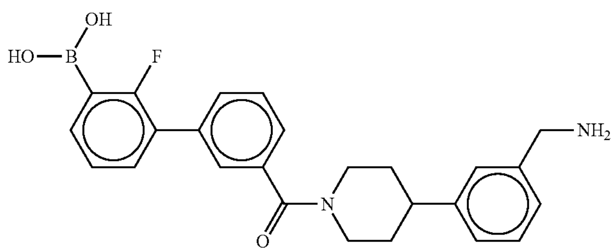 | T133 | Hetero |
| 92 | 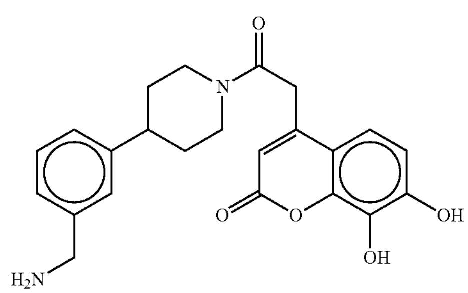 | T98 | Hetero |
| 93 | 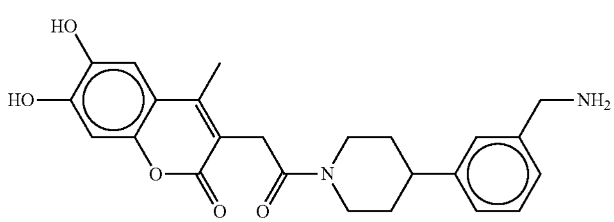 | T99 | Hetero |
| 94 | 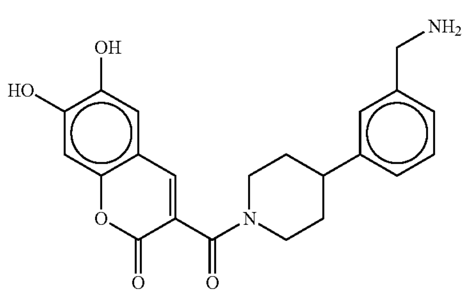 | T100 | Hetero |

-continued
| No. | Structure | Compound Code | Homo/Hetero-Dimerizing Monomer |
|---|---|---|---|
| 95 | 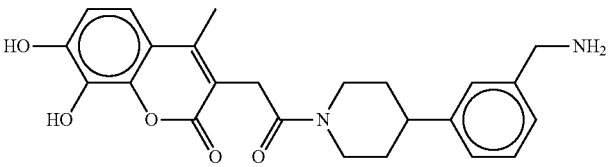 | T101 | Hetero |
| 96 | 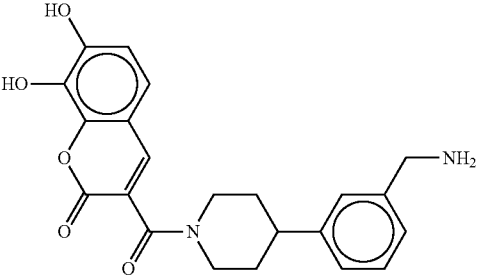 | T102 | Hetero |
| 97 | 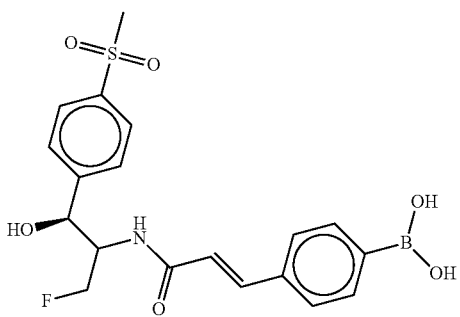 | | Hetero |
| 98 | 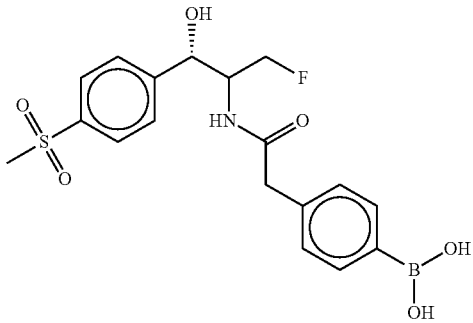 | | Hetero |
| 99 | 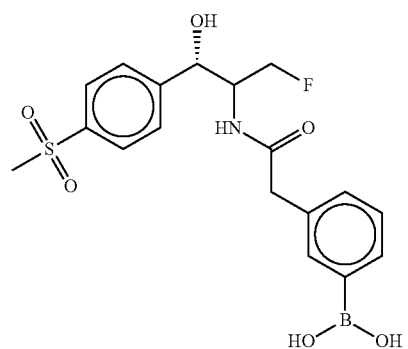 | | Hetero |

-continued
| No. | Structure | Compound Code | Homo/Hetero-Dimerizing Monomer |
|---|---|---|---|
| 101 | 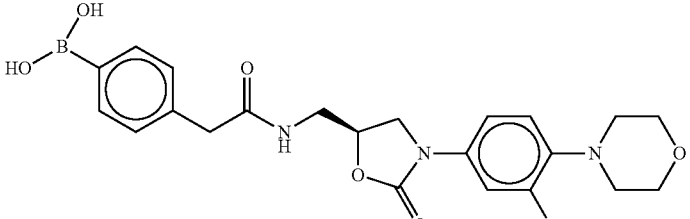 | | Hetero |
| 102 | 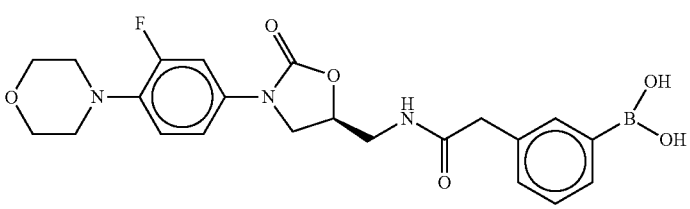 | | Hetero |
| 103 | 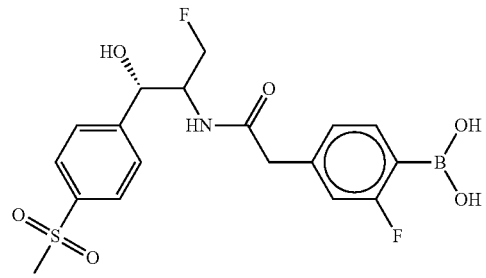 | | Hetero |
| 104 | 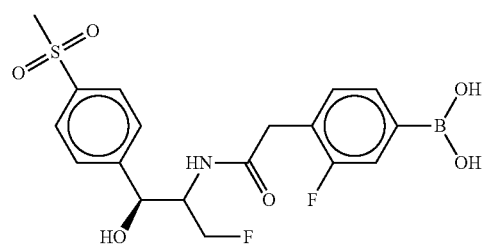 | | Hetero |
| 105 | 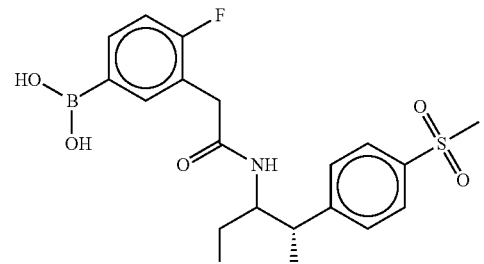 | | Hetero |
| 106 | 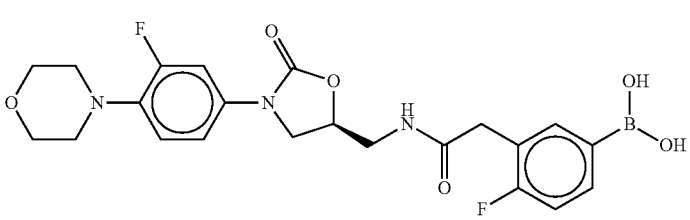 | | Hetero |

-continued
| No. | Structure | Compound Code | Homo/Hetero-Dimerizing Monomer |
|---|---|---|---|
| 107 | 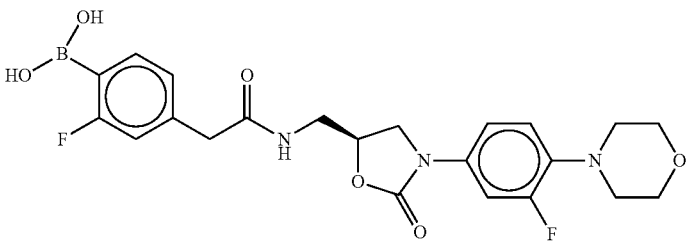 | | Hetero |
| 108 | 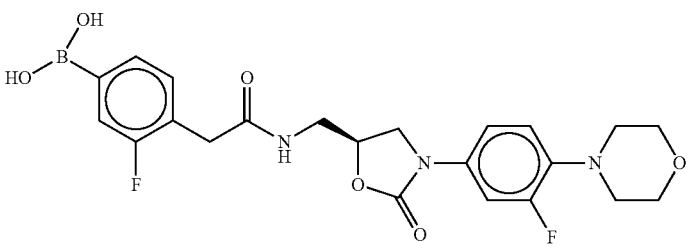 | | Hetero |
| 109 | 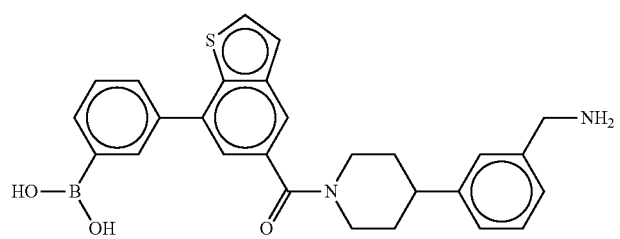 | | Hetero |
| 110 | 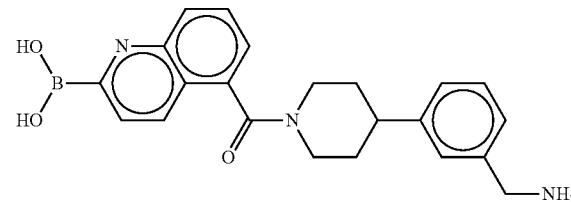 | | Hetero |
| 111 | 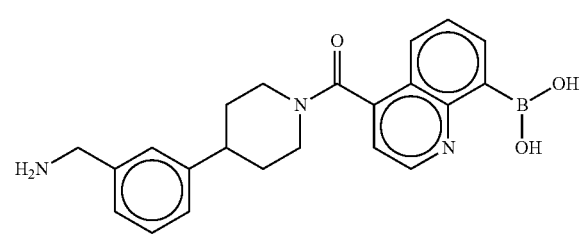 | | Hetero |
| 112 | 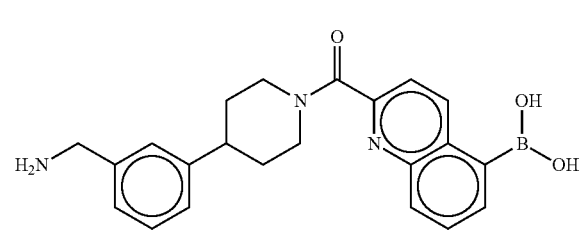 | | Hetero |

| No. | Structure | Compound Code | Homo/Hetero-Dimerizing Monomer |
|---|---|---|---|
| 113 | 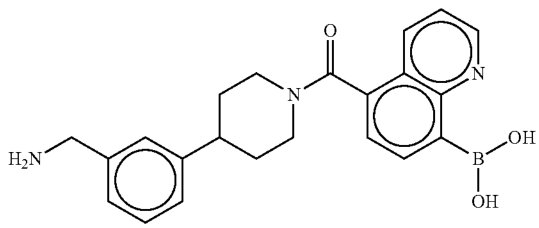 | | Hetero |
| 114 | 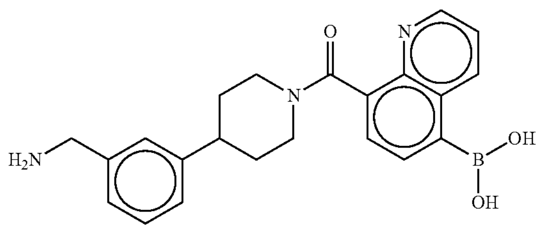 | T51 | Hetero |
| 115 | 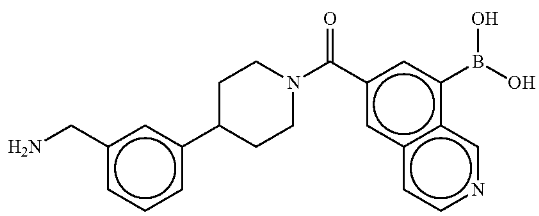 | | Hetero |
| 116 | 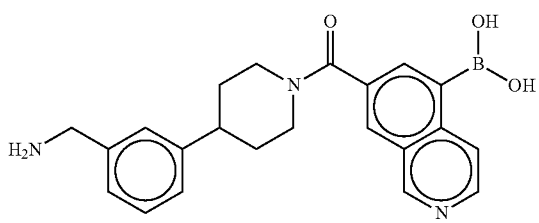 | | Hetero |
| 117 | 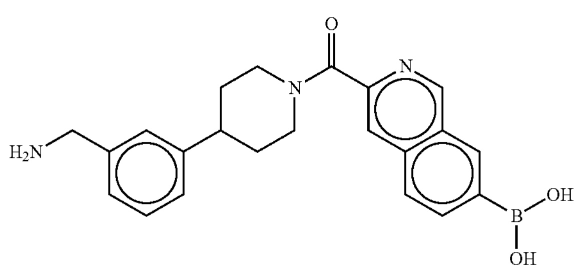 | | Hetero |
| 118 | 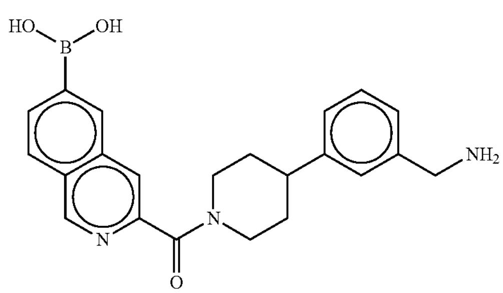 | | Hetero |

| No. | Structure | Compound Code | Homo/Hetero-Dimerizing Monomer |
|---|---|---|---|
| 119 | 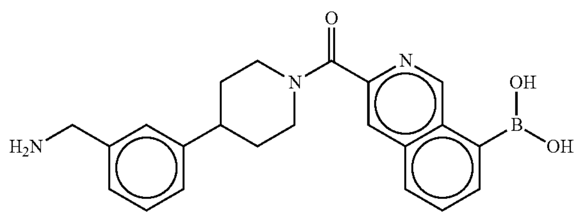 | | Hetero |
| 120 | 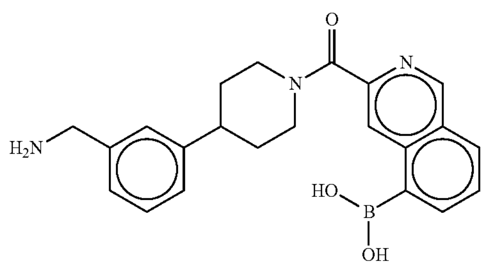 | | Hetero |
| 121 | 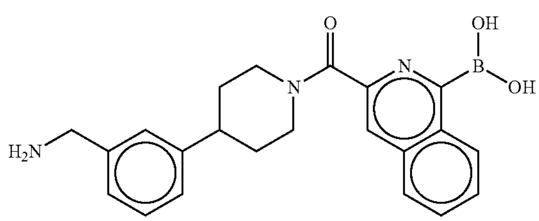 | | Hetero |
| 122 | 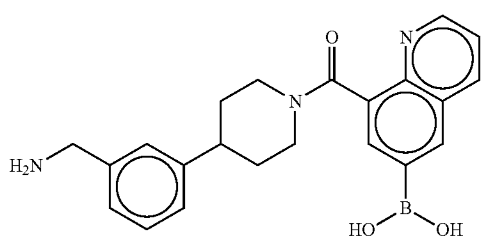 | | Hetero |
| 123 | 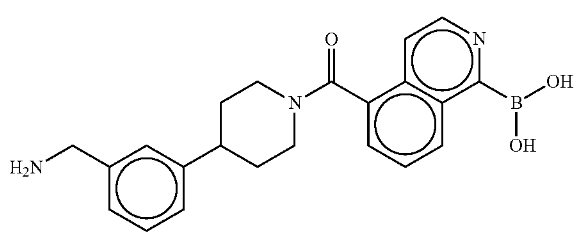 | | Hetero |
| 124 | 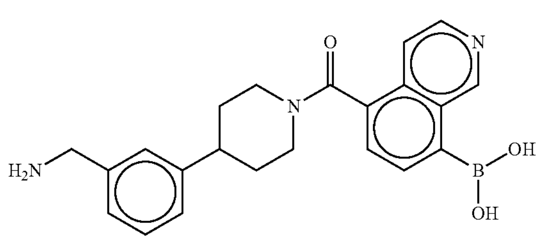 | | Hetero |

| No. | Structure | Compound Code | Homo/Hetero-Dimerizing Monomer |
|---|---|---|---|
| 125 | 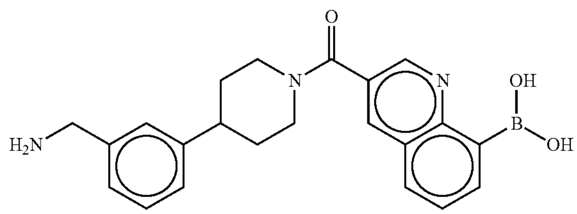 | T156 | Hetero |
| 126 | 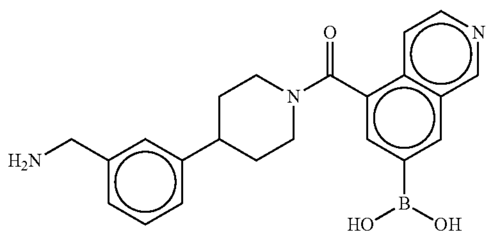 | | Hetero |
| 127 | 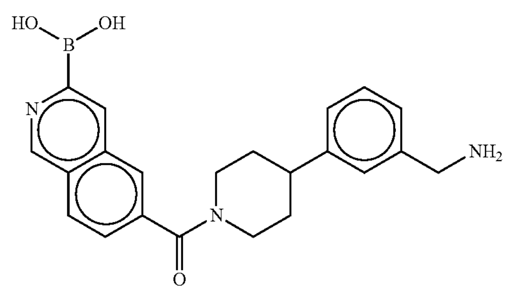 | | Hetero |
| 128 | 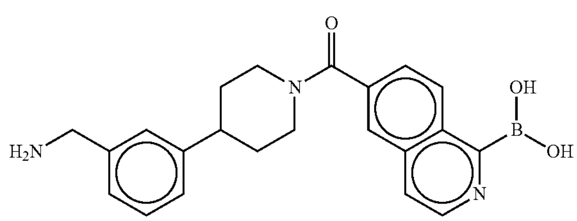 | | Hetero |
| 129 | 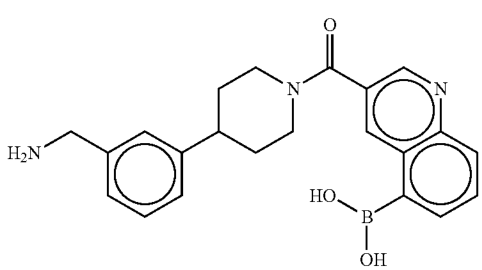 | | Hetero |
| 130 | 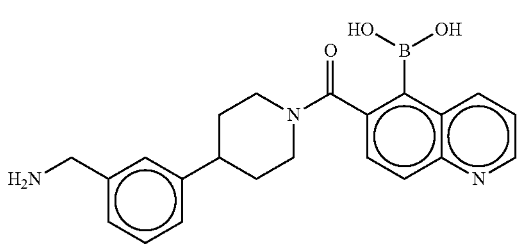 | | Hetero |

-continued

| No. | Structure | Compound Code | Homo/Hetero-Dimerizing Monomer |
|---|---|---|---|
| 131 | 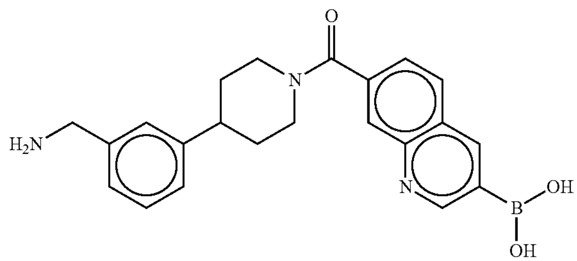 | | Hetero |
| 132 | 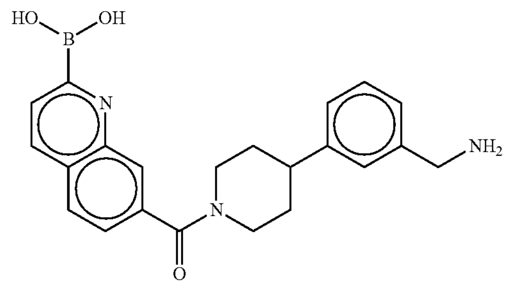 | | Hetero |
| 133 | 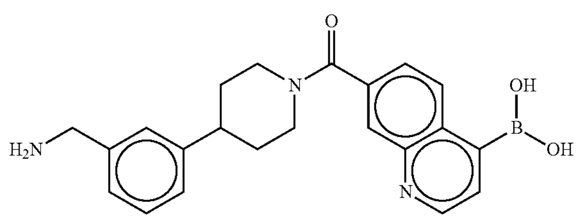 | | Hetero |
| 134 | 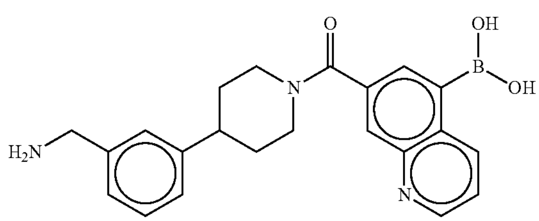 | | Hetero |
| 135 | 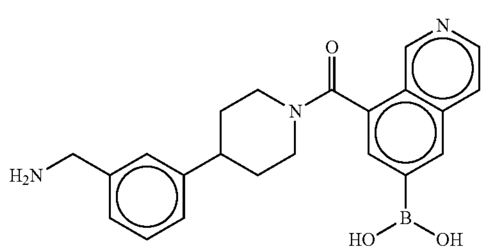 | | Hetero |
| 136 | 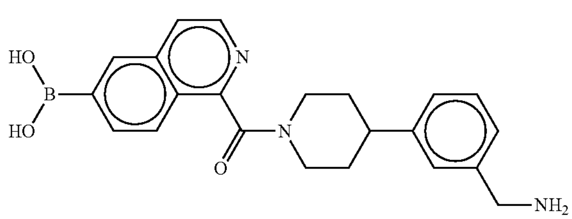 | | Hetero |

-continued

| No. | Structure | Compound Code | Homo/Hetero-Dimerizing Monomer |
|---|---|---|---|
| 137 | 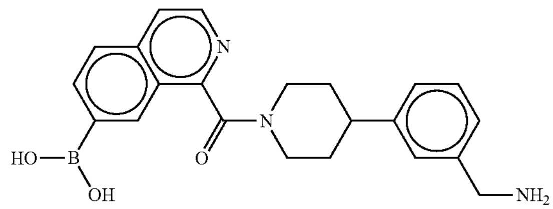 | | Hetero |
| 138 | 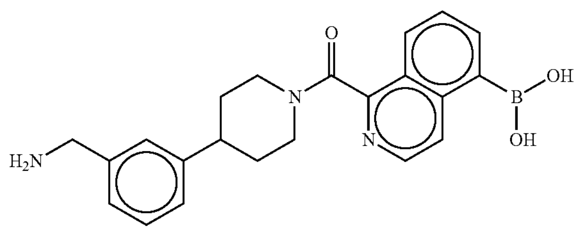 | | Hetero |
| 139 | 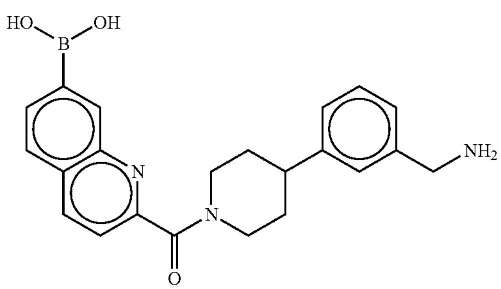 | | Hetero |
| 140 | 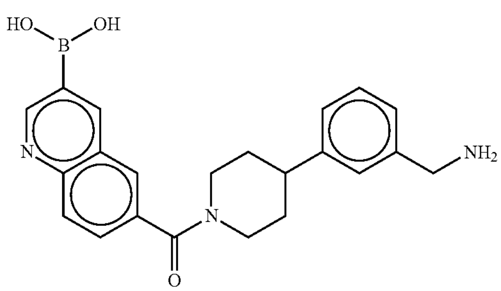 | | Hetero |
| 141 | 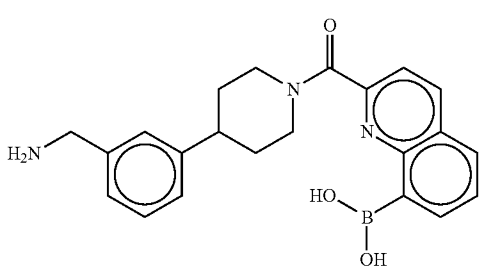 | | Hetero |
| 142 | 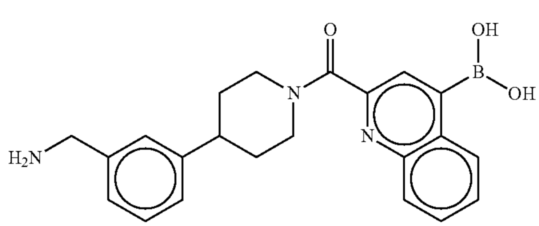 | | Hetero |

| No. | Structure | Compound Code | Homo/Hetero-Dimerizing Monomer |
|---|---|---|---|
| 143 | 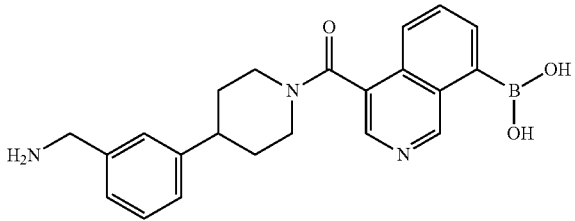 [SMILES: NCc1cccc(C2CCN(C(=O)c3cncc4c(B(O)O)cccc34)CC2)c1] | | Hetero |
| 144 | 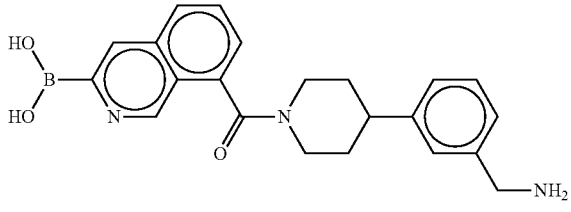 | | Hetero |
| 145 | 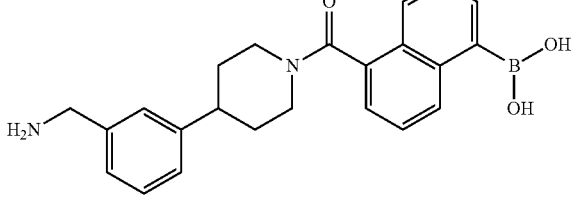 | | Hetero |
| 146 | 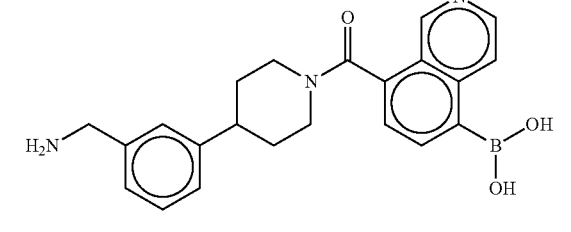 | | Hetero |
| 147 | 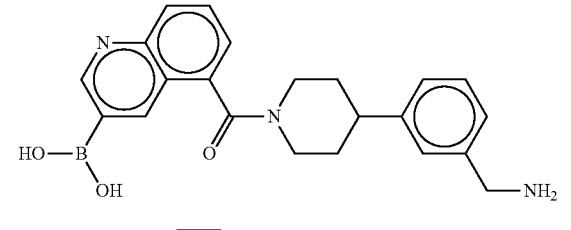 | | Hetero |
| 148 | 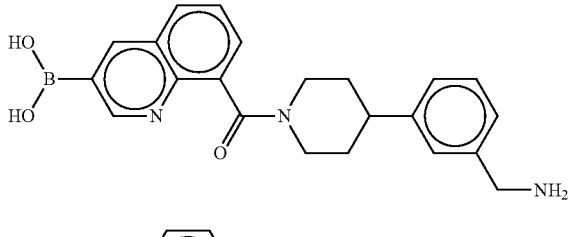 | | Hetero |
| 149 | 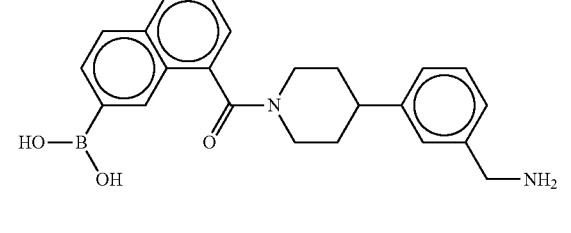 | | Hetero |

-continued

| No. | Structure | Compound Code | Homo/Hetero-Dimerizing Monomer |
|---|---|---|---|
| 150 | 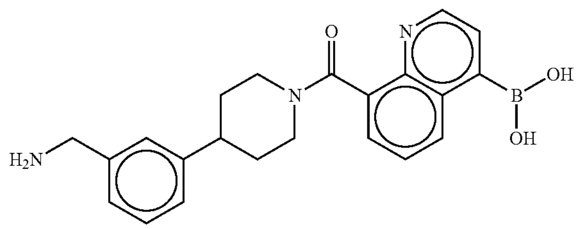 | | Hetero |
| 151 | 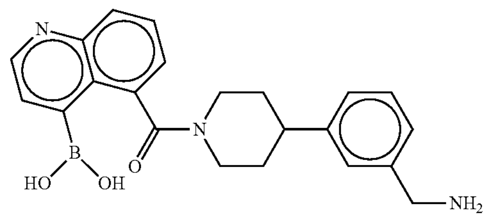 | | Hetero |
| 152 | 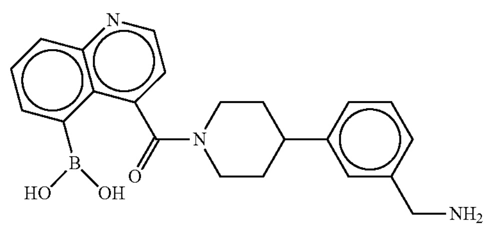 | | Hetero |
| 153 | 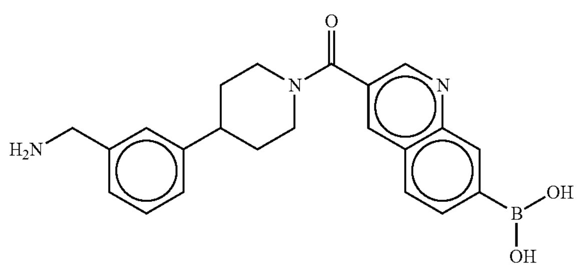 | | Hetero |
| 154 | 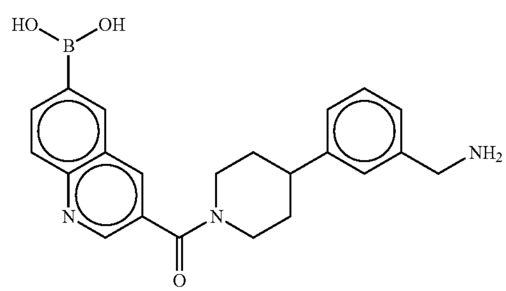 | | Hetero |
| 155 | 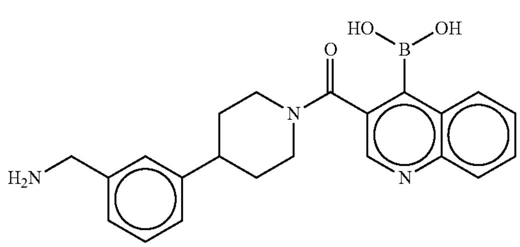 | | Hetero |

-continued

| No. | Structure | Compound Code | Homo/Hetero-Dimerizing Monomer |
|---|---|---|---|
| 156 | 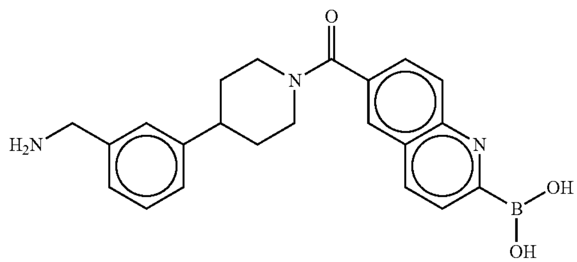 | | Hetero |
| 157 | 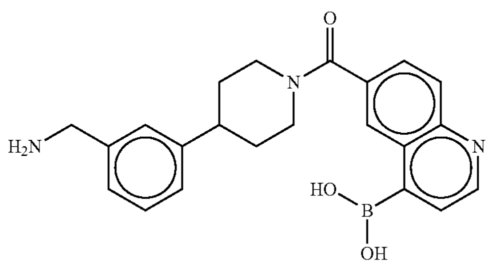 | | Hetero |
| 158 | 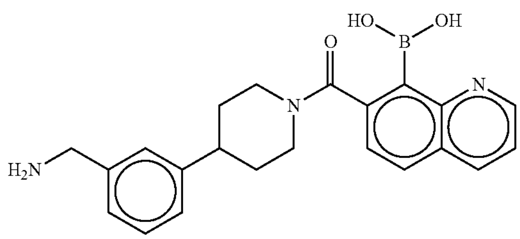 | | Hetero |
| 159 | 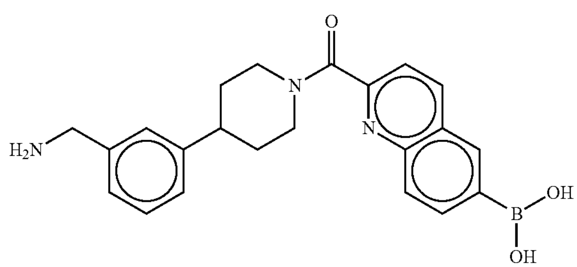 | | Hetero |
| 160 | 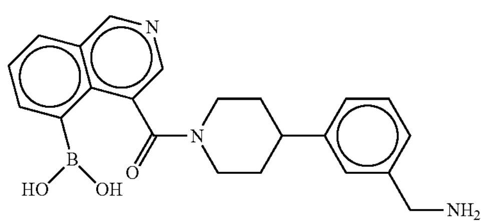 | | Hetero |
| 161 | 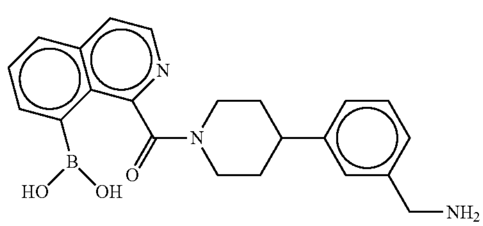 | | Hetero |

-continued

| No. | Structure | Compound Code | Homo/Hetero-Dimerizing Monomer |
|---|---|---|---|
| 162 | 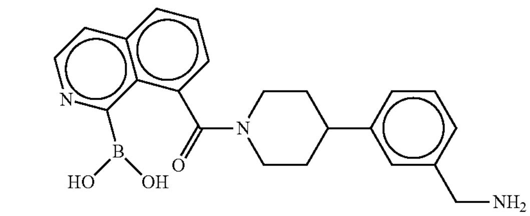 | | Hetero |
| 163 | 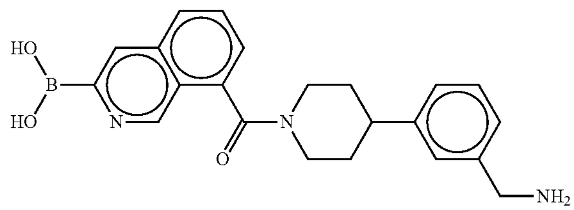 | | Hetero |
| 164 | 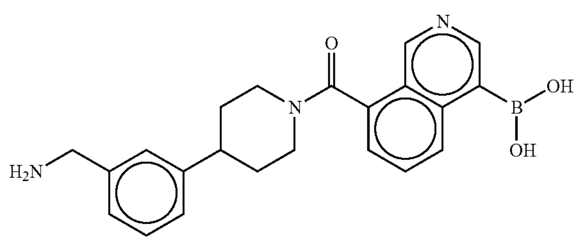 | | Hetero |
| 165 | 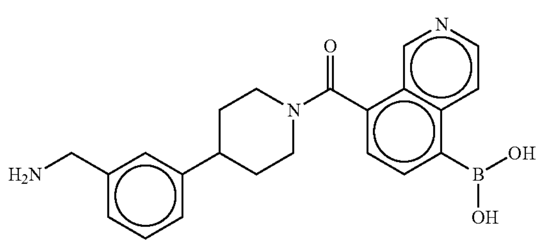 | | Hetero |
| 166 | 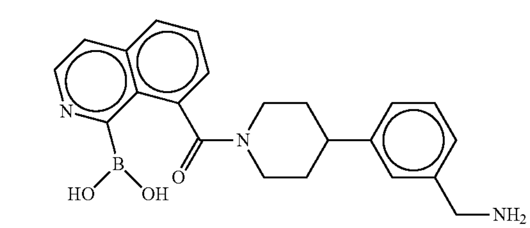 | | Hetero |
| 167 | 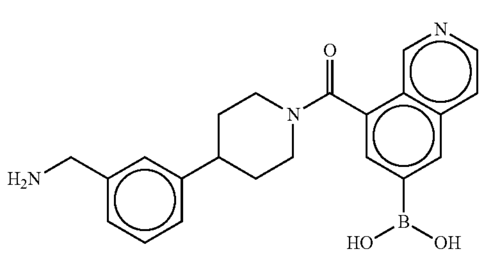 | | Hetero |

-continued

| No. | Structure | Compound Code | Homo/Hetero-Dimerizing Monomer |
|---|---|---|---|
| 168 | 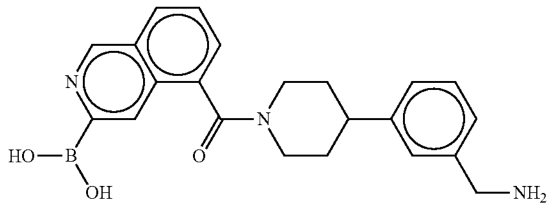 | | Hetero |
| 169 | 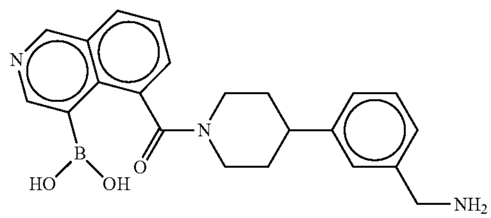 | | Hetero |
| 170 | 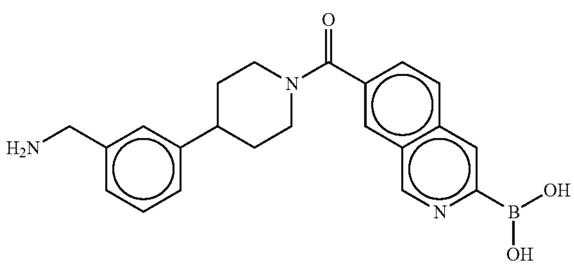 | | Hetero |
| 171 | 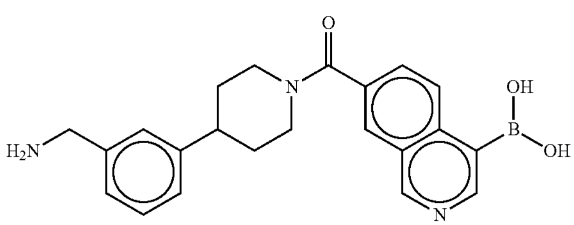 | | Hetero |
| 172 | 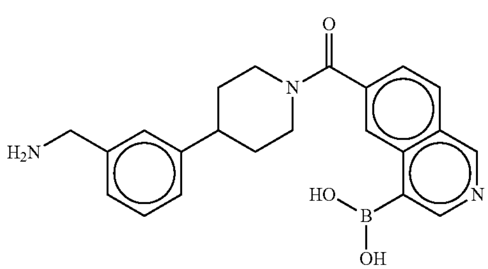 | | Hetero |
| 173 | 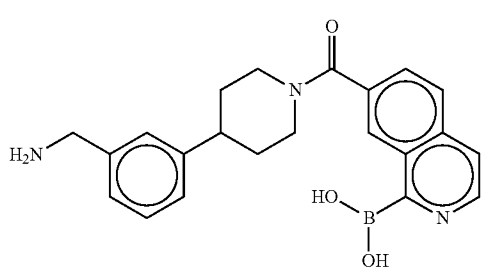 | | Hetero |

| No. | Structure | Compound Code | Homo/Hetero-Dimerizing Monomer |
|---|---|---|---|
| 174 | 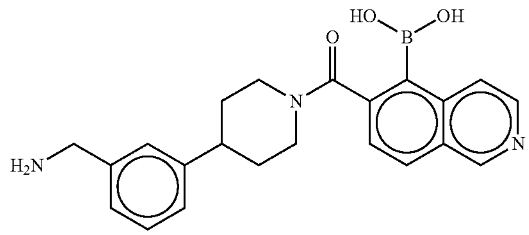 | | Hetero |
| 175 | 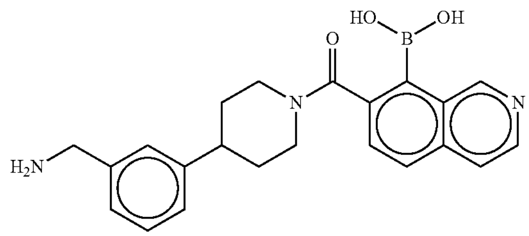 | | Hetero |
| 176 | 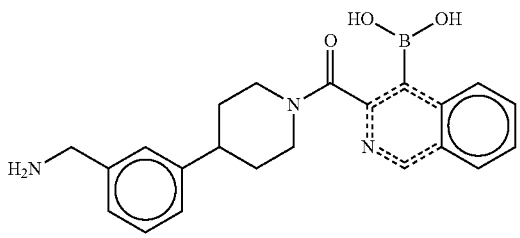 | | Hetero |
| 177 | 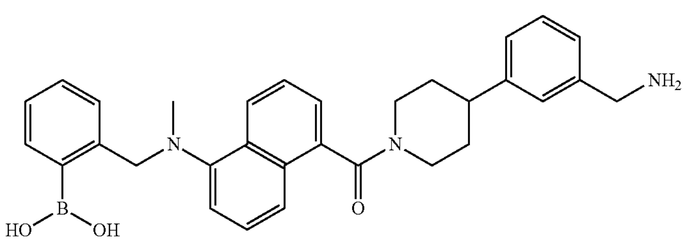 [SMILES: CN(Cc1ccccc1B(O)O)c1cccc2c(C(=O)N3CCC(c4cccc(CN)c4)CC3)cccc12] | T143 | Hetero |
| 178 | 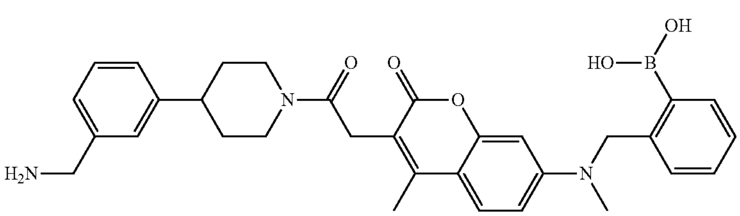 [SMILES: Cc1c(CC(=O)N2CCC(c3cccc(CN)c3)CC2)c(=O)oc2cc(N(C)Cc3ccccc3B(O)O)ccc12] | T144 | Hetero |
| 179 | 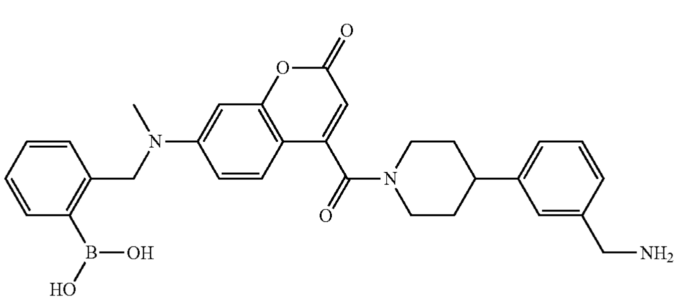 [SMILES: CN(Cc1ccccc1B(O)O)c1ccc2c(C(=O)N3CCC(c4cccc(CN)c4)CC3)cc(=O)oc2c1] | | Hetero |

-continued
| No. | Structure | Compound Code | Homo/Hetero-Dimerizing Monomer |
|---|---|---|---|
| 180 | 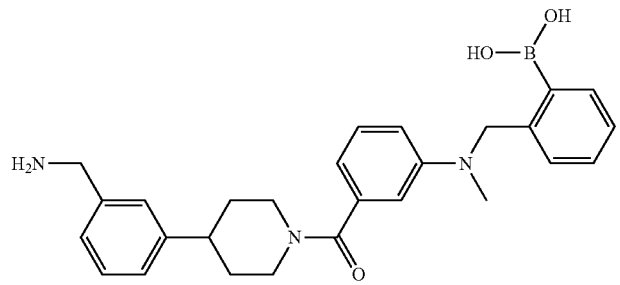 [SMILES: CN(Cc1ccccc1B(O)O)c1cccc(C(=O)N2CCC(c3cccc(CN)c3)CC2)c1] | T146 | Hetero |
| 181 | 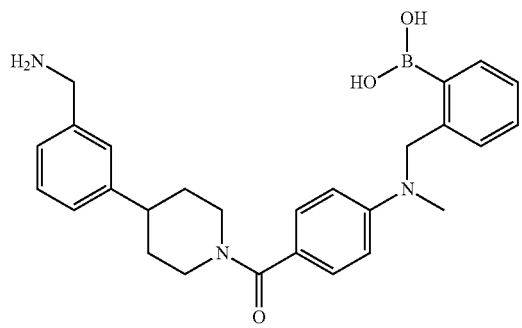 [SMILES: CN(Cc1ccccc1B(O)O)c1ccc(C(=O)N2CCC(c3cccc(CN)c3)CC2)cc1] | T147 | Hetero |
| 182 | 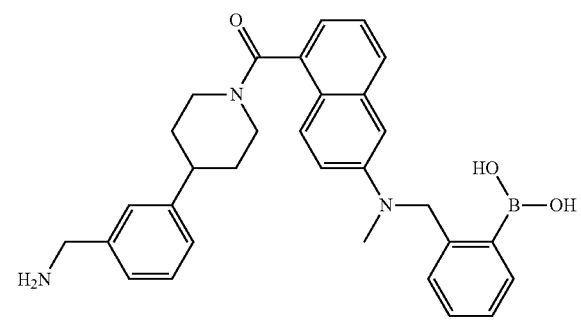 [SMILES: CN(Cc1ccccc1B(O)O)c1ccc2c(C(=O)N3CCC(c4cccc(CN)c4)CC3)cccc2c1] | T154 | Hetero |
| 183 | 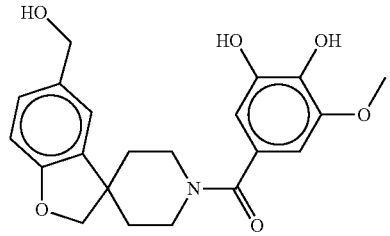 | Taget-104-Spiro | Hetero |
| 184 | 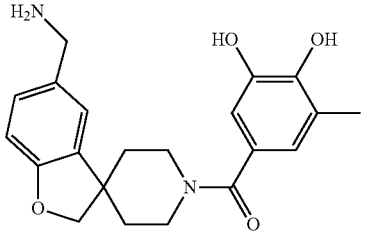 [SMILES: Cc1cc(C(=O)N2CCC3(CC2)COc2ccc(CN)cc23)cc(O)c1O] | T-105-Spiro | Hetero |

-continued

| No. | Structure | Compound Code | Homo/Hetero-Dimerizing Monomer |
|---|---|---|---|
| 185 | 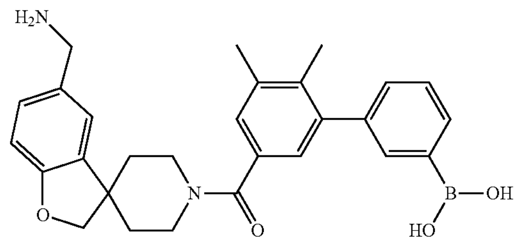 [SMILES: Cc1cc(C(=O)N2CCC3(CC2)COc2ccc(CN)cc23)cc(-c2cccc(B(O)O)c2)c1C] | T-107-Spiro | Hetero |
| 186 | 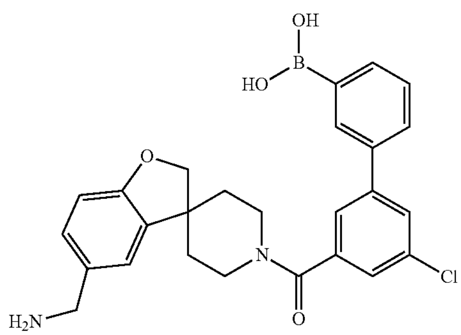 [SMILES: NCc1ccc2c(c1)C1(CCN(C(=O)c3cc(Cl)cc(-c4cccc(B(O)O)c4)c3)CC1)CO2] | T-108-Spiro | Hetero |
| 187 | 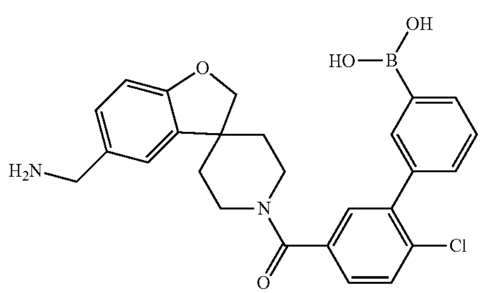 [SMILES: NCc1ccc2c(c1)C1(CCN(C(=O)c3ccc(Cl)c(-c4cccc(B(O)O)c4)c3)CC1)CO2] | T-109-Spiro | Hetero |
| 188 | 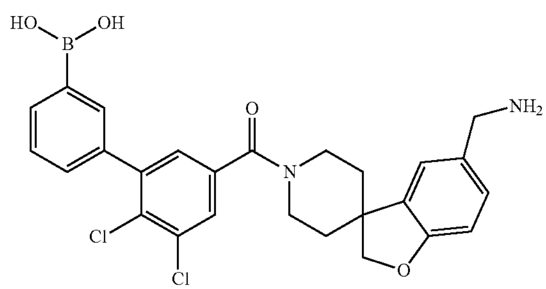 [SMILES: NCc1ccc2c(c1)C1(CCN(C(=O)c3cc(Cl)c(Cl)c(-c4cccc(B(O)O)c4)c3)CC1)CO2] | T-110-Spiro | Hetero |
| 189 | 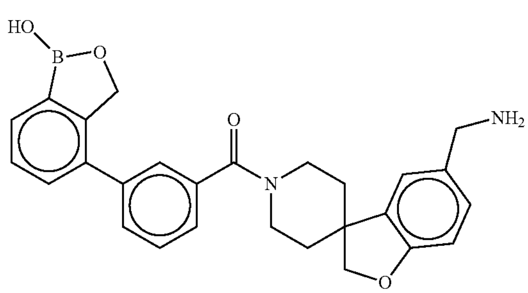 | T-112-Spiro | Hetero |

-continued
| No. | Structure | Compound Code | Homo/Hetero-Dimerizing Monomer |
|---|---|---|---|
| 190 | 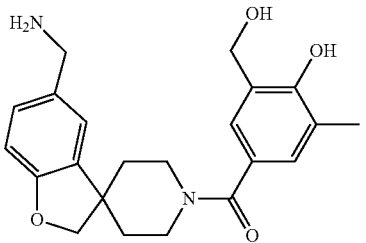 [SMILES: Cc1cc(C(=O)N2CCC3(CC2)COc2ccc(CN)cc23)cc(CO)c1O] | T-113-Spiro | Hetero |
| 191 | 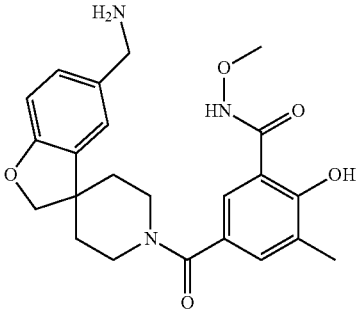 [SMILES: CONC(=O)c1cc(C(=O)N2CCC3(CC2)COc2ccc(CN)cc23)cc(C)c1O] | T-114-Spiro | Hetero |
| 192 | 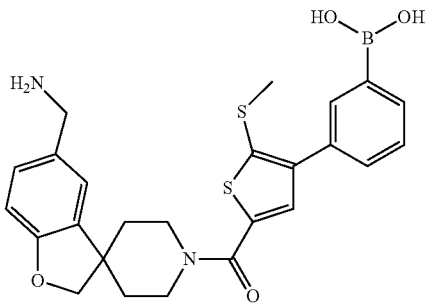 [SMILES: CSc1sc(C(=O)N2CCC3(CC2)COc2ccc(CN)cc23)cc1-c1cccc(B(O)O)c1] | T-116-Spiro | Hetero |
| 193 | 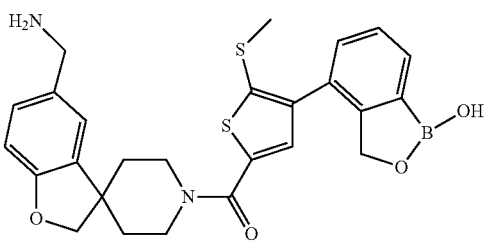 [SMILES: CSc1sc(C(=O)N2CCC3(CC2)COc2ccc(CN)cc23)cc1-c1cccc2c1COB2O] | T-117-Spiro | Hetero |
| 194 | 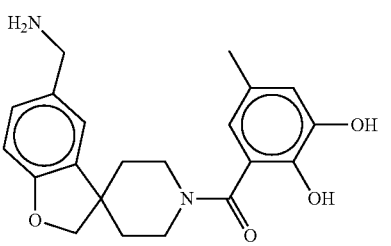 | T-123-Spiro | Hetero |

-continued

| No. | Structure | Compound Code | Homo/Hetero-Dimerizing Monomer |
|---|---|---|---|
| 195 | 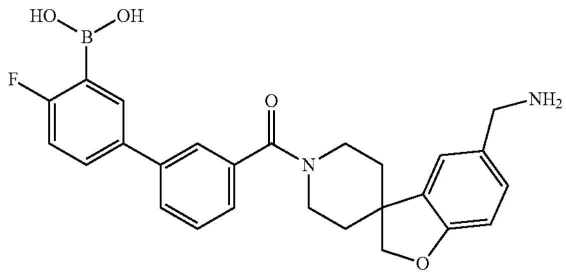 [SMILES: NCc1ccc2c(c1)C1(CCN(C(=O)c3cccc(-c4ccc(F)c(B(O)O)c4)c3)CC1)CO2] | T-131-Spiro | Hetero |
| 196 | 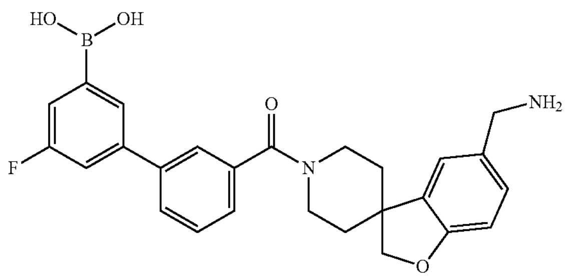 [SMILES: NCc1ccc2c(c1)C1(CCN(C(=O)c3cccc(-c4cc(F)cc(B(O)O)c4)c3)CC1)CO2] | T-132-Spiro | Hetero |
| 197 | 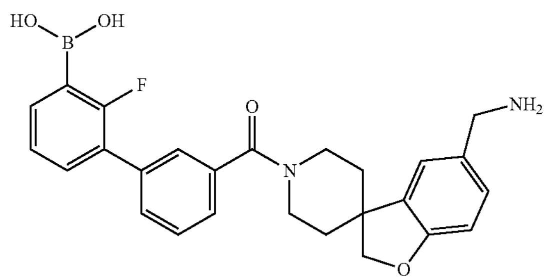 [SMILES: NCc1ccc2c(c1)C1(CCN(C(=O)c3cccc(-c4cccc(B(O)O)c4F)c3)CC1)CO2] | T-133-Spiro | Hetero |
| 198 | 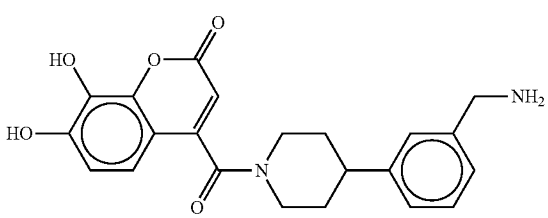 | T-96 | Hetero |
| 199 | 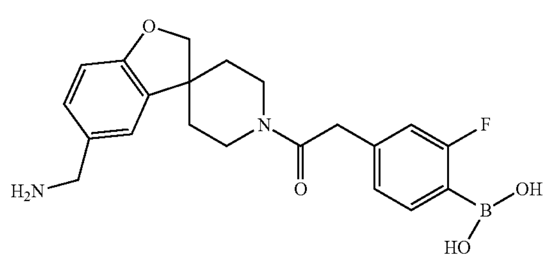 [SMILES: NCc1ccc2c(c1)C1(CCN(C(=O)Cc3ccc(B(O)O)c(F)c3)CC1)CO2] | T54BA-Spiro | Hetero |
| 200 | 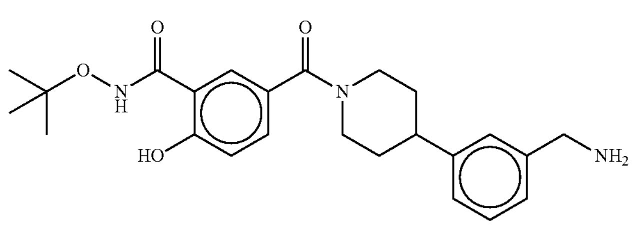 | T92OTB | Hetero |

-continued

| No. | Structure | Compound Code | Homo/Hetero-Dimerizing Monomer |
|---|---|---|---|
| 201 | 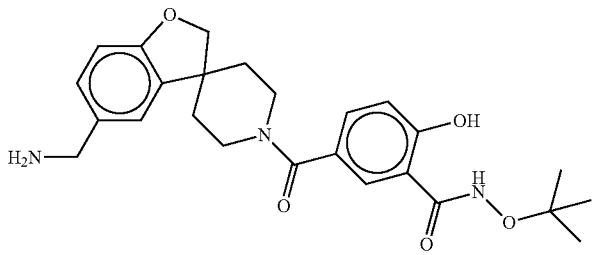 | T92OTBSpiro | Hetero |
| 202 | 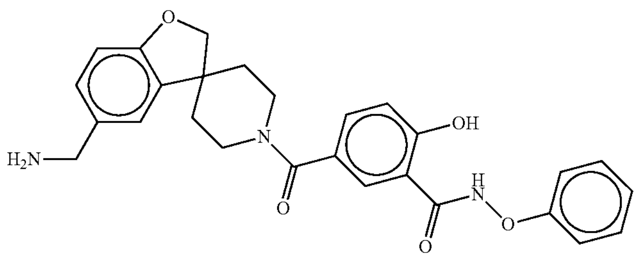 | T92PIISpiro | Hetero |
| 203 | 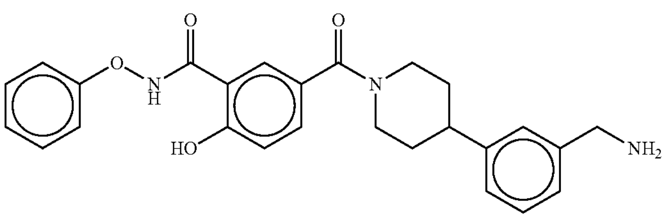 | T92OPII | Hetero |
| 204 | 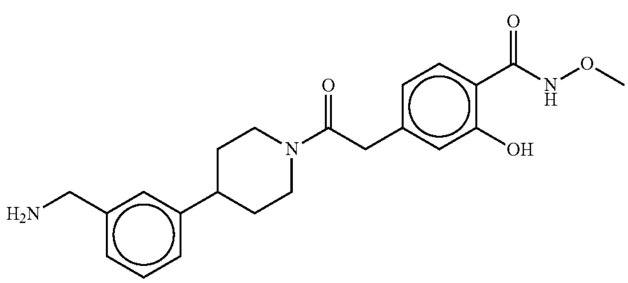 | T85a | Hetero |
| 205 | 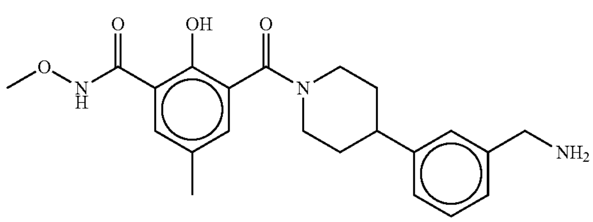 | T136A | Hetero |
| 206 | 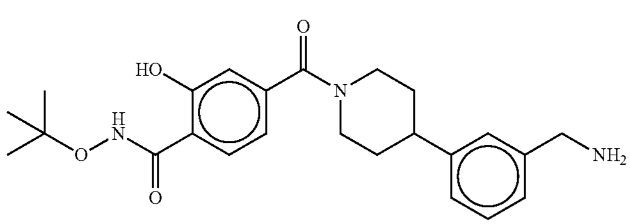 | T75AOTB | Hetero |

-continued

| No. | Structure | Compound Code | Homo/Hetero-Dimerizing Monomer |
|---|---|---|---|
| 207 | 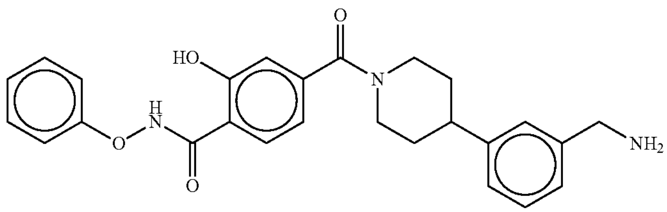 | T75AP | Hetero |
| 208 | 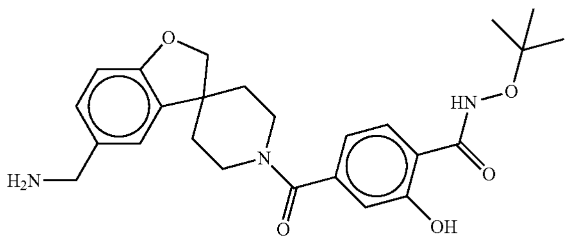 | T75AOTBSpiro | Hetero |
| 209 | 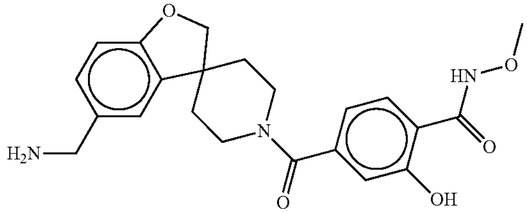 | T75ASpiro | Hetero |
| 210 | 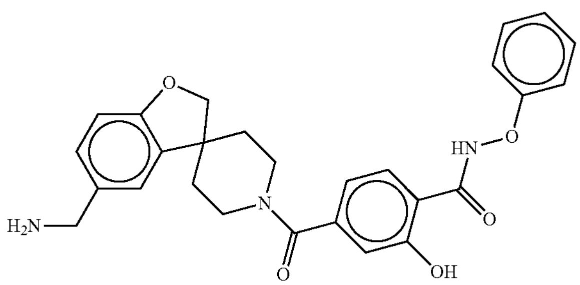 | T75APSpiro | Hetero |
| 211 | 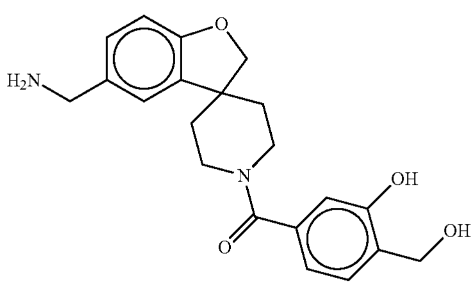 | T74Spiro | Hetero |
| 212 | 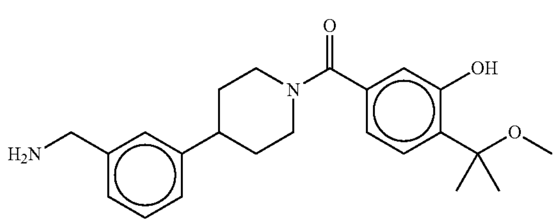 | T126MonoMethyl | Hetero |

-continued

| No. | Structure | Compound Code | Homo/Hetero-Dimerizing Monomer |
|---|---|---|---|
| 213 | 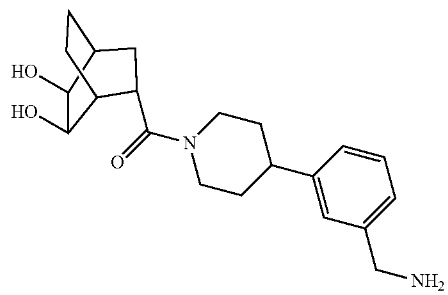 [SMILES: NCc1cccc(C2CCN(C(=O)C3CC4CCC3C(O)C4O)CC2)c1] | T142ENDOANTI | Hetero |
| 214 | 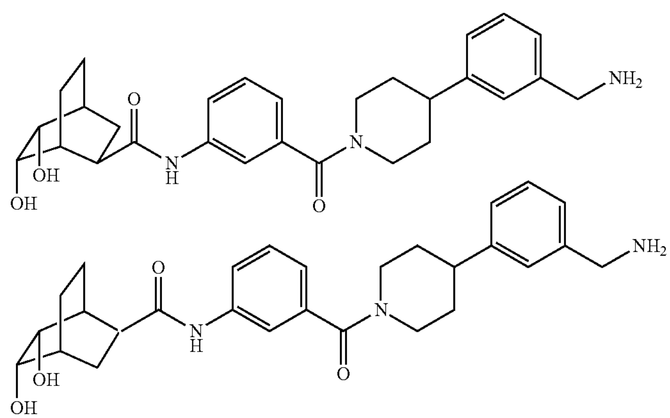 | T141EXOANTI | Hetero |
| 215 | 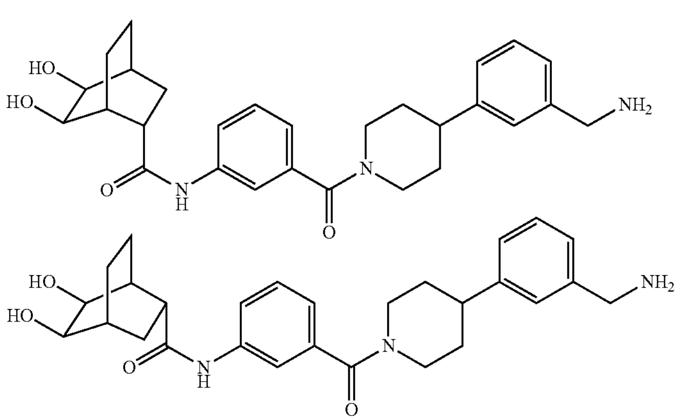 | T141ENDOANTI | Hetero |

-continued

| No. | Structure | Compound Code | Homo/Hetero-Dimerizing Monomer |
|---|---|---|---|
| 216 | 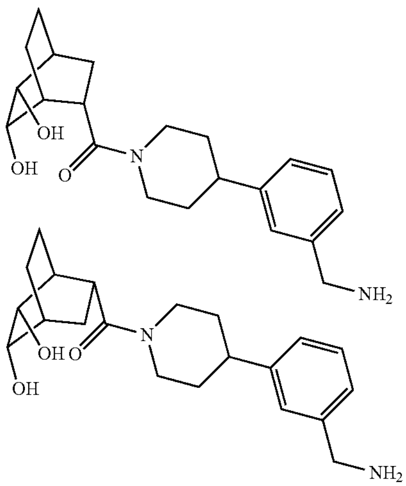 | T142ENDOSYN | Hetero |
| 217 | 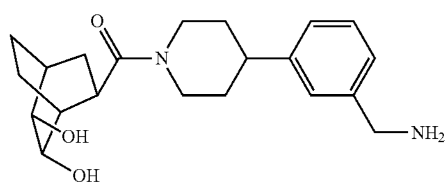 [SMILES: NCc1cccc(C2CCN(C(=O)C3CC4CCC3C(O)C4O)CC2)c1] | T142EXOANTI | Hetero |
| 218 | 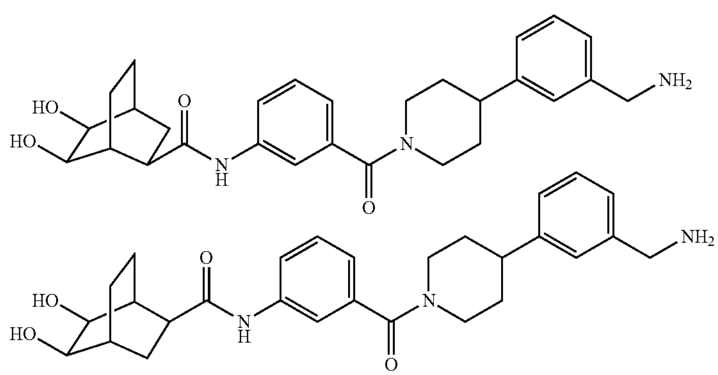 | T141EXOSYN | Hetero |
| 219 | 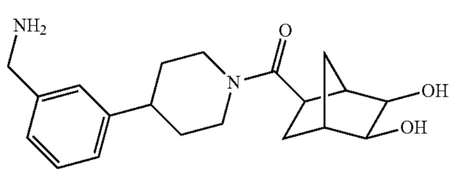 [SMILES: NCc1cccc(C2CCN(C(=O)C3CC4CC3C(O)C4O)CC2)c1] | T140RACEENDO | Hetero |
| 220 | 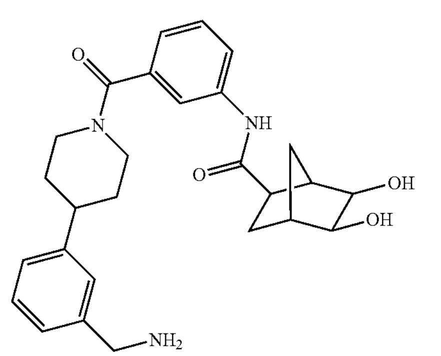 [SMILES: NCc1cccc(C2CCN(C(=O)c3cccc(NC(=O)C4CC5CC4C(O)C5O)c3)CC2)c1] | T139ENDO | Hetero |

| No. | Structure | Compound Code | Homo/Hetero-Dimerizing Monomer |
|---|---|---|---|
| 221 | 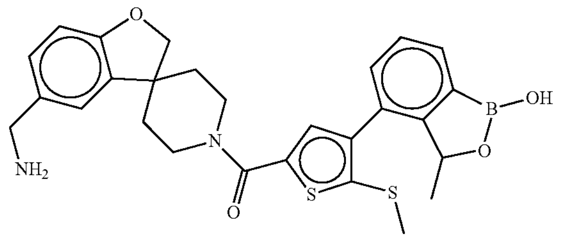 | T117Gem MonoMethylSpiro | Hetero |
| 222 | 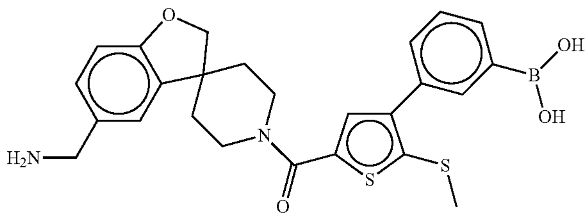 | T117MethylSpiro | Hetero |
| 223 | 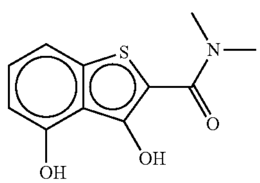 | T163 | Hetero |
| 224 | 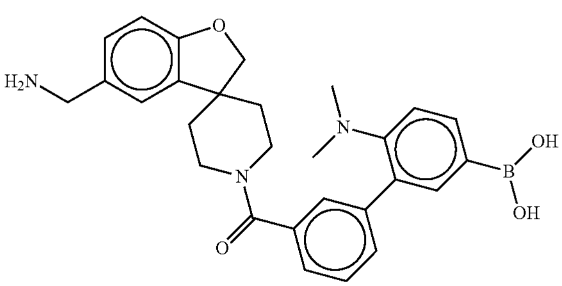 | T155-Spiro | Hetero |
| 225 | 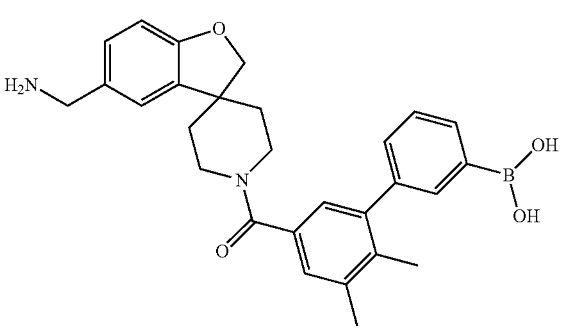 [SMILES: Cc1cc(C(=O)N2CCC3(CC2)COc2ccc(CN)cc23)cc(-c2cccc(B(O)O)c2)c1C] | T107-Spiro | Hetero |

Example 28. Synthesis of Tryptase Inhibitors with Boronic Acid Functionality

Final targets with boronic acid functionality were synthesized. These compounds were synthesized by two approaches. In approach-1 the aryl boronic acids or their pinacolato boronate esters with carboxylic acid were coupled to protected core (Core-1 or Core-4 shown in synthetic scheme). Product was deprotected to obtain the target boronic acids. In approach-2 desired halo aryl carboxylic acids were first coupled to the appropriate protected core. The boronate ester/acid was introduced on the coupled product and deprotected to give the desired target boronic acids. The required aryl halo carboxylic acids in step-1 of both the approaches were either procured commercially or synthesized in-house by known methods in the literature. The details of the synthesis of these targets are given below.

Approach-1

Required aryl boronic acids or their pinacolato boronate esters with carboxylic acid groups were synthesized and coupled with protected core (Core-1 or Core-4 shown in synthetic scheme). Coupled products were deprotected. During deprotection reaction of intermediates containing boronate ester functionality, either partial or complete hydrolysis of boronate esters to boronic acids occurred. Mixture of boronate ester and boronic acid was then subjected to purification by prep HPLC under acidic condition during which, remainder of the boronate ester was converted to boronic acid.

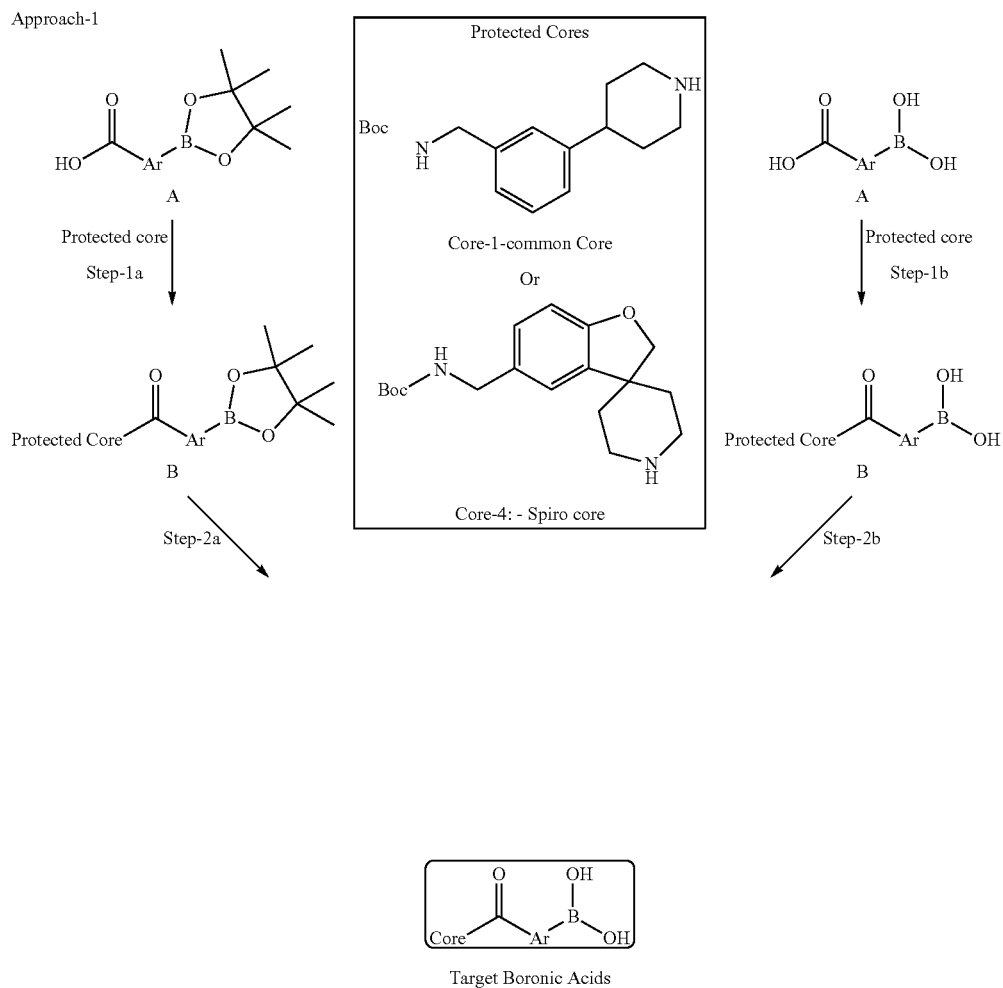

Scheme 29

Synthesis of Boronate Ester or Boronic Acid Precursors (A)

The details of intermediates sourced/synthesized as per literature methods/synthesized by adapted methods are given below.

| Code | Structure |
|---|---|
| A-54 | 2-(3-fluoro-4-(4,4,5,5-tetramethyl-1,3,2-dioxaborolan-2-yl)phenyl)acetic acid |
| A-107 | 5,6-dimethyl-3'-(4,4,5,5-tetramethyl-1,3,2-dioxaborolan-2-yl)-[1,1'-biphenyl]-3-carboxylic acid |
| A-109 | 6-chloro-3'-(4,4,5,5-tetramethyl-1,3,2-dioxaborolan-2-yl)-[1,1'-biphenyl]-3-carboxylic acid |
| A-116 | 4-(3-boronophenyl)-5-(methylthio)thiophene-2-carboxylic acid |
| A-131 | 4'-fluoro-3'-(4,4,5,5-tetramethyl-1,3,2-dioxaborolan-2-yl)-[1,1'-biphenyl]-3-carboxylic acid |
| A-132 | 3'-fluoro-5'-(4,4,5,5-tetramethyl-1,3,2-dioxaborolan-2-yl)-[1,1'-biphenyl]-3-carboxylic acid |
| A-133 | 2'-fluoro-3'-(4,4,5,5-tetramethyl-1,3,2-dioxaborolan-2-yl)-[1,1'-biphenyl]-3-carboxylic acid |
| A-143 | 5-((2-boronobenzyl)(methyl)amino)-1-naphthoic acid |
| A-146 | 3-((2-boronobenzyl)(methyl)amino)benzoic acid |
| A-147 | 4-((2-boronobenzyl)(methyl)amino)benzoic acid |
| A-154 | 6-((2-boronobenzyl)(methyl)amino)-1-naphthoic acid |
| A-155 | 5'-borono-2'-(dimethylamino)-[1,1'-biphenyl]-3-carboxylic acid |

| Code | Structure |
|---|---|
| A-156 | 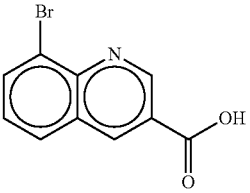<br>8-bromoquinoline-3-carboxylic acid<br>Available commercially |

Synthesis of 2-(3-fluoro-4-(4, 4, 5, 5-tetramethyl-1, 3, 2-dioxaborolan-2-yl) phenyl) acetic acid (A-54)

Scheme 30

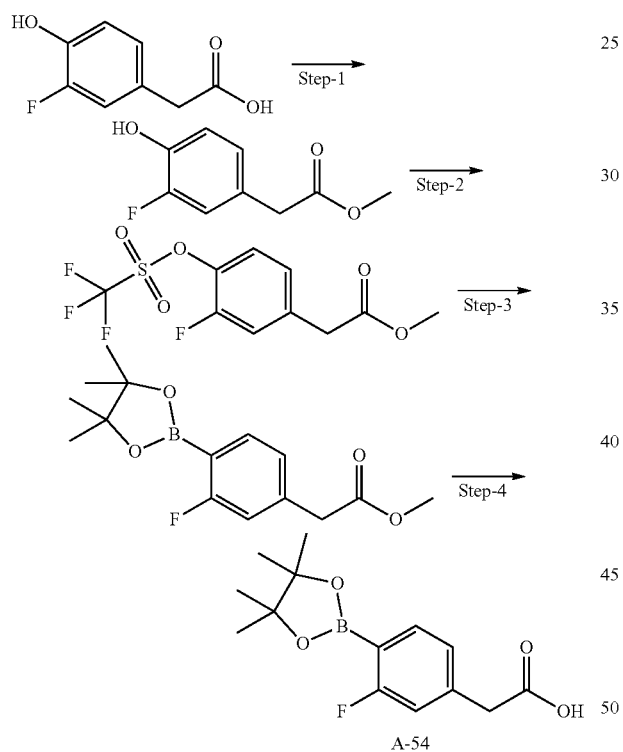

Experimental Procedures

Step-1: To an ice-cold solution of 2-(3-fluoro-4-hydroxyphenyl) acetic acid (2.0 g, 11.75 mmol) in MeOH (40 mL), thionyl chloride (1.7 mL, 23.51 mmol) was added drop wise. The reaction mixture was warmed to room temperature and refluxed for 5 h. The reaction mixture was concentrated in vacuo and the residue obtained was diluted with ethyl acetate, washed with water and saturated sodium bicarbonate solution. The organic layer was washed with brine, dried over anhydrous sodium sulfate, filtered and concentrated under reduced pressure to give a residue which was purified by silica gel column chromatography (0-10% Ethyl acetate in Hexane) to yield methyl 2-(3-fluoro-4-hydroxyphenyl) acetate. White solid;

Yield: 2.1 g, (95%).

$^1$H NMR (400 MHz, CD$_3$OD): δ 7.04-6.92 (m, 1H), 6.90-6.80 (m, 2H), 4.85 (bs, 1H), 3.65 (s, 3H), 3.52 (s, 2H)

Step-2: To an ice-cold solution of methyl 2-(3-fluoro-4-hydroxyphenyl) acetate (2.1 g, 11.41 mmol) in pyridine (40 mL), trifluoromethane sulphonic anhydride (5.7 mL, 34.23 mmol) was added drop wise. The reaction mixture was warmed to room temperature over the period of 3 h. The reaction mixture was concentrated under vacuo and the residue obtained was dried to afford methyl 2-(3-fluoro-4-(((trifluoromethyl) sulfonyl) oxy) phenyl) acetate. White solid;

Yield: 3.3 g, (92%)

$^1$H NMR (400 MHz, CD$_3$OD): δ 7.48-7.32 (m, 2H), 7.28-7.18 (m, 1H), 3.75 (s, 2H), 3.70 (s, 3H)

Step-3: To a solution of methyl 2-(3-fluoro-4-(((trifluoromethyl)sulfonyl)oxy)phenyl)acetate (3.3 g, 10.43 mmol) in Dioxane (70 mL) was added Bis(Pinacolato)diborane (3.17 g, 12.52 mmol) and the reaction mixture was degassed under argon stream. To this solution, dichlorobis (triphenylphosphine) palladium (11) (0.25 g, 0.31 mmol), 1, 1'-Bis (diphenylphosphino) ferrocene (0.17 g, 0.31 mmol) and potassium acetate (3.07 g, 31.3 mmol) were added and the mixture was stirred at 90° C. for 15 h under argon. After completion of reaction (TLC), the reaction mixture was cooled to room temperature and diluted with ethyl acetate, washed with water followed by brine, dried over anhydrous sodium sulfate and evaporated under reduced pressure to give a residue which was purified by silica gel column chromatography on silica gel (0-30% Ethyl acetate in Hexane) to give methyl 2-(3-fluoro-4-(4,4,5,5-tetramethyl-1,3,2-dioxaborolan-2-yl)phenyl)acetate. White solid;

Yield: 1.5 g (49%)

$^1$H NMR (400 MHz, CDCl$_3$): δ 7.40-7.30 (m, 1H), 7.18-7.08 (m, 2H), 4.77 (s, 2H), 3.73 (s, 3H), 1.35 (s, 12H)

Step-4: To a solution of methyl 2-(3-fluoro-4-(4,4,5,5-tetramethyl-1,3,2-dioxaborolan-2-yl)phenyl)acetate (0.25 g, 0.85 mmol) in THF (15 mL) was added LiOH (0.07 g, 1.69 mmol) and the resulting solution was stirred at room temperature for 5 h. The reaction mixture was concentrated in vacuo, residue acidified with 10% citric acid solution and extracted with ethyl acetate. The ethyl acetate layer was dried over anhydrous sodium sulfate, filtered, concentrated under reduced pressure and triturated with diethyl ether to yield the 2-(3-fluoro-4-(4,4,5,5-tetramethyl-1,3,2-dioxaborolan-2-yl)phenyl)acetic acid. White solid;

Yield: 0.16 g (67%)

MS (ES+): m/z=281 [MH+]

Synthesis of (5'-(4-(3-(amino methyl) phenyl) piperidine-1-carbonyl)-2', 3'-dimethyl-[1, 1'-biphenyl]-3-yl) boronic acid (A-107)

Scheme 31

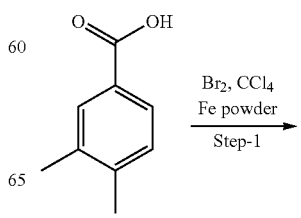

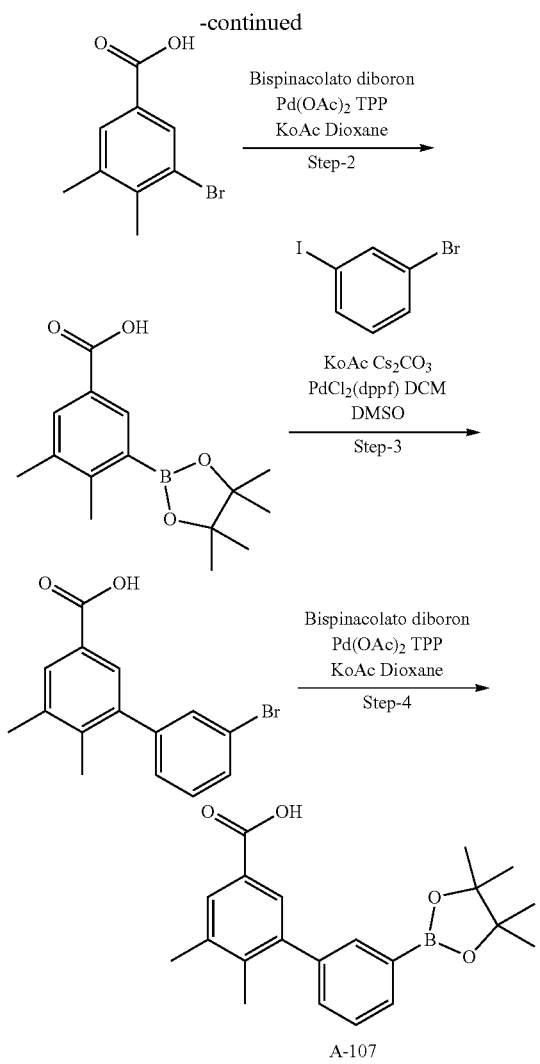

A-107

Experimental Procedures

Step-1: To a mixture of bromine (20.5 g, 128.3 mmol) in CCl4 (225 mL) iron powder (1.98 g, 34.9 mmol) was added and cooled to 0° C. A solution of 3, 4 dimethyl benzoic acid (3.5 g, 23.3 mmol in 70 mL CCl4) was added drop wise and the reaction mixture was allowed to stir at room temperature overnight. TLC (Mobile phase 30% ethyl acetate in n-hexane) indicated absence of starting material (RF 0.4) and product formation ($R_f$-0.35). The reaction mixture was quenched with sodium thiosulphate at 0° C. and stirred for 15 min. The reaction mixture was filtered through celite. The organic layer was washed with brine, dried over sodium sulphate, filtered, and concentrated in vacuo to give 3-bromo-4, 5-dimethylbenzoic acid as a yellow solid. NMR is in agreement with the desired structure. Yield: (2.8 g, 52.8%).

$^1$H NMR (400 MHz, CDCl$_3$): δ 4.04 (s, 3H), 7.12 (d, J=8.4 Hz, 1H), 8.07-8.10 (m, 2H), 9.90 (brs, 1H).

Step-2: To a degassed solution of palladium acetate (0.98 g, 4.37 mmol) Triphenyl phosphine (4.58 g, 17.5 mmol) in degassed 1,4 Dioxane (30 mL) was added to a degassed solution of 3-bromo-4,5-dimethylbenzoic acid (1 g, 4.37 mmol), Bispinacolato diborane (11 g, 43.7 mmol) and potassium acetate (1.28 g, 13.11 mmol in 70 mL Dioxane). The reaction mixture was heated at 90° C. for 16 h. TLC (Mobile phase 30% ethyl acetate in n-hexane) indicated absence of starting material (RF 0.35) and product formation (Rf-0.45). The reaction mixture was filtered through celite and concentrated. The compound was extracted in ethyl acetate, washed with water. The organic layer was separated, dried over sodium sulphate, filtered, concentrated in vacuo and the crude residue purified by column chromatography on silica gel using hexane-ethyl acetate as eluent to give 3,4-dimethyl-5-(4,4,5,5-tetramethyl-1,3,2-dioxaborolan-2-yl)benzoic acid. LCMS is in agreement with the desired structure.

Yield: (0.61 g 50.8%).

MS: (ES+); m/z=277 [MH+]

Step-3: A solution of 3,4-dimethyl-5-(4,4,5,5-tetramethyl-1,3,2-dioxaborolan-2-yl)benzoic acid (0.61 g, 2.21 mmol) 1-bromo-3-iodobenzene (0.62 g, 2.21 mmol), potassium acetate (0.28 g, 2.87 mmol), cesium carbonate (2.15 g, 6.63 mmol) in degassed DMSO (10 mL) was degassed for 15 min. PdCl$_2$ (dppf).DCM adduct (0.36 g, 0.44 mmol) was added and the reaction mixture was further degassed for 15 min. The reaction mixture was heated at 90° C. overnight. TLC (Mobile phase 20% ethyl acetate in hexane) indicated absence of starting material (Rf 0.45) and product formation (Rf 0.3). The reaction mixture was quenched with water and the compound was extracted in ethyl acetate. The organic layer was separated, dried over sodium sulphate, filtered, concentrated in vacuo and purified by column chromatography on silica gel eluting with hexanes-ethyl acetate as eluent to give 3'-bromo-5,6-dimethyl-[1,1'-biphenyl]-3-carboxylic acid.

Yield: (0.32 g, 47.7%).

MS (ES+): m/z=305/307 [MH+]

Step-4: To a degassed solution of palladium acetate (0.23 g, 1.05 mmol) Triphenyl phosphine (1.1 g, 4.21 mmol) in degassed 1,4 Dioxane (20 mL) was added to a degassed solution of 3'-bromo-5,6-dimethyl-[1,1'-biphenyl]-3-carboxylic acid (0.32 g, 1.05 mmol), Bispinacolato diborane (2.66 g, 10.5 mmol) and potassium acetate (0.3 g, 3.15 mmol in 30 mL Dioxane). The reaction mixture was heated at 90° C. for 16 h. TLC (Mobile phase 30% ethyl acetate in n-hexane) indicated absence of starting material (RF 0.5) and product formation (Rf-0.55). The reaction mixture was filtered through celite and concentrated in vacuo. The compound was extracted in ethyl acetate, washed with water. The organic layer was separated, dried over sodium sulphate, filtered, concentrated in vacuo and purified by column chromatography on silica gel eluting with hexane-ethyl acetate as eluent to give 5, 6-dimethyl-3'-(4,4,5,5-tetramethyl-1,3,2-dioxaborolan-2-yl)-[1,1'-biphenyl]-3-carboxylic acid. Purified material still contained pinacolato boronate peaks. This material was used in the next step without further purification.

Yield: (0.37 g, Crude)

$^1$H NMR (400 MHz, DMSO-d6): δ 1.25 (t, J=7.0 Hz, 3H), 4.10-4.23 (q, J=7 Hz, 2H), 6.57 (d, J=16 Hz, 1H), 6.91 (d, J=8.4 Hz, 1H), 7.55 (d, J=16 Hz, 1H), 7.74-7.80 (dd, J=2.0 and 8.6 Hz, 1H), 8.06 (s, 1H), 8.28 (d, J=2 Hz, 1H), 8.50 (s, 1H), 13.5 (s, 1H).

377

Synthesis of 6-chloro-3'-(4, 4, 5, 5-tetramethyl-1, 3, 2-dioxaborolan-2-yl)-[1,1'-biphenyl]-3-carboxylic acid (A-109)

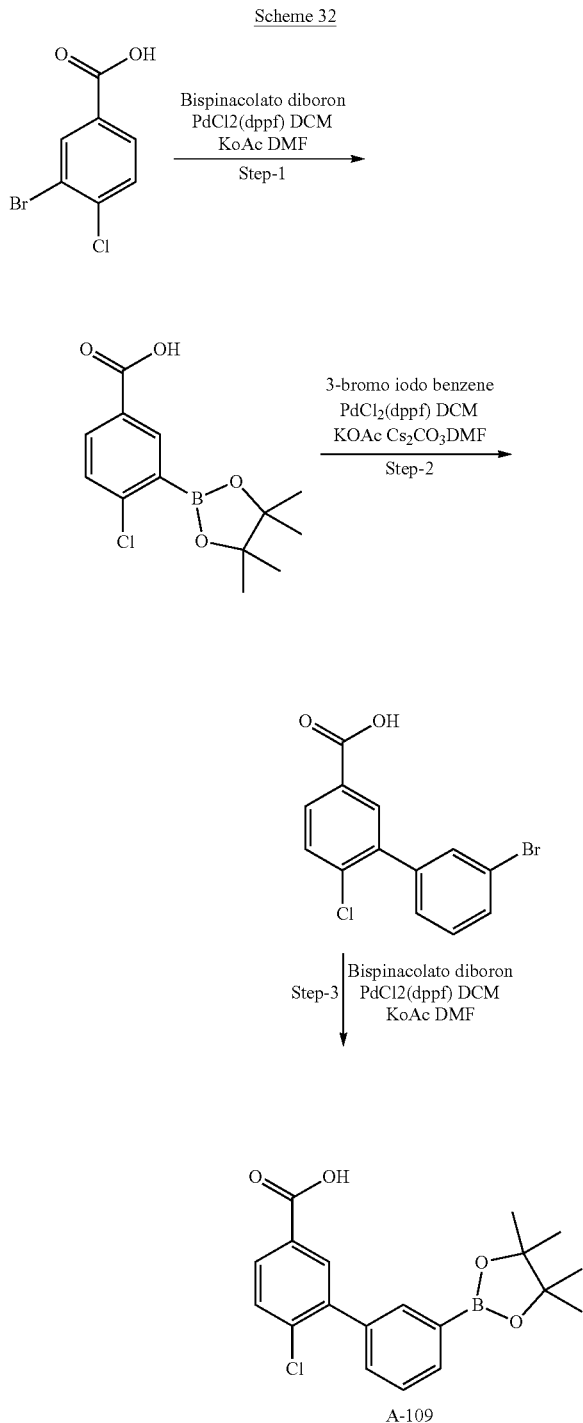

Experimental Procedures

Step-1: A solution of 3-bromo-4-chlorobenzoic acid (1.5 g, 6.43 mmol), potassium acetate (3.15 g, 32.1 mmol), and Bispinacolato diborane (8.14 g, 32.1 mmol) in degassed DMF (15 mL) was degassed for 15 min. PdCl2 (dppf) DCM adduct (0.52 g, 0.64 mmol) was added and the reaction mixture was further degassed for 15 min. The reaction mixture was heated at 90° C. overnight. TLC (Mobile phase 50% ethyl acetate in n-hexane) indicated absence of starting material (Rf 0.2) and product formation (Rf-0.5). The reaction mixture was concentrated in vacuo, diluted with 2N NaOH and washed with ethyl acetate. The aqueous layer was acidified with 1N HCl and the compound was extracted in ethyl acetate. The organic layer was separated, dried over sodium sulphate, filtered, concentrated in vacuo, and the crude was purified by column chromatography on silica gel eluting with hexanes-ethyl acetate to give 4-chloro-3-(4,4,5,5-tetramethyl-1,3,2-dioxaborolan-2-yl)benzoic acid as white solid.

Yield: (1.4 g 77%).

$^1$H NMR (400 MHz, DMSO-d$_6$): δ 7.07 (d, J=8.4 Hz, 1H), 7.90-8.00 (dd, J=2.0 and 8.8 Hz, 1H), 8.15 (s, 1H), 8.50 (d, J=2 Hz, 1H), 8.67 (brs, 1H), 9.82 (s, 1H), 13.9 (s, 1H).

Step-2: A solution of 4-chloro-3-(4,4,5,5-tetramethyl-1,3,2-dioxaborolan-2-yl)benzoic acid (1.6 g, 5.67 mmol) 3-bromo iodo benzene (1.59 g, 5.67 mmol), potassium acetate (0.72 g, 7.37 mmol), cesium carbonate (5.53 g, 17.02 mmol) in degassed DMSO (20 mL) was degassed for 15 min. PdCl$_2$ (dppf).DCM adduct (0.46 g, 0.56 mmol) was added and the reaction mixture was further degassed for 15 min. The reaction mixture was heated at 90° C. overnight. TLC (Mobile phase 50% ethyl acetate in hexane) indicated absence of starting material (Rf 0.5) and product formation (Rf 0.3). The reaction mixture was quenched with water and acidified with 1N HCl. Solid precipitated out which was filtered, dried and purified by column chromatography on silica gel eluting with hexanes-ethyl acetate to give 3'-bromo-6-chloro-[1,1'-biphenyl]-3-carboxylic acid as a white solid.

Yield: (1.12 g, 63.6%).

$^1$H NMR (400 MHz, DMSO-d$_6$): δ 7.07 (d, J=8.4 Hz, 1H), 7.90-8.00 (dd, J=2.0 and 8.8 Hz, 1H), 8.15 (s, 1H), 8.50 (d, J=2 Hz, 1H), 8.67 (brs, 1H), 9.82 (s, 1H), 13.9 (s, 1H).

Step-3: A solution of 3'-bromo-6-chloro-[1,1'-biphenyl]-3-carboxylic acid (1.12 g, 3.60 mmol), potassium acetate (1.05 g, 10.8 mmol), Bispinacolato diborane (2.73 g, 10.8 mmol) in degassed DMF (20 mL) was degassed for 15 min. PdCl2 (dppf) DCM adduct (0.14 g, 0.17 mmol) was added and the reaction mixture was further degassed for 15 min. The reaction mixture was heated at 90° C. overnight. TLC (Mobile phase 50% ethyl acetate in n-hexane) indicated absence of starting material (Rf 0.2) and product formation (Rf-0.5). The reaction mixture was concentrated in vacuo, diluted with 2N NaOH and washed with ethyl acetate. The aqueous layer was acidified with 1N HCl and the compound was extracted in ethyl acetate. The organic layer was separated, dried over sodium sulphate, filtered, concentrated in vacuo and purified by column chromatography on silica gel eluting with hexanes-ethyl acetate to give 6-chloro-3'-(4,4,5,5-tetramethyl-1,3,2-dioxaborolan-2-yl)-[1,1'-biphenyl]-3-carboxylicacid.

Yield: (0.83 g, 64%)

$^1$H NMR (400 MHz, DMSO-d6): δ 1.25 (t, J=7.0 Hz, 3H), 4.10-4.23 (q, J J=7 Hz, 2H), 6.57 (d, J=16 Hz, 1H), 6.91 (d, J=8.4 Hz, 1H), 7.55 (d, J=16 Hz, 1H), 7.74-7.80 (dd, J=2.0 and 8.6 Hz, 1H), 8.06 (s, 1H), 8.28 (d, J=2 Hz, 1H), 8.50 (s, 1H), 13.5 (s, 1H).

Synthesis of: 4-(3-boronophenyl)-5-(methylthio)thiophene-2-carboxylic acid (A-116)

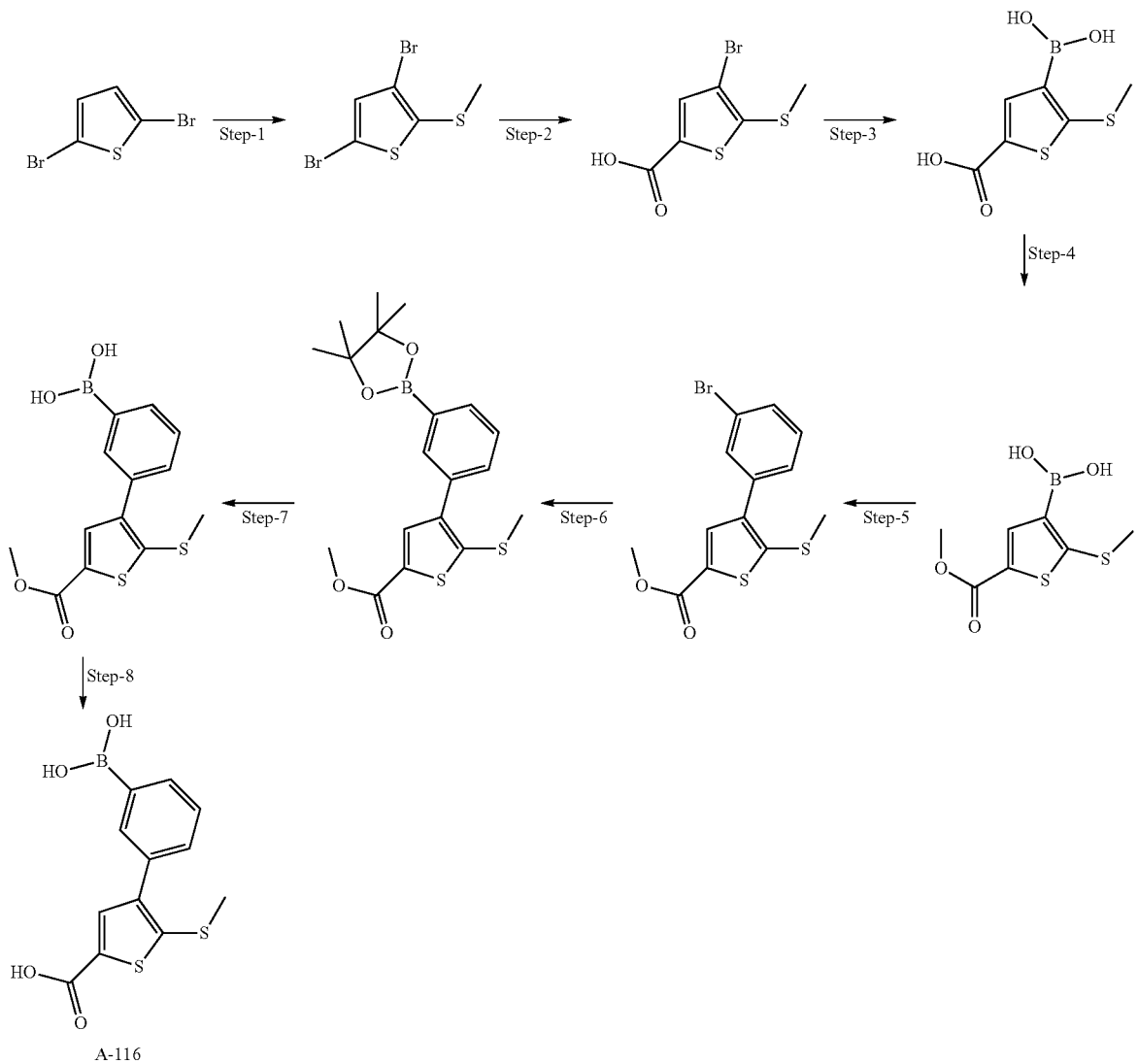

A-116

Experimental Procedure

Step-1: 2, 4-dibromo-5-methylthio thiophene was synthesized as per procedures available in the literature (Kano, Shinzo; Yuasa, Yoko; Yokomatsu, Tsutomu; Shibuya, Shiroshi Heterocycles, 1983, vol. 20, #10 p. 2035-2037)

Step-2: Lithiation of 2,4-dibromo-5-methylthio thiophene (28.13 g, 97.7 mmol) was done with n-BuLi (7.46 g, 116.64 mmol) at −78° C. in THF (562 mL after 5 min under stirring at same temperature was carefully added dry-ice and the temperature of the reaction mixture was allowed to raise to room temperature then the reaction mixture was quenched with dil HCl and concentrated. The residue obtained was diluted with dil HCl, and filtered and washed with methanol to get the product.

Yield: 17.2 g, 70%

MS (ES+): m/z=253.20/255.20 [MH+]

Step-3: Lithiation of bromo-5-(methylthio)thiophene-2-carboxylic acid (14.99 g, 59.25 mmol) was done with n-BuLi (11.37 g, 177.76 mmol) at −78° C. in THF (300 mL) after 30 min, under stirring at same temperature was carefully added tri-isopropyl borate (32.53 g, 177.76 mmol) drop wise and the temperature of the reaction mixture was allowed to raise to room temperature. The reaction mixture was quenched with dil HCl and concentrated in vacuo. The residue obtained was diluted with dil HCl, filtered and washed with water and re-dissolved in aq NaOH and re-precipitated by acidifying with dil HCl to get pure product.

Yield: 10.36 g. 80%

MS (ES+): m/z=219.10 [MH+]

Step-4: To ice cold methanol (30 vol) was added conc. Sulphuric acid (2 vol) and then 4-borono-5-(methylthio)thiophene-2-carboxylic acid (9.9 g, 45.85 mmol) was added. The reaction mixture was heated to reflux till completion of reaction. After completion the reaction mixture was concentrated to its 25% vol and poured on crushed ice. The solid precipitated was filtered and washed with water to get pure product.

Yield: 7.45 g, 70%

MS (ES+): m/z=233.25 [MH+]

Step-5: Suzuki coupling of (5-(methoxycarbonyl)-2-(methylthio)thiophen-3-yl)boronic acid step-4 product (5 g, 21.54 mmol) with 3-bromo Iodobenzene (7.31 g, 25.85 mmol) was carried out in presence of Palladium (0) Tetrakis (Triphenyl phosphine) (10 mol %) in Dioxane (20 vol) water (5 vol) and sodium carbonate (4.56 g, 43.08 mmol) as base and heated at 80° C. for 15 hrs. After completion of reaction, the reaction mixture was filtered through a pad of celite and filtrate was concentrated in vacuo. The residue was diluted with water and extracted with ethyl acetate to get crude product. Crude product obtained was purified by column chromatography over silica gel eluting with 5-10% ethyl acetate in hexane.

Yield: 3.69 g, 50%

LCMS: Mol. Wt: 343.26; Peak observed: 343/345.10 [MH]

Step-6: Stirred suspension of methyl 4-(3-bromophenyl)-5-(methylthio)thiophene-2-carboxylate, step-5 (2.6 g, 7.8 mmol) product in toluene (30 vol) was degassed with argon and charged with potassium acetate (3 eq), PdCl2-DPPF—CH$_2$Cl$_2$ (5 mol %) and Bis (Pinacolato) Diborane (4.93 g, 19.5 mmol), dppf (3 mol %). Reaction mass was heated to reflux & monitored by LCMS till most of the starting material was consumed. The mixture was filtered through a pad of celite and the filtrate was concentrated under reduced pressure to yield the crude product. The crude product was purified by column chromatography over silica gel eluting with 1-5% ethyl acetate in hexane.

Yield: 2.14 g, 70%

MS (ES+): m/z=391.15 [MH+]

Step-7: To ice cold methanol (30 mL) was added conc. Sulphuric acid (2 mL) and then methyl 5-(methylthio)-4-(3-(4,4,5,5-tetramethyl-1,3,2-dioxaborolan-2-yl)phenyl)thiophene-2-carboxylate, step-6 product (2.1 g, 5.38 mmol) was added at 0° C. Reaction mixture was heated to reflux until completion of reaction. After completion the reaction mixture was concentrated to 25% of its vol and poured over crushed ice. The precipitate was filtered and washed with water to get pure product.

Yield: 1.3 g, 80%

MS (ES+): m/z=309.20 [MH+]

Step-8: A mixture of step-7 product (1.29 g, 4.21 mmol), Potassium hydroxide (2.36 g, 42.13 mmol), THF (10 mL) and water (20 mL) was heated to 60° C. for 2 h. The reaction was monitored by LCMS till most of the starting was consumed. The reaction mixture was concentrated in vacuo and diluted with water. The pH of the reaction mixture was then adjusted to ~2 using Conc. HCl. Resulting in a precipitate. The precipitate was filtered, washed with water and dried in vacuum oven.

Yield: 744 mg, 60%

MS (ES+): m/z=295.20 [MH+]

Synthesis of 4'-fluoro-3'-(4, 4, 5, 5-tetramethyl-1, 3, 2-dioxaborolan-2-yl)-[1, 1'-biphenyl]-3-carboxylic acid (A-131)

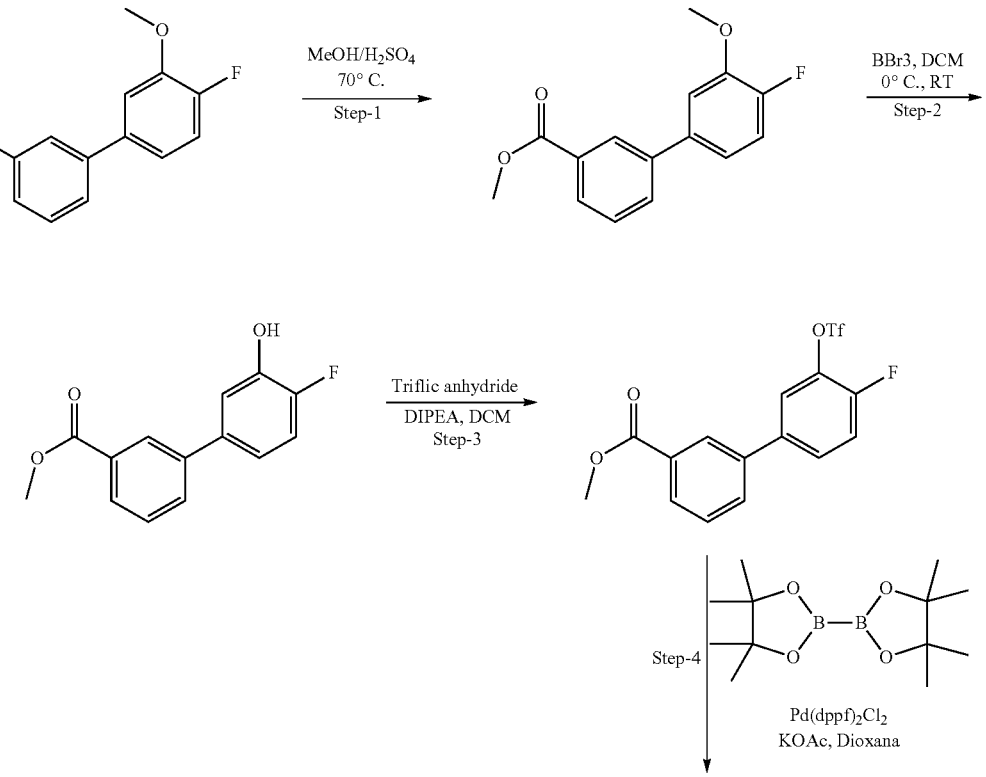

Scheme 34

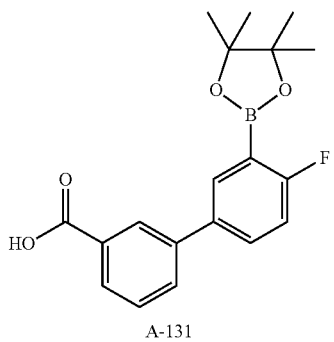

A-131

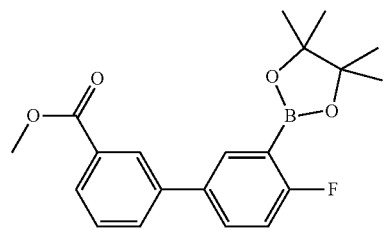

-continued

LiOH
THF:Water
⟵ Step-5

Experimental Procedure

Step-1: 4'-fluoro-3'methoxy biphenyl-3-carboxylic acid (1 g, 4.865 mmol) was dissolved in methanol (25 mL and the solution was cooled to 0° C. thionyl chloride (0.8 ml, 12.19 mmol) was added drop wise and then refluxed at 70° C. overnight. The methanol was concentrated in vacuo and the residue was diluted with ethyl acetate. The organic layer was washed with water (lx 25 mL), 10% NaHCO$_3$ solution then separated. The organic layer was dried over sodium sulfate, filtered, and concentrated in vacuo to get pure product (Off white solid)

Yield: 1.01 g (95%)

MS (ES+): m/z=261 [MH$^+$]

$^1$H NMR (400 MHz, CDCl$_3$): δ 8.22 (s, 1H), 8.02 (d, J=7.7 Hz, 1H), 7.73 (d, J=87.6 Hz, 1H), 7.51 (t, J=7.6 Hz, 1H), 7.22-7.08 (m, 3H), 3.96 (d, J=6.2 Hz, 6H).

Step-2: A stirred solution of methyl-4'-fluoro-3'-methoxy-[1,1'-biphenyl]-3-carboxylate (900 mg, 3.46 mmol) in dichloromethane (25 mL) was cooled to 0° C. and dropwise charged with boron tribromide (1.0 ml, 10.38 mmol) under a nitrogen atmosphere and stirred at room temperature for 5 hrs. The reaction mixture was cooled and quenched with methanol then concentrated in vacuo and charged with methanol and concentrated in vacuo several times to remove excess of bromine.

Yield: 800 mg (94%), $^1$H NMR (400 MHz, DMSO-d$_6$): δ 8.08 (t, J=1.9 Hz, 1H), 7.92 (d, J=87.7 Hz, 1H), 7.87-7.82 (m, 1H), 7.59 (t, J=7.8 Hz, 1H), 7.25 (d, J=6.0 Hz, 2H), 7.10 (ddd, J=8.3, 4.3, 2.4 Hz, 1H), 3.86 (s, 3H).

Step-3: A stirred solution of methyl-4'-fluoro-5'-hydroxy-[1,1'-biphenyl]-3-carboxylate (800 mg, 3.25 mmol) in dichloromethane (30 mL) was charged with DIPEA (1.7 ml, 9.76 mmol) at 0° C. then charged with triflic anhydride (1.67 ml, 9.76 mmol) and stirred at room temperature for 6 hr. The reaction mixture was quenched with water followed by wash with 1N HCl (25 mL) and brine solution. Organic layer was separated and dried over Na$_2$SO$_4$, filtered and concentrated in vacuo resulting in crude product, yellow oil. The crude compound was further purified by column chromatography on silica gel eluting with (n-hexane-ethyl acetate 9:1) to give 850 mg pure product as white solid.

Yield: 850 mg (85%)

$^1$H NMR (400 MHz, DMSO-d$_6$): δ 8.24-8.19 (m, 1H), 8.13 (dd, J=7.1, 2.3 Hz, 1H), 8.01-7.97 (m, 2H), 7.91 (ddd, J=8.9, 4.8, 2.5 Hz, 1H), 7.75-7.62 (m, 2H), 3.90 (d, J=1.4 Hz, 3H).

Step-4: A solution of methyl-4'-fluoro-3'-((((trifluoromethyl)sulfonyl)oxy)-[1,1'-biphenyl]-3-carboxylate (500 mg, 1.322 mmol), potassium acetate (444 mg, 4.629 mmol), bis pinacolato diborane (3.34 g, 13.22 mmol) in anhydrous dioxane (15 mL) was degassed for 15 min. under argon. To this were added Pd(dppf)Cl$_2$ (64.7 mg, 0.0793 mmol), dppf (43.4 mg, 0.0793 mmol) and again degassed for 10 min. and stirred at 80° C. for 12-14 hr. The reaction mixture was filtered through a pad of celite and the filtrate was concentrated in vacuo. The residue was diluted with ethyl acetate and washed with water followed by brine. The organic layer was dried over sodium sulfate, filtered, and concentrated in vacuo to get crude product. The crude product was further purified by column chromatography on silica gel eluting with (n-hexane-ethyl acetate 8:2) to get 650 mg product contaminated with some bis pinacolato diborane.

Yield: 600 mg $^1$H NMR (400 MHz, DMSO-d$_6$): δ 1.33 (s, 12H), 3.89 (s, 3H), 7.36-7.23 (m, 1H), 8.02-7.79 (m, 3H), 8.15-8.07 (m, 1H), 7.70-7.57 (m, 1H)

Step-5: To a solution of 4'-fluoro-3'-(4,4,5,5-tetramethyl-1,3,2-dioxaborolan-2-yl)-[L1,1'-biphenyl]-3-carboxylate (600 mg, 1.685 mmol) in THF:water (10 mL) was added lithium hydroxide (212 mg, 5.056 mmol) and stirred at room temperature overnight. The solvent was concentrated in vacuo and the pH of residue was adjusted up to 2. Major product spot was isolated by acid base work-up.

Yield: 200 mg $^1$H NMR (400 MHz, DMSO-d$_6$): δ 13.12 (brs, 1H), 8.12 (t, J=1.9 Hz, 1H), 7.97-7.84 (m, 4H), 7.61 (t, J=7.7 Hz, 1H), 7.29 (t, J=8.7 Hz, 1H), 1.33 (s, 12H).

Synthesis of 3'-fluoro-5'-(4, 4, 5, 5-tetramethyl-1, 3, 2-dioxaborolan-2-yl)-[1, 1'-biphenyl]-3-carboxylic acid (A-132)

Synthetic Scheme

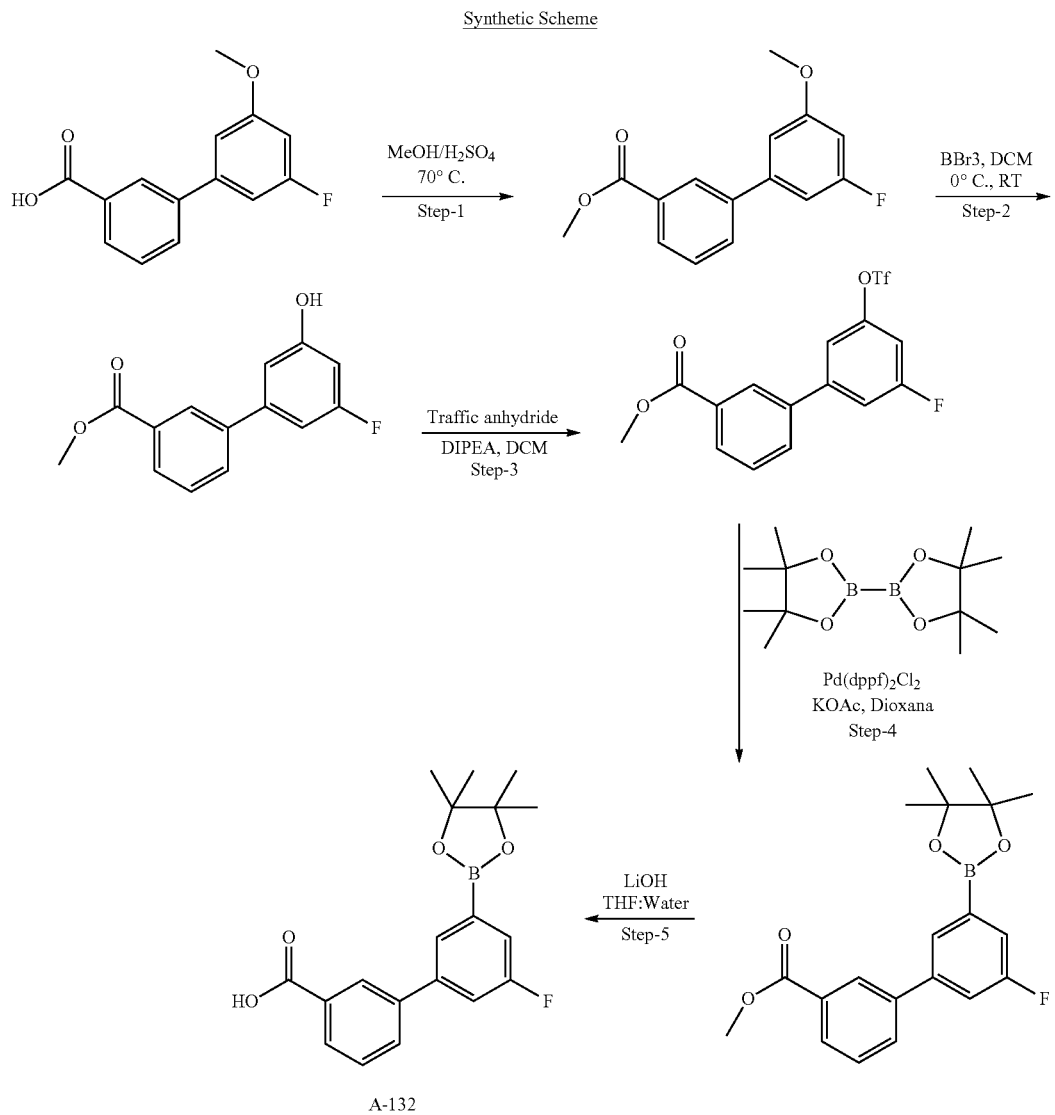

A-132

Experimental Procedures

Step-1: 3'-Fluoro-5'methoxy biphenyl-3-carboxylic acid (1 g, 4.865 mmol) was dissolved in methanol (25 ml) and solution was cooled to 0° C. Thionyl chloride (0.8 ml, 12.19 mmol) was added drop wise and reaction mixture was refluxed at 70° C. overnight. Methanol was removed in vacuo and the residue was diluted with ethyl acetate and washed with water (1×25 mL) followed by 10% NaHCO$_3$ solution and separated. The organic layer dried over Na$_2$SO$_4$, filtered, and concentrated in vacuo to get pure product (off-white solid)

Yield: 1 g (94%)

MS (ES+): m/z=261.00 [MH$^+$]

$^1$H NMR (400 MHz, DMOS-d$_6$): δ 8.17 (s, 1H), 8.01-7.92 (m, 2H), 7.62 (t, J=7.8 Hz, 1H), 7.17-7.03 (m, 2H), 6.88 (dt, J=11.0, 2.3 Hz, 1H), 3.87 (d, J=15.5 Hz, 6H).

Step-2: A stirred solution of methyl-3'-fluoro-5'-methoxy-[1, 1'-biphenyl]-3-carboxylate (900 mg, 3.461 mmol) in dichloromethane (25 mL) was cooled to 0° C. and dropwise charged with boron tribromide (1 ml, 10.38 mmol) under a nitrogen atmosphere The reaction mixture was stirred at room temperature 5 hr then cooled and quenched with methanol. The solvent was concentrated in vacuo and charged and stripped with methanol several times to remove excess of bromine.

Yield: 800 mg (93.4%).

1H NMR (400 MHz, DMSO-d$_6$): δ 8.13 (s, 1H), 7.94 (dd, J=20.0, 7.7 Hz, 2H), 7.62 (t, J=7.8 Hz, 1H), 7.03-6.89 (m, 2H), 6.61 (d, J=10.6 Hz, 1H), 3.89 (s, 3H).

Step-3: A stirred solution of methyl-3'-fluoro-5'-hydroxy-[1,1'-biphenyl]-3-carboxylate (800 mg, 3.252 mmol) in dichloromethane (30 mL) was charged with DIPEA (1.7 ml, 9.756 mmol) at 0° C. followed by triflic anhydride (1.67 ml, 9.756 mmol) and stirred at room temperature for 6 hr. The reaction mixture was quenched with water and separated and the organic was wash wit 1N HCl (25 mL) and brine solution. The organic layer was dried over $Na_2SO_4$, filtered, and concentrated in vacuo resulting in crude product, yellow oil) which was further purified by column chromatography on silica gel (n-hexane:ethyl acetate 9:1) to give 850 mg pure product as a white solid.

Yield: 850 mg (85%).

$^1$H NMR (400 MHz, DMSO-$d_6$): δ 8.26 (s, 1H), 8.04 (t, J=6.3 Hz, 2H), 7.87-7.79 (m, 2H), 7.66 (q, J=9.0, 8.3 Hz, 2H), 3.90 (s, 3H).

Step-4: A solution of methyl-3'-fluoro-5'-(((trifluoromethyl)sulfonyl)oxy)-[1,1'-biphenyl]-3-carboxylate (500 mg, 1.322 mmol), potassium acetate (444 mg, 4.629 mmol), bis pinacolato diborane (3.34 g, 13.22 mmol) in anhydrous dioxane (15 mL) was degassed for 15 min. under argon and charged with Pd(dppf)Cl$_2$ (64.7 mg, 0.0793 mmol) and dppf (43.4 mg, 0.0793 mmol) and degassed for 10 min. and stirred at 80° C. for 12-14 hr. The reaction mixture was filtered through a pad of celite and the filtrate was concentrated in vacuo. The residue was diluted with ethyl acetate and washed with water and brine and the organic layer was dried over sodium sulfate, filtered, and concentrated in vacuo to get crude product which was further purified by column chromatography on silica gel eluting with (n-hexane-ethyl acetate 8:2) to get 650 mg product contaminated with some bis pinacolato diborane.

Yield: 650 mg.

$^1$H NMR (400 MHz DMSO-$d_6$): δ 1.32 (s, 12H), 3.9 (s, 3H), 7.38-7.40 (m, 1H), 7.63-7.74 (m, 3H), 7.99-8.01 (m, 2H), 8.18 (s, 1H)

Step-5: A solution of 3'-fluoro-5'-(4,4,5,5-tetramethyl-1,3,2-dioxaborolan-2-yl)-[1,1'-biphenyl]-3-carboxylate (250 mg, 0.7022 mmol) in THF:water (10 mL) was charged with lithium hydroxide (88 mg, 2.106 mmol) and stirred at room temperature overnight. The THF solvent was concentrated under vacuum and the pH of residue was adjusted up to 2 and the major product spot was isolated by acid-base work-up.

Yield: 90 mg $^1$H NMR (400 MHz DMSO-$d_6$): δ 1.32 (s, 12H), 3.9 (s, 3H), 7.38-7.40 (d, J=7.6 Hz, 1H), 7.63-7.74 (m, 1H), 7.99-8.01 (d, J=7.6 Hz, 1H), 8.18 (s, 1H), 13.12 (bs, 1H)

Synthesis of 2'-fluoro-3'-(4, 4, 5, 5-tetramethyl-1, 3, 2-dioxaborolan-2-yl)-[1, 1'-biphenyl]-3-carboxylic acid. (A-133)

Synthetic Scheme

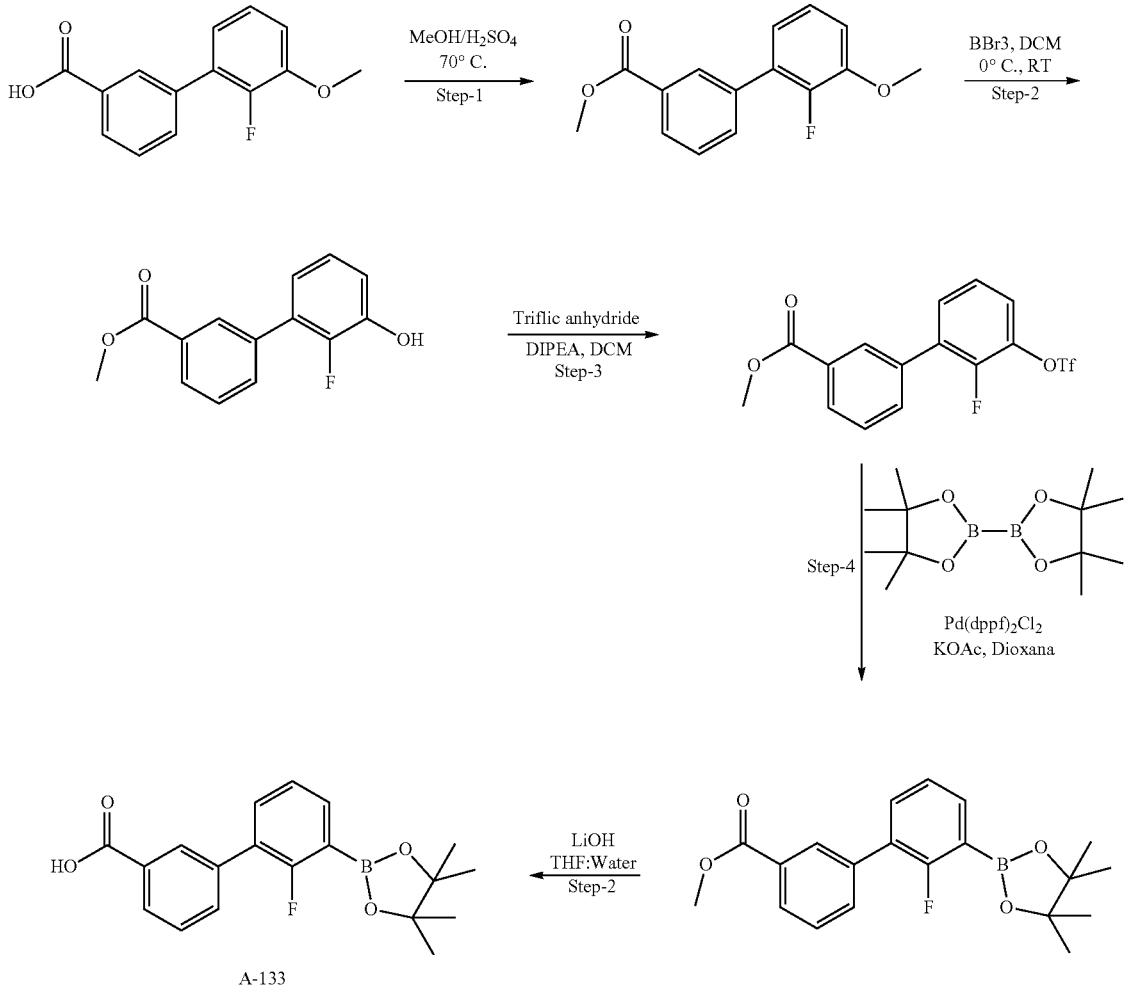

A-133

Experimental Procedures

Step-1: A solution of 2'-fluoro-3'methoxy biphenyl-3-carboxylic acid (1 g, 4.865 mmol) in methanol (25 mL) was cooled to 0° C. and dropwise charged with thionyl chloride (0.8 ml, 12.19 mmol) and refluxed at 70° C. overnight. The reaction was allowed to cool to room temperature and the solvent was concentrated in vacuo. The residue was diluted with ethyl acetate and the organic layer was washed with water (lx 25 mL), 10% NaHCO$_3$ Solution (lx 15 ml) and separated and dried over Na$_2$SO$_4$, filtered, and concentrated in vacuo resulting in pure product (off white solid)

Yield: 700 mg (66%), $^1$H NMR (400 MHz, CDCl$_3$): δ 8.24-8.19 (m, 1H), 8.05 (dt, J=7.4, 1.5 Hz, 1H), 7.75 (dq, J=7.4, 1.8 Hz, 1H), 7.52 (t, J=7.8 Hz, 1H), 7.06-6.94 (m, 3H), 3.94 (s, 6H).

Step-2: A stirred solution of methyl2'-fluoro-3'-methoxy-[1, 1'-biphenyl]-3-carboxylate (700 mg, 2.692 mmol) in dichloromethane (25 mL) was cooled to 0° C. and dropwise charged with boron tribromide (0.8 ml, 8.070 mmol) under a nitrogen atmosphere and stirred at room temperature for 5 hr. The reaction mixture was cooled and quenched with methanol and the solvent was evaporated and stripped with methanol several times to remove excess of bromine.

Yield: 650 mg (98%), $^1$H NMR (400 MHz, DMSO-d$_6$): δ 8.06 (s, 1H), 7.97 (d, J=7.6 Hz, 1H), 7.79 (d, J=7.6 Hz, 1H), 7.63 (td, J=7.7, 2.1 Hz, 1H), 7.09 (t, J=8.0 Hz, 1H), 7.00 (t, J=8.2 Hz, 1H), 6.92 (t, J=7.2 Hz, 1H), 3.87 (s, 3H).

Step-3: A stirred solution of methyl-2'-fluoro-3'-hydroxy-[1,1'-biphenyl]-3-carboxylate (650 mg, 2.640 mmol), 2, 4-dibromo-5-methylthio thiophene, and DIPEA (1.41 ml, 7.920 mmol) in dichloromethane (30 mL) was cooled to 0° C. and charged with triflic anhydride (1.33 ml, 7.920 mmol) and stirred at room temperature for 6 hrs. The reactiontion mixture was quenched with water and separated and the organic was washed with 1N HCl (25 mL), brine, dried over Na$_2$SO$_4$, filtered, and concentrated in vacuo resulting in crude yellow oil. The crude compound was purified by column chromatography on silica gel eluting with (n-hexane-ethyl acetate 9:1) to give 850 mg pure compound as a white solid.

Yield: 850 mg (85%).

$^1$H NMR (400 MHz, DMSO-d$_6$): δ 8.13 (d, J=2.2 Hz, 1H), 8.06 (d, J=7.8 Hz, 1H), 7.89 (d, J=7.7 Hz, 1H), 7.79-7.62 (m, 3H), 7.51 (t, J=8.1 Hz, 1H), 3.89 (s, 3H).

Step-4: A solution of methyl2'-fluoro-3'-(((trifluoromethyl)sulfonyl)oxy)-[1,1'-biphenyl]-3-carboxylate (400 mg, 1.038 mmol), potassium acetate (355 mg, 3.703 mmol), bis pinacolato diborane (1.34 g, 5.2810 mmol) in anhydrous dioxane (15 mL) was degassed for 15 min. under argon. The reaction mixture was charged with Pd(dppf)Cl$_2$ (51 mg, 0.0634 mmol), dppf (35 mg, 0.0634 mmol) and again degassed for 10 min. and heated to 80° C. for 12-14 hrs. The reaction mixture was filtered through a pad of celite and the filtrate was concentrated in vacuo. The residue was diluted with ethyl acetate and washed with water followed by brine. The organic layer was dried over sodium sulfate, filtered and concentrated in vacuo resulting in crude product. The crude product was purified by column chromatography on silica gel eluting with (n-hexane-ethyl acetate 8:2) to get 600 mg product contaminated with some Bis pinacolato diborane.

Yield: 600 mg.

$^1$H NMR (400 MHz, DMSO-d$_6$): δ 8.06-8.08 (m, 1H) 7.97 (d, J=6.8 Hz, 1H), 7.78 (d, J=7.6 Hz, 1H), 7.52-7.65 (m, 2H), 7.25-7.35 (m, 1H), 3.86 (s, 1H), 1.29 (s 12H)

Step-5: A solution of 2'-fluoro-3'-(4, 4, 5, 5-tetramethyl-1, 3, 2-dioxaborolan-2-yl)-[1, 1'-biphenyl]-3-carboxylate (200 mg, 0.561 mmol) in THF: Water (10 mL) was charged with Solid lithium hydroxide (94 mg, 2.247) and stirred at room temperature overnight. The THF was concentrated in vacuo and the aqueous pH adjusted up to 2. Major product spot was isolated by acid base work-up.

Yield: 130 mg (67.7%)

$^1$H NMR (400 MHz, DMSO-d$_6$): δ 1.31 (s, 12H), 3.92 (s, 1H), 7.33 (s, 1H), 7.59-7.98 (m, 6H), 8.08 (s, 1H), 13.04 (bs, 1H)

Synthesis of 5-((2-boronobenzyl) (methyl)amino)-1-naphthoic acid (A-143)

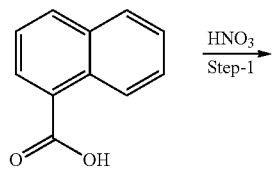

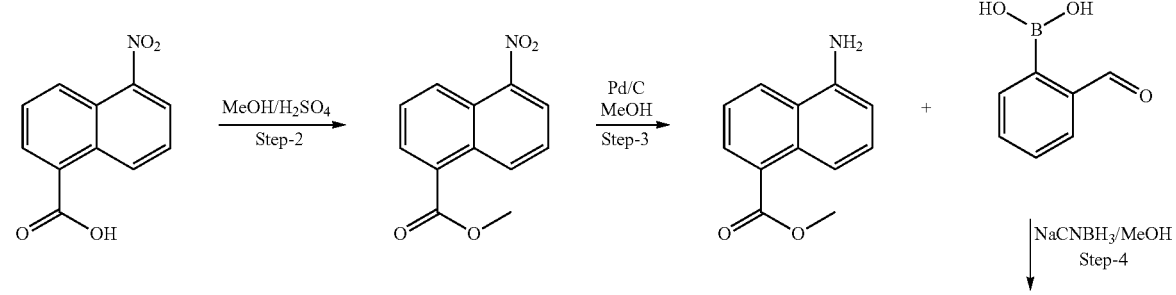

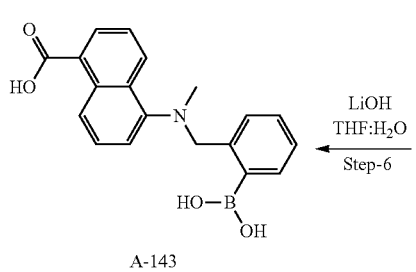

A-143

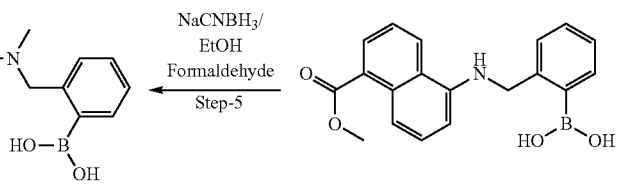

Experimental Procedures

Step 1: To cold fuming nitric acid (3 ml, 660 mmol) at 0-5° C. was charged with α-naphthoic acid (1 gm, 5.8 mmol) portion-wise over a 15 min. period and stirred at 0-5° C. for 30 min. and then at room temperature for an additional 2 hr. The reaction mixture was poured into 20 ml of ice-cold water upon which a precipitate formed. The precipitate was filtered and washed with 10 ml of water. The solid obtained was dissolved in 10 ml of 8% sodium carbonate and stirred for 10 mins and filtered. Filtrate was acidified using 10% HCl (pH=2) and the precipitate was filtered and re-crystallized from ethanol, filtered and dried under vacuum to get a yellow solid.

Yield: 1.14 g, 90.47%

HPLC Purity: 98.09%, $^1$H NMR (400 MHz, DMSO-$d_6$): δ 13.57 (s, 1H), 9.19 (d, J=8.8 Hz, 1H), 8.54-8.21 (m, 3H), 7.85 (dt, J=16.3, 7.8 Hz, 2H)

Step 2: A stirred solution of step-1 product (1 g, 4.60 mmol) in methanol (15 ml) was charged with conc. Sulfuric acid and heated to reflux at 70° C. for 24 hrs. The solvent was concentrated in vacuo and the residue was basified to pH=8 using 10% sodium bicarbonate and extracted with ethyl acetate (3×20 ml). The combined organic layer was washed with brine (2×10 ml), dried over sodium sulfate, filtered and concentrated in vacuo resulting in crude product which was purified by column chromatography on silica gel to get a pale yellow color solid.

Yield: 150 mg, 14.15%,

HPLC Purity: 77.57%, $^1$H NMR (400 MHz, CDCl$_3$): δ 9.26 (d, J=8.7 Hz, 1H), 8.67 (d, J=8.8 Hz, 1H), 8.30 (d, J=7.3 Hz, 1H), 8.21 (d, J=7.5 Hz, 1H), 8.18-8.07 (m, 1H), 7.71 (dt, J=22.9, 8.1 Hz, 1H), 4.05 (d, J=8.5 Hz, 3H).

Step 3: A stirred solution of 10% Pd—C (8 mg) in dry methanol (2 mL) was charged with a solution of step-2 product (80 mg, 0.340 mmol) in methanol (10 ml) under nitrogen and then the reaction was charged with a hydrogen pressure (bladder) for 24 hr at room temperature. The reaction mixture was filtered through a pad of celite and the filtrate was concentrated in vacuo to get yellow oil.

Yield: 60 mg, 86.95%

MS (ES+): m/z=202.05 [MH$^+$]

Step 4: A stirred solution of step-3 product (120 mg, 1 eq) in methanol (20 mL) was charged with 2-formyl phenyl boronic acid (89 mg, 1 eq) and the reaction was stirred at room-temperature for 30 min. then charged with sodium cyanoborohydride (150 mg, 4 eq) and stirred at room-temperature for an additional 48 hrs. The solvent was concentrated in vacuo then partitioned between DCM (20 mL) and water (2×15 mL) and separated. The organic layer was dried over sodium sulfate, filtered, and concentrated in vacuo to get the crude product which was purified by column chromatography on silica gel to get yellow color oil.

Yield: 80 mg, 40%

HPLC Purity: 82.57%,

MS (ES+): m/z=336.15 [MH$^+$]

Step 5: A stirred solution of the step-4 product (100 mg, 0.590 mmol) in ethanol (6 mL), water (2 mL), and acetic acid (2 mL) was charged with p-formaldehyde (14 mg, 0.590 mmol) and stirred at room-temperature for 15 mins then charged with sodium cyanoborohydride (75 mg, 2.30 mmol) portion-wise over a 15 min. period and stirred at room-temperature for 24 hrs. The solvent was concentrated in vacuo and the residue was charged with water (10 mL) then acidified to pH=2 using 1N KHSO$_4$ and extracted with ethyl acetate (3×10 mL). The combined organic layers were washed with brine (2×10 mL), dried over sodium sulfate, filtered, and concentrated in vacuo to get a yellow solid.

Yield: 100 mg, 97.15%,

MS (ES+): m/z=350.10 [MH$^+$]

Step 6: A stirred solution of the step-5 product (100 mg, 1 eq) in THF (3 mL) and water (3 mL) was charged with solid lithium hydroxide (14 mg, 2 eq) and the reaction was stirred at room-temperature for 24 hrs. The THF was concentrated in vacuo and the aqueous was acidified to pH=2 using 1N KHSO$_4$ and extracted with ethyl acetate (3×15 mL). The combined organic layers were washed with brine (2×10 mL), dried over sodium sulfate, filtered, and concentrated in vacuo to get brown solid.

Yield: 80 mg, 83.33%

HPLC Purity: 32.52%,

MS (ES+): m/z=336.10 [MH$^+$]

Synthesis of 3-((2-boronobenzyl) (methyl) amino) benzoic acid (A-146)

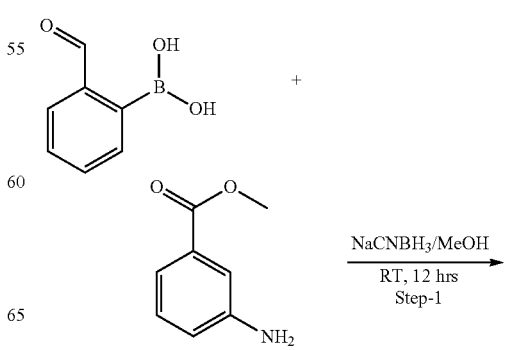

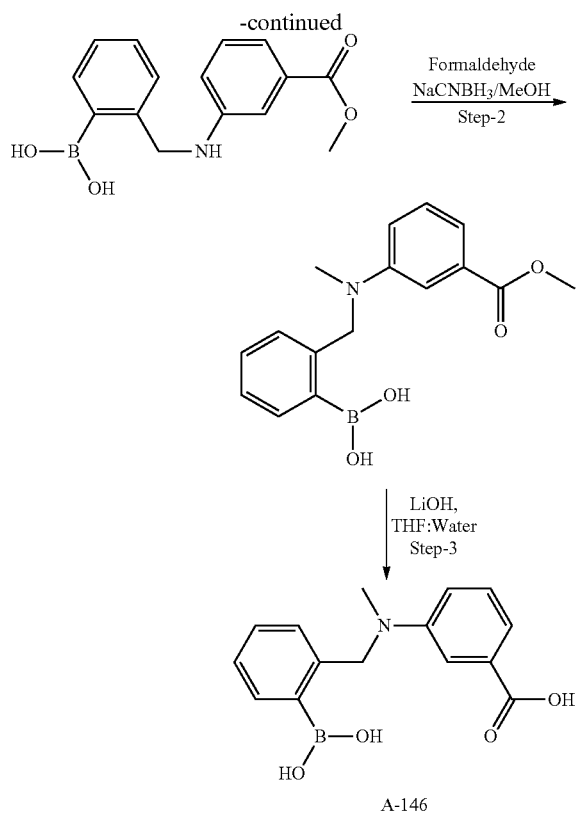

Experimental Procedures

Step-1

A stirred solution of methyl-3-amino benzoate (200 mg, 1.52 mmol) in methanol (5 mL) was charged with 2-formyl phenyl boronic acid (198 mg, 1.32 mmol) and stirred at room-temperature for 10 mins then charged with sodium cyano borohydride (332 mg, 5.29 mmol) portion-wise over a 15 min period and stirred at room-temperature for 24 hrs. The solvent was concentrated in vacuo. The residue was dissolved in DCM (20 mL) and washed with water (2×15 mL), brine (2×15 mL), dried over sodium sulfate, filtered, and concentrated in vacuo to get the crude product which was purified by column chromatography on silica gel to get a brown solid.

Yield: 250 mg, 66.31%

MS (ES+): m/z=286.15 [MH$^+$]

$^1$H NMR (400 MHz, DMSO-d$_6$): δ 7.55-7.39 (m, 1H), 7.37-7.26 (m, 4H), 7.23-7.10 (m, 4H), 4.58 (s, 2H), 4.12-3.99 (m, 1H), 3.83 (d, J=30.9 Hz, 3H), 1.99 (s, 2H)

Step-2

A stirred solution of the step-1 product (250 mg, 0.87 mmol) in ethanol (15 mL), water (5 mL), and acetic acid (5 mL) was charged with p-formaldehyde (40 mg, 1.30 mmol) and was stirred at room-temperature for 15 mins. The reaction mixture was charged with sodium cyanoborohydride (220 mg, 3.50 mmol) portion-wise over a 15 min. period and stirred at room-temperature for 24 hr. The solvent was concentrated in vacuo and to residue was charged with water (10 mL) and was acidified to pH=2 using 1N KHSO$_4$ and extracted with ethyl acetate (3×20 mL). The combined organic layers were washed with brine (2×20 mL), dried over sodium sulfate, filtered, and concentrated in vacuo resulting in yellow solid (Qty—160 mg).

Yield: 160 mg, 61.06%,

HPLC Purity: 85.56%,

MS (ES+): m/z=300.00 [MH$^+$]

Step 3:

To a stirred solution of the step-2 product (160 mg, 0.53 mmol) in THF (5 mL) and water (2 mL) was charged with lithium hydroxide (26 mg, 1.00 mmol) and the reaction was stirred at room-temperature for 24 hr. The solvent was concentrated in vacuo and the residue was acidified to pH 2 using 1N KHSO$_4$ and extracted with ethyl acetate (3×15 mL). The combined organic layer was washed with brine (2×10 mL), dried over sodium sulfate, filtered, and concentrated in vacuo resulting in a pale yellow solid.

Yield: 150 mg, 98.68%,

MS (ES+): m/z=286.15 [MH$^+$]

Synthesis of 4-((2-boronobenzyl)(methyl)amino) benzoic acid (A-147)

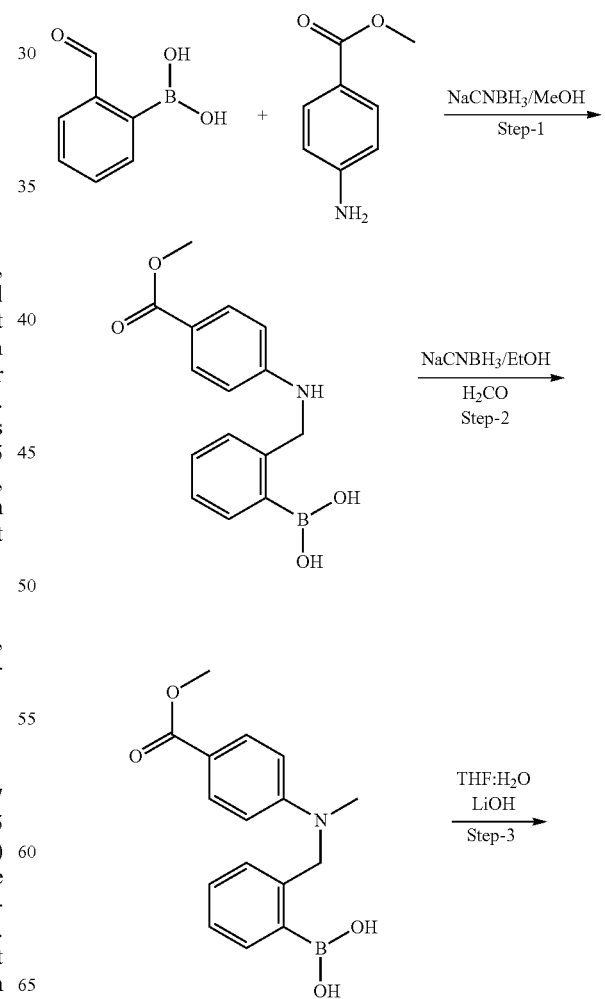

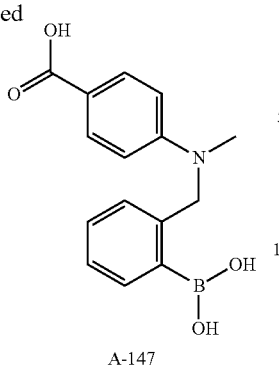

A-147

Experimental Procedures

Step-1

A stirred solution of methyl-4-amino benzoate (200 mg, 1.52 mmol) in methanol (5 mL) was charged with 2-formyl phenyl boronic acid (198 mg, 1.32 mmol) and stirred at room-temperature for 10 mins then charged with sodium cyano borohydride (332 mg, 0.529 mmol) portion-wise over a 15 min. period and continued to stir at room-temperature for an additional 24 hr. The solvent was concentrated under vacuum and the residue was dissolved in DCM (20 mL) and washed with water (2×15 mL), brine (2×15 mL), dried over sodium sulfate, filtered, and concentrated in vacuo resulting in the crude product which was purified by column chromatography to get an off-white color solid.

Yield: 270 mg, 71.61%
MS (ES+): m/z=286.15 [MH$^+$]
$^1$H NMR (400 MHz, DMSO-d$_6$): δ 7.89 (t, J=8.7 Hz, 2H), 7.67 (dd, J=13.5, 8.6 Hz, 2H), 7.46 (d, J=4.1 Hz, 2H), 7.38-7.24 (m, 2H), 4.59 (s, 2H), 4.10 (q, J=5.2 Hz, 1H), 3.81 (s, 3H), 1.23 (s, 2H)

Step 2

A stirred solution of the step-1 product (50 mg, 0.175 mmol) in ethanol (3 mL), water (1 mL) and acetic acid (1 mL) was charged with p-formaldehyde (8 mg, 0.26 mmol) and stirred at room-temperature for 15 min. The reaction was then charged with sodium cyanoborohydride (44 mg, 0.70 mmol) portion-wise over a 15 min period and stirred at room-temperature for 24 hrs. The solvent was concentrated in vacuo and the residue was diluted in water (10 mL) and was acidified to pH=2 using 1N KHSO$_4$ and extracted with ethyl acetate (3×10 mL). The combined organic layer was washed with brine (2×10 mL), dried over sodium sulfate, filtered, and concentrated in vacuo resulting in an off-white solid.

Yield: 50 mg, 96.15%
MS (ES+): m/z=300.00 [MH$^+$]

Step 3

A stirred solution of the step-2 product (250 mg, 0.83 mmol) in THF (10 mL) and water (4 mL) was charged with lithium hydroxide (40 mg, 1.6 mmol) and stirred at room-temperature for 24 hr. The solvent was concentrated in vacuo and the residue was acidified to pH=2 using 1N KHSO$_4$ and extracted with ethyl acetate (3×15 mL). The combined organic layers were washed with brine (2×10 mL), dried over sodium sulfate filtered, and concentrated in vacuo resulting in yellow solid.

Yield: 210 mg, 88.23%
HPLC Purity: 82.94%,
MS (ES+): m/z=286.15 [MH$^+$]

Synthesis of 6-((2-boronobenzyl)(methyl)amino)-1-naphthoic acid (A-154)

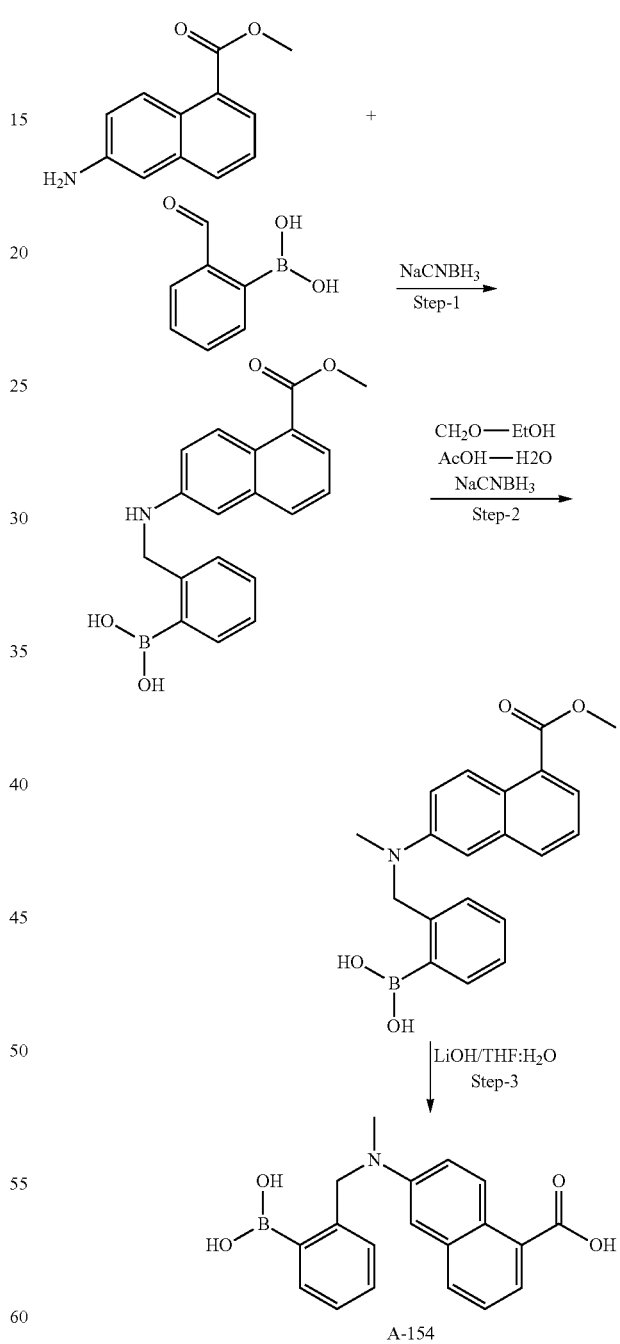

A-154

Experimental Procedures

Step 1: A stirred solution of methyl 6-amino-1-naphthoate (500 mg, 2.48 mmol) in methanol (20 mL) was charged with 2-formyl phenyl boronic acid (373 mg, 2.48 mmol) and stirred at room-temperature for 30 min. The reaction mixture was then charged with sodium cyanoborohydride (625 mg, 9.9 mmol) and stirred at room-temperature for an additional 48 hr. The solvent was concentrated in vacuo and residue was diluted with DCM (20 mL) and washed with water (2×15 mL), dried over sodium sulfate, filtered, and concentrated in vacuo to get the crude product which was purified by column chromatography to get yellow solid (Qty-600 mg).

Yield: 600 mg, 72.02%

MS (ES+): m/z=336.10 [MH$^+$]

HPLC Purity: 99.59%, $^1$H NMR (400 MHz, DMSO-d$_6$): δ 9.66-9.60 (m, 1H), 8.67 (d, J=9.5 Hz, 1H), 8.36 (dd, J=9.7, 2.8 Hz, 2H), 8.06 (d, J=8.3 Hz, 2H), 7.92 (dd, J=15.9, 7.3 Hz, 2H), 7.74 (s, 1H), 7.49 (dq, J=15.2, 7.7 Hz, 3H), 7.35 (t, J=7.2 Hz, 1H), 4.69 (s, 2H), 4.00-3.88 (m, 3H)

Step 2: A stirred solution of the step-1 product (600 mg, 1.79 mmol) in ethanol (36 mL), water (12 mL), and acetic acid (12 mL) was charged with p-formaldehyde (81 mg, 2.68 mmol) and stirred at room-temperature for 15 mins. The reaction mixture was charged with sodium cyanoborohydride (450 mg, 7.16 mmol) portion-wise over a 15 min. period and stirred at room-temperature for 24 hrs. The solvent was concentrated in vacuo and the residue was diluted with water (10 mL) and acidified to pH=2 using 1N KHSO$_4$ and extracted with ethyl acetate (3×20 mL). The combined organic layer was washed with brine (2×20 mL), dried over sodium sulfate, filtered, and concentrated in vacuo resulting in a yellow solid (Qty-680 mg crude) which was used in the next step without further purification.

Crude product used as such for next step

HPLC Purity: 93.25%,

MS (ES+): m/z=350.15 [MH$^+$]

$^1$H NMR (400 MHz, DMSO-d$_6$): δ 8.52 (d, J=9.6 Hz, 1H), 8.14 (s, 1H), 7.88 (d, J=8.4 Hz, 1H), 7.77 (d, J=7.1 Hz, 1H), 7.53 (d, J=6.9 Hz, 1H), 7.40 (t, J=7.7 Hz, 1H), 7.32 (dd, J=9.4, 2.9 Hz, 1H), 7.21 (dq, J=15.0, 7.0 Hz, 3H), 7.05 (t, J=5.9 Hz, 2H), 4.80 (s, 2H), 3.89 (s, 3H), 3.07 (s, 3H)

Step 3: A stirred solution of the step-2 product (670 mg, 1.9 mmol) in THF (20 mL) and water (20 mL) was charged with lithium hydroxide (92 mg, 3.8 mmol) and stirred at room-temperature for 24 hrs. The solvent was concentrated in vacuo and residue was acidified to pH=2 using 1N KHSO$_4$ and extracted with ethyl acetate (3×25 mL). The combined organic layer was washed with brine (2×20 mL), dried over sodium sulfate, filtered, and concentrated in vacuo resulting in a yellow solid.

Yield: 600 mg, 93.33%,

MS (ES+): m/z=336.10 [MH$^+$]

HPLC Purity: 80.32%, $^1$H NMR (400 MHz, DMSO-d$_6$): δ 12.84 (s, 1H), 8.63 (d, J=9.5 Hz, 1H), 7.81 (dd, J=27.3, 7.8 Hz, 2H), 7.52 (d, J=7.1 Hz, 1H), 7.42-7.14 (m, 4H), 7.06 (d, J=6.1 Hz, 2H), 4.79 (s, 2H), 4.08-3.86 (m, 2H), 3.09 (d, J=23.7 Hz, 3H)

Synthesis of 5'-bromo-2'-(dimethylamino)-[1, 1'-biphenyl]-3-carboxylic acid (A 155)

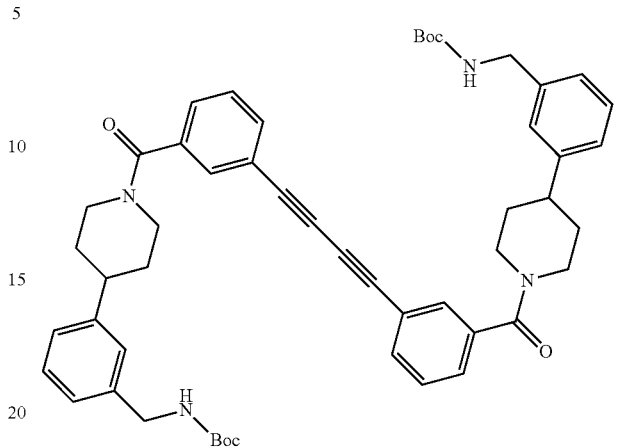

Experimental Procedures

Step 1: A stirred solution of 4-bromo-2-iodo aniline (2 g, 6.71 mmol) and potassium carbonate (1.4 g, 10.14 mmol) in DMF (20 mL) was cooled to 0° C. and dropwise charged over a 20 min. period with iodomethane (1.9 g, 13.0 mmol) keeping the temperature between 0-5° C. then stirred at 0° C. for 1 hr and then at room-temperature for 48 hrs. The reaction mixture was charged with water (30 mL) and was extracted with ethyl acetate (3×25 mL). The combined organic layers were washed with brine (2×25 mL), dried over sodium sulfate, filtered, and concentrated in vacuo to get the crude product which was purified by column chromatography to get a brown oil.

Yield: 1.8 g, 82.19%

HPLC Purity: 68.15%,

MS (ES+): m/z=312/314 [MH$^+$]

Step 2: A stirred solution of the step-1 product (1.8 g, 5.70 mmol) in ethanol (108 mL), water (36 mL), and acetic acid (36 mL) was charged with p-formaldehyde (260 mg, 8.60 mmol) and stirred at room-temperature for 15 min. The reaction mixture was portion-wise charged over a 20 min period with sodium cyanoborohydride (1.45 g, 23 mmol) and stirred at room-temperature for 24 hr. The solvent was concentrated in vacuo and the residue was diluted in water (20 mL) and was acidified to pH=2 using 1N KHSO$_4$ and extracted with ethyl acetate (3×30 mL). The combined organic layer was washed with brine (2×20 mL), dried over sodium sulfate, filtered, and concentrated in vacuo resulting in a yellow oil.

Yield: 1.7 g, 90.42%

HPLC Purity: 99.70%,

MS (ES+): m/z=326 [MH$^+$]

Step 3: A stirred solution of step-2 product (1.7 g, 5.20 mmol) in toluene (50 mL) was charged with a solution of sodium carbonate (1.11 g, 10.04 mmol) in water (15 mL), 3-ethoxycarbonyl phenyl boronic acid (939 mg, 5.20 mmol) and the reaction was degassed with argon for 1 hr and then charged with tetrakis (340 mg, 20 w/w) and heated to 100° C. for 24 hr. The reaction was allowed to cool to room-temperature and charged with water (20 mL) and was extracted with ethyl acetate (3×20 mL). The combined organic layer was washed with brine (2×20 mL), dried over sodium sulfate, filtered, and concentrated in vacuo to get 750 mg of the crude product which was purified by column chromatography to get desired product as colorless oil.

Yield: 150 mg, 8.33%
HPLC Purity: 96.76%,
MS (ES+): m/z=348/350 [MH⁺]

Step 4: A stirred solution of the step-3 product (100 mg, 0.28 mmol) in THF (5 mL) and water (3 mL) was charged with lithium hydroxide (10 mg, 0.43 mmol) and stirred at room-temperature for 24 hrs. The solvent was concentrated in vacuo and the residue was acidified to pH=2 using 1N KHSO$_4$ and extracted with ethyl acetate (3×10 mL). The combined organic layer was washed with brine (2×10 mL), dried over sodium sulfate, filtered, and concentrated in vacuo resulting in an off-white solid.

Yield: 70 mg, 76.92%
HPLC Purity: 95.09%,
MS (ES+): m/z=321/323 [MH⁺]

Coupling of Boronate Ester or Boronic Acid Precursors (A) to the Appropriate Protected Core (Step-1a & b)

To a stirred solution of carboxylic acid in DCM or DMF was added DMAP or DIPEA, EDCI, HOBt (in some cases). The solution was stirred for 15 min. at 0° C.-room temperature followed by addition of protected 4-(3-aminomethyl phenyl) piperidine or 5-aminomethyl Spiro [benzofuran-3, 4'-piperidine]. Stirring was continued at room temperature and reaction was monitored by LCMS till most of the starting materials were consumed. Reaction mixture was then quenched with water and aq. Layer was extracted twice with dichloromethane. The combined organic layer was dried over sodium sulfate, filtered, and concentrated in vacuo to afford the crude product which was used for next step without further purification.

The details of compounds synthesized by step-1a are as below:

| Comp. No. | Structure | Brief Reaction conditions | Analytical data |
|---|---|---|---|
| B-132 Spiro | tert-butyl ((1'-(3'-fluoro-5'-(4,4,5,5-tetramethyl-1,3,2-dioxaborolan-2-yl)-[1,1'-biphenyl]-3-carbonyl)-2H-spiro[benzofuran-3,4'-piperdin]-5-yl)methyl)carbamate | A-132 (1 eq), Spiro core (1 eq.), EDCI (1.5 eq.), DMAP (0.5 eq.), in Dichloromethane 50 vol. R.T. 12 hrs. 66% after acid-base work-up | Yield: ~66% Mol. Wt: 642.56 MS (ES+): m/z = 583 (MH⁺ − Boc + AcN) |
| B-133 Spiro | tert-butyl ((1'-(2'-fluoro-3'-(4,4,5,5-tetramethyl-1,3,2-dioxaborolan-2-yl)-[1,1'-biphenyl]-3-carbonyl)-2H-spiro[benzofuran-3,4'-piperdin]-5-yl)methyl)carbamate | A-133 (1 eq), Spiro core (1 eq.), EDCI (1.5 eq.), DMAP (0.5 eq.), in Dichloromethane 50 vol. R.T. 12 hrs. 53.1% after acid-base work-up. | Yield: ~53% Mol. Wt: 642.56 MS (ES+): m/z = 583(MH⁺ − Boc + AcN) |
| B-131-Spiro | tert-butyl ((1'-(4'-fluoro-3'-(4,4,5,5-tetramethyl-1,3,2-dioxaborolan-2-yl)-[1,1'-biphenyl]-3-carbonyl)-2H-spiro[benzofuran-3,4'-piperdin]-5-yl)methyl)carbamate | A-131 (1 eq), Spiro core (1 eq.), EDCI (1.5 eq.), DMAP (0.5 eq.), in Dichloromethane 50 vol. R.T. 12 hrs. 62% after acid-base work-up. | Yield: ~62% Mol. Wt: 642.56 MS (ES+): m/z = 587 [MH⁺ − t-Bu] |

| Comp. No. | Structure | Brief Reaction conditions | Analytical data |
|---|---|---|---|
| B-107 | tert-butyl 3-(1-(5,6-dimethyl-3'-(4,4,5,5-tetramethyl-1,3,2-dioxaborolan-2-yl)-[1,1'-biphenyl]-3-carbonyl)piperidin-4-yl)benzylcarbamate | A-107 370 mg, tert-butyl 3-(piperidin-4-yl) benzyl carbamate 1.2 eq., EDCI 1.5 eq. DMAP 0.5 eq. in Dichloromethane 80 vol. R.T. 12 hrs. yield: ~53.8% after chromatographic purification over silica gel | Mol. Wt: 652.37 MS (ES+): m/z = 653 [MH⁺] |
| B-107-Spiro | tert-butyl ((1'-(5,6-dimethyl-3'-(4,4,5,5-tetramethyl-1,3,2-dioxaborolan-2-yl)-[1,1'-biphenyl]-3-carbonyl)-2H-spiro[benzofuran-3,4'-piperidin]-5-yl)methyl)carbamate | A-107 150 mg, Spiro core 1.2 eq., EDCI 1.5 eq. DMAP 0.5 eq. in Dichloromethane 200 vol. R.T. 12 hrs. yield: ~44.4% after chromatographic purification over silica gel | Mol. Wt: 652.37 MS (ES+): m/z = 653 [MH⁺] |
| B-54 | tert-butyl 3-(1-(2-(3-fluoro-4-(4,4,5,5-tetramethyl-1,3,2-dioxaborolan-2-yl)phenyl)acetyl)piperidin-4-yl)benzylcarbamate | A-54 (1 eq.) tert-butyl 3-(piperidin-4-yl) benzyl carbamate (1.0 eq.), EDCI (1.5 eq.), DMAP (1.2 eq.), DCM, rt, 15 h, Yield: 32% | Mol. Wt: 552.48 MS (ES+): m/z = 553 [MH⁺] ¹H NMR (400 MHz, CDCl₃): δ 7.42-7.32 (m, 1H), 7.19-6.90 (m, 6H), 4.88-4.72 (m, 1H), 4.28 (s, 2H), 4.05-3.95 (m, 1H), 3.80 (s, 2H), 3.20-3.08 (m, 1H), 2.58-2.60 (m, 2H), 1.94-1.78 (m, 2H), 1.70-1.52 (m, 2H), 1.58 (s, 9H), 1.45 (s, 12H) |
| B-54-spiro | tert-butyl ((1'-(2-(3-fluoro-4-(4,4,5,5-tetramethyl-1,3,2-dioxaborolan-2-yl)phenyl)acetyl)-2H-spiro[benzofuran-3,4'-piperidin]-5-yl)methyl)carbamate | A-54 (1 eq.) tert-butyl 4-methoxy-3-(4-methylpiperidin-4-yl)benzyl carbamate (1.0 eq.), EDCI (1.5 eq.), DMAP (1.2 eq.), DCM, rt, 15 h, Yield: 34% | Mol. Wt: 580.50 MS (ES+): m/z = 581 [MH⁺] |

-continued

| Comp. No. | Structure | Brief Reaction conditions | Analytical data |
|---|---|---|---|
| B-109-Spiro | tert-butyl ((1'-(6-chloro-3'-(4,4,5,5-tetramethyl-1,3,2-dioxaborolan-2-yl)-[1,1'-biphenyl]-3-carbonyl)-2H-spiro[benzofuran-3,4'-piperidin]-5-yl)methyl)carbamate | A-109 (1 eq.) Spiro core 1.2 eq., EDCI 1.5 eq. HOBt 1.5 eq. DIPEA 2.5 eq. in DMF 70 vol. R.T. 12 hrs. yield: ~60% after chromatographic purification over silica gel | Mol. Wt: ~658.3 MS (ES+): m/z = 681 [MH+ + Na] |

| Comp. No. | Structure | Brief Reaction conditions | Analytical data |
|---|---|---|---|
| B-116 Spiro | (3-(5-(5-(((tert-butoxycarbonyl)amino)methyl)-2H-spiro[benzofuran-3,4'-piperidin]-1'-ylcarbonyl)-2-(methylthio)thiophen-3-yl)phenyl)boronic acid | tert-buty ((2H-spiro[benzofuran-3,4'-piperidin]-5-yl)methyl)carbamate (1.3 eq.), EDCI•HCl (1.5 eq.), DMAP (2 eq.), DCM(20 vol), RT, 4 h, | Yield: ~60% Mol. Wt: 594.55 MS (ES+): m/z = 595.70 [MH+] |
| B-146 | (2-(((3-(4-(3-(((tert-butoxycarbonyl)amino)methyl)phenyl)piperidine-1-carbonyl)phenyl)(methyl)amino)methyl)phenyl)boronic acid | A-146, tert-butyl 3-(piperidin-4-yl) benzyl carbamate (1 eq), EDCI 1.5 eq. DMAP 1.1 eq., HOBt, 1.1 eq. in Dichloromethane 70 vol. R.T. 12 hrs. | Yield: ~50% Mol. Wt: 557.49 MS (ES+): m/z = 558.40 |
| B-147 | (2-(((4-(4-(3-(((tert-butoxycarbonyl)amino)methyl)phenyl)piperidine-1-carbonyl)phenyl)(methyl)amino)methyl)phenyl)boronic acid | A-147, tert-butyl 3-(piperidin-4-yl) benzyl carbamate (1 eq), EDCI 1.5 eq. DMAP 1.1 eq., HOBt, 1.1 eq. in Dichloromethane 70 vol. R.T. 12 hrs | Yield: ~50% Mol. Wt: ~557.49 MS (ES+): m/z = 558.40 [MH+] |

-continued

| Comp. No. | Structure | Brief Reaction conditions | Analytical data |
|---|---|---|---|
| B-143 | 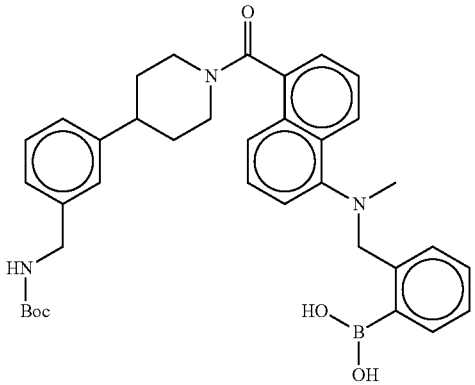<br>(2-(((5-(4-(3-(((tert-butoxycarbonyl)amino)methyl)phenyl)piperidine-1-carbonyl)naphthalen-1-yl)(methyl)amino)methyl)phenyl)boronic acid | A-143, tert-butyl 3-(piperidin-4-yl) benzyl carbamate 1 eq., EDCI 1.5 eq. DMAP 1.1 eq., HOBt, 1.1 eq. in Dichloromethane 125 vol. R.T. 12 hrs. | Yield: ~96.5%<br>Mol. Wt: 607.5<br>MS (ES+):<br>m/z = 608.40 [MH$^+$] |
| B-154 | 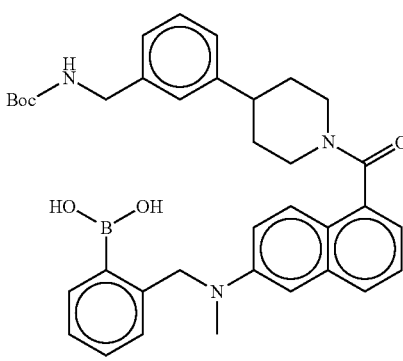<br>(2-(((5-(4-(3-(((tert-butoxycarbonyl)amino)methyl)phenyl)piperidine-1-carbonyl)naphthalen-2-yl)(methyl)amino)methyl)phenyl)boronic acid | A-154, tert-butyl 3-(piperidin-4-yl) benzyl carbamate 1 eq., EDCI 1.5 eq. DMAP 1.1 eq., HOBt, 1.1 eq. in Dichloromethane 125 vol. R.T. 12 hrs | Yield: ~97.34%<br>Mol. Wt: 607.5<br>MS (ES+):<br>m/z = 608.35 [MH$^+$]<br>$^1$H NMR (400 MHz, dmso-d$_6$): δ 8.13 (s, 2H), 7.69-7.62 (m, 3H), 7.51 (dd, J = 15.3, 8.2 Hz, 5H), 7.39-6.89 (m, 5H), 4.88-4.70 (m, 2H), 4.16 (s, 2H), 3.16-2.61 (m, 8H), 2.05-1.49 (m, 6H), 1.27 (s, 9H) |

Deprotection of the Protected Amide (B) with Boronate Functionality (Step-2a)

Products from step-1a were stirred with aq. hydrochloric acid or trifluoracetic acid (TFA) in a co-solvent like dioxane, acetonitrile, methanol, THF, DCM etc. Reaction was monitored by LCMS till most of the starting material was consumed. Reaction mass was then concentrated in vacuo to remove the solvents and residue obtained was purified by reverse phase preparative HPLC. The pure fraction of mobile phase was lyophilized to get the products as TFA salts.

In most of the cases boronate esters were hydrolyzed partly to get mixture of desired product and corresponding boronate esters. In such cases mixture was subjected to prep-HPLC purification under acidic condition during which, most of the boronate esters got converted to target boronic acids. Multiple purifications needed in such cases to isolate pure boronic acid.

In some cases TFA salts were converted to hydrochloride salts by stirring with 2N HCl for 30 min under nitrogen atmosphere followed by lyophilization.

The details of compounds synthesized by step (2a) are as below. All reactions were done on 100-200 mg scale.

| Comp. No. | Structure | Brief Reaction conditions | Analytical data |
|---|---|---|---|
| 132 Spiro | (3'-(5-(aminomethyl)-2H-spiro[benzofuran-3,4'-piperidin]-1'-ylcarbonyl)-5-fluoro-[1,1'-biphenyl]-3-yl)boronic acid | Acetonitrile (20 vol), TFA (10 vol) water (3 vol) 80° C., 12 hrs. | Mol. Wt: 460.3<br>MS (ES+): m/z = 461 [MH+]<br>HPLC Purity: 98.5%<br>$^1$H NMR(400 MHz, DMSO-d$_6$(D2O): δ 1.55-1.78(m, 4H), 3.07-3.27 (m, 4H)3.95(s, 2H), 4.39-4.50(m, 2H), 6.81 (d, J = 8.2 Hz, 1H),, 7.19 (dd, J = 8.4, 2.0 Hz, 1H)), 7.36(s, 1H), 7.43 (d, J = 7.6 Hz, 1H), 7.50 (dd, J = 9.4, 2.7 Hz, 1H)), 7.55-7.59(m, 2H), 7.69(s, 1H), 7.78-7.80(d = 8.2, 1H), 7.93(s, 1H) |
| 133 Spiro | (3'-(5-(aminomethyl)-2H-spiro[benzofuran-3,4'-piperidin]-1'-ylcarbonyl)-2-fluoro-[1,1'-biphenyl]-3-yl)boronic acid | Acetonitrile (20 vol), TFA (10 vol) water (3 vol) 80° C., 12 hrs. | Mol. Wt: 460.3<br>MS (ES+): m/z = 461 [MH+]<br>HPLC Purity: 99%<br>$^1$H NMR(400 MHz, DMSO-d$_6$(D2O): δ 1.55-1.78(m, 4H), 3.07-3.27(m, 4H)3.95(s, 2H), 4.39-4.50(m, 2H),6.81(J = 8.2 Hz, 1H), 7.21 (d, J = 8.1 Hz, 1H), 7.36(s, 1H), 7.47-7.38 (m, 2H), 7.65-7.50 (m, 5H), 7.93(s, 1H) |
| 131-Spiro | (3'-(5-(aminomethyl)-2H-spiro[benzofuran-3,4'-piperidin]-1'-ylcarbonyl)-4-fluoro-[1,1'-biphenyl]-3-yl)boronic acid | Acetonitrile (20 vol), TFA (10 vol) water (3 vol) 80° C., 12 hrs. | Mol. Wt: 460.3<br>MS (ES+): m/z = 461 [MH+]<br>HPLC Purity: 99.6%<br>$^1$H NMR(400 MHz, DMSO-d$_6$(D20): δ 1.66-1.77(m, 4H), 3.07-3.38(m, 4H)3.93(s, 2H), 4.41-4.49(m, 2H), 6.81 (d, J = 8.2 Hz, 1H), 7.20 (t, J = 8.8 Hz, 2H), 7.39 (d, J = 9.0 Hz, 2H), 7.55 (t, J = 7.7 Hz, 1H),7.65 (s, 1H), 7.73 (d, J = 7.9 Hz, 2H), 7.85 (d, J = 5.3 Hz, 1H) |
| 109-spiro | (5'-(5-(aminomethyl)-2H-spiro[benzofuran-3,'4-piperidin]-1'-ylcarbonyl)-2'-chloro-[1,1'-biphenyl]-3-yl)boronic acid | Dioxane 85 vol 30% HCl 2 vol. RT overnight isolate as TFA salt by prep HPLC Yield: ~8% | Mol. Wt: 476.17<br>MS (ES+): m/z = 477 [MH+], 479 [(M + 2)H+]<br>HPLC Purity: 95.8%<br>$^1$H NMR(400 MHz, DMSO-d$_6$): δ 1.37 (s, 9H), 1.53 (br, 2H), 1.83 (br, 2H), 2.60-2.90 (m, 2H), 3.10-3.30 (m, 1H), 4.10 (d, J = 5.6 Hz, 2H), 4.40 (br, 1H), 4.63 (br, 1H), 6.91 (d, J = 8.4 Hz, 1H), 7.00-7.40 (m, 6H), 7.44 (d, J = 15.2 Hz, 1H), 7.80 (d, J = 8.8 Hz, 1H), 8.07 (brs, 1H), 8.20 (s, 1H), 8.48 (brs, 1H), 13.5 (s, 1H). |

| Comp. No. | Structure | Brief Reaction conditions | Analytical data |
|---|---|---|---|
| 107 | (5'-(4-(3-(aminomethyl)phenyl)piperidine-1-carbonyl)-2',3'-dimethyl-[1,1'-biphenyl]-3-yl)boronic acid | Dioxane 100 vol 30% HCl 7 vol. RT overnight isolate as TFA salt by prep HPLC Yield: ~30.7% | Mol. Wt: 442.24 MS (ES+): m/z = 443 [MH$^+$] HPLC Purity: 99.49% $^1$H NMR (400 MHz, DMSO-d6): δ 1.37 (s, 9H), 1.53 (br, 2H), 1.83 (br, 2H), 2.60-2.90 (m, 2H), 3.10-3.30 (m, 1H), 4.10 (d, J = 5.6 Hz, 2H), 4.40 (br, 1H), 4.63 (br, 1H), 6.91 (d, J = 8.4 Hz, 1H), 7.00-7.40 (m, 6H), 7.44 (d, J = 15.2 Hz, 1H), 7.80 (d, J = 8.8 Hz, 1H), 8.07 (brs, 1H), 8.20 (s, 1H), 8.48 (brs, 1H), 13.5 (s, 1H). |
| 107-Spiro | (5'-(5-(aminomethyl)-2H-spiro[benzofuran-3,4'-piperidin]-1'-ylcarbonyl)-2',3'-dimethyl-[1,1'-biphenyl]-3-yl)boronic acid | Dioxane 100 vol 30% HCl 8 vol. RT overnight isolate as TFA salt by prep HPLC Yield: ~10% | Mol. Wt: ~470.37 MS (ES+): m/z = 471 [MH$^+$] HPLC Purity: 95.19% $^1$H NMR (400 MHz, DMSO-d$_6$): δ 1.37 (s, 9H), 1.53 (br, 2H), 1.83 (br, 2H), 2.60-2.90 (m, 2H), 3.10-3.30 (m, 1H), 4.10 (d, J = 5.6 Hz, 2H), 4.40 (br, 1H), 4.63 (br, 1H), 6.91 (d, J = 8.4 Hz, 1H), 7.00-7.40 (m, 6H), 7.44 (d, J = 15.2 Hz, 1H), 7.80 (d, J = 8.8 Hz, 1H), 8.07 (brs, 1H), 8.20 (s, 1H), 8.48 (brs, 1H), 13.5 (s, 1H). |
| 54-Boronic acid | (4-(2-(4-(3-aminomethyl)phenyl)piperidin-1-yl)-2-oxoethyl)-fluorophenyl)boronic acid | Conc. HCl (1 mL/g), 1,4-dioxane (30 mL/g), rt, 4 h, Yield: 67% | White solid; Mol. Wt: 370.23 MS (ES+): m/z = 371 [MH$^+$] HPLC Purity: 98.80% $^1$H NMR (400 MHz, D$_2$O): 7.64 (t, J = 7.2 Hz, 1H), 7.48-7.38 (m, 1H), 7.33-7.28 (m, 3H), 7.14 (d, J = 8.0 Hz, 1H), 7.10-7.02 (m, 1H), 4.59-4.52 (m, 1H), 4.28-4.16 (m, 3H), 3.96 (ABq, J = 15.6 Hz, 2H), 3.32-3.21 (m, 1H), 2.96-2.80 (m, 2H), 1.93 (d, J = 12.0 Hz, 1H), 1.84 (d, J = 14.8 Hz, 1H)), 1.65-1.54 (m, 1H), 1.42-1.29 (m, 1H) |
| 54-Boronic acid Spiro | (4-(2-(5-(aminomethyl)-2H-spiro[benzofuran-3,4'-piperidin]-1'-yl)-2-oxoethyl)-2-fluorophenyl)boronic acid | Conc. HCl (1 mL/g), 1,4-dioxane (30 mL/g), rt, 4 h, Yield: 58% | White solid; Mol. Wt: 398.24 MS (ES+): m/z = 399 [MH$^+$] HPLC Purity: 98.34% $^1$H NMR (400 MHz, D$_2$O): 7.65 (t, J = 7.2 Hz, 1H), 7.26 (d, J = 8.4 Hz, 1H), 7.21 (s, 1H), 7.15 (d, J= 7.6 Hz, 1H), 7.10-7.04 (m, 1H), 6.90 (d, J = 8.4 Hz, 1H), 4.57 (s, 2H), 4.44-4.35 (m, 1H), 4.11 (s, 2H), 4.06-3.99 (m, 1H), 3.96 (ABq, J = 16.0 Hz, 2H), 3.36-3.26 (m, 1H), 3.00-2.92 (m, 1H), 1.88-1.70 (m, 3H), 1.68-1.58 (m, 1H) |

Deprotection of the Protected Amide (B) with Boronic Acid Functionality (Step-2b)

Products from step-1b were stirred with aq. hydrochloric acid or Trifluoracetic acid (TFA) in a co-solvent like Dioxane, Acetonitrile, methanol, THF, DCM etc. Reaction was monitored by LCMS till most of the starting material was consumed. Reaction mass was concentrated under vacuum. The residue obtained was purified by reverse phase preparative HPLC. The pure fraction of mobile phase was lyophilized to get the products as TFA salts.

In some cases TFA salts were converted to hydrochloride salts by stirring with

2N HCl for 30 min under nitrogen atmosphere followed by lyophilization. The details of compounds synthesized by above method (2 b) are as below. All reactions were done on 100-200 mg scale.

| Comp. No. | Structure | Brief Reaction conditions | Analytical data |
|---|---|---|---|
| 116 Spiro | (3-(5-(5-(aminomethyl)-2H-spiro[benzofuran-3,4'-piperidin]-1'-ylcarbonyl)-2-methylthio)thiophen-3-yl)phenyl)boronic acid | TFA (20 eq.), dichloromethane (20 vol), R.T. 4 hr. Prep HPLC. isolated as TFA salt, | Yield: ~24% Mol. Wt: 494.15 MS (ES+): m/z = 494.95 [MH+] $^1$H NMR (400 MHz, DMSO-d$_6$): δ 8.17 (s, 4H), 7.95 (s, 1H), 7.78 (d, J = 7.3 Hz, 1H), 7.60 (d, J = 7.5 Hz, 1H), 7.46 (dd, J = 15.9, 8.2 Hz, 3H), 7.24 (d, J = 8.2 Hz, 1H), , 6.84 (d, J = 8.2 Hz, 1H), 4.52 (s, 2H), 4.27 (d, J = 13.2 Hz, 2H), 3.92 (d, J = 5.8 Hz, 2H). 2.58-2.45 (m, 3H), 1.90-1.72 (m, 4H), |
| 146 | (2-(((3-(4-(3(aminomethyl)phenyl)piperidine-1-carbonyl)phenyl)(methyl)amino)methyl)phenyl)boronic acid | dichloromethane(70 vol), TFA, (2 eq added at 0° C.) Stirring at R.T. for 24 hrs Purification by prep HPLC | Yield: ~10.34%, Mol. Wt: 457.37, MS (ES+): m/z = 458.25 [MH+], HPLC Purity: 97.56 % $^1$H NMR (400 MHz, DMSO-d$_6$): δ 8.11 (s, 2H), 7.51 (d, J = 7.3 Hz, 1H), 7.35 (d, J = 6.8 Hz, 2H), 7.22 (ddt, J = 31.5, 15.2, 6.9 Hz, 5H), 7.00 (d, J = 7.7 Hz, 1H), 6.77 (d, J = 8.1 Hz, 1H), 6.69-6.60 (m, 2H), 4.64 (d, J = 39.2 Hz, 2H), 4.15-3.80 (m, 6H), 2.99 (s, 3H), 2.78 (t, J = 12.0 Hz, 1H), 1.62 (t, J = 67.8 Hz, 6H). |
| 147 | (2-(((4-(4-(3(aminomethyl)phenyl)piperidine-1-carbonyl)phenyl)(methyl)amino)methyl)phenyl)boronic acid | dichloromethane(70 mL), TFA, (2 eq added at 0° C.) Stirring at R.T. for 24 hrs Purification by prep HPLC | Yield: ~10.34%, Mol. Wt: 457.37, MS (ES+): m/z = 458.30 [MH+], HPLC Purity: 98.83% $^1$H NMR (400 MHz, DMSO-d$_6$): δ 8.11 (s, 2H), 7.51 (d, J = 7.3 Hz, 1H), 7.35 (d, J = 6.8 Hz, 2H), 7.22 (ddt, J = 31.5, 15.2, 6.9 Hz, 5H), 7.00 (d, J = 7.7 Hz, 1H), 6.77 (d, J = 8.1 Hz, 1H), 6.69-6.60 (m, 2H), 4.64 (d, J = 39.2 Hz, 2H), 4.15-3.80 (m, 6H), 2.99 (s, 3H), 2.78 (t, J = 12.0 Hz, 1H), 1.62 (t, J = 67.8 Hz, 6H) |
| 143 | (2-(((5-(4-(3(aminomethyl)phenyl)piperidine-1-carbonyl)napthalen-1-yl)(methyl)amino)methyl)phenyl) boronic acid | dichloromethane (70 mL), TFA, (3 eq added at 0° C.) stirring at R.T. for 24 hrs Purification by prep HPLC after concentrating in vacuum | Yield: ~10.34%, Mol. Wt: 507.43, MS (ES+): m/z = 508.30 [MH+], HPLC Purity: 99.5% $^1$H NMR (400 MHz, DMSO-d$_6$): δ 8.36-8.28 (m, 1H), 8.13 (s, 2H), 7.51 (q, J = 11.5, 8.7 Hz, 4H), 7.32 (tdd, J = 27.9, 17.0, 7.6 Hz, 8H), 4.84 (t, J = 13.6 Hz, 1H), 4.39 (s, 2H), 4.02 (q, J = 5.9 Hz, 2H), 3.43-2.77 (m, 5H), 2.70 (s, 3H), 2.03-1.28 (m, 6H) |

| Comp. No. | Structure | Brief Reaction conditions | Analytical data |
|---|---|---|---|
| 154 | (2-(((5-(4-(3-(aminomethyl)phenyl)piperidine-1-carbonyl)napthalen-2-yl)(methyl)amino)methyl phenyl)boronic acid | Dichloromethane (45 vol), TFA, (3 eq added at 0° C.) Stirring at R.T. for 24 hrs Purification by prep HPLC after concentrating in vacuum | Yield: ~19.07%, Mol. Wt: 507.43, MS (ES+): m/z = 508.25 [MH$^+$], HPLC Purity: 97.10% $^1$H NMR (400 MHz, DMSO-d$_6$): δ 8.10 (s, 3H), 7.68 (d, J = 8.7 Hz, 1H), 7.52 (dd, J = 15.8, 8.2 Hz, 2H), 7.40-7.17 (m, 4H), 7.14 (d, J = 6.8 Hz, 2H), 7.05 (dd, J = 13.4, 5.3 Hz, 2H), 4.79 (s, 2H), 4.02 (s, 2H), 3.06 (s, 3H), 2.82 (m, 5H), 1.95-1.62 (m, 6H) |

Approach-2

Desired halo aryl carboxylic acids were first coupled with tert-butyl 3-(piperidin-4-yl) benzyl carbamate and coupled products were reacted with Bis Pinacolato diborane to get boronate esters which were hydrolyzed to corresponding boronic acids.

The details of intermediates halo aryl carboxylic acids (A) sourced/synthesised as per literature methods/synthesised by developed methods are given above.

Approach-2

Protected Cores

Core-1-common Core

Or

Core-4:- Spiro Core

Step-1

A

B

Step-2

C

H+ Step-3

Target Boronic Acids

Coupling of Halo Carboxylic Acid Precursors (A) to the Appropriate Protected Core to Get the Halo Amides (B)

Step-1: To a stirred solution of carboxylic acid in DCM or DMF was added DMAP or DIPEA, EDCI, HOBt (in some cases). The solution was stirred for 15 min. at 0° C.-RT followed by addition of Core-1 or Core-4 as shown in synthetic scheme. Stirring was continued at room temperature and reaction was monitored by LCMS till most of the, starting materials were consumed. Solvents were concentrated under vacuum and reaction mixture was then quenched with water and aq. layer was extracted twice with dichloromethane/ethyl acetate and combined organic layers were optionally washed with dil. HCl whenever DIPEA was used and dried over sodium sulfate and concentrated under vacuum to afford the product which was purified by column chromatography. The details of compounds synthesized by above method are as below.

| Comp. No. | Structure | Brief Reaction conditions | Analytical data |
|---|---|---|---|
| B-144 | 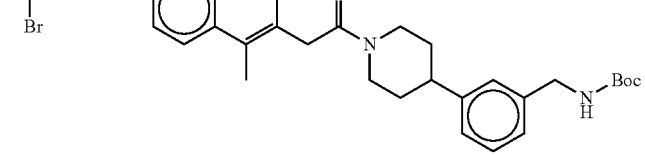<br>tert-butyl 3-(1-(2-(7-((2-bromobenzyl)(methyl)amino-4-methyl-2-oxo-2H-chromen-3-yl)acetyl)piperidin-4-yl)benzylcarbamate | carboxylic acid (0.34 g) 0.19 mmol) in DCM (~90 mL), HOBt (1.5 eq.)EDCI (1.5 eq.), DMAP (0.5 eq.) and tert-butyl 3-(piperidin-4-yl) benzyl carbamate (1.2 eq.) was stirred at R.T. for 12 hrs. Yield: ~77% after chromatographic purification | Mol. Wt: 687.23 MS (ES+): m/z = 588/590 [MH$^+$ − Boc], |
| B-51 | 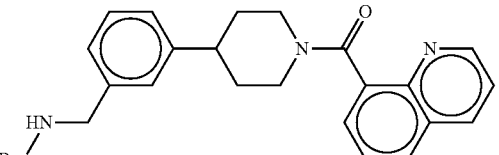<br>tert-butly 3-(1-(5-bromoquinoline-6-carbonyl)piperidin-4-yl) benzylcarbamate | 5-bromoquinoline-8-carboxylic acid (0.05 g, 0.19 mmol) in DMF (100 mL), HOBt (1.5 eq.) EDCI (1.5 eq.), DIPEA (2 eq.) and tert-butyl 3-(piperidin-4 yl) benzyl carbamate (1 eq.) were stirred at R.T. for 12 hrs Yield: ~50% after chromatographic purification | Mol. Wt: 523.15 MS (ES+): m/z = 546/548 [MH$^+$ + Na]] |
| B-155-Spiro | 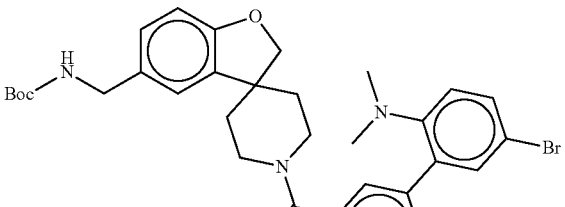<br>tert-butyl ((1'-(5'-bromo-2'-(dimethylamino)-[1,1'-biphenyl]-3-carbonyl)-2H-spiro[benzofuran-3,4'-piperidin]-5-yl)methyl)carbamate | A-155, spiro core (1 eq.), EDCI 1.5 eq, DMAP 1.1 eq., HOBt, 1.1 eq. in dichloromethane (75 mL) R.T. 12 hrs | Yield: ~90.20% Mol. Wt: ~620.58 MS (ES+): m/z = 620.30/622 [MH$^+$] |
| B-156 | 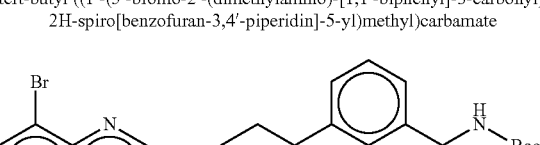<br>tert-butyl 3-(1-(6-bromoquinoline-3-carbonyl)piperidin-4-yl) benzylcarbamate | A156, tert-butyl 3-(piperidin-4-yl)benzyl carbamate (1.3 eq.), EDCI•HCl (1.5 eq.), DMAP (2 eq.), DCM(20 mL), RT, 4 h, | Yield: ~80%, Mol. Wt: ~524.45 MS (ES+): m/z = 524.20/526 [MH$^+$] |

Boronation of Halo Amides (Step-1) to Get Desired Boronate Esters (C)

Step-2: Product of step-1, was converted to boronate ester by palladium (0) catalyzed reaction with bis pinacolato borane in 1, 4-dioxane using potassium acetate as base. Reaction was monitored by LCMS till most of the starting material was consumed. After completion of reaction, the reaction mixture was filtered through celite and concentrated. Product was extracted in ethyl acetate, and ethyl acetate layer was washed with water. The organic layer was separated, dried over sodium sulfate concentrated and purified by column chromatography using hexane/ethyl acetate to yield the boronate esters contaminated with bis pinacolato borane, which were characterized by LCMS and subjected for next step without further purification The details of compounds synthesized are as below.

| Comp. No. | Structure | Brief Reaction conditions | Analytical data |
|---|---|---|---|
| C-144 | tert-butyl 3-(1-(2-(4-methyl-7-(methyl(2-(4,4,5,5-tetramethyl-1,3,2-dioxaborolan-2-yl)benzyl)amino)-2-oxo-2H-chromen-3-yl)acetyl)piperidin-4-yl)benzyl)carbamate | B-144 50 mg, Pd(OAc)$_2$ 1 eq. TPP 4 eq., potassium acetate 3 eq. bis pinacolato diborane 10 eq. in dioxane, 90° C. for 16 h. | Mol. Wt: 735.41 MS (ES+): m/z = 758 [MH$^+$ + Na] |
| C-51 | tert-butyl 3-(1-(5-(4,4,5,5-tetramethyl-1,3,2-dioxaborolan-2-yl)quinoline-8-carbonyl)piperidin-4-yl)benzylcarbamate | B-51 50 mg, Pd(PPh$_3$)$_4$ 0.1 eq. TPP 4 eq., potassium acetate 3 eq. bis pinacolato diborane 5 eq. in dioxane, reflux for 12 h. | Mol. Wt: 571.32 MS (ES+): m/z = 571 [MH$^+$] |
| C-155-Spiro | tert-butyl ((1'-(2'-(dimethylamino)-5'-(4,4,5,5-tetramethyl-1,3,2-dioxaborolan-2-yl)-[1,1'-biphenyl]-3-carbonyl)-2H-spiro[benzofuran-3,4'-piperidin]-5-yl)methyl)carbamate | B-155, bis pinacolato diborane(5 eq), KOAc (3.5 eq), Pd(dppf)Cl$_2$ (0.06 eq), DMSO 60 mL, 80° C., 6 hr | Yield: –crude Mol. Wt: 667.64 MS (ES+): m/z = 668.50 [MH$^+$] |
| C-156 | (3-(4-(3-(((tert-butoxycarbonyl)amino)methyl)phenyl)piperidine-1-carbonyl)quinolin-8-yl)boronic acid | B-156, bis pinacolato diborane (2.5 eq.), PdCl$_2$(dppf) (5 mol %), dppf (3 mol %), potassium acetate (3.0 eq.), Toluene (30 mL), Reflux, 5 hrs. Yield impure product was used for next step. | Mol. Wt: 489.37 MS (ES+): m/z = 390.20 [MH$^+$ – Boc] |

Deprotection of Boronate Esters (Step-2) to Get the Target Boronic Acids

Step-3: Products of step-2 were stirred with dioxane and concentrated HCl at room temperature overnight, when LCMS indicated complete consumption of starting. The reaction mixture was concentrated, and purified by Preparative HPLC. The details of compounds synthesized are below. All reactions were done on 100-200 mg scale.

| Comp. No. | Structure | Brief Reaction conditions | Analytical data |
|---|---|---|---|
| 144 | (2-(((3-(2-(4-(3-(aminomethyl)phenyl)piperidin-1-yl)-2-oxoethyl)-4-methyl-2-oxo-2H-chromen-7-yl)methyl)amino)methyl)phenyl)boronic acid | dioxane 100 vol 30% HCl 2 vol. RT overnight isolate as TFA salt by prep HPLC Yield: ~26% | Mol. Wt: 553.27<br>MS (ES+): m/z = 554 [MH+]<br>HPLC Purity: 96.4%<br>$^1$H NMR (400 MHz, DMSO-$d_6$): δ 1.40-1.70 (br, 2H), 1.84 (br, 2H), 2.60-2.91 (m, 2H), 3.10-3.30 (m, 1H), 3.98 (d, J = 5.6 Hz, 2H), 4.40-4.70 (br, 2H), 6.91 (d, J = 8.4 Hz, 1H), 7.20-7.50 (m, 6H), 7.78 (d, J = 8.8 Hz, 1H), 8.07 (br, 1H), 8.32 (br, 2H), 8.37 (br, 2H), 8.65 (br, 1H). |
| 51 | (8-(4-(3-(aminomethyl)phenyl)piperidine-1-carbonyl)quinolin-5-yl)boronic acid | dioxane (100 vol) 30% HCl (2 vol). RT overnight isolate as TFA salt by prep HPLC Yield: ~11.3% | Mol. Wt: 389.19<br>MS (ES+): m/z = 390 [MH+]<br>HPLC Purity: 99.8%<br>$^1$H NMR (400 MHz, CD$_3$OD): δ 1.70-2.00 (m, 4H), 2.85-3.00 (m, 2H), 3.75-3.85 (brd, 1H), 4.10 (s, 2H), 4.70-4.80 (brd, 2H), 6.80 (s, 1H), 7.02 (s, 1H), 7.26-7.44 (m, 4H), 7.95 (s, 1H) |
| 155-Spiro | (3'-(5-(aminomethyl)-2H-spiro[benzofuran-3,4'-piperidin]-1'-ylcarbonyl)-6-(dimethylamino)-[1,1'-biphenyl]-3yl)boronic acid | C-155, Acetonitrile (80 vol), 2NHCl(3o vol) RT 12 hrs. | Mol. Wt. 485.3<br>MS (ES+): m/z = 486.35 [MH+]<br>HPLC Purity: 96.72%<br>$^1$H NMR (400 MHz, DMSO-$d_6$): δ 8.02 (s, 2H), 7.75-7.66 (m, 1H), 7.64 (s, 1H), 7.56 (m, 3H), 7.42 (s, 1H), 7.36 (d, J = 7.5 Hz, 1H), 7.22 (d, J = 8.3 Hz, 1H), 7.04 (dd, J = 8.0, 4.3 Hz, 1H), 6.84 (d, J = 8.2 Hz, 1H), 4.57-3.89 (m, 2H), 3.69 (m, 2H), 3.19 (d, J = 62.5 Hz, 4H), 2.5 (s, 6H), 1.90-1.64 (m, 3H), 1.21 (d, J = 37.9 Hz, 3H) |
| 156 | (3-(4-(3-(aminomethyl)phenyl)piperidine-1-carbonyl)quinolin-8-yl) boronic acid | TFA(20 eq.), dichloromethane(20 vol), R.T. 4 hr. Prep HPLC. isolated as TFA salt | Yield: ~10%<br>Mol. Wt: 389.26<br>MS (ES+): m/z = 390.10 [MH+]<br>$^1$H NMR (400 MHz, DMSO-$d_6$): δ 9.04 (s, 1H), 8.62 (s, 1H), 8.35 (d, J = 6.7 Hz, 1H), 8.19 (dd, J = 13.1, 7.2 Hz, 1H), 7.75 (t, J = 7.5 Hz, 1H), 7.35 (ddd, J = 27.0, 12.8, 7.9 Hz, 4H), 3.40-3.23 (m, 2H), 4.03 (q, J = 5.7 Hz, 2H), 3.40-3.23 (m, 1H), 2.93 (d, J = 36.1 Hz, 4H), 1.98-1.63 (m, 6H). |

Example 29. Synthesis of Tryptase Inhibitor with Amido Phenol Functionality

Thirteen final targets with amido phenol functionality were synthesized.

Approach-1

Suitably substituted 2-hydroxy aromatic amides with carboxylic acid functionality were synthesized and coupled with the protected core followed by the deprotection of Boc protection on amino methyl functionality as in the reaction scheme below

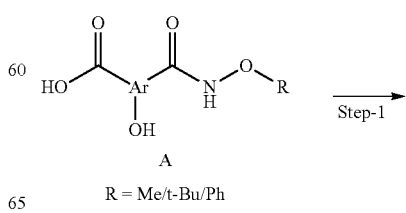

R = Me/t-Bu/Ph

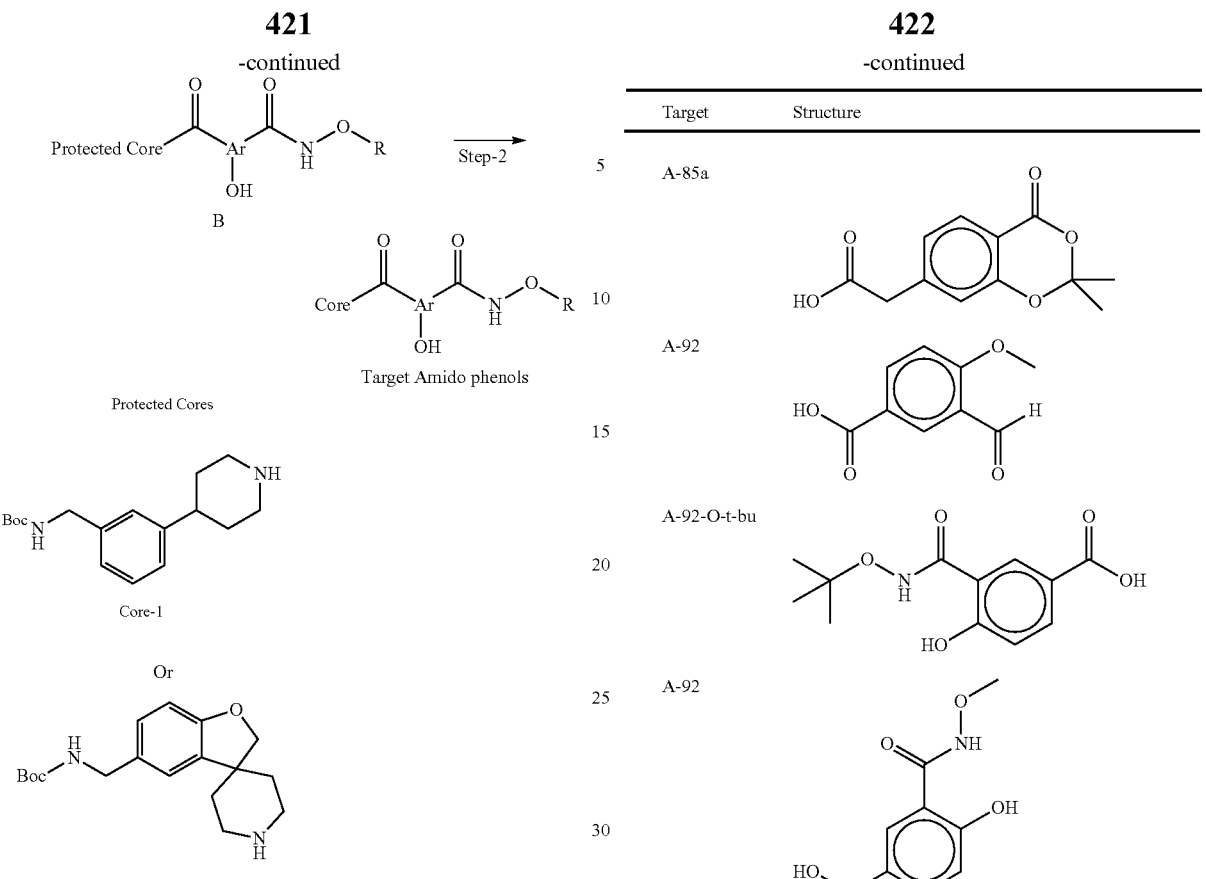
The details of intermediates (A) sourced/synthesised as per literature methods/synthesised by adapted methods are given below.
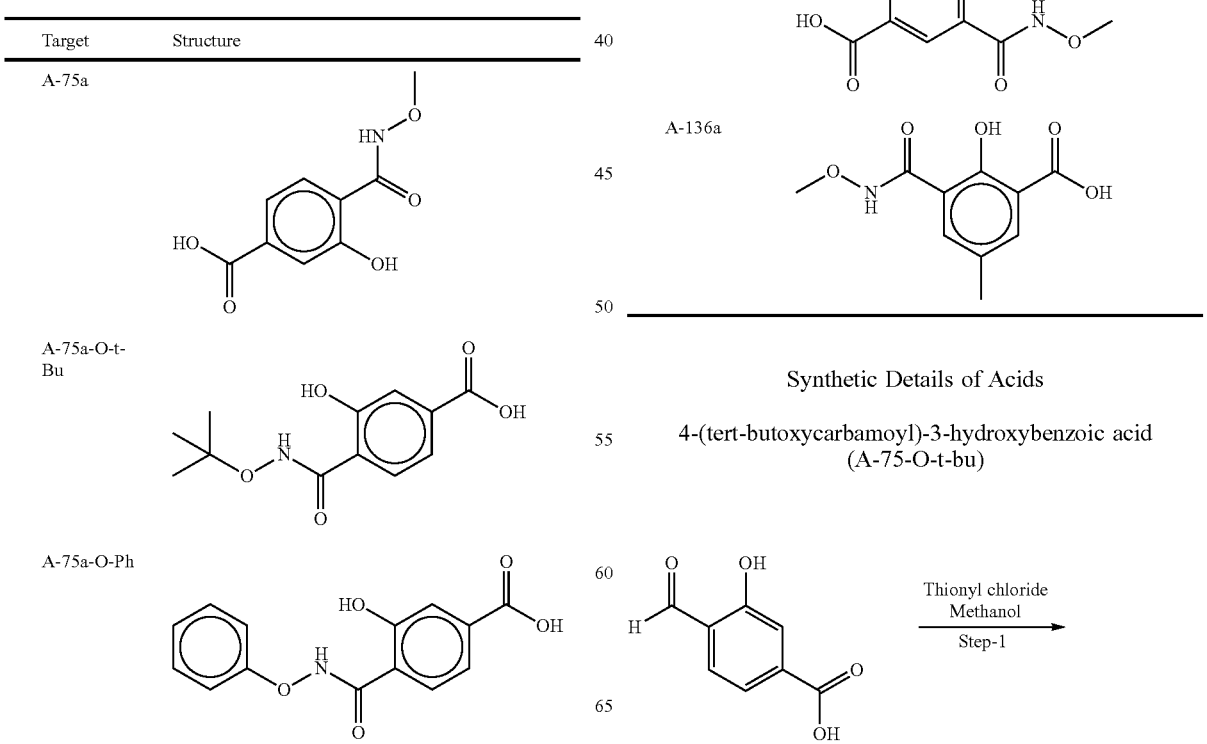
Synthetic Details of Acids
4-(tert-butoxycarbamoyl)-3-hydroxybenzoic acid (A-75-O-t-bu)

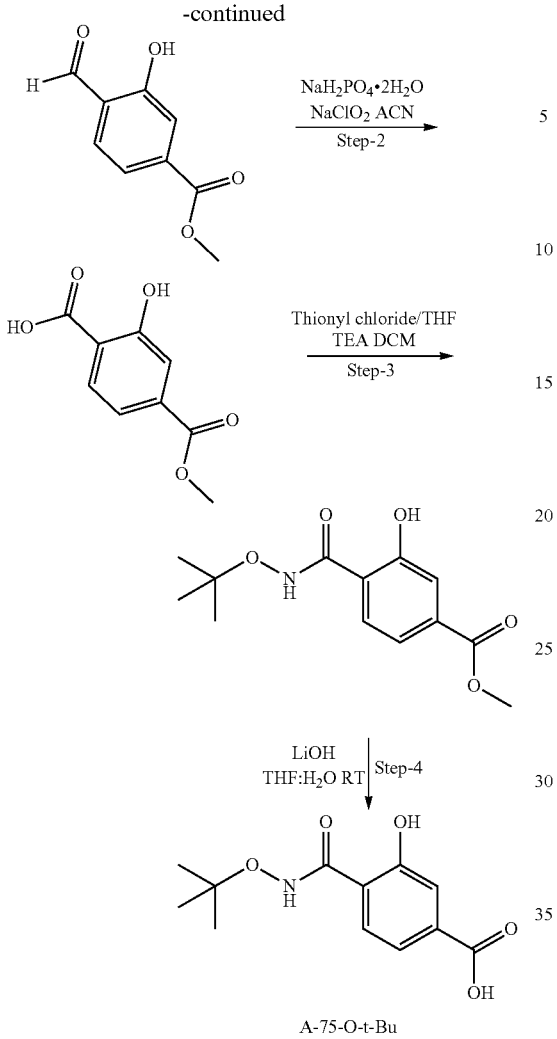

A-75-O-t-Bu

Experimental Procedures

Step-1: A solution of 4-formyl-3-hydroxy benzoic acid (0.1 g, 0.6 mmol) in methanol (50 mL) was cooled to 0° C. and charged with thionyl chloride (0.097 g, 0.72 mmol) and heated at reflux for 6 h. TLC (Mobile phase 5% methanol in chloroform) indicated absence of starting material (Rf 0.1) along with new spot (Rf 0.5). The reaction mixture was cooled to room temperature and concentrated in vacuo. The residue was partitioned between ethyl acetate and water and separated. The organic layer was dried over sodium sulfate concentrated, filtered, and concentrated in vacuo resulting in 95 mg desired product.

Yield: (95 mg, 87.9%).

$^1$H NMR (400 MHz, DMSO-$d_6$): δ 3.93 (s, 3H), 7.4 (d, J=8.0 Hz, 1H), 7.5 (s, 1H), 7.7 (d, J=8.0 Hz, 1H)

Step-2: A solution of methyl 4-formyl-3-hydroxybenzoate (0.05 g, 0.27 mmol) and NaH$_2$PO$_4$·2H$_2$O (0.11 g, 0.69 mmol) in DMSO: water, 2:1 (7.5 ml) was charged with sodium chlorite (0.075 g, 0.66 mmol) at 0° C. The reaction mixture was allowed to stir at room temperature for 12 h. The reaction mixture was acidified with 1N HCl till pH-2. and the precipitated white solid was filtered, washed with water several times and dried to give 2-hydroxy-4-(methoxycarbonyl) benzoic acid.

Yield: (0.035 g, 65%).

Mol Wt: 196;

MS (ES+): m/z=197.2 [MH$^+$]

Step-3: A solution of 2-hydroxy-4-(methoxycarbonyl) benzoic acid (0.20 g, 1 mmol) in THF (10 mL) was charged with thionyl chloride (0.121 g, 10 mmol) at 0° C. then the reaction mixture was heated to 45° C. for 4 h, The reaction mixture was concentrated in vacuo and the residue was diluted in dry DCM (5 ml) and charged with a solution of o-t-butyl amine.HCl (0.512 g, 4 mmol), TEA (0.412 g, 4 mmol) in DCM (15 ml) at 0° C. The reaction mixture was charged with 1N HCl solution (15 ml) and separated. The organic layer dried over sodium sulfate, filtered, and concentrated in vacuo to get 0.205 g crude product which was purified by column chromatography on silica gel using hexane-ethyl acetate as eluent to give methyl 4-(benzoyloxy)-3-formylbenzoate.

Yield: (0.16 g, 58.8%)

Mol Wt: 267

MS (ES+): m/z=268.05 [MH$^+$]

Step-4: A solution of step-3 product (0.160 g, 0.59 mmol) in THF: water (2:1) (15 mL) was charged with LiOH (0.043 g, 1.7 mmol) and stirred at room temperature for 6 h. The reaction mixture was concentrated in vacuo and the aqueous layer was and acidified with 1N HCl until pH-2. A solid precipitated out which was filtered and dried to give 4-(tert-butoxycarbamoyl)-3-hydroxybenzoic acid.

Yield: (0.015 g, 44%).

Mol Wt: 253

MS (ES+): m/z=254.0 [MH$^+$]

3-hydroxy-4-(phenoxycarbamoyl) benzoic acid (A-75-O-ph)

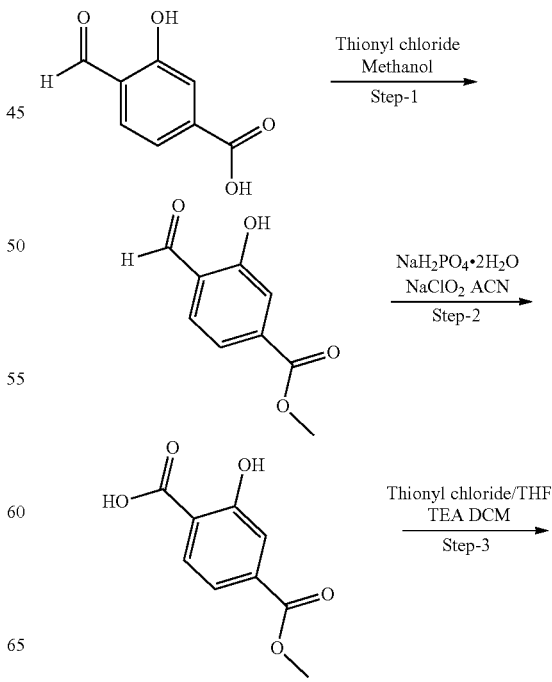

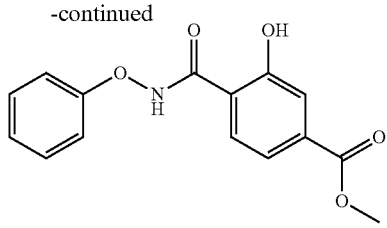

A-75-O-Ph

Experimental Procedures

Step-1: A solution of 4-formyl-3-hydroxy benzoic acid (0.1 g, 0.6 mmol) in methanol (50 mL) at 0° C. was charged with thionyl chloride (0.097 g, 0.72 mmol) and the reaction mixture was heated at reflux for 6 hr. The reaction mixture was cooled and concentrated in vacuo and partitioned between ethyl acetate and water and separated. The organic layer was dried over sodium sulfate, filtered, and concentrated in vacuo resulting in 95 mg of the desired product.

Yield: (0.095 g, 87.9%).

$^1$H NMR (400 MHz, DMSO-$d_6$): δ 3.93 (s, 3H), 7.4 (d, J=8.0 Hz, 1H), 7.5 (s, 1H), 7.7 (d, J=8.0 Hz, 1H)

Step-2: A solution of methyl 4-formyl-3-hydroxybenzoate (0.05 g, 0.27 mmol) and $NaH_2PO_4 \cdot 2H_2O$ (0.11 g, 0.69 mmol) in DMSO:water, 2:1 (7.5 ml) was cooled to 0° C. and charged with sodium chlorite (0.075 g, 0.66 mmol). The reaction mixture was allowed to stir at room temperature for 12 hr. then acidified to pH 2 with 1N HCl. The precipitated white solid was filtered, washed with water several times and dried to give 2-hydroxy-4-(methoxycarbonyl) benzoic acid.

Yield: (0.035 g, 65%).
Mol Wt: 196
MS (ES+): m/z=197.2 [MH$^+$]

Step-3: A solution of 2-hydroxy-4-(methoxycarbonyl) benzoic acid (0.05 g, 0.25 mmol) in THF (10 mL) was cooled to 0° C. and charged with thionyl chloride (0.303 g, 2.5 mmol) then the reaction mixture was heated to 45° C. for 4 hr. The reaction mixture was concentrated in vacuo and the residue was diluted with dry DCM (5 ml) and charged with a solution of o-phenyl amine.HCl (0.055 g, 0.38 mmol), $NaHCO_3$ (0.038 mg, 0.45 mmol) and in DCM (15 ml) at 0° C. then the reaction was charged with 1N HCl solution (15 ml) and the organic was separated, dried over sodium sulfate, filtered, and concentrated in vacuo resulting in 0.07 g of crude product which was purified by column chromatography on silica gel eluting with hexane-ethyl acetate resulting in methyl 3-hydroxy-4-(phenoxycarbamoyl)benzoate.

Yield: (0.5 g, 68%)
Mol Wt: 287
MS (ES+): m/z=288.1 [MH$^+$]

Step-4: A solution of methyl 3-hydroxy-4-(phenoxycarbamoyl)benzoate (0.05 g, 0.17 mmol) in THF:water (2:1) (7.5 mL) was charged with LiOH (0.012 g, 0.51 mmol) and stirred at room temperature for 6 h. The reaction mixture was concentrated and the aqueous was acidified to pH 2 with 1N HCl and the precipitate was filtered and dried to give 3-hydroxy-4-(phenoxycarbamoyl) benzoic acid.

Yield: (0.03 g, 63.8%).
Mol Wt: 273
MS (ES+): m/z=274.0 [MH$^+$]

Synthesis of 2-(2, 2-dimethyl-4-oxo-4H-benzo[d] [1, 3] dioxin-7-yl) acetic acid (A-85a)

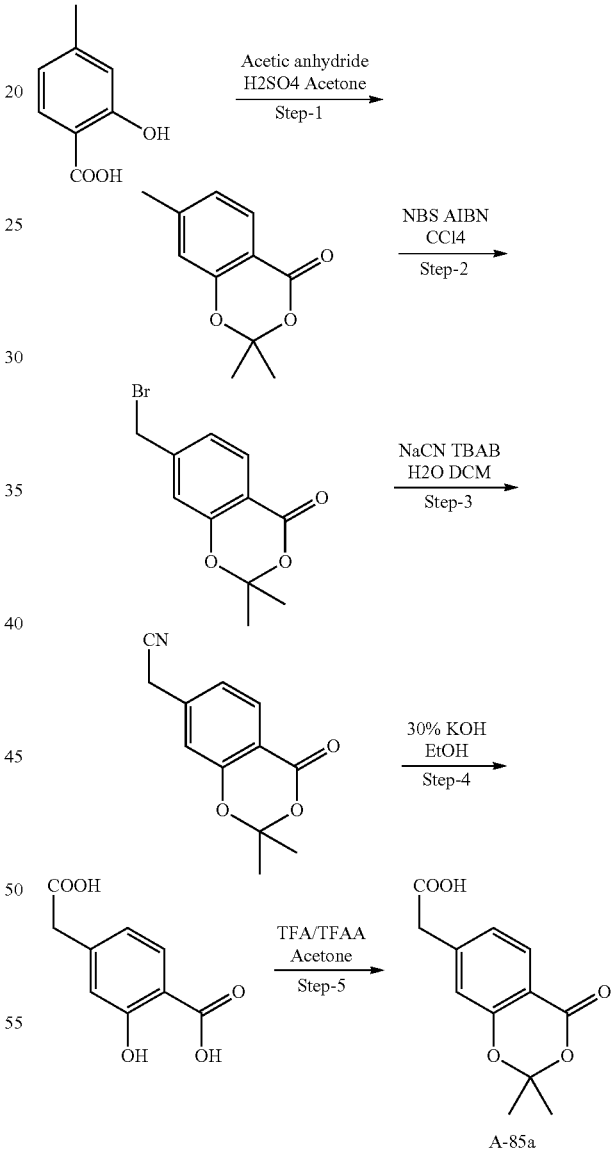

Experimental Procedures

Step-1: A solution of 2-hydroxy-4-methylbenzoic acid (5 g, 32.8 mmol) and acetic anhydride (1.5 mL) in acetone (12.5 mL) at −8° C. was charged with concentrated sulfuric acid (0.05 mL) and stirred at room temperature overnight. The reaction mixture was concentrated to in vacuo to obtain a dark brown solid which was repeatedly washed with hexane and diethyl ether to get yellow solid. The solid was then purified by column chromatography on silica gel using chloroform/hexane as eluent to give crude product which was washed with saturated solution of sodium bicarbonate to give 2,2,7-trimethyl-4H-benzo[d][1,3]dioxin-4-one.

Yield: (4.5 g, 71.4%),

MS (ES+): m/z=193 [MH+]

Step-2: A solution of 2, 2, 7-trimethyl-4H-benzo[d][1,3]dioxin-4-one (4.5 g, 23.4 mmol) in carbon tetrachloride (200 mL) was charged with N-bromosuccinimide (4.83 g, 27.1 mmol) and AIBN (0.8 g, 4.92 mmol) and the mixture was refluxed for 2 hr. The reaction mixture was washed with water and the compound was extracted in dichloromethane. The organic layer was separated, dried over sodium sulfate, filtered, and concentrated in vacuo and the crude was purified by column chromatography using hexane ethyl acetate as eluent resulting in 7-(bromomethyl)-2,2-dimethyl-4H-benzo[d][1,3]dioxin-4-one.

Yield: (1.8 g, 28.3%),

MS (ES+): m/z=271 [MH+]

Step-3: A solution of 7-(bromomethyl)-2,2-dimethyl-4H-benzo[d][1,3]dioxin-4-one (1.8 g, 6.64 mmol) in dichloromethane (15 mL) was added slowly to a suspension of sodium cyanide (0.57 g, 11.6 mmol in 1.2 mL water) and TBAB (0.08 g, 0.26 mmol). The reaction mixture was allowed to stir at room temperature for 48 h. The reaction mixture was quenched with water and the organic layer was separated, washed with water and brine. The organic layer was separated, dried over sodium sulfate, filtered, and concentrated in vacuo and the crude purified by column chromatography using hexane ethyl acetate as eluent resulting in 2-(2,2-dimethyl-4-oxo-4H-benzo[d][1,3]dioxin-7-yl)acetonitrile.

Yield: (0.5 g, 35%).

MS (ES+): m/z=218 [MH+]

Step-4: A solution of 2-(2,2-dimethyl-4-oxo-4H-benzo[d][1,3]dioxin-7-yl)acetonitrile (0.55 g, 2.53 mmol) in ethanol (4.5 mL) was charged with 30% KOH (4.5 mL) and heated at 60° C. for 3 h. The reaction mixture was concentrated in vacuo, and the aqueous was acidified with 1N HCl and the compound was extracted in ethyl acetate. The organic layer was separated, dried over sodium sulfate, filtered, and concentrated in vacuo resulting in 4-(carboxymethyl)-2-hydroxybenzoic acid as a yellow solid.

Yield: (0.42 g, 85.7%).

$^1$H NMR (400 MHz, DMSO-$d_6$): δ 1.25 (t, J=7.0 Hz, 3H), 4.10-4.23 (q, J=7 Hz, 2H), 6.57 (d, J=16 Hz, 1H), 6.91 (d, J=8.4 Hz, 1H), 7.55 (d, J=16 Hz, 1H), 7.74-7.80 (dd, J=2.0 and 8.6 Hz, 1H), 8.06 (s, 1H), 8.28 (d, J=2 Hz, 1H), 8.50 (s, 1H), 13.5 (s, 1H).

Step-5: A solution of 4-(carboxymethyl)-2-hydroxybenzoic acid (0.25 g, 1.27 mmol) in acetone (4 mL), was charged with TFAA (4 mL) and TFA (6 mL) and heated at 100° C. for 24 h. The reaction mixture was concentrated in vacuo to give 2-(2,2-dimethyl-4-oxo-4H-benzo[d][1, 3]dioxin-7-yl) acetic acid. The crude compound was used as such for the next step without further purification.

Yield: (0.55 g, Crude),

MS (ES+): m/z=237 [MH+]

Synthesis of 3-formyl-4-hydroxybenzoic acid: (A-92)

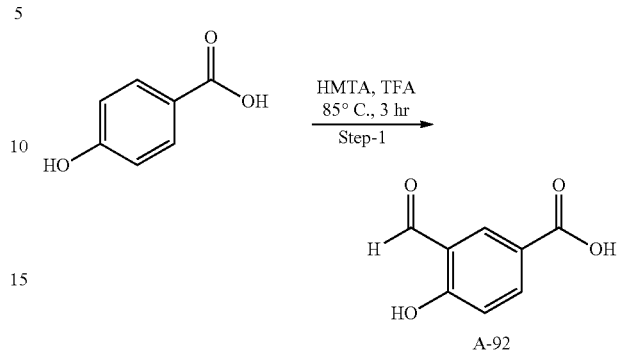

Experimental Procedures

A solution of 4-hydroxy benzoic acid (2 g, 14.4 mmol) in TFA (8 mL) was charged with HMTA (2 g, 14.4 mmol) and heated at 85° C. for 3 h. TLC (Mobile phase 30% ethyl acetate in n-hexane) indicated absence of starting material (Rf 0.3) and product formation (Rf 0.5). The reaction mixture was cooled and charged with 1N HCl (75 mL) and was extracted in diethyl ether. The organic layer was separated, dried over sodium sulfate, filtered, and concentrated in vacuo and the crude was purified by column chromatography using hexane ethyl acetate as eluent resulting 3-formyl-4-hydroxybenzoic acid.

Yield: (0.6 g, 33.8%).

$^1$H NMR (400 MHz, CDCl$_3$): δ 3.93 (s, 3H), 7.04 (d, 1H, J=8.8 Hz), 8.18-8.20 (dd, J=1.6 Hz, J=8.8 Hz, 1H), 8.32 (s, 1H), 9.56 (s, 1H), 11.39 (s, 1H).

Synthesis of 3-(tert-butoxycarbamoyl)-4-hydroxybenzoic acid (A-92-O-t-bu)

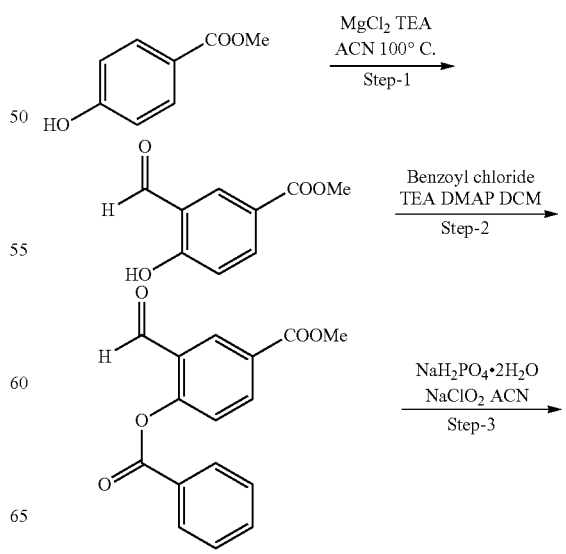

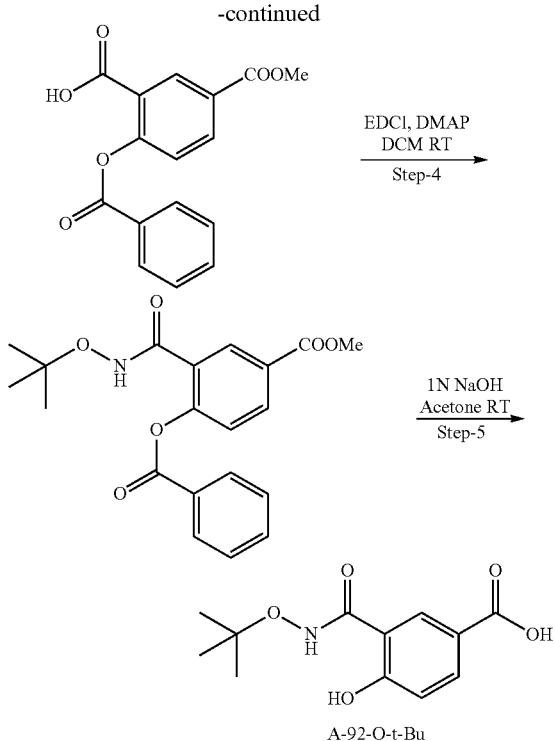

A-92-O-t-Bu

Experimental Procedures

Step-1: A solution of methyl-4-hydroxy benzoate (2 g, 13.15 mmol) and anhydrous magnesium chloride (1.87 g, 19.7 mmol) in acetonitrile (100 mL) was charged with triethyl amine (7 mL, 49.9 mmol). The reaction mixture was then charged with para formaldehyde (8 g, 89.4 mmol) in a single portion and the reaction mixture was heated at reflux for 24 hr. The reaction mixture was cooled and quenched with 1N HCl and extracted with ethyl acetate. The organic layer was washed with water and separated dried over sodium sulfate, filtered, and concentrated in vacuo and the crude material was purified by column chromatography using hexane ethyl acetate as eluent to give methyl 3-formyl-4-hydroxybenzoate as white solid.

Yield: (0.51 g, 22%).

$^1$H NMR (400 MHz, CDCl$_3$): δ 3.93 (s, 3H), 7.04 (d, J=8.8 Hz, 1H), 8.18-8.20 (dd, J=1.6 Hz, J=8.8 Hz, 1H), 8.32 (s, 1H), 9.56 (s, 1H), 11.39 (s, 1H).

Step-2: A solution of methyl 3-formyl-4-hydroxybenzoate (1.8 g, 0.01 mol) in dichloromethane (120 mL) was cooled to 0° C. and charged with DMAP (0.12 g, 0.001 mol), triethylamine (5.5 mL, 0.04 mol) and benzoyl chloride (2.3 mL, 0.02 mol). The reaction mixture was allowed to stir at room temperature overnight. The reaction mixture was quenched with water. The organic layer was separated and washed with water and the organic layer was separated, dried over sodium sulfate, filtered, and concentrated in vacuo. The crude material was purified by column chromatography using hexane/ethyl acetate as eluent resulting in methyl 4-(benzoyloxy)-3-formylbenzoate.

Yield: (1.4 g, 49.2%).

$^1$H NMR (400 MHz, DMSO-d$_6$): δ 3.83 (s, 3H), 7.06 (d, J=8.8 Hz, 1H), 8.02-8.07 (dd, J=1.6 and 8.6 Hz, 1H), 8.38 (d, J=1.2 Hz, 1H).

Step-3: A solution of methyl 4-(benzoyloxy)-3-formylbenzoate (0.05 g, 0.17 mmol) and NaH$_2$PO$_4$.2H$_2$O (0.068 g, 0.44 mmol) in DMSO:H$_2$O, 2:1 (6 mL) was charged with sodium chlorite (0.038 g, 0.42 mmol) and was allowed to stir at room temperature for 2 hr. The reaction mixture was acidified to pH 2 with 1N HCl and the white precipitate was filtered, washed with water several times and dried to give 2-(benzoyloxy)-5-(methoxycarbonyl)benzoic acid as the desired product.

Yield: (0.05 g, 96.1%).

$^1$H NMR (400 MHz, DMSO-d$_6$): δ 3.83 (s, 3H), 7.06 (d, J=8.8 Hz, 1H), 8.02-8.07 (dd, J=1.6, 8.6 Hz, 1H), 8.38 (d, J=1.2 Hz, 1H).

Step-4: A solution of 2-(benzoyloxy)-5-(methoxycarbonyl)benzoic acid (0.3 g, 1.00 mmol) in DCM (15 mL) was charged with DMAP (0.061 g, 0.5 mmol), EDCI (0.28 g, 1.5 mmol) and o-(tert-butyl)hydroxylamine hydrochloride (0.18 g, 1.5 mmol) and the mixture was stirred at room temperature for 2 hr. The reaction mixture was washed with water (3×), 2N HCl 3 (3×) and separated. The organic layer was dried over sodium sulfate, filtered, and concentrated in vacuo resulting in crude material that was purified by column chromatography on silica gel using hexane/ethyl acetate as eluent to give methyl 4-(benzoyloxy)-3-(tert-butoxycarbamoyl)benzoate.

Yield: (0.2 g, 54%).

MS (ES+): m/z=372 [MH$^+$]

Step-5: A solution of methyl 4-(benzoyloxy)-3-(tert-butoxycarbamoyl) benzoate (0.05 g, 0.13 mmol) in acetone (1.2 mL) was charged with 1N NaOH (1.2 mL) and the reaction mixture was stirred at room temperature overnight. The reaction mixture was concentrated in vacuo and the aqueous was acidified to pH 2 using 1N HCl. A solid precipitated out and was filtered and dried to give 3-(tert-butoxycarbamoyl)-4-hydroxybenzoic acid.

Yield: (0.015 g, 44%).

MS (ES+): m/z=254 [MH$^+$]

Synthesis of
4-hydroxy-3-(methoxycarbamoyl)-5-methylbenzoic acid (A-114)

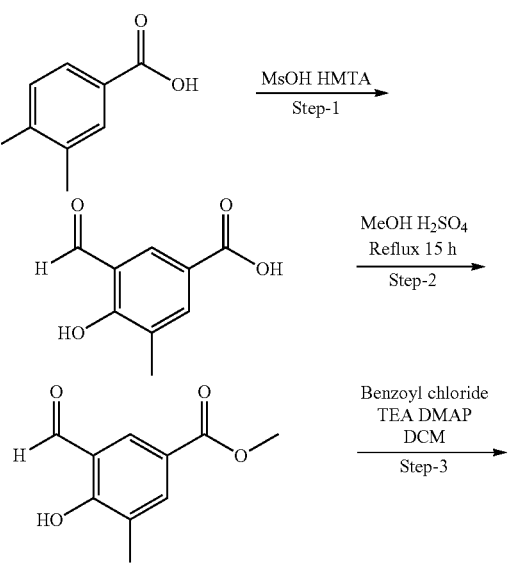

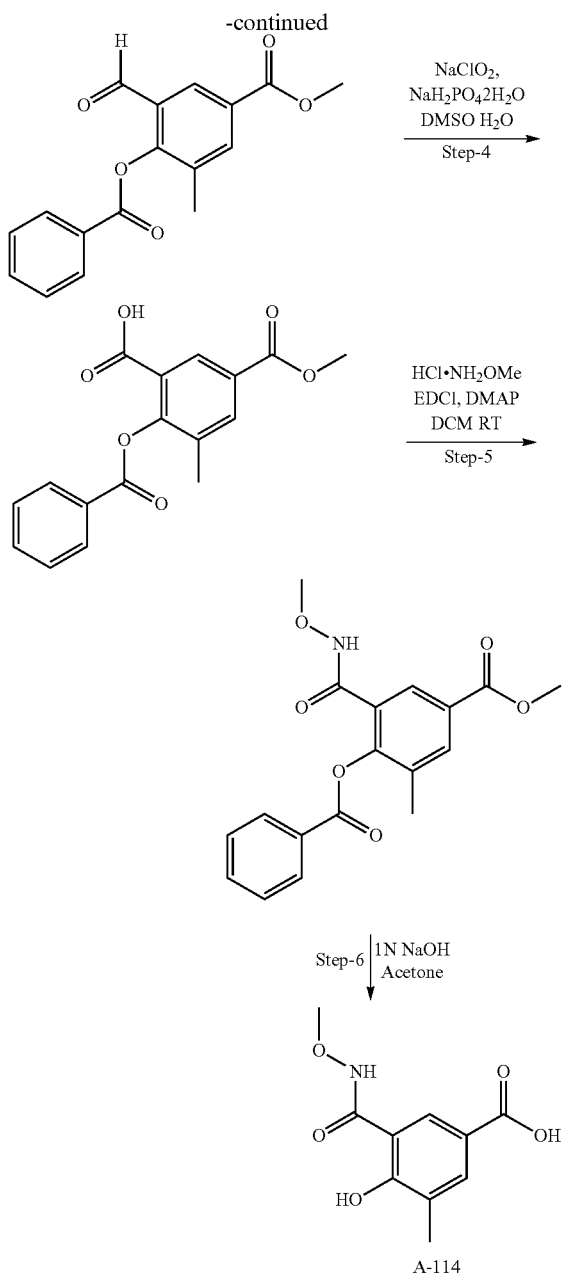

Experimental Procedures

Step-1: A suspension of 4-hydroxy-3-methylbenzoic acid (1 g, 6.57 mmol) suspended in methanesulfonic acid (5 mL) was cooled to 0° C. and portionwise charged with hexamethylenetetramine (1.84 g, 13.15 mmol) and warmed to warmed to room temperature followed by heating at 90° C. for 5 hr then cooled to room temperature and stirred overnight. The reaction mixture was poured into ice cooled water and the compound was extracted in ethyl acetate. The organic layer was washed with water, dried over sodium sulfate, filtered, and concentrated in vacuo to give 3-formyl-4-hydroxy-5-methylbenzoic acid as yellow solid.

Yield: (0.5 g, 42.3%).

$^1$H NMR (400 MHz, CDCl$_3$): δ 3.93 (s, 3H), 7.04 (d, J=8.8 Hz, 1H), 8.19 (dd, 1H, J=1.6, 8.8 Hz, 1H), 8.32 (s, 1H), 9.56 (s, 1H), 11.39 (s, 1H).

Step-2: A solution of 3-formyl-4-hydroxy-5-methylbenzoic acid (0.2 g, 1.11 mmol) in methanol (4 mL) was charged with conc. sulfuric acid (0.14 mL) and refluxed for 16 hr. The reaction mixture was concentrated and the aqueous was extracted in ethyl acetate. The combined organic layer was washed with saturated solution of sodium bicarbonate dried over sodium sulfate, filtered, concentrated in vacuo to give methyl 3-formyl-4-hydroxy-5-methylbenzoate as an off white solid.

Yield: (0.18 g, 85.7%).

$^1$H NMR (400 MHz, DMSO-d$_6$): δ 3.83 (s, 3H), 7.06 (d, J=8.8 Hz, 1H), 8.02-8.07 (dd, J=1.6, 8.6 Hz, 1H), 8.38 (d, J=1.2 Hz, 1H).

Step-3: A solution of methyl 3-formyl-4-hydroxy-5-methylbenzoate (0.5 g, 2.57 mmol) in dichloromethane (50 mL) was cooled to 0° C. and charged with DMAP (0.031 g, 0.25 mmol), triethylamine (1.4 mL, 1.03 mmol), and benzoyl chloride (0.6 mL, 5.15 mmol) then allowed to stir at room temperature overnight. The reaction mixture was quenched with water and the organic layer was separated and washed with water. The organic layer was dried over sodium sulfate, filtered, and concentrated in vacuo and the crude was purified by column chromatography on silica gel using hexanes/ethyl acetate as eluent to give methyl 4-(benzoyloxy)-3-formyl-5-methylbenzoate.

Yield: (0.5 g, 65.7%).

$^1$H NMR (400 MHz, CDCl$_3$): δ 3.91 (s, 3H), 3.92 (s, 3H), 7.03 (d, J=8.8 Hz, 1H), 8.05-8.09 (dd, J=1.8, 8.6 Hz, 1H), 8.16 (s, 1H), 9.48 (s, 1H), 12.2 (s, 1H)

Step-4: A solution of methyl 4-(benzoyloxy)-3-formyl-5-methylbenzoate (0.5 g, 1.67 mmol) and NaH$_2$PO$_4$.2H$_2$O (0.65 g, 4.19 mmol) in DMSO:water (2:1) (30 mL) was charged with sodium chlorite (0.36 g, 4.02 mmol) and allowed to stir at room temperature for 2 hr. The reaction mixture was acidified to pH 2 with 1N HCl upon which a white precipitate formed. The precipitate was filtered, washed with water several times and dried to give 2-(benzoyloxy)-5-(methoxycarbonyl)-3-methylbenzoic acid as the desired product.

Yield: (0.4 g, 77%).

$^1$H NMR (400 MHz, DMSO-d$_6$): δ 3.70 (s, 3H), 7.05 (d, J=8.4 Hz, 1H), 7.89-7.93 (dd, J=1.4, 8.6 Hz, 1H), 8.26 (s, 1H).

Step-5: A solution of 2-(benzoyloxy)-5-(methoxycarbonyl)-3-methylbenzoic acid (0.2 g, 0.63 mmol), DMAP (0.077 g, 0.63 mmol), EDCI (0.18 g, 0.95 mmol) in DCM (20 mL) was charged with o-methyl hydroxylamine hydrochloride (0.08 g, 0.95 mmol) and stirred at room temperature for 2 hr. The reaction mixture was washed with water (3×), 2N HCl (3×) and separated. The combined organic layer was dried over sodium sulfate, filtered, and concentrated in vacuo and the crude was further purified by column chromatography on silica gel using hexanes/ethyl acetate as eluent to give methyl 4-(benzoyloxy)-3-(methoxycarbamoyl)-5-methylbenzoate.

Yield: (0.12 g, 57.1%)

$^1$H NMR (400 MHz, CDCl$_3$): δ 1.46 (s, 9H), 1.64-2.00 (m, 4H), 2.70-2.82 (m, 1H), 2.90-3.40 (br, 2H), 4.29 (s, 2H), 4.50-5.00 (br, 2H), 6.97 (d, J=8.4 Hz, 1H), 7.00-7.20 (m, 4H), 7.26-7.30 (m, 1H), 7.42 (d, J=8.4 Hz, 1H), 7.70 (s, 1H), 10.7 (s, 1H), 12.1 (s, 1H).

Step-6: A solution of methyl 4-(benzoyloxy)-3-(methoxycarbamoyl)-5-methylbenzoate (0.12 g, 0.34 mmol) in acetone (2.5 mL) was charged with 1N NaOH (2.5 mL) and stirred at room temperature overnight. The reaction mixture was concentrated in vacuo and the aqueous was acidified to pH 2 with 1N HCl. Upon acidification a precipitate formed and was filtered and dried to give 4-hydroxy-3-(methoxycarbamoyl)-5-methylbenzoic acid.

Yield: (0.03 g, 38.4%),

MS (ES+): m/z=226 [MH$^+$]

Synthesis of 2-hydroxy-3-(methoxycarbamoyl)-5-methylbenzoic acid (A-136 a)

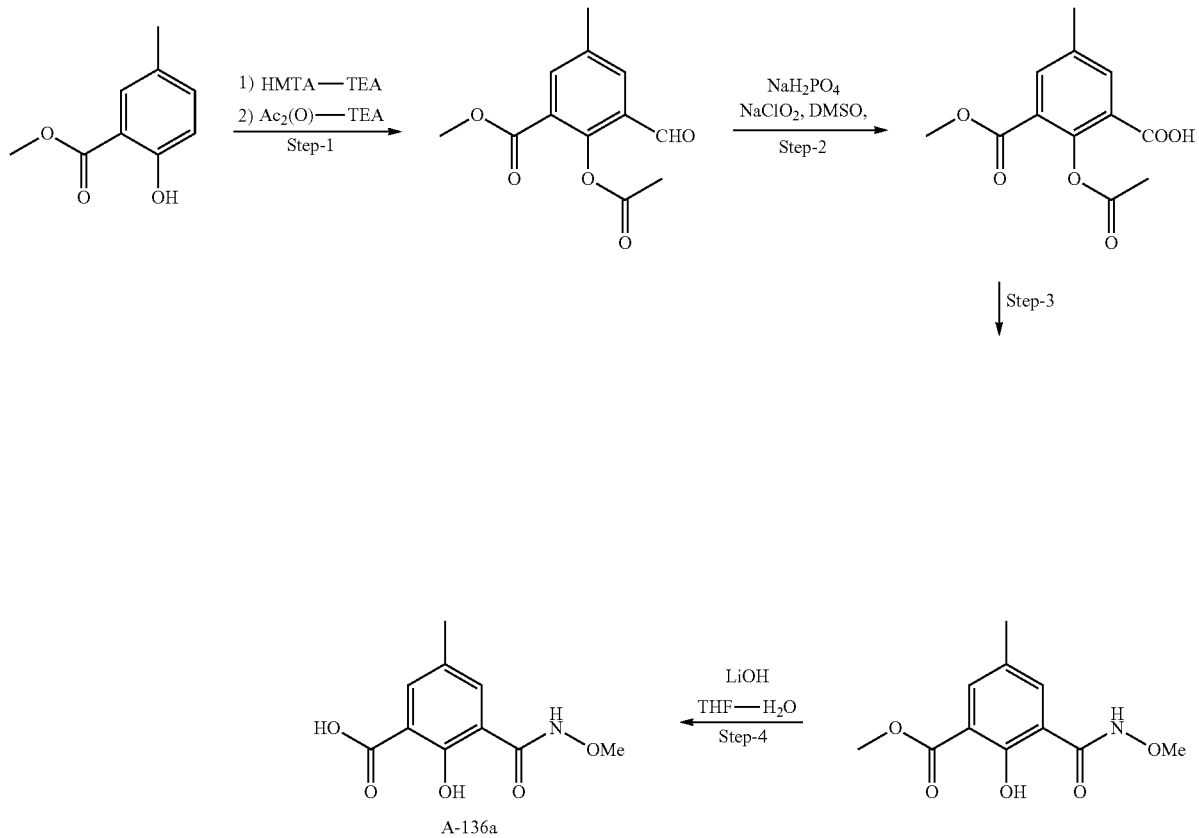

Experimental Procedures

Step-1: Formylation of methyl 2-hydroxy-5-methylbenzoate was carried out as per procedure described in the literature. (*J. Org. Chem.* 1999, 64, 5858-5866). Subsequent 0-Acetylation carried out by stirring the hydroxyl aldehyde with Ac$_2$O, NEt$_3$ in DCM.

Step-2: Step-1 product was dissolved in 40 vol DMSO: water (4:1), sodium dihydrogen phosphate (5 eq) and charged with sodium chlorite (5 eq) and stirred at room temperature and monitored by LCMS till starting material was consumed (15 hrs). Reaction mixture was then concentrated, residue was acidified with aqueous HCl and product extracted in ethyl acetate. Ethyl acetate extract dried over sodium sulfate, filtered, and concentrated in vacuo to afford the crude product which was sufficiently pure for the use in next step.

Yield: 93%, White solid;
Mol. Wt: 252.22
MS (ES+): m/z=253 [MH$^+$]

Step-3: A solution of step-2 product in 20 vol DCM was charged with EDCI (1.5 eq.) and stirred at room temperature for 10 minutes followed by addition of DMAP (1.5 eq) and O-Methyl hydroxyl amine hydrochloride (1.5 eq) and stirred at room temperature for hr. The reaction mixture was diluted with ethyl acetate, washed with water, dried over sodium sulfate, filtered, and concentrated in vacuo to afford the crude product which was purified by column chromatography on silica gel eluting with (0-10%, ethyl acetate in hexanes) to yield methyl 2-hydroxy-3-(methoxycarbamoyl)-5-methylbenzoate.

Yield: 88%, White solid;
Mol. Wt: 239.22
MS (ES+): m/z=240 [MH$^+$]

Step-4: A solution of step-3 product in THF:water (2:1) was charged with LiOH (3.0 eq.) and stirred at room temperature for 5 hr, The reaction mixture was concentrated and the aqueous was acidified to pH 2 with 1N HCl and the precipitate was filtered and dried to give white solid product.

Yield: 85% White solid;
Mol. Wt: 225.20
MS (ES+): m/z=226 [MH$^+$]Synthesis of intermediate amides and final targets with their respective approaches are as follows Step-1: Couplings of desired suitably substituted carboxylic acids were carried out with protected 4-(3-aminomethyl phenyl) piperidine or 5-aminomethyl spiro [benzofuran-3, 4'-piperidine] as per conditions mentioned in the table below. Work-up of reactions was carried out as described in general methods. Details of the compound are given in the table below.

| Comp. No. | Structure | Brief Reaction conditions | Analytical data |
|---|---|---|---|
| B-75a-O-t-Bu | tert-butyl 3-(1-(4-(tert-butoxycarbamoyl)-3-hydroxybenzoyl)piperidin-4-yl)benzylcarbamate | EDCI (1.5 eq.), DMAP (1.2 eq), DCM (~200 Vol), phenyl piperidine core(1 eq), Stirring at RT For 3 hrs, Crude product used for next step without purification | Yield: ~96%, Mol. Wt.: 525.64 MS (ES+): m/z = 526.35 [MH+] |
| B-75a-O-t-Bu Spiro | tert-butyl ((1'-(4-(tert-butoxycarbamoyl)-3-hydroxybenzoyl)-2H-spiro[benzofuran-3,4'-piperidin]-5-yl)methyl)carbamate | EDCI (1.5 eq.), DMAP (1.2 eq), DCM (~200 Vol), phenyl piperidine core(1 eq), Stirring at RT For 3 hrs, Crude product used for next step without purification | Yield: ~82.5%, Mol. Wt.: 553.65 MS (ES+): m/z = 586.350[MH+ + Na] |
| B-75a-O-Ph | tert-butyl 3-(1-(3-hydroxy-4-(phenoxycarbamoyl)benzoyl)piperidin-4-yl)benzylcarbamate | EDCI (1.5 eq.), DMAP (1.2 eq), DCM (~200 Vol), phenyl piperidine core(1 eq), Stirring at RT For 3 hrs, Crude product used for next step without purification | Yield: ~90%, Mol. Wt.: 545.63 MS (ES+): m/z = 558.3 [MH+ + Na] |
| B-75a-O-Ph-spiro | tert-butyl ((1'-(3-hydroxy-4-(phenoxycarbamoyl)benzoyl)-2H-spiro[benzofuran-3,4'-piperidin]-5-yl)methyl)carbamate | EDCI (1.5 eq.), DMAP (1.2 eq), DCM (~300 Vol), phenyl piperidine core(1 eq), Stirring at RT For 3 hrs, Crude product used for next step without purification | Yield: ~96%, Mol. Wt.: 573.64 MS (ES+): m/z = 596.20 [MH+ + Na] |
| B-75a Spiro | tert-butyl ((1'-(3-hydroxy-4-(methoxycarbamoyl)benzoyl)-2H-spiro[benzofuran-3,4'-piperidin]-5-yl)methyl)carbamate | EDCI (1.5 eq.), DMAP (1.2 eq), DCM (~200 Vol), phenyl piperidine core(1 eq), Stirring at RT For 3 hrs, Crude product used for next step without purification | Yield: ~86%, Mol. Wt.: 511.57 MS (ES+): m/z = 534.25 [MH+ + Na] |

| Comp. No. | Structure | Brief Reaction conditions | Analytical data |
|---|---|---|---|
| B-92-O-t-bu | tert-butyl 3-(1-(3-(tert-butoxycarbamoyl)-4-hydroxybenzoyl)piperidin-4-yl)benzylcarbamate | EDCI (1.5 eq.), DMAP (0.5 eq), DCM (~300 Vol), phenyl piperidine core(1 eq), Stirring at RT For 4 hrs, Crude product used for next step without purification | Yield: ~64.5%, Mol. Wt.: 525.64 MS (ES+): m/z = 426 [MH$^+$ − Boc] |
| B-92-O-t-bu spiro | tert-butyl ((1'-(3-tert-butoxycarbamoyl)-4-hydroxybenzoyl)-2H-spiro[benzofuran-3,4'-piperidin]-5-yl)methyl)carbamate | EDCI (1.5 eq.), DMAP (0.5 eq), DCM (~300 Vol), Spiro core(1.2 eq), Stirring at RT For 4 hrs, Crude product used for next step without purification | Yield: ~89.8%, Mol. Wt.: 553.65 MS (ES+): m/z = 576 [MH$^+$ + Na] |
| B-92 Spiro | tert-butyl ((1'-(4-hydroxy-3-methoxycarbamoyl)benzoyl)-2H-spiro[benzofuran-3,4'-piperidin]-5-yl)methyl)carbamate | EDCI (1.5 eq.), DMAP (0.5 eq), DCM (~100 Vol), Spiro core(1.2 eq), Stirring at RT For 4 hrs, Crude product purified by column chromotography using hexane ethyl acetate | Yield: ~51.6%, Mol. Wt.: 511.57 MS (ES+): m/z = 534 [MH$^+$ + Na] |
| B-114 Spiro | tert-butyl ((1'-(4-hydroxy-3-(methoxycarbamoyl)-5-methylbenzoyl)-2H-spiro[benzofuran-3,4'-piperidin]-5-yl)methyl)carbamate | EDCI (1.5 eq.), DMAP (0.5 eq), DCM (~150 Vol), Spiro core(1.2 eq), Stirring at RT For 4 hrs, Crude product purified by column chromotography using hexane ethyl acetate | Yield: ~71.4%, Mol. Wt.: 525.59 MS (ES+): m/z = 526 [MH$^+$] |
| B-136a | tert-butyl 3-(1-(2-hydroxy-3-(methoxycarbamoyl)-5-methylbenzoyl)piperidin-4-yl)benzylcarbamate | tert-butyl-3-(piperidin-4-yl) benzyl carbamate (1.1 eq.), PyBOP (1.5 eq.), pyridine (2.0 eq.), DMF (30 mL/g), rt, 15 h. | Yield: 30%, White solid; Mol. Wt: 497.58 MS (ES+): m/z = 498 [MH$^+$] |

Step-2: Products of step-1 were deprotected as per conditions mentioned in the table below. The details of the compounds synthesized are as below. All reactions were done on 100-200 mg scale.

| Comp. No. | Structure | Brief Reaction conditions | Analytical data |
|---|---|---|---|
| 75a-O-t-Bu | 4-(4-(3-(aminomethyl)phenyl)piperidine-1-carbonyl)-N-(tert-butoxy)-2-hydroxybenzamide | DCM(~175 vol), TFA (6 Vol), stirring at RT for 3 h, Followed by concentration and purification by prep HPLC | Yield: 41%, Mol. Wt. 425.52, MS (ES+): m/z = 426.25 [MH+] HPLC: 97.9% (200-400 nm) $^1$H NMR (400 MHz, DMSO-d$_6$, D$_2$O): δ 7.76 (s, 1H), 7.74 (d, J = 8.2 Hz, 1H) 7.49 (d, J = 6.7 Hz, 1H), 7.30 (dt, J = 25.5, 8.2 Hz, 1H), 7.07 (dd, J = 13.7, 7.5 Hz, 2H), 6.95 (d, J = 8.4 Hz, 1H), 4.01 (q, J = 5.6 Hz, 2H) 3.20 (m, 3H), 2.86 (s, 2H), 1.91-1.53 (m, 4H), 1.25 (s, 9H). |
| 75a-O-Ph | 4-(4-(3-(aminomethyl)phenyl)piperidine-1-carbonyl)-2-hydroxy-N-phenoxybenzamide | DCM(~50 vol), TFA (6 Vol), stirring at RT for 3 h, Followed by concentration and purification by prep HPLC | Yield: 10%, Mol. Wt. 445.41, MS (ES+): m/z = 446.20 [MH+] HPLC: 96.68% (200-400 nm) $^1$H NMR (400 MHz, DMSO-d$_6$, D$_2$O): δ 7.94 (s, 1H), 7.81 (s, 1H), 7.74 (d, J = 8.2 Hz, 1H), 7.49 (d, J = 6.7 Hz, 1H), 7.30 (dt, J = 25.5, 8.2 Hz, 5H), 7.07 (dd, J = 13.7, 7.5 Hz, 2H), 6.95 (d, J = 8.4 Hz, 1H), 3.97 (s, 2H), 3.20 (m, 3H), 2.86 (s, 2H), 1.91-1.53 (m, 4H). |
| 75a-O-t-Bu Spiro | 4-(5(aminomethyl)-2H-spiro[benzofuran-3,4′-piperidin]-1′-ylcarbonyl-N-(tert-butoxy)-2-hydroxybenzamide | DCM(~100 vol), TFA(6 Vol), stirring at RT for 3 h, Followed by concentration and purification by prep HPLC | Yield: 48%, Mol. Wt. 453.53, MS (ES+): m/z = 517.20 [MH+ + Na + AcN] HPLC: 99.13% (200-400 nm) $^1$H NMR (400 MHz, DMSO-d$_6$): δ 11.09 (s, 1H), 8.05 (d, J = 16.0 Hz, 3H), 7.77 (d, J = 7.9 Hz, 1H), 7.43 (d, J = 2.0 Hz, 1H), 7.23 (dd, J = 8.3, 1.9 Hz, 1H), 6.96-6.84 (m, 2H), 4.50 (d, J = 4.5 Hz, 2H), 4.36 (d, J = 13.3 Hz, 1H), 3.95 (q, J = 5.6 Hz, 2H), 3.29-3.01 (m, 4H), 1.76 (q, J = 22.4, 20.8 Hz, 4H), 1.25 (s, 9H) |
| 75a Spiro | 4-(5-(aminomethyl)-2H-spiro[benzofuran-3,4′-piperidin]-1′-ylcarbonyl)-2-hydroxy-N-methoxybenzamide | DCM(~100 vol), TFA(6 Vol), stirring at RT for 3 h, Followed by concentration and purification by prep HPLC | Yield: 74%, Mol. Wt. 411.45, MS (ES+): m/z = 434.3 [MH+ + Na], HPLC: 97.85% (200-400 nm) $^1$H NMR (400 MHz, DMSO-d$_6$): δ 8.04 (s, 3H), 7.71 (d, J = 8.0 Hz, 1H), 7.43 (d, J = 2.1 Hz, 1H), 7.23 (dd, J = 8.3, 2.0 Hz, 1H), 6.95-6.81 (m, 2H), 4.50 (d, J = 5.4 Hz, 2H), 4.35 (d, J = 12.9 Hz, 1H), 4.01 (s, 3H), 3.67 (s, 3H), 3.15 (dt, J = 58.2, 12.2 Hz, 4H), 1.90-1.60 (m, 4H). |
| 75a-O-Ph-spiro | 4-(5-(aminomethyl)-2H-spiro[benzofuran-3,4′-piperidin]-1′-ylcarbonyl)-2-hydroxy-N-phenoxybenzamide | DCM(~50 vol), TFA(6 Vol), stirring at RT for 3 h, Followed by concentration and purification by prep HPLC | Yield: 29%, Mol. Wt. 473.52, MS (ES+): m/z = 474.20 [MH+] HPLC: 99.80% (200-400 nm) $^1$H NMR (400 MHz, DMSO-d$_6$): δ 8.03 (s, 3H), 7.79 (d, J = 7.9 Hz, 1H), 7.43 (s, 1H), 7.35 (t, J = 7.8 Hz, 1H), 7.23 (d, J = 7.9 Hz, 1H), 7.12 (d, J = 8.2 Hz, 1H), 7.06 (t, J = 7.3 Hz, 2H), 7.01-6.85 (m, 3H), 6.84 (s, 1H), 4.51 (d, J = 3.7 Hz, 2H), 4.36 (s, 1H), 3.95 (q, J = 5.5 Hz, 2H), 3.58 (s, 2H), 3.10 (s, 2H), 1.74 (d, J = 37.8 Hz, 4H). |

| Comp. No. | Structure | Brief Reaction conditions | Analytical data |
|---|---|---|---|
| 92-O-t-bu | 5-(4-(3-(aminomethyl)phenyl)piperidine-1-carbonyl)-N-(tert-butoxy)-2-hydroxybenzamide | dioxane ~200 vol, conc. HCl 3.5 vol, 4 hrs stirring at RT, Followed by concentration and purification by prep HPLC | Yield: 50%, Mol. Wt. 425.52, MS (ES+): m/z = 448 [MH$^+$ + Na], HPLC: 94.5% (220 nm) $^1$H NMR (400 MHz, DMSO-d$_6$): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H), 11.7 (br, 1H), 11.9 (br, 1H). |
| 92-O-t-Bu spiro | 5-(5-(aminomethyl)-2H-spiro[benzofuran-3,4'-piperidin]-1'-ylcarbonyl)-N-(tert-butoxy)-2-hydroxybenzamide | dioxane ~75 vol, conc. HCl 3.5 vol, 4 hrs stirring at RT, Followed by concentration and purification by prep HPLC | Yield: 38%, Mol. Wt. 453.53, MS (ES+): m/z = 476 [MH$^+$ + Na] HPLC: 99.0% (220 nm) $^1$H NMR (400 MHz, DMSO-d$_6$): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H), 11.7 (br, 1H), 11.9 (br, 1H). |
| 92 Spiro | 5-(5-(aminomethyl)-2H-spiro[benzofuran-3,4'-piperidin]-1'-ylcarbonyl)-2-hydroxy-N-methoxybenzamide | dioxane ~100 vol, conc. HCl 4 vol, 12 hrs stirring at RT, Followed by concentration and purification by prep HPLC | Yield: 27%. Mol. Wt: –411.45, MS (ES+): m/z = 412 [MH$^+$] HPLC: 95.5% (220 nm), $^1$H NMR (400 MHz, DMSO-d$_6$): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H), 11.7 (br, 1H), 11.9 (br, 1H). |
| 114 Spiro | 5-(5-(aminomethyl)-2H-spiro[benzofuran-3,4'-piperidin]-1'-ylcarbonyl)-2-hydroxy-N-methoxy-3-methylbenzamide | dioxane ~100 vol, conc. HCl 4 vol, 4 hrs stirring at RT, Followed by concentration and purification by prep HPLC | Yield: 33.3%, Mol Wt.: –425.48 MS (ES+): m/z = 448 [MH$^+$ + Na] HPLC: 95.98% (220 nm), $^1$H NMR (400 MHz, DMSO-d$_6$): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H), 11.7 (br, 1H), 11.9 (br, 1H). |
| 136a | 3-(4-(3-(aminomethyl)phenyl)piperidine-1-carbonyl)-2-hydroxy-N-methoxy-5-methylbenzamide | conc. HCl (1 mL/g), 1,4-dioxane (30 mL/g), rt, 4 h, Yield: 86% | White solid; Mol. Wt.: 397.47 MS (ES+): m/z = 398 [MH$^+$] HPLC Purity: 93.44% $^1$H NMR (400 MHz, CD$_3$OD): δ 7.50-7.22 (m, 6H), 4.16-4.06 (m, 3H), 3.83 (s, 3H), 3.58-3.45 (m, 1H), 3.21-3.10 (m, 1H), 3.04-2.85 (m, 2H), 2.32 (s, 3H), 2.14-1.70 (m, 4H) |

Approach-2

Carboxy O-methyl salicylaldehydes/Protected salicylic acids were first coupled with the protected core. Subsequent O-methylation & oxidation (In case of aldehydes) or deprotection (In case of protected salicylic acids) of the coupled product yielded carboxylic acid which was coupled with suitable amine and then Boc protection on amino methyl functionality was carried out to get the desired products. In case of O-Methyl compounds O-de-methylation and Boc deprotection was carried out together using boron tribromide as in the reaction scheme below.

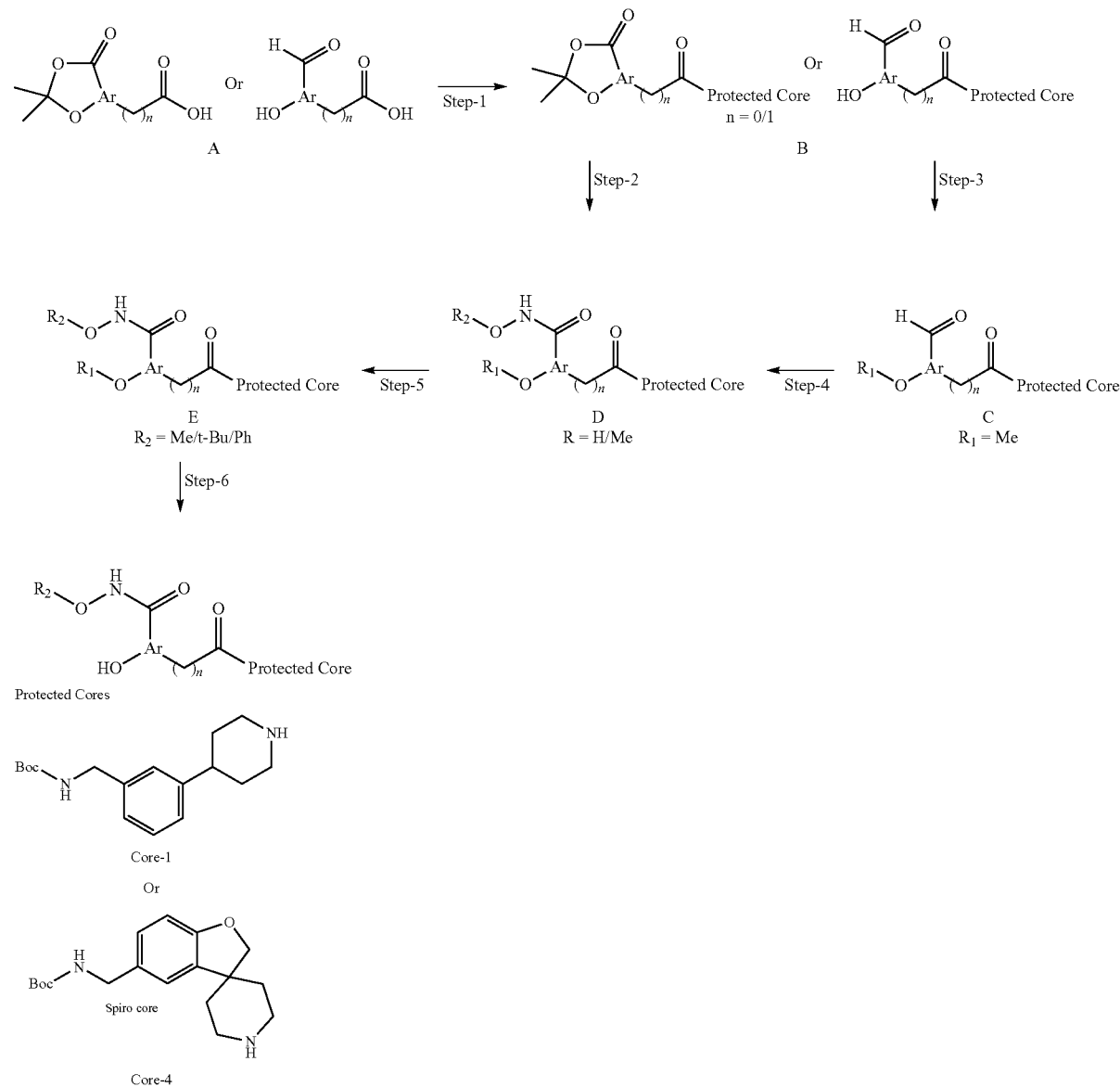

Step-1: Coupling of protected salicylic acids/salicylaldehydes with appropriate core (core-1/core-4 as shown in synthetic scheme.) A stirred solution of protected salicylic acid/salicylaldehyde in DCM was charged with EDCI, HOBt (in some cases) and DMAP or DIPEA. The solution was stirred for 15 min. at 0° C. followed by addition of protected core. Stirring was continued at room temperature and reaction was monitored by LCMS till most of the starting materials were consumed. Reaction mixture was then quenched with water and aq. layer was extracted with dichloromethane and combined organic layers were dried over sodium sulfate, filtered, and concentrated under vacuum to afford the crude product, which were sufficiently pure to be used for next step.

| Comp. No. | Structure | Brief Reaction conditions | Analytical data |
|---|---|---|---|
| B-92-Spiro-O-Ph | tert-butyl ((1'-(3-formyl-4-hydroxybenzoyl)-2H-spiro[benzofuran-3,4'-piperidin]-5-yl)methyl)carbamate | EDCI (1.5 eq.), DMAP (0.5 eq), DCM (100 Vol), spiro core(1.2 eq), Stirring at RT For 4 hrs, Crude product used for next step without purification | Yield: ~53.5%, Mol. Wt.: 466.53 MS (ES+): m/z = 489 [MH$^+$ + Na] |
| B-92-O-Ph | tert-butyl 3-(1-(3-formyl-4-hydroxybenzoyl)piperidin-4yl)benzyl-carbamate | EDCI (1.5 eq.), DMAP (0.5 eq), DCM (100 Vol), phenyl piperidine core(1 eq), Stirring at RT For 4 hrs, Crude product used for next step without purification | Yield: ~72%, Mol. Wt.: 438.52 MS (ES+): m/z = 502 [MH$^+$ + Na + AcN] |
| B-85a | tert-butyl 3-(1-(2-(2,2-dimethyl-4-oxo-4H-benzo[d][1,3]dioxin-7-yl)acetyl)piperidin-4-yl)benzylcarbamate | EDCI (1.5 eq.), HOBt (1.5 eq), DMF (15 Vol), DIPEA (4 eq), phenyl piperidine core(1.2 eq), Stirring at RT For 4 hrs, Crude product purified by column chromatography using hexane ethyl acetate. | Yield: ~50%, Mol. Wt.: 508.61 MS (ES+): m/z = 531 [MH$^+$ + Na] |

Step-2: Deprotection of acid in coupled protected core amide: A solution of step-1 product in dioxane:water was charged with lithium hydroxide and the reaction mixture was stirred at room temperature for 4 h. The reaction mixture was concentrated in vacuo and the aqueous layer was acidified with 1N HCl upon which a precipitate formed. The precipitate was filtered, washed with hexane and dried to give step-2 product.

| Comp. No. | Structure | Brief Reaction conditions | Analytical data |
|---|---|---|---|
| D-85a | 4-(2-(4-(3-(((tert-butoxycarbonyl)amino)methyl)phenyl)piperidin-1-yl)-2-oxoethyl)-2-hydroxybenzoic acid | LiOH (10 eq) dioxane: water (1:1) ~45 vol. Stirring at RT for 4 hrs. Solvents concentrated under vacuum distillation and subsequent acidification with 1N HCl resulted in solid which was used for next step without purification. | Yield: ~58.3% Mol. Wt.: 468.54 MS (ES+): m/z = 491 [MH$^+$ + Na] |

Step-3: O-Methylation of step-1 product: A solution of step-1 product and potassium carbonate in acetone was charged with methyl iodide and heated at 70° C. for 4 hr. The reaction mixture was filtered and concentrated in vacuo and the compound was extracted in dichloromethane and washed with water. The organic layer was washed with water, dried over sodium sulfate, filtered, and concentrated to give step-4 product. The crude product was used as such for the next step without purification.

| Comp. No. | Structure | Brief Reaction conditions | Analytical data |
|---|---|---|---|
| D-92-Spiro-O-Ph | tert-butyl ((1'-(3-formyl-4-methoxybenzoyl)-2H-spiro[benzofuran-3,4'-piperidin]-5-yl)methyl)carbamate | Acetone (60 vol), potassium carbonate (3 eq), methyl iodide (1.2 eq), 70 °C., 4 hrs, isolated by distillation of solvent, dilution with water and extraction with dichloromethane and concentration. Crude product used for next step | Yield: ~95% (Crude) Mol. Wt.: 480.55 LCMS (m/z): 503 [MH⁺ + Na] |
| D-92-O-Ph | tert-butyl 3-(1-(3-formyl-4-methoxybenzoyl)piperidin-4-yl)benzylcarbamate | Acetone (60 vol), potassium carbonate (3 eq), methyl iodide (2 eq), 70° C., 4 hrs, Isolated by distillation of solvent, dilution with water and extraction with dichloromethane and concentration. Crude product used for next step | Yield: 100% (Crude), $^1$H NMR (400 MHz, CDCl$_3$): δ 3.93 (s, 3H), 7.04 (d, J = 8.8 Hz, 1H), 8.18-8.20 (dd, J = 1.6 Hz, J = 8.8 Hz, 1H), 8.32 (s, 1H), 9.56 (s, 1H), 11.39 (s, 1H). |

Step-4: Oxidation of step-3 product: A solution of step-3 product and NaH$_2$PO$_4$.2H$_2$O in DMSO:water was charged with sodium chlorite and allowed to stir at room temperature for 2 hr. The reaction mixture was acidified to pH 2 with 1N HCl upon which a precipitate formed. The white precipitate was filtered, washed with water several times and dried to give step-3 product

| Comp. No. | Structure | Brief Reaction conditions | Analytical data |
|---|---|---|---|
| D-92-Spiro-O-Ph | 5-(5-(((tert-butoxycarbonyl)amino)methyl)-2H-spiro[benzofuran-3,4'-piperidin]-1'-ylcarbonyl)-2-methoxybenzoic acid | sodium chlorite (2.4 eq), Sodium dihydrogen phosphate dehydrate (2.5 eq), DMSO (40 vol), Water (20 vol), Stirring at R.T. for 2 hrs, followed by acidification with 1N HCl to pH-2 & Filtration to get solid product which was sufficient pure to be used for next step | Yield: 88.2%, $^1$H NMR (400 MHz, DMSO-d$_6$): δ 3.70 (s, 3H), 7.05 (d, J = 8.4 Hz, 1H), 7.89-7.93 (dd, J = 1.4, 8.6 Hz, 1H), 8.26 (s, 1H). |
| D-92-O-Ph | 5-(4-(3-(((tert-butoxycarbonyl)amino)methyl)phenyl)piperidine-1-carbonyl)-2-methoxybenzoic acid | sodium chlorite (2.4 eq), Sodium dihydrogen phosphate dehydrate (2.5 eq), DMSO (20 vol), Water (10 vol), Stirring at R.T. for 2 hrs, followed by acidification with 1N HCl to pH-2 & Filtration to get solid product which was sufficient pure to be used for next step | Yield: 57%, $^1$H NMR (400 MHz, CDCl$_3$): δ 3.93 (s, 3H), 7.04 (d, 1H, J = 8.8 Hz), 8.18-8.20 (dd, J = 1.6 Hz, 8.8 Hz, 1H), 8.32 (s, 1H), 9.56 (s, 1H), 11.39 (s, 1H). |

Step-5: Amide coupling of step-2 and step-4 products with O-phenyl and O-methyl hydroxyl amines: A solution of step-2 and step-4 in dioxane/pyridine, and Boc anhydride was charged with O-phenylhydroxylamine and stirred at room temperature overnight. Reaction mixture was concentrated in vacuo and given for prep purification to give step-5 product.

| Comp. No | Structure | Brief Reaction conditions | Analytical data |
|---|---|---|---|
| D-92-Spiro-O-Ph | 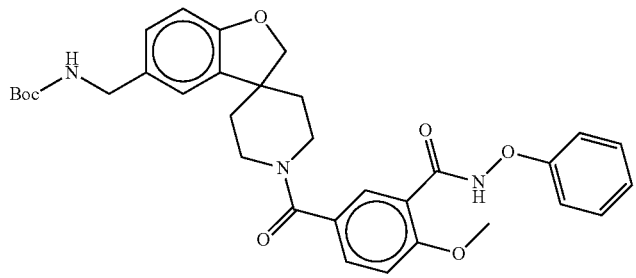<br>tert-butyl ((1'-(4-methoxy-3-(phenoxycarbamoyl)benzoyl)-2H-spiro[benzofuran-3,4'-piperidin]-5-yl)methyl)carbamate | dioxane (20 vol), pyridine (1 eq), Boc anhydride (1.3 eq.) O-phenyl hydroxylamine (1.3 eq) Stirring R.T., 12 hrs, Purified by prep HPLC after concentration in vacuum. | Yield: ~17.8%<br>Mol. Wt.: 587.66<br>MS (ES+):<br>m/z = 488<br>[MH$^+$ − Boc] |
| D-92-O-Ph | 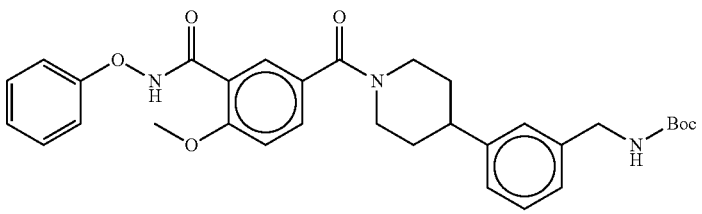<br>tert-butyl 3-(1-(4-methoxy-3-(phenoxycarbamoyl)benzoyl)piperidin-4-yl)benzylcarbamate | dioxane (25 vol), pyridine (1 eq), Boc anhydride (1.3 eq.) O-phenyl hydroxylamine (1.3 eq) Stirring R.T., 12 hrs, Purified by prep HPLC after concentration in vacuum. | Yield: ~26.7<br>Mol. Wt: 559.65<br>MS (ES+):<br>m/z = 460<br>[MH$^+$ − Boc] |
| D-85a | 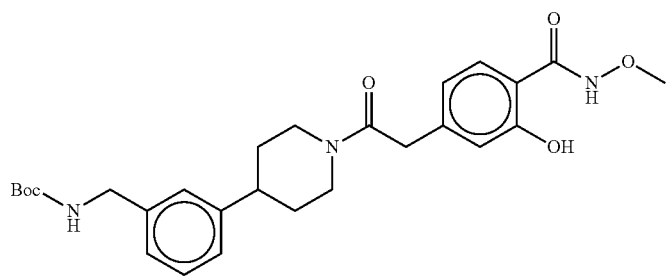<br>tert-butyl 3-(1-(2-(3-hydroxy-4-(methoxycarbamoyl)phenyl)acetyl)piperidin-4-yl)benzylcarbamate | EDCI (1.5 eq), HOBt (1.5 eq) DMF (35 vol). Triethyl amine (4 eq) O-methyl hydroxylamine•HCl (1.2 eq). Stirring at RT for 12 hrs, Product purified by prep. HPLC after usual work-up. | Yield: ~8%<br>Mol. Wt.: 497.58<br>MS (ES+):<br>m/z = 520<br>[MH$^+$ + Na] |

Step-6: Deprotection of Protected core: A solution of step-5 in dichloromethane was charged with BBr$_3$ in DCM and the reaction mixture was allowed to stir at room temperature for 3 hrs. The reaction mixture was Concentrated and purified by prep HPLC to give final target compounds.

| Comp. No. | Structure | Brief Reaction conditions | Analytical data |
|---|---|---|---|
| 92-Spiro-O- | 5-(5-(aminomethyl)-2H-spiro[benzofuran-3,4'-piperidin]-1'-ylcarbonyl)-2-hydroxy-N-phenoxybenzamide | 1M BBr$_3$ in DCM (1.5 eq) stirring at RT for 3 hrs, Purification by prep HPLC after concentrating in vacuum | Yield: 24%, Mol. Wt: –473.52, MS (ES+): m/z = 474 [MH$^+$] HPLC: 96.1% (220 nm) $^1$H NMR (400 MHz, DMSO-d$_6$): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H), 11.7 (br, 1H), 11.9 (br, 1H). |
| 92-O-Ph | 5-(4-(3-(aminomethyl)phenyl)piperidine-1-carbonyl)-2-hydroxy-N-phenoxybenzamide | 1M BBr$_3$ in DCM (1.5 eq) stirring at RT for 3 hrs, Purification by prep HPLC after concentrating in vacuum | Yield:: –10%, Mol. Wt. 445.51 MS (ES+): m/z = 446 [MH$^+$] HPLC: 86.8% (220 nm) $^1$H NMR (400 MHz, DMSO-d$_6$): δ 1.50-1.90 (m, 4H), 2.75-2.90 (m, 1H), 2.91-3.30 (br, 2H), 3.50-3.60 (br. 2H), 3.73 (s, 3H), 4.00-4.10 (m, 2H), 6.99 (d, J = 8.4 Hz, 1H), 7.20-7.40 (m, 4H), 7.47 (d, J = 8.4 Hz, 1H), 7.77 (s, 1H), 8.20 (br, 2H), 11.7 (br, 1H), 11.9 (br, 1H). |
| 85a | 4-(2-(4-(3-(aminomethyl)phenyl)piperidine-1-yl)-2-oxoethyl)-2-hydroxy-N-methoxybenzamide | dioxane ~1.80 vol, Conc. HCl 12 vol, 12 hrs stirring at RT, Followed by concentration and purification by prep HPLC | Yield: –64%, Mol. Wt.: –397.47, MS (ES+): m/z = 398 [MH$^+$] HPLC: (200-400 nm) 96.6%. $^1$H NMR (400 MHz, DMSO-d$_6$): δ 1.40-1.70 br, 2H), 1.84 (br, 2H), 2.60-2.91 (m, 2H), 3.10-3.30 (m, 1H), 3.98 (d, J = 5.6 Hz, 2H), 4.40-4.70 (br, 2H), 6.91 (d, J = 8.4 Hz, 1H), 7.20-7.50 (m, 6H), 7.78 (d, J = 8.8 Hz, 1H), 8.07 (br. 1H), 8.32 (br, 2H), 8.37 (br, 2H), 8.65 (br, 1H). |

Example 30. Synthesis of Tryptase Inhibitors with Phenolic & Hydroxymethyl Phenol Functionality Eleven Final Targets with phenolic & hydroxymethyl phenol functionality were synthesized. Title compounds were synthesized by two different approaches as given below.

Approach-1

Functionalized dihydroxy aromatic carboxylic acids were coupled with the required core and coupled product was deprotected as described in the scheme below.

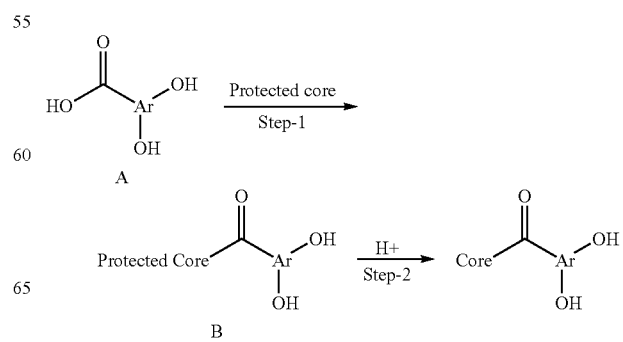

Protected Cores

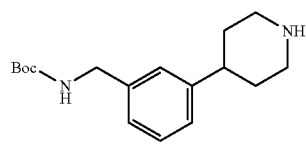

Core-1

Or

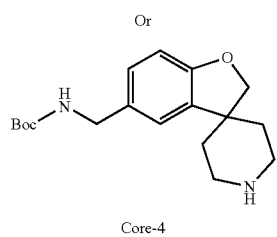

Core-4

The details of intermediates sourced/synthesised as per literature methods/synthesised by adapted methods are given below.

| Target | Structure |
|---|---|
| A-74 | 2,2-dimethyl-4H-benzo[d][1,3]dioxine-7-carboxylic acid<br><br>Draft_experimental_SAI(Pune) Shipment after 2nd September 2010 pg No-23 |
| A-96 | 7,8-dihydroxy-2-oxo-2H-chromene-4-carboxylic acid |
| A-98 | 2-(7,8-dihydroxy-2-oxo-2H-chromene-4-yl)acetic acid |
| A-99 | 2-(8-methyl-6-oxo-6H-[1,3]dioxolo[4,5-g]chromen-7-yl)acetic acid |
| A-104 | 3,4-dihydroxy-5-methoxybenzoic acid<br><br>Procured from commercial source |
| 113 Spiro | 2,2,8-trimethyl-4H-benzo[d][1,3]dioxine-6-carboxylic acid |
| 126 | 3-methoxy-4-(2-methoxypropan-2-yl)benzoic acid |
| A-127 | 2,3-dihydroxy-4-methoxybenzoic acid |

Synthetic details of acids

Synthesis of 7,8-dihydroxy-2-oxo-2H-chromene-4-carboxylic acid (A-96)

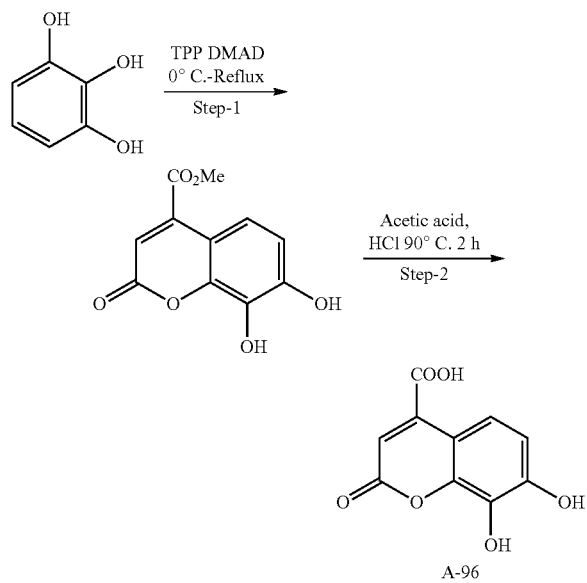

Experimental Procedures

Step-1

A solution of pyrogallol (0.5 g, 3.96 mmol) in toluene (10 mL) was charged with triphenyl phosphine (2.07 g, 7.93 mmol) and cooled to −5° C. and stirred for 10 min. then dropwise charged with a solution of DMAP (1.12 g, 7.93 mmol) in toluene (5 mL) and stirred at room temperature for 30 min, then refluxed for 8 hr. The reaction mixture was concentrated in vacuo and purified by column chromatography on silica gel eluting with hexanes/ethyl acetate resulting in methyl 7,8-dihydroxy-2-oxo-2H-chromene-4-carboxylate.

Yield: (0.16 g, 17%)

MS (ES+): m/z=237 [MH$^+$]

Step-2

A solution of methyl 7,8-dihydroxy-2-oxo-2H-chromene-4-carboxylate (0.1 g, 0.42 mmol) and acetic acid (3 mL) was charged with conc. HCl (1 mL) and heated at 90° C. for 2 hr. The reaction mixture was concentrated in vacuo to obtain a solid which was washed with pentane and dried to give 7,8-dihydroxy-2-oxo-2H-chromene-4-carboxylic acid. The crude product was used in the next step without further purification.

Yield: (0.095 g, Crude).

MS (ES+): m/z=223 [MH$^+$]

Synthesis 2-(7,8-dihydroxy-2-oxo-2H-chromen-4-yl) acetic acid (A-98)

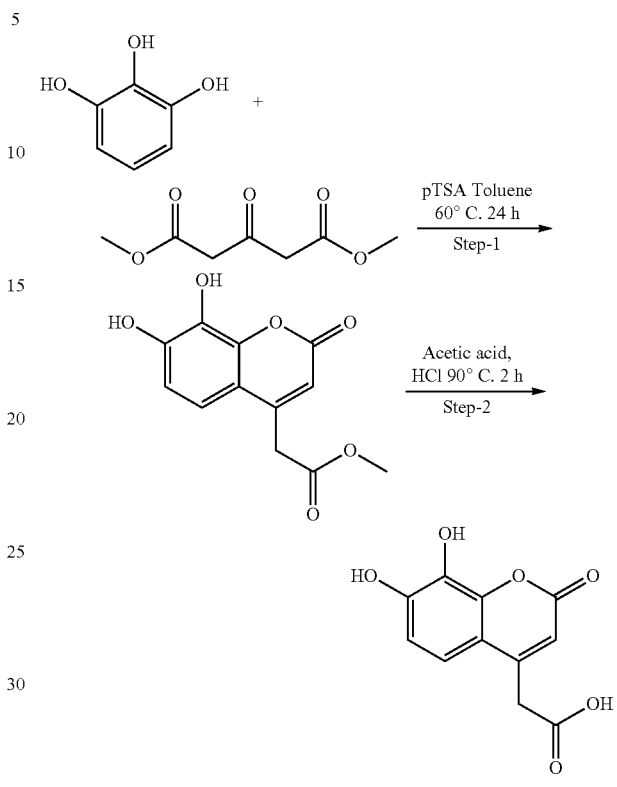

Experimental Procedures

Step-1

A solution of pyrogallol (1 g, 7.93 mmol) and dimethyl 1,3-acetone di carboxylate (1.4 mL, 9.52 mmol) in toluene (10 mL) was charged with pTSA (0.15 g, 0.79 mmol) and heated in a Schott Duran bottle at 60° C. overnight. TLC (Mobile phase 50% ethyl acetate in n-hexane) indicated absence of starting material (Rf 0.4) and product formation (Rf 0.3). The reaction mixture was concentrated in vacuo and the residue was washed with diethyl ether:hexanes (80:20 mix). The solid was filtered and dried to give methyl 2-(7,8-dihydroxy-2-oxo-2H-chromen-4-yl)acetate.

Yield: (0.65 g, 32.8%),

MS (ES+): m/z=251 [MH$^+$]

Step-2

A solution of methyl 2-(7,8-dihydroxy-2-oxo-2H-chromen-4-yl) acetate (0.1 g, 0.4 mmol) in acetic acid (1.5 mL) was charged with conc. HCl (0.75 mL) and heated at 90° C. for 2 hr. The reaction mixture was concentrated to dryness to give 2-(7,8-dihydroxy-2-oxo-2H-chromen-4-yl) acetic acid. The product was used in the next step without further purification.

Yield: (0.085 g, Crude).

MS (ES+): m/z=237 [MH$^+$]

To Synthesis 2-(8-methyl-6-oxo-6H-[1,3] dioxolo[4,5-g] chromen-7-yl) acetic acid (A-99)

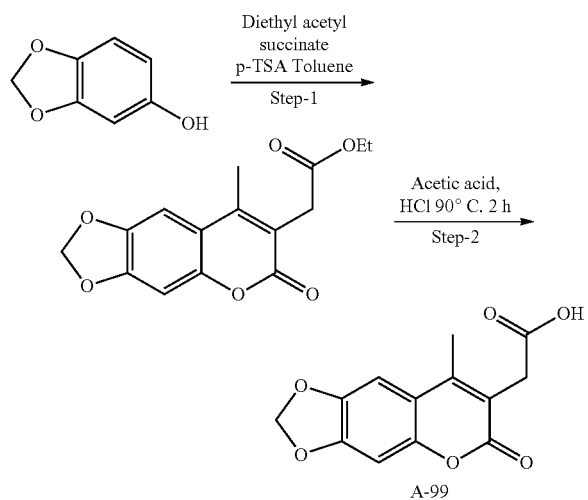

A-99

Experimental Procedures

Step-1: A solution of sesamol (0.5 g, 3.62 mmol) in toluene (10 mL) and diethyl acetyl succinate (0.87 mL, 4.30 mmol) in toluene (10 mL) was charged with p-TSA·H2O (0.34 g, 1.79 mmol) and heated at 80° C. overnight. TLC (Mobile phase 50% ethyl acetate in n-hexane) indicated absence of starting material (Rf 0.6) and product formation (Rf 0.4). The reaction mixture was concentrated and the compound was extracted in ethyl acetate, washed with brine. The organic layer was separated, dried over sodium sulfate, filtered, and concentrated in vacuo and purified by column chromatography on silica gel eluting with hexanes/ethyl acetate resulting in ethyl 2-(8-methyl-6-oxo-6H-[1,3]dioxolo[4,5-g]chromen-7-yl)acetate.

Yield: (0.6 g, 57%)
MS (ES+): m/z=313 [MH++Na]

Step-2: A solution of ethyl 2-(8-methyl-6-oxo-6H-[1,3]dioxolo[4,5-g]chromen-7-yl)acetate (0.2 g, 0.68 mmol) in acetic acid (6 mL) was charged with conc. HCl (2 mL) and heated at 90° C. for 2 hr. The reaction mixture was concentrated in vacuo to obtain a solid which was washed with pentane and dried to give 2-(8-methyl-6-oxo-6H-[1, 3] dioxolo [4,5-g]chromen-7-yl) acetic acid. The product was used in the next step without further purification.

Yield: (0.17 g, crude).
$^1$H NMR (400 MHz, DMSO-$d_6$): δ 7.34 (d, J=2.4 Hz, 1H), 7.10 (d, J=2.4 Hz, 1H), 6.17 (d, J=2.5 Hz, 2H), 3.57 (s, 2H), 2.64 (s, 3H)

Synthesis of 2, 2, 8-trimethyl-4H-benzo[d] [1,3] dioxine-6-carboxylic acid (A-113)

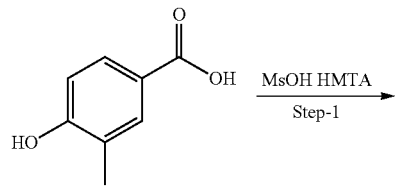

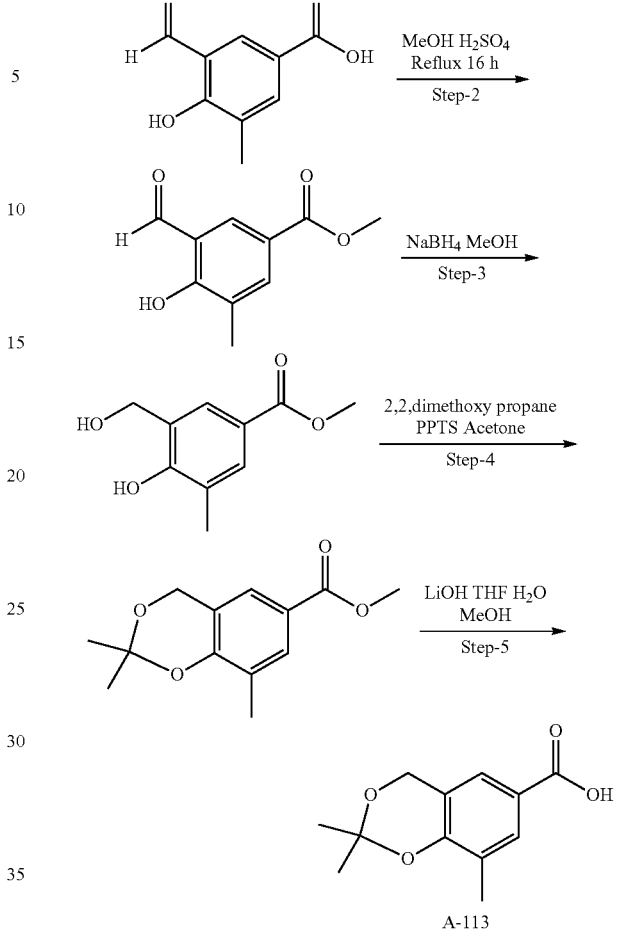

A-113

Experimental Procedures

Step-1: A suspension of 4-hydroxy-3-methylbenzoic acid (1 g, 6.57 mmol) in methanesulfonic acid (5 mL) was cooled to 0° C. and portion wise charged with hexamethylenetetramine (1.84 g, 13.15 mmol) and warmed to room temperature followed by heating at 90° C. for 5 hr then cooled to room temperature and stirred overnight. TLC (Mobile phase 10% methanol in dichloromethane) indicated absence of starting material (Rf 0.6) and product formation (Rf 0.5). The reaction mixture was poured into ice cooled water and the compound was extracted in ethyl acetate. The organic layer was washed with water, dried over sodium sulfate, filtered, and concentrated in vacuo to give 3-formyl-4-hydroxy-5-methylbenzoic acid as yellow solid.

Yield: (0.5 g, 42.3%).
$^1$H NMR (400 MHz, CDCl$_3$): δ 3.93 (s, 3H), 7.04 (d, 1H, J=8.8 Hz), 8.18-8.20 (dd, J=1.6 Hz, J=8.8 Hz, 1H), 8.32 (s, 1H), 9.56 (s, 1H), 11.39 (s, 1H).

Step-2: A solution of 3-formyl-4-hydroxy-5-methylbenzoic acid (0.2 g, 1.11 mmol) in methanol (4 mL) was charged with conc. sulfuric acid (0.14 mL) and refluxed for 16 hr. TLC (Mobile phase 5% methanol in dichloromethane) indicated absence of starting material (Rf 0.2) and product formation (Rf 0.7). The reaction mixture was concentrated in vacuo and the aqueous was extracted with ethyl acetate. The organic layer was washed with saturated solution of sodium bicarbonate, dried over sodium sulfate, filtered, and concentrated in vacuo resulting in methyl 3-formyl-4-hydroxy-5-methylbenzoate as an off white solid.

Yield: (0.18 g, 85.7%).

¹H NMR (400 MHz, DMSO-d₆): δ 3.83 (s, 3H), 7.06 (d, J=8.8 Hz, 1H), 8.02-8.07 (dd, J=1.6, 8.6 Hz, 1H), 8.38 (d, J=1.2 Hz, 1H).

Step-3: A solution of methyl 3-formyl-4-hydroxy-5-methylbenzoate (0.18 g, 0.92 mmol) in methanol (10 mL) was cooled to 0° C. and charged with sodium borohydride (0.035 g, 0.92 mmol) and stirred at 0° C. for 45 min. TLC (mobile phase 40% ethyl acetate in n-hexane) indicated absence of starting material (Rf 0.7) and product formation (Rf 0.5). The reaction mixture was quenched with saturated solution of ammonium chloride and concentrated in vacuo. The residue was partitioned between ethyl acetate and water and separated. The organic layer was dried over sodium sulfate, filtered, and concentrated in vacuo resulting in methyl 4-hydroxy-3-(hydroxymethyl)-5-methylbenzoate as white solid. The compound was used in the next step without further purification.

Yield: (0.16 g, 88.8%).

¹H NMR (400 MHz, CDCl₃): δ 3.91 (s, 3H), 3.92 (s, 3H), 7.03 (d, J=8.8 Hz, 1H), 8.05-8.09 (dd, J=1.8, 8.6 Hz, 1H), 8.16 (s, 1H), 9.48 (s, 1H), 12.2 (s, 1H)

Step-4: A solution of methyl 4-hydroxy-3-(hydroxymethyl)-5-methylbenzoate (0.9 g, 4.59 mmol) and 2,2 dimethoxy propane (1.7 mL, 13.77 mmol) in acetone (30 mL) was charged with pyridinium-para-toluene sulfonate (0.11 g, 0.45 mmol) and stirred room temperature overnight. TLC (Mobile phase 30% ethyl acetate in n-hexane) indicated absence of starting material (Rf 0.3) and product formation (Rf 0.5). The reaction mixture was concentrated in vacuo and the crude was purified by column chromatography on silica gel eluting with hexanes/ethyl acetate resulting in methyl 2,2,8-trimethyl-4H-benzo[d][1,3]dioxine-6-carboxylate.

Yield: (0.96 g, 88.8%).

¹H NMR (400 MHz, DMSO-d₆): δ 3.70 (s, 3H), 7.05 (d, J=8.4 Hz, 1H), 7.89-7.93 (dd, J=1.4, 8.6 Hz, 1H), 8.26 (s, 1H).

Step-5: A solution of methyl 2, 2, 8-trimethyl-4H-benzo[d][1,3]dioxine-6-carboxylate (0.96 g, 4.06 mmol) in THF:water:MeOH (10:10:3 mL) was charged with lithium hydroxide (0.25 g, 6.10 mmol) and stirred at room temperature overnight. TLC (Mobile phase 30% ethyl acetate in hexane) indicated absence of starting material (Rf 0.5) and product formation (Rf 0.3). The reaction mixture was concentrated in vacuo and acidified with 10% citric acid resulting in a white precipitate which was filtered to give 2, 2, 8-trimethyl-4H-benzo[d] [1, 3] dioxine-6-carboxylic acid as white solid. The precipitate was washed with water, dried and used in the next step without further purification.

Yield: (0.82 g, 91.1%).

¹H NMR (400 MHz, CDCl₃): δ 1.46 (s, 9H), 1.64-2.00 (m, 4H), 2.70-2.82 (m, 1H), 2.90-3.40 (br, 2H), 4.29 (s, 2H), 4.50-5.00 (br, 2H), 6.97 (d, J=8.4 Hz, 1H), 7.00-7.20 (m, 4H), 7.26-7.30 (m, 1H), 7.42 (d, J=8.4 Hz, 1H), 7.70 (s, 1H), 10.7 (s, 1H), 12.1 (s, 1H).

Synthesis of 3-methoxy-4-(2-methoxypropan-2-yl) benzoic acid

Synthetic Scheme (A-126)

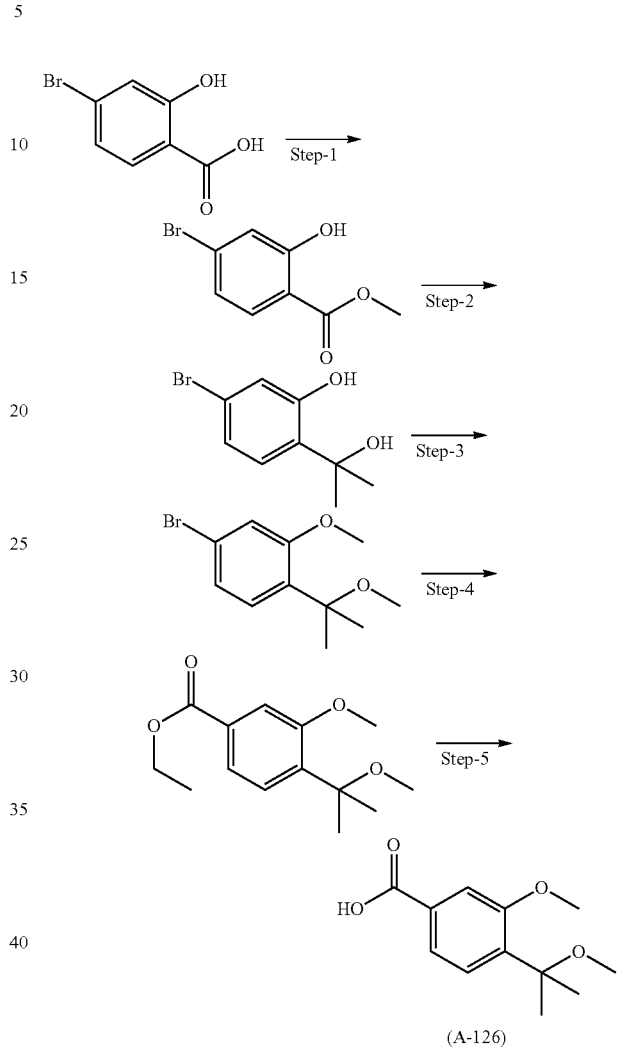

(A-126)

Experimental Procedures

Experimental for steps 1 & 2 is cited in the document "Draft_experimental_SAI (Pune) Shipment till March 2011"

Step-3: An ice-cold solution of 5-bromo-2-(2-hydroxypropan-2-yl) phenol (3.8 g, 16.44 mmol) in anhydrous DMF (10 mL) was charged with sodium hydride (1.18 g, 49.33 mmol) followed by methyl iodide (2.6 mL, 41.1 mmol) and stirred at room temperature for 2 hr. The reaction mixture was then partitioned between dichloromethane and water and separated. The organic layer was dried over sodium sulfate, filtered, and concentrated in vacuo resulting in crude product which was purified by column chromatography on silica gel eluting with (0-10% ethyl acetate in hexanes) to afford 4-bromo-2-methoxy-1-(2-methoxypropan-2-yl)benzene as a white solid Yield: 3.4 g (80%)

Mol. Wt.: 258.03

MS (ES+): m/z=258/260 [MH⁺]

Step-4: A solution of 4-bromo-2-methoxy-1-(2-methoxypropan-2-yl)benzene (1.0 g, 3.87 mmol) in THF (50 mL)

was cooled to −78° C. under nitrogen atmosphere then charged with, n-butyl lithium, 1.6 M (7.26 mL, 11.62 mmol) stirred at this temperature for 30 min. The reaction mixture was then charged with ethyl chloroformate (0.74 mL, 7.74 mmol) and allowed to warm to room temperature and stirred for an additional 3 hr. The reaction mixture was quenched with sat.NH₄Cl solution and extracted with dichloromethane. The combined organic layer was dried over sodium sulfate, filtered, and concentrated in vacuo resulting in the crude product which was purified by column chromatography on silica gel eluting with (0-5%, ethyl acetate in hexanes) to yield ethyl 3-methoxy-4-(2-methoxypropan-2-yl)benzoate as a white solid.

Yield: 0.6 g (31%)
Mol. Wt.: 252.31
MS (ES+): m/z=253 [MH⁺]

Step-5: A solution of ethyl ethyl 3-methoxy-4-(2-methoxypropan-2-yl) benzoate (0.6 g, 2.38 mmol) in MeOH:water (4:1) (10.0 mL) was charged with NaOH (0.19 g, 4.75 mmol) and was heated to reflux for 3 hr. The organic solvent was concentrated in vacuo and the resultant residue was acidified with 10% citric acid solution then extracted with ethyl acetate. The combined organic layer was dried over sodium sulfate, filtered and concentrated in vacuo resulting in a residue which was triturated with diethyl ether to yield 3-methoxy-4-(2-methoxypropan-2-yl)benzoic acid.
White solid;
Yield: 0.41 g (77%)
Mol. Wt.: 224.25
MS (ES+): m/z=225 [MH]

Synthesis of 2,3-dihydroxy-4-methoxybenzoic acid (A-127)

Synthetic Scheme

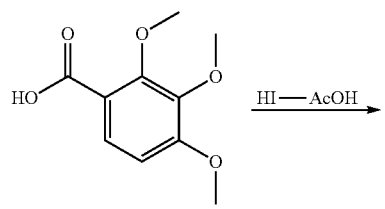

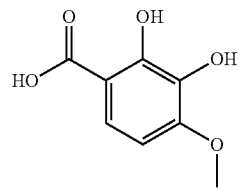

A-127

Experimental Procedures

A solution of 2, 3, 4-trimethoxybenzoic acid (2.0 g, 9.42 mmol) in acetic acid (12.0 mL) was charged with 55% hydriodic acid (5.0 ml) at room temperature and then heated to 80° C. for 10 hr. The pH of the reaction mixture was adjusted to 1.5 by addition of aqueous sodium hydroxide upon which a precipitate formed. The precipitate was filtered and the resulting solid was washed with water and dried in vacuo to give 2, 3-dihydroxy-4-methoxybenzoic acid as a white solid Yield: 1.31 g (76%)
Mol. Wt.: 184.15

MS (ES+): m/z=185 [MH⁺]Synthesis of intermediate amides and Final Targets with their respective general synthetic scheme are as follows.

Step-1: Coupling of carboxylic acids (A) was carried out with Core-1 or Core-4 as shown in general synthetic scheme above. Work-up of reactions were carried out as described in the general methods. The details of the compounds synthesized are shown below. Reactions were done on 100-200 mg scale

| Compound No. | Structure | Brief reaction conditions | Analytical data |
|---|---|---|---|
| B-96 | tert-butyl 3-(1-(7,8-dihydroxy-2-oxo-2H-chromene-4-carbonyl)piperidin-4-yl)benzylcarbamate | Carboxylic acid (1 eq.), DMF (~25 vol), EDCI (1.5 eq.) HOBT (1.5 eq) Core (1.0 eq.) and DIPEA (4.0 eq.) storing at R.T. 12 hrs. Purified by Prep. HPLC | White solid; Yield: 6% Mol. Wt: 494.54, MS (ES+): m/z = 517 [MH⁺+ Na] |

-continued

| Compound No. | Structure | Brief reaction conditions | Analytical data |
|---|---|---|---|
| B-98 | tert-butyl 3-(1-(2-(7,8-dihydroxy-2-oxo-2H-chromen-4-yl)acetyl)piperidin-4-yl)benzylcarbamate | Carboxylic acid (1 eq.), DMF (~25 vol), EDCI (1.5 eq.) HOBT (1.5 eq) Core (1.0 eq.) and DIPEA (4.0 eq.) stirring at R.T. 12 hrs. Purified by Prep. HPLC | White solid; Yield: 13.6% Mol. Wt: 508.56 MS (ES+): m/z = 531 [MH$^+$+ Na] |
| B-99 | tert-butyl 3-(1-(2-(6,7-dihydroxy-4-methyl-2-oxo-2H-chromen-3-yl)acetyl)piperidin-4-yl)benzylcarbamate | carboxylic acid (1 eq.), DMF (~25 vol), EDCI (1.5 eq.) HOBt (1.5 eq) Core (1.0 eq.) and DIPEA (4.0 eq.) stirring at RT 12 hr. Purified by column chromatography | Yield: (0.1 g, 28%) MS (ES+): m/z = 557 [MH$^+$ + Na] |
| B-127 | tert-butyl 3-(1-(2,3-dihydroxy-4-methoxybenzoyl)piperidin-4-yl)benzylcarbamate | carboxylic acid (1 eq.) DMF (20 vol) PyBOP (2 eq.) TEA (2 eq) tert-butyl 3-(piperidin-4-yl) benzyl carbamate (1.5 eq.) RT, 15 hr. purified by silica gel column chromatography (0-2%, methanol in chloroform) | White solid; Yield: 61% Mol. Wt: 456.53 MS (ES+): m/z = 479 [MH$^+$ + Na] |
| B-104 | tert-butyl 3-(1-(3,4-dihydroxy-5-methoxybenzoyl)piperidin-4-yl)benzylcarbamate | carboxylic acid (1 eq.), DMF (~25 vol), EDCI (1.5 eq.) HOBt (1.5 eq) Core (1.2 eq.) and DIPEA (2.5 eq.) stirring at RT 12 hr. purified by silica gel column chromatography using 0-5%, methanol in dichloromethane | White solid; Yield: 44% Mol. Wt: 456.53 MS (ES+): m/z = 479 [MH$^+$ + Na] |
| B-104-spiro | tert-butyl ((1'-(3,4-dihydroxy-5-methoxybenzoyl)-2H-spiro[benzofuran-3,4'-piperidin]-5-yl)methyl)carbamate | carboxylic acid (1 eq.), DMF (~25 vol), EDCI (1.5 eq.) DMAP (0.5 eq) Core (1.1 eq.) stirring at RT 12 hr. purified by prep HPLC | White solid; Yield: 12% Mol. Wt: 484.54 MS (ES+): m/z = 507 [MH$^+$ + Na] |

Step-2: Products of step-1 were deprotected as per conditions mentioned in the table below. The details of the compounds synthesized are as below. Reactions were done on 100-200 mg scale

| Compound No. | Structure | Brief reaction conditions | Analytical data |
|---|---|---|---|
| 96 | 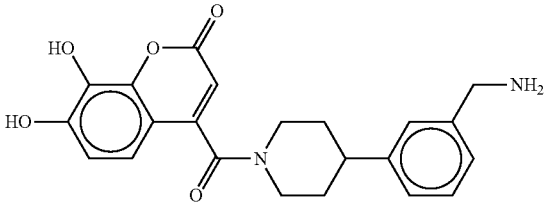<br>4-(4-(3-(aminomethyl)phenyl)piperidine-1-carbonyl)-7,8-dihydroxy-2H-chromen-2-one | Methanol ~80 vol, conc. HCl ~8 vol, 12 hrs stirring at RT, followed lyophilization | Yield: 34%, Mol. Wt: 394.54<br>MS (ES+): m/z = 395.10 [MH$^+$]<br>HPLC: 96.4% (254 nm) $^1$H NMR (400 MHz, DMSO-d$_6$): δ 1.40-1.90 (m, 4H), 2.28 (s, 3H), 2.60-2.89 (m, 2H), 3.16-3.27 (m, 1H), 4.00 (bs, 2H), 4.05 (s, 2H), 4.21 (brd, 1H), 4.51 (brd, 1H), 6.84 (d, J = 8.8 Hz, 1H), 7.13 (d, J = 8.8 Hz, 1H), 7.25-7.43 (m, 4H), 8.36 (br, 2H) |
| 98 | 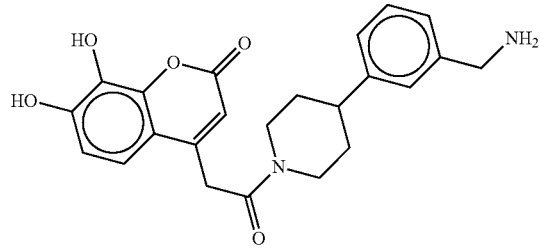<br>4-(2-(4-(3-(aminomethyl)phenyl)piperidin-1-yl)-2-oxoethyl)-7,8-dihydroxy-2H-chromen-2-one | methanol ~100 vol, conc. HCl ~15 vol, 12 hrs stirring at RT, followed by lyophilization | Yield: 60%, Mol Wt. 408.45<br>MS (ES+): m/z = 409 [MH$^+$]<br>HPLC: 98.6% (220 nm)<br>$^1$H NMR (400 MHz, DMSO-d$_6$ ): δ 1.40-1.90 (m, 4H), 2.28 (s, 3H), 2.60-2.89 (m, 2H), 3.16-3.27 (m, 1H), 4.10 (bs, 2H), 4.18 (s, 2H), 4.21 (brd, 1H), 4.51 (brd, 1H), 6.84 (d, J = 8.8 Hz. 1H), 7.13 (d, J = 8.8 Hz, 1H), 7.25-7.43 (m, 4H). 8.36 (br, 2H) |
| 99 | 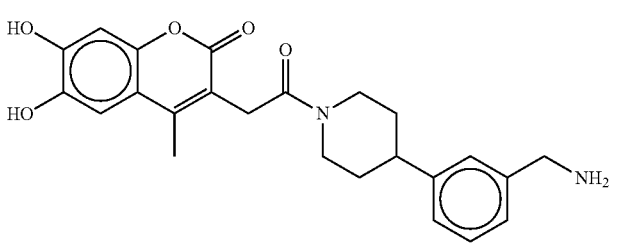<br>3-(2-(4-(3-(aminomethyl)phenyl)piperidin-1-yl)-2-oxoethyl)-6,7-dihydroxy-4-methyl-2H-chromen-2-one | dichloromethane ~100 vol, BBr$_3$, RT — 0° C., 12hr, trituration with methanol followed by Prep HPLC. | Yield: 33%.<br>MS (ES+): m/z = 423 [MH$^+$]<br>HPLC: 99.92% (220 nm)<br>$^1$H NMR (400 MHz, CD$_3$OD): δ 7.43-7.28 (m, 4H), 7.12 (s, 1H), 6.75 (s, 1H), 4.67 (d, J = 12.8 Hz, 1H), 4.33 (d, J = 13.3 Hz, 1H), 4.11 (s, 2H), 3.91-3.70 (m, 2H), 2.92 (tt, J = 12.1, 3.7 Hz, 2H), 2.79 (td, J = 13.4, 12.7, 2.7 Hz, 1H), 2.37 (s, 3H), 2.04-1.79 (m, 3H), 1.66 (qd, J = 12.9. 4.2 Hz, 1H). |

| Compound No. | Structure | Brief reaction conditions | Analytical data |
|---|---|---|---|
| 127 | (4-(3-(aminomethyl)phenyl)piperidin-1-yl) (2,3-dihydroxy-4-methoxyphenyl)-methanone | dioxane ~15 vol, conc. HCl 1 vol, 3 hrs stirring at RT, Followed by concentration and purification by prep HPLC | White solid; Yield: 16% Mol. Wt.: 356.42, MS (ES+): m/z = 357 [MH$^+$] HPLC Purity: 98.83% $^1$H NMR (400 MHz, D$_2$O): δ 7.46-7.33 (m, 3H), 7.29 (d, J = 7.6 Hz, 1H), 6.81 (d, J = 8.4 Hz, 1H), 6.71 (d, J = 8.4 Hz, 1H), 4.15 (s, 2H), 3.95-3.80 (m, 4H), 3.25-3.02 (m, 2H), 3.00-2.88 (m, 1H), 2.00-1.82 (m, 2H), 1.78-1.62 (m, 2H) |
| 104 | (4-(3-(aminomethyl)phenyl)piperidin-1-yl)(3,4-dihydroxy-5-methoxyphenyl)methanone | methanol 22 vol, conc. HCl 18 vol, 12 hrs stirring at RT, followed by concentration and trituration with hexanes and diethyl ether | Yield: 88%, MS (ES+): m/z = 379 [MH$^+$ + Na] HPLC: 98.8% (254 nm) $^1$H NMR (400 MHz, CD$_3$OD): δ 1.70-2.00 (m, 4H), 2.85-3.00 (m, 2H), 3.75-3.85 (brd, 1H), 4.10 (s, 2H), 4.70-4.80 (brd, 2H), 6.80 (S, 1H), 7.02 (s, 1H), 7.26-7.44 (m, 4H), 7.95 (S. 1H). |
| 104-spiro | (5-aminomethyl)-2H-spiro[benzofuran-3,4'-piperidin]-1'-yl)(3,4-dihydroxy-5-methoxyphenyl)methanone | methanol ~75 vol, conc. HCl 11 vol, 12 hrs stirring at RT, Followed by concentration and trituration with hexane followed by diethyl ether | Yield: 93%, Mol Wt. 384.43 MS (ES+): m/z = 407 [MH$^+$+ Na] HPLC: 98.28% (220 nm) $^1$H NMR (400 MHz, CD$_3$OD): δ 1.70-2.00 (m, 4H), 2.85-3.00 (m, 2H), 3.75-3.85 (brd, 1H), 4.10 (s, 2H), 4.70-4.80 (brd, 2H), 6.80 (s, 1H), 7.02 (s, 1H), 7.26-7.44 (m, 4H), 7.95 (S, 1H). |

Approach-2

Protected dihydroxy acids were synthesized and coupled with the core and later protecting groups were cleaved to get the target compounds. The details of intermediates (A) sourced/synthesised as per literature methods/synthesised by adapted methods are given above.

Scheme-1

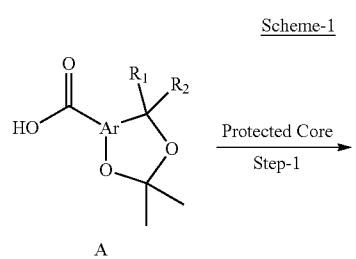

A

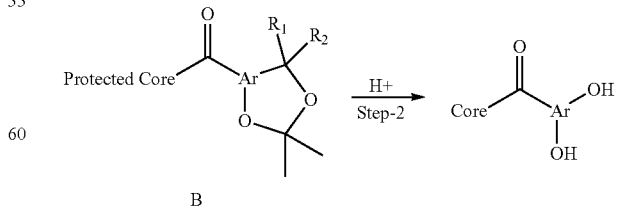

B

469
-continued

R₁ & R₂ = H/Me
Protected Cores

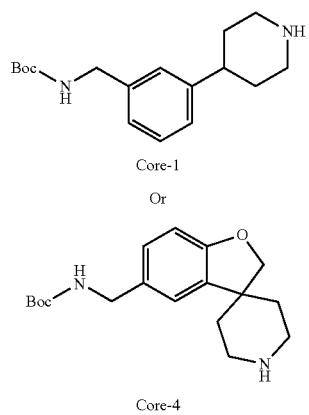

Core-1
Or

Core-4

Scheme-2

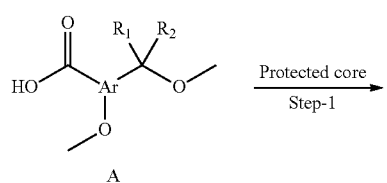

A

470
-continued

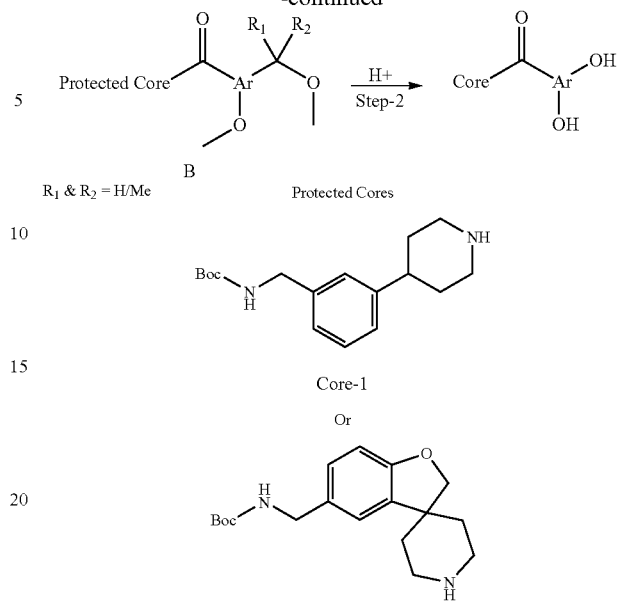

R₁ & R₂ = H/Me    Protected Cores

Core-1
Or

Core-4

Step-1: Coupling of carboxylic acids (A) was carried out with Core-1 or Core-4 as shown in the synthetic scheme. The details of the synthesis are given as below. Reactions were done on 100-200 mg scale

| Compound No. | Structure | Brief reaction conditions | Analytical data |
|---|---|---|---|
| B-74-spiro | tert-butyl ((1'-(2,2-dimethyl-4H-benzo[d][1,3]dioxine-7-carbonyl)-2H-spiro[benzofuran-3,4'-piperidin]-5-yl)methyl)carbamate | carboxylic acid (1 eq.), DCM (~150 vol), EDCI (1.5 eq.) DMAP (1.2 eq) Core (1 eq.) stirring at RT 12 hr. followed by concentration, used crude product as it is for next step. | Yield: 95 % Mol. Wt.: 508.61 MS (ES+): m/z = 408.25 [MH⁺ – boc] |
| B-113 Spiro | tert-butyl ((1'-(2,2,8-trimethyl-4H-benzo[d][1,3]dioxine-6-carbonyl)-2H-spiro[benzofuran-3,4'-piperidin]-5-yl)methyl)carbamate | carboxylic acid (1 eq.), DMF (~85 vol), EDCI (1.5 eq.) DMAP (1 eq) Core (1 eq.) stirring at RT 12 hr. purified by purified by column chromatography using hexanes/ethyl acetate | Yield: 80% Mol. Wt.: 522.63 MS (ES+): m/z = 545 [MH⁺ + Na] |

| Compound No. | Structure | Brief reaction conditions | Analytical data |
|---|---|---|---|
| B-126 | tert-butyl 3-(1-(3-methoxy-4-(2-methoxypropan-2-yl)benzoyl)piperidin-4-yl)benzylcarbamate | carboxylic acid (1 eq.), DMF (~85 vol), EDCI (1.5 eq.) DMAP (1 eq) Core (1 eq.) stirring at RT 12 hr. purified by silica gel column chromatography (0-5%, methanol in chloroform) | White solid; Yield: 37% Mol. Wt.: 496.64 MS (ES+): m/z = 497.3 [MH$^+$] |

Step-2: Products of step-1 were deprotected as per conditions mentioned in the table below. The details of the compounds synthesized are as below. Reactions were done on 100-200 mg scale

| Compound No. | Structure | Brief reaction conditions | Analytical data |
|---|---|---|---|
| 74 Spiro | (5-(aminomethyl)-2H-spiro[benzofuran-3,4'-piperidin]-1'-yl)(3-hydroxy-4-(hydroxymethyl)phenyl)methanone | methanolic HCl ~25 vol. 6 h stirring at room temperature, Followed by concentration and purification by prep HPLC | Yield: 19%, Mol Wt.: ~368.43 MS (ES+): m/z = 391.05 [MH$^+$ + Na] HPLC: 99.02% (254 nm). $^1$H H NMR (400 MHZ, DMSO-d6): δ 1.73(m,4H), 3.20(m.2H), 3.95(d, J = 5.2 Hz, 2H), 4.31(m, 2H), 4.49(s, 4H), 6.82(t, J = 9.6, 8.0 Hz 3H), 7.22(d, 7 = 7.6 Hz, 1H), 7.35(d, 7 = 7.5 Hz, 1H), 7.42(S, 1H), 8.04(bs, 3H), 9.6(bs, 1h). |
| 113 Spiro | (5-(aminomethyl)-2H-spiro[benzofuran-3,4'-piperidin]-1'-yl)(4-hydroxy-3-(hydroxymethyl)-5-methylphenyl)methanone | dioxane ~20 vol, conc. HCl ~3 vol, 4 hrs stirring at RT, Followed by concentration and purification by prep HPLC | Yield: 52.6%, Mol Wt.: 382.45 MS (ES+): m/z = 405 [MH$^+$ + Na] HPLC: 99.64% (220 nm), $^1$H NMR (400 MHz, DMSO-d$_6$): δ 1.50-1.90 (m, 4H), 2.75-2.90 (m, 1H), 2.91-3.30 (br, 2H), 3.50-3.60 (br, 2H), 3.73 (s, 3H), 4.00-4.10 (m, 2H), 6.99 (d. J = 8.4 Hz, 1H), 7.20-7.40 (m, 4H), 7.47 (d, J = 8.4 Hr, 1H), 7.77 (s, 1H), 8.20 (br, 2H), 11.7 (br, 1H), 11.9 (br, 1H). |

-continued

| Compound No. | Structure | Brief reaction conditions | Analytical data |
|---|---|---|---|
| 126 | 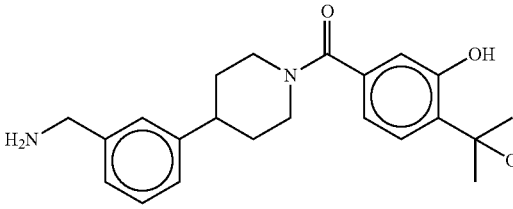<br>(4-(3-(aminomethyl)phenyl)piperidin-1-yl) (3-hydroxy-4-(2-hydroxypropan-2-yl)phenyl)methanone | BBr$_3$ (2 eq.) in dichloromethane (50 vol) added at 0° C. and further stirring at RT for 7 hrs. Products isolated by concentration in vacuo and subsequent purification by prep HPLC | White solid; Yield: 13%, Mol. Wt.: 368.47, MS (ES+): m/z = 369 [MH$^+$] HPLC Purity: 86.46%, $^1$H NMR (400 MHz, CD$_3$OD): δ 7.44-7.26 (m, 5H), 6.86 (d, J = 8.4 Hz, 1H). 6.82 (s, 1H), 4.80-4.72 (m, 1H), 4.10 (s, 2H), 4.00-3.86 (m, 1H), 3.26-3.15 (m, 1H), 3.00-2.85 (m, 2H), 2.04-1.66 (m, 4H), 1.61 (s, 6H) |
| 126 mono methyl | 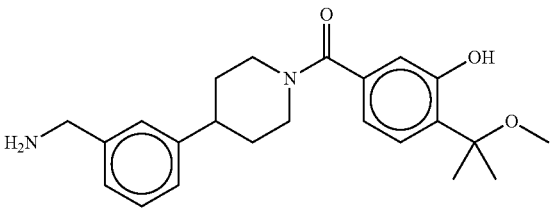<br>(4-(3-(aminomethyl)phenyl)piperidin-1-yl) (3-hydroxy-4-(2-methoxypropan-2-yl)phenyl)methanone | | White solid; Yield: 26%, Mol. Wt.: 382.50, MS (ES+): m/z = 383 [MH$^+$] HPLC Purity: 97.66% $^1$H NMR (400 MHz, CD$_3$OD): 7.64 (d, J = 8.0 Hz, 1H), 7.44-7.32 (m, 3H), 7.29 (d, J = 6.4 Hz, 1H), 7.06-6.98 (m, 2H), 4.10 (s, 2H), 3.98-3.84 (m, 4H), 3.04-2.86 (m, 2H), 2.06-1.64 (m, 4H), 1.59 (s, 6H) |
| T-163 | 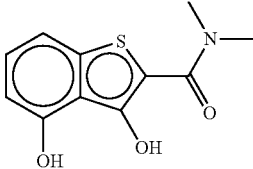 | *J. Org. Chem*,1987,52,1670-1373 | |

Example 31. Synthesis of Tryptase Inhibitors with Cis-Diol Functionality

Sixteen Final Targets with cis-diol functionality were synthesized. Racemic bicyclo[2.2.1]-5-heptene/octene-2-carboxylic acids either in pure Endo/Exo form or their mixtures were coupled with protected 4-(3-aminomethyl phenyl) piperidine coupled products were converted to diols by cis hydroxylation to get anti and syn isomers of racemic Endo and Exo isomers. Later Boc protection on the amino methyl functionality was cleaved under acidic conditions to get the target compounds. (Scheme-1)

Also analogues of these diols with 3-amino benzoyl linkage between the core and diol were synthesized by first coupling racemic bicyclo[2.2.1]-5-heptene/octene-2-carboxylic acids with 3-amino methyl benzoate and subsequent hydrolysis to get corresponding carboxylic acid which was processed as per the reaction sequence mentioned below. (Scheme-2)

Wherever possible, Endo-Exo/anti-syn isomers were separated by chromatographic techniques and characterized. Remaining compounds isolated as mixtures.

Scheme-1

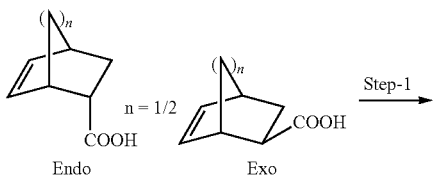

-continued
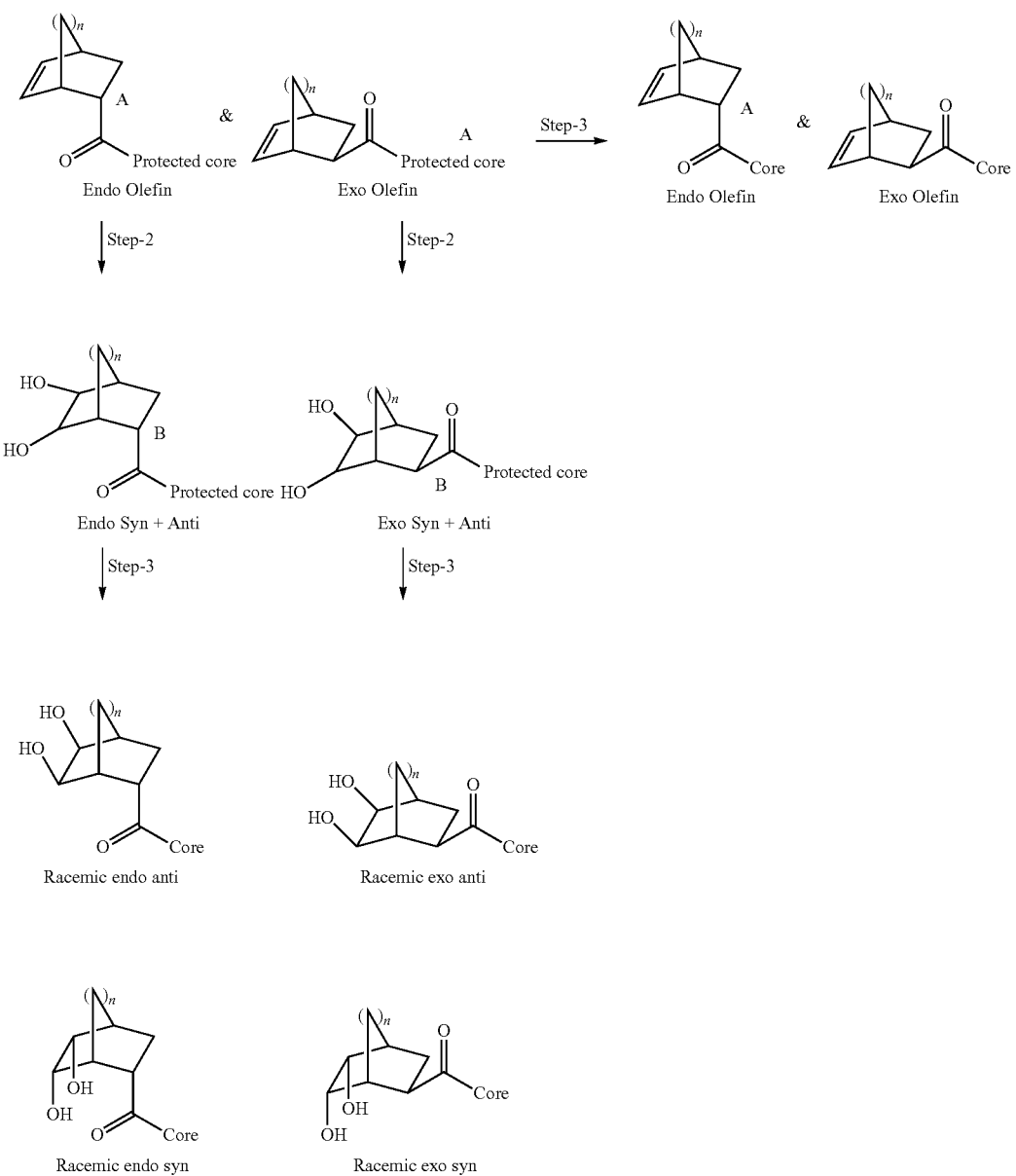
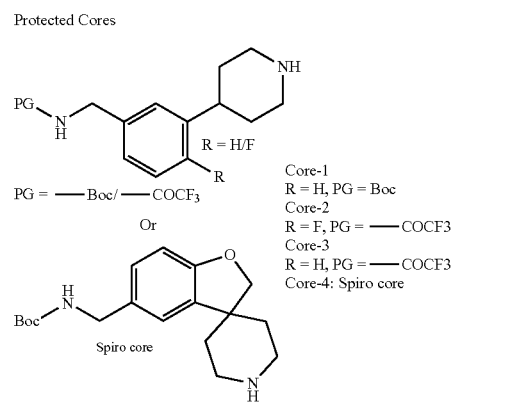

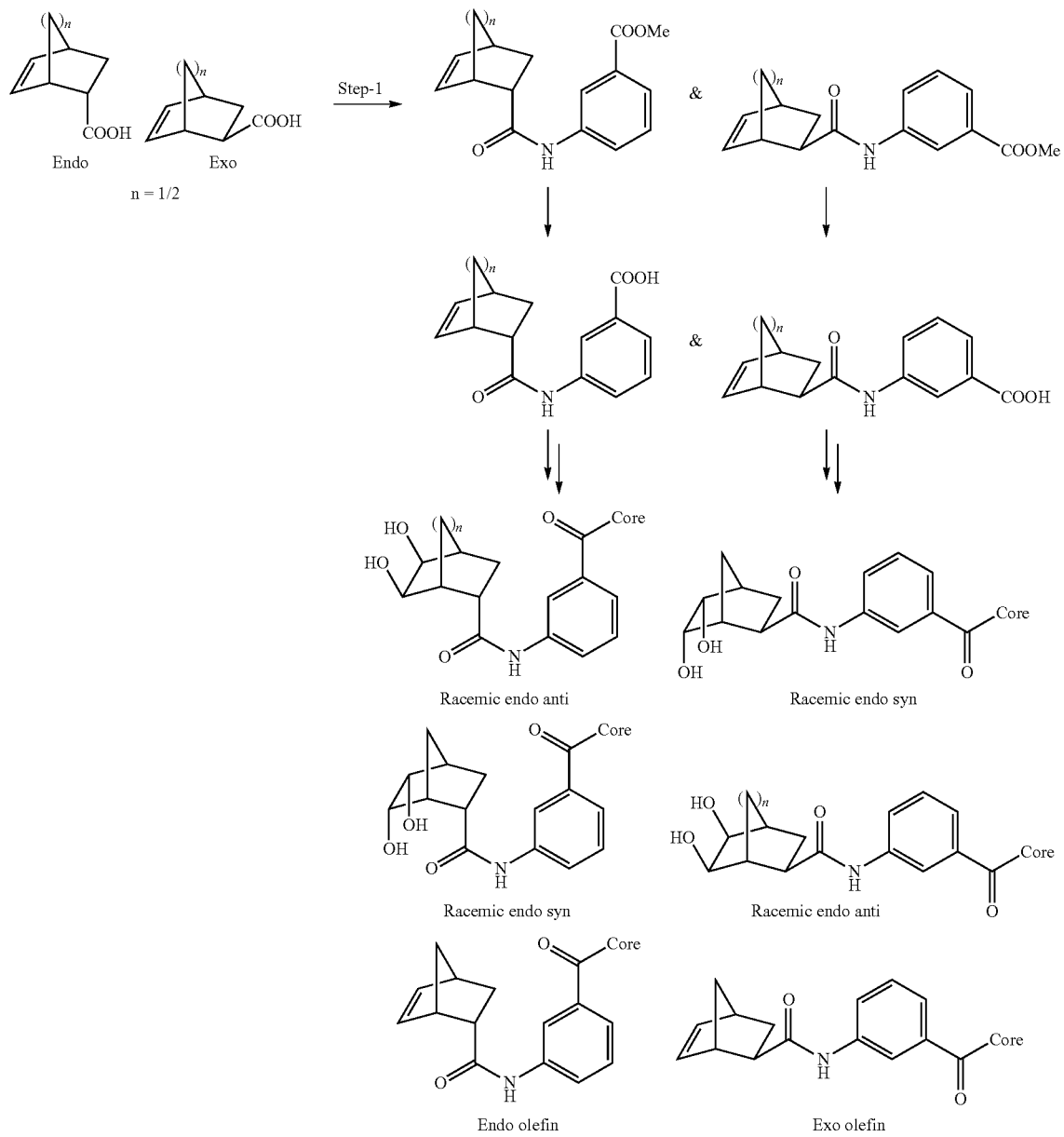
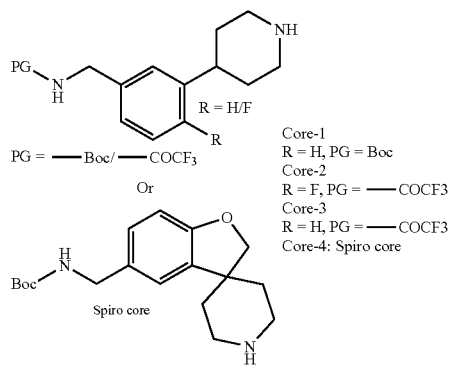

Racemic bicyclo [2.2.1]-5-heptene-2-carboxylic acid was procured from Aldrich chemical company which was containing major Endo isomer. Endo & Exo isomers of racemic bicyclo [2.2.1]-5-octene-2-carboxylic acids were synthesized as per procedure reported in the literature. (*Chem. Pharm. Bull.* 44, 296-306, 1996)

The details of intermediates (A) sourced/synthesised as per literature methods/synthesised by adapted methods are given below.

| Target | Structure |
|---|---|
| A-139 | 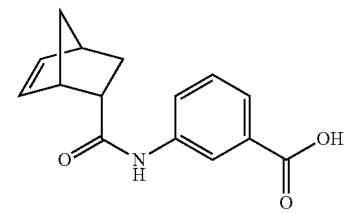 [SMILES: O=C(O)c1cccc(NC(=O)C2CC3C=CC2C3)c1] |
| A-140 | Major / Procured commercially |
| A-141 Endo | 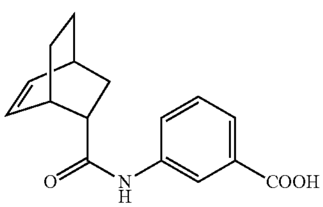 [SMILES: O=C(O)c1cccc(NC(=O)C2CC3C=CC2CC3)c1] |
| A-141 Exo | 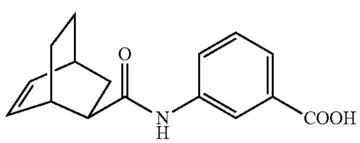 [SMILES: O=C(O)c1cccc(NC(=O)C2CC3C=CC2CC3)c1] |
| A-142 Endo | *Chem. Pharm. Bull,* 44, 296-306 (1996) |
| A-142 Exo | *Chem. Pharm. Bull,* 44, 296-306 (1996) |

Coupling of 3-amino methyl benzoate and racemic bicyclo[2.2.1]-5-heptene/octene-2-carboxylic acids is described below.

Synthesis of Endo & Exo 3-bicyclo [2.2.1] hept-5-ene-2-carboxamido benzoic acid (A-139)

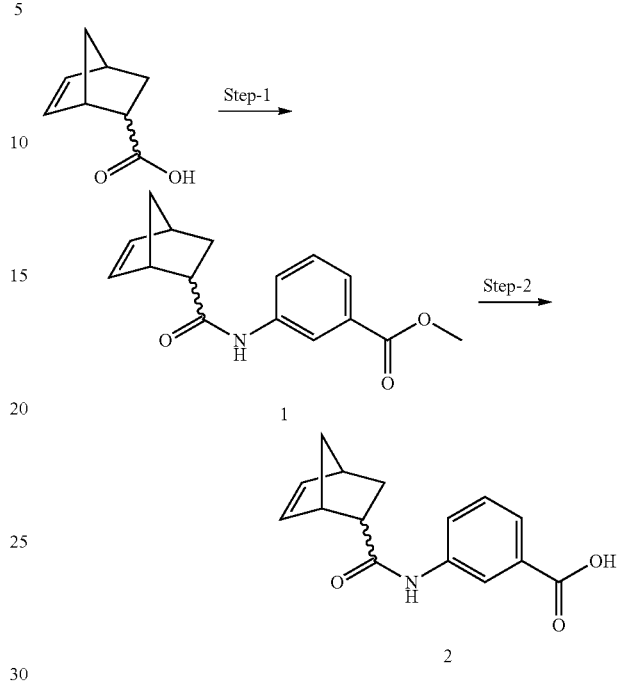

Experimental Procedures

Step-1

An ice-cold solution of 5-norbornene-2-carboxylic acid (1.0 eq.) in dichloromethane (30 Vol) was charged with 4-dimethylaminopyridine (DMAP) (0.5 eq.), hydroxy benzotriazole (HOBt) (1. eq.), and 1-ethyl-3-(3-dimethylaminopropyl) carbodiimide hydrochloride EDCI·HCl (1.5 eq) and stirred at 0° C. for 30 minutes then charged with methyl-3-aminobenzoate (1.2 eq.) and stirred at room temperature for an additional for 2 hr. The mixture was partitioned between dichloromethane and water and separated. The combined organic layer was washed with water (2×25 mL), 2N HCl (1×25 mL), dried over sodium sulfate, filtered, and concentrated in vacuo to afford the crude product colorless oil; (mixture of endo+exo) which was used for next step without further purification.

Yield: 51%

Mol. Wt: 271.31, MS (ES+): m/z=272 [MH$^+$]

Step-2

A solution of ester (1.0 eq.) in THF:H$_2$O (1:1)(15 vol) was charged with LiOH (3.0 eq.) and stirred at room temperature for 2-3 hr. The reaction mixture was concentrated in vacuo and the residue was diluted with water and extracted with DCM. The aqueous layer was separated and acidified with 2N HCl and extracted with DCM. The combined organic layer was dried over sodium sulfate, filtered, and concentrated in vacuo to give a mixture of Endo+Exo acid derivatives.

Yield: 78%

Mol. Wt: 257.28, MS (ES+): m/z=258 [MH$^+$]

481

Synthesis of Endo & Exo 3-bicyclo [2.2.2] oct-5-ene-2-carboxamido benzoic acid (A-141 Endo & A-141 Exo)

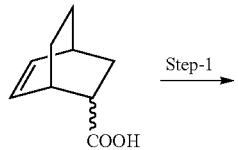

Step-1 →

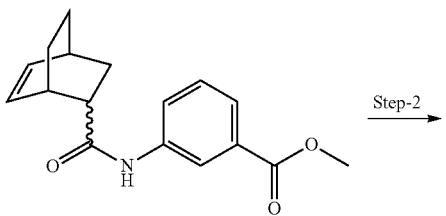

Step-2 →

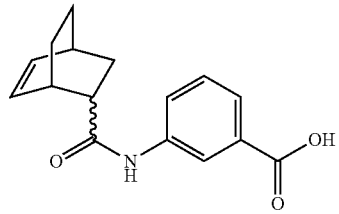

Experimental Procedures

Step-1

An ice-cold solution of carboxylic acid (1.0 eq.) in dichloromethane (30 mL/g) was charged with triethyl amine (3.0 eq.) and thionyl chloride (1.5 eq.) and stirred at 0° C. for 30 minutes then charged with methyl-3-aminobenzoate (1.0 eq.) and allowed to warm to stir at room temperature overnight. Reaction mixture was diluted with dichloromethane, washed with saturated sodium bicarbonate solution. The combined organic layer was dried over sodium sulfate, filtered and concentrated in vacuo to afford the crude product which was purified by column chromatography on silica gel eluting with (0-10%, ethyl acetate in hexane) to afford endo-amide or exo-amide derivatives.

| Sr. No. | Structure | Analytical data |
|---|---|---|
| 1 | 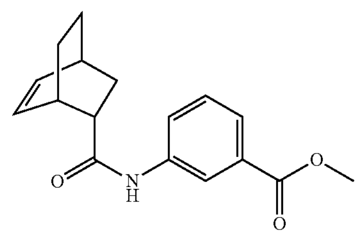 [SMILES: COC(=O)c1cccc(NC(=O)C2CC3C=CC2CC3)c1] | White solid; Yield: 48%<br>Mol. Wt.: 285.34<br>MS (ES+): m/z =286 [MH$^+$] |
| 2 | 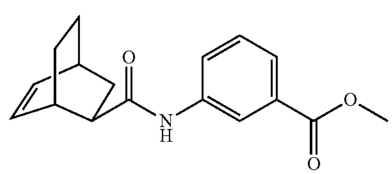 [SMILES: COC(=O)c1cccc(NC(=O)C2CC3C=CC2CC3)c1] | White solid; Yield: 50%<br>Mol. Wt.: 285.34<br>MS (ES+): m/z = 286 [MH$^+$] |

Step-2

A solution of ester (1.0 eq.) in MeOH:water (30 mL/g, 4:1) was charged with NaOH (2.0 eq.) was refluxed for 2 hr. The reaction mixture was concentrated in vacuo and the residue was acidified with 10% citric acid solution and extracted with ethyl acetate. The combined organic layer was dried over sodium sulfate, filtered, and concentrated in vacuo to give Endo acid or Exo acid derivatives.

| Sr. No. | Structure | Analytical data |
|---|---|---|
| 1 | (bicyclo[2.2.1]hept-5-ene-2-carboxamide linked to 3-carboxyphenyl) | White solid; Yield: 89% Mol. Wt.: 271.31 MS (ES+): m/z = 272 [MH⁺] |
| 2 | (bicyclo[2.2.2]oct-5-ene-2-carboxamide linked to 3-carboxyphenyl) | White solid; Yield: 74% Mol. Wt.: 271.31 MS (ES+): m/z = 272 [MH⁺] |

Synthesis of intermediate amides and final targets with their respective steps as shown in the general synthetic scheme are as follows.

Step-1: Conditions of the coupling reactions and compounds synthesized are as in the table below. The details of the synthesis and work up procedures have been given in the section "Synthesis of common intermediates" and "General Procedure"

| Compound No. | Structure | Names | Brief reaction conditions | Analytical data |
|---|---|---|---|---|
| A-139 (Endo + Exo) olefin | Endo + Exo | Major compound: (±) endo tert-butyl 3-(1-(3-bicyclo[2.2.1]hept-5-ene-2-carboxomido) benzoyl)piperidin-4-yl)benzylcarbamate Minor compound: (±) exo tert-butyl 3-(l-(3-bicyclo[2.2.1]hept-5-ene-2-carboxamido) benzoyl)piperidin-4-yl)benzylcarbamate | Carboxylic acid (1.0 eq.),4-(3-aminomethyl phenyl) piperidine, (1.3 eq.), EDCI (1.5 eq.), HOBt (1 eq) DMAP (1 eq.), DCM RT 2 hr | Colorless oil, Yield: 87.25%, Mol. Wt.: 529.67 MS (ES+): m/z = 552 [MH⁺+ Na] |
| A-140 (Endo + Exo)olefin | Endo + Exo | Major compound: (±) endo tert-butyl 3-(1-bicyclo[2.2.1]hept-5-ene-2-carbonyl) piperidin-4-yl) benzylcarbamate Minor compound: (±) exo tert-butyl 3-(1-bicyclo[2.2.1]hept-5-ene-2-carbonyl) piperidin-4-yl)benzylcarbamate | Carboxylic acid (1.0 eq.), 4-(3-aminomethyl phenyl) piperidine, (1.00 eq.), EDCI (1.5 eq.),HOBt (1 eq) DMAP (1 eq.), DCM RT, 3 hr | Colorless oil, Yield: 31.57%, Mol. Wt.: 410.55 MS (ES+): m/z = 433 [MH⁺ + Na] |
| A-141 Endo | 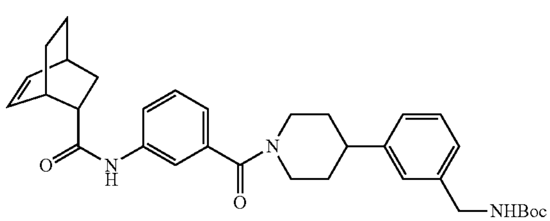 [SMILES: CC(C)(C)OC(=O)NCc1cccc(C2CCN(C(=O)c3cccc(NC(=O)C4CC5C=CC4CC5)c3)CC2)c1] | (±) endo tert-butyl 3-(l-(3-bicyclo[2.2.2] oct-5-ene-2-carboxamido) benzoyl) piperidin-4-yl) benzylcarbomate | Carboxylic acid (1.0 eq.) in anhydrous DMF (30 mL/g), EDCI (1.5 eq.), HOBt (1.5 eq.), tert-butyl 3-(piperidin-4-yl) benzyl carbamate (1.0 eq.), DIEA (2.5 eq.) Stirring at RT for 15 hr | White solid; Yield: 90% Mol. Wt.: 543.70 LCMS (m/z): 544: [MH⁺] |
| A-141 Exo | 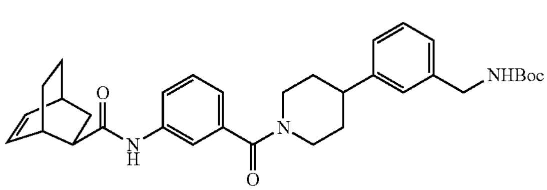 [SMILES: CC(C)(C)OC(=O)NCc1cccc(C2CCN(C(=O)c3cccc(NC(=O)C4CC5C=CC4CC5)c3)CC2)c1] | (±) exo tert-butyl 3-(l-(3-bicyclo[2.2.2] oct-5-ene-2-carboxamido)benzoyl) pipendin-4-yl) benzylcarbamate | | White solid; Yield: 93% Mol. Wt: 543.70 MS (ES+): m/z = 544 [MH⁺] |

| Compound No. | Structure | Names | Brief reaction conditions | Analytical data |
|---|---|---|---|---|
| A-142 Endo | 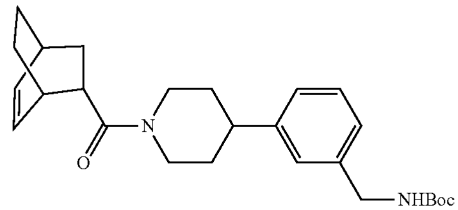 [SMILES: CC(C)(C)OC(=O)NCc1cccc(C2CCN(C(=O)C3CC4C=CC3CC4)CC2)c1] | (±) endo tert-butyl 3-(1-bicyclo[2.2.2] oct-5-ene-2-carbonyl) piperidin-4-yl) benzylcarbamate | Anhydrous DMF (30 mL/g), EDCI (1.5 eq.)., HOBt (1.5 eq.), tert-butyl 3-(piperidin-4-yl) benzyl carbamate (1.0 eq.), DIEA (2.5 eq.), Stirring at R.T for 15 hrs Purified by column chromatography over silica gel (0-15%, ethyl acetate in hexane) | White solid; Yield: 36% Mol. Wt: 424.58 MS (ES+): m/z = 425 [MH+] |
| A-142 Exo | 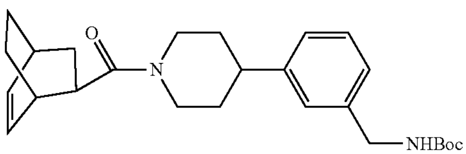 [SMILES: CC(C)(C)OC(=O)NCc1cccc(C2CCN(C(=O)C3CC4C=CC3CC4)CC2)c1] | (±) exo tert-butyl 3-(1-bicyclo[2.2.2] oct-5-ene-2-carbonyl)piperidin-4-yl)benzylcarbamate | | White solid; Yield: 54% Mol. Wt.: 424.58 LCMS (m/z): 425 [MH+] |

Step-2: Reaction conditions for cis hydroxylation and compounds synthesized are as in the table below.

| Compound No | Structure | Names | Brief reaction conditions | Analytical data |
|---|---|---|---|---|
| B-139 Racemic (Endo + Exo) | 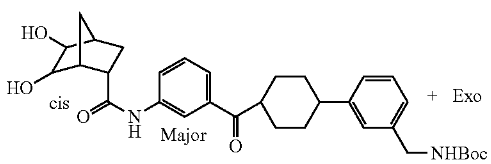 | Major compound: (±) endo tert-butyl 3-(1-(3--5,6-syn-dihydroxybicyclo [2.2.1] heptane-2-carboxyamido) benzoyl)piperidin-4-yl)benzylcarbamate Major compound: (+) exo tert-butyl 3-(1-(3--5,6-syn-dihydroxybicyclo [2.2.1]heptane-2-carboxamido) benzoyl)piperidin-4-yl)benzylcarbamate | THF (50 mL/g) and water (40 mL/g), OsO$_4$ (0.02 eq.), NMO (1.1 eq.) Stirring at RT for 3 hr. Extraction with ethyl acetate and concentration in vacuo and subsequent purification by column chromatography using 0-2%, methanol in chloroform | White solid; Yield: 94% Mol. Wt: 563.68 MS (ES+): m/z = 586 [MH+ + Na] |
| B-140 Racemic (Endo + Exo) | 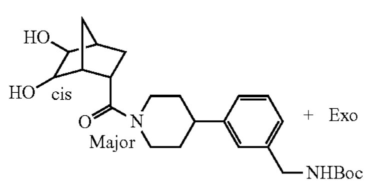 | Major compound: (±) endotert-butyl 3-(1-5,6-syn dihydroxybicyclo [2.2.1]heptane-2-carbonyl) piperidin-4-yl] benzylcarbamate Minor compound: (±) exotert-butyl 3-(1-5, 6-syndihydroxybicyclo [2.2.1]heptane-2-carbonyl) piperidin-4-yl]benzylcarbamate. | THF (50 mL/g) and water (40 mL/g), OsO$_4$ (0.02 eq.), NMO (1.1 eq.) Stirring at RT for 3 hr. Extraction with ethyl acetate and concentration in vacuo and subsequent purification by column chromatography using 0-2%, methanol in chloroform | White solid; Yield: 35% Mol. Wt: 444.56 MS (ES+): m/z = 467 [MH+ + Na] |

| Compound No | Structure | Names | Brief reaction conditions | Analytical data |
|---|---|---|---|---|
| B-141 Racemic Endo Anti | Endo Anti; Formed exclusively | (±) endo tert-butyl 3-(1-(3-(-5,6-anti-dihydroxybicyclo[2.2.2]octane-2-carboxamido)benzoyl)piperidin-4-yl)benzylcarbamate | THF (50 mL/g) and water (40 mL/g), OsO₄ (0.02 eq.), NMO (1.1 eq.) Stirring at RT for 3 hr. Extraction with ethyl acetate and concentration in vacuo and subsequent purification by column chromatography using 0-2%, methanol in chloroform | White solid; Yield: 47% Mol. Wt: 577.71 MS (ES+): m/z = 578 [MH⁺] |
| B-141 Racemic Exo syn | 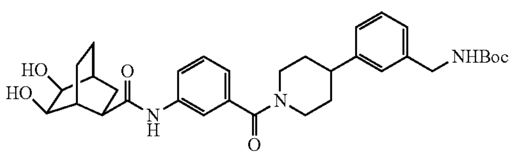 [SMILES: CC(C)(C)OC(=O)NCc1cccc(C2CCN(C(=O)c3cccc(NC(=O)C4CC5CCC4C(O)C5O)c3)CC2)c1] | (±) exo tert-butyl 3-(1-(3-(-5,6-syn-dihydroxybicyclo[2.2.2]octane-2-carboxamido)benzoyl)piperidin-4-yl)benzylcarbamate | | White solid; Yield: 35% Mol. Wt: 577.71 MS (ES+): m/z = 578 [MH⁺] |
| B-141 Racemic Exo anti | 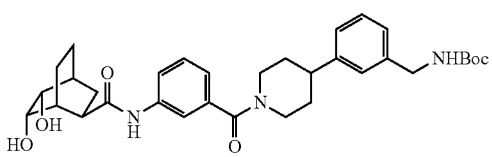 [SMILES: CC(C)(C)OC(=O)NCc1cccc(C2CCN(C(=O)c3cccc(NC(=O)C4CC5CCC4C(O)C5O)c3)CC2)c1] | (±) exo tert-butyl 3-(1-(3-(-5,6-anti-dihydroxybicyclo[2.2.2]octane-2-carboxamido)benzoyl)piperidin-4-yl)benzylcarbamate | | White solid; Yield: 15% Mol.Wt: 577.71 MS (ES+): m/z = 578 [MH⁺] |
| B-142-Racemic Endo anti | 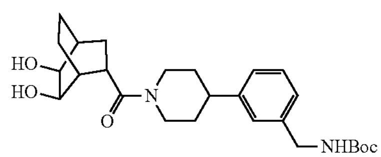 [SMILES: CC(C)(C)OC(=O)NCc1cccc(C2CCN(C(=O)C3CC4CCC3C(O)C4O)CC2)c1] | (±) endo tert-butyl 3-(1-(-5,6-anti-dihydroxybicyclo[2.2.2]octane-2-carbonyl)piperidin-4-yl)benzylcarbamate | THF (60 mL/g) and water (40 mL/g), OsO₄ (0.02 eq.), NMO (1.1 eq.) Stirring at RT for 3 hr. After completion. Extraction with ethyl acetate and concentration in vacuo and subsequent purification by column chromatography using 0-2%, methanol in chloroform | White solid; Yield: (19%) Mol. Wt.: 458.59 LCMS (m/z): 459 [MH⁺] |
| B-142-Racemic Endo syn | 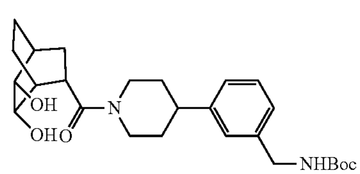 [SMILES: CC(C)(C)OC(=O)NCc1cccc(C2CCN(C(=O)C3CC4CCC3C(O)C4O)CC2)c1] | (±) endo tert-butyl 3-(1-(-5,6-syn-dihydroxybicyclo[2.2.2]octane-2-carbonyl)piperidin-4-yl)benzylcarbamate | | White solid; Yield: (12%) Mol. Wt.: 458.59 MS m/z = 459 [MH⁺] |

| Compound No | Structure | Names | Brief reaction conditions | Analytical data |
|---|---|---|---|---|
| B-142-Racemic Exo Anti | Exo anti; Formed exclusively | (±) exo tert-butyl 3-(1-(-5,6-anti-dihydroxybicyclo[2.2.2]octane-2-carbonyl)piperidin-4-yl)benzylcarbamate | THF (60 mL/g) and water (20 mL/g), OsO$_4$ (0.02 eq.), NMO (1.1 eq.) Stirring at RT for 3 hr. After completion. Extraction with ethyl acetate and concentration in vacuo and subsequent purification by column chromatography using 0-2%, methanol in chloroform | White solid; Yield: 71%, Mol. Wt.: 458.59, MS (ES+): m/z = 459 [MH$^+$] |

Step-3: Reaction conditions for deprotection and compounds synthesized are as in the table below.

| Compound No. | Structure | Names | Brief reaction conditions | Analytical data |
|---|---|---|---|---|
| 139 Endo olefin | Endo | (±) endo-N-(3-(4-(3-(aminomethyl)phenyl)piperidine-1-carbonyl)phenyl)bicyclo[2.2.1]hept-5-ene-2-carboxomide. | trifluoro acetic acid (4 eq.). in dichloromethane. Stirring at room temp, for 12hr. conc. for removal of DCM, and purification by prep HPLC, TLC (10% methanol in chloroform. | White Solid, Yield: 31.2%, Mol. Wt.: 429.55 MS (ES+): m/z = 430 [MH$^+$] $^1$H NMR (400 MHz, DMSO-d$_6$ (D$_2$O): δ 7.71 (d, J = 2.5 Hz, 1H). 7.54-7.51 (m. 1H), 7.39-7.25 (m, 5H), 7.03 (d, J = 7.4 Hz, 1H). 6.15 (dd, J = 5.7, 2.9 Hz, 1H), 5.83 (dd, J = 5.5, 2.8 Hz, 1H), 4.61 (s, 1H), 4.00 (s, 2H), 3.70 (s, 1H), 3.21 (d, J = 42.8 Hz. 2H), 3.03 (dt, J = 8.4, 4.0 Hz, 1H), 2.85 (d, J = 11.9 Hz, 3H), 1.81 (tt, J = 11.8, 9.3, 4.3 Hz, 2H), 1.48 (d, J = 70.9 Hz, 4H), 1.31 (d, J = 2.2 Hz, 2H) |
| 139 Exo olefin | Exo | (±) exdo-N-(3-(4-(3-(aminomethyl)phenyl)piperidine-1-carbonyl)phenyl)bicyclo[2.2.1]hept-5-ene-2-carboxamide. | trifluoro acetic acid (4 eq.). in dichloromethane. Stirring at room temp, for 12 hr. Conc. for removal of DCM, and purification by prep HPLC. TLC (10% methanol in chloroform. | White Solid, Yield: 31.2%, Mol. Wt.: 429.55 MS (ES+): m/z = 430 [MH$^+$] $^1$H NMR (400 MHz, DMSO-d$_6$): δ 8.19 (s, 3H), 7.78-7.74 (m, 1H), 7.58-7.50 (m, 1H), 7.36 (td, J = 7.6, 4.0 Hz, 3H), 7.28 (t, J = 7.7 Hz, 2H), 7.06 (d, J = 7.5 Hz, 1H), 6.21-6.15 (s, 2H), 4.62 (s, 1H), 4.00 (s, 2H), 3.24-3.11 (m, 1H), 2.87 |

| Compound No. | Structure | Names | Brief reaction conditions | Analytical data |
|---|---|---|---|---|
| | | | | (m, 5H), 2.31-2.22 (m, 1H), 1.87 (dt, J = 11.6, 3.9 Hz, 2H), 1.77-1.48 (m, 3H), 1.30-1.21 (m, 3H). |
| 140 Endo olefin | 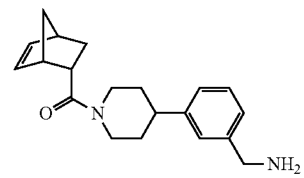 | (±) endo (4-(3-(aminomethyl)phenyl)piperidin-1-yl)(-bicyclo[2.2.1]hept-5-en-2-yl)methanone | trifluoro acetic acid (4 eq.), in dichloromethane. Stirring at room temp, for 12 hr. conc. for removal of DCM, and purification by prep HPLC. TLC (10% Methanol in chloroform. | Colorless oil, Yield: 10.4%, Mol. Wt: 310.43 MS (ES+): m/z = 311 [MH+] $^1$H NMR 400 MHz, DMSO-$d_6$): δ 7.29 (dt, J = 27.0, 6.5 Hz, 4H), 6.15-6.04 (m, 1H), 5.95-5.85 (m, 1H), 4.42 (d, J = 12.6 Hz, 1H), 4.17 (d, J = 13.7 Hz, 1H), 3.97 (s, 2H), 3.19-2.99 (m, 4H), 2.79 (d, J = 10.5 Hz, 2H), 1.96-1.68 (m, 3H), 1.57-1.33 (m, 2H), 1.27 (q, J = 8.1 Hz, 3H) |
| 140 Exo olefin | 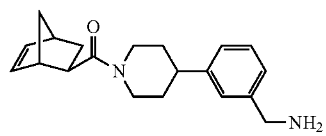 | (±) exo (4-(3-(aminomethyl)phenyl)piperidin-1-yl)(-bicyclo[2.2.1]hept-5-en-2-yl)methanone | trifluoro acetic acid (4 eq.), in dichloromethane. Stirring at room temp, for 12 hr. conc. for removal of DCM, and purification by prep HPLC. TLC (10% methanol in chloroform. | Colorless oil, Yield: 47.39%, Mol. Wt: 310.43 MS (ES+): m/z = 311 [MH+] $^1$H NMR (400 MHz, DMSO-$d_6$, $D_2O$): δ 7.30 (dd, J = 28.1, 7.8 Hz, 4H), 6.16 (s, 2H), 4.00 (s, 2H), 3.24-3.05 (m, 5H), 2.90-2.72 (m, 3H), 1.78 (s, 4H), 1.46 (d, J = 8.4 Hz, 2H), 1.25 (d, J = 14.1 Hz, 2H). |
| 139 Racemic Endo | 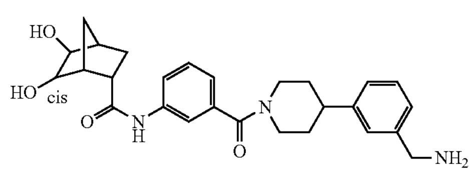 | (±) endo-N-(3-(4-(3-(aminomethyl)phenyl)piperidine-1-carbonyl)phenyl)-5,6-syn-dihydroxybicyclo[2.2.1]heptane-2-carboxamide | trifluoro acetic acid (3 eq.), in dichloromethane. Stirring at room temp, for 12hr. conc. for removal of DCM, and purification by prep HPLC. TLC (10% methanol in chloroform. | Colorless oil, Yield: 13.5%, Mol. Wt: 463.57 MS (ES+): m/z = 464 [MH+] $^1$H NMR (400 MHz, DMSO-$d_6$, $D_2O$): δ 8.13 (s, 2H), 7.77 (s, 1H), 7.56 (dd, J = 14.7, 8.0 Hz, 1H), 7.41-7.25 (m, 5H), 7.10-7.05 (m, 1H), 4.54 (d, J = 73.9 Hz, 1H), 4.02 (q, J = 5.6 Hz, 2H), 2.95-2.43 (m, 6H), 2.37 (d, J = 4.2 Hz, 1H). 2.25 (dd, J = 8.4, 5.0 Hz, 1H), 2.05 (d, J = 20.7 Hz, 1H), 1.90-1.68 (m, 4H), 1.63-1.48 (m, 5H), 1.21 (dd, J = 21.5, 10.0 Hz, 2H), |

-continued

| Compound No. | Structure | Names | Brief reaction conditions | Analytical data |
|---|---|---|---|---|
| 140 Racemic Endo | Endo | (±) endo (4-(3-(aminomethyl)phenyl)piperidin-1-yl)-(5,6-syn-dihydroxybicyclo[2.2.1]heptan-2-yl)methanone | trifluoro acetic acid (3 eq.). in dichloromethane. Stirring at room temp. for 12 hr. Conc, for removal of DCM, and purification by prep HPLC. TLC (10% methanol in chloroform. | Colorless oil, Yield: 32.05%, Mol. Wt: 344.45 MS (ES+): m/z = 345 [MH+] $^1$H NMR (400 MHz, DMSO-$d_6$): δ 7.39-7.23 (m, 4H), 4.57 (d, J = 13.3 Hz, 1H), 4.14 (s, 1H), 3.99 (d, J = 3.4 Hz, 2H), 3.23-3.04 (m, 1H) 2.96 (d, J = 6.0 Hz, 1H), 2.82 (d, J = 11.9 Hz, 1H), 2.65 (d, J = 12.4 Hz, 2H), 2.15 (s, 1H), 1.98 (d, J = 4.2 Hz, 1H), 1.92 (s, 1H), 1.85-1.71 (m, 2H), 1.61 (d, J = 11.1 Hz, 1H), 1.54-1.36 (m, 5H), 1.21 (s, 1H) |
| 141 Endo olefin | 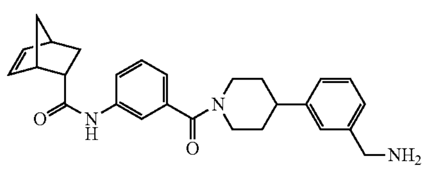 [SMILES: NCc1cccc(C2CCN(C(=O)c3cccc(NC(=O)C4CC5C=CC4C5)c3)CC2)c1] | (±) endo N-(3-(4-(3-(aminomethyl)phenyl)piperidine-1-carbonyl)phenyl)bicyclo[2.2.2]oct-5-ene-2-carboxamide | 1,4-dioxane (30 mL/g), conc. HCl (1 mL/g) Stirring at room temperature for 3 h., Reaction mixture was evaporated under vacuo and purified by preparative HPLC | White solid; Yield: 44%, Mol. Wt: 443.53, MS (ES+): m/z = 444 [MH$^+$], HPLC Purity: 99.83%, $^1$H NMR (400 MHz, CD$_3$OD): δ 7.81 (s, 1H), 7.50 (d, J = 7.6 Hz, 1H), 7.45-7.32 (m, 4H), 7.29 (d, J = 7.6 Hz, 1H), 7.13 (d, J = 6.8 Hz, 1H), 6.31 (t, J = 6.8 Hz, 1H), 6.16 (t, J = 6.8 Hz, 1H), 4.84-4.72 (m, 1H), 4.11 (s, 2H), 3.95-3.83 (m, 1H), 3.27-3.16 (m, 1H), 3.00-2.72 (m, 4H), 2.68-2.55 (m, 1H), 2.04-1.50 (m, 8H), 1.38-1.20 (m, (2H) |
| 141 Exo olefin | 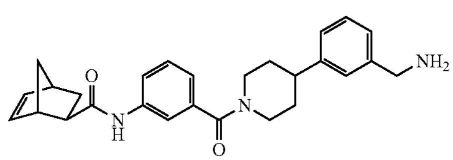 [SMILES: NCc1cccc(C2CCN(C(=O)c3cccc(NC(=O)C4CC5C=CC4C5)c3)CC2)c1] | (±) exo N-(3-(4-(3-(aminomethyl)phenyl)piperidine-1-carbonyl)phenyl)bicyclo[2.2.2]oct-5-ene-2-carboxamide | | White solid; Yield: 75%, Mol. Wt: 443.55, MS (ES+): m/z = 444 [MH$^+$], HPLC Purity: 96.84%, $^1$H NMR (400 MHz, CD$_3$OD): δ 7.87 (s, 1H), 7.52 (d, J = 7.2 Hz, 1H), 7.44-7.34 (m, 4H), 7.31 (d, J = 7.6 Hz, 1H), 7.14 (d, J = 7.6 Hz, 1H), 6.40 (t, J = 6.8 Hz, 1H), 6.35 (t, J = 6.8 Hz, 1H), 4.11 (s, 2H), 3.98-3.84 (m, 1H), 3.04-2.88 (m, 2H), |

| Compound No. | Structure | Names | Brief reaction conditions | Analytical data |
|---|---|---|---|---|
| | | | | 2.80-2.70 (m, 1H), 2.62-2.48 (m, 2H), 2.08-1.60 (m, 8H), 1.48-1.35 (m, 1H), 1.34-1.20 (m, 1H), 1.18-1.05 (m, 1H) |
| 142 Endo olefin | 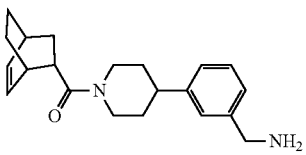 [SMILES: NCc1cccc(C2CCN(C(=O)C3CC4C=CC3CC4)CC2)c1] | (±) endo (4-(3-(aminomethyl)phenyl)piperidin-1-yl)(-bicyclo[2.2.2]oct-5-en-2-yl)methanone (±) exo (4-(3-(aminomethyl)phenyl)piperidin-1-yl)(-bicyclo[2.2.2]oct-5-en-2-yl)methanone | | White solid; Yield: 39%, Mol. Wt.: 324.45 MS (ES+): m/z = 325 [MH$^+$], HPLC Purity: 99.71%, $^1$H NMR (400 MHz, CDCl$_3$): δ 8.37 (bs, 2H), 7.30-7.10 (m, 4H), 6.30-6.18 (m, 2H), 4.62-4.50 (m, 1H), 4.08-3.90 (m, 3H), 3.16-3.00 (m, 1H), 2.82-2.48 (m, 6H), 1.92-1.66 (m, 3H), 1.63-1.36 (m. 4H), 1.33-1.21 (m. 2H) |
| 142 Exo olefin | 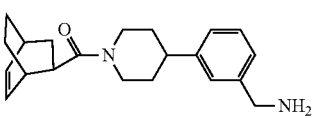 [SMILES: NCc1cccc(C2CCN(C(=O)C3CC4C=CC3CC4)CC2)c1] | | | White solid; Yield: 44%, Mol. Wt: 324.45 MS (ES+): m/z = 325 [MH$^+$], HPLC Purity: 99.50%, $^1$H NMR (400 MHz, CD$_3$OD): δ 7.44-7.24 (m, 4H), 6.44-6.28 (m, 2H), 4.80-4.68 (m, 1H), 4.20-4.02 (m, 3H), 3.23-3.12 (m, 1H), 2.96-2.82 (m, 1H), 2.80-2.67 (m, 2H), 2.63-2.52 (m, 2H), 2.12-1.86 (m, 3H), 1.82-1.51 (m, 4H), 1.48-1.03 (m, (3H) |
| 141 Racemic Endo anti | 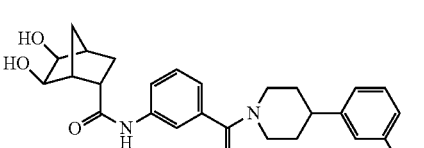 | (±) endo-N-(3-(4-(3-(aminomethyl)phenyl)piperidine-1-carbonyl)phenyl)-5,6-anti-dihydroxybicyclo[2.2.2]octane-2-carboxemide. | | White solid; Yield: 36%, Mol. Wt: 477.60 MS (ES+): m/z = 478 [MH$^+$], HPLC Purity: 95.87%, $^1$H NMR (400 MHz, CD$_3$OD): δ 7.85 (s, 1H), 7.51 (d, J = 7.8 Hz, 1H), 7.45-7.34 (m, 4H), 7.29 (d, J = 7.8 Hz, 1H), 7.14 (d, J = 7.2 Hz, 1H), 4.82-4.72 (m, 1H), 4.11 (s, 2H), 4.06-3.98 (m, 1H), 3.95-3.85 (m, 1H), 3.04-2.72 (m, 4H), 2.08-1.68 (m, 9H), 1.50-1.24 (m, 2H) |

-continued

| Compound No. | Structure | Names | Brief reaction conditions | Analytical data |
|---|---|---|---|---|
| 141 Racemic Exo syn | 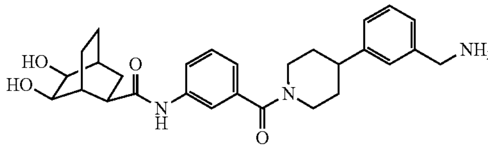 [SMILES: NCc1cccc(C2CCN(C(=O)c3cccc(NC(=O)C4CC5CCC4C(O)C5O)c3)CC2)c1] | (±) exo-N-(3-(4-(3-(aminomethyl)phenyl)piperidine-1-carbonyl)phenyl)-5,6-syn-dihydroxybicyclo[2.2.2]octane-2-carboxamide. | | White solid; Yield: 30%, Mol. Wt: 477.60 MS (ES+): m/z = 478 [MH+], HPLC Purity: 95.54%, $^1$H NMR (400 MHz, CD$_3$OD): δ 8.52 (s, 1H), 7.85 (S, 1H), 7.52 (d, J = 8.0 Hz, 1H), 7.44-7.33 (m, 3H), 7.29 (d, J = 7.2 Hz, 1H), 7.14 (d, J = 8.0 Hz, 1H), 4.10 (s, 2H), 3.98-3.80 (s, 3H), 3.14-2.87 (m, 2H), 2.70-2.59 (m, 1H), 2.24-2.11 (m, 1H), 2.06-1.94 (m, 2H), 1.90-1.69 (m, 5H), 1.66-1.30 (m, 2H) |
| 141 Racemic Exo anti | 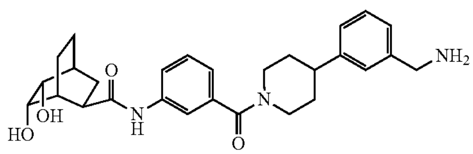 [SMILES: NCc1cccc(C2CCN(C(=O)c3cccc(NC(=O)C4CC5CCC4C(O)C5O)c3)CC2)c1] | (±) exo-N-(3-(4-(3-(aminomethyl)phenyl)piperidine-1-carbonyl)phenyl)-5,6-anti-dihydroxybicyclo[2.2.2]octane-2-carboxamide. | | White solid; Yield: 15%, Mol. Wt: 477.60 MS (ES+): m/z = 478 [MH+], HPLC Purity: 99.57%, $^1$H NMR (400 MHz, CD$_3$OD): δ 8.54 (s, 1H), 7.84 (s, 1H), 7.52 (d, J = 7.6 Hz, 1H(, 7.44-7.32 (m, 3H), 7.29 (d, J = 7.2 Hz, 1H), 7.14 (d, J = 7.6 Hz, 1H), 4.09 (s, 2H), 3.97-3.82 (m, 3H), 3.38-3.18 (m, 1H), 3.10-2.88 (m, 2H), 2.05-1.62 (m, 8H), 1.45-1.29 (m, 2H) |
| 142 Racemic Endo anti | 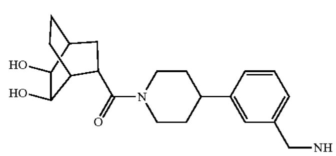 | (±) endo (4-(3-(aminomethyl)phenyl)piperidin-1-yl)(-5,6-anti-dihydroxybicyclo[2.2.2]octan-2-yl)methanone | | White solid; Yield: 37%, Mol. Wt.: 358.47 MS (ES+): m/z = 359 [MH+], HPLC Purity: 95.59%, $^1$H NMR (400 MHz, CD$_3$OD): δ 7.42-7.20 (m, 4H), 4.75-4.65 (m, 1H), 4.58-4.38 (m, 1H), 4.18-4.05 (m, 3H), 4.00-3.86 (m, 1H), 3.27-3.12 (m, 1H), 3.08-3.00 (m, 1H), 2.94-2.82 (m, 1H), 2.80-2.67 (m. 1H), 2.06-1.76 (m, 8H), 1.74-1.54 (m, 2H), 1.50-1.28 (m,2H) |

| Compound No. | Structure | Names | Brief reaction conditions | Analytical data |
|---|---|---|---|---|
| 142 Racemic Endo syn | 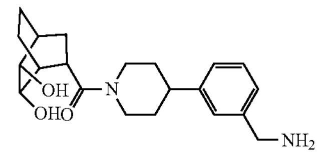 [SMILES: NCc1cccc(C2CCN(C(=O)C3CC4CCC3C(O)C4O)CC2)c1] | (±) endo (4-(3 (aminomethyl)phenyl) piperidin-1-yl)(-5,6-syn-dihydroxybicyclo [2.2.2]octan-2-yl)methanone | | White solid; Yield: 31%, Mol. Wt.: 358.47 MS (ES+): m/z = 359 [MH$^+$], HPLC Purity: 99.24%, $^1$H NMR (400 MHz, CD$_3$OD): δ 7.42-7.24 (m, 4H), 4.75-4.66 (m, 1H), 4.20-4.04 (m, 3H), 3.86-3.72 (m, 2H), 3.10-3.00 (m, 1H), 2.96-2.84 (m, 1H), 2.80-2.68 (m, 1H), 2.34-1.48 (m, 13H) |
| 142 Racemic Exo Anti | 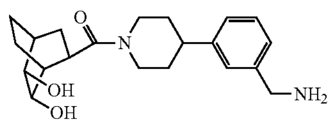 [SMILES: NCc1cccc(C2CCN(C(=O)C3CC4CCC3C(O)C4O)CC2)c1] | (±) endo (4-(3 (aminomethyl)phenyl) piperidin-1-yl)(-5,6-anti-dihydroxybicyclo [2.2.2]octan-2-yl)methanone | | White solid; Yield: 12%, Mol. Wt.: 358.47 MS (ES+): m/z = 359 [MH$^+$], HPLC Purity: 95.03%, $^1$H NMR (400 MHz, CD$_3$OD): δ 7.42-7.20 (m, 4H), 4.78-4.64 (m, 1H), 4.40-4.16 (m, 1H), 4.10-3.97 (m, 3H), 3.94-3.80 (m, 1H), 3.75-3.55 (m, 1H), 3.23-3.03 (m, 1H), 2.90-2.60 (m, 2H), 2.10-1.50 (m, 10H), 1.42-1.20 (m, 2H) |

Example 32. Synthesis of Tryptase Inhibitors with benzooxaborol-1-ol functionality Five Final targets with benzoxaborol functionality were synthesized 112 Spiro, T-117 Spiro, T-117 Spiro methyl and T-117-gem mono methyl, were synthesized with benzoxaborol functionality. Synthetic approaches for all the targets were not very similar, so every target is described with its respective scheme and procedure as given below.

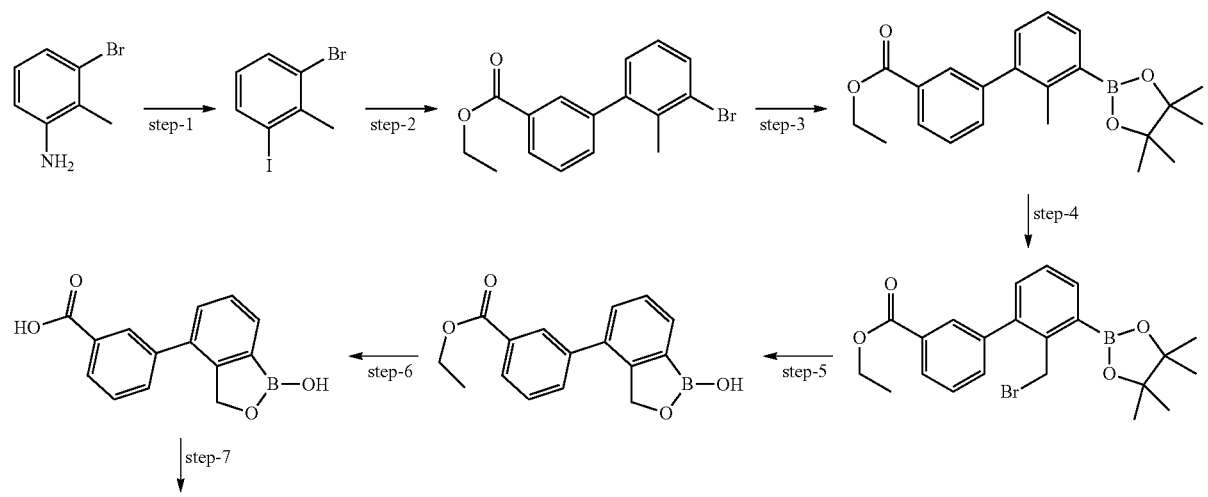

Scheme-Target112spiro

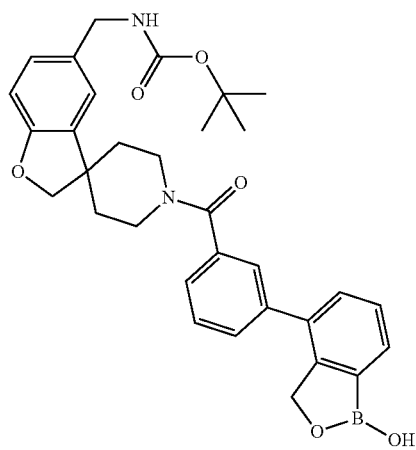

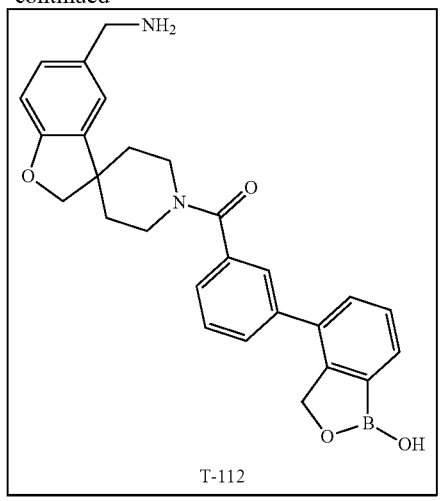

T-112

Step-1

1-bromo-6-iodo-2-methylbenzene was synthesized as per procedures available in the literature (*Bioorganic and Medicinal Chemistry*, 16, 6764-6777, 2008; *J. Am. Chem. Soc.*, 122, 6871- 6883, 2000.)

Step-2

Suzuki coupling of Step-1 product (8.5 g, 28.6 mmol) with m-carbethoxy phenyl boronic acid (6.65 g, 34.32 mmol)) was carried out in presence of palladium (0) tetrakis (triphenyl phosphine) (10 mol %) in dioxane (20 vol) and sodium carbonate (6.06 g, 57.2 mmol) as the base. After completion of reaction, the reaction mixture was filtered through a pad of celite and the filtrate was concentrated in vacuo. The residue obtained was partitioned between ethyl acetate and water and separated. The aqueous was re-etracted with ethyl acetate and the combined organic fractions were dried over sodium sulfate, filtered and concentrated in vacuo. The crude product obtained was purified by column chromatography over silica gel eluting with 5-10% ethyl acetate in hexanes.
Yield: 80%
Mol. Wt: 319.19
MS (ES+): m/z=319.2/321.2 [MH$^+$]

Step-3

A stirred suspension of step-2 (7.0 g, 21.9 mmol) in toluene (30 vol) was degassed with argon then charged with potassium acetate (6.47 g, 65.7 mmol), PdCl$_2$-dppf-CH$_2$Cl$_2$ (5 mol %) and bis (pinacolato) diborane (13.9 g, 54.75 mmol) and the reaction was refluxed. The reaction mixture was the filtered through a pad of celite and the filtrate was concentrated in vacuo resulting in crude product. The crude product was purified by column chromatography over silica gel eluting with 1-5% ethyl acetate in hexane.
Yield: 80%
Mol. Wt: 366.26
MS (ES+): m/z=367.20 [MH$^+$]

Step-4

A stirred solution of step-3 product (6.0 g, 16.3 mmol) in carbon tetrachloride (20 vol) was charged with dibenzoyl peroxide (075 g, 3.2 mmol) and N-bromo succinimide (1.2 eq) and heated to 75° C. for 5 hr. The reaction mixture was partitioned between water dichloromethane and separated. The organic phase was washed with water, brine, dried over anhydrous sodium sulfate, filtered, and concentrated in vacuo resulting in crude product. The crude product was purified by column chromatography over silica gel eluting with 1-5% ethyl acetate in hexanes.
Yield: 80%
Mol. Wt: 445.15
MS (ES+): m/z=446.20/447.20 [MH]

Step-5

A stirred solution of Step-4 product (5.8 g, 13 mmol) in acetonitrile (30 vol) was charged with trifluoro acetic acid (10 vol) and water (5 vol) and heated to 91° C. and monitored by LCMS. The reaction mixture was concentrated in vacuo and the residue was partitioned between water and ethyl acetate and separated. The organic layer was dried over sodium sulfate, filtered and concentrated in vacuo. The crude product was purified by column chromatography over silica gel eluting with 10-35% ethyl acetate in hexanes.
Yield: 60%
Mol. Wt: 282.10
MS (ES+): m/z=283.25 [MH$^+$]

Step-6

A mixture of step-5 product (2 g, 7.08 mmol) in THF (10 vol) & water (20 vol) was charged with lithium hydroxide (1.7 g, 70.8 mmol) and heated to 60° C. The reaction mixture was concentrated in vacuo. The reaction mixture was diluted with water and was adjusted to pH 2 using conc. HCl upon which a precipitate formed. The precipitate was filtered, washed with water and dried in vacuum oven.
Yield: 60%
Mol. Wt: 254.05
MS (ES+): m/z=255.10 [MH$^+$]

Step-7

A mixture of step-6 product (250 mg, 0.98 mmol), tert-butyl ((2H-spiro[benzofuran-3,4'-piperidin]-5-yl)methyl)

carbamate (404 mg, 1.27 mmol), EDCI (280 mg, 1.47 mmol), DMAP (240 mg, 1.96 mmol) in dichloromethane (20 vol) was stirred at room temperature and was monitored by LCMS. The reaction mixture was concentrated in vacuo diluted with water and the pH was adjusted to 4 using dil. HCl upon which a precipitate formed. The precipitate was filtered and washed with water and dried in vacuum oven.

Yield: 60%
Mol. Wt: 554.44,
MS (ES+): m/z=555.10 [MH$^+$]

Step-8

Product of step-7 (370 mg, 0.66 mmol) was dissolved in dichloromethane (20 vol) and TFA (20 vol) and stirred at room temperature until complete. The reaction mixture was concentrated in vacuo and the crude residue was purified by preparative HPLC to give Target 112.

Yield: 33%
Mol. Wt: 454.33
MS (ES+): m/z=455.20 [MH$^+$]
HPLC purity: 96%

$^1$H NMR (400 MHz, DMSO-d$_6$): δ 8.29 (s, 2H), 7.81 (d, J=6.9 Hz, 1H), 7.64-7.41 (m, 7H), 7.26 (d, J=8.2 Hz, 1H), 6.82 (d, J=8.2 Hz, 1H), 5.13 (s, 2H), 4.44 (d, J=46.7 Hz, 4H), 4.13-3.88 (m, 4H), 3.69 (d, J=16.3 Hz, 1H), 3.14 (s, 2H), 1.74 (d, J=42.6 Hz, 4H).

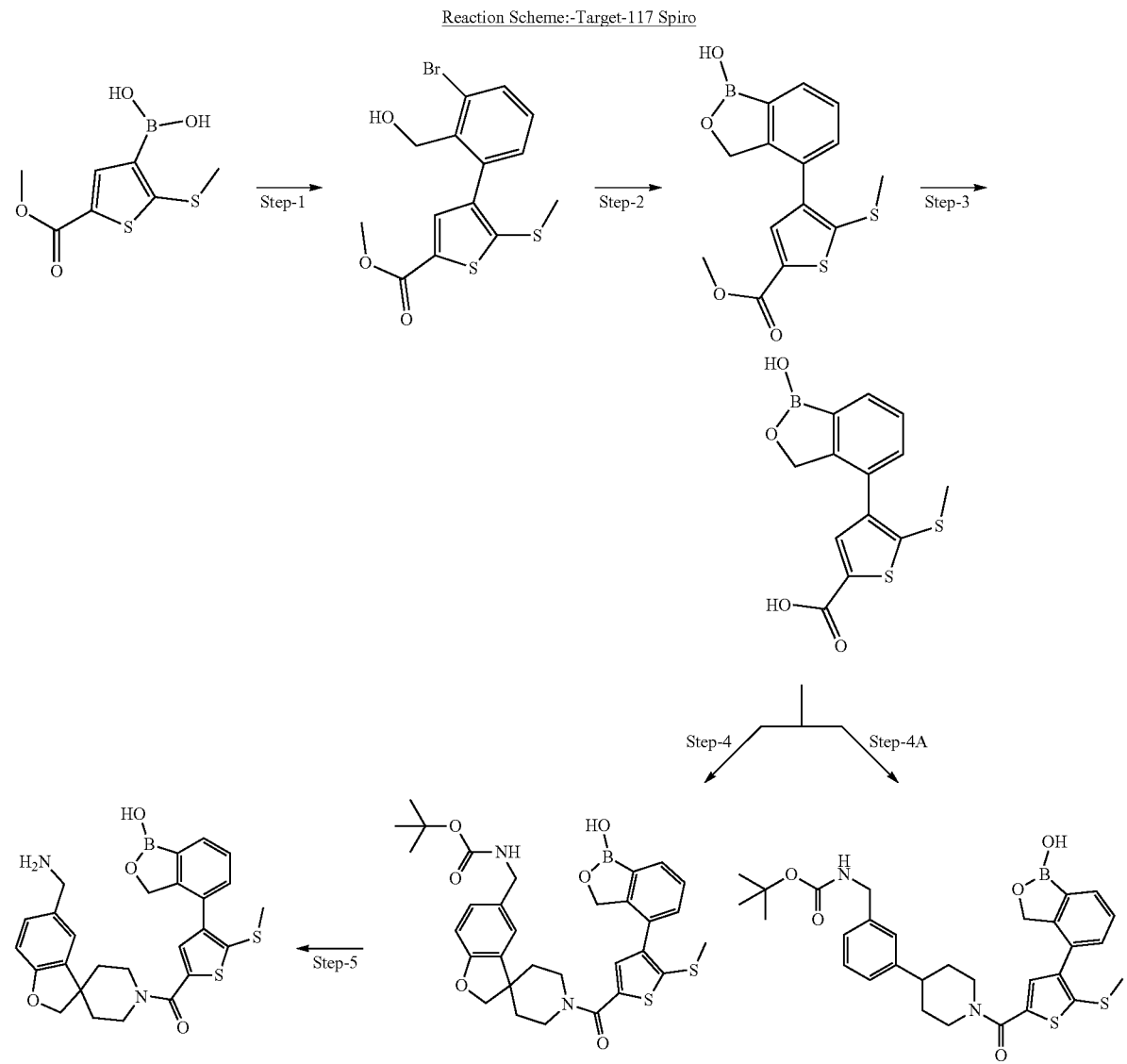

Reaction Scheme:-Target-117 Spiro

-continued

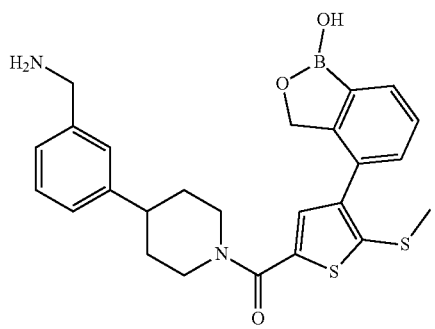

T-117

Step-1

A solution of (5-(methoxycarbonyl)-2-(methylthio)thiophen-3-yl)boronic acid (8 g, 34.48 mmol), 2,6-dibromobenzyl alcohol (11 g, 41.37 mmol), palladium (0) tetrakis (triphenyl phosphine) (10 mol %), and sodium carbonate (7.3 g, 68.96 mmol) in dioxane (20 vol) was degassed and heated until complete. The reaction mixture was filtered through a pad of celite and the filtrate was concentrated in vacuo. The residue was partitioned between water and ethyl acetate and separated. The organic layer was dried over sodium sulfate, filtered, and concentrated in vacuo resulting in crude product. The crude product was purified by column chromatography over silica gel eluting with 5-10% ethyl acetate in hexanes.
Yield: 20%
Mol. Wt: 373.29
MS (ES+): m/z=373.10/375.10 [MH+]

Step-2

A stirred suspension of step-1 product (1.9 g, 5.09 mmol) in toluene (30 vol) was degassed with argon and charged with potassium acetate (1.5 g, 15.27 mmol), $PdCl_2$-dppf-$CH_2Cl_2$ (5 mol %), dppf (3 mol %) and bis (pinacolato) diborane (3.21 g, 12.72 mmol) and degassed again then heated to reflux & monitored by LCMS till most of the starting material was consumed. The mixture was filtered through a pad of celite and the filtrate was concentrated in vacuo resulting in crude product. The crude product was purified by column chromatography over silica gel eluting with 1-5% ethyl acetate in hexanes.
Yield: 40%
Mol. Wt: 320.19
MS (ES+): m/z=321.10 [MH+]

Step-3

A mixture of step-2 product (650 mg, 2.03 mmol, potassium hydroxide (570 mg, 10.15 mmol) in THF (10 vol) and water (20 vol) was heated to 60° C. Reaction was monitored by LCMS till most of the starting material was consumed. The reaction mixture was concentrated in vacuo and the residue was diluted with water and the pH was adjusted to 2 using conc. HCl upon which a precipitate formed. The precipitate was filtered and washed with water and dried in vacuum oven.
Yield: 35%
Mol. Wt: 306.17
MS (ES+): m/z=307.20 [MH+]

Step-4

A mixture of step-3 product (150 mg, 0.490 mmol), tert-butyl ((2H-spiro[benzofuran-3,4'-piperidin]-5-yl) methyl)carbamate (202 mg, 0.63 mmol), EDCI (142 mg, 0.735 mmol), DMAP (120 mg, 0.98 mmol) in dichloromethane (20 vol) was stirred at room temperature and monitored by LCMS till most of the starting material was consumed. The reaction mixture was concentrated in vacuo and diluted with water and adjusted to pH ~4 using dil. HCl upon which a precipitate formed. The precipitate was filtered and washed with water and dried in vacuum oven.
Yield: 55%
Mol. Wt: 606.17
MS (ES+): m/z=607.20 [MH+]
Step-4A: same as step-4, only tert-butyl 3-(piperidin-4-yl) benzyl carbamate used instead of ((2H-spiro [benzofuran-3,4'-piperidin]-5-yl)methyl)carbamate
Yield: 51%
Mol. Wt: 578.55
MS (ES+): m/z=579.3 [MH+]

Step-5

Product of step-4 (160 mg, 0.263 mmol) was dissolved in dichloromethane (20 vol)-TFA (20 eq) a stirred at room temperature. After completion of reaction, the reaction mixture was concentrated in vacuo and purified by preparative HPLC to give Target-117 Spiro.
Yield: 30%,
Mol. Wt: 506.44
MS (ES+): m/z=507.15 [MH+]
HPLC purity: 99.2%
$^1$H NMR (400 MHz, DMSO-$d_6$): δ 9.38 (s, 1H), 8.19-8.06 (m, 2H), 7.87 (d, J=7.3 Hz, 1H), 7.52 (t, J=7.4 Hz, 1H), 7.37 (d, J=7.5 Hz, 1H), 7.30-7.29 (m, 1H), 7.20 (d, J=8.2 Hz, 1H), 6.90 (s, 1H), 6.78 (d, J=8.2 Hz, 1H), 5.00 (d, J=26.4 Hz, 2H), 4.26 (s, 2H), 3.96 (p, J=5.6 Hz, 2H), 2.89-2.75 (m, 4H), 2.50 (s, 3H), 1.25 (s, 4H).
Step-5A: same as step-5 only tert-butyl 3-(piperidin-4-yl) benzyl carbamate used instead of ((2H-spiro [benzofuran-3,4'-piperidin]-5-yl)methyl)carbamate
Yield: 20%,
Mol. Wt: 478.43
MS (ES+): m/z=479.15 [MH+]
HPLC data: 96.79%

¹H NMR (400 MHz, CDCl₃): δ 8.16 (bs, 1H), 8.03 (m, 1H), 7.79 (d, J=6.8 Hz, 1H), 7.51-7.42 (m, 3H), 7.03-6.97 (m, 3H), 6.62 (s, 1H), 5.34 (m, 1H), 4.16 (s, 2H) 3.77 (m, 2H), 3.63-3.48 (m, 4H), 2.72 (bs, 1H), 2.57 (s, 3H), 2.2-2.0 (m, 4H)

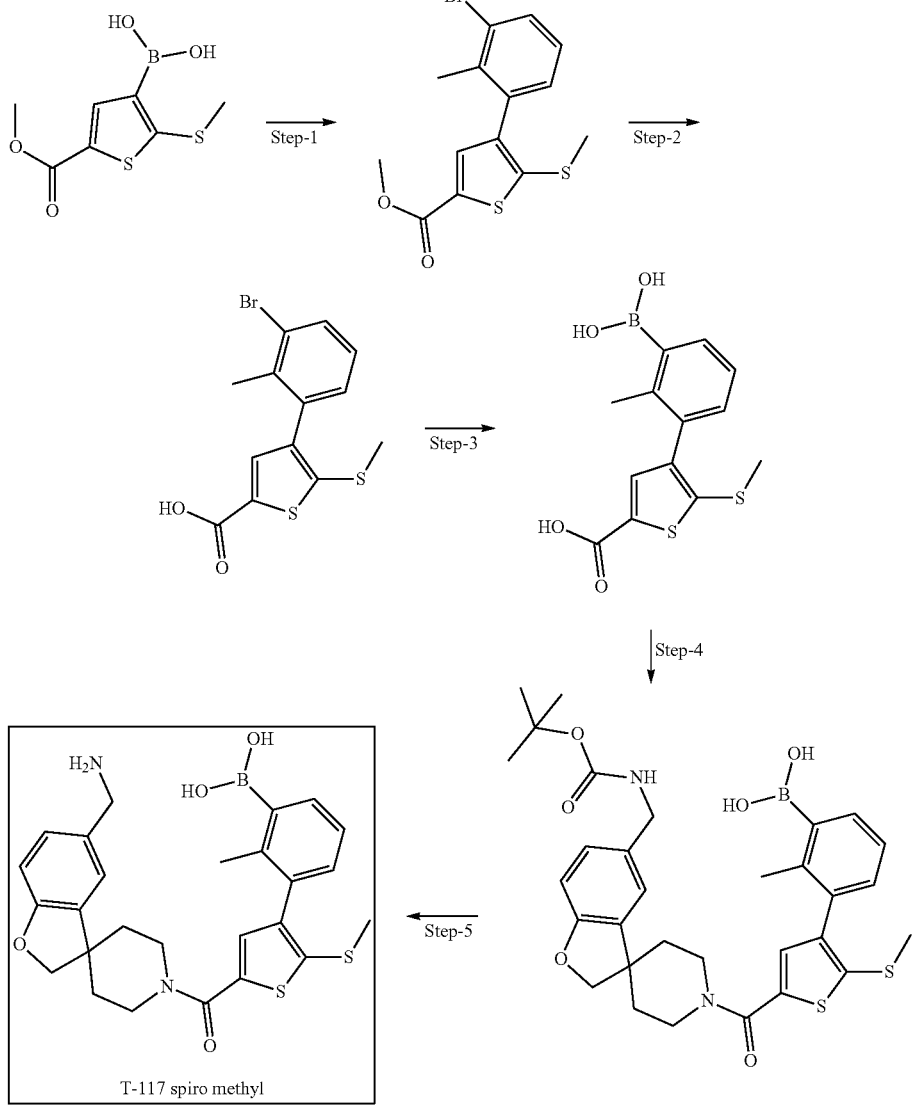

Step-1

Suzuki coupling of (5-(methoxycarbonyl)-2-(methylthio) thiophen-3-yl)boronic acid (5 g, 21.54 mmol) with 2-bromo-6-iodotoluene (7.6 g, 25.85) was carried out in presence of palladium (0) tetrakis (triphenyl phosphene) (10 mol %), and sodium carbonate (4.56 g, 43.08 mmol) in dioxane (20 vol) and heated at 80° C. for 3 hr. After completion of reaction, the reaction mixture was filtered through a pad of celite and filtrate was concentrated in vacuo. The residue obtained was partitioned between water and ethyl acetate and separated. The organic was dried over sodium sulfate, filtered, and concentrated in vacuo resulting in product. The crude product obtained was purified by column chromatography over silica gel eluting with 5-10% ethyl acetate in hexane.

Yield: 70%
Mol. Wt: 357.29
MS (ES+): m/z=357.10/359.10 [MH⁺]

Step-2

A mixture of step-1 product (5 g, 13.9 mmol) in THF (10 eq) & water (20 vol) was charged with potassium hydroxide (7.8 g, 13.9 mmol) was heated to 60° C. for 2 hr. The reaction was monitored by LCMS till most of the starting material was consumed. The reaction mixture was concentrated in vacuo and diluted with water and the pH was adjusted to 2 using conc. HCl. Upon which a precipitate formed. The precipitate was filtered, washed with water and dried in vacuum oven.

Yield: 80%
Mol. Wt: 343.26
MS (ES+): m/z=343.10/345.10 [MH+]

Step-3

A solution of Step-2 product (1 g, 2.9 mmol) in in THF (30 vol) was cooled to −78° C. and charged with n-BuLi (556 mg, 8.7 mmol) and stirred at −78° C. for 30 min. Stirring at same temperature the reaction was dropwise charged with tri-isopropyl borate (1.58 mg, 8.7 mmol) and then allowed to warm to room temperature. The reaction mixture was quenched with dil HCl and concentrated in vacuo. The residue obtained was diluted with dil HCl, filtered and washed with water. The residue was redissolved in aq NaOH and reprecipitated by acidifying with dil HCl to get pure product.

Yield: 20%
Mol. Wt: 308.18
MS (ES+): m/z=309.10 [MH+]

Step-4

A mixture of step-3 product (150 mg, 0.486 mmol), tert-butyl ((2H-spiro [benzofuran-3, 4'-piperidin]-5-yl) methyl) carbamate (200 mg, 0.632 mmol), EDCI (140 mg, 0.729 mmol), DMAP (120 mg, 0.972) in dichloromethane (20 vol) was stirred at room temperature. The reaction was monitored by LCMS until most of the starting material was consumed. The reaction mixture was concentrated in vacuo and diluted with water and the pH was adjusted to ~-4 using dil. HCl upon which a precipitate formed. The precipitate was filtered, washed with water and dried in vacuum oven.

Yield: 60%
Mol. Wt: 608.58
MS (ES+): m/z=609.20 [MH+]

Step-5

Product of step-4 (164 mg, 0.27 mmol) was dissolved in dichloromethane (20 vol)-TFA (20 eq) and stirred at room temperature until completion of reaction and then concentrated in vacuo and purified by preparative HPLC to give the Target-117 Spiro Methyl.

Yield: 31.6%
Mol. Wt: 508.46
MS (ES+): m/z=509.15 [MH+]
HPLC purity: 98.4%
$^1$H NMR (400 MHz, DMSO-$d_6$): δ 8.23 (s, 2H), 7.55 (d, J=7.1 Hz, 1H), 7.22 (t, J=7.6 Hz, 2H), 7.17-7.07 (m, 2H), 7.00 (s, 1H), 6.77 (d, J=8.3 Hz, 1H), 4.29 (s, 2H), 3.94 (q, J=5.8 Hz, 2H), 2.85 (t, J=12.3 Hz, 4H), 2.60 (s, 3H), 2.30 (s, 3H), 1.32 (bs, 6H)

Reaction Scheme:-Target-117 gem mono methyl Spiro

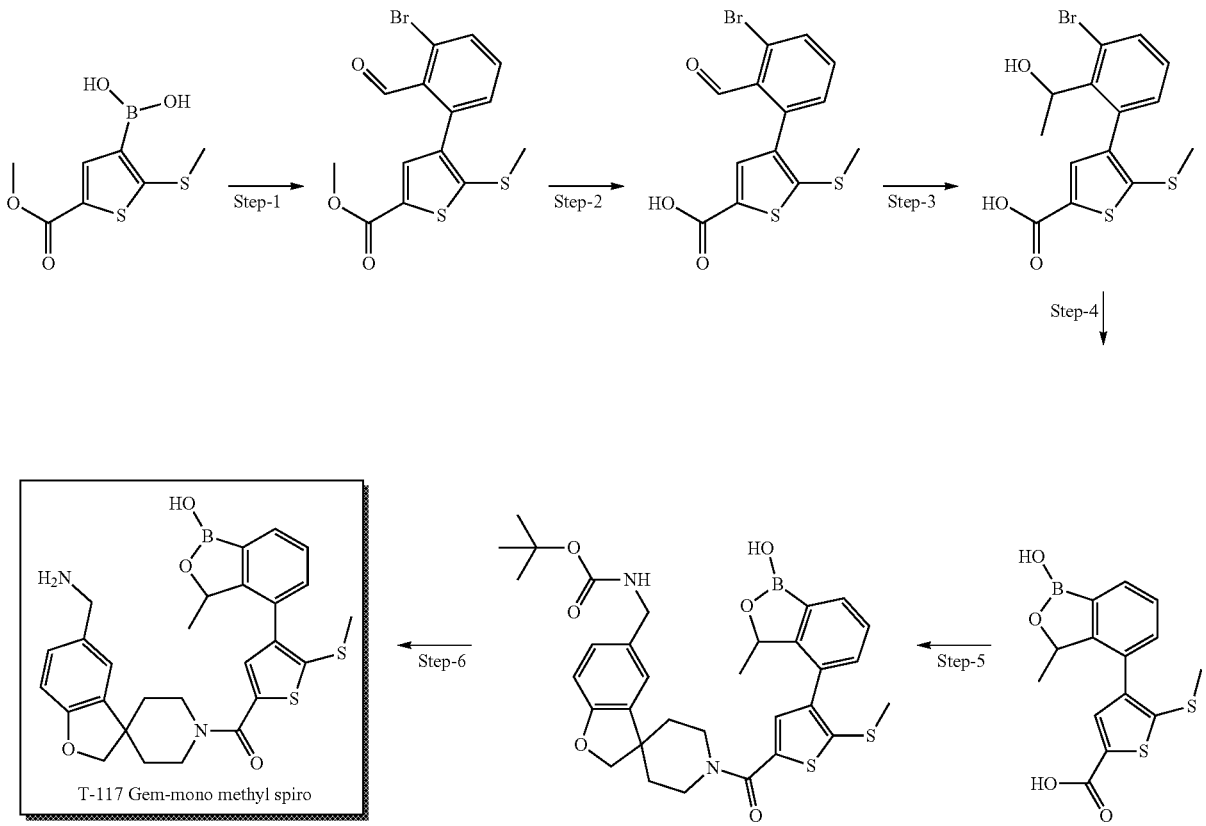

Step-1

A solution of (5-(methoxycarbonyl)-2-(methylthio)thiophen-3-yl)boronic acid (5 g, 21.54 mmol), 2-bromo-6-iodobenzaldehyde (8 g, 25.85 mmol), palladium(0) tetrakis (triphenyl phosphine) (10 mol %), sodium carbonate (4.53 g, 43.08 mmol) in dioxane (20 vol) was degassed and heated at 80° C. for 24 hr. The reaction mixture was filtered through a pad of celite and the filtrate was concentrated in vacuo. The residue was diluted with water and extracted with ethyl acetate to get crude product. The crude product was purified by column chromatography over silica gel eluting with 5-10% ethyl acetate in hexane.
Yield: 60%
Mol. Wt: 371.27
MS (ES+): m/z=371.10/373.10 [MH+]

Step-2

A mixture of step-1 product (3.5 g, 9.4 mmol) in THF (10 eq) & water (20 vol) was charged with potassium hydroxide (2.1 g, 37.6 mmol) and heated to 60° C. for 2 hr. The reaction mixture was concentrated in vacuo and diluted with water and the pH was adjusted to ~2 using conc. HCl upon which a precipitate formed. The precipitate was filtered, washed with water and dried in vacuum oven.
Yield: 80%
Mol. Wt: 357.24
MS (ES+): m/z=357.20/359.20 [MH+]

Step-3

Solution of Step-2 product (2.57 g, 7.2 mmol) in THF (30 vol) was cooled to 0° C. and charged with methylmagnesiumbromide (944 mg, 7.92 mmol) and stirred for 30 min The reaction mixture was quenched with dil HCl at 0° C. and concentrated in vacuo. The residue was diluted with dil HCl, filtered and washed with water. The crude product was purified by column chromatography over silica gel using 5-10% ethyl acetate in hexane.
Yield: 95%
Mol. Wt: 373.29
MS (ES+): m/z=373.10/375.10 [MH+]

Step-4

A stirred suspension of step-3 product (2.5 g, 6.69 mmol) in toluene was degassed with argon and charged with potassium acetate (1.96 g, 20.07 mmol), $PdCl_2$-dppf-$CH_2Cl_2$ (5 mol %) and bis (pinacolato) diborane (4.23 g, 16.72 mmol) and heated to reflux and monitored by LCMS till most of the starting material was consumed. The mixture was the filtered through a pad of celite and the filtrate was concentrated in vacuo to give the crude product. The crude product was purified by column chromatography over silica gel using 1-5% ethyl acetate in hexanes.
Yield: 80%
Mol. Wt: 320.19
MS (ES+): m/z=321.10 [MH+]

Step-5

A mixture of step-4 product (700 mg, 2.18 mmol), tert-butyl ((2H-spiro[benzofuran-3,4'-piperidin]-5-yl)methyl)carbamate (900 mg, 2.83 mmol), EDCI (617 mg, 13.27 mmol), DMAP (536 mg, 4.36 mmol) in dichloromethane (20 vol) was stirred at room temperature and the reaction was monitored by LCMS till most of the starting material was consumed. The reaction mixture was concentrated and diluted with water and the aqueous was adjusted to pH 4 using dil. HCl upon which a precipitate formed. The precipitate was filtered, washed with water and dried in vacuum oven
Yield: 50%
Mol. Wt: 620.59
MS (ES+): m/z=621.20 [MH+]

Step-6

Product of step-5 (600 mg, 0.96 mmol) was dissolved in dichloromethane (20 vol)-TFA (20 eq) and stirred at room temperature. The reaction mixture was concentrated in vacuo and purified by preparative HPLC to give Target-117 Gem mono methyl spiro.
Yield: 31.6%
Mol. Wt: 520.47
MS (ES+): m/z=521.25 [MH+]
HPLC purity: 99.3%
$^1$H NMR (400 MHz, DMSO-$d_6$): δ 8.17 (s, 4H), 7.95 (s, 1H), 7.78 (d, J=7.3 Hz, 1H), 7.60 (d, J=7.5 Hz, 1H), 7.46 (dd, J=15.9, 8.2 Hz, 3H), 7.24 (d, J=8.2 Hz, 1H), 6.84 (d, J=8.2 Hz, 1H), 5.55 (q, J=6.4 Hz, 1H), 4.31 (d, J=8.0 Hz, 2H), 4.08-3.87 (m, 2H), 3.03 (t, J=12.3 Hz, 1H), 2.39-2.28 (m, 1H), 2.62 (s, 3H), 1.28 (d, J=52.8 Hz, 4H), 1.04 (d, J=6.7 Hz, 3H)
The details of the Final Targets synthesized are as below.

| Target | Structure | Analytical Data |
|---|---|---|
| 112 Spiro | 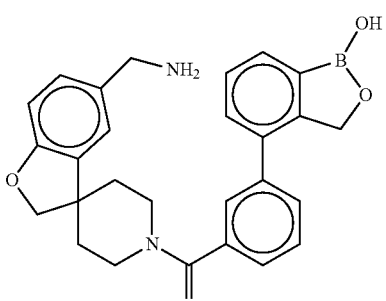<br>(5-(aminomethyl)-2H-spiro[benzofuran-3,4'-piperidin]-1'-yl)(3-(1-hydroxy-1,3-dihydrobenzo[c][1,2]oxaborol-4-yl)phenyl)methanone | Mol. Wt: 454.33<br>MS (ES+): m/z = 455.20 [MH+]<br>HPLC data: 96%<br>$^1$H NMR (400 MHz, DMSO-$d_6$):<br>δ 8.29 (s, 2H), 7.81 (d, J = 6.9 Hz, 1H), 7.64-7.41 (m, 7H), 7.26 (d, J = 8.2 Hz, 1H), 6.82 (d, J = 8.2 Hz, 1H), 5.13 (s, 2H), 4.44 (d, J = 46.7 Hz. 4H), 4.13-3.88 (m, 4H), 3.69 (d, J = 16.3 Hz, 1H), 3.14 (s, 2H), 1.74 (d, J = 42.6 Hz. 4H). |

| Target | Structure | Analytical Data |
|---|---|---|
| 117-Spiro | (5-(aminomethyl)-2H-spiro[benzofuran-3,4'-piperidine]-1'-yl)(4-(1-hydroxy-1,3-dihydrobenzo[c][1,2]oxaborol-4-yl)-5-(methylthio)thiophen-2-yl)methanone | Mol. Wt: 506.44<br>MS (ES+): m/z = 507.15 [MH$^+$]<br>HPLC data: 99.2%<br>$^1$H NMR (400 MHz, DMSO-d$_6$): δ 9.38 (s, 1H), 8.19-8.06 (m, 2H), 7.87 (d, J = 7.3 Hz, 1H), 7.52 (t, J = 7.4 Hz, 1H), 7.37 (d, J = 7.5 Hz, 1H), 7.30-7.29 (m, 1H), 7.20 (d, J = 8.2 Hz, 1H), 6.90 (s, 1H), 6.78 (d, J = 8.2 Hz, 1H), 5.00 (d, J = 26.4 Hz, 2H), 4.26 (s, 2H), 3.96 (d, J = 5.6 Hz, 2H), 2.89-2.75 (m, 4H), 2.50 (s, 3H), 1.25 (s, 4H). |
| 117 | (4-(3-(aminomethyl)phenyl)piperidin-1-yl)(4-(1-hydroxy-1,3-dihydrobenzo[c][1,2]oxaborol-4-yl)-5-(methylthio)thiophen-2-yl)methanone | Mol. Wt: 478.43<br>MS (ES+): m/z = 479.15 [MH$^+$]<br>HPLC data: 96.79%<br>$^1$H NMR (400 MHz, CDCl$_3$): δ 8.16 (bs, 1H), 8.03 (m, 1H), 7.79 (d, J = 6.8 Hz, 1H), 7.51-7.42 (m, 3H), 7.03-6.97 (m, 3H), 6.62 (s, 1H), 5.34 (m, 1H), 4.16 (s, 2H) 3.77 (m, 2H), 3.63-3.48 (m, 4H), 2.72 (bs, 1H), 2.57 (s, 3H), 2.2-2.0 (m, 4H) |
| 117-Spiro- | (3-(5-(5-(aminomethyl)-2H-spiro[benzofuran-3,4'-piperidin]-1'-ylcarbonyl)-2-(methylthio)thiophen-3-yl)-2-methylphenyl)boronic acid | Mol. Wt: 508.46<br>MS (ES+): m/z = 509.15 [MH$^+$]<br>HPLC Data: 98.4%<br>$^1$H NMR (400 MHz, DMSO-d$_6$): δ 8.23 (s, 2H), 7.55 (d, J = 7.1 Hz, 1H), 7.22 (t, J = 7.6 Hz, 2H), 7.17-7.07 (m, 2H), 7.00 (s, 1H), 6.77 (d, J = 8.3 Hz, 1H), 4.29 (s, 2H), 3.94 (q, J = 5.8 Hz, 2H), 2.85 (t, J = 12.3 Hz, 4H), 2.60 (s, 3H), 2.30 (s, 3H), 1.32 (bs, 6H) |
| 117-Gem-Monomethyl-Spiro | (5-(aminomethyl)-2H-spiro[benzofuran-3,4'-piperidin]-1'-yl)(4-(1-hydroxy-3-methyl-1,3-dihydrobenzo[c][1,2]oxaborol-4-yl)-5-(methylthio)thiophen-2-yl)methanone | Md. Wt: 520.47<br>MS (ES+): m/z = 521.25 [MH$^+$]<br>HPLC data: 99.3%<br>$^1$H NMR (400 MHz, DMSO-d$_6$): δ 8.17 (s, 4H), 7.95 (5, 1H), 7.78 (d, J = 7.3 Hz, 1H), 7.60 (d, J = 7.5 Hz, 1H), 7.46 (dd, J = 15.9, 8.2 Hz, 3H), 7.24 (d, J = 8.2 Hz, 1H), , 6.84 (d, J = 8.2 Hz, 1H), 5.55 (q, J = 6.4 Hz, 1H), 4.31 (d, J = 8.0 Hz, 2H), 4.08-3.87 (m, 2H), 3.03 (t, J = 12.3 Hz, 1H), 2.39-2.28 (m, 1H), 2.62 (s, 3H), 1.28 (d, J = 52.8 H2, 4H), 1.04 (d, J = 6.7 Hz, 3H), |

General Procedure for Coupling Conditions and Work-Up

A stirred solution of carboxylic acid from step-3 in DCM or DMF was added and EDCI, HOBt (in some cases) and DMAP or DIPEA was for 15 min. at 0° C. followed by addition of protected core. Stirring was continued at room temperature and reaction was monitored by LCMS until most of the starting materials were consumed. Reaction mixture was then quenched with water and aq. layer was extracted with dichloromethane and combined organic layers were dried over sodium sulfate, filtered, and concentrated in vacuo to afford the crude product which was either used for next step without purification or purified by chromatographic techniques.

General Procedures for Hydrolysis

Desired ester was dissolved in mixture of Water and solvents like THF/methanol/acetone that are miscible in water then charged with lithium/sodium hydroxide and stirred at room temperature and monitored by TLC & LCMS until most of the starting material was consumed. Solvent was concentrated in vacuo and partitioned between ethyl acetate and water and separated. The aqueous layer was washed with ethyl acetate (1×) and acidified with 2N HCl and extracted with ethyl acetate again. The acidic ethyl acetate extract was dried over sodium sulfate, filtered, and concentrated in vacuo to get crude product. In most of the cases products were sufficient pure to be used for the next step.

General Procedures for Boc Deprotection

Desired compound was stirred with aq. hydrochloric acid or trifluoracetic acid (TFA) in a co-solvent like acetonitrile, methanol, THF, DCM etc. Reaction was monitored by LCMS until most of the starting materials were consumed. The reaction mixture was concentrated in vacuo to remove the solvents and residue obtained was purified by reverse phase preparative HPLC. In some cases products were purified by column chromatography over silica gel.

The pure fraction of mobile phase was lyophilized to get the products as TFA salts. TFA salts were converted to hydrochloride salts by stirring with 2N HCl for 30 min under nitrogen atmosphere followed by lyophilization.

Sometimes only Boc deprotection observed to be taking place with boronate ester functionality intact. In such cases further hydrolysis of isolated Boc de-protected boronate esters were carried out followed by purification using preparative HPLC.

EQUIVALENTS

While specific embodiments have been discussed, the above specification is illustrative and not restrictive. Many variations will become apparent to those skilled in the art upon review of this specification. The full scope of the embodiments should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A therapeutic composition comprising a first monomer selected from the group consisting of:

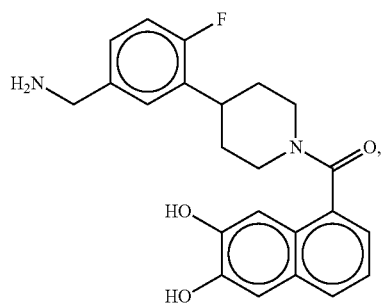

-continued

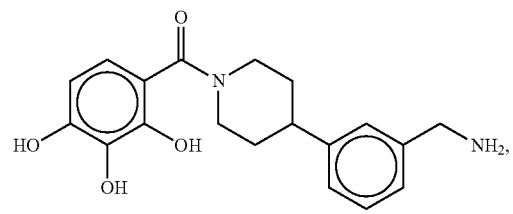

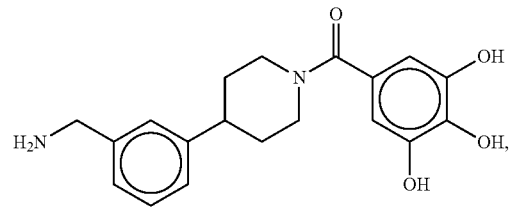

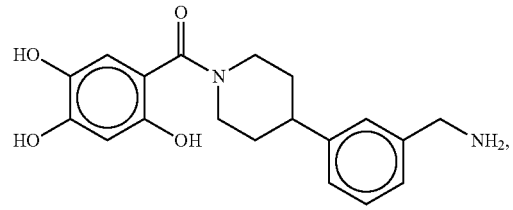

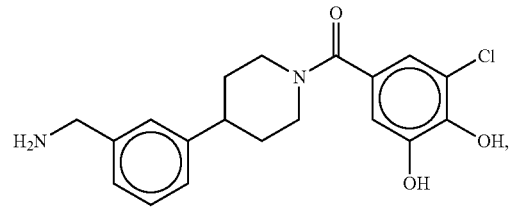

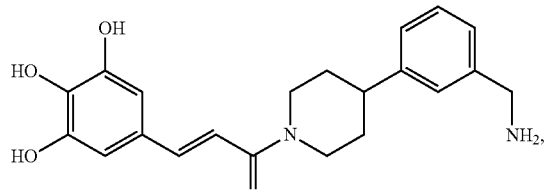

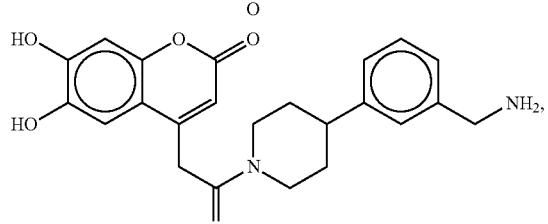

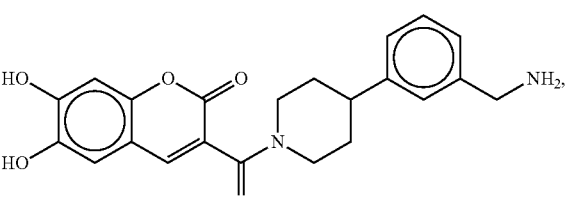

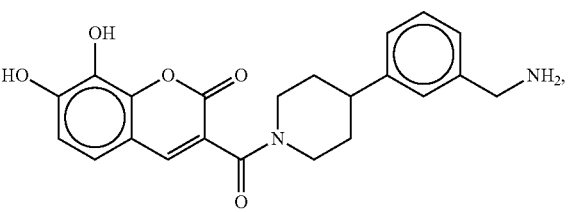

517
-continued
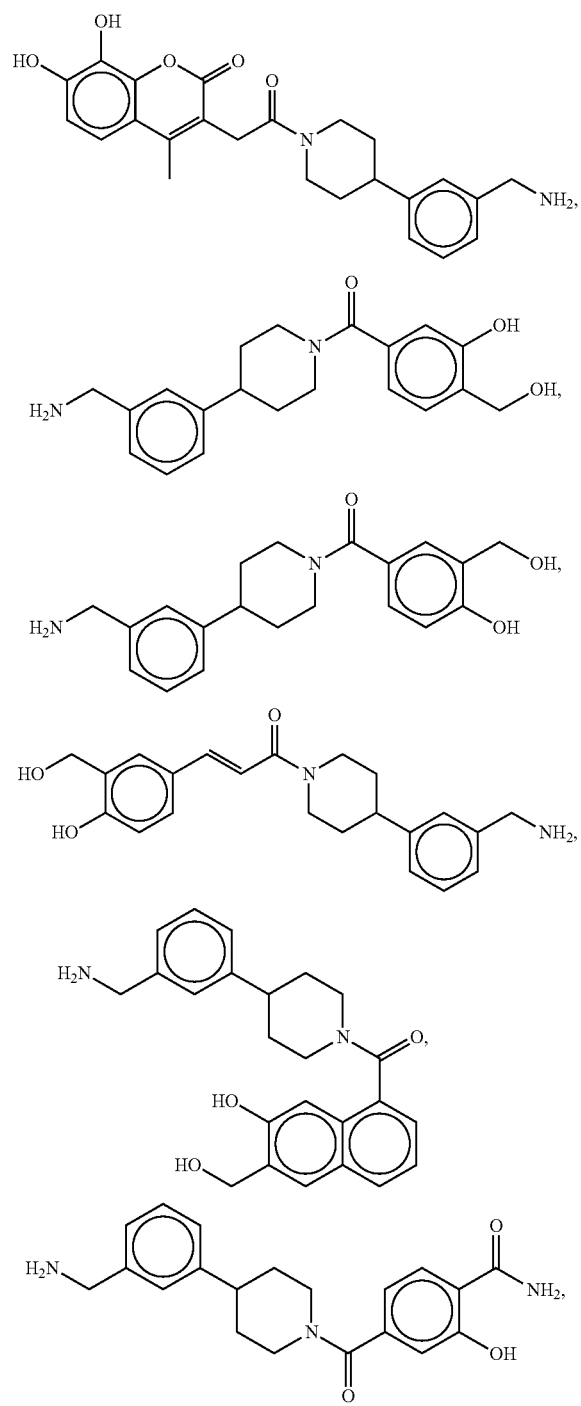
518
-continued
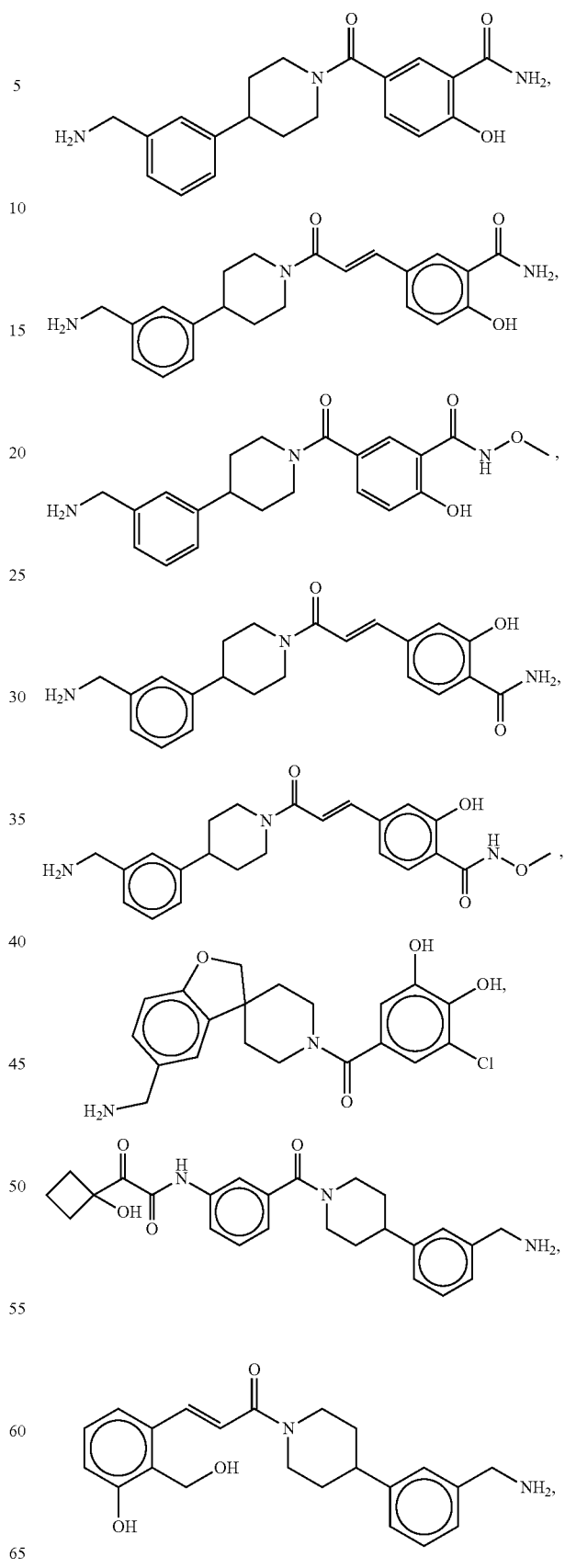

519
-continued
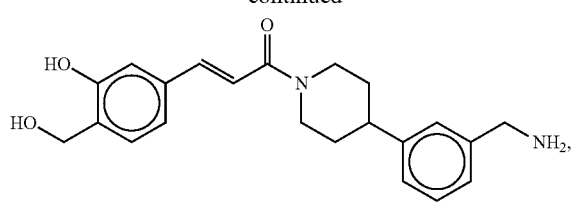
and
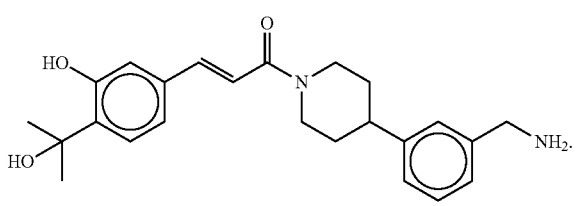
and
a second monomer selected from the group consisting of:
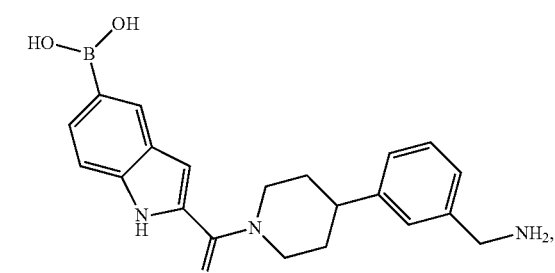
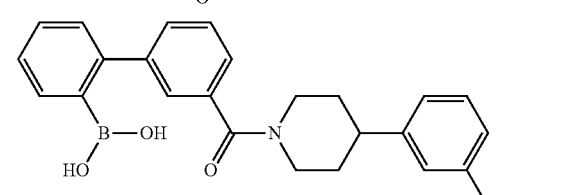
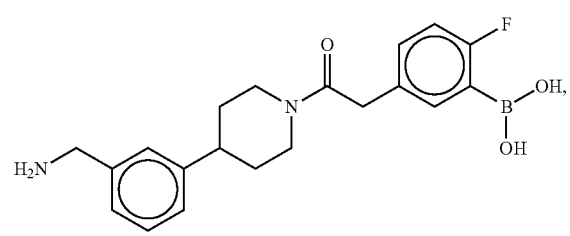
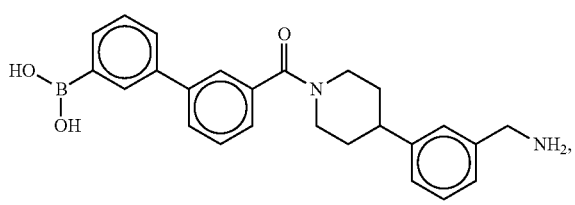
520
-continued
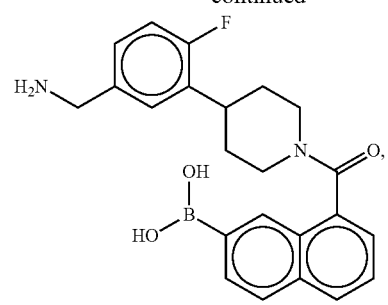
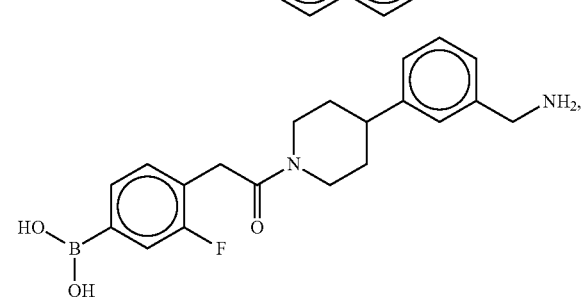
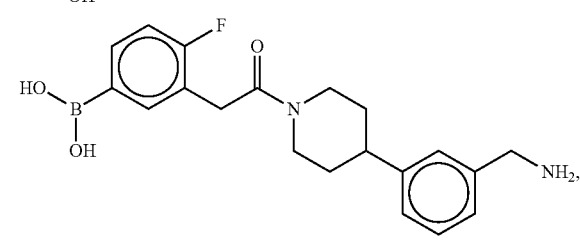
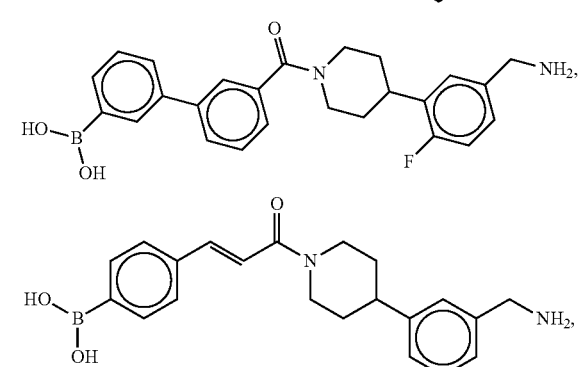
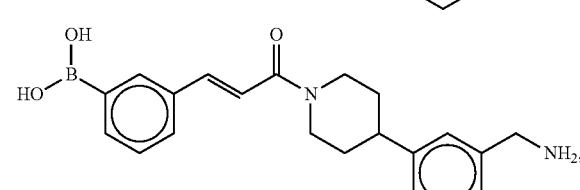
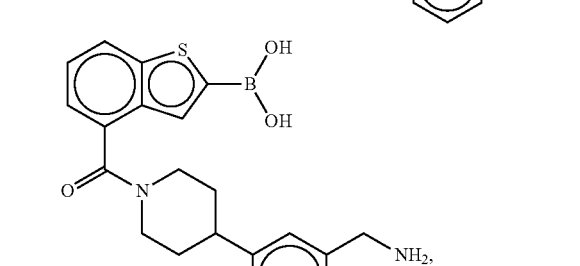

-continued
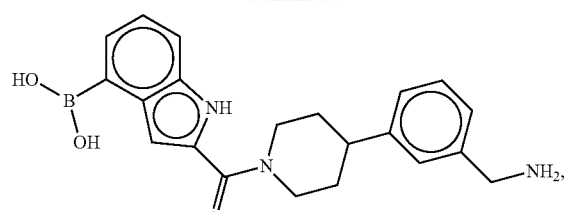
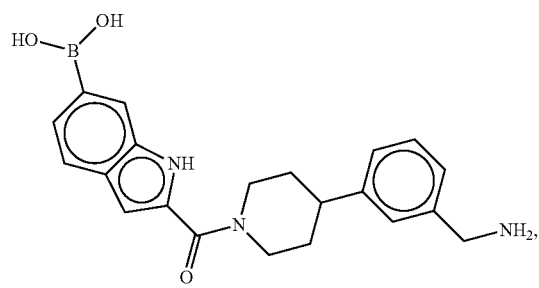
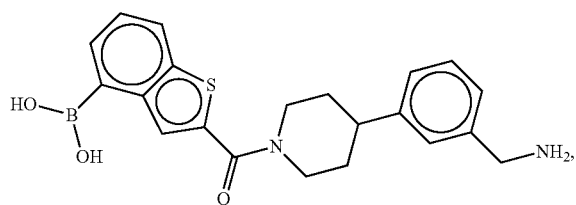
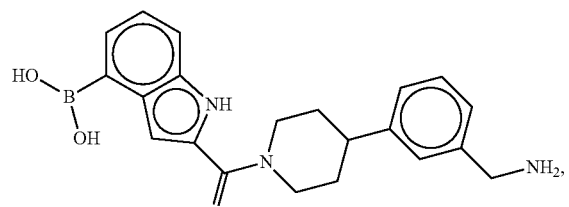
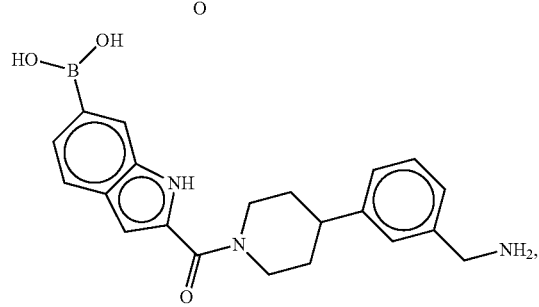
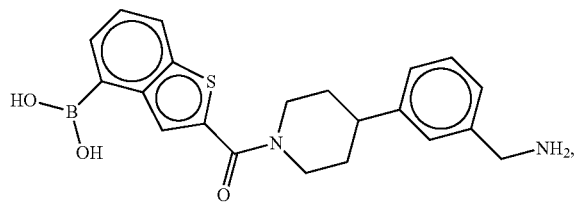
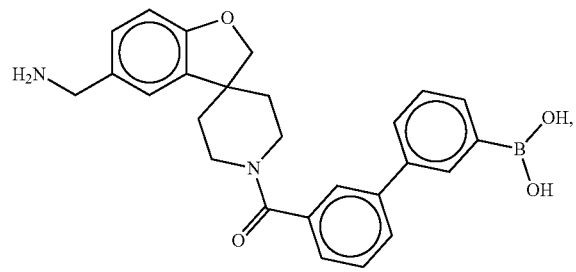
-continued
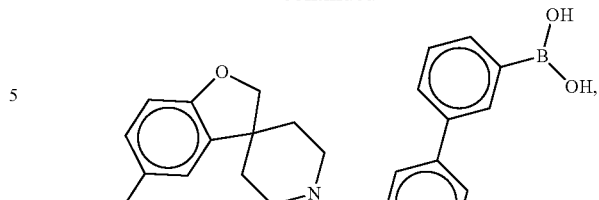
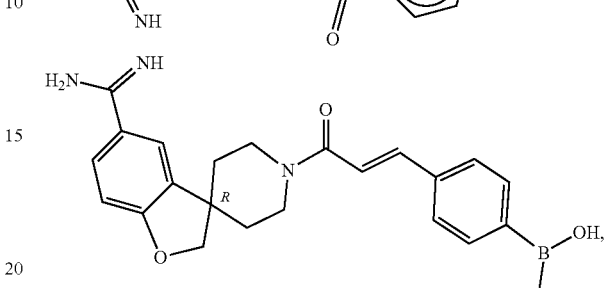
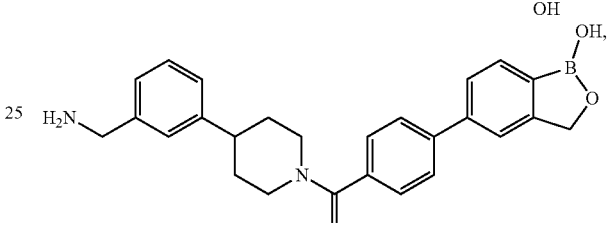
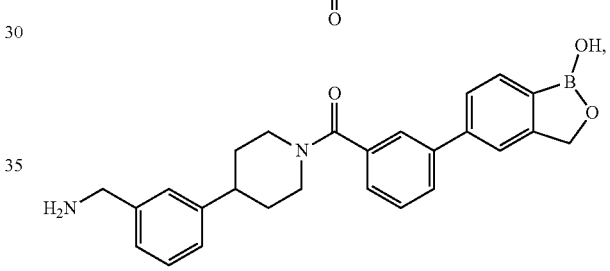
and
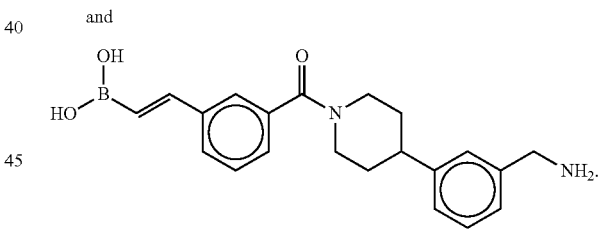
and
pharmaceutically acceptable salts, stereoisomers, or hydrates thereof.
2. The therapeutic composition of claim 1, wherein the first monomer is
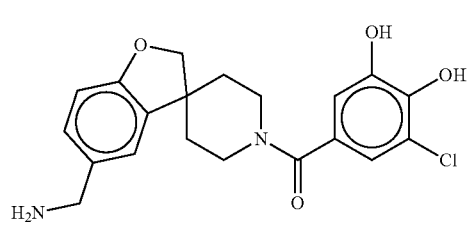

and the second monomer is
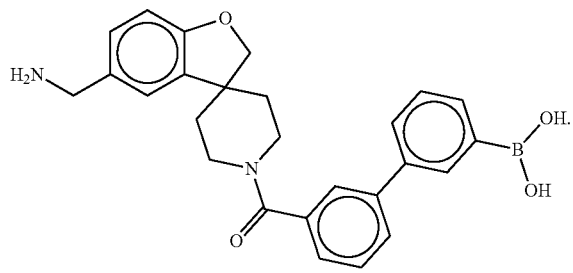
3. A therapeutic composition comprising a first monomer selected from the group consisting of:
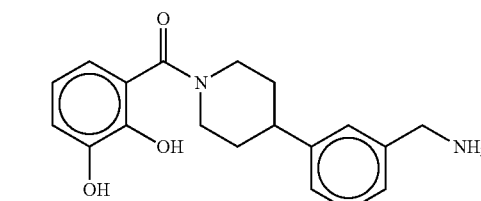
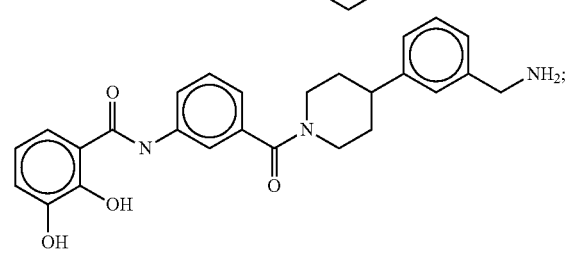
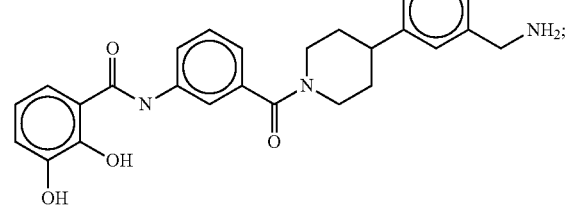
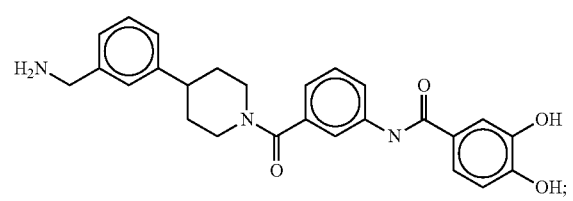
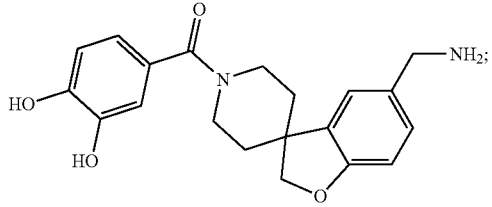
and
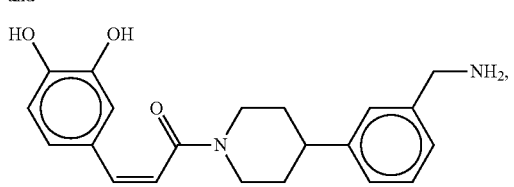
and a second monomer selected from the group consisting of:
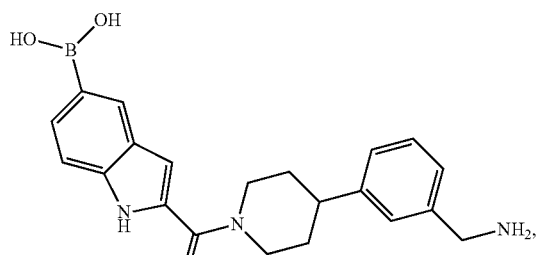
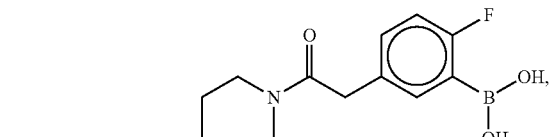
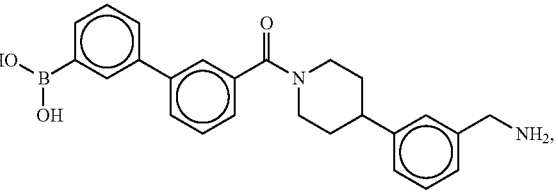
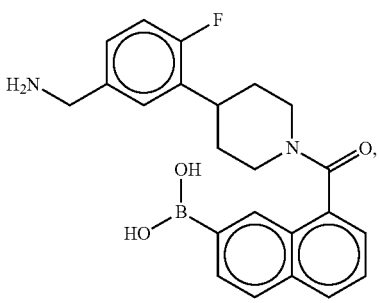
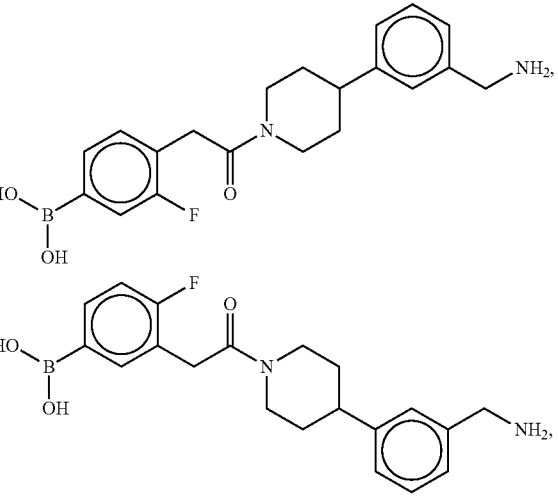

525
-continued
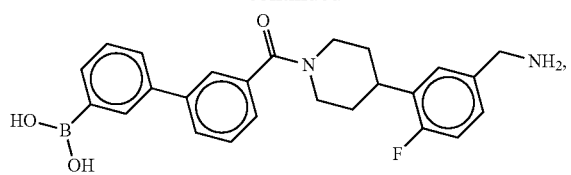
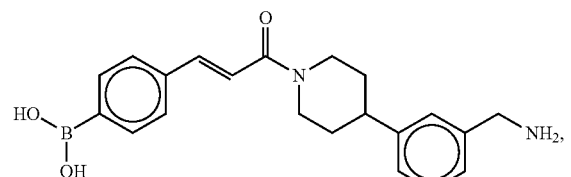
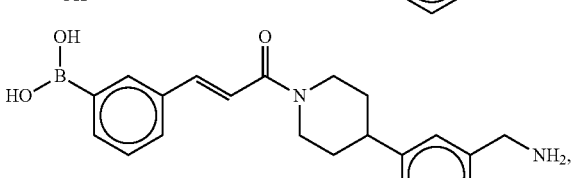
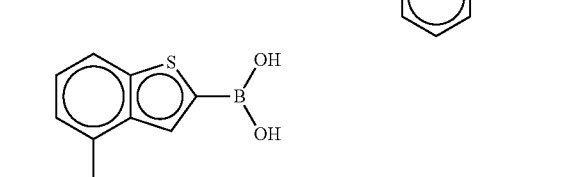
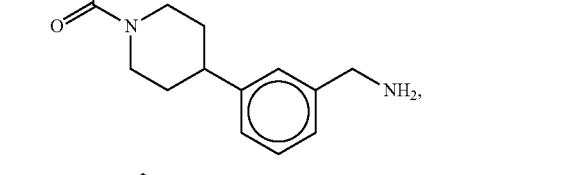
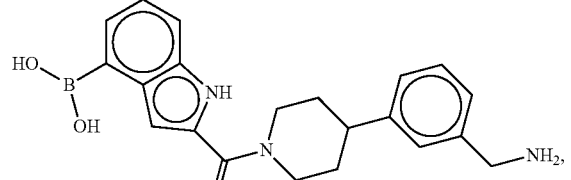
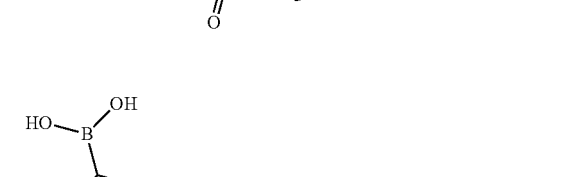
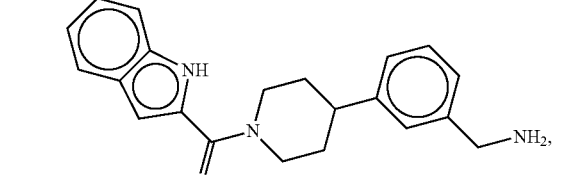
526
-continued
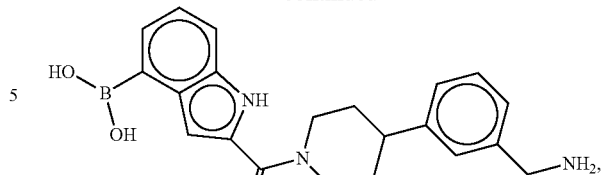
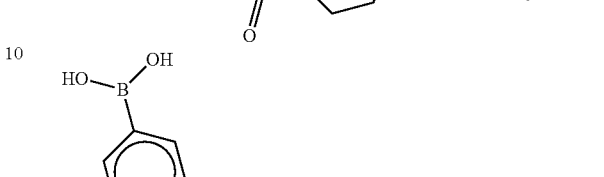
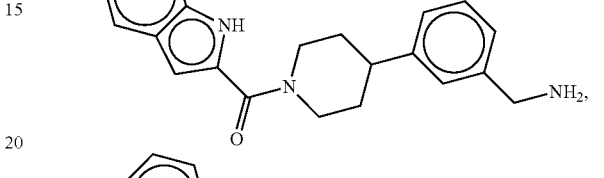
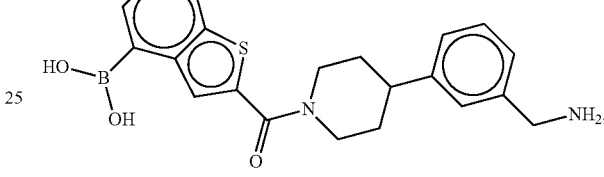
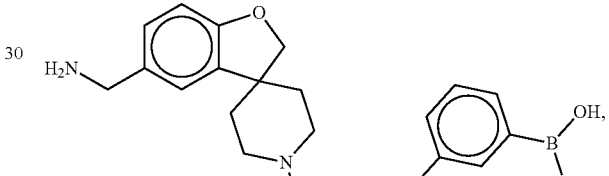
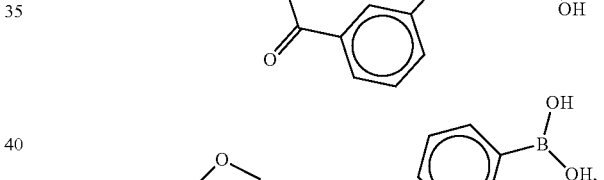
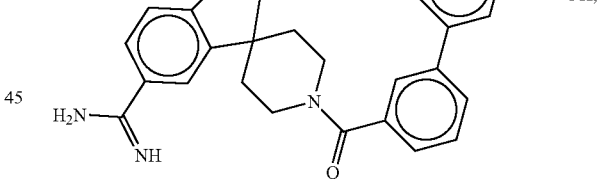
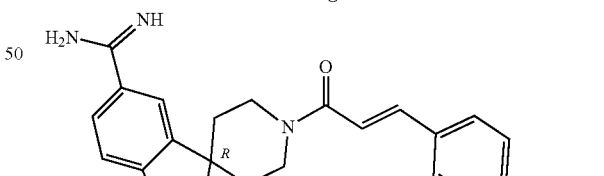

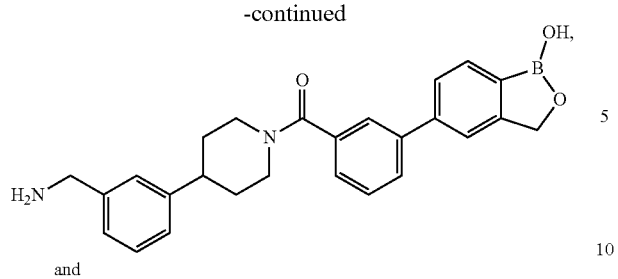
and
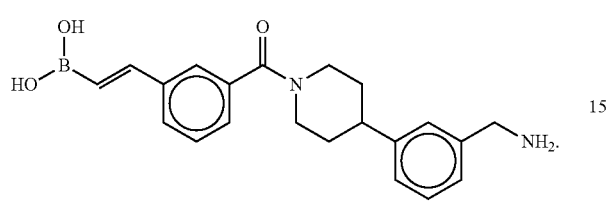
and
pharmaceutically acceptable salts, stereoisomers, or hydrates thereof.
* * * * *